US011634497B2

(12) United States Patent
Bender et al.

(10) Patent No.: US 11,634,497 B2
(45) Date of Patent: Apr. 25, 2023

(54) ANTI-CCR7 ANTIBODY DRUG CONJUGATES

(71) Applicant: NOVARTIS AG, Basel (CH)

(72) Inventors: Steven Bender, Oceanside, CA (US); Tracy Charlton, San Diego, CA (US); Anna Galkin, Encinitas, CA (US); Bernhard Hubert Geierstanger, Solana Beach, CA (US); Scott Martin Glaser, San Diego, CA (US); Shailaja Kasibhatla, San Diego, CA (US); Mark Knuth, El Cajon, CA (US); Sabine Rottmann, San Diego, CA (US); Sarah Rue, San Diego, CA (US); Glen Spraggon, San Diego, CA (US); Tetsuo Uno, San Diego, CA (US)

(73) Assignee: NOVARTIS AG, Basel (CH)

( * ) Notice: Subject to any disclaimer, the term of this patent is extended or adjusted under 35 U.S.C. 154(b) by 443 days.

(21) Appl. No.: 16/482,173

(22) PCT Filed: Feb. 1, 2018

(86) PCT No.: PCT/IB2018/050639
§ 371 (c)(1),
(2) Date: Jul. 30, 2019

(87) PCT Pub. No.: WO2018/142322
PCT Pub. Date: Aug. 9, 2018

(65) Prior Publication Data
US 2020/0216548 A1 Jul. 9, 2020

Related U.S. Application Data

(60) Provisional application No. 62/454,476, filed on Feb. 3, 2017.

(51) Int. Cl.
*C07K 16/28* (2006.01)
*A61K 47/68* (2017.01)
*A61P 35/00* (2006.01)
*A61K 39/00* (2006.01)

(52) U.S. Cl.
CPC ...... *C07K 16/2866* (2013.01); *A61K 47/6803* (2017.08); *A61K 47/6849* (2017.08); *A61P 35/00* (2018.01); *A61K 2039/505* (2013.01)

(58) Field of Classification Search
CPC ............ C07K 16/2866; C07K 2317/24; C07K 2317/30; C07K 2317/33; C07K 2317/732; C07K 2317/76; C07K 2317/77; C07K 2317/92; A61K 47/6803; A61K 47/6849; A61K 2039/505; A61K 39/39525; A61P 35/00; A61P 35/02
See application file for complete search history.

(56) References Cited

U.S. PATENT DOCUMENTS

| 5,759,804 A | 6/1998 | Godiska et al. |
| 6,043,551 A | 3/2000 | Seshan |
| 6,153,441 A | 11/2000 | Appelbaum et al. |
| 8,066,996 B2 | 11/2011 | Calleja et al. |
| 2002/0168358 A1 | 11/2002 | Gladue et al. |
| 2002/0182624 A1 | 12/2002 | Zlotnik |
| 2009/0123483 A1 | 5/2009 | Calleja et al. |
| 2009/0175877 A1 | 7/2009 | Mueller et al. |
| 2010/0285020 A1 | 11/2010 | Aifantis et al. |
| 2011/0114651 A1 | 5/2011 | Oltman |
| 2012/0114651 A1 | 5/2012 | de Wildt et al. |
| 2015/0017167 A1 | 1/2015 | Nishiguchi et al. |
| 2015/0344580 A1 | 12/2015 | Abbasova et al. |
| 2016/0031997 A1 | 2/2016 | King et al. |
| 2020/0129632 A1 | 4/2020 | Abrams et al. |

FOREIGN PATENT DOCUMENTS

| AU | 2018215701 B2 | 4/2021 | |
| EP | 2623592 A1 * | 8/2013 | ........... A61K 31/713 |
| EP | 2623592 A1 | 8/2013 | |
| WO | 2000/004926 A2 | 2/2000 | |
| WO | 2000/009151 A1 | 2/2000 | |
| WO | 2001/038352 A2 | 5/2001 | |
| WO | 2002/010138 A2 | 2/2002 | |
| WO | 2002/062850 A2 | 8/2002 | |
| WO | 2002/067771 A2 | 9/2002 | |
| WO | 2002/101350 A2 | 12/2002 | |
| WO | 2003/047420 A2 | 6/2003 | |
| WO | 2004/104574 A2 | 12/2004 | |
| WO | 2005/015207 A2 | 2/2005 | |

(Continued)

OTHER PUBLICATIONS

Kim et al., Bimol Ther 2015 23(6), pp. 493-509 (Year: 2015).*
Wilson, et al., "Anti-CCR7 antibodies for the treatment of cancer", Expert Opinion Therapeutic Patents, 2007, vol. 17, No. 7, pp. 871-874.
Birkenbach, et al., "Epstein-Barr virus-induced genes: first lymphocyte-specific G protein-coupled peptide receptors", Journal of Virology, Apr. 1993, vol. 67, No. 4, pp. 2209-2220, American Society for Microbiology.
Itoh, et al., "Presence of Three Distinct Molecular Species of G, Protein a Subunit, Strucutre of Rat cDNAs and Human Genomic DNAs", The Journal of Biological Chemistry, May 15, 1988, vol. 263, No. 14, pp. 6656-6664, The American Society for Biochemistry and Molecular Biology, Inc.

(Continued)

*Primary Examiner* — Julie Wu
*Assistant Examiner* — John L Van Druff
(74) *Attorney, Agent, or Firm* — Elizabeth T. Karnas

(57) ABSTRACT

This application discloses anti-CCR7 antibodies, antigen binding fragments thereof, and antibody drug conjugates of said antibodies or antigen binding fragments. The invention also relates to methods of treating or preventing cancer using the antibodies, antigen binding fragments, and antibody drug conjugates. Also disclosed herein are methods of making the antibodies, antigen binding fragments, and antibody drug conjugates, and methods of using the antibodies and antigen binding fragments as diagnostic reagents.

26 Claims, 15 Drawing Sheets

Specification includes a Sequence Listing.

(56) References Cited

FOREIGN PATENT DOCUMENTS

| | | |
|---|---|---|
| WO | 2005/105207 A2 | 2/2005 |
| WO | 2006/056061 A1 | 6/2006 |
| WO | 2006/099019 A2 | 9/2006 |
| WO | 2007/003216 A1 | 1/2007 |
| WO | 2007/005605 A2 | 1/2007 |
| WO | WO-2007003426 A1 * | 1/2007 ......... C07K 16/2866 |
| WO | 2007/041364 A2 | 4/2007 |
| WO | 2007/048022 A2 | 4/2007 |
| WO | 2007/051063 A2 | 5/2007 |
| WO | 2008/015694 A2 | 2/2008 |
| WO | 2008/034074 A2 | 3/2008 |
| WO | 2008/034076 A2 | 3/2008 |
| WO | 2008/080218 A1 | 7/2008 |
| WO | 2009/076696 A1 | 6/2009 |
| WO | 2009/139853 A2 | 11/2009 |
| WO | 2011/003833 A1 | 1/2011 |
| WO | 2011/123903 A1 | 10/2011 |
| WO | 2012/043533 A1 | 5/2012 |
| WO | 2012/088290 A2 | 6/2012 |
| WO | 2012/088302 A2 | 6/2012 |
| WO | 2012/148547 A1 | 11/2012 |
| WO | 2012/172337 A2 | 12/2012 |
| WO | 2012/172341 A2 | 12/2012 |
| WO | 2012/172343 A2 | 12/2012 |
| WO | 2012/172346 A2 | 12/2012 |
| WO | 2012/172347 A1 | 12/2012 |
| WO | 2013/014535 A1 | 1/2013 |
| WO | 2013/074044 A1 | 5/2013 |
| WO | 2013/123018 A1 | 8/2013 |
| WO | 2013/184200 A1 | 12/2013 |
| WO | 2014/093870 A2 | 6/2014 |
| WO | 2014/150397 A2 | 9/2014 |
| WO | 2014/150937 A1 | 9/2014 |
| WO | 2014/151834 A2 | 9/2014 |
| WO | 2014/153114 A1 | 9/2014 |
| WO | WO-2014134483 A2 * | 9/2014 ......... A61K 31/5365 |
| WO | WO-2014150937 A1 * | 9/2014 ......... A61K 31/537 |
| WO | 2015/031698 A1 | 3/2015 |
| WO | 2015/033136 A1 | 3/2015 |
| WO | 2015/033137 A1 | 3/2015 |
| WO | 2015/036582 A2 | 3/2015 |
| WO | 2015/063187 A1 | 5/2015 |
| WO | 2015/138615 A2 | 9/2015 |
| WO | 2015/158855 A1 | 10/2015 |
| WO | WO-2015177360 A1 * | 11/2015 ......... A61K 31/475 |
| WO | 2016075670 A1 | 5/2016 |
| WO | 2016/179472 A1 | 11/2016 |

OTHER PUBLICATIONS

Charest-Morin, et al., "C—C chemokine receptor-7 mediated endocytosis of antibody cargoes into intact cells", Frontiers in Pharmacology, Sep. 24, 2013, vol. 4, Article 122, pp. 1-8.
U.S. Appl. No. 62/454,476.
Clinicaltrials.gov identifier NCT04240704.
Lo, Megan et al., "Effector-attenuating Substitutions That Maintain Antibody Stability and Reduce Toxicity in Mice", The Journal of Biological Chemistry, vol. 292, pp. 3900-3908, Jan. 11, 2017.

* cited by examiner

ANTI-CCR7 ANTIBODY DRUG CONJUGATES

CROSS-REFERENCE TO RELATED APPLICATIONS

This application is a national phase application, filed under 35 U.S.C. 371, of the International Patent Application No. PCT/IB2018/050639 filed Feb. 1, 2018, which claims the benefit of U.S. Provisional Application No. 62/454,476 filed Feb. 3, 2017, the content of which is hereby incorporated by reference in its entirety.

SEQUENCE LISTING

The instant application contains a Sequence Listing which has been submitted electronically in ASCII format and is hereby incorporated by reference in its entirety. Said ASCII copy, created on Jan. 10, 2018, is named PAT057594-WO-PCT_SL.txt and is 387,054 bytes in size.

FIELD OF THE INVENTION

The present invention generally relates to anti-CCR7 antibodies, antibody fragments, and immunoconjugates thereof, and their uses for the treatment or prevention of cancer.

BACKGROUND OF THE INVENTION

CC-chemokine receptor 7 (CCR7) was first identified in 1993 as a lymphocyte specific receptor (see, e.g., Birkenbach et al., J Virol. 1993 April; 67(4):2209-20). Its expression is restricted to subsets of immune cells, such as naïve T cells, central memory T cells (Tcm), regulatory T cells (Treg), naïve B cells, NK cells and mature antigen-presenting dendritic cells (DCs). CCR7 regulates homing of immune cells to and within lymphoid organs and thus plays a key role in balancing immunity and tolerance (see, e.g., Förster et al., Nat Rev Immunol. 2008 May; 8(5):362-71).

CCR7 is a class A, rhodopsin-like G-protein coupled receptor (GPCR), with two ligands, CCL21 and CCL19. The CCR7 structure has not been fully solved, however, certain motifs have been found essential for receptor activity (see, e.g., Legler et al., Int J Biochem Cell Biol. 2014 Jul. 1).

CCR7 and Cancer

CCR7 (also referred to as EBI1, BLR2, CC-CKR-7, CMKBR7, CD197 and CDw197) is also known to be overexpressed in a number of malignant tumors, including B cell malignancies (e.g., CLL, MCL, Burkitt's lymphoma), T cell malignancies (e.g., ATLL), HNSCC, ESCC, gastric carcinoma, NSCLC, colorectal carcinoma, pancreatic cancer, thyroid cancer, breast cancer, and cervical cancer, among others. The overexpression of CCR7 in, e.g., colorectal carcinoma, ESCC, pancreatic cancer, HNSCC, and gastric cancer was associated with advanced tumor stage, lymph node metastasis and poor survival (see, e.g., Malietzis et al., Journal of Surgical Oncology 2015; 112:86-92; Irino et al., BMC Cancer 2014, 14:291; Guo et al., Oncology Letters 5: 1572-1578, 2013; Xia et al., Oral Dis. 2015 January; 21(1):123-31; Du et al., Gastric Cancer. 2016 Mar. 16).

In addition, CCR7 expression in, e.g., HNSCC has been shown to play a role in resistance to chemotherapy (see, e.g., Wang et al., JNCI J Natl Cancer Inst (2008) 100 (7): 502-512.). In certain cancer types, such as pancreatic cancer and nasopharyngeal carcinoma (NPC), CCR7 is known to promote cancer stem-like cell metastasis and sphere formation (see, e.g., Zhang et al., PLOS ONE 11 (8); Lun et al., PLOS ONE 7(12)). CCR7's role in cell migration, invasiveness and EMT (epithelial-mesenchymal transition) is described in various cancer types, such as breast and pancreatic cancer in vitro and in vivo (see, e.g., Pang et al., Oncogene (2015), 1-13); Sperveslage et al., Int. J. Cancer: 131, E371-E381 (2012)). Key pathways that have been described to be essential for CCR7 signaling include b-Arrestin mediated p38/ERK1/2 and Rho signaling (see, e.g., Noor et al., J Neuroinflammation 2012 Apr. 25; 9:77).

Numerous cancer-related processes are known to induce CCR7 expression. In HNSCC, CCR7 expression is shown to be induced by NF-kB and AP1 transcription factors via direct binding to sites in the CCR7 promoter (Mburu et al., J. Biol. Chem. 2012, 287:3581-3590). In particular, CCR7 expression is regulated by various factors in the tumor microenvironment. In this context, it is known that CCR7 expression is induced via the b-Defensin 3/NF-kB pathway in HNSCC (see, e.g., Mburu et al., Carcinogenesis vol. 32 no. 2 pp. 168-174, 2010) and Endothelin Receptor A and Hypoxia-inducible factor-1 in breast tumor cells (see, e.g., Wilson et al., Cancer Res 2006; 66:11802-11807).

Antibody Drug Conjugates

Antibody drug conjugates ("ADCs") have been used for the local delivery of cytotoxic agents in the treatment of cancer (see, e.g., Lambert, Curr. Opinion In Pharmacology 5:543-549, 2005). ADCs allow targeted delivery of the drug moiety where maximum efficacy with minimal toxicity may be achieved. ADCs include an antibody selected for its ability to bind to a cell targeted for therapeutic intervention, linked to a drug selected for its cytostatic or cytotoxic activity. Binding of the antibody to the targeted cell thereby delivers the drug to the site where its therapeutic effect is needed.

Many antibodies that recognize and selectively bind to targeted cells, e.g., cancer cells, have been disclosed for use in ADCs. In spite of the extensive work on ADCs, antibody binding to a particular target of interest is not sufficient to predict success in ADC applications. Examples of factors that can effect therapeutic effectiveness of ADCs (besides target-intrinsic features) include various aspects that need customized fine-tuning, such as the optimal antibody affinity as a balance between target-mediated disposition (TMDD) and efficacy-driving exposure, evaluation of Fc-mediated functions (antibody-dependent cell-mediated cytotoxicity, ADCC), method of conjugation (site-specific or not), the ratio of the drug/payload molecules that conjugate to each antibody ("DAR" or "drug antibody ratio"), the cleavability or stability of the linker, stability of the ADC, and the tendency of an ADC to aggregate.

There remains a need for antibodies, attachment methods, and cytotoxic payloads with improved properties for use as effective ADC therapeutic compositions and methods.

SUMMARY OF THE INVENTION

The present application discloses an antibody or antigen binding fragment thereof that binds to human CCR7 protein, wherein the antibody or antigen binding fragment thereof has reduced or no significant effector function as compared to a wild-type antibody of the same isotype. In one embodiment, the antibody or antigen binding fragment thereof has a reduced or no significant level of antibody-dependent cell-mediated cytotoxicity (ADCC) activity. IN one embodiment, the antibody or antigen binding fragment thereof comprises a silenced Fc region. In some embodiments, the antibody comprises a mutation in the Fc region selected from: D265A; P329A; P329G; N297A; D265A and P329A; D265A and N297A; L234 and L235A; P329A, L234A and L235A; and P329G, L234A and L235A. In one embodiment, the antibody or antigen binding fragment thereof has no significant cell killing activity. In one embodiment, the antibody or antigen binding fragment thereof binds with greater affinity to cells expressing higher levels of CCR7 than cells expressing lower levels of CCR7. In some embodidments, the antibody or antigen binding fragment thereof binds with greater affinity to cancer cells that express higher levels of CCR7 than normal cells that express lower levels of CCR7. In some embodiments, the antibody or antigen binding fragment thereof does not significantly deplete normal hematopoietic cells that express CCR7.

In one embodiment, the present application discloses an antibody or antigen binding fragment thereof that binds CCR7 comprising:

a. a heavy chain variable region that comprises an HCDR1 (Heavy Chain Complementarity Determining Region 1) of SEQ ID NO:1, an HCDR2 (Heavy Chain Complementarity Determining Region 2) of SEQ ID NO:2, and an HCDR3 (Heavy Chain Complementarity Determining Region 3) of SEQ ID NO:3; and a light chain variable region that comprises an LCDR1 (Light Chain Complementarity Determining Region 1) of SEQ ID NO:17, an LCDR2 (Light Chain Complementarity Determining Region 2) of SEQ ID NO:18, and an LCDR3 (Light Chain Complementarity Determining Region 3) of SEQ ID NO:19;

b. a heavy chain variable region that comprises an HCDR1 of SEQ ID NO:4, an HCDR2 of SEQ ID NO:5, and an HCDR3 of SEQ ID NO:6; and a light chain variable region that comprises an LCDR1 of SEQ ID NO:20, an LCDR2 of SEQ ID NO:21, and an LCDR3 of SEQ ID NO:22;

c. a heavy chain variable region that comprises an HCDR1 of SEQ ID NO:7, an HCDR2 of SEQ ID NO:8, and an HCDR3 of SEQ ID NO:9; and a light chain variable region that comprises an LCDR1 of SEQ ID NO:23, an LCDR2 of SEQ ID NO:24, and an LCDR3 of SEQ ID NO:25;

d. a heavy chain variable region that comprises an HCDR1 of SEQ ID NO:10, an HCDR2 of SEQ ID NO:11, and an HCDR3 of SEQ ID NO:12; and a light chain variable region that comprises an LCDR1 of SEQ ID NO:26, an LCDR2 of SEQ ID NO:27, and an LCDR3 of SEQ ID NO:28;

e. a heavy chain variable region that comprises an HCDR1 of SEQ ID NO:33, an HCDR2 of SEQ ID NO:34, and an HCDR3 of SEQ ID NO:35; and a light chain variable region that comprises an LCDR1 of SEQ ID NO:49, an LCDR2 of SEQ ID NO:50, and an LCDR3 of SEQ ID NO:51;

f. a heavy chain variable region that comprises an HCDR1 of SEQ ID NO:36, an HCDR2 of SEQ ID NO:37, and an HCDR3 of SEQ ID NO:38; and a light chain variable region that comprises an LCDR1 of SEQ ID NO:52, an LCDR2 of SEQ ID NO:53, and an LCDR3 of SEQ ID NO:54;

g. a heavy chain variable region that comprises an HCDR1 of SEQ ID NO:39, an HCDR2 of SEQ ID NO:40, and an HCDR3 of SEQ ID NO:41; and a light chain variable region that comprises an LCDR1 of SEQ ID NO:55, an LCDR2 of SEQ ID NO:56, and an LCDR3 of SEQ ID NO:57;

h. a heavy chain variable region that comprises an HCDR1 of SEQ ID NO:42, an HCDR2 of SEQ ID NO:43, and an HCDR3 of SEQ ID NO:44; and a light chain variable region that comprises an LCDR1 of SEQ ID NO:58, an LCDR2 of SEQ ID NO:59, and an LCDR3 of SEQ ID NO:60;

i. a heavy chain variable region that comprises an HCDR1 of SEQ ID NO:65, an HCDR2 of SEQ ID NO:66, and an HCDR3 of SEQ ID NO:67; and a light chain variable region that comprises an LCDR1 of SEQ ID NO:81, an LCDR2 of SEQ ID NO:82, and an LCDR3 of SEQ ID NO:83;

j. a heavy chain variable region that comprises an HCDR1 of SEQ ID NO:68, an HCDR2 of SEQ ID NO:69, and an HCDR3 of SEQ ID NO:70; and a light chain variable region that comprises an LCDR1 of SEQ ID NO:84, an LCDR2 of SEQ ID NO:85, and an LCDR3 of SEQ ID NO:86;

k. a heavy chain variable region that comprises an HCDR1 of SEQ ID NO:71, an HCDR2 of SEQ ID NO:72, and an HCDR3 of SEQ ID NO:73; and a light chain variable region that comprises an LCDR1 of SEQ ID NO:87, an LCDR2 of SEQ ID NO:88, and an LCDR3 of SEQ ID NO:89;

l. a heavy chain variable region that comprises an HCDR1 of SEQ ID NO:74, an HCDR2 of SEQ ID NO:75, and an HCDR3 of SEQ ID NO:76; and a light chain variable region that comprises an LCDR1 of SEQ ID NO:90, an LCDR2 of SEQ ID NO:91, and an LCDR3 of SEQ ID NO:92;

m. a heavy chain variable region that comprises an HCDR1 of SEQ ID NO:596, an HCDR2 of SEQ ID NO:597, and an HCDR3 of SEQ ID NO:598; and a light chain variable region that comprises an LCDR1 of SEQ ID NO:612, an LCDR2 of SEQ ID NO:613, and an LCDR3 of SEQ ID NO:614;

n. a heavy chain variable region that comprises an HCDR1 of SEQ ID NO:599, an HCDR2 of SEQ ID NO:600, and an HCDR3 of SEQ ID NO:601; and a light chain variable region that comprises an LCDR1 of SEQ ID NO:615, an LCDR2 of SEQ ID NO:616, and an LCDR3 of SEQ ID NO:617;

o. a heavy chain variable region that comprises an HCDR1 of SEQ ID NO:602, an HCDR2 of SEQ ID NO:603, and an HCDR3 of SEQ ID NO:604; and a light chain variable region that comprises an LCDR1 of SEQ ID NO:618, an LCDR2 of SEQ ID NO:619, and an LCDR3 of SEQ ID NO:620; or p. a heavy chain variable region that comprises an HCDR1 of SEQ ID NO:605, an HCDR2 of SEQ ID NO:606, and an HCDR3 of SEQ ID NO:607; and a light chain variable region that comprises an LCDR1 of SEQ ID NO:621, an LCDR2 of SEQ ID NO:622, and an LCDR3 of SEQ ID NO:623.

An antibody or antigen binding fragment thereof that binds CCR7 of the present application may also comprise:

a. A heavy chain variable region (VH) comprising the amino acid sequence of SEQ ID NO:13, and a light chain variable region (VL) comprising the amino acid sequence of SEQ ID NO:29;

b. A heavy chain variable region (VH) comprising the amino acid sequence of SEQ ID NO:45, and a light chain variable region (VL) comprising the amino acid sequence of SEQ ID NO:61;

c. A heavy chain variable region (VH) comprising the amino acid sequence of SEQ ID NO:77, and a light chain variable region (VL) comprising the amino acid sequence of SEQ ID NO:93; or d. A heavy chain variable region (VH) comprising the amino acid sequence of SEQ ID NO:608, and a light chain variable region (VL) comprising the amino acid sequence of SEQ ID NO:624.

In another embodiment, the antibody or antigen binding fragment thereof that binds CCR7 comprises:

a. A heavy chain comprising the amino acid sequence of SEQ ID NO:15, and a light chain comprising the amino acid sequence of SEQ ID NO:31;

b. A heavy chain comprising the amino acid sequence of SEQ ID NO:47, and a light chain comprising the amino acid sequence of SEQ ID NO:63;

c. A heavy chain comprising the amino acid sequence of SEQ ID NO:79, and a light chain comprising the amino acid sequence of SEQ ID NO:95; or d. A heavy chain comprising the amino acid sequence of SEQ ID NO:610, and a light chain comprising the amino acid sequence of SEQ ID NO:626.

The antibody or antigen binding fragment thereof as described herein may comprise one or more cysteine substitutions. In one embodiment, the antibody or antigen binding fragment thereof comprises one or more cysteine substitutions selected from S152C, S375C, or both S152C and S375C of the heavy chain of the antibody or antigen binding fragment thereof, wherein the position is numbered according to the EU system. An antibody as disclosed herein can be a monoclonal antibody.

The present application discloses an antibody drug conjugate comprising the formula:

Ab-(L-(D)$_m$)$_n$ or a pharmaceutically acceptable salt thereof; wherein

Ab is an antibody or antigen binding antigen binding fragment thereof as disclosed herein;

L is a linker;

D is a drug moiety;

m is an integer from 1 to 8; and n is an integer from 1 to 12.

In some embodidments, m is 1. In one embodiment, n is about 3 to about 4. In one embodiment, the linker is selected from the group consisting of a cleavable linker, a non-cleavable linker, a hydrophilic linker, a procharged linker, and a dicarboxylic acid based linker.

In one embodiment, the linker is derived from a cross-linking reagent selected from the group consisting of N-succinimidyl-3-(2-pyridyldithio)propionate (SPDP), N-succinimidyl 4-(2-pyridyldithio)pentanoate (SPP), N-succinimidyl 4-(2-pyridyldithio)butanoate (SPDB), N-succinimidyl-4-(2-pyridyldithio)-2-sulfo-butanoate (sulfo-SPDB), N-succinimidyl iodoacetate (SIA), N-succinimidyl(4-iodoacetyl) aminobenzoate (SIAB), maleimide PEG NHS, N-succinimidyl 4-(maleimidomethyl)cyclohexanecarboxylate (SMCC), N-sulfosuccinimidyl 4-(maleimidomethyl)cyclohexanecarboxylate (sulfo-SMCC), and 2,5-dioxopyrrolidin-1-yl 17-(2,5-dioxo-2,5-dihydro-1H-pyrrol-1-yl)-5,8,11,14-tetraoxo-4,7,10,13-tetraazaheptadecan-1-oate (CX1-1).

In other embodiments, the linker has the following Formula (IIA):

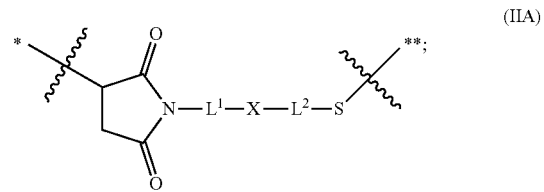

wherein * is linked to the thiol functionality on the antibody, and ** is linked to the thiol functionality of a drug moiety; and wherein:

L$^1$ is a C$_{1-6}$alkylene wherein one of the methylene groups may be replaced with oxygen;

L$^2$ is a C$_{1-6}$alkylene or is —(CH$_2$CH$_2$O)$_y$—CH$_2$—CH$_2$— wherein y is 1 to 11;

X is —C(O)—NH—, —NHC(O)— or a triazole; and alkylene is linear or branched.

In another embodiment, the linker has the following Formula:

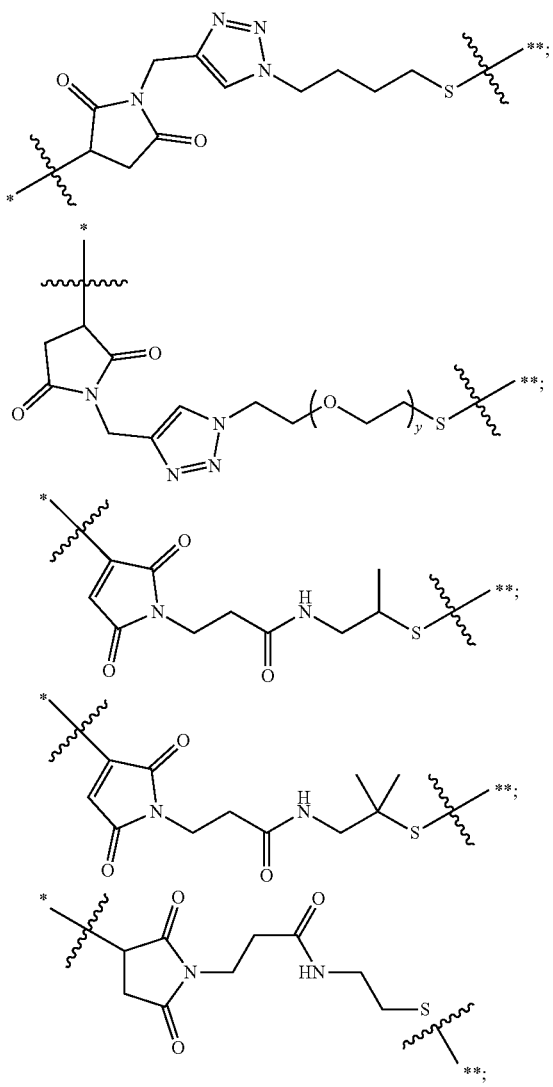

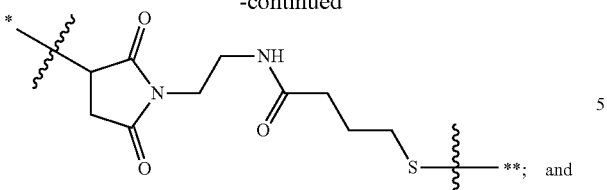

5

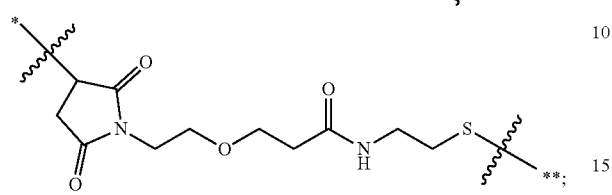

10

15 wherein y is 1 to 11; * is linked to the thiol functionality on the antibody, and ** is linked to the thiol functionality of the drug moiety.

In one embodiment, the drug moiety is selected from a group consisting of a V-ATPase inhibitor, a pro-apoptotic agent, a Bcl2 inhibitor, an MCL1 inhibitor, a HSP90 inhibitor, an IAP inhibitor, an mTor inhibitor, a microtubule stabilizer, a microtubule destabilizer, an auristatin, an amanitin, a pyrrolobenzodiazepine, an RNA polymerase inhibitor, a dolastatin, a maytansinoid, a MetAP (methionine aminopeptidase), an inhibitor of nuclear export of proteins CRM1, a DPPIV inhibitor, proteasome inhibitors, inhibitors of phosphoryl transfer reactions in mitochondria, a protein synthesis inhibitor, a kinase inhibitor, a CDK2 inhibitor, a CDK9 inhibitor, a kinesin inhibitor, an HDAC inhibitor, a DNA damaging agent, a DNA alkylating agent, a DNA intercalator, a DNA minor groove binder and a DHFR inhibitor. In some embodiments, the cytotoxic agent is a maytansinoid, wherein the maytansinoid is N(2')-deacetyl-N(2')-(3-mercapto-1-oxopropyl)-maytansine (DM1), N(2')-deacetyl-N(2')-(4-mercapto-1-oxopentyl)-maytansine (DM3) or N(2')-deacetyl-N2-(4-mercapto-4-methyl-1-oxopentyl)-maytansine (DM4).

In one embodiment, the antibody drug conjugates disclosed herein comprise the following formula (VIII):

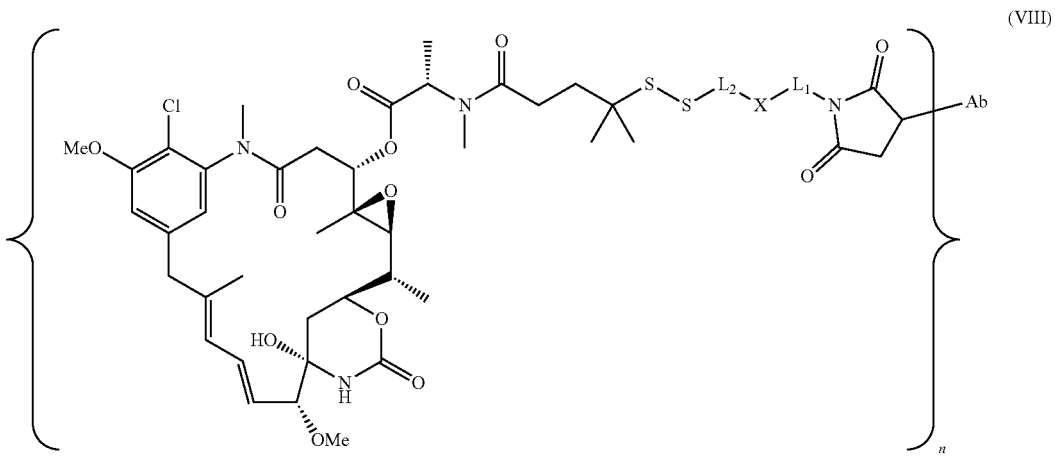

Ab-Maleimido linker-DM4 wherein $L^1$ is a $C_{1-6}$alkylene wherein one of the methylene groups may be replaced with oxygen;
$L^2$ is a $C_{1-6}$alkylene or is —(CH$_2$CH$_2$O)$_y$—CH$_2$—CH$_2$— wherein y is 1 to 11;
X is —C(O)—NH—, —NHC(O)— or a triazole; and alkylene is linear or branched; and wherein n is about 3 to about 4; or a pharmaceutically acceptable salt thereof.

In one embodiment, the antibody drug conjugates disclosed hereing have the following formula:

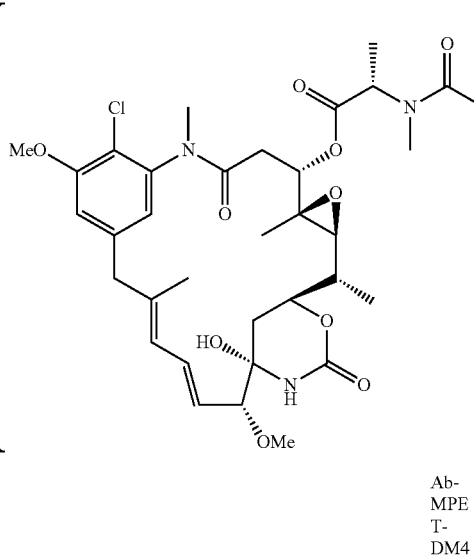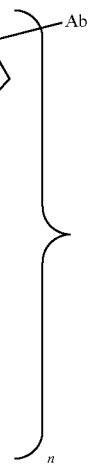

Ab-
MPE
T-
DM4 wherein n is about 3 to about 4, and Ab is an antibody comprising a heavy chain comprising the amino acid sequence of SEQ ID NO:47, and a light chain comprising the amino acid sequence of SEQ ID NO:63; or a pharmaceutically acceptable salt thereof.

The present application also discloses pharmaceutical composition comprising the antibodies, or antigen binding fragments thereof, disclosed herein and a pharmaceutically acceptable carrier. The present application also discloses pharmaceutical composition comprising the antibody drug conjugates as disclosed herein.

The present application also discloses methods of treating or preventing cancer in a patient in need thereof, comprising administering to said patient the antibody drug conjugates or the pharmaceutical compositions disclosed herein, wherein the cancer expresses CCR7.

In some embodiments of the methods of treatment or preventing cancer, the antibody drug conjugate or pharmaceutical composition are administered to the patient in combination with one or more additional therapeutic compounds. In one embodiment, the one or more additional therapeutic compounds is selected from a standard of care chemotherapeutic, a costimulatory molecule, or a checkpoint inhibitor. In one embodiment, the costimulatory molecule is selected from an agonist of OX40, CD2, CD27, CDS, ICAM-1, LFA-1 (CD11a/CD18), ICOS (CD278), 4-1BB (CD137), GITR, CD30, CD40, BAFFR, HVEM, CD7, LIGHT, NKG2C, SLAMF7, NKp80, CD160, B7-H3, STING, or CD83 ligand. In another embodiment, the checkpoint inhibitor is selected from an inhibitor of PD-1, PD-L1, PD-L2, CTLA4, TIM3, LAG3, VISTA, BTLA, TIGIT, LAIR1, CD160, 2B4 and/or TGFR beta.

The present application also discloses the antibody drug conjugates or the pharmaceutical compositions disclosed herein, for use as a medicament. In one embodiment, the antibody drug conjugates or the pharmaceutical compositions disclosed herein, are for use in the treatment or prevention of a CCR7 expressing cancer in a patient in need thereof.

In one embodiment, the application discloses use of the antibodies or antigen binding fragments thereof, the antibody drug conjugates, or the pharmaceutical composition as disclosed herein, to treat or prevent a CCR7 expressing cancer in a patient in need thereof.

In one embodiment, the application discloses use of the antibodies or antigen binding fragments thereof, the antibody drug conjugates, or the pharmaceutical compositions as disclosed herein, in the manufacture of a medicament.

In one embodiment, the cancer is selected from the group consisting of chronic lymphocytic leukemia (CLL), peripheral T cell lymphomas (PTCL) such as adult T-cell leukemia/lymphoma (ATLL) and anaplastic large-cell lymphoma (ALCL), Non-Hodgkin's lymphoma (NHL) such as mantle cell lymphoma (MCL), Burkitt's lymphoma and diffuse large B-cell lymphoma (DLBCL), gastric carcinoma, non-small cell lung cancer, small cell lung cancer, head and neck cancer, nasopharyngeal carcinoma (NPC), esophageal cancer, colorectal carcinoma, pancreatic cancer, thyroid cancer, breast cancer, renal cell cancer, and cervical cancer. In specific embodiments, the cancer is selected from the group consisting of chronic lymphocytic leukemia (CLL), peripheral T cell lymphomas (PTCL) such as adult T-cell leukemia/lymphoma (ATLL) and anaplastic large-cell lymphoma (ALCL), Non-Hodgkin's lymphoma (NHL) such as mantle cell lymphoma (MCL), Burkitt's lymphoma and diffuse large B-cell lymphoma (DLBCL), and non-small cell lung cancer.

The present application also discloses nucleic acids that encodes the antibodies or antigen binding fragments as disclosed herein. In one embodiment, the nucleic acid comprises the nucleotide sequence of SEQ ID NOs: 14, 16, 30, 32, 46, 48, 62, 64, 78, 80, 94, 96, 481, 483, 497, or 499. This application also discloses vectors comprising the nucleic acids, and host cells comprising the vectors or nucleic acids. This application also discloses a process for producing the antibodies or antigen binding fragments disclosed herein comprising cultivating the host cell and recovering the antibody from cell culture. In one embodiment, the process of recovering the antibody from cell culture comprises the steps of:

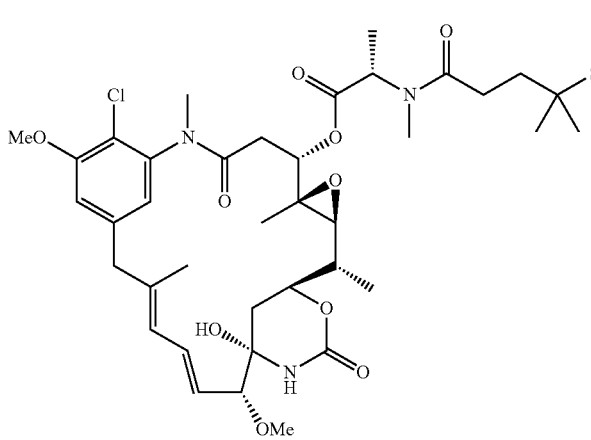

a) removing cells and filtering the culture;
b) purifying the culture by affinity chromatography;
c) inactivating any viruses in the culture by adjusting the pH to 3.4-3.6, then readjusting the pH to 5.8-6.2 and filtering the culture;
d) purifying the culture by cation exchange chromatography and performing on-column reduction of the culture;
e) performing anion exchange chromatography on the culture;
f) removing viruses by nanofiltration;
g) filtering the culture containing the antibody; and
h) obtaining purified antibody.

In yet another embodiment, disclosed herein is a process for producing an anti-CCR7 antibody drug conjugate comprising:
(a) pre-forming a linker-drug moiety of the following Formula:

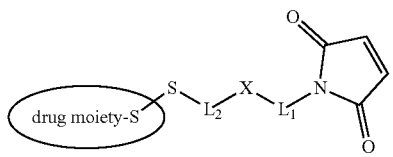

wherein:
the drug moiety is DM1, DM3 or DM4 and the drug moiety is attached to the linker via its thiol functionality;
$L^1$ is a $C_{1-6}$alkylene wherein one of the methylene groups may be replaced with oxygen;
$L^2$ is a $C_{1-6}$alkylene or is —$(CH_2CH_2O)_y$—$CH_2$—$CH_2$— wherein y is 1 to 11;
X is —C(O)—NH—, —NHC(O)— or a triazole; and alkylene is linear or branched;

(b) conjugating said linker-drug moiety to the antibody recovered from the cell culture disclosed herein to produce an antibody drug conjugate; and
(c) purifying the antibody drug conjugate.

In one embodiment, the process comprises:
(a) pre-forming a linker-drug moiety of the following Formula:

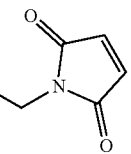

and
(b) conjugating said linker-drug moiety to the antibody recovered from the cell culture disclosed herein to produce an antibody drug conjugate; and
(c) purifying the antibody drug conjugate.

In another embodiment, the process for producing an anti-CCR7 antibody drug conjugate comprises:
(a) pre-forming a linker-drug moiety of the following Formula:

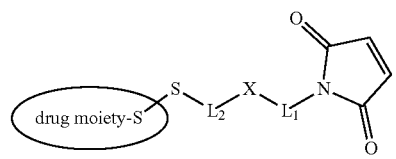

wherein:
the drug moiety is DM1, DM3 or DM4 and the drug moiety is attached to the linker via its thiol functionality;
$L^1$ is a $C_{1-6}$alkylene wherein one of the methylene groups may be replaced with oxygen;
$L^2$ is a $C_{1-6}$alkylene or is —$(CH_2CH_2O)_y$—$CH_2$—$CH_2$— wherein y is 1 to 11;
X is —C(O)—NH—, —NHC(O)— or a triazole; and alkylene is linear or branched;
(b) conjugating said linker-drug moiety to an antibody as disclosed herein to produce an antibody drug conjugate; and
(c) purifying the antibody drug conjugate.

In another embodiment, the process for producing an anti-CCR7 antibody drug conjugate comprises:
(a) pre-forming a linker-drug moiety of the following Formula:

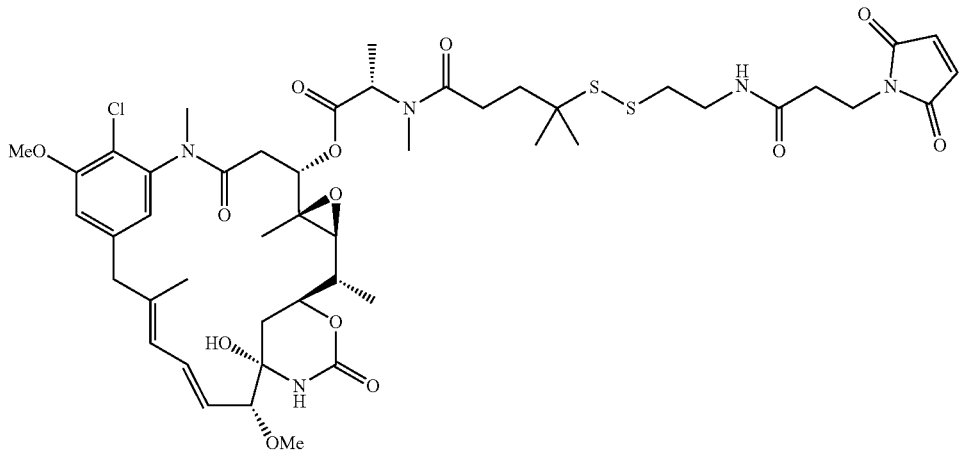 [SMILES: COc1cc2cc(c1Cl)N(C)C(=O)C[C@H](OC(=O)[C@H](C)N(C)C(=O)CCC(C)(C)SSCCNC(=O)CCN1C(=O)C=CC1=O)[C@]1(C)O[C@H]1[C@H](C)[C@@H]1C[C@@](O)(NC(=O)O1)[C@H](OC)/C=C/C=C(\C)C2]

(b) conjugating said linker-drug moiety to an antibody or antigen binding fragment thereof as disclosed herein, to produce an antibody drug conjugate; and (c) purifying the antibody drug conjugate.

In another embodiment, the step of pre-forming said linker-drug moiety comprises:

a) Reacting a drug moiety via its thiol functionality with:

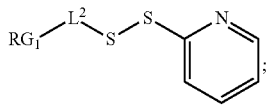

to form:

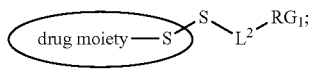

b) Reacting the formed

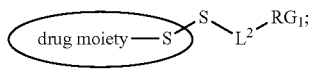

with:

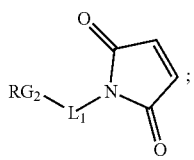

to form the linker-drug moiety:

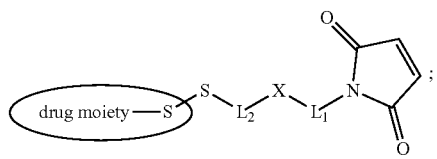

wherein:

$L^1$ is a $C_{1-6}$alkylene wherein one of the methylene groups may be replaced with oxygen;

$L^2$ is a $C_{1-6}$alkylene or is —(CH$_2$CH$_2$O)$_y$—CH$_2$—CH$_2$— wherein y is 1 to 11; and X is —C(O)—NH—, —NHC(O)— or a triazole;

wherein the alkylene is linear or branched; and

RG1 and RG2 are 2 reactive groups forming group X.

In another embodiment, the step of pre-forming said linker-drug moiety comprises:

a) Reacting the drug moiety via its thiol functionality with:

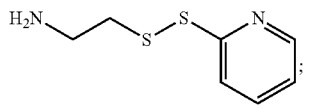 [SMILES: NCCSSc1ccccn1]

to form:
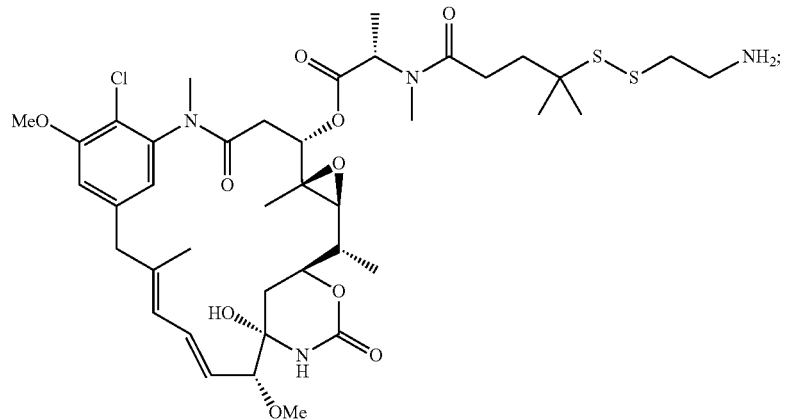 [SMILES: COc1cc2cc(c1Cl)N(C)C(=O)C[C@H](OC(=O)[C@H](C)N(C)C(=O)CCC(C)(C)SSCCN)[C@]1(C)O[C@H]1[C@H](C)[C@@H]1C[C@@](O)(NC(=O)O1)[C@H](OC)/C=C/C=C(\C)C2]
b) Reacting the formed
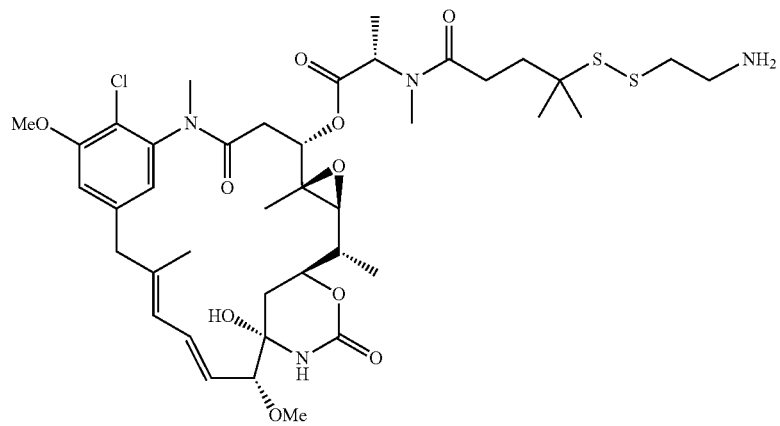
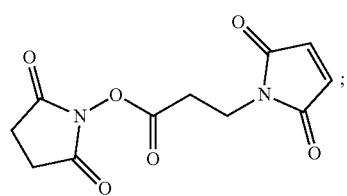

with:
  to form the linker-drug moiety:

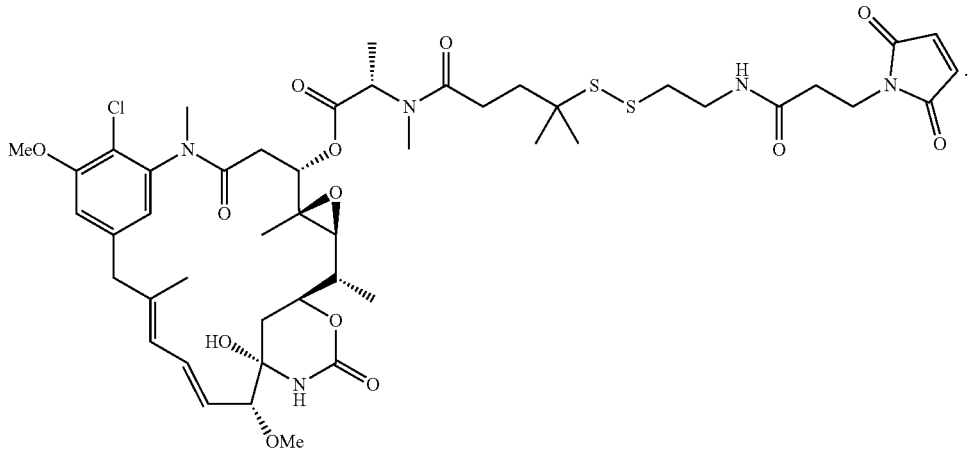 [SMILES: COc1cc2cc(c1Cl)N(C)C(=O)C[C@H](OC(=O)[C@H](C)N(C)C(=O)CCC(C)(C)SSCCNC(=O)CCN1C(=O)C=CC1=O)[C@]1(C)O[C@H]1[C@H](C)[C@@H]1C[C@@](O)(NC(=O)O1)[C@H](OC)/C=C/C=C(\C)C2]

In some embodiment, an antibody drug conjugate made according to above processes has an average DAR, measured with a UV spectrophotometer, of about 3 to about 4.

In another embodiment, this application discloses a process for producing an anti-CCR7 antibody drug conjugate comprising:
  (a) chemically linking SMCC or MPET to a drug moiety DM-1 or DM-4 to form a linker-drug;
  (b) conjugating said linker-drug to an antibody or antigen binding fragment thereof as disclosed herein; and
  (c) purifying the antibody drug conjugate.

In one embodiment, the antibody drug conjugate made according this process has an average DAR, measured with a UV spectrophotometer, of about 3 to about 4.

The present application also discloses a diagnostic reagent comprising an antibody or antigen binding fragment thereof as disclosed herein. In some embodiments, the antibody or antigen binding fragment thereof is labeled with a radiolabel, a fluorophore, a chromophore, an imaging agent, or a metal ion.

DETAILED DESCRIPTION OF THE INVENTION

Definitions

Figure 1:
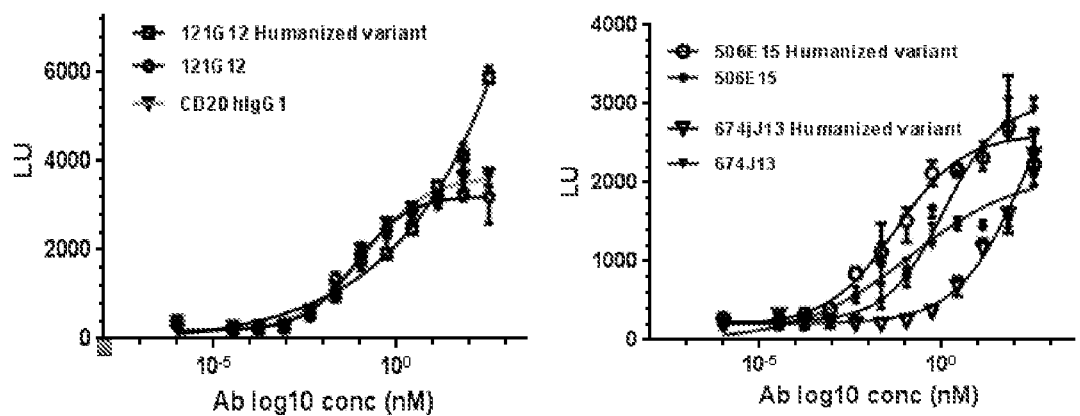
FIG. 1 depicts experimental data on in vitro ADCC activity of non-humanized and humanized anti-CCR7 antibodies in CysMab format using a surrogate ADCC reporter assay.

Unless stated otherwise, the following terms and phrases as used herein are intended to have the following meanings:

The term "alkyl" refers to a monovalent saturated hydrocarbon chain having the specified number of carbon atoms. For example, $C_{1-6}$ alkyl refers to an alkyl group having from 1 to 6 carbon atoms. Alkyl groups may be straight or branched. Representative branched alkyl groups have one, two, or three branches. Examples of alkyl groups include, but are not limited to, methyl, ethyl, propyl(n-propyl and isopropyl), butyl(n-butyl, isobutyl, sec-butyl, and t-butyl), pentyl(n-pentyl, isopentyl, and neopentyl), and hexyl. The term "alkylene" is the bivalent form of "alkyl".

The term "antibody" as used herein refers to a polypeptide of the immunoglobulin family that is capable of binding a corresponding antigen non-covalently, reversibly, and in a specific manner. For example, a naturally occurring IgG antibody is a tetramer comprising at least two heavy (H) chains and two light (L) chains inter-connected by disulfide bonds. Each heavy chain is comprised of a heavy chain variable region (abbreviated herein as VH) and a heavy chain constant region. The heavy chain constant region is comprised of three domains, CH1, CH2 and CH3. Each light chain is comprised of a light chain variable region (abbreviated herein as VL) and a light chain constant region. The light chain constant region is comprised of one domain, CL. The VH and VL regions can be further subdivided into regions of hypervariability, termed complementarity determining regions (CDR), interspersed with regions that are more conserved, termed framework regions (FR). Each VH and VL is composed of three CDRs and four FRs arranged from amino-terminus to carboxy-terminus in the following order: FR1, CDR1, FR2, CDR2, FR3, CDR3, and FR4. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (Clq) of the classical complement system.

The term "antibody" includes, but is not limited to, monoclonal antibodies, human antibodies, humanized antibodies, chimeric antibodies, and anti-idiotypic (anti-Id) antibodies (including, e.g., anti-Id antibodies to antibodies of the invention). The antibodies can be of any isotype/class (e.g., IgG, IgE, IgM, IgD, IgA and IgY), or subclass (e.g., IgG1, IgG2, IgG3, IgG4, IgA1 and IgA2).

"Complementarity-determining domains" or "complementary-determining regions" ("CDRs") interchangeably refer to the hypervariable regions of VL and VH. The CDRs are the target protein-binding site of the antibody chains that harbors specificity for such target protein. There are three CDRs (CDR1-3, numbered sequentially from the N-terminus) in each human VL or VH, constituting about 15-20% of the variable domains. The CDRs are structurally complementary to the epitope of the target protein and are thus directly responsible for the binding specificity. The remaining stretches of the VL or VH, the so-called framework regions, exhibit less variation in amino acid sequence (Kuby, Immunology, 4th ed., Chapter 4. W.H. Freeman & Co., New York, 2000).

The positions of the CDRs and framework regions can be determined using various well known definitions in the art, e.g., Kabat, Chothia, international ImMunoGeneTics database (IMGT) (on the worldwide web at www.imgt.org/), and AbM (see, e.g., Johnson et al., Nucleic Acids Res., 29:205-206 (2001); Chothia and Lesk, J. Mol. Biol., 196:901-917 (1987); Chothia et al., Nature, 342:877-883 (1989); Chothia et al., J. Mol. Biol., 227:799-817 (1992); Al-Lazikani et al., J. Mol. Biol., 273:927-748 (1997)). Definitions of antigen combining sites are also described in the following: Ruiz et al., Nucleic Acids Res., 28:219-221 (2000); and Lefranc, M. P., Nucleic Acids Res., 29:207-209 (2001); MacCallum et al., J. Mol. Biol., 262:732-745 (1996); and Martin et al., Proc. Natl. Acad. Sci. USA, 86:9268-9272 (1989); Martin et al., Methods Enzymol., 203:121-153 (1991); and Rees et al., In Sternberg M. J. E. (ed.), Protein Structure Prediction, Oxford University Press, Oxford, 141-172 (1996).

Both the light and heavy chains are divided into regions of structural and functional homology. The terms "constant" and "variable" are used functionally. In this regard, it will be appreciated that the variable domains of both the light (VL) and heavy (VH) chain portions determine antigen recognition and specificity. Conversely, the constant domains of the light chain (CL) and the heavy chain (CH1, CH2 or CH3) confer important biological properties such as secretion, transplacental mobility, Fc receptor binding, complement binding, and the like. By convention, the numbering of the constant region domains increases as they become more distal from the antigen binding site or amino-terminus of the antibody. The N-terminus is a variable region and at the C-terminus is a constant region; the CH3 and CL domains actually comprise the carboxy-terminal domains of the heavy and light chain, respectively.

The term "antigen binding fragment", as used herein, refers to one or more portions of an antibody that retain the ability to specifically interact with (e.g., by binding, steric hindrance, stabilizing/destabilizing, spatial distribution) an epitope of an antigen. Examples of binding fragments include, but are not limited to, single-chain Fvs (scFv), camelid antibodies, disulfide-linked Fvs (sdFv), Fab fragments, F(ab') fragments, a monovalent fragment consisting of the VL, VH, CL and CH1 domains; a F(ab)2 fragment, a bivalent fragment comprising two Fab fragments linked by a disulfide bridge at the hinge region; a Fd fragment consisting of the VH and CH1 domains; a Fv fragment consisting of the VL and VH domains of a single arm of an antibody; a dAb fragment (Ward et al., Nature 341:544-546, 1989), which consists of a VH domain; and an isolated complementarity determining region (CDR), or other epitope-binding fragments of an antibody.

Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv ("scFv"); see, e.g., Bird et al., Science 242:423-426, 1988; and Huston et al., Proc. Natl. Acad. Sci. 85:5879-5883, 1988). Such single chain antibodies are also intended to be encompassed within the term "antigen binding fragment." These antigen binding fragments are obtained using conventional techniques known to those of skill in the art, and the fragments are screened for utility in the same manner as are intact antibodies.

Antigen binding fragments can also be incorporated into single domain antibodies, maxibodies, minibodies, single domain antibodies, intrabodies, diabodies, triabodies, tetrabodies, v-NAR and bis-scFv (see, e.g., Hollinger and Hudson, Nature Biotechnology 23:1126-1136, 2005). Antigen binding fragments can be grafted into scaffolds based on polypeptides such as fibronectin type III (Fn3) (see U.S. Pat. No. 6,703,199, which describes fibronectin polypeptide monobodies).

Antigen binding fragments can be incorporated into single chain molecules comprising a pair of tandem Fv segments (VH-CH1-VH-CH1) which, together with complementary light chain polypeptides, form a pair of antigen binding regions (Zapata et al., Protein Eng. 8:1057-1062, 1995; and U.S. Pat. No. 5,641,870).

The term "monoclonal antibody" or "monoclonal antibody composition" as used herein refers to polypeptides, including antibodies and antigen binding fragments that have substantially identical amino acid sequence or are derived from the same genetic source. This term also includes preparations of antibody molecules of single molecular composition. A monoclonal antibody composition displays a single binding specificity and affinity for a particular epitope.

The term "human antibody", as used herein, includes antibodies having variable regions in which both the framework and CDR regions are derived from sequences of human origin. Furthermore, if the antibody contains a constant region, the constant region also is derived from such human sequences, e.g., human germline sequences, or mutated versions of human germline sequences or antibody containing consensus framework sequences derived from human framework sequences analysis, for example, as described in Knappik et al., J. Mol. Biol. 296:57-86, 2000). Also included are antibodies derived from human sequences wherein one or more CDRs has been mutated for affinity maturation or for manufacturing/payload conjugation purposes. See Kilpatrick et al., "Rapid development of affinity matured monoclonal antibodies using RIMMS," Hybridoma. Aug. 16, 1997(4):381-9.

The human antibodies of the invention may include amino acid residues not encoded by human sequences (e.g., mutations introduced by random or site-specific mutagenesis in vitro or by somatic mutation in vivo, or a conservative substitution to promote stability or manufacturing).

The term "recognize" as used herein refers to an antibody or antigen binding fragment thereof that finds and interacts (e.g., binds) with its epitope, whether that epitope is linear or conformational. The term "epitope" refers to a site on an antigen to which an antibody or antigen binding fragment of the invention specifically binds. Epitopes can be formed both from contiguous amino acids or noncontiguous amino acids juxtaposed by tertiary folding of a protein. Epitopes formed from contiguous amino acids are typically retained on exposure to denaturing solvents, whereas epitopes formed by tertiary folding are typically lost on treatment with denaturing solvents. An epitope typically includes at least 3, 4, 5, 6, 7, 8, 9, 10, 11, 12, 13, 14 or 15 amino acids in a unique spatial conformation. Methods of determining spatial conformation of epitopes include techniques in the art, for example, x-ray crystallography and 2-dimensional nuclear magnetic resonance (see, e.g., Epitope Mapping Protocols in Methods in Molecular Biology, Vol. 66, G. E. Morris, Ed. (1996)).

The term "affinity" as used herein refers to the strength of interaction between antibody and antigen at single antigenic sites. Within each antigenic site, the variable region of the antibody "arm" interacts through weak non-covalent forces with antigen at numerous sites; the more interactions, the stronger the affinity.

The term "isolated antibody" refers to an antibody that is substantially free of other antibodies having different antigenic specificities. An isolated antibody that specifically binds to one antigen may, however, have cross-reactivity to other antigens. Moreover, an isolated antibody may be substantially free of other cellular material and/or chemicals.

The term "corresponding human germline sequence" refers to the nucleic acid sequence encoding a human variable region amino acid sequence or subsequence that shares the highest determined amino acid sequence identity with a reference variable region amino acid sequence or subsequence in comparison to all other all other known variable region amino acid sequences encoded by human germline immunoglobulin variable region sequences. The corresponding human germline sequence can also refer to the human variable region amino acid sequence or subsequence with the highest amino acid sequence identity with a reference variable region amino acid sequence or subsequence in comparison to all other evaluated variable region amino acid sequences. The corresponding human germline sequence can be framework regions only, complementarity determining regions only, framework and complementarity determining regions, a variable segment (as defined above), or other combinations of sequences or subsequences that comprise a variable region. Sequence identity can be determined using the methods described herein, for example, aligning two sequences using BLAST, ALIGN, or another alignment algorithm known in the art. The corresponding human germline nucleic acid or amino acid sequence can have at least about 90%, 91, 92%, 93%, 94%, 95%, 96%, 97%, 98%, 99%, or 100% sequence identity with the reference variable region nucleic acid or amino acid sequence. Corresponding human germline sequences can be determined, for example, through the publicly available international ImMunoGeneTics database (IMGT) (on the worldwide web at www.imgt.org/) and V-base (on the worldwide web at vbase.mrc-cpe.cam.ac.uk).

The phrase "specifically binds" or "selectively binds," when used in the context of describing the interaction between an antigen (e.g., a protein) and an antibody, antibody fragment, or antibody-derived binding agent, refers to a binding reaction that is determinative of the presence of the antigen in a heterogeneous population of proteins and other biologics, e.g., in a biological sample, e.g., a blood, serum, plasma or tissue sample. Thus, under certain designated immunoassay conditions, the antibodies or binding agents with a particular binding specificity bind to a particular antigen at least two times the background and do not substantially bind in a significant amount to other antigens present in the sample. In one embodiment, under designated immunoassay conditions, the antibody or binding agent with a particular binding specificity binds to a particular antigen at least ten (10) times the background and does not substantially bind in a significant amount to other antigens present in the sample. Specific binding to an antibody or binding agent under such conditions may require the antibody or agent to have been selected for its specificity for a particular protein. As desired or appropriate, this selection may be achieved by subtracting out antibodies that cross-react with molecules from other species (e.g., mouse or rat) or other subtypes. Alternatively, in some embodiments, antibodies or antibody fragments are selected that cross-react with certain desired molecules.

A variety of immunoassay formats may be used to select antibodies specifically immunoreactive with a particular protein. For example, solid-phase ELISA immunoassays are routinely used to select antibodies specifically immunoreactive with a protein (see, e.g., Harlow & Lane, Using Antibodies, A Laboratory Manual (1998), for a description of immunoassay formats and conditions that can be used to determine specific immunoreactivity). Typically a specific or selective binding reaction will produce a signal at least twice over the background signal and more typically at least 10 to 100 times over the background.

The term "equilibrium dissociation constant (KD, M)" refers to the dissociation rate constant (kd, time-1) divided by the association rate constant (ka, time-1, M-1). Equilibrium dissociation constants can be measured using any known method in the art. The antibodies of the present invention generally will have an equilibrium dissociation constant of less than about $10^{-7}$ or $10^{-8}$ M, for example, less than about $10^{-9}$ M or $10^{-10}$ M, in some embodiments, less than about $10^{-11}$ M, $10^{-12}$ M or $10^{-13}$ M.

The term "bioavailability" refers to the systemic availability (i.e., blood/plasma levels) of a given amount of drug administered to a patient. Bioavailability is an absolute term that indicates measurement of both the time (rate) and total amount (extent) of drug that reaches the general circulation from an administered dosage form.

As used herein, the phrase "consisting essentially of" refers to the genera or species of active pharmaceutical agents included in a method or composition, as well as any excipients inactive for the intended purpose of the methods or compositions. In some embodiments, the phrase "consisting essentially of" expressly excludes the inclusion of one or more additional active agents other than an antibody drug conjugate of the invention. In some embodiments, the phrase "consisting essentially of" expressly excludes the inclusion of one or more additional active agents other than an antibody drug conjugate of the invention and a second co-administered agent.

The term "amino acid" refers to naturally occurring, synthetic, and unnatural amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine Amino acid analogs refer to compounds that have the same basic chemical structure as a naturally occurring amino acid, i.e., an α-carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid Amino acid mimetics refers to chemical compounds that have a structure that is different from the general chemical structure of an amino acid, but that functions in a manner similar to a naturally occurring amino acid.

The term "conservatively modified variant" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid that encodes a polypeptide is implicit in each described sequence.

For polypeptide sequences, "conservatively modified variants" include individual substitutions, deletions or additions to a polypeptide sequence which result in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention. The following eight groups contain amino acids that are conservative substitutions for one another: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and 8) Cysteine (C), Methionine (M) (see, e.g., Creighton, Proteins (1984)). In some embodiments, the term "conservative sequence modifications" are used to refer to amino acid modifications that do not significantly affect or alter the binding characteristics of the antibody containing the amino acid sequence.

The term "optimized" as used herein refers to a nucleotide sequence that has been altered to encode an amino acid sequence using codons that are preferred in the production cell or organism, generally a eukaryotic cell, for example, a yeast cell, a Pichia cell, a fungal cell, a Trichoderma cell, a Chinese Hamster Ovary cell (CHO) or a human cell. The optimized nucleotide sequence is engineered to retain completely or as much as possible the amino acid sequence originally encoded by the starting nucleotide sequence, which is also known as the "parental" sequence.

The terms "percent identical" or "percent identity," in the context of two or more nucleic acids or polypeptide sequences, refers to the extent to which two or more sequences or subsequences that are the same. Two sequences are "identical" if they have the same sequence of amino acids or nucleotides over the region being compared. Two sequences are "substantially identical" if two sequences have a specified percentage of amino acid residues or nucleotides that are the same (i.e., 60% identity, optionally 65%, 70%, 75%, 80%, 85%, 90%, 95%, or 99% identity over a specified region, or, when not specified, over the entire sequence), when compared and aligned for maximum correspondence over a comparison window, or designated region as measured using one of the following sequence comparison algorithms or by manual alignment and visual inspection. Optionally, the identity exists over a region that is at least about 30 nucleotides (or 10 amino acids) in length, or more preferably over a region that is 100 to 500 or 1000 or more nucleotides (or 20, 50, 200 or more amino acids) in length.

For sequence comparison, typically one sequence acts as a reference sequence, to which test sequences are compared.

When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well known in the art. Optimal alignment of sequences for comparison can be conducted, e.g., by the local homology algorithm of Smith and Waterman, Adv. Appl. Math. 2:482c (1970), by the homology alignment algorithm of Needleman and Wunsch, J. Mol. Biol. 48:443 (1970), by the search for similarity method of Pearson and Lipman, Proc. Natl. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., Brent et al., Current Protocols in Molecular Biology, 2003).

Two examples of algorithms that are suitable for determining percent sequence identity and sequence similarity are the BLAST and BLAST 2.0 algorithms, which are described in Altschul et al., Nuc. Acids Res. 25:3389-3402, 1977; and Altschul et al., J. Mol. Biol. 215:403-410, 1990, respectively. Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a word length (W) of 11, an expectation (E) or 10, M=5, N=−4 and a comparison of both strands. For amino acid sequences, the BLASTP program uses as defaults a word length of 3, and expectation (E) of 10, and the BLOSUM62 scoring matrix (see Henikoff and Henikoff, (1989) Proc. Natl. Acad. Sci. USA 89:10915) alignments (B) of 50, expectation (E) of 10, M=5, N=−4, and a comparison of both strands.

The BLAST algorithm also performs a statistical analysis of the similarity between two sequences (see, e.g., Karlin and Altschul, Proc. Natl. Acad. Sci. USA 90:5873-5787, 1993). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

The percent identity between two amino acid sequences can also be determined using the algorithm of E. Meyers and W. Miller, Comput. Appl. Biosci. 4:11-17 (1988) which has been incorporated into the ALIGN program (version 2.0), using a PAM120 weight residue table, a gap length penalty of 12 and a gap penalty of 4. In addition, the percent identity between two amino acid sequences can be determined using the Needleman and Wunsch, J. Mol. Biol. 48:444-453 (1970) algorithm which has been incorporated into the GAP program in the GCG software package (available at www.gcg.com), using either a BLOSUM62 matrix or a PAM250 matrix, and a gap weight of 16, 14, 12, 10, 8, 6, or 4 and a length weight of 1, 2, 3, 4, 5, or 6.

Other than percentage of sequence identity noted above, another indication that two nucleic acid sequences or polypeptides are substantially identical is that the polypeptide encoded by the first nucleic acid is immunologically cross reactive with the antibodies raised against the polypeptide encoded by the second nucleic acid, as described below. Thus, a polypeptide is typically substantially identical to a second polypeptide, for example, where the two peptides differ only by conservative substitutions. Another indication that two nucleic acid sequences are substantially identical is that the two molecules or their complements hybridize to each other under stringent conditions, as described below. Yet another indication that two nucleic acid sequences are substantially identical is that the same primers can be used to amplify the sequence.

The term "nucleic acid" is used herein interchangeably with the term "polynucleotide" and refers to deoxyribonucleotides or ribonucleotides and polymers thereof in either single- or double-stranded form. The term encompasses nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphorothioates, phosphoramidates, methyl phosphonates, chiral-methyl phosphonates, 2-O-methyl ribonucleotides, peptide-nucleic acids (PNAs).

Unless otherwise indicated, a particular nucleic acid sequence also implicitly encompasses conservatively modified variants thereof (e.g., degenerate codon substitutions) and complementary sequences, as well as the sequence explicitly indicated. Specifically, as detailed below, degenerate codon substitutions may be achieved by generating sequences in which the third position of one or more selected (or all) codons is substituted with mixed-base and/or deoxyinosine residues (Batzer et al., (1991) Nucleic Acid Res. 19:5081; Ohtsuka et al., (1985) J. Biol. Chem. 260: 2605-2608; and Rossolini et al., (1994) Mol. Cell. Probes 8:91-98).

The term "operably linked" in the context of nucleic acids refers to a functional relationship between two or more polynucleotide (e.g., DNA) segments. Typically, it refers to the functional relationship of a transcriptional regulatory sequence to a transcribed sequence. For example, a promoter or enhancer sequence is operably linked to a coding sequence if it stimulates or modulates the transcription of the coding sequence in an appropriate host cell or other expression system. Generally, promoter transcriptional regulatory sequences that are operably linked to a transcribed sequence are physically contiguous to the transcribed sequence, i.e., they are cis-acting. However, some transcriptional regulatory sequences, such as enhancers, need not be physically contiguous or located in close proximity to the coding sequences whose transcription they enhance.

The terms "polypeptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer. Unless otherwise indicated, a particular polypeptide sequence also implicitly encompasses conservatively modified variants thereof.

The term "antibody drug conjugate" or "immunoconjugate" as used herein refers to the linkage of an antibody or an antigen binding fragment thereof with another agent, such as a chemotherapeutic agent, a toxin, an immunotherapeutic agent, an imaging probe, and the like. The linkage can be covalent bonds, or non-covalent interactions such as through electrostatic forces. Various linkers, known in the art, can be employed in order to form the antibody drug conjugate. Additionally, the antibody drug conjugate can be provided in the form of a fusion protein that may be expressed from a polynucleotide encoding the immunoconjugate. As used herein, "fusion protein" refers to proteins created through the joining of two or more genes or gene fragments which originally coded for separate proteins (including peptides and polypeptides). Translation of the fusion gene results in a single protein with functional properties derived from each of the original proteins.

The term "subject" includes human and non-human animals Non-human animals include all vertebrates, e.g., mammals and non-mammals, such as non-human primates, sheep, dog, cow, chickens, amphibians, and reptiles. Except when noted, the terms "patient" or "subject" are used herein interchangeably.

The term "cytotoxin", or "cytotoxic agent" as used herein, refers to any agent that is detrimental to the growth and proliferation of cells and may act to reduce, inhibit, or destroy a cell or malignancy.

The term "anti-cancer agent" as used herein refers to any agent that can be used to treat or prevent a cell proliferative disorder such as cancer, including but not limited to, cytotoxic agents, chemotherapeutic agents, radiotherapy and radiotherapeutic agents, targeted anti-cancer agents, and immunotherapeutic agents.

The term "drug moiety" or "payload" as used herein refers to a chemical moiety that is conjugated to an antibody or antigen binding fragment of the invention, and can include any therapeutic or diagnostic agent, for example, an anti-cancer, anti-inflammatory, anti-infective (e.g., anti-fungal, antibacterial, anti-parasitic, anti-viral), or an anesthetic agent. For example, the drug moiety can be an anti-cancer agent, such as a cytotoxin. In certain embodiments, a drug moiety is selected from a V-ATPase inhibitor, a HSP90 inhibitor, an IAP inhibitor, an mTor inhibitor, a microtubule stabilizer, a microtubule destabilizer, an auristatin, a dolastatin, a maytansinoid, a MetAP (methionine aminopeptidase), an RNA polymerase inhibitor, a pyrrolobenzodiazepine (PBD), an amanitin, an inhibitor of nuclear export of proteins CRM1, a DPPIV inhibitor, an inhibitor of phosphoryl transfer reactions in mitochondria, a protein synthesis inhibitor, a kinase inhibitor, a CDK2 inhibitor, a CDK9 inhibitor, a proteasome inhibitor, a kinesin inhibitor, an HDAC inhibitor, a DNA damaging agent, a DNA alkylating agent, a DNA intercalator, a DNA minor groove binder and a DHFR inhibitor. Methods for attaching each of these to a linker compatible with the antibodies and method of the invention are known in the art. See, e.g., Singh et al., (2009) Therapeutic Antibodies: Methods and Protocols, vol. 525, 445-457. In addition, a payload can be a biophysical probe, a fluorophore, a spin label, an infrared probe, an affinity probe, a chelator, a spectroscopic probe, a radioactive probe, a lipid molecule, a polyethylene glycol, a polymer, a spin label, DNA, RNA, a protein, a peptide, a surface, an antibody, an antibody fragment, a nanoparticle, a quantum dot, a liposome, a PLGA particle, a saccharide or a polysaccharide.

The term "maytansinoid drug moiety" means the substructure of an antibody-drug conjugate that has the structure of a maytansinoid compound. Maytansine was first isolated from the east African shrub Maytenus serrata (U.S. Pat. No. 3,896,111). Subsequently, it was discovered that certain microbes also produce maytansinoids, such as maytansinol and C-3 maytansinol esters (U.S. Pat. No. 4,151,042). Synthetic maytansinol and maytansinol analogues have been reported. See U.S. Pat. Nos. 4,137,230; 4,248,870; 4,256, 746; 4,260,608; 4,265,814; 4,294,757; 4,307,016; 4,308, 268; 4,308,269; 4,309,428; 4,313,946; 4,315,929; 4,317, 821; 4,322,348; 4,331,598; 4,361,650; 4,364,866; 4,424, 219; 4,450,254; 4,362,663; and 4,371,533, and Kawai et al., (1984) Chem. Pharm. Bull. 3441-3451), each of which are expressly incorporated by reference. Examples of specific maytansinoids useful for conjugation include DM1, DM3 and DM4.

"Tumor" refers to neoplastic cell growth and proliferation, whether malignant or benign, and all pre-cancerous and cancerous cells and tissues.

The term "anti-tumor activity" means a reduction in the rate of tumor cell proliferation, viability, or metastatic activity. For example, anti-tumor activity can be shown by a decline in growth rate of abnormal cells that arises during therapy or tumor size stability or reduction, or longer survival due to therapy as compared to control without therapy. Such activity can be assessed using accepted in vitro or in vivo tumor models, including but not limited to xenograft models, allograft models, MMTV models, and other known models known in the art to investigate anti-tumor activity.

The term "malignancy" refers to a non-benign tumor or a cancer. As used herein, the term "cancer" includes a malignancy characterized by deregulated or uncontrolled cell growth. Exemplary cancers include: carcinomas, sarcomas, leukemias, and lymphomas.

The term "cancer" includes primary malignant tumors (e.g., those whose cells have not migrated to sites in the subject's body other than the site of the original tumor) and secondary malignant tumors (e.g., those arising from metastasis, the migration of tumor cells to secondary sites that are different from the site of the original tumor).

The term "CCR7" (also known as BLR2, CC-CKR-7, CCR-7, CD197, CDw197, CMKBR7, EBI1, or C-C motif chemokine receptor 7) refers to a member of the G protein-coupled receptor family. The nucleic acid and amino acid sequence of human CCR7 have been published in GenBank with the following Accession Nos.: NP_001829, NP_001288643, NP_001288645, NP_001288646, NP_001288647 (amino acid sequences), and NM_001838, NM_001301714, NM_001301716, NM_001301717, NM_001301718 (nucleotide sequences). As used herein, the term "CCR7" is used to refer collectively to all naturally occurring isoforms of CCR7 protein, or a variant thereof.

The term "variant" refers to a polypeptide that has a substantially identical amino acid sequence to a reference polypeptide, or is encoded by a substantially identical nucleotide sequence, and is capable of having one or more activities of the reference polypeptide. For example, a variant can have about 85%, 90%, 91%, 92%, 93%, 94%, 95%, 96%, 97%, 98%, 99% or higher sequence identity to a reference polypeptide, while retain one or more activities of the reference polypeptide.

As used herein, the terms "treat," "treating," or "treatment" of any disease or disorder refers in one embodiment, to ameliorating the disease or disorder (i.e., slowing or arresting or reducing the development of the disease or at least one of the clinical symptoms thereof). In another embodiment, "treat," "treating," or "treatment" refers to alleviating or ameliorating at least one physical parameter including those which may not be discernible by the patient. In yet another embodiment, "treat," "treating," or "treatment" refers to modulating the disease or disorder, either physically, (e.g., stabilization of a discernible symptom), physiologically, (e.g., stabilization of a physical parameter), or both.

As used herein, the term "prevent", "preventing" or "prevention" of any disease or disorder refers to the prophylactic treatment of the disease or disorder; or delaying the onset or progression of the disease or disorder The term "therapeutically acceptable amount" or "therapeutically effective dose" interchangeably refers to an amount sufficient to effect the desired result (i.e., a reduction in tumor size, inhibition of tumor growth, prevention of metastasis, inhibition or prevention of viral, bacterial, fungal or parasitic infection). In some embodiments, a therapeutically acceptable amount does not induce or cause undesirable side effects. In some embodiments, a therapeutically acceptable amount induces or causes side effects but only those that are acceptable by the healthcare providers in view of a patient's condition. A therapeutically acceptable amount can be determined by first administering a low dose, and then incrementally increasing that dose until the desired effect is achieved. A "prophylactically effective dosage," and a "therapeutically effective dosage," of the molecules of the invention can prevent the onset of, or result in a decrease in severity of, respectively, disease symptoms, including symptoms associated with cancer.

The term "co-administer" refers to the presence of two active agents in the blood of an individual. Active agents that are co-administered can be concurrently or sequentially delivered.

The present invention provides antibodies, antibody fragments (e.g., antigen binding fragments), and drug conjugates thereof, i.e., antibody drug conjugates or ADCs, that bind to CCR7. In particular, the present invention provides antibodies and antibody fragments (e.g., antigen binding fragments) that bind to CCR7, and internalize upon such binding. The antibodies and antibody fragments (e.g., antigen binding fragments) of the present invention can be used for producing antibody drug conjugates. Furthermore, the present invention provides antibody drug conjugates that have desirable pharmacokinetic characteristics and other desirable attributes, and thus can be used for treating or preventing a cancer expressing CCR7. The present invention further provides pharmaceutical compositions comprising the antibody drug conjugates of the invention, and methods of making and using such pharmaceutical compositions for the treatment or prevention of cancer.

Antibody Drug Conjugates

The present invention provides antibody drug conjugates also referred to as immunoconjugates, where an antibody, antigen binding fragment or its functional equivalent that specifically binds to CCR7 is linked to a drug moiety. In one aspect, the antibodies, antigen binding fragments or their functional equivalents of the invention are linked, via covalent attachment by a linker, to a drug moiety that is an anti-cancer agent. The antibody drug conjugates of the invention can deliver an effective dose of an anti-cancer agent (e.g., a cytotoxic agent) to tumor tissues expressing CCR7, whereby greater selectivity (and lower efficacious dose) may be achieved.

In one aspect, the invention provides an immunoconjugate of Formula (I):

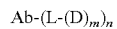

Wherein Ab represents CCR7 binding antibody described herein;

L is a linker;

D is a drug moiety;

m is an integer from 1 to 8; and n is an integer from 1-20. In one embodiment, n is an integer from 1 to 10, 2 to 8, or 2 to 5.

In a specific embodiment, n is 2, 3, or 4. In some embodiments, m is 1; in other embodiments m is 2, 3 or 4.

While the drug to antibody ratio has an exact value for a specific conjugate molecule (e.g., n multiplied by m in Formula (I)), it is understood that the value will often be an average value when used to describe a sample containing many molecules, due to some degree of heterogeneity, typically associated with the conjugation step. The average loading for a sample of an immunoconjugate is referred to herein as the drug to antibody ratio, or "DAR." In some embodiments, when the drug is a maytansinoid, it is referred to as "MAR." In some embodiments, the DAR is between about 2 and about 6, and typically is about 3, 3.5, 4, 4.5, 5, 5.5, 6, 6.5, 7.0, 7.5, 8.0. In some embodiments, at least 50% of a sample by weight is compound having the average DAR plus or minus 2, and preferably at least 50% of the sample is a conjugate that contains the average DAR plus or minus 1. Embodiments include immunoconjugates wherein the DAR is about 3.5, 3.6, 3.7, 3.8 or 3.9. In some embodiments, a DAR of 'about n' means the measured value for DAR is within 20% of n.

The present invention is also directed to immunoconjugates comprising the antibodies, antibody fragments (e.g., antigen binding fragments) and their functional equivalents as disclosed herein, linked or conjugated to a drug moiety. In one embodiment, the drug moiety D is a maytansinoid drug moiety, including those having the structure:

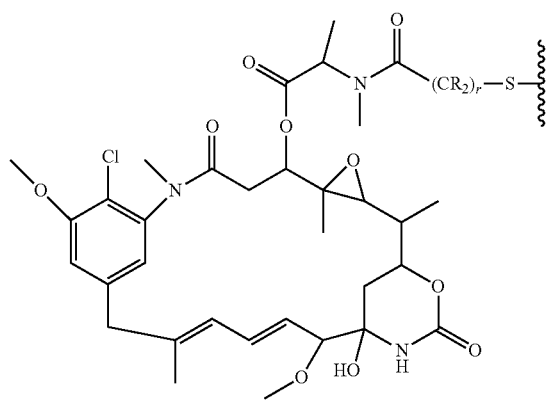

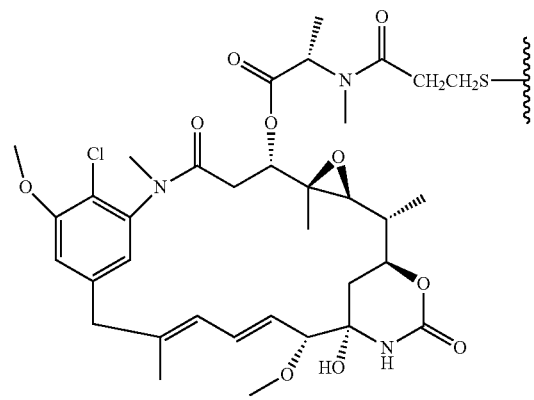

DM1

In another embodiment the maytansinoid drug moiety is N$^{2'}$-deacetyl-N$^{2'}$-(4-mercapto-1-oxopentyl)-maytansine (also known as DM3). DM3 is represented by the following structural formula.

where the wavy line indicates the covalent attachment of the sulfur atom of the maytansinoid to a linker of an antibody drug conjugate. R at each occurrence is independently H or a $C_1$-$C_6$ alkyl. The alkylene chain attaching the amide group to the sulfur atom may be methanyl, ethanyl, or propyl, i.e., r is 1, 2, or 3. (U.S. Pat. Nos. 633,410, 5,208,020, Chari et al. (1992) Cancer Res. 52; 127-131, Lui et al. (1996) Proc. Natl. Acad. Sci. 93:8618-8623).

All stereoisomers of the maytansinoid drug moiety are contemplated for the immunoconjugates of the invention, i.e. any combination of R and S configurations at the chiral carbons of the maytansinoid. In one embodiment the maytansinoid drug moiety has the following stereochemistry.

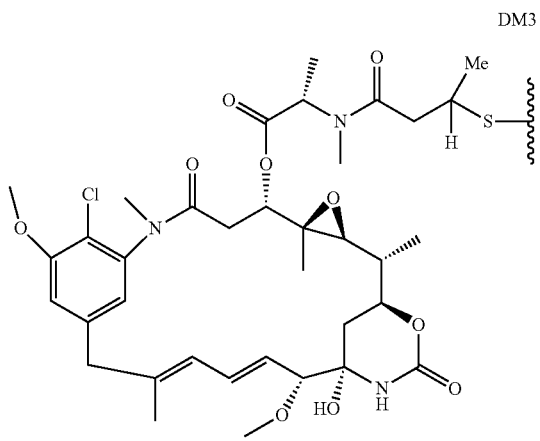

DM3

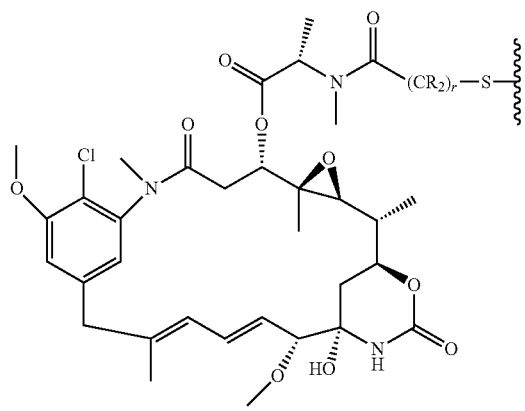

In another embodiment the maytansinoid drug moiety is N$^{2'}$-deacetyl-N$^{2'}$-(4-methyl-4-mercapto-1-oxopentyl)-maytansine (also known as DM4). DM4 is represented by the following structural formula.

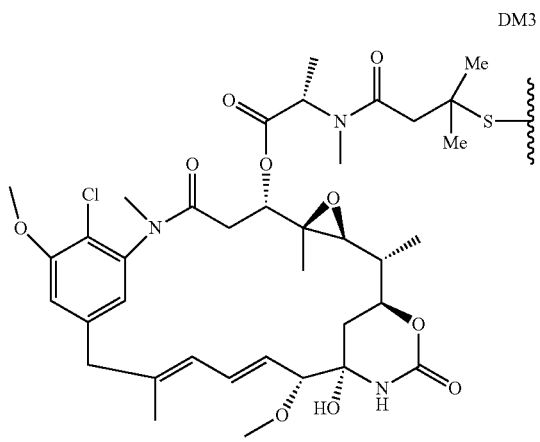 [SMILES: *SC(C)(C)CC(=O)N(C)[C@@H](C)C(=O)O[C@H]1CC(=O)N(C)c2cc(cc(OC)c2Cl)C/C(C)=C/C=C/[C@@H](OC)[C@@]2(O)C[C@H](OC(=O)N2)[C@@H](C)[C@@H]2O[C@@]12C]

DM3

In one embodiment, the maytansinoid drug moiety is N$^{2'}$-deacetyl-N$^{2'}$-(3-mercapto-1-oxopropyl)-maytansine (also known as DM1). DM1 is represented by the following structural formula.

The drug moiety D can be linked to the antibody Ab through linker L. L is any chemical moiety capable of linking the drug moiety to the antibody through covalent bonds. A cross-linking reagent is a bifunctional or multi-functional reagent that can be used to link a drug moiety and an antibody to form antibody drug conjugates. Antibody drug conjugates can be prepared using a cross-linking reagent having a reactive functionality capable of binding to both the drug moiety and the antibody. For example, a cysteine, thiol or an amine, e.g. N-terminus or an amino acid side chain, such as lysine of the antibody, can form a bond with a functional group of a cross-linking reagent. Alternatively, the Antibody drug conjugates can be prepared by pre-forming a linker-drug moiety (or drug-linker moiety, both terms being used interchangeably), and reacting the linker-drug moiety with the antibody. In some instant, the linker moiety is built onto the drug stepwise using several linking moieties until obtaining the desired linker-drug moiety.

In one embodiment, L is a cleavable linker. In another embodiment, L is a non-cleavable linker. In some embodiments, L is an acid-labile linker, photo-labile linker, peptidase cleavable linker, esterase cleavable linker, a disulfide bond cleavable linker, a hydrophilic linker, a procharged linker, a glycosidase cleavable linker, a phosphodiesterase cleavable linker, a phosphatase cleavable linker, or a dicarboxylic acid based linker.

Suitable cross-linking reagents that form a non-cleavable linker between the drug moiety, for example maytansinoid, and the antibody are well known in the art, and can form non-cleavable linkers that comprise a sulfur atom (such as SMCC) or those that are without a sulfur atom. Preferred cross-linking reagents that form non-cleavable linkers between the drug moiety, for example maytansinoid, and the antibody comprise a maleimido- or haloacetyl-based moiety. According to the present invention, such non-cleavable linkers are said to be derived from maleimido- or haloacetyl-based moieties.

Cross-linking reagents comprising a maleimido-based moiety include but not limited to, N-succinimidyl-4-(maleimidomethyl)cyclohexanecarboxylate (SMCC), sulfosuccinimidyl 4-(N-maleimidomethyl) cyclohexane-1-carboxylate (sulfo-SMCC), N-succinimidyl-4-(maleimidomethyl)cyclohexane-1-carboxy-(6-amidocaproate), which is a "long chain" analog of SMCC (LC-SMCC), κ-maleimidoundecanoic acid N-succinimidyl ester (KMUA), γ-maleimidobutyric acid N-succinimidyl ester (GMBS), ε-maleimidocaproic acid N-succinimidyl ester (EMCS), m-maleimidobenzoyl-N-hydroxysuccinimide ester (MBS), N-(α-maleimidoacetoxy)-succinimide ester (AMSA), succinimidyl-6-(β-maleimidopropionamido)hexanoate (SMPH), N-succinimidyl-4-(p-maleimidophenyl)-butyrate (SMPB), N-(-p-maleomidophenyl)isocyanate (PMIP) and maleimido-based cross-linking reagents containing a polyethythene glycol spacer, such as MAL-PEG-NHS. These cross-linking reagents form non-cleavable linkers derived from maleimido-based moieties. Representative structures of maleimido-based cross-linking reagents are shown below.

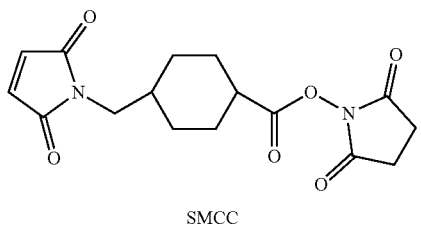

SMCC

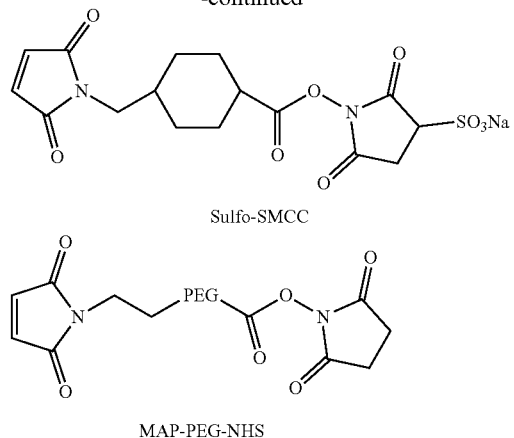

Sulfo-SMCC

MAP-PEG-NHS

In another embodiment, the linker L is derived from N-succinimidyl-4-(maleimidomethyl)cyclohexanecarboxylate (SMCC), sulfosuccinimidyl 4-(N-maleimidomethyl)cyclohexane-1-carboxylate (sulfo-SMCC) or MAL-PEG-NHS.

Cross-linking reagents comprising a haloacetyle-based moiety include N-succinimidyl iodoacetate (SIA), N-succinimidyl(4-iodoacetyl)aminobenzoate (SIAB), N-succinimidyl bromoacetate (SBA) and N-succinimidyl 3-(bromoacetamido)propionate (SBAP). These cross-linking reagents form a non-cleavable linker derived from haloacetyl-based moieties. Representative structures of haloacetyl-based cross-linking reagents are shown below.

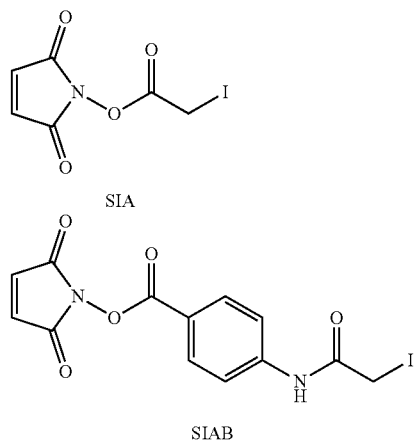

SIA

SIAB

In one embodiment, the linker L is derived from N-succinimidyl iodoacetate (SIA) or N-succinimidyl(4-iodoacetyl)aminobenzoate (SIAB).

Suitable cross-linking reagents that form a cleavable linker between the drug moiety, for example maytansinoid, and the antibody are well known in the art. Disulfide containing linkers are linkers cleavable through disulfide exchange, which can occur under physiological conditions. According to the present invention, such cleavable linkers are said to be derived from disulfide-based moieties. Suitable disulfide cross-linking reagents include N-succinimidyl-3-(2-pyridyldithio)propionate (SPDP), N-succinimidyl-4-(2-pyridyldithio)pentanoate (SPP), N-succinimidyl-4-(2-pyridyldithio)butanoate (SPDB) and N-succinimidyl-4-(2-pyridyldithio)-2-sulfo-butanoate (sulfo-SPDB), the structures of which are shown below. These disulfide cross-linking reagents form a cleavable linker derived from disulfide-based moieties.

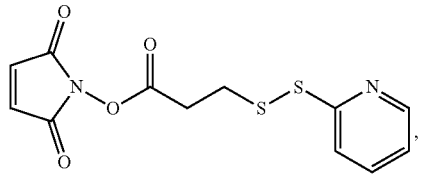

N-succinimidyl-3-(2-pyridyldithio)propionate
(SPDP)

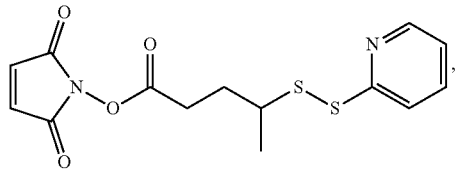

N-succinimidyl-4-(2-pridyldithio)pentanoate
(SPP)

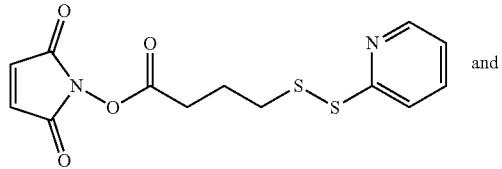

N-succinimidyl-4-(2-pyridyldithio)butanoate
(SPDB)

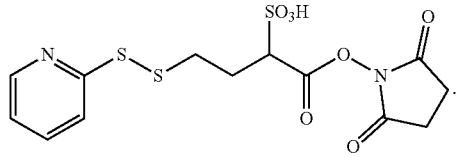

N-succinimidyl-4-(2-pyridyldithio)-2-sulfo-butanoate
(sulfo-SPDB)

In one embodiment, the linker L is derived from N-succinimidyl-4-(2-pyridyldithio)butanoate (SPDB).

Suitable cross-linking reagents that form a charged linker between the drug moiety, for example maytansinoid, and the antibody are known as procharged cross-linking reagents. In one embodiment, the linker L is derived from the procharged cross-linking reagent CX1-1. The structure of CX1-1 is below.

2,5-dioxopyrrolidin-1-yl 17-(2,5-dioxo-2,5-dihydro-1H-pyrrol-1-yl)-5,8,11,14-tetraoxo-4,7,10,13-tetraazaheptadecan-1-oate (CX1-1)

Each of the cross-linking reagents depicted above contains, at one end of the cross-linking reagent, a NHS-ester which reacts with a primary amine of the antibody to form an amide bond and, at the other end, a maleimide group or pyridinyldisulfide group which reacts with the sulfhydryl of the maytansionoid drug moiety to form a thioether or disulfide bond.

In another embodiment, suitable cross-linking moieties that form a cleavable linker between the drug moiety (for example maytansinoid) and the antibody are represented by the following formula (II):

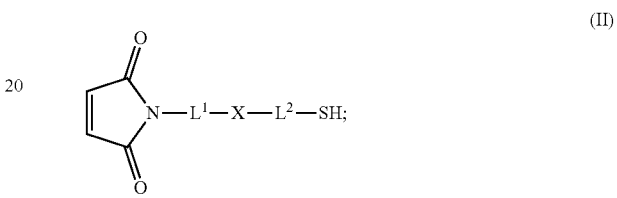

(II)

wherein:
L$^1$ is a C$_{1-6}$alkylene wherein one of the methylene groups may be replaced with oxygen;
L$^2$ is a C$_{1-6}$alkylene or is —(CH$_2$CH$_2$O)$_y$—CH$_2$—CH$_2$— wherein y is 1 to 11; and
X is —C(O)—NH—, —NHC(O)— or a triazole;
wherein the alkylene is linear or branched.

In one aspect of this embodiment y is 5, 7, 9 or 11. In another aspect of this embodiment y is less than 5.

In yet another embodiment, suitable cross-linking moieties according to formula I are selected from the group consisting of:

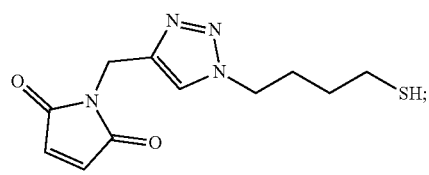

MaleimidoMethylTriazoleButaneThiol
(MMTBT)

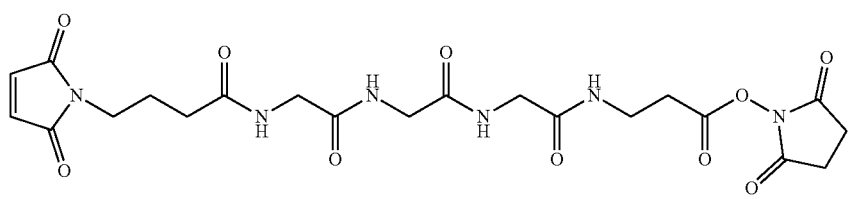 [SMILES: O=C(CCCN1C(=O)C=CC1=O)NCC(=O)NCC(=O)NCC(=O)NCCC(=O)ON1C(=O)CCC1=O]

-continued

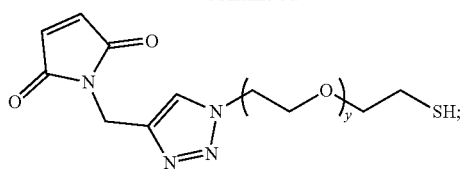

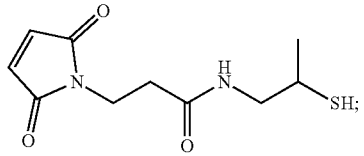
MPPT: MaleimidoPropionamidoPropaneThio

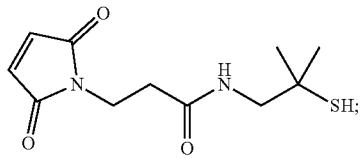
MPBT: maleimidoPropionamidoButylThio

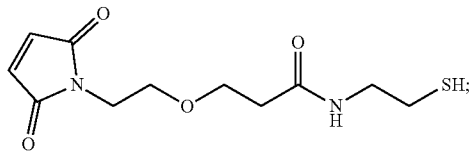
MEPET: MaleimidoEthoxyPropionamidoEthylThio

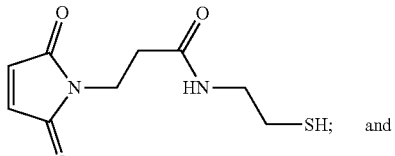
MPET: MaleimidoPropionamidoEthylThio

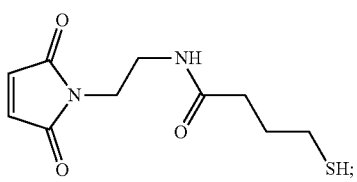
MBT: MaleimidoEthylButanamidoThio wherein y is 1 to 11.

For the cross-linking moieties depicted above (i.e. MBT, MPET, MEPET; MMTBT, MPPT, MPBT), the maleimide group allows for reaction with the sulfhydryl (or thiol) of a Cysteine in an antibody thereby forming a thioether bond; and the thiol functionality of the cross-linking moiety is connected to the thiol of the maytansinoid drug moiety to form a cleavable disulfide bond. In view of the cross-reactional nature of the linking moiety of Formula (I) (thiol and maleimide could cross react), one of ordinary skill in the art would appreciate that the linking moiety has to be built stepwise onto the drug moiety as depicted in Scheme 1.

According to the above embodiment, the linkers resulting from the cross linking moieties (i.e. MBT, MPET, MEPET) can be depicted as follow:

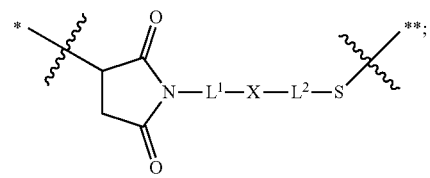

wherein * is linked to the thiol functionality on the antibody, and ** is linked to the thiol functionality of a drug moiety (e.g. maytansinoid drug moiety DM1, DM3 or DM4).

According to the above embodiment, the linkers resulting from the cross linking moieties (i.e. MBT, MPET, MEPET) can be depicted as follows:

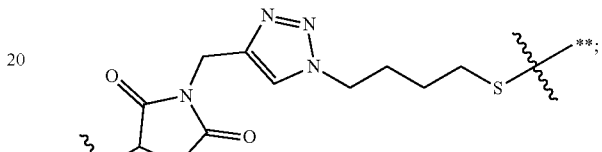

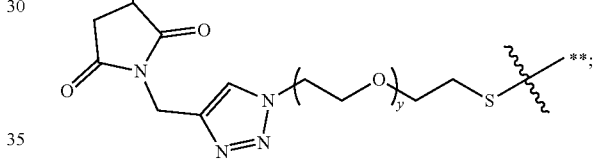

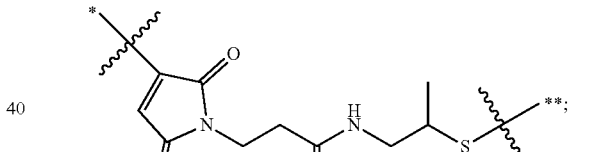

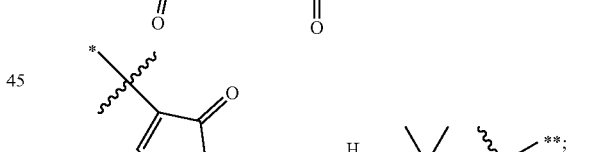

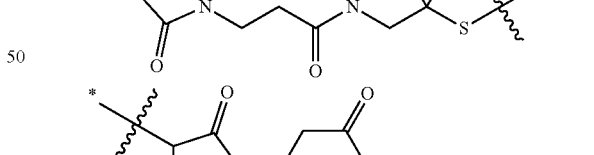

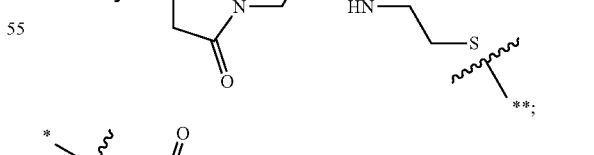

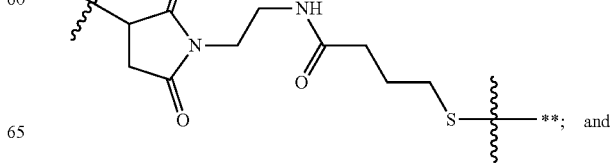
and

-continued

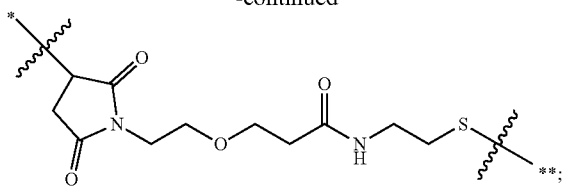

wherein y is 1 to 11; * is linked to the thiol functionality on the antibody, and ** is linked to the thiol functionality of the drug moiety (e.g. maytansinoid drug DM1, DM3 or DM4).

In a preferred embodiment, the linker has the following formula:

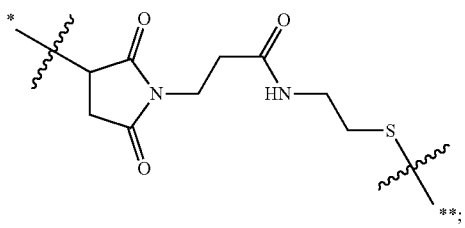 [SMILES: *SCCNC(=O)CCN1C(=O)CC(*)C1=O]

wherein * is linked to the thiol functionality on the antibody, and ** is linked to the thiol functionality of the maytansinoid drug (DM1, DM3 or DM4)

In one embodiment, the invention relates to the linker-drug moiety of Formula:

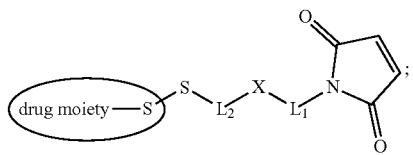

wherein
$L^1$ is a $C_{1-6}$alkylene wherein one of the methylene groups may be replaced with oxygen;
$L^2$ is a $C_{1-6}$alkylene or is $-(CH_2CH_2-)_y-CH_2-CH_2-$ wherein y is 1 to 11; and
X is $-C(O)-NH-$, $-NHC(O)-$ or a triazole;
wherein the alkylene is linear or branched.

In another embodiment, the invention pertains to the stepwise formation of the above linker-drug conjugate as disclosed in Scheme 1 herein.

In one embodiment, the invention relates to the linker-drug moiety compounds having one of the following Formulae (III), (IV) and (V):

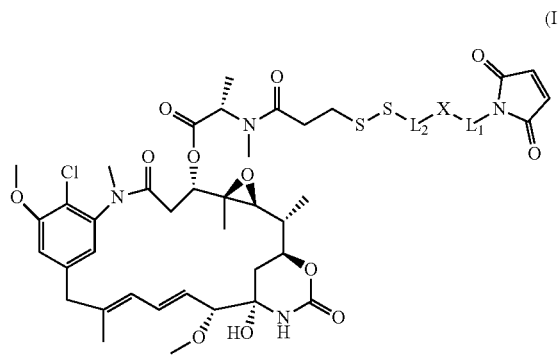

(III)

Maleimido Linker_DM1

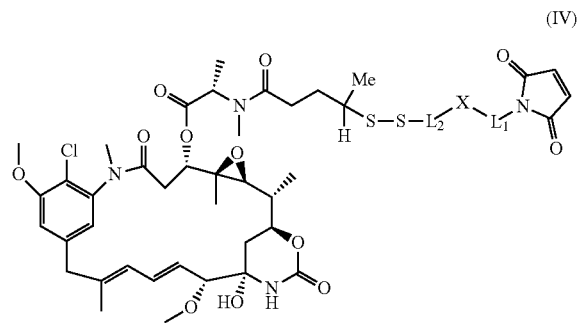

(IV)

Maleimido Linker-DM3

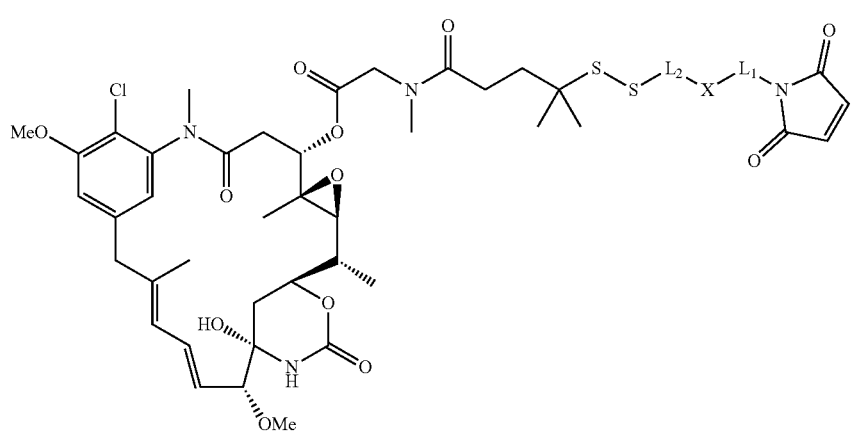

(V)

Maleimido linker-DM4 wherein $L^1$ is a $C_{1-6}$alkylene wherein one of the methylene groups may be replaced with oxygen;

$L^2$ is a $C_{1-6}$alkylene or is —(CH$_2$CH$_2$O)$_y$—CH$_2$—CH$_2$— wherein y is 1 to 11; and X is —C(O)—NH—, —NHC(O)— or a triazole;
Wherein the alkylene is linear or branched.

In one embodiment, the invention relates to the linker-drug moiety compounds which are selected from the following formulae:

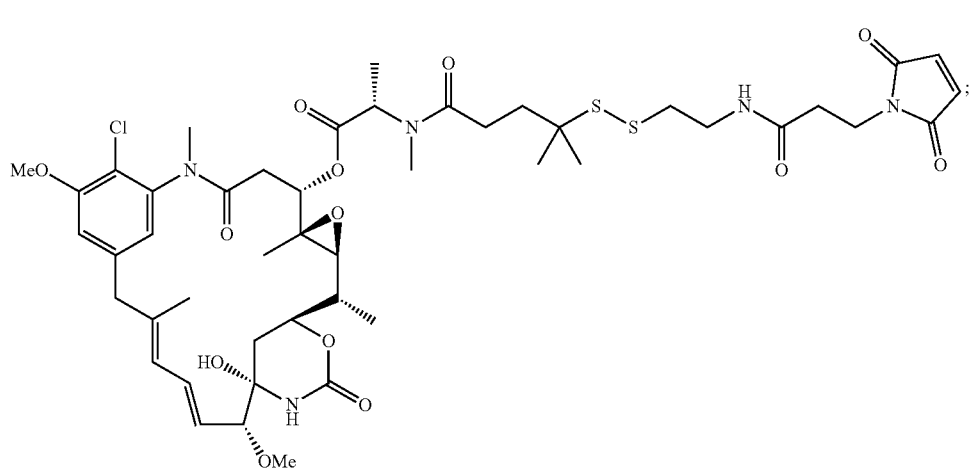

MPET-DM4

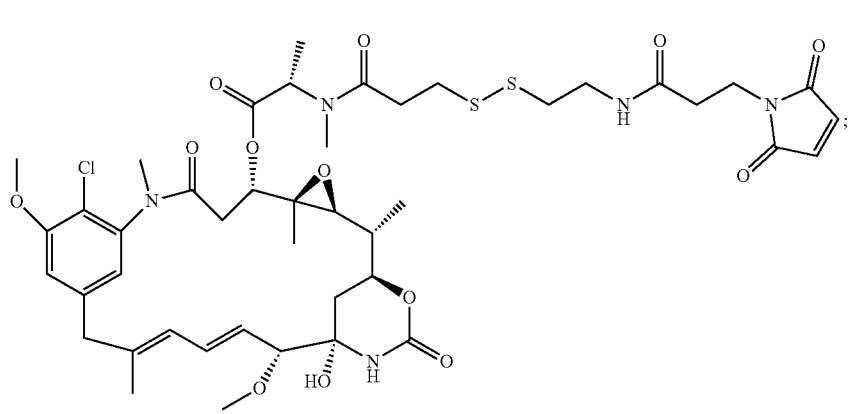

MPET-DM1

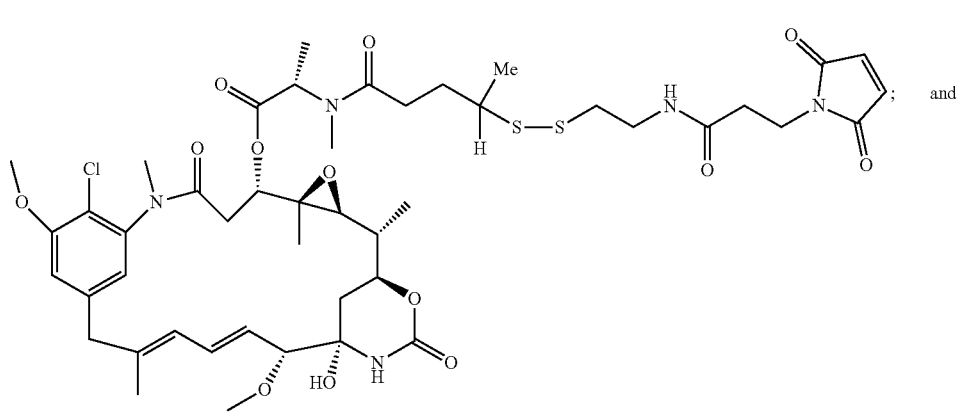

MPET-DM3 and

MPET-DM1
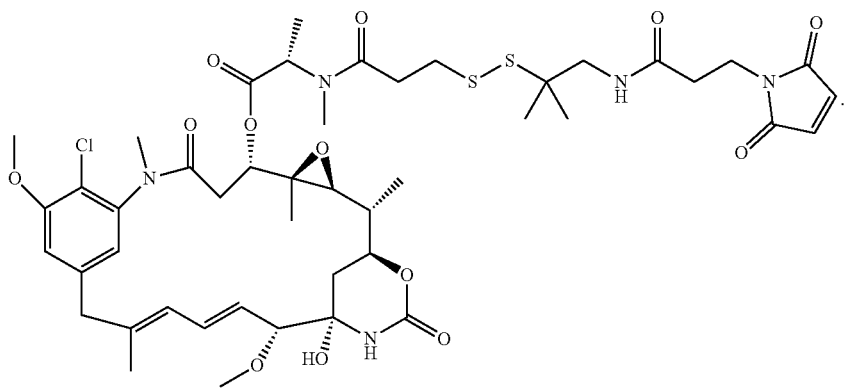
In another embodiment, the invention relates to the linker-drug moiety compounds which are selected from the following formulae:
MEPET-DM4
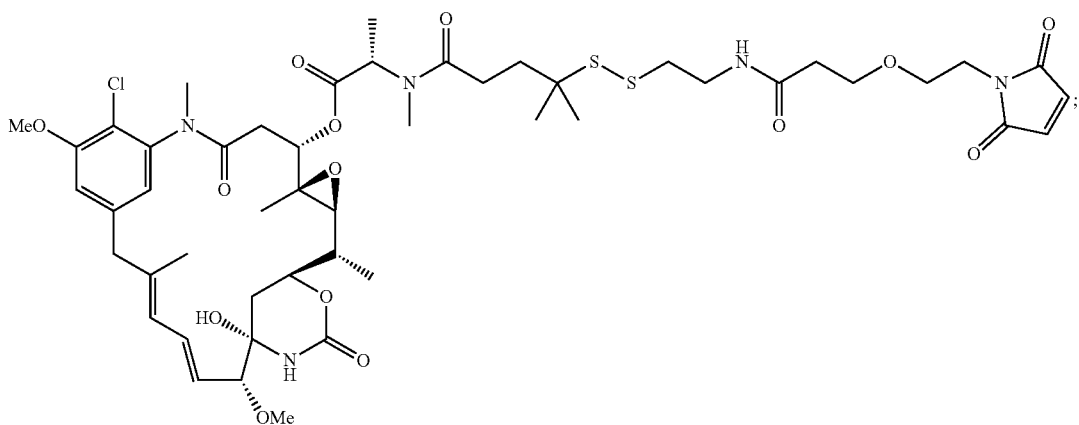
MEPET-DM1
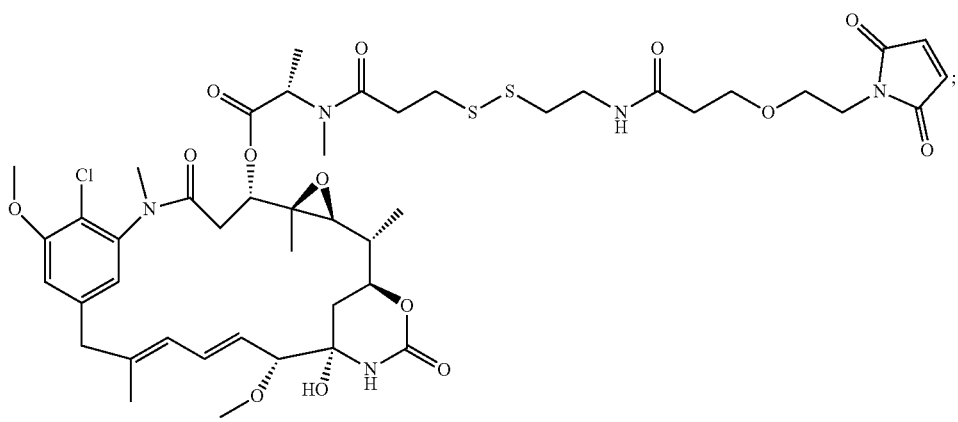

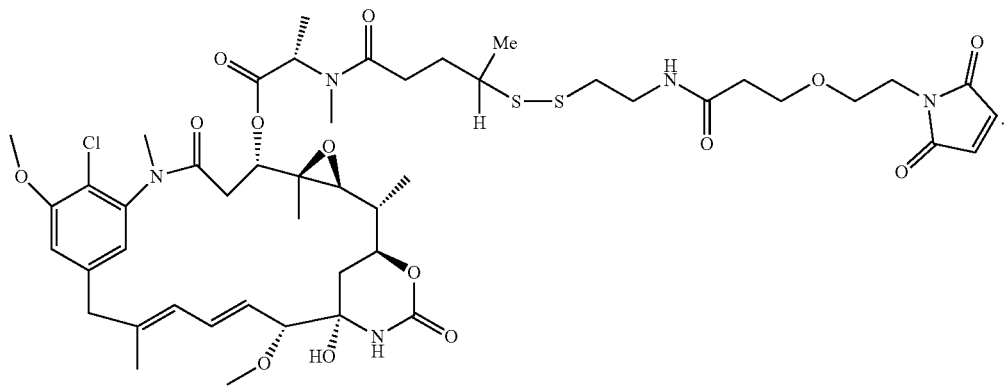
MEPET-DM3
In another embodiment, the linker-drug of the present invention is represented by any one of the following formulae:
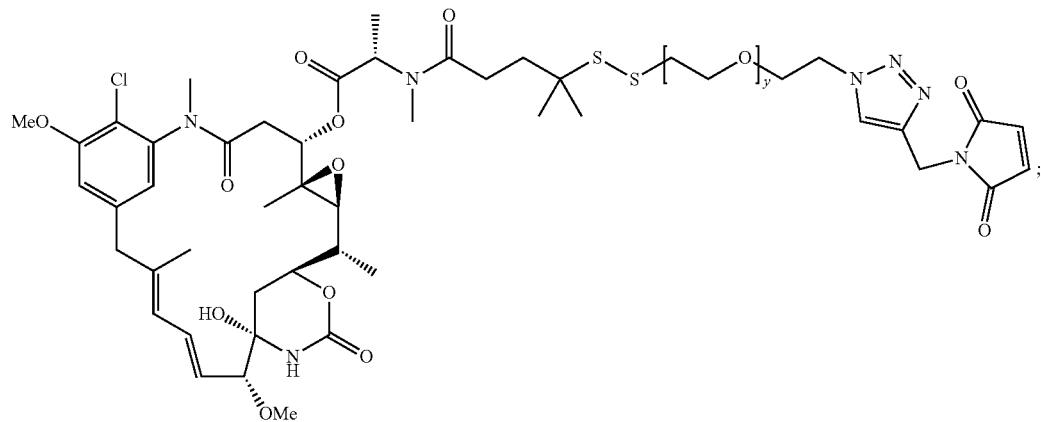
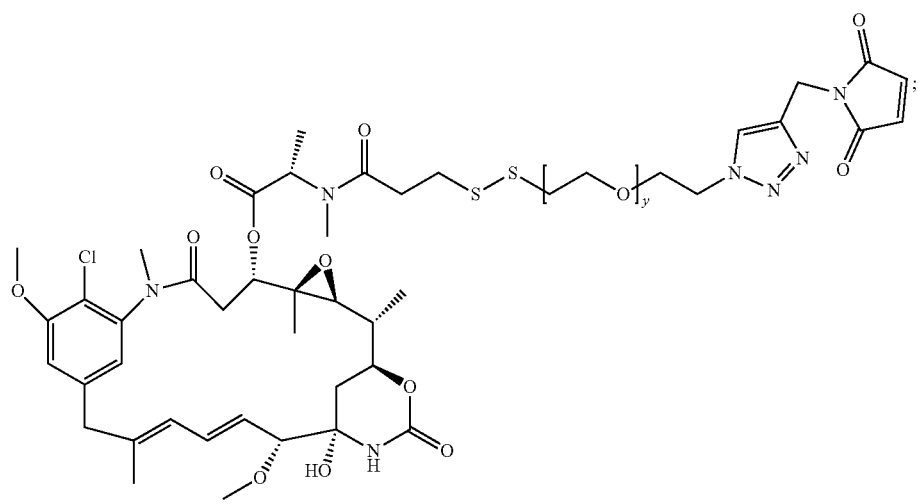

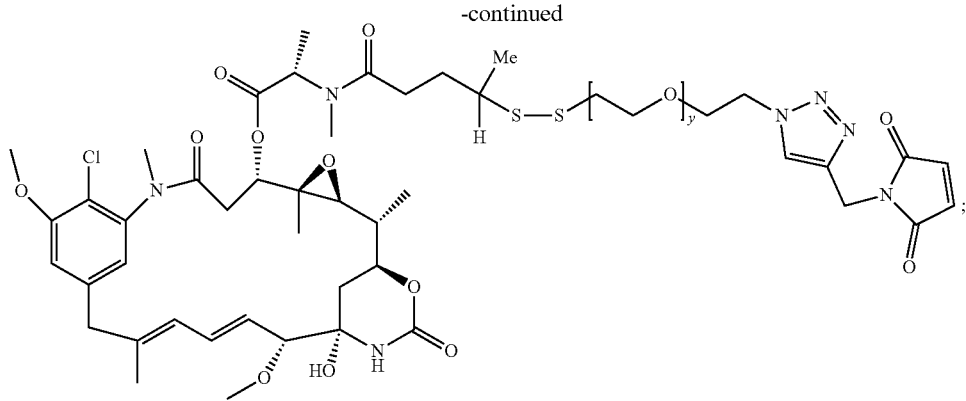
wherein y is 1 to 11, preferably 1 to 5.
In one embodiment, the linker-drug of the present invention is represented by any one of the following structural formulae:
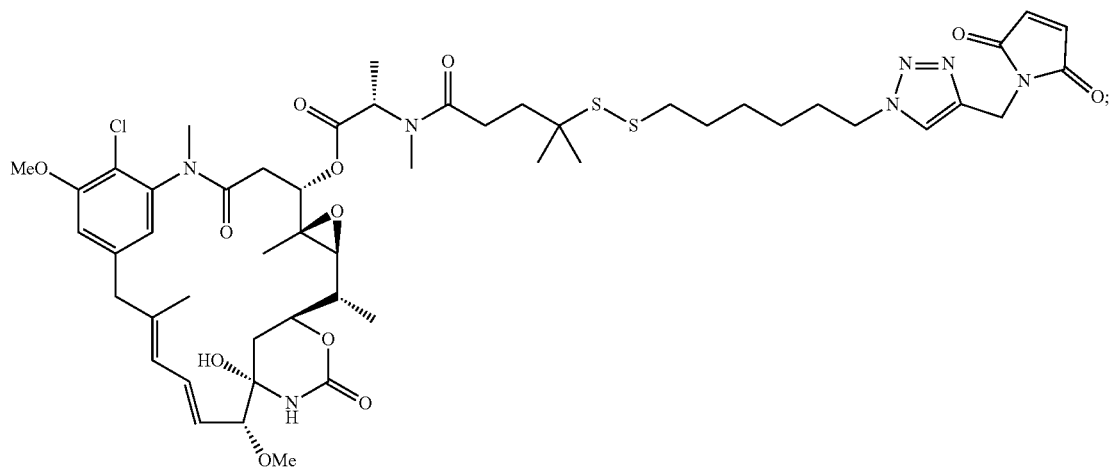
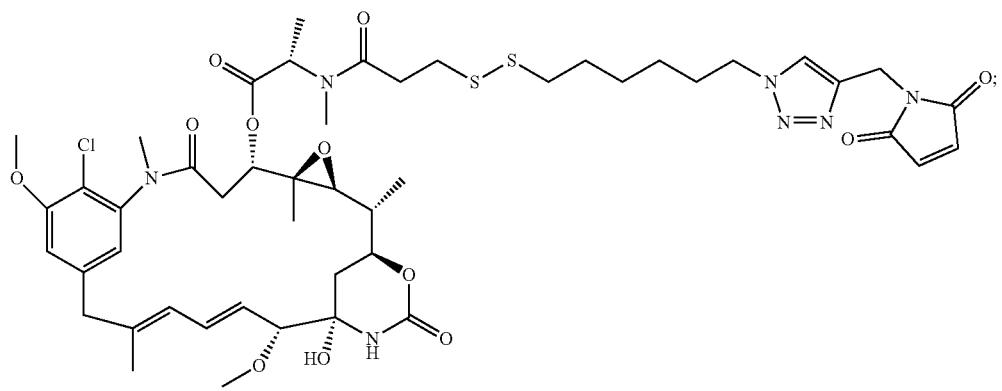

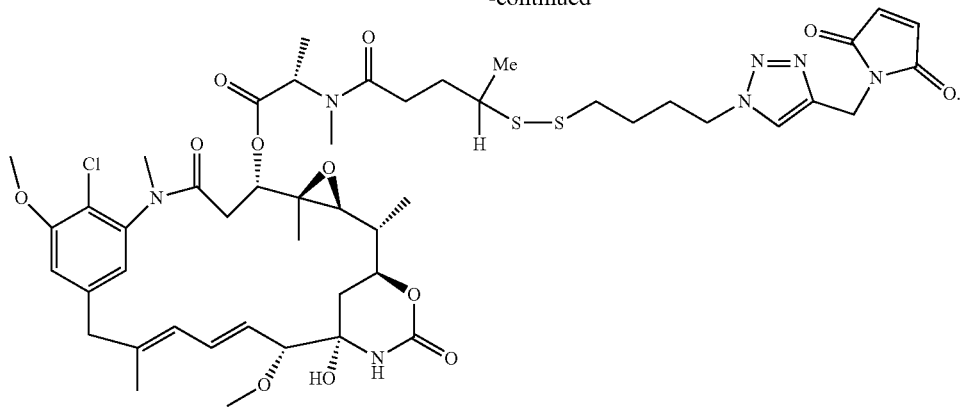
In one embodiment, the conjugate of the present invention is represented by any one of the following structural formulae:
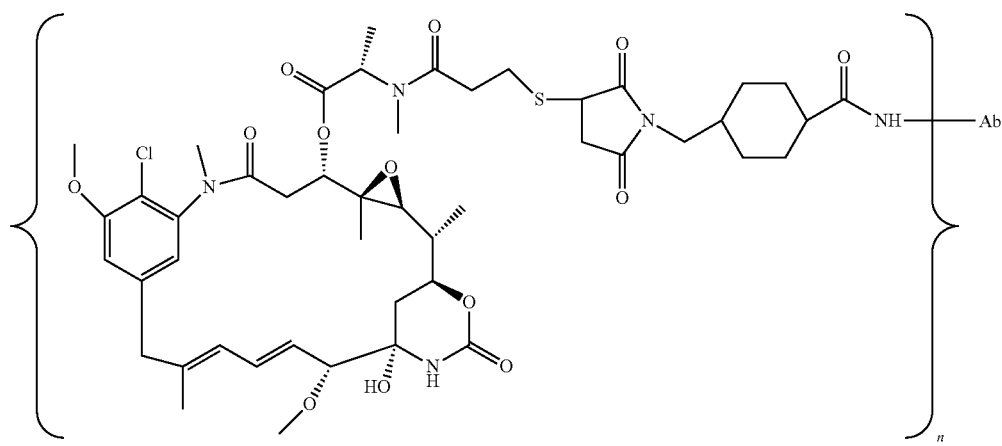
Ab-MCC-DM1
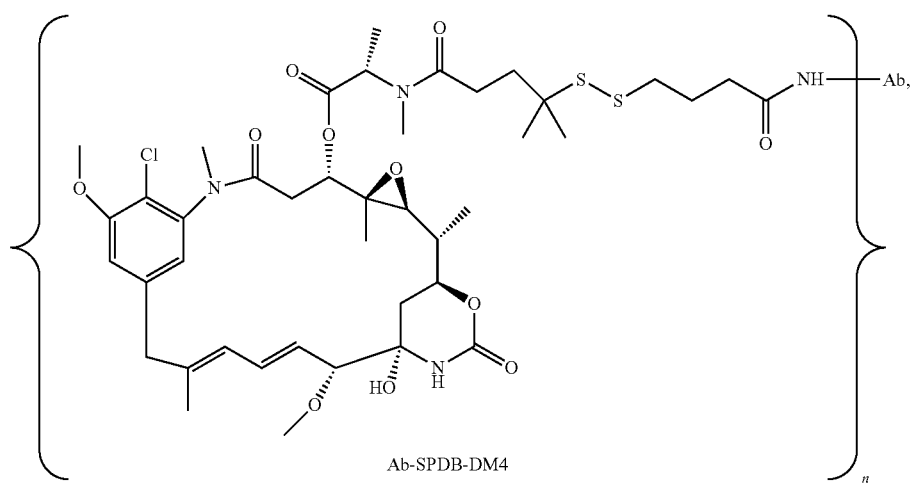
Ab-SPDB-DM4

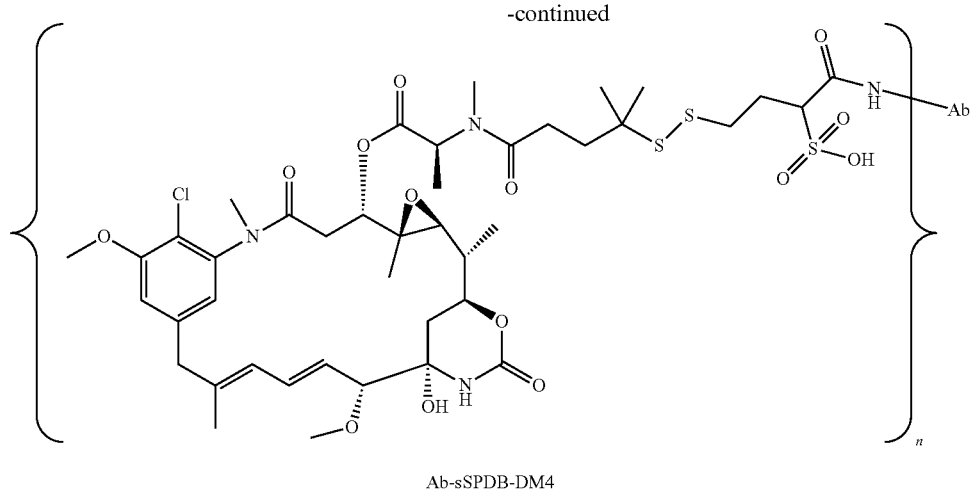

Ab-sSPDB-DM4

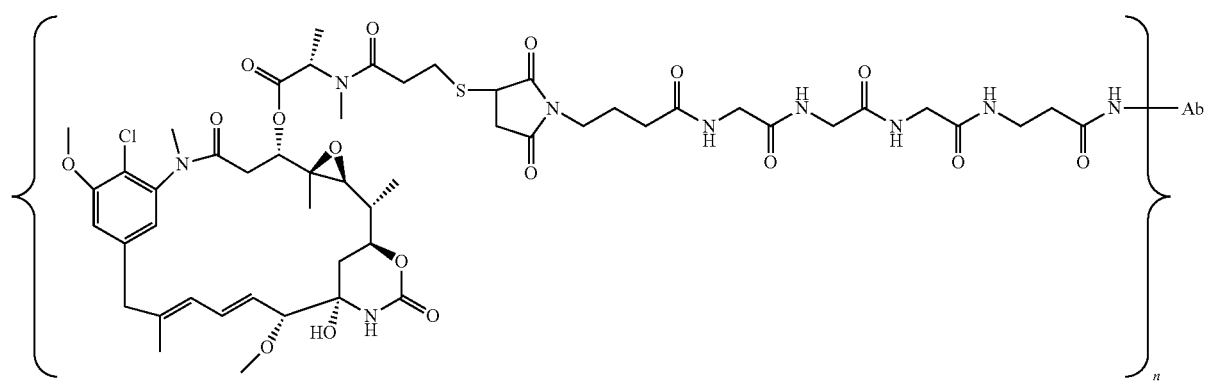

Ab-CX1-1-DM1 wherein:
Ab is an antibody or antigen binding fragment thereof that specifically binds CCR7;
n, which indicates the number of linker-drug (L-D-) groups attached to the Ab through the formation of an amide bond with a primary amine of the Ab, is an integer from 1 to 20. In one embodiment, n is an integer from 1 to 10, 2 to 8 or 2 to 5. In a specific embodiment, n is 3 or 4.

In another embodiment, the conjugate of the present invention is represented by any of the following Formulae (VI), (VII) and (VIII):

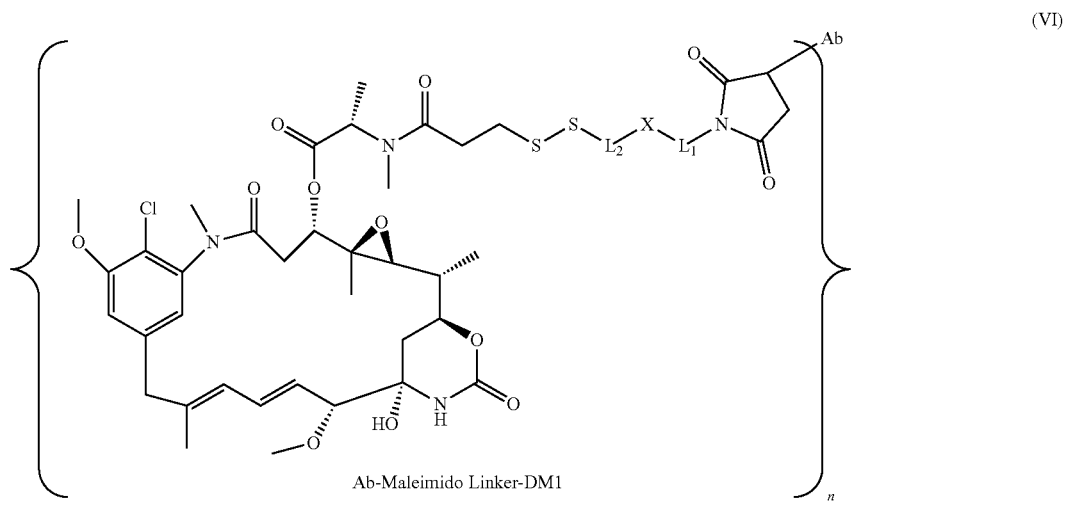

Ab-Maleimido Linker-DM1

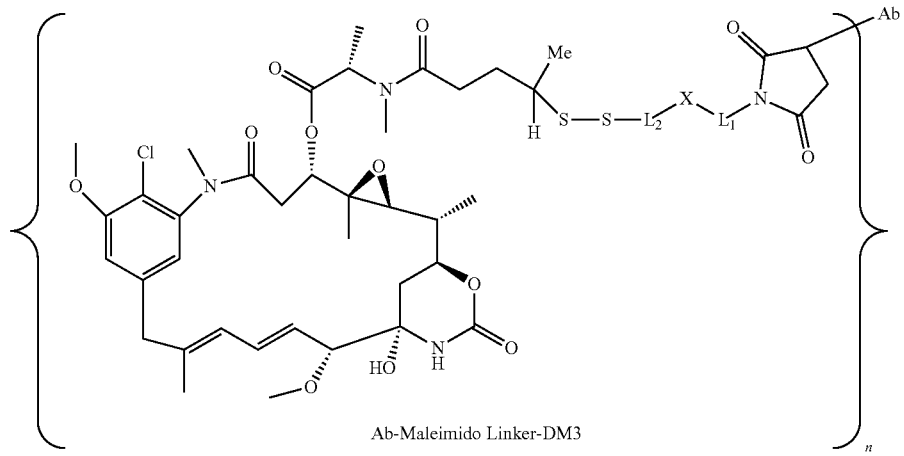

Ab-Maleimido Linker-DM3

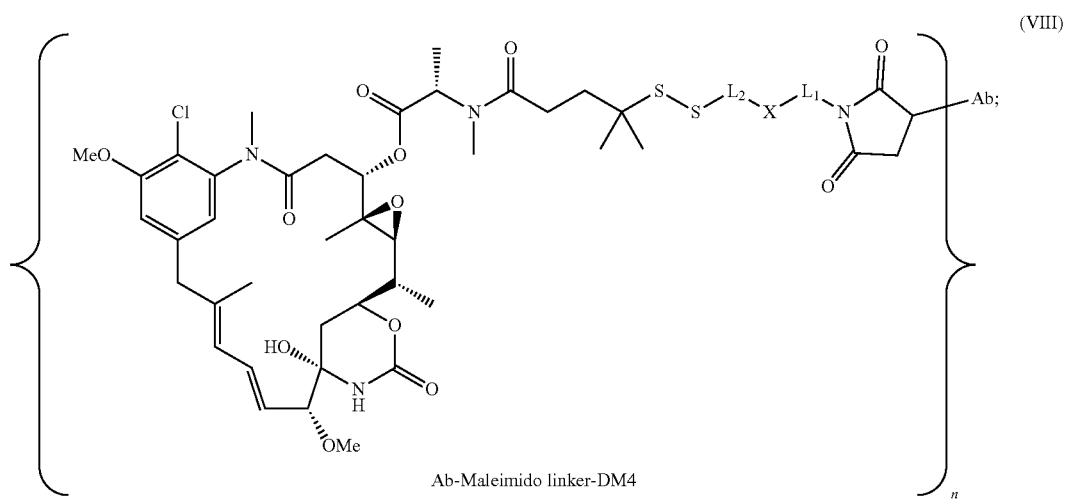

Ab-Maleimido linker-DM4 wherein:

$L^1$ is a $C_{1-6}$alkylene wherein one of the methylene groups may be replaced with oxygen;

$L^2$ is a $C_{1-6}$alkylene or is —$(CH_2CH_2O)_y$—$CH_2$—$CH_2$— wherein y is 1 to 11; and X is —C(O)—NH—, —NHC(O)— or a triazole;

wherein the alkylene is linear or branched; and

Ab is an antibody or antigen binding fragment thereof;

n, which indicates the number of linker-drug (L-D-) groups attached to the Ab through the formation of an amide bond with a primary amine of the Ab, is an integer from 1 to 20. In one embodiment, n is an integer from 1 to 10, 2 to 8 or 2 to 5. In a specific embodiment, n is 3 or 4. In some embodiments, the antibody or antigen binding fragment thereof binds to an antigen that is expressed on tumor cells. In one embodiment, the antibody or antigen binding fragment thereof specifically binds CCR7. In other embodiments, the antibody or antigen binding fragment thereof specifically binds P-cadherin, Cadherin 6, FGFR2, or FGFR4.

In another embodiment, the conjugate of the present invention has the Formula (VIA) or (VIB) corresponding to the open forms of the succinimide of the conjugate of Formula (VI):

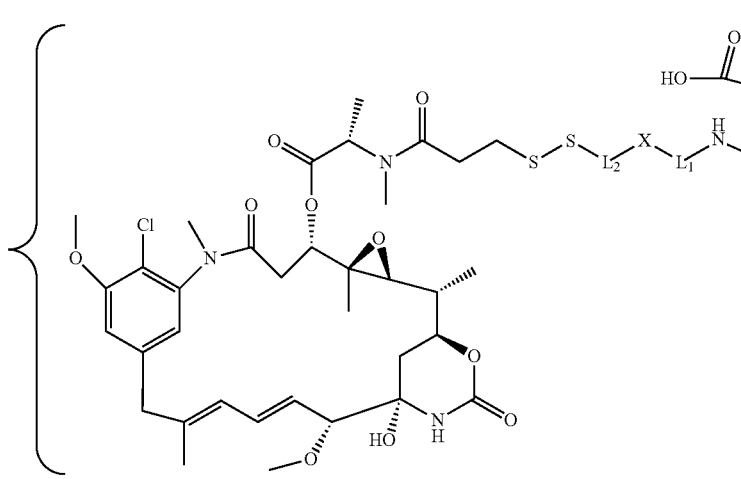

(VIA)

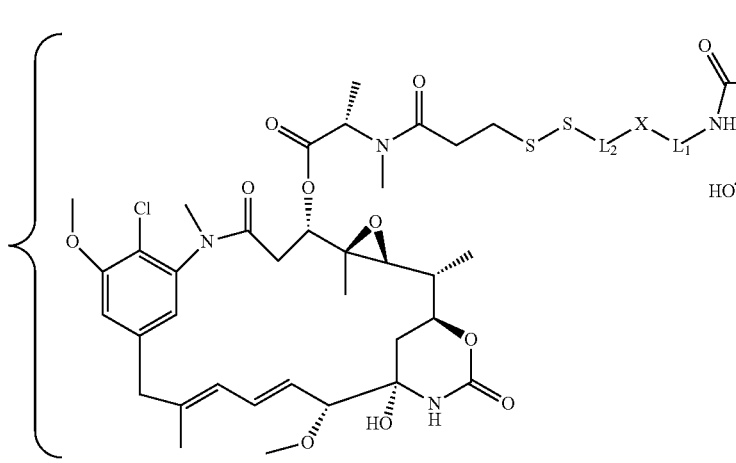

(VIB)

wherein:
L¹ is a $C_{1-6}$alkylene wherein one of the methylene groups may be replaced with oxygen;
L² is a $C_{1-6}$alkylene or is —(CH₂CH₂O)$_y$—CH₂—CH₂— wherein y is 1 to 11; and
X is —C(O)—NH—, —NHC(O)— or a triazole;
wherein the alkylene is linear or branched; and
Ab is an antibody or antigen binding fragment;
n, which indicates the number of linker-drug (L-D-) groups attached to the Ab through the formation of an amide bond with a primary amine of the Ab, is an integer from 1 to 20. In one embodiment, n is an integer from 1 to 10, 2 to 8 or 2 to 5. In a specific embodiment, n is 3 or 4. In some embodiments, the antibody or antigen binding fragment thereof binds to an antigen that is expressed on tumor cells. In one embodiment, the antibody or antigen binding fragment thereof specifically binds CCR7. In other embodiments, the antibody or antigen binding fragment thereof specifically binds P-cadherin, Cadherin 6, FGFR2, or FGFR4.

In another embodiment, the conjugate of the present invention has the Formula (VIIA) or (VIIB) corresponding to the open forms of the succinimide of the conjugate of Formula (VII):

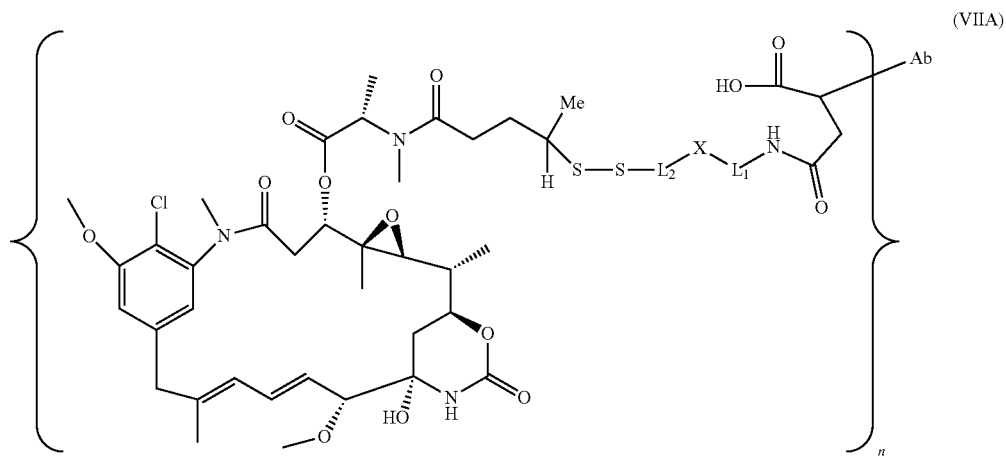

(VIIA)

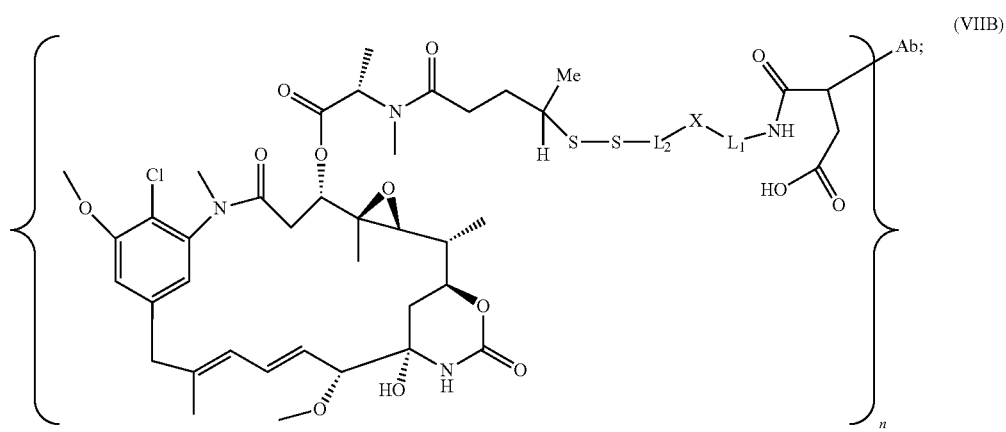

(VIIB)

wherein:
L¹ is a $C_{1-6}$alkylene wherein one of the methylene groups may be replaced with oxygen;
L² is a $C_{1-6}$alkylene or is —(CH$_2$CH$_2$O)$_y$—CH$_2$—CH$_2$— wherein y is 1 to 11; and
X is —C(O)—NH—, —NHC(O)— or a triazole;
wherein the alkylene is linear or branched; and
Ab is an antibody or antigen binding fragment thereof;
n, which indicates the number of linker-drug (L-D) groups attached to the Ab through the formation of an amide bond with a primary amine of the Ab, is an integer from 1 to 20. In one embodiment, n is an integer from 1 to 10, 2 to 8 or 2 to 5. In a specific embodiment, n is 3 or 4. In some embodiments, the antibody or antigen binding fragment thereof binds to an antigen that is expressed on tumor cells. In one embodiment, the antibody or antigen binding fragment thereof specifically binds CCR7. In other embodiments, the antibody or antigen binding fragment thereof specifically binds P-cadherin, Cadherin 6, FGFR2, or FGFR4.

In another embodiment, the conjugate of the present invention has the Formula (VIIIA), (VIIIB) corresponding to the open forms of the succinimide of the conjugate of Formula (VIII):

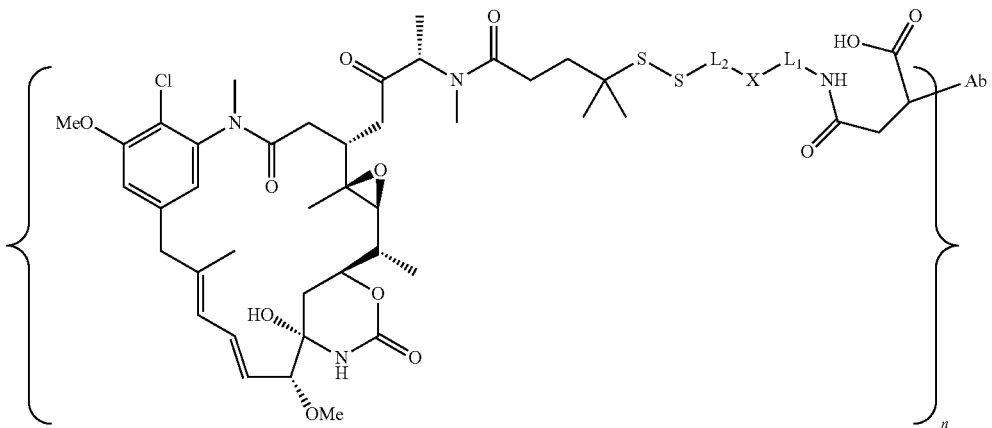

(VIIIA)

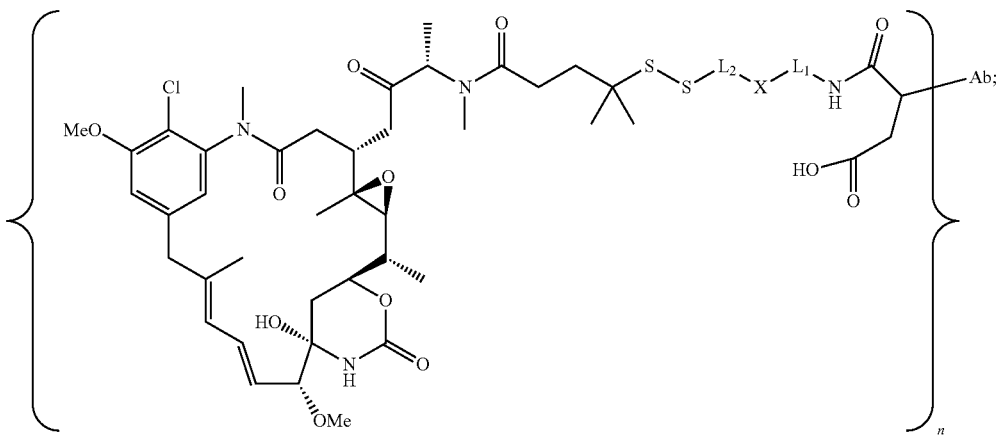

(VIIIB)

wherein:
L$^1$ is a C$_{1-6}$alkylene wherein one of the methylene groups may be replaced with oxygen;
L$^2$ is a C$_{1-6}$alkylene or is —(CH$_2$CH$_2$O)$_y$—CH$_2$—CH$_2$— wherein y is 1 to 11; and
X is —C(O)—NH—, —NHC(O)— or a triazole;
wherein the alkylene is linear or branched; and
Ab is an antibody or antigen binding fragment thereof;
n, which indicates the number of linker-drug (L-D-) groups attached to the Ab through the formation of an amide bond with a primary amine of the Ab, is an integer from 1 to 20. In one embodiment, n is an integer from 1 to 10, 2 to 8 or 2 to 5. In a specific embodiment, n is 3 or 4. In some embodiments, the antibody or antigen binding fragment thereof binds to an antigen that is expressed on tumor cells. In one embodiment, the antibody or antigen binding fragment thereof specifically binds CCR7. In other embodiments, the antibody or antigen binding fragment thereof specifically binds P-cadherin, Cadherin 6, FGFR2, or FGFR4.

In one embodimemt, each antibody drug conjugate disclosed herein wherein the linker-drug moiety is attached to the antibody via a succimide, can also exist as the open forms of the succinimide as generally depicted in Formulae (VIA), (VIB), (VIIA), (VIIB), (VIIIA) and (VIIIB).

In yet another embodiment, the conjugate of the present invention is represented by any one of the following structural formulae:

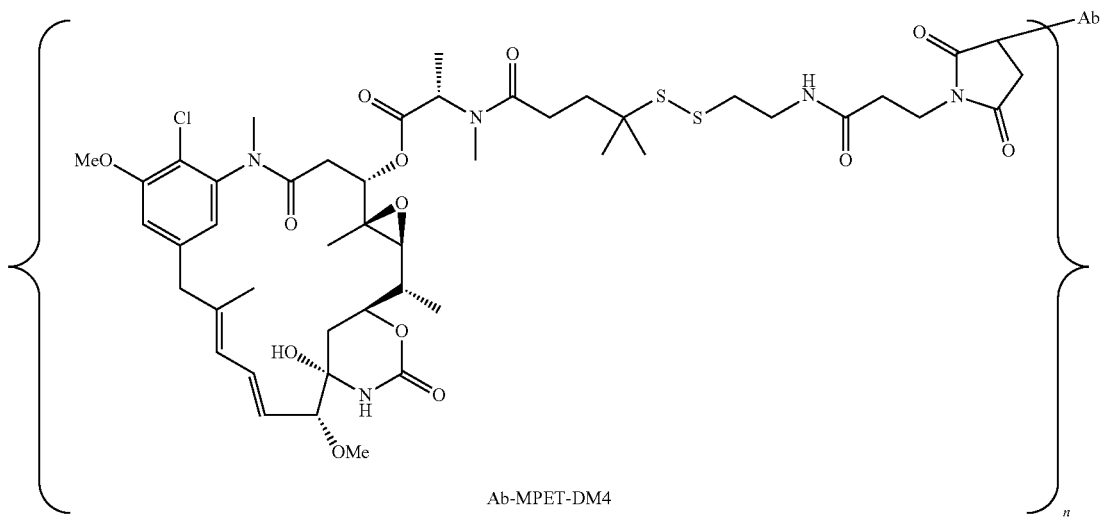
Ab-MPET-DM4
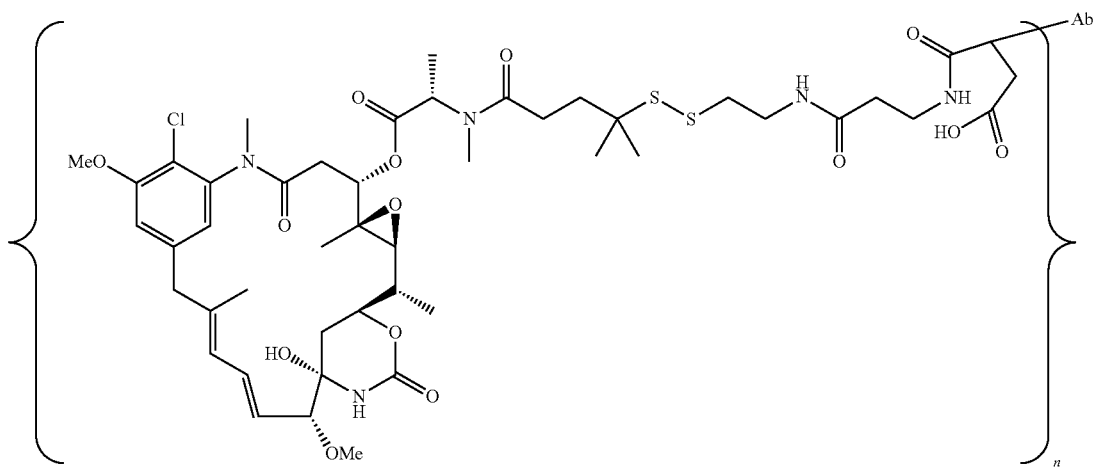
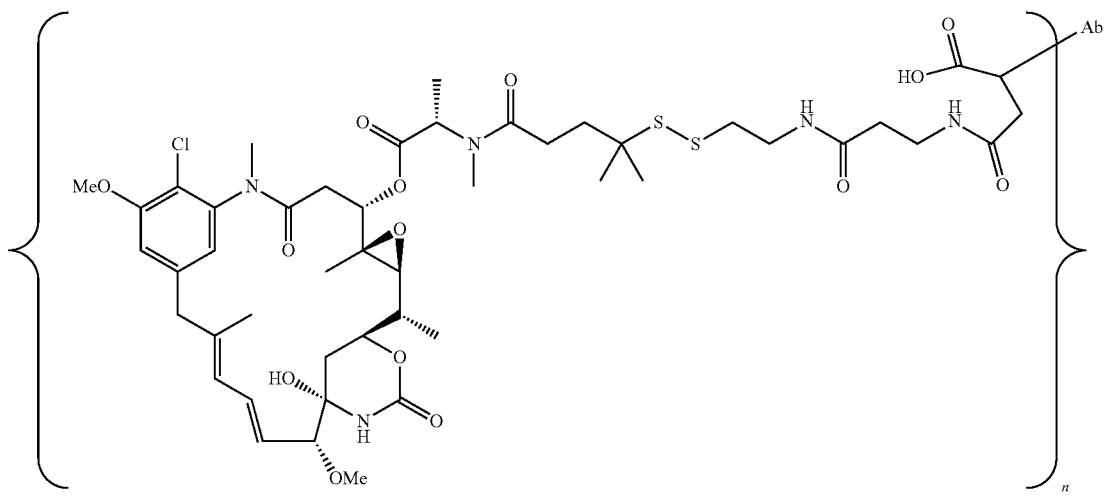

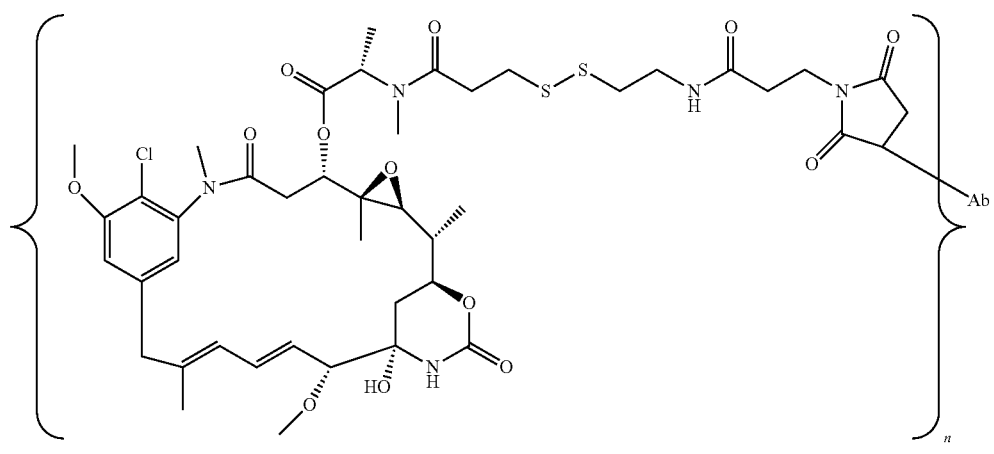
Ab-MPET-DM1
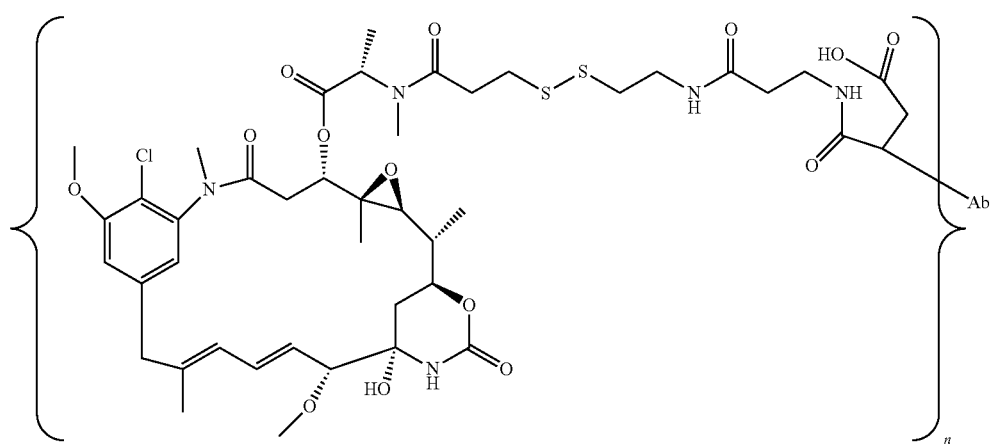
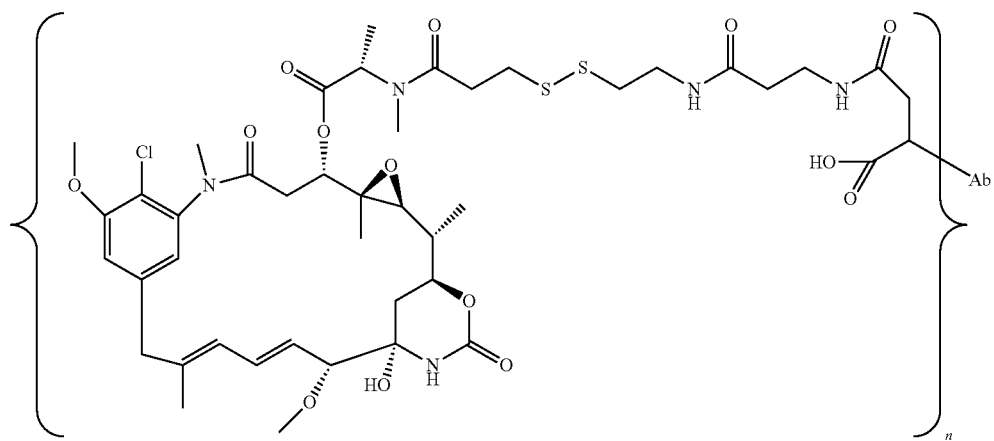

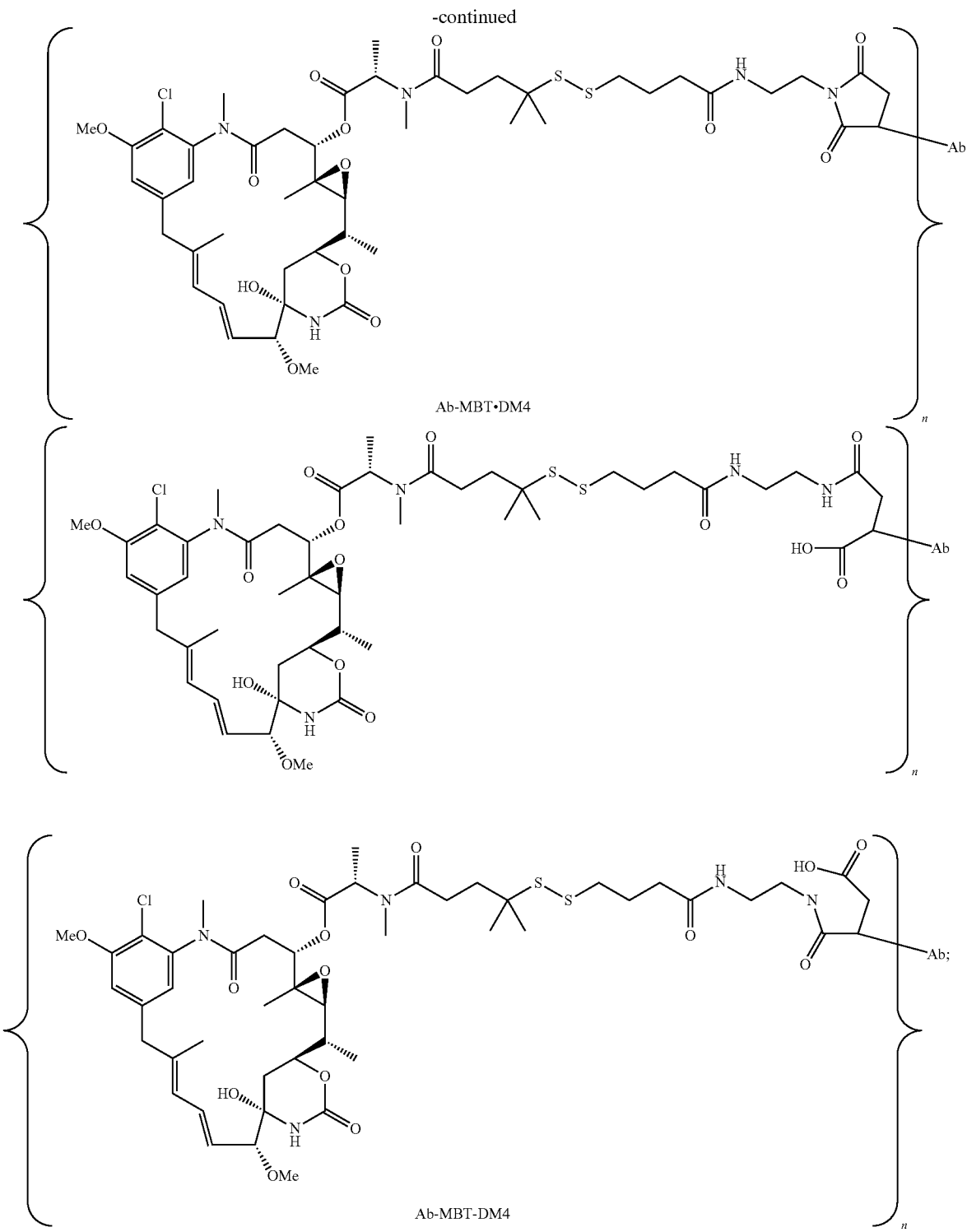

wherein:
 Ab is an antibody or antigen binding fragment thereof;
 n, which indicates the number of D-L groups attached to the Ab through the formation of a thioester bond with a sulfhydryl of the Ab, is an integer from 1 to 12, or 1 to 8, or preferably 1 to 4. In a specific embodiment, n is 3 or 4. In some embodiments, the antibody or antigen binding fragment thereof binds to an antigen that is expressed on tumor cells. In one embodiment, the antibody or antigen binding fragment thereof specifically binds CCR7. In other embodiments, the antibody or antigen binding fragment thereof specifically binds P-cadherin, Cadherin 6, FGFR2, or FGFR4.

In another embodiment, the conjugate of the present invention is represented by any one of the following structural formulae:

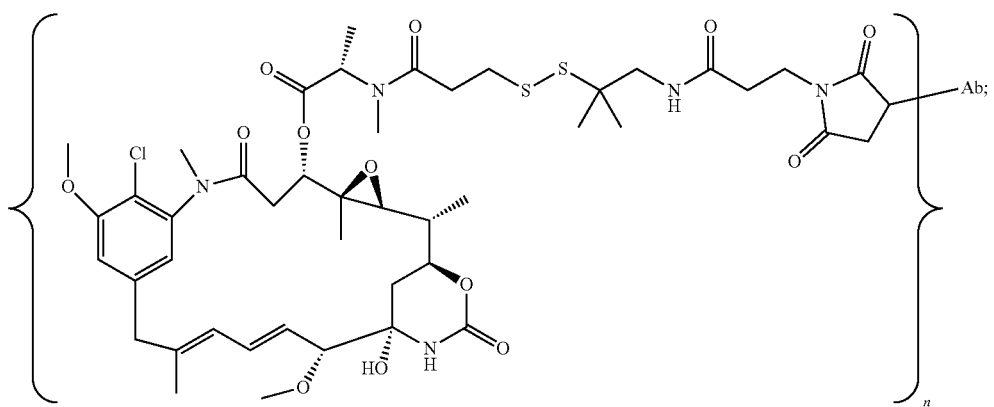
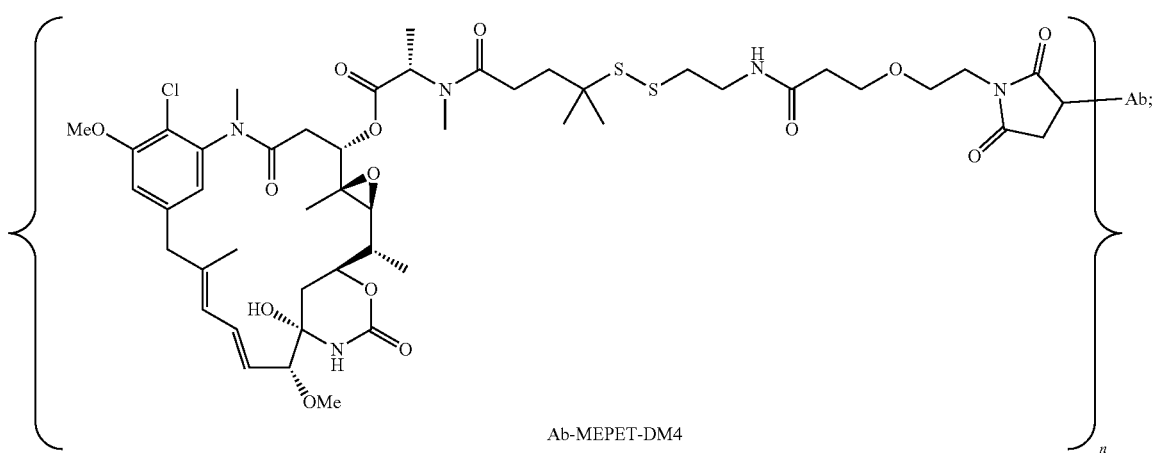
Ab-MEPET-DM4
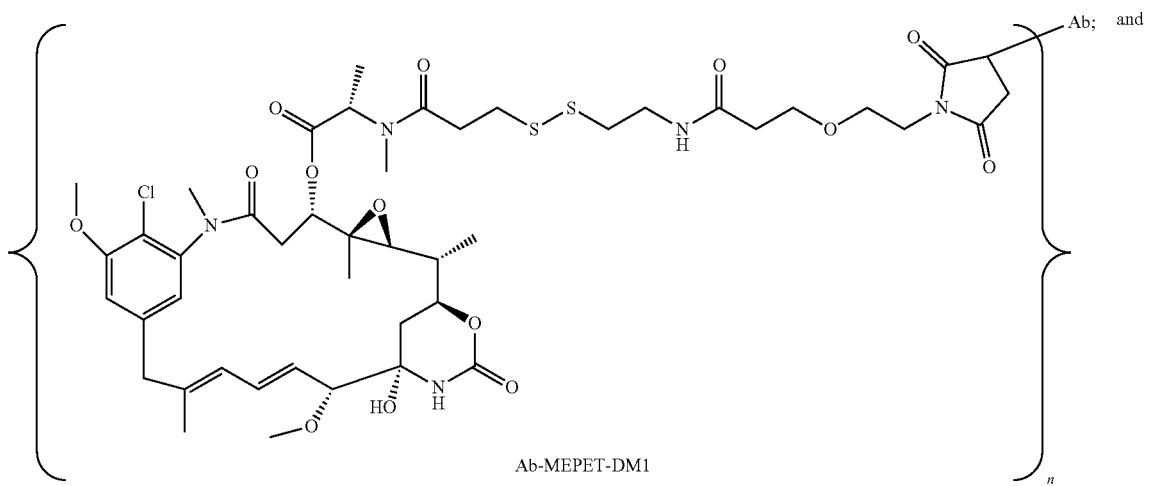
Ab-MEPET-DM1

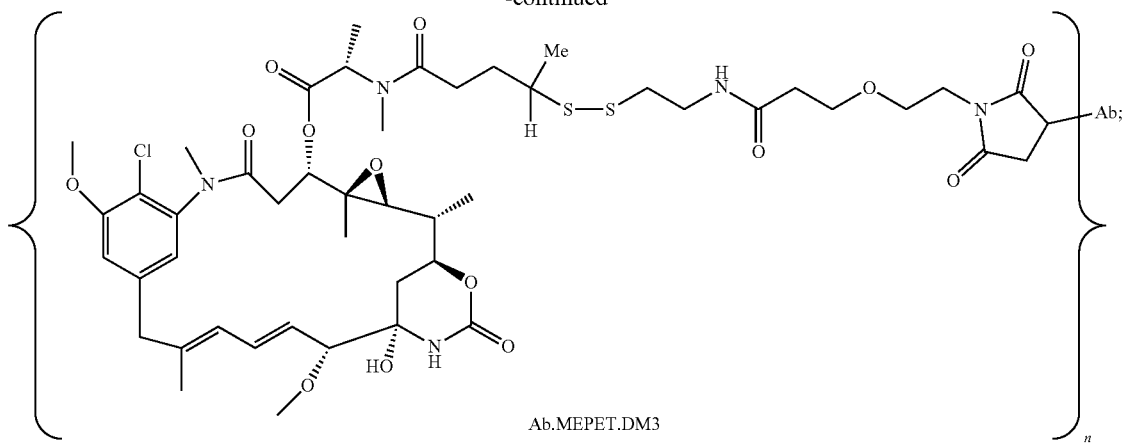

Ab.MEPET.DM3 as well as the corresponding open forms of the succinimide; wherein:
Ab is an antibody or antigen binding fragment thereof;
n, which indicates the number of D-L groups attached to the Ab through the formation of a thioester bond with a sulfhydryl of the Ab, is an integer from 1 to 12, or 1 to 8, or preferably 1 to 4. In a specific embodiment, n is 3 or 4. In some embodiments, the antibody or antigen binding fragment thereof binds to an antigen that is expressed on tumor cells. In one embodiment, the antibody or antigen binding fragment thereof specifically binds CCR7. In other embodiments, the antibody or antigen binding fragment thereof specifically binds P-cadherin, Cadherin 6, FGFR2, or FGFR4.

In another embodiment; the conjugate of the present invention is represented by any one of the following structural formulae:

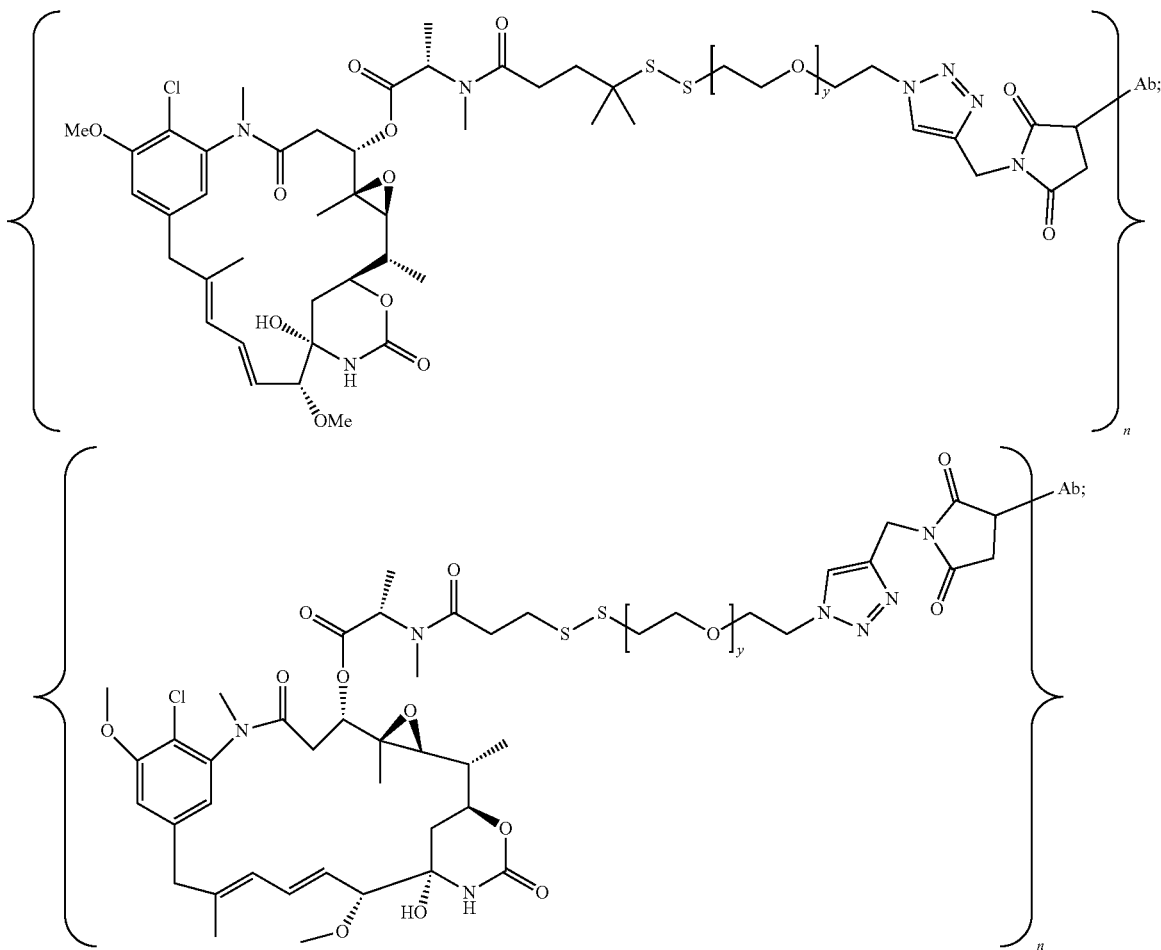

-continued

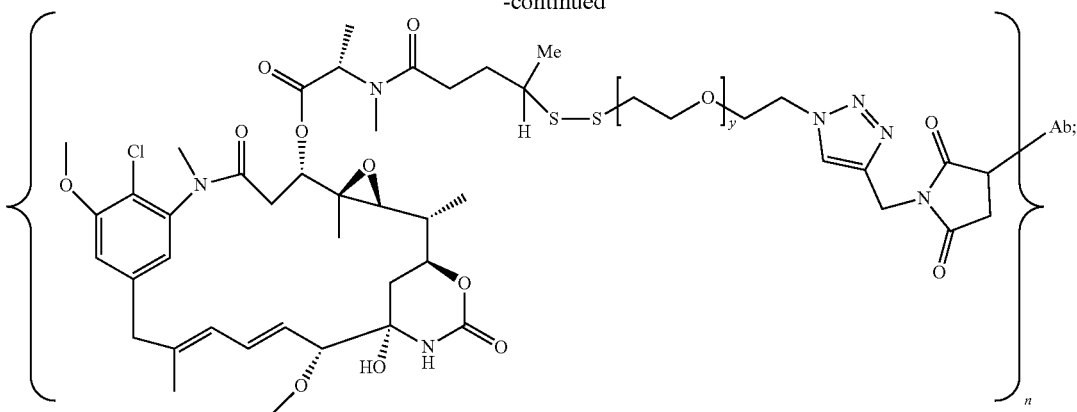

as well as the corresponding open forms of the succinimide; wherein:
y is 1 to 11, preferably 1 to 5;
Ab is an antibody or antigen binding fragment thereof;
n, which indicates the number of D-L groups attached to the Ab through the formation of a thioester bond with a sulfhydryl of the Ab, is an integer from 1 to 12, or 1 to 8, or preferably 1 to 4. In a specific embodiment, n is 3 or 4. In some embodiments, the antibody or antigen binding fragment thereof binds to an antigen that is expressed on tumor cells. In one embodiment, the antibody or antigen binding fragment thereof specifically binds CCR7. In other embodiments, the antibody or antigen binding fragment thereof specifically binds P-cadherin, Cadherin 6, FGFR2, or FGFR4.

In yet another embodiment; the conjugate of the present invention is represented by the following Formulae:

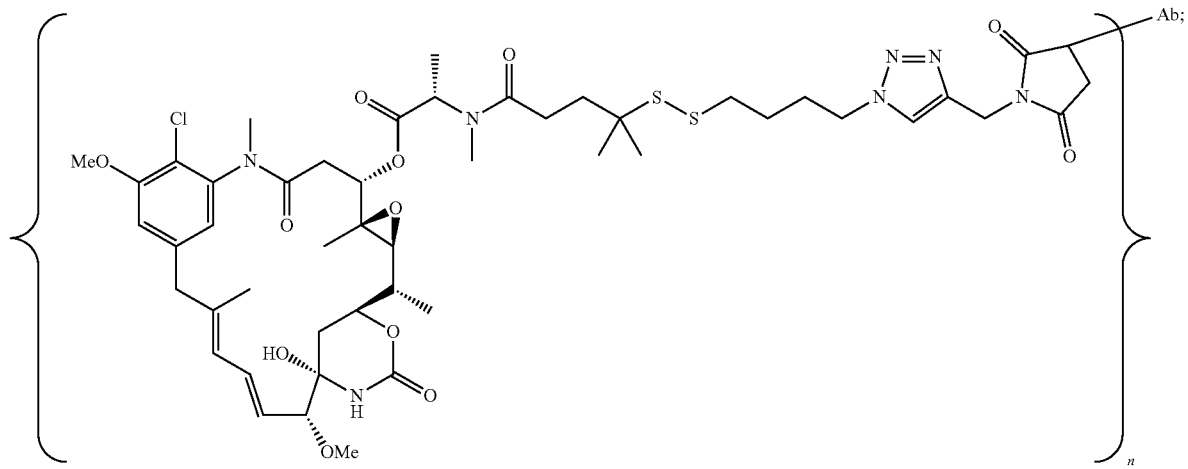

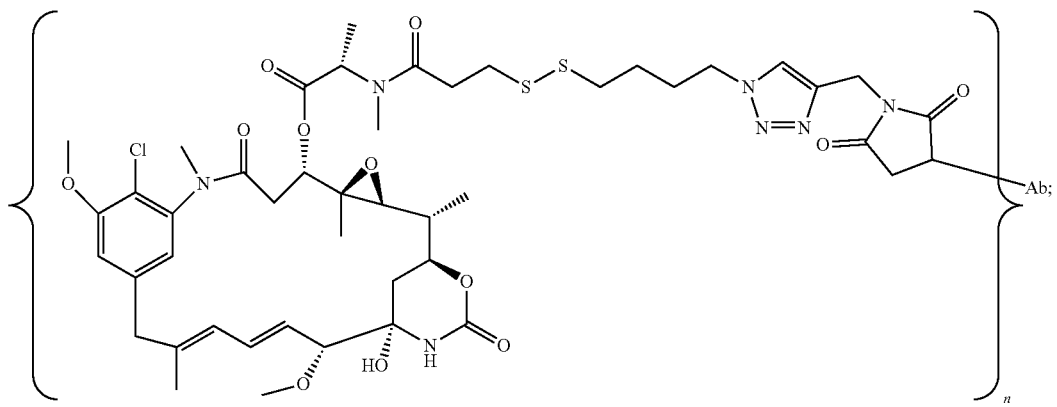

-continued

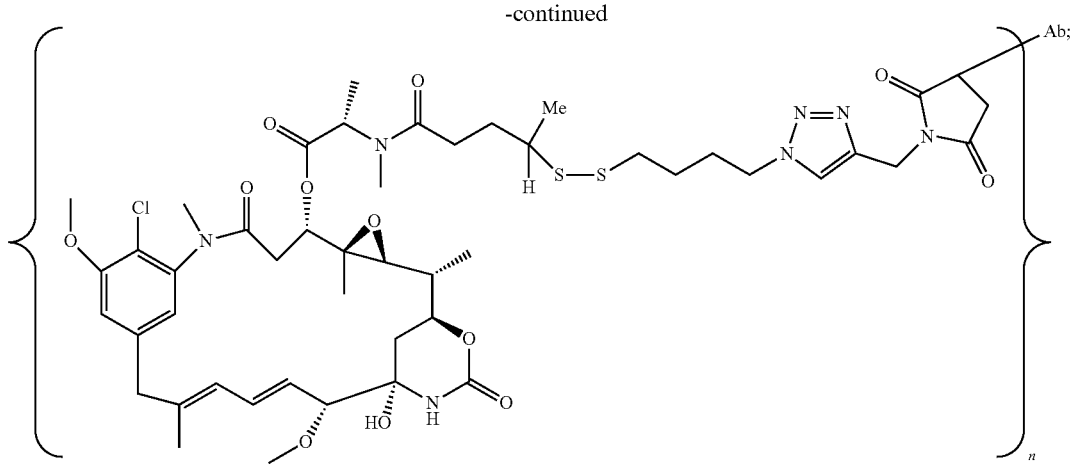

as well as the corresponding open forms of the succinimide; wherein:

Ab is an antibody or antigen binding fragment thereof;

n, which indicates the number of D-L groups attached to the Ab through the formation of a thioester bond with a sulfhydryl of the Ab, is an integer from 1 to 12, or 1 to 8, or preferably 1 to 4. In a specific embodiment, n is 3 or 4. In some embodiments, the antibody or antigen binding fragment thereof binds to an antigen that is expressed on tumor cells. In one embodiment, the antibody or antigen binding fragment thereof specifically binds CCR7. In other embodiments, the antibody or antigen binding fragment thereof specifically binds P-cadherin, Cadherin 6, FGFR2, or FGFR4.

In a preferred embodiment, the conjugate of the present invention is represented by the following Formula:

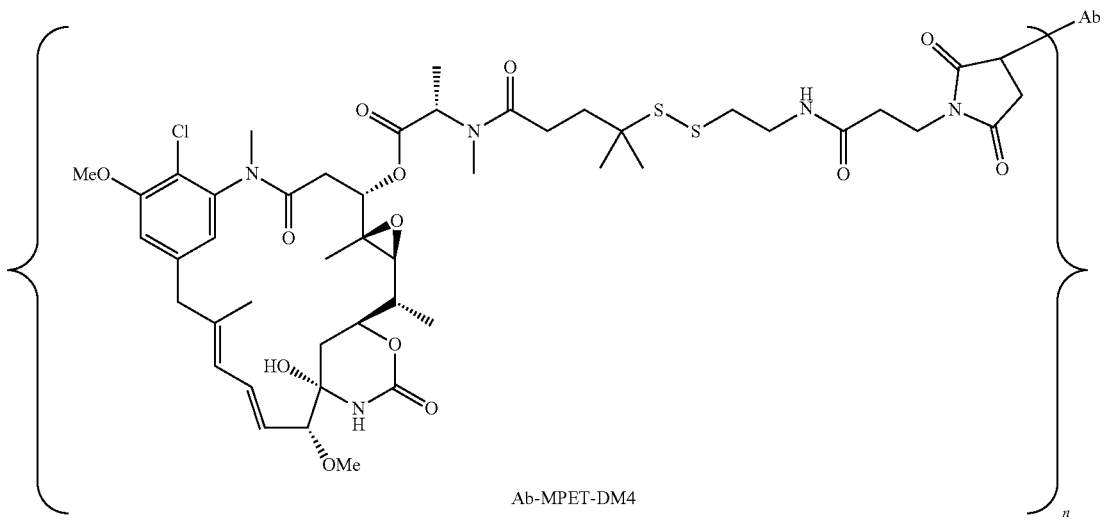

Ab-MPET-DM4 wherein:
Ab is an antibody or antigen binding fragment thereof;
n, which indicates the number of D-L groups attached to the Ab through the formation of a thioester bond with a sulfhydryl of the Ab, is an integer from 1 to 20. In some embodiments, n is an integer from 1 to 12. In some embodiments, n is an integer from 1 to 8. In some embodiments, n is an integer from 1 to 4. In a specific embodiment, n is 3 or 4. In another embodiment, the average n value is about 3 to about 4. In some embodiments, the antibody or antigen binding fragment thereof binds to an antigen that is expressed on tumor cells. In one embodiment, the antibody or antigen binding fragment thereof specifically binds CCR7. In other embodiments, the antibody or antigen binding fragment thereof specifically binds P-cadherin, Cadherin 6, FGFR2, or FGFR4.

In one embodiment, the average molar ratio of drug (e.g., DM1, DM3 or DM4) to the antibody in the conjugate (i.e., average n value, also known as Maytansinoid Antibody Ratio (MAR)) is about 1 to about 10, about 2 to about 8 (e.g., 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, or 8.1), about 2.5 to about 7, about 3 to about 5, about 2.5 to about 4.5 (e.g., about 2.5, about 2.6, about 2.7, about 2.8, about 2.9, about 3.0, about 3.1, about 3.3, about 3.4, about 3.5, about 3.6, about 3.7, about 3.8, about 3.9, about 4.0, about 4.1, about 4.2, about 4.3, about 4.4, about 4.5), about 3.0 to about 4.0, about 3.2 to about 4.2, or about 4.5 to 5.5 (e.g., about 4.5, about 4.6, about 4.7, about 4.8, about 4.9, about 5.0, about 5.1, about 5.2, about 5.3, about 5.4, or about 5.5).

In an aspect of the invention, the conjugate of the present invention has substantially high purity and has one or more of the following features: (a) greater than about 90% (e.g., greater than or equal to about 91%, 92%, 93%, 94%, 95%, 96%, 97%, 98%, 99%, or 100%), preferably greater than about 95%, of conjugate species are monomeric, (b) unconjugated linker level in the conjugate preparation is less than about 10% (e.g., less than or equal to about 9%, 8%, 7%, 6%, 5%, 4%, 3%, 2%, 1%, or 0%) (relative to total linker), (c) less than 10% of conjugate species are crosslinked (e.g., less than or equal to about 9%, 8%, 7%, 6%, 5%, 4%, 3%, 2%, 1%, or 0%), (d) free drug (e.g., DM1, DM3 or DM4) level in the conjugate preparation is less than about 2% (e.g., less than or equal to about 1.5%, 1.4%, 1.3%, 1.2%, 1.1%, 1.0%, 0.9%, 0.8%, 0.7%, 0.6%, 0.5%, 0.4%, 0.3%, 0.2%, 0.1%, or 0%) (mol/mol relative to total cytotoxic agent) and/or (e) no substantial increase in the level of free drug (e.g., DM1, DM3 or DM4) occurs upon storage (e.g., after about 1 week, about 2 weeks, about 3 weeks, about 1 month, about 2 months, about 3 months, about 4 months, about 5 months, about 6 months, about 1 year, about 2 years, about 3 years, about 4 years, or about 5 years). "Substantial increase" in the level of free drug (e.g., DM1, DM3 or DM4) means that after certain storage time (e.g., about 1 week, about 2 weeks, about 3 weeks, about 1 month, about 2 months, about 3 months, about 4 months, about 5 months, about 6 months, about 1 year, about 2 years, about 3 years, about 4 years, or about 5 years), the increase in the level of free drug (e.g., DM1, DM3 or DM4) is less than about 0.1%, about 0.2%, about 0.3%, about 0.4%, about 0.5%, about 0.6%, about 0.7%, about 0.8%, about 0.9%, about 1.0%, about 1.1%, about 1.2%, about 1.3%, about 1.4%, about 1.5%, about 1.6%, about 1.7%, about 1.8%, about 1.9%, about 2.0%, about 2.2%, about 2.5%, about 2.7%, about 3.0%, about 3.2%, about 3.5%, about 3.7%, or about 4.0%.

As used herein, the term "unconjugated linker" refers to the antibody that is covalently linked with a linker derived from a cross-linking reagent (e.g., SMCC, Sulfo-SMCC, SPDB, Sulfo-SPDB or CX1-1), wherein the antibody is not covalently coupled to the drug (e.g., DM1, DM3 or DM4) through a linker (i.e., the "unconjugated linker" can be represented by Ab-MCC, Ab-SPDB, or Ab-CX1-1).

1. Drug Moiety

The present invention provides immunoconjugates that specifically bind to CCR7. The antibody drug conjugates of the invention comprise anti-CCR7 antibodies, antibody fragments (e.g., antigen binding fragments) or functional equivalents that are conjugated to a drug moiety, e.g., an anti-cancer agent, an autoimmune treatment agent, an anti-inflammatory agent, an antifungal agent, an antibacterial agent, an anti-parasitic agent, an anti-viral agent, or an anesthetic agent. The antibodies, antibody fragments (e.g., antigen binding fragments) or functional equivalents of the invention can be conjugated to several identical or different drug moieties using any methods known in the art.

In certain embodiments, the drug moiety of the immunoconjugates of the present invention is selected from a group consisting of a V-ATPase inhibitor, a pro-apoptotic agent, a Bcl2 inhibitor, an MCL1 inhibitor, a HSP90 inhibitor, an IAP inhibitor, an mTor inhibitor, a microtubule stabilizer, a microtubule destabilizer, an RNA polymerase inhibitor, an amanitin, a pyrrolobenzodiazepine, an auristatin, a dolastatin, a maytansinoid, a MetAP (methionine aminopeptidase), an inhibitor of nuclear export of proteins CRM1, a DPPIV inhibitor, an Eg5 inhibitor, proteasome inhibitors, an inhibitor of phosphoryl transfer reactions in mitochondria, a protein synthesis inhibitor, a kinase inhibitor, a CDK2 inhibitor, a CDK9 inhibitor, a kinesin inhibitor, an HDAC inhibitor, a DNA damaging agent, a DNA alkylating agent, a DNA intercalator, a DNA minor groove binder and a DHFR inhibitor.

In certain embodiment, the drug moiety of the immunoconjugates of the present invention is an auristatin disclosed in PCT Publication Numbers: WO 2015/095301 and WO2015/189791, both applications are hereby incorporated by reference. Non-limiting examples of auristatin drug moiety-linker constructs are:

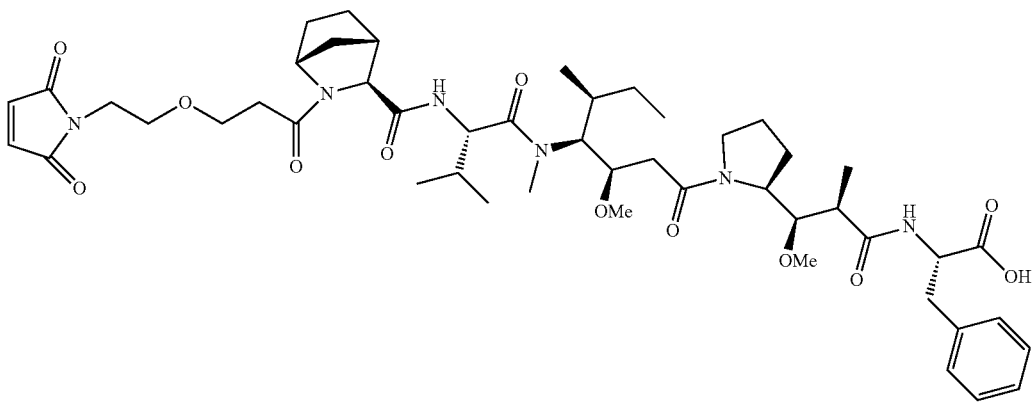 [SMILES: CC[C@H](C)[C@@H]([C@@H](CC(=O)N1CCC[C@H]1[C@H](OC)[C@@H](C)C(=O)N[C@@H](Cc1ccccc1)C(=O)O)OC)N(C)C(=O)[C@@H](NC(=O)[C@@H]1[C@H]2CC[C@H](C2)N1C(=O)CCOCCN1C(=O)C=CC1=O)C(C)C]

(which is AURIX2 as disclosed in instant application); and

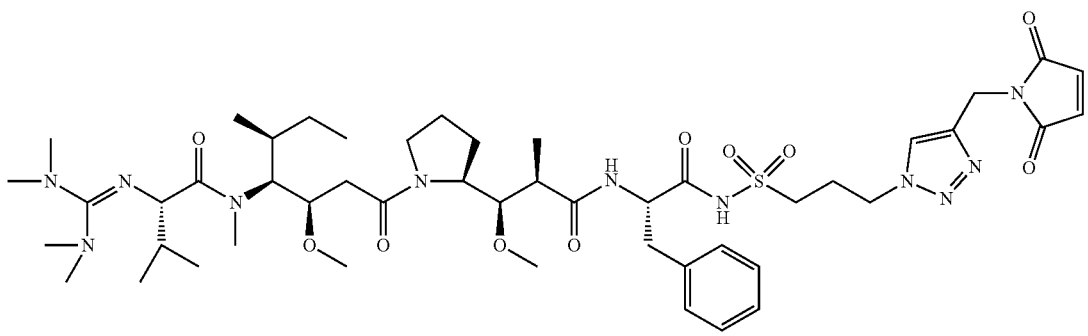 [SMILES: CC[C@H](C)[C@@H]([C@@H](CC(=O)N1CCC[C@H]1[C@H](OC)[C@@H](C)C(=O)N[C@@H](Cc1ccccc1)C(=O)NS(=O)(=O)CCCn1cc(CN2C(=O)C=CC2=O)nn1)OC)N(C)C(=O)[C@@H](N=C(N(C)C)N(C)C)C(C)C]

(which is AURIX1 as disclosed in instant application).

In one embodiment, the drug moiety of the immunoconjugates of the present invention is a maytansinoid drug moiety, such as but not limited to, DM1, DM3 or DM4.

Further, the antibodies, antibody fragments (e.g., antigen binding fragments) or functional equivalents of the present invention may be conjugated to a drug moiety that modifies a given biological response. Drug moieties are not to be construed as limited to classical chemical therapeutic agents. For example, the drug moiety may be a protein, peptide, or polypeptide possessing a desired biological activity. Such proteins may include, for example, a toxin such as abrin, ricin A, pseudomonas exotoxin, cholera toxin, or diphtheria toxin, a protein such as tumor necrosis factor, α-interferon, β-interferon, nerve growth factor, platelet derived growth factor, tissue plasminogen activator, a cytokine, an apoptotic agent, an anti-angiogenic agent, or, a biological response modifier such as, for example, a lymphokine.

In one embodiment, the antibodies, antibody fragments (e.g., antigen binding fragments) or functional equivalents of the present invention are conjugated to a drug moiety, such as a cytotoxin, a drug (e.g., an immunosuppressant) or a radiotoxin. Examples of cytotoxins include but are not limited to, taxanes (see, e.g., International (PCT) Patent Application Nos. WO 01/38318 and PCT/US03/02675), DNA-alkylating agents (e.g., CC-1065 analogs), anthracyclines, tubulysin analogs, duocarmycin analogs, auristatin E, auristatin F, maytansinoids, and cytotoxic agents comprising a reactive polyethylene glycol moiety (see, e.g., Sasse et al., J. Antibiot. (Tokyo), 53, 879-85 (2000), Suzawa et al., Bioorg. Med. Chem., 8, 2175-84 (2000), Ichimura et al., J. Antibiot. (Tokyo), 44, 1045-53 (1991), Francisco et al., Blood (2003) (electronic publication prior to print publication), U.S. Pat. Nos. 5,475,092, 6,340,701, 6,372,738, and 6,436,931, U.S. Patent Application Publication No. 2001/0036923 A1, Pending U.S. patent application Ser. Nos. 10/024,290 and 10/116,053, and International (PCT) Patent Application No. WO 01/49698), taxon, cytochalasin B, gramicidin D, ethidium bromide, emetine, mitomycin, etoposide, tenoposide, vincristine, vinblastine, t. colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. Therapeutic agents also include, for example, antimetabolites (e.g., methotrexate, 6-mercaptopurine, 6-thioguanine, cytarabine, 5-fluorouracil decarbazine), ablating agents (e.g., mechlorethamine, thiotepa chlorambucil, meiphalan, carmustine (BSNU) and lomustine (CCNU), cyclophosphamide, busulfan, dibromomannitol, streptozotocin, mitomycin C, and cis-dichlorodiamine platinum (II) (DDP) cisplatin, anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine). (See e.g., Seattle Genetics US20090304721).

Other examples of cytotoxins that can be conjugated to the antibodies, antibody fragments (antigen binding fragments) or functional equivalents of the invention include duocarmycins, calicheamicins, maytansines and auristatins, and derivatives thereof.

Various types of cytotoxins, linkers and methods for conjugating therapeutic agents to antibodies are known in the art, see, e.g., Saito et al., (2003) Adv. Drug Deliv. Rev. 55:199-215; Trail et al., (2003) Cancer Immunol. Immunother. 52:328-337; Payne, (2003) Cancer Cell 3:207-212; Allen, (2002) Nat. Rev. Cancer 2:750-763; Pastan and Kreitman, (2002) Curr. Opin. Investig. Drugs 3:1089-1091; Senter and Springer, (2001) Adv. Drug Deliv. Rev. 53:247-264.

The antibodies, antibody fragments (e.g., antigen binding fragments) or functional equivalents of the present invention can also be conjugated to a radioactive isotope to generate cytotoxic radiopharmaceuticals, referred to as radioimmunoconjugates. Examples of radioactive isotopes that can be conjugated to antibodies for use diagnostically or therapeutically include, but are not limited to, iodine-131, indium-111, yttrium-90, and lutetium-177. Methods for preparing radioimmunoconjugates are established in the art. Examples of radioimmunoconjugates are commercially available, including Zevalin™ (DEC Pharmaceuticals) and Bexxar™ (Corixa Pharmaceuticals), and similar methods can be used to prepare radioimmunoconjugates using the antibodies of the invention. In certain embodiments, the macrocyclic chelator is 1,4,7,10-tetraazacyclododecane-N,N',N'',N'''-tetraacetic acid (DOTA) which can be attached to the antibody via a linker molecule. Such linker molecules are commonly known in the art and described in Denardo et al., (1998) Clin Cancer Res. 4(10):2483-90; Peterson et al., (1999) Bioconjug. Chem. 10(4):553-7; and Zimmerman et al., (1999) Nucl. Med. Biol. 26(8):943-50, each incorporated by reference in their entireties.

The antibodies, antibody fragments (e.g., antigen binding fragments) or functional equivalents of the present invention can also conjugated to a heterologous protein or polypeptide (or fragment thereof, preferably to a polypeptide of at least 10, at least 20, at least 30, at least 40, at least 50, at least 60, at least 70, at least 80, at least 90 or at least 100 amino acids) to generate fusion proteins. In particular, the invention provides fusion proteins comprising an antibody fragment (e.g., antigen binding fragment) described herein (e.g., a Fab fragment, Fd fragment, Fv fragment, F(ab)2 fragment, a VH domain, a VH CDR, a VL domain or a VL CDR) and a heterologous protein, polypeptide, or peptide.

Additional fusion proteins may be generated through the techniques of gene-shuffling, motif-shuffling, exon-shuffling, and/or codon-shuffling (collectively referred to as "DNA shuffling"). DNA shuffling may be employed to alter the activities of antibodies of the invention or fragments thereof (e.g., antibodies or fragments thereof with higher affinities and lower dissociation rates). See, generally, U.S. Pat. Nos. 5,605,793, 5,811,238, 5,830,721, 5,834,252, and 5,837,458; Patten et al., (1997) Curr. Opinion Biotechnol. 8:724-33; Harayama, (1998) Trends Biotechnol. 16(2):76-82; Hansson et al., (1999) J. Mol. Biol. 287:265-76; and Lorenzo and Blasco, (1998) Biotechniques 24(2):308-313 (each of these patents and publications are hereby incorporated by reference in its entirety). Antibodies or fragments thereof, or the encoded antibodies or fragments thereof, may be altered by being subjected to random mutagenesis by error-prone PCR, random nucleotide insertion or other methods prior to recombination. A polynucleotide encoding an antibody or fragment thereof that specifically binds to an antigen may be recombined with one or more components, motifs, sections, parts, domains, fragments, etc. of one or more heterologous molecules.

Moreover, the antibodies, antibody fragments (e.g., antigen binding fragments) or functional equivalents of the present invention can be conjugated to marker sequences, such as a peptide, to facilitate purification. In preferred embodiments, the marker amino acid sequence is a hexa-histidine peptide (SEQ ID NO: 628), such as the tag provided in a pQE vector (QIAGEN, Inc., 9259 Eton Avenue, Chatsworth, CA, 91311), among others, many of which are commercially available. As described in Gentz et al., (1989) Proc. Natl. Acad. Sci. USA 86:821-824, for instance, hexa-histidine (SEQ ID NO: 628) provides for convenient purification of the fusion protein. Other peptide tags useful for purification include, but are not limited to, the hemagglutinin ("HA") tag, which corresponds to an epitope derived from the influenza hemagglutinin protein (Wilson et al., (1984) Cell 37:767), and the "FLAG" tag (A. Einhauer et al., J. Biochem. Biophys. Methods 49: 455-465, 2001). According to the present invention, antibodies or antigen binding fragments can also be conjugated to tumor-penetrating peptides in order to enhance their efficacy.

In other embodiments, the antibodies, antibody fragments (e.g., antigen binding fragments) or functional equivalents of the present invention are conjugated to a diagnostic or detectable agent. Such immunoconjugates can be useful for monitoring or prognosing the onset, development, progression and/or severity of a disease or disorder as part of a clinical testing procedure, such as determining the efficacy of a particular therapy. Such diagnosis and detection can be accomplished by coupling the antibody to detectable substances including, but not limited to, various enzymes, such as, but not limited to, horseradish peroxidase, alkaline phosphatase, beta-galactosidase, or acetylcholinesterase; prosthetic groups, such as, but not limited to, streptavidin/biotin and avidin/biotin; fluorescent materials, such as, but not limited to, Alexa Fluor 350, Alexa Fluor 405, Alexa Fluor 430, Alexa Fluor 488, Alexa Fluor 500, Alexa Fluor 514, Alexa Fluor 532, Alexa Fluor 546, Alexa Fluor 555, Alexa Fluor 568, Alexa Fluor 594, Alexa Fluor 610, Alexa Fluor 633, Alexa Fluor 647, Alexa Fluor 660, Alexa Fluor 680, Alexa Fluor 700, Alexa Fluor 750, umbelliferone, fluorescein, fluorescein isothiocyanate, rhodamine, dichlorotriazinylamine fluorescein, dansyl chloride or phycoerythrin; luminescent materials, such as, but not limited to, luminol; bioluminescent materials, such as but not limited to, luciferase, luciferin, and aequorin; radioactive materials, such as, but not limited to, iodine ($^{131}$I, $^{125}$I, $^{123}$I, and $^{121}$I), carbon ($^{14}$C), sulfur ($^{35}$S), tritium ($^{3}$H), indium ($^{115}$In, $^{113}$In, $^{112}$In, and $^{111}$In,), technetium ($^{99}$Tc), thallium ($^{201}$Ti) gallium ($^{68}$Ga, $^{67}$Ga), palladium ($^{103}$Pd), molybdenum ($^{99}$Mo), xenon ($_{133}$Xe), fluorine ($^{18}$F), $^{153}$Sm, 177Lu, $^{159}$Gd, $^{149}$Pm, $^{140}$La, $^{175}$Yb, $^{166}$Ho, $^{90}$Y, $^{47}$Sc, $^{186}$Re, $^{188}$Re, $^{142}$Pr, $^{105}$Rh, $^{97}$Ru, $^{68}$Ge, $^{57}$Co, $^{65}$Zn, $^{85}$Sr, $^{32}$P, $^{153}$Gd, $^{169}$Yb, $^{51}$Cr, $^{54}$Mn, $^{75}$Se, $^{64}$Cu, $^{113}$Sn, and $^{117}$Sn; and positron emitting metals using various positron emission tomographies, and non-radioactive paramagnetic metal ions.

The antibodies, antibody fragments (e.g., antigen binding fragments) or functional equivalents of the invention may also be attached to solid supports, which are particularly useful for immunoassays or purification of the target antigen. Such solid supports include, but are not limited to, glass, cellulose, polyacrylamide, nylon, polystyrene, polyvinyl chloride or polypropylene.

2. Linker

As used herein, a "linker" is any chemical moiety that is capable of linking an antibody, antibody fragment (e.g., antigen binding fragments) or functional equivalent to another moiety, such as a drug moiety. Linkers can be susceptible to cleavage (cleavable linker), such as, acid-induced cleavage, photo-induced cleavage, peptidase-induced cleavage, esterase-induced cleavage, glycosidase induced cleavage, phosphodiesterase induced cleavage, phosphatase induced cleavage and disulfide bond cleavage, at conditions under which the compound or the antibody remains active. Alternatively, linkers can be substantially resistant to cleavage (e.g., stable linker or noncleavable linker). In some aspects, the linker is a procharged linker, a hydrophilic linker, or a dicarboxylic acid based linker.

In one aspect, the linker used in the present invention is derived from a crosslinking reagent such as N-succinimidyl-3-(2-pyridyldithio)propionate (SPDP), N-succinimidyl 4-(2-pyridyldithio)pentanoate (SPP), N-succinimidyl 4-(2-pyridyldithio)butanoate (SPDB), N-succinimidyl-4-(2-pyridyldithio)-2-sulfo-butanoate (sulfo-SPDB), N-succinimidyl iodoacetate (SIA), N-succinimidyl(4-iodo-acetyl)aminobenzoate (SIAB), maleimide PEG NHS, N-succinimidyl 4-(maleimidomethyl)cyclohexanecarboxylate (SMCC), N-sulfosuccinimidyl 4-(maleimidomethyl)cyclohexanecarboxylate (sulfo-SMCC) or 2,5-dioxopyrrolidin-1-yl 17-(2,5-dioxo-2,5-dihydro-1H-pyrrol-1-yl)-5,8,11,14-tetraoxo-4,7,10,13-tetraazaheptadecan-1-oate (CX1-1).

Non-cleavable linkers are any chemical moiety capable of linking a drug, such as a maytansinoid, to an antibody in a stable, covalent manner and does not fall under the categories listed above for cleavable linkers. Thus, non-cleavable linkers are substantially resistant to acid-induced cleavage, photo-induced cleavage, peptidase-induced cleavage, esterase-induced cleavage and disulfide bond cleavage. Furthermore, non-cleavable refers to the ability of the chemical bond in the linker or adjoining to the linker to withstand cleavage induced by an acid, photolabile-cleaving agent, a peptidase, an esterase, or a chemical or physiological compound that cleaves a disulfide bond, at conditions under which the drug, such as maytansionoid or the antibody does not lose its activity.

Acid-labile linkers are linkers cleavable at acidic pH. For example, certain intracellular compartments, such as endosomes and lysosomes, have an acidic pH (pH 4-5), and provide conditions suitable to cleave acid-labile linkers.

Photo-labile linkers are linkers that are useful at the body surface and in many body cavities that are accessible to light. Furthermore, infrared light can penetrate tissue.

Some linkers can be cleaved by peptidases, i.e., peptidase cleavable linkers. Only certain peptides are readily cleaved inside or outside cells, see e.g., Trout et al., 79 Proc. Natl. Acad. Sci. USA, 626-629 (1982) and Umemoto et al. 43 Int. J. Cancer, 677-684 (1989). Furthermore, peptides are composed of a-amino acids and peptidic bonds, which chemically are amide bonds between the carboxylate of one amino acid and the amino group of a second amino acid. Other amide bonds, such as the bond between a carboxylate and the ε-amino group of lysine, are understood not to be peptidic bonds and are considered non-cleavable.

Some linkers can be cleaved by esterases, i.e., esterase cleavable linkers. Again, only certain esters can be cleaved by esterases present inside or outside of cells. Esters are formed by the condensation of a carboxylic acid and an alcohol. Simple esters are esters produced with simple alcohols, such as aliphatic alcohols, and small cyclic and small aromatic alcohols.

Procharged linkers are derived from charged cross-linking reagents that retain their charge after incorporation into an antibody drug conjugate. Examples of procharged linkers can be found in US 2009/0274713.

3. Conjugation and Preparation of ADCs

Numerous methods of conjugating linker-payloads to antigen binding moiety are known in the art (reviewed in for example: Antibody-Drug Conjugate, Methods in Molecular Biology, Vol. 1045, Editor L. Ducry, Humana Press (2013)). Traditionally, drugs are conjugated to native lysine or native cysteine residues of the antibody. The resulting preparations are complex mixtures. More recently, site-specific conjugation methods are being employed to improve the therapeutic index and homogeneity of ADC preparations (For review: Panowski, S.; Bhakta, S.; Raab, H.; Polakis, P.; Junutula, J. R. mAbs 2014, 6, 34). Besides glycoengineering, (Zhou, Q. et al. *Bioconjugate chemistry* 2014, 25, 510; Zhu, Z. et al. mAbs 2014, 6, 1190); some of the more common methods of preparing site-specific ADCs are based on the incorporation of engineered cysteines, (Junutula, J. R. et al., *Nature biotechnology* 2008, 26, 925; Shinmi, D. et al., *Bioconjugate chemistry* 2016, 27, 1324), non-canonical amino acids (Tian, F. et al., *Proceedings National Academy of Sciences USA* 2014, 111, 1766; Axup, J. Y. et al., *Proceedings National Academy of Sciences USA* 2012, 109, 16101) or short peptide sequences into the antibody backbone (Drake, P. M. et al., *Bioconjugate chemistry* 2014, 25, 1331; Strop, P. et al., *Chemistry & biology* 2013, 20, 161; Beerli, R. R. et al., *PLoS one* 2015, 10, e0131177; Grunewald, J. et al., *Bioconjugate chemistry* 2015, 26, 2554). These methods provide control over stoichiometry and attachment site of the cytotoxin resulting in better pharmacokinetic (PK), safety, and efficacy profiles of the conjugates relative to traditionally prepared ADCs.

The conjugates of the present invention can be prepared by any methods known in the art, such as those described in U.S. Pat. Nos. 7,811,572, 6,411,163, 7,368,565, and 8,163,888, US application publications 2011/0003969, 2011/0166319, 2012/0253021 and 2012/0259100, and PCT publications WO2014/124316 and WO2015/138615. The entire teachings of these patents and patent application publications are herein incorporated by reference.

Process for Conjugation to Engineered Cysteine Antibody Residues

Conjugates of the invention can be prepared using cysteine residues engineered into an antibody by, for example, site-directed mutagenesis. Such site-specific conjugates are homogenous and have improved properties (Junutula J R, Raab H, Clark S, Bhakta S, Leipold D D, Weir S, Chen Y, Simpson M, Tsai S P, Dennis M S, Lu Y, Meng Y G, Ng C, Yang J, Lee C C, Duenas E, Gorrell J, Katta V, Kim A, McDorman K, Flagella K, Venook R, Ross S, Spencer S D, Lee Wong W, Lowman H B, Vandlen R, Sliwkowski M X, Scheller R H, Polakis P, Mallet W. (2008) Nature Biotechnology 26:925-932.)

Because engineered cysteines in antibodies expressed in mammalian cells are modified by adducts (disulfides) such as glutathione (GSH) and/or cysteine during their biosynthesis (Chen et al. 2009), the engineered cysteine residues in the product as initially expressed are unreactive to thiol reactive reagents such as maleimido or bromo-or iodoacetamide groups. To conjugate payload to an engineered cysteine after expression, glutathione or cysteine adducts need to be removed by reducing these disulfide adducts, which generally entails also reducing native disulfides in the expressed protein. Deprotection of adducted engineered cysteines can be accomplished by first exposing antibody to a reducing agent, e.g., dithiothreitol (DTT), TCEP, or reduced cysteine, followed by a procedure that allows for re-oxidation of all native disulfide bonds of an antibody to restore and/or stabilize the functional antibody structure.

Several methods can be employed to reduce and re-oxidize antibodies with engineered Cys residues for preparation of antibody drug conjugates. Attempts to follow re-oxidation protocols previously described in the literature using high concentration of CuSO$_4$ resulted in protein precipitation (Junutula J R, Raab H, Clark S, Bhakta S, Leipold D D, Weir S, Chen Y, Simpson M, Tsai S P, Dennis M S, Lu Y, Meng Y G, Ng C, Yang J, Lee C C, Duenas E, Gorrell J, Katta V, Kim A, McDorman K, Flagella K, Venook R, Ross S, Spencer S D, Lee Wong W, Lowman H B, Vandlen R, Sliwkowski M X, Scheller R H, Polakis P, Mallet W. (2008) Nature Biotechnology 26:925). We have successfully prepared and obtained antibody drug conjugates with several different methods for reduction and antibody re-oxidation.

In one example, freshly prepared DTT is added to purified Cys mutant antibodies to a final concentration of 10 mM. After incubation with DTT at room temperature for 1 hour, mixture is dialyzed at 4° C. against PBS for three days with daily buffer exchange to remove DTT and re-oxidize native disulfide bonds of the antibody. An alternative method is to remove reducing reagents through a desalting column such as Sephadex G-25, equilibrated with PBS. Once protein is fully reduced, 1 mM oxidized ascorbate (dehydro-ascorbic acid) is optionally added to desalted samples and re-oxidation incubations are carried out for 20-24 hours.

In another exemplary method, deprotection of engineered Cys residues is accomplished by adding fully reduced cysteine at 20 mM concentration to antibodies bound to protein A-Sepharose resin. Reduction of the Cys adducts is achieved by incubation for approximately 30-60 minutes at room temperature, then reductant is rapidly removed by washing resin with 50 beds of PBS. Re-oxidation of the reduced antibody is achieved by incubating washed slurry at room temperature with or without addition of 50-2000 nM CuCl$_2$ as an accelerant. With the exception of use of copper sulfate, examples herein use each of the protocols described herein with similar results. Reoxidation restores intra-chain disulfides, while dialysis, desalting or protein A chromatography removes reducing agent as well as cysteines and glutathiones initially connected to engineered cysteine(s) of the antibody. HPLC reverse phase chromatography is typically used to monitor the reoxidation process: Antibodies are loaded onto a PLRP-S column (4000 Å, 50 mm×2.1 mm, Agilent) heated to 80° C. and eluted using a linear gradient of 30-45% CH3CN in water containing 0.1% TFA at 1.5 mL/min. and peak detection at 215, 254, and 280 nm.

After re-oxidation, the antibody is conjugated to a pre-formed linker-drug moiety. By way of example, the pre-formed linker-drug moiety (such as for example MMTBT-DM4; MPET-DM4; MBT-DM4; MEPET-DM4, MPBT-DM1; and other linker-drug moieties as described herein), are added to re-oxidized Cys mutant antibody at 10 molar equivalents relative to antibody in PBS buffer (pH 7.2). Incubations are carried out for 1 hour. The conjugation process is monitored by reverse-phase HPLC, which is able to separate conjugated antibodies from non-conjugated ones. Conjugation reaction mixtures are analyzed on a PRLP-S column (4000 Å, 50 mm×2.1 mm, Agilent) heated to 80° C. and elution of the column are carried out by a linear gradient of 30-60% acetonitrile in water containing 0.1% TFA at a flow rate of 1.5 ml/min. Elution of proteins from the column is monitored at 280 nm, 254 nm and 215 nm.

In one embodiment, examples of linker-drug moiety for cysteine conjugation can be prepared according to Schemes 1 to 3:

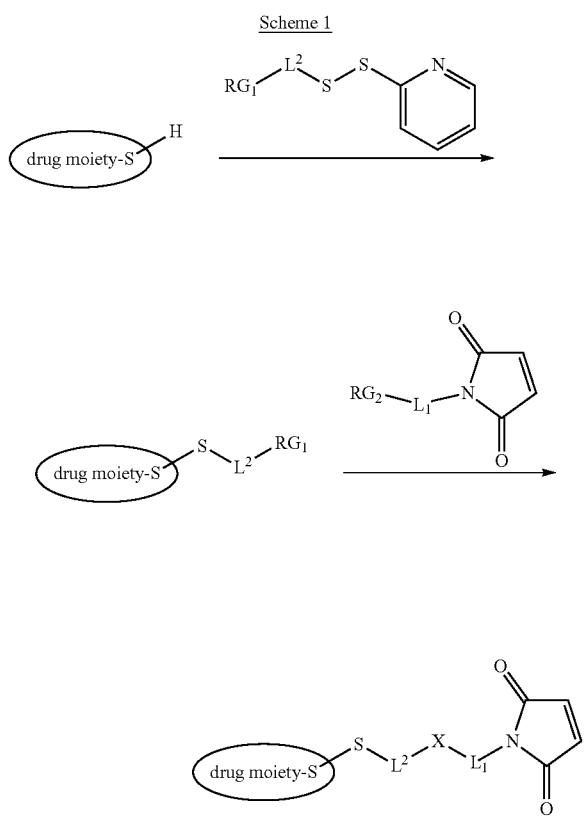

wherein:
the drug moiety is attached to the linker via a thiol functionality;
L$^1$ is a C$_{1-6}$alkylene wherein one of the methylene groups may be replaced with oxygen;
L$^2$ is a C$_{1-6}$alkylene or is —(CH$_2$CH$_2$O)$_y$—CH$_2$—CH$_2$— wherein y is 1 to 11; and
X is —C(O)—NH—, —NHC(O)— or a triazole;
wherein the alkylene is linear or branched; and
RG1 and RG2 are 2 reactive groups forming group X.
Reacting groups which form an amide or a triazole are well known in the art.

One example of pre-forming the linker-drug moiety is represented in Scheme 2 wherein the drug moiety is DM4; RG1 is an amino group and RG2 is an activated acid, resulting in the formation of the amide bond (X):

Scheme 2.
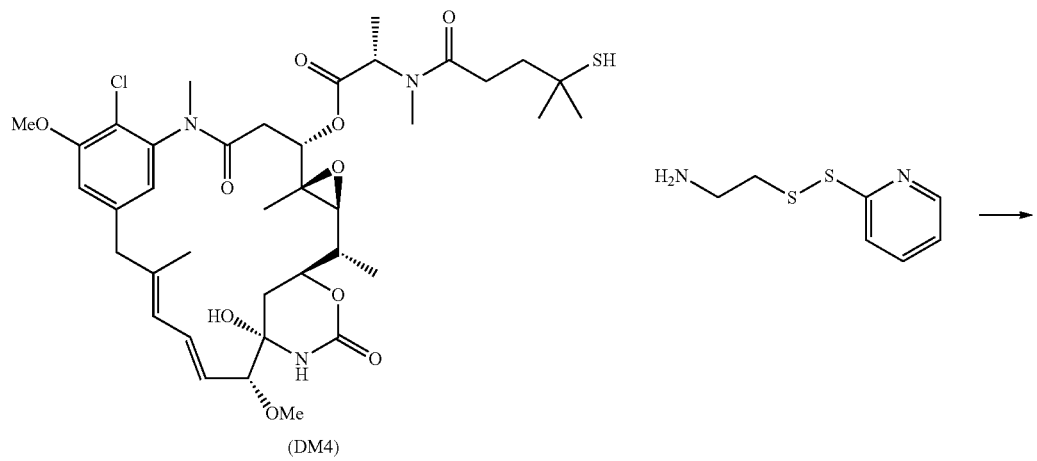
(DM4)
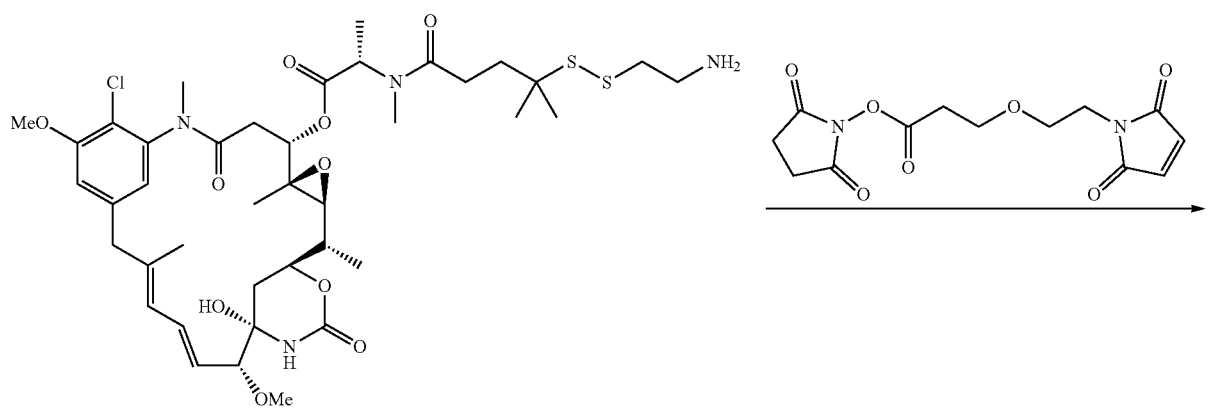
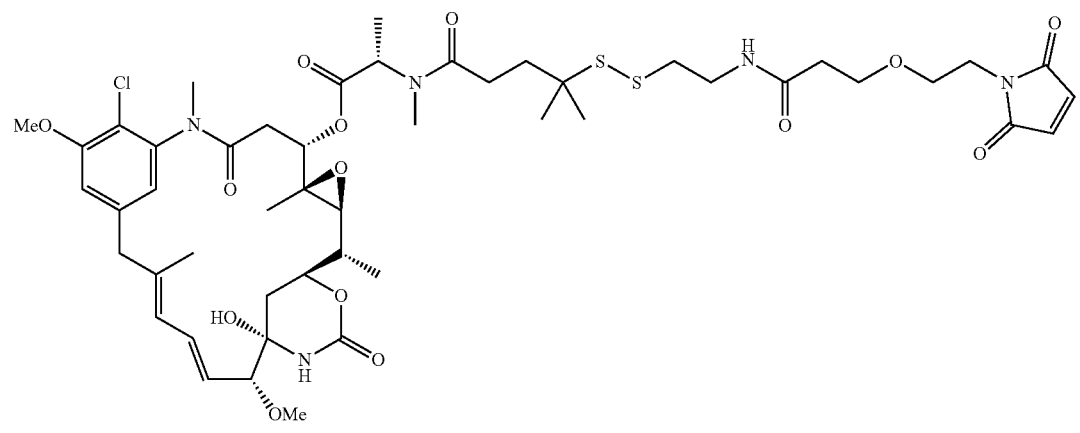
MEPET-DM4

Another example of pre-forming the linker-drug moiety is represented in Scheme 3 wherein the drug moiety is DM4; RG1 is an azide group and RG2 is an alkyne group, resulting in the formation of the tetrazole (X):

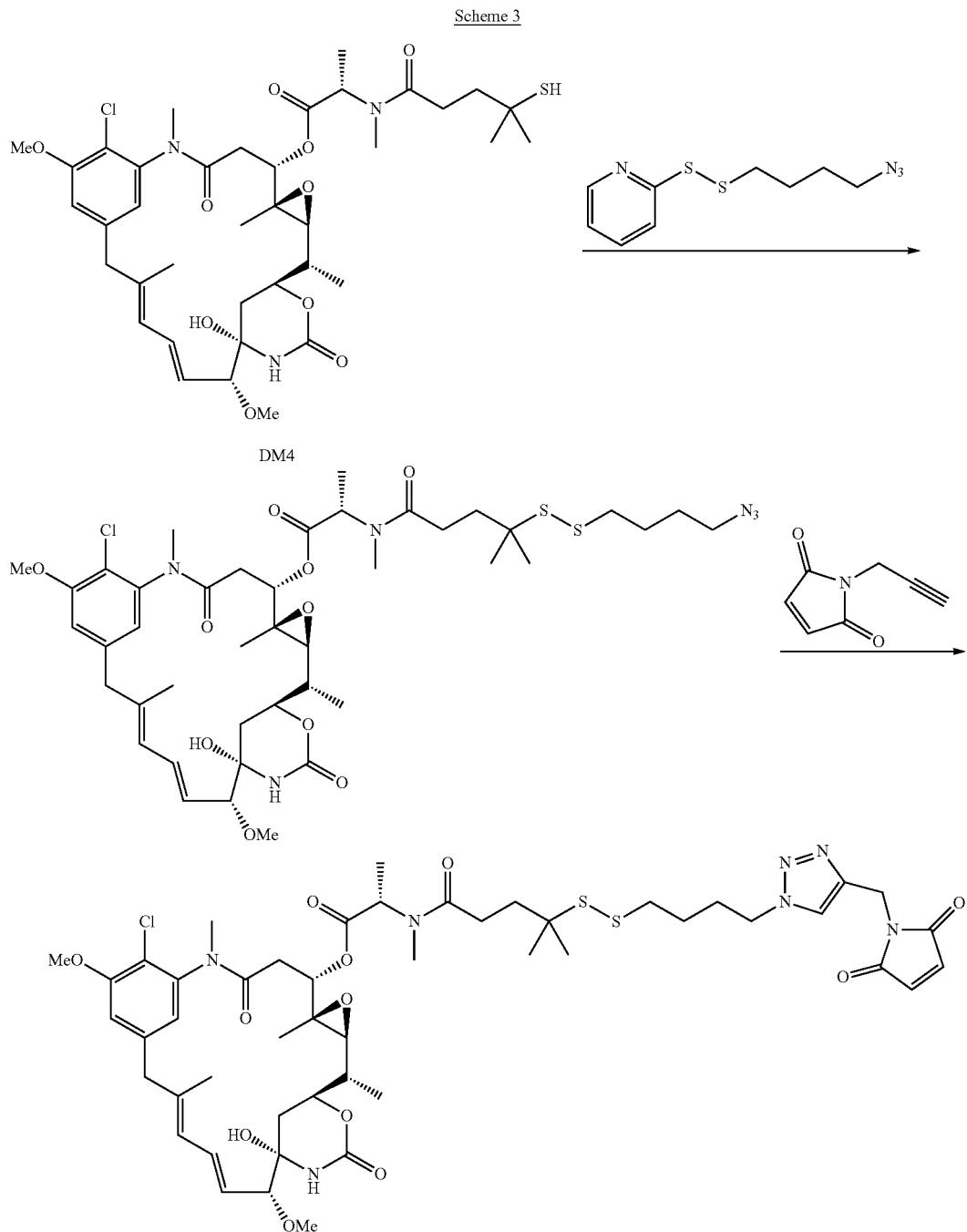

Conjugation efficiency of various drug moieties having a linked maleimide to a Cys mutant antibody vary depending on the solubility of the drug moieties used, however, many reactions result in more than 90% conjugate. To evaluate aggregation state, resulting conjugates are analyzed in a size exclusion chromatography column (GE, Superdex200, 3.2/30) at a flow rate of 0.1 ml/min in PBS. All conjugates are mainly monomeric. The majority of conjugates contain less than 3% dimeric and oligomeric material, indicating that conjugation of drug moiety having a linked maleimide to Cys mutant antibody does not cause aggregation.

Immunoconjugates are also characterized in terms of average loading of a drug moiety to antibody binding moiety, generally referred to as drug-to-antibody ratio (DAR). The DAR value is extrapolated, for example, from LC-MS data for reduced and deglycosylated samples. LC/MS allows quantitation of the average number of molecules of payload (drug moiety) attached to an antibody in an ADC. HPLC separates an antibody into light and heavy chains, and also separates heavy chain (HC) and light chain (LC) according to the number of Linker-Payload groups per chain. Mass spectral data enables identification of the component species in the mixture, e.g., LC, LC+1, LC+2, HC, HC+1, HC+2, etc. From average loading of LC and HC chains, the average DAR can be calculated for an ADC. The DAR for a given immunoconjugate sample represents the average number of drug (payload) molecules attached to a tetrameric antibody containing two light chains and two heavy chains.

Process for Conjugation to Native Cysteine Antibody Residues linker-drug moieties as described herein can also be conjugated to native cysteine residues of non-engineered antibodies using a procedure that involves partial reduction of the antibodies (Doronina, S. O., Toki, B. E., Torgov, M. Y., Mendelsohn, B. A., Cerveny, C. G., Chace, D. F., DeBlanc, R. L., Gearing,R. P., Bovee, T. D., Siegall, C. B., Francisco, J. A., Wahl, A. F., Meyer, D. L., and Senter, P. D. (2003) Development of potent monoclonal antibody auristatin conjugates for cancer therapy. *Nat. Biotechnol.* 21, 778-784). The following protocol is a non-limiting example how such conjugates can be prepared: Inter- and intra-chain disulfides bonds of the antibody (at a concentration of typically 5 to 10 mg/ml) are first partially reduced in PBS containing 2 mM EDTA by adding TCEP to a final concentration of 10 mM and incubating the mixture at 37° C. for 1 hour. After desalting and addition of 1% w/v PS-20 detergent, the partially reduced antibodies (1-2 mg/ml) is reacted overnight at 4° C. with 0.5 to 1 mg of a maleimide containing linker payload compound per 10 mg antibody. Resulting conjugates are purified by Protein A chromatography by standard methods and buffer exchanged to PBS, and are profiled typically by mass-spectrometry (MS), analytical size-exclusion chromatography (AnSEC), and analytical hydrophobic interaction chromatography (AnHIC) for their drug-to-antibody-ratio, aggregation propensity, and hydrophobicity as well as by activity assays.

One-Step Process for Cross-Linking to Lysine Antibody Residues

In one embodiment, the conjugates of the present invention can be prepared by a one-step process for cross-linking the drug to lysine residues on the antibody. The process comprises combining the antibody, drug and cross-linking agent in a substantially aqueous medium, optionally containing one or more co-solvents, at a suitable pH. In one embodiment, the process comprises the step of contacting the antibody of the present invention with a drug (e.g., DM1 or DM4) to form a first mixture comprising the antibody and the drug, and then contacting the first mixture comprising the antibody and the drug with a cross-linking agent (e.g., SMCC, Sulfo-SMCC, SPDB, Sulfo-SPDB or CX1-1) in a solution having a pH of about 4 to about 9 to provide a mixture comprising (i) the conjugate (e.g., Ab-MCC-DM1, Ab-SPDB-DM4, or Ab-CX1-1-DM1), (ii) free drug (e.g., DM1 or DM4), and (iii) reaction by-products.

In one embodiment, the one-step process comprises contacting the antibody with the drug (e.g., DM1 or DM4) and then the cross-linking agent (e.g., SMCC, Sulfo-SMCC, SPDB, Sulfo-SPDB or CX1-1) in a solution having a pH of about 6 or greater (e.g., about 6 to about 9, about 6 to about 7, about 7 to about 9, about 7 to about 8.5, about 7.5 to about 8.5, about 7.5 to about 8.0, about 8.0 to about 9.0, or about 8.5 to about 9.0). For example, the inventive process comprises contacting a cell-binding agent with the drug (DM1 or DM4) and then the cross-linking agent (e.g., SMCC, Sulfo-SMCC, SPDB, Sulfo-SPDB or CX1-1) in a solution having a pH of about 6.0, about 6.1, about 6.2, about 6.3, about 6.4, about 6.5, about 6.6, about 6.7, about 6.8, about 6.9, about 7.0, about 7.1, about 7.2, about 7.3, about 7.4, about 7.5, about 7.6, about 7.7, about 7.8, about 7.9, about 8.0, about 8.1, about 8.2, about 8.3, about 8.4, about 8.5, about 8.6, about 8.7, about 8.8, about 8.9, or about 9.0. In a specific embodiment, the inventive process comprises contacting a cell-binding agent with the drug (e.g., DM1 or DM4) and then the cross-linking agent (e.g., SMCC, Sulfo-SMCC, SPDB, Sulfo-SPDB or CX1-1) in a solution having a pH of about 7.8 (e.g., a pH of 7.6 to 8.0 or a pH of 7.7 to 7.9).

The one-step process (i.e., contacting the antibody with the drug (e.g., DM1 or DM4) and then the cross-linking agent (e.g., SMCC, Sulfo-SMCC, SPDB, Sulfo-SPDB or CX1-1) can be carried out at any suitable temperature known in the art. For example, the one-step process can occur at about 20° C. or less (e.g., about −10° C. (provided that the solution is prevented from freezing, e.g., by the presence of organic solvent used to dissolve the cytotoxic agent and the bifunctional crosslinking reagent) to about 20° C., about 0° C. to about 18° C., about 4° C. to about 16° C.), at room temperature (e.g., about 20° C. to about 30° C. or about 20° C. to about 25° C.), or at an elevated temperature (e.g., about 30° C. to about 37° C.). In one embodiment, the one-step process occurs at a temperature of about 16° C. to about 24° C. (e.g., about 16° C., about 17° C., about 18° C., about 19° C., about 20° C., about 21° C., about 22° C., about 23° C., about 24° C., or about 25° C.). In another embodiment, the one-step process is carried out at a temperature of about 15° C. or less (e.g., about −10° C. to about 15° C., or about 0° C. to about 15° C.). For example, the process comprises contacting the antibody with the drug (e.g., DM1 or DM4) and then the cross-linking agent (e.g., SMCC, Sulfo-SMCC, SPDB, Sulfo-SPDB or CX1-1) at a temperature of about 15° C., about 14° C., about 13° C., about 12° C., about 11° C., about 10° C., about 9° C., about 8° C., about 7° C., about 6° C., about 5° C., about 4° C., about 3° C., about 2° C., about 1° C., about 0° C., about −1° C., about −2° C., about −3° C., about −4° C., about −5° C., about −6° C., about −7° C., about −8° C., about −9° C., or about −10° C., provided that the solution is prevented from freezing, e.g., by the presence of organic solvent(s) used to dissolve the cross-linking agent (e.g., SMCC, Sulfo-SMCC, Sulfo-SPDB SPDB, or CX1-1). In one embodiment, the process comprises contacting the antibody with the drug (e.g., DM1 or DM4) and then the cross-linking agent (e.g., SMCC, Sulfo-SMCC, SPDB, Sulfo-SPDB or CX1-1) at a temperature of about −10° C. to about 15° C., about 0° C. to about 15° C., about 0° C. to about 10° C., about 0° C. to about 5° C., about 5° C. to about 15° C., about 10° C. to about 15° C., or about 5° C. to about 10° C. In another embodiment, the process comprises contacting the antibody with the drug (e.g., DM1 or DM4) and then the cross-linking agent (e.g., SMCC, Sulfo-SMCC, SPDB, Sulfo-SPDB or CX1-1) at a temperature of about 10° C. (e.g., a temperature of 8° C. to 12° C. or a temperature of 9° C. to 11° C.).

In one embodiment, the contacting described above is effected by providing the antibody, then contacting the antibody with the drug (e.g., DM1 or DM4) to form a first mixture comprising the antibody and the drug (e.g., DM1 or DM4), and then contacting the first mixture comprising the antibody and the drug (e.g., DM1 or DM4) with the cross-linking agent (e.g., SMCC, Sulfo-SMCC, SPDB, Sulfo-SPDB or CX1-1). For example, in one embodiment, the antibody is provided in a reaction vessel, the drug (e.g., DM1 or DM4) is added to the reaction vessel (thereby contacting the antibody), and then the cross-linking agent (e.g., SMCC, Sulfo-SMCC, SPDB, Sulfo-SPDB or CX1-1) is added to the mixture comprising the antibody and the drug (e.g., DM1 or DM4) (thereby contacting the mixture comprising the antibody and the drug). In one embodiment, the antibody is provided in a reaction vessel, and the drug (e.g., DM1 or DM4) is added to the reaction vessel immediately following providing the antibody to the vessel. In another embodiment, the antibody is provided in a reaction vessel, and the drug (e.g., DM1 or DM4) is added to the reaction vessel after a time interval following providing the antibody to the vessel (e.g., about 5 minutes, about 10 minutes, about 20 minutes, about 30 minutes, about 40 minutes, about 50 minutes, about 1 hour, about 1 day or longer after providing the cell-binding agent to the space). The drug (e.g., DM1 or DM4) can be added quickly (i.e., within a short time interval, such as about 5 minutes, about 10 minutes) or slowly (such as by using a pump).

The mixture comprising the antibody and the drug (e.g., DM1 or DM4) can then be contacted with the cross-linking agent (e.g., SMCC, Sulfo-SMCC, SPDB, Sulfo-SPDB or CX1-1) either immediately after contacting the antibody with the drug (e.g., DM1 or DM4) or at some later point (e.g., about 5 minutes to about 8 hours or longer) after contacting the antibody with the drug (e.g., DM1 or DM4). For example, in one embodiment, the cross-linking agent (e.g., SMCC, Sulfo-SMCC, SPDB, Sulfo-SPDB or CX1-1) is added to the mixture comprising the antibody and the drug (e.g., DM1 or DM4) immediately after the addition of the drug (e.g., DM1 or DM4) to the reaction vessel comprising the antibody. Alternatively, the mixture comprising the antibody and the drug (e.g., DM1 or DM4) can be contacted with the cross-linking agent (e.g., SMCC, Sulfo-SMCC, SPDB, Sulfo-SPDB or CX1-1) at about 5 minutes, about 10 minutes, about 20 minutes, about 30 minutes, about 1 hour, about 2 hours, about 3 hours, about 4 hours, about 5 hours, about 6 hours, about 7 hours, about 8 hours, or longer after contacting the antibody with the drug (e.g., DM1 or DM4).

After the mixture comprising the antibody and the drug (e.g., DM1 or DM4) is contacted with the cross-linking agent (e.g., SMCC, Sulfo-SMCC, SPDB, Sulfo-SPDB or CX1-1) the reaction is allowed to proceed for about 1 hour, about 2 hours, about 3 hours, about 4 hours, about 5 hours, about 6 hours, about 7 hours, about 8 hours, about 9 hours, about 10 hours, about 11 hours, about 12 hours, about 13 hours, about 14 hours, about 15 hours, about 16 hours, about 17 hours, about 18 hours, about 19 hours, about 20 hours, about 21 hours, about 22 hours, about 23 hours, about 24 hours, or longer (e.g., about 30 hours, about 35 hours, about 40 hours, about 45 hours, or about 48 hrs).

In one embodiment, the one-step process further comprises a quenching step to quench any unreacted drug (e.g., DM1 or DM4) and/or unreacted cross-linking agent (e.g., SMCC, Sulfo-SMCC, SPDB, Sulfo-SPDB or CX1-1). The quenching step is typically performed prior to purification of the conjugate. In one embodiment, the mixture is quenched by contacting the mixture with a quenching reagent. As used herein, the "quenching reagent" refers to a reagent that reacts with the free drug (e.g., DM1 or DM4) and/or cross-linking agent (e.g., SMCC, Sulfo-SMCC, SPDB, Sulfo-SPDB or CX1-1). In one embodiment, maleimide or haloacetamide quenching reagents, such as 4-maleimidobutyric acid, 3-maleimidopropionic acid, N-ethylmaleimide, iodoacetamide, or iodoacetamidopropionic acid, can be used to ensure that any unreacted group (such as thiol) in the drug (e.g., DM1 or DM4) is quenched. The quenching step can help prevent the dimerization of the drug (e.g., DM1). The dimerized DM1 can be difficult to remove. Upon quenching with polar, charged thiol-quenching reagents (such as 4-maleimidobutyric acid or 3-maleimidopropionic acid), the excess, unreacted DM1 is converted into a polar, charged, water-soluble adduct that can be easily separated from the covalently-linked conjugate during the purification step. Quenching with non-polar and neutral thiol-quenching reagents can also be used. In one embodiment, the mixture is quenched by contacting the mixture with a quenching reagent that reacts with the unreacted cross-linking agent (e.g., SMCC, Sulfo-SMCC, SPDB, Sulfo-SPDB or CX1-1). For example, nucleophiles can be added to the mixture in order to quench any unreacted SMCC. The nucleophile preferably is an amino group containing nucleophile, such as lysine, taurine and hydroxylamine.

In a preferred embodiment, the reaction (i.e., contacting the antibody with the drug (e.g., DM1 or DM4) and then cross-linking agent (e.g., SMCC, Sulfo-SMCC, SPDB, Sulfo-SPDB or CX1-1)) is allowed to proceed to completion prior to contacting the mixture with a quenching reagent. In this regard, the quenching reagent is added to the mixture about 1 hour to about 48 hours (e.g., about 1 hour, about 2 hours, about 3 hours, about 4 hours, about 5 hours, about 6 hours, about 7 hours, about 8 hours, about 9 hours, about 10 hours, about 11 hours, about 12 hours, about 13 hours, about 14 hours, about 15 hours, about 16 hours, about 17 hours, about 18 hours, about 19 hours, about 20 hours, about 21 hours, about 22 hours, about 23 hours, about 24 hours, or about 25 hours to about 48 hours) after the mixture comprising the antibody and the drug (e.g., DM1 or DM4) is contacted with the cross-linking agent (e.g., SMCC, Sulfo-SMCC, SPDB, Sulfo-SPDB or CX1-1).

Alternatively, the mixture is quenched by lowering the pH of the mixture to about 5.0 (e.g., 4.8, 4.9, 5.0, 5.1 or 5.2). In another embodiment, the mixture is quenched by lowering the pH to less than 6.0, less than 5.5, less than 5.0, less than 4.8, less than 4.6, less than 4.4, less than 4.2, less than 4.0. Alternatively, the pH is lowered to about 4.0 (e.g., 3.8, 3.9, 4.0, 4.1 or 4.2) to about 6.0 (e.g., 5.8, 5.9, 6.0, 6.1 or 6.2), about 4.0 to about 5.0, about 4.5 (e.g., 4.3, 4.4, 4.5, 4.6 or 4.7) to about 5.0. In one embodiment, the mixture is quenched by lowering the pH of the mixture to 4.8. In another embodiment, the mixture is quenched by lowering the pH of the mixture to 5.5.

In one embodiment, the one-step process further comprises a holding step to release the unstably bound linkers from the antibody. The holding step comprises holding the mixture prior to purification of the conjugate (e.g., after the reaction step, between the reaction step and the quenching step, or after the quenching step). For example, the process comprises (a) contacting the antibody with the drug (e.g., DM1, DM3 or DM4) to form a mixture comprising the antibody and the drug (e.g., DM1, DM3 or DM4); and then contacting the mixture comprising the antibody and drug (e.g., DM1, DM3 or DM4) with the cross-linking agent (e.g., SMCC, Sulfo-SMCC, SPDB, Sulfo-SPDB or CX1-1), in a solution having a pH of about 4 to about 9 to provide a mixture comprising (i) the conjugate (e.g., Ab-MCC-DM1, Ab-SPDB-DM4 or Ab-CX1-1-DM1), (ii) free drug (e.g., DM1, DM3 or DM4), and (iii) reaction by-products, (b) holding the mixture prepared in step (a) to release the unstably bound linkers from the cell-binding agent, and (c) purifying the mixture to provide a purified conjugate.

In another embodiment, the process comprises (a) contacting the antibody with the drug (e.g., DM1, DM3 or DM4) to form a mixture comprising the antibody and the drug (e.g., DM1, DM3 or DM4); and then contacting the mixture comprising the antibody and the drug (e.g., DM1, DM3 or DM4) with the cross-linking agent (e.g., SMCC, Sulfo-SMCC, SPDB, Sulfo-SPDB or CX1-1), in a solution having a pH of about 4 to about 9 to provide a mixture comprising (i) the conjugate, (ii) free drug (e.g., DM1, DM3 or DM4), and (iii) reaction by-products, (b) quenching the mixture prepared in step (a) to quench any unreacted drug (e.g., DM1, DM3 or DM4) and/or unreacted cross-linking agent (e.g., SMCC, Sulfo-SMCC, SPDB, Sulfo-SPDB or CX1-1), (c) holding the mixture prepared in step (b) to release the unstably bound linkers from the cell-binding agent, and (d) purifying the mixture to provide a purified conjugate (e.g., Ab-MCC-DM1, Ab-SPDB-DM4 or Ab-CX1-1-DM1).

Alternatively, the holding step can be performed after purification of the conjugate, followed by an additional purification step.

In a preferred embodiment, the reaction is allowed to proceed to completion prior to the holding step. In this regard, the holding step can be performed about 1 hour to about 48 hours (e.g., about 1 hour, about 2 hours, about 3 hours, about 4 hours, about 5 hours, about 6 hours, about 7 hours, about 8 hours, about 9 hours, about 10 hours, about 11 hours, about 12 hours, about 13 hours, about 14 hours, about 15 hours, about 16 hours, about 17 hours, about 18 hours, about 19 hours, about 20 hours, about 21 hours, about 22 hours, about 23 hours, about 24 hours, or about 24 hours to about 48 hours) after the mixture comprising the antibody and the drug (e.g., DM1, DM3 or DM4) is contacted with the cross-linking agent (e.g., SMCC, Sulfo-SMCC, SPDB, Sulfo-SPDB or CX1-1).

The holding step comprises maintaining the solution at a suitable temperature (e.g., about 0° C. to about 37° C.) for a suitable period of time (e.g., about 1 hour to about 1 week, about 1 hour to about 24 hours, about 1 hour to about 8 hours, or about 1 hour to about 4 hours) to release the unstably bound linkers from the antibody while not substantially releasing the stably bound linkers from the antibody. In one embodiment, the holding step comprises maintaining the solution at about 20° C. or less (e.g., about 0° C. to about 18° C., about 4° C. to about 16° C.), at room temperature (e.g., about 20° C. to about 30° C. or about 20° C. to about 25° C.), or at an elevated temperature (e.g., about 30° C. to about 37° C.). In one embodiment, the holding step comprises maintaining the solution at a temperature of about 16° C. to about 24° C. (e.g., about 15° C., about 16° C., about 17° C., about 18° C., about 19° C., about 20° C., about 21° C., about 22° C., about 23° C., about 24° C., or about 25° C.). In another embodiment, the holding step comprises maintaining the solution at a temperature of about 2° C. to about 8° C. (e.g., about 0° C., about 1° C., about 2° C., about 3° C., about 4° C., about 5° C., about 6° C., about 7° C., about 8° C., about 9° C., or about 10° C.). In another embodiment, the holding step comprises maintaining the solution at a temperature of about 37° C. (e.g., about 34° C., about 35° C., about 36° C., about 37° C., about 38° C., about 39° C., or about 40° C.).

The duration of the holding step depends on the temperature and the pH at which the holding step is performed. For example, the duration of the holding step can be substantially reduced by performing the holding step at elevated temperature, with the maximum temperature limited by the stability of the cell-binding agent-cytotoxic agent conjugate. The holding step can comprise maintaining the solution for about 1 hour to about 1 day (e.g., about 1 hour, about 2 hours, about 3 hours, about 4 hours, about 5 hours, about 6 hours, about 7 hours, about 8 hours, about 9 hours, about 10 hours, about 12 hours, about 14 hours, about 16 hours, about 18 hours, about 20 hours, about 22 hours, or about 24 hours), about 10 hours to about 24 hours, about 12 hours to about 24 hours, about 14 hours to about 24 hours, about 16 hours to about 24 hours, about 18 hours to about 24 hours, about 20 hours to about 24 hours, about 5 hours to about 1 week, about 20 hours to about 1 week, about 12 hours to about 1 week (e.g., about 12 hours, about 16 hours, about 20 hours, about 24 hours, about 2 days, about 3 days, about 4 days, about 5 days, about 6 days, or about 7 days), or about 1 day to about 1 week.

In one embodiment, the holding step comprises maintaining the solution at a temperature of about 2° C. to about 8° C. for a period of at least about 12 hours for up to a week. In another embodiment, the holding step comprises maintaining the solution at a temperature of about 2° C. to about 8° C. overnight (e.g., about 12 to about 24 hours, preferably about 20 hours).

The pH value for the holding step preferably is about 4 to about 10. In one embodiment, the pH value for the holding step is about 4 or more, but less than about 6 (e.g., 4 to 5.9) or about 5 or more, but less than about 6 (e.g., 5 to 5.9). In another embodiment, the pH values for the holding step range from about 6 to about 10 (e.g., about 6.5 to about 9, about 6 to about 8). For example, pH values for the holding step can be about 6, about 6.5, about 7, about 7.5, about 8, about 8.5, about 9, about 9.5, or about 10.

In specific embodiments, the holding step can comprise incubating the mixture at 25° C. at a pH of about 6-7.5 for about 12 hours to about 1 week, incubating the mixture at 4° C. at a pH of about 4.5-5.9 for about 5 hours to about 5 days, or incubating the mixture at 25° C. at a pH of about 4.5-5.9 for about 5 hours to about 1 day.

The one-step process may optionally include the addition of sucrose to the reaction step to increase solubility and recovery of the conjugates. Desirably, sucrose is added at a concentration of about 0.1% (w/v) to about 20% (w/v) (e.g., about 0.1% (w/v), 1% (w/v), 5% (w/v), 10% (w/v), 15% (w/v), or 20% (w/v)). Preferably, sucrose is added at a concentration of about 1% (w/v) to about 10% (w/v) (e.g., about 0.5% (w/v), about 1% (w/v), about 1.5% (w/v), about 2% (w/v), about 3% (w/v), about 4% (w/v), about 5% (w/v), about 6% (w/v), about 7% (w/v), about 8% (w/v), about 9% (w/v), about 10% (w/v), or about 11% (w/v)). In addition, the reaction step also can comprise the addition of a buffering agent. Any suitable buffering agent known in the art can be used. Suitable buffering agents include, for example, a citrate buffer, an acetate buffer, a succinate buffer, and a phosphate buffer. In one embodiment, the buffering agent is selected from the group consisting of HEPPSO (N-(2-hydroxyethyl)piperazine-N'-(2-hydroxypropanesulfonic acid)), POPSO (piperazine-1,4-bis-(2-hydroxy-propane-sulfonic acid) dehydrate), HEPES (4-(2-hydroxyethyl)piperazine-1-ethanesulfonic acid), HEPPS (EPPS) (4-(2-hydroxyethyl)piperazine-1-propanesulfonic acid), TES (N-[tris(hydroxymethyl)methyl]-2-aminoethanesulfonic acid), and a combination thereof.

In one embodiment, the one-step process can further comprise the step of purifying the mixture to provide purified conjugate (e.g., Ab-MCC-DM1, Ab-SPDB-DM4 or Ab-CX1-1-DM1). Any purification methods known in the art can be used to purify the conjugates of the present invention. In one embodiment, the conjugates of the present invention using tangential flow filtration (TFF), non-adsorptive chromatography, adsorptive chromatography, adsorptive filtration, selective precipitation, or any other suitable purification process, as well as combinations thereof. In another embodiment, prior to subjecting the conjugates to purification process described above, the conjugates are first filtered through one or more PVDF membranes. Alternatively, the conjugates are filtered through one or more PVDF membranes after subjecting the conjugates to the purification process described above. For example, in one embodiment, the conjugates are filtered through one or more PVDF membranes and then purified using tangential flow filtration. Alternatively, the conjugates are purified using tangential flow filtration and then filtered through one or more PVDF membranes.

Any suitable TFF systems may be utilized for purification, including a Pellicon type system (Millipore, Billerica, Mass.), a Sartocon Cassette system (Sartorius A G, Edgewood, N.Y.), and a Centrasette type system (Pall Corp., East Hills, N.Y.).

Any suitable adsorptive chromatography resin may be utilized for purification. Preferred adsorptive chromatography resins include hydroxyapatite chromatography, hydrophobic charge induction chromatography (HCIC), hydrophobic interaction chromatography (HIC), ion exchange chromatography, mixed mode ion exchange chromatography, immobilized metal affinity chromatography (IMAC), dye ligand chromatography, affinity chromatography, reversed phase chromatography, and combinations thereof. Examples of suitable hydroxyapatite resins include ceramic hydroxyapatite (CHT Type I and Type II, Bio-Rad Laboratories, Hercules, CA), HA Ultrogel hydroxyapatite (Pall Corp., East Hills, N.Y.), and ceramic fluoroapatite (CFT Type I and Type II, Bio-Rad Laboratories, Hercules, Calif.). An example of a suitable HCIC resin is MEP Hypercel resin (Pall Corp., East Hills, N.Y.). Examples of suitable HIC resins include Butyl-Sepharose, Hexyl-Sepaharose, Phenyl-Sepharose, and Octyl Sepharose resins (all from GE Healthcare, Piscataway, N.J.), as well as Macro-prep Methyl and Macro-Prep t-Butyl resins (Biorad Laboratories, Hercules, Calif.). Examples of suitable ion exchange resins include SP-Sepharose, CM-Sepharose, and Q-Sepharose resins (all from GE Healthcare, Piscataway, N.J.), and Unosphere S resin (Bio-Rad Laboratories, Hercules, Calif.). Examples of suitable mixed mode ion exchangers include Bakerbond ABx resin (J T Baker, Phillipsburg N.J.). Examples of suitable IMAC resins include Chelating Sepharose resin (GE Healthcare, Piscataway, N.J.) and Profinity IMAC resin (Bio-Rad Laboratories, Hercules, Calif.). Examples of suitable dye ligand resins include Blue Sepharose resin (GE Healthcare, Piscataway, N.J.) and Affi-gel Blue resin (Bio-Rad Laboratories, Hercules, Calif.). Examples of suitable affinity resins include Protein A Sepharose resin (e.g., MabSelect, GE Healthcare, Piscataway, N.J.) and lectin affinity resins, e.g. Lentil Lectin Sepharose resin (GE Healthcare, Piscataway, N.J.), where the antibody bears appropriate lectin binding sites. Examples of suitable reversed phase resins include C4, C8, and C18 resins (Grace Vydac, Hesperia, Calif.).

Any suitable non-adsorptive chromatography resin may be utilized for purification. Examples of suitable non-adsorptive chromatography resins include, but are not limited to, SEPHADEX™ G-25, G-50, G-100, SEPHACRYL™ resins (e.g., S-200 and S-300), SUPERDEX™ resins (e.g., SUPERDEX™ 75 and SUPERDEX™ 200), BIO-GEL® resins (e.g., P-6, P-10, P-30, P-60, and P-100), and others known to those of ordinary skill in the art.

Two-Step Process and One-Pot Process for Cross-Linking to Lysine Antibody Residues In one embodiment, the conjugates of the present invention can be prepared as described in the U.S. Pat. No. 7,811,572 and U.S. Patent Application Publication No. 2006/0182750. The process comprises the steps of (a) contacting the antibody of the present invention with the cross-linking agent (e.g., SMCC, Sulfo-SMCC, SPDB, Sulfo-SPDB or CX1-1) to covalently attach the linker (i.e., Ab-SMCC, Ab-SPDB or Ab-CX1-1) to the antibody and thereby prepare a first mixture comprising the antibody having the linker bound thereto; (b) optionally subjecting the first mixture to a purification process to prepare a purified first mixture of the antibody having the linker bound thereto; (c) conjugating the drug (e.g., DM1, DM3, or DM4) to the antibody having the linker bound thereto in the first mixture by reacting the antibody having the linker bound thereto with the drug (e.g., DM1, DM3, or DM4) in a solution having a pH of about 4 to about 9 to prepare a second mixture comprising (i) conjugate (e.g., Ab-MCC-DM1, Ab-SPDB-DM4 or Ab-CX1-1-DM1), (ii) free drug (e.g., DM1, DM3 or DM4); and (iii) reaction by-products; and (d) subjecting the second mixture to a purification process to purify the conjugate from the other components of the second mixture. Alternatively, the purification step (b) can be omitted. Any purification methods described herein can be used for steps (b) and (d). In one embodiment, TFF is used for both steps (b) and (d). In another embodiment, TFF is used for step (b) and absorptive chromatography (e.g., CHT) is used for step (d).

One-Step Reagent and In-Situ Process for Cross-Linking to Lysine Antibody Residues In one embodiment, the conjugates of the present invention can be prepared by conjugating pre-formed linker-drug compound (e.g., SMCC-DM1, Sulfo-SMCC-DM1, SPDB-DM4 or CX1-1-DM1) to the antibody of the present invention, as described in U.S. Pat. No. 6,441,163 and U.S. Patent Application Publication Nos. 2011/0003969 and 2008/0145374, followed by a purification step. Any purification methods described herein can be used. The linker-drug compound is prepared by reacting the drug (e.g., DM1, DM3, or DM4) with the cross-linking agent (e.g., SMCC, Sulfo-SMCC, SPDB, Sulfo-SPDB or CX1-1). The linker-drug compound (e.g., SMCC-DM1, Sulfo-SMCC-DM1, SPDB-DM4 or CX1-1-DM1) is optionally subjected to purification before being conjugated to the antibody.

Anti-CCR7 Antibodies

The present invention provides antibodies or antibody fragments (e.g., antigen binding fragments) that specifically bind to CCR7. Antibodies or antibody fragments (e.g., antigen binding fragments) of the invention include, but are not limited to, the human monoclonal antibodies or fragments thereof, isolated as described in the Examples.

The present invention in certain embodiments provides antibodies or antibody fragments (e.g., antigen binding fragments) that specifically bind CCR7, said antibodies or antibody fragments (e.g., antigen binding fragments) comprise a VH domain having an amino acid sequence of SEQ ID NO: 13, 45, 77 or 608. The present invention in certain embodiments also provides antibodies or antibody fragments (e.g., antigen binding fragments) that specifically bind to CCR7, said antibodies or antibody fragments (e.g., antigen binding fragments) comprise a VH CDR having an amino acid sequence of any one of the VH CDRs listed in Tables 1 and 4, infra. In particular embodiments, the invention provides antibodies or antibody fragments (e.g., antigen binding fragments) that specifically bind to CCR7, said antibodies comprising (or alternatively, consist of) one, two, three, four, five or more VH CDRs having an amino acid sequence of any of the VH CDRs listed in Tables 1 and 4, infra.

The present invention provides antibodies or antibody fragments (e.g., antigen binding fragments) that specifically bind to CCR7, said antibodies or antibody fragments (e.g., antigen binding fragments) comprise a VL domain having an amino acid sequence of SEQ ID NO: 29, 61, 93 or 624. The present invention also provides antibodies or antibody fragments (e.g., antigen binding fragments) that specifically bind to CCR7, said antibodies or antibody fragments (e.g., antigen binding fragments) comprise a VL CDR having an amino acid sequence of any one of the VL CDRs listed in Tables 1 and 4, infra. In particular, the invention provides antibodies or antibody fragments (e.g., antigen binding fragments) that specifically bind to CCR7, said antibodies or antibody fragments (e.g., antigen binding fragments) comprise (or alternatively, consist of) one, two, three or more VL CDRs having an amino acid sequence of any of the VL CDRs listed in Tables 1 and 4, infra.

Other antibodies or antibody fragments (e.g., antigen binding fragments) of the invention include amino acids that have been mutated, yet have at least 60, 70, 80, 90 or 95 percent identity in the CDR regions with the CDR regions depicted in the sequences described in Tables 1 and 4. In some embodiments, the antibodies comprise mutant amino acid sequences wherein no more than 1, 2, 3, 4 or 5 amino acids have been mutated in the CDR regions when compared with the CDR regions depicted in the sequence described in Tables 1 and 4.

The present invention also provides nucleic acid sequences that encode the VH, VL, the full length heavy chain, and the full length light chain of the antibodies that specifically bind to CCR7. Such nucleic acid sequences can be optimized for expression in mammalian cells.

Throughout the text of this application, should there be a discrepancy between the text of the specification and the sequence listing, the text of the specification shall prevail.

TABLE 1

Examples of Anti-CCR7 Antibodies of the Present Invention

506E15 (Humanized CysMab DAPA)

| | | |
|---|---|---|
| SEQ ID NO: 1 | HCDR1 (Combined) | GFTFSSYAMS |
| SEQ ID NO: 2 | HCDR2 (Combined) | TISSGGSFTYYPDSVKG |
| SEQ ID NO: 3 | HCDR3 (Combined) | RASTVVGTDFDV |
| SEQ ID NO: 4 | HCDR1 (Kabat) | SYAMS |
| SEQ ID NO: 5 | HCDR2 (Kabat) | TISSGGSFTYYPDSVKG |
| SEQ ID NO: 6 | HCDR3 (Kabat) | RASTVVGTDFDV |
| SEQ ID NO: 7 | HCDR1 (Chothia) | GFTFSSY |
| SEQ ID NO: 8 | HCDR2 (Chothia) | SSGGSF |
| SEQ ID NO: 9 | HCDR3 (Chothia) | RASTVVGTDFDV |
| SEQ ID NO: 10 | HCDR1 (IMGT) | GFTFSSYA |
| SEQ ID NO: 11 | HCDR2 (IMGT) | ISSGGSFT |
| SEQ ID NO: 12 | HCDR3 (IMGT) | ARRASTVVGTDFDV |
| SEQ ID NO: 13 | VH | EVQLVESGGGLVKPGGSLRLSCAASGFTFSSYAMSWIRQ APGKGLEWVATISSGGSFTYYPDSVKGRFTISRDNAKNSL YLQMNSLRAEDTAVYYCARRASTVVGTDFDVWGQGTT VTVSS |
| SEQ ID NO: 14 | DNA VH | GAAGTGCAGCTGGTGGAATCTGGCGGCGGACTGGTCA AGCCTGGCGGCTCCCTGAGACTGTCTTGCGCCGCCTCC GGCTTCACCTTCTCCAGCTACGCCATGTCCTGGATCCG GCAGGCCCCTGGCAAGGGACTGGAGTGGGTGGCCAC CATCTCCTCCGGCGGCAGCTTCACCTACTACCCCGACTC CGTGAAGGGCCGGTTCACCATCTCCCGGGACAACGCC AAGAACTCCCTGTACCTGCAGATGAACTCCCTGCGGGC CGAGGACACCGCCGTGTACTACTGTGCCAGACGGGCC TCCACCGTCGTGGGCACCGATTTCGATGTGTGGGGCCA GGGCACAACCGTGACCGTGTCCTCC |
| SEQ ID NO: 15 | Heavy Chain (DAPA, CysMab mutations underlined) | EVQLVESGGGLVKPGGSLRLSCAASGFTFSSYAMSWIRQ APGKGLEWVATISSGGSFTYYPDSVKGRFTISRDNAKNSL YLQMNSLRAEDTAVYYCARRASTVVGTDFDVWGQGTT VTVSSASTKGPSVFPLAPSSKSTSGGTAALGCLVKDYFP<u>C</u>P VTVSWNSGALTSGVHTFPAVLQSSGLYSLSSVVTVPSSSL GTQTYICNVNHKPSNTKVDKRVEPKSCDKTHTCPPCPAP ELLGGPSVFLFPPKPKDTLMISRTPEVTCVVV<u>A</u>VSHEDPE VKFNWYVDGVEVHNAKTKPREEQYNSTYRVVSVLTVLH QDWLNGKEYKCKVSNKAL<u>A</u>APIEKTISKAKGQPREPQVY TLPPSREEMTKNQVSLTCLVKGFYP<u>C</u>DIAVEWESNGQPE NNYKTTPPVLDSDGSFFLYSKLTVDKSRWQQGNVFSCSV MHEALHNHYTQKSLSLSPGK |
| SEQ ID NO: 16 | DNA Heavy Chain | GAAGTGCAGCTGGTGGAATCTGGCGGCGGACTGGTCA AGCCTGGCGGCTCCCTGAGACTGTCTTGCGCCGCCTCC GGCTTCACCTTCTCCAGCTACGCCATGTCCTGGATCCG |

TABLE 1-continued

Examples of Anti-CCR7 Antibodies of the Present Invention

|  |  |  |
|---|---|---|
|  |  | GCAGGCCCCTGGCAAGGGACTGGAGTGGGTGGCCAC<br>CATCTCCTCCGGCGGCAGCTTCACCTACTACCCCGACTC<br>CGTGAAGGGCCGGTTCACCATCTCCCGGGACAACGCC<br>AAGAACTCCCTGTACCTGCAGATGAACTCCCTGCGGGC<br>CGAGGACACCGCCGTGTACTACTGTGCCAGACGGGCC<br>TCCACCGTCGTGGGCACCGATTTCGATGTGTGGGGCCA<br>GGGCACAACCGTGACCGTGTCCTCCGCCTCCACCAAGG<br>GACCCTCCGTGTTCCCTCTGGCCCCTTCCAGCAAGTCCA<br>CCTCTGGCGGCACCGCCGCTCTGGGCTGCCTGGTCAAG<br>GACTACTTCCCCTGCCCTGTGACAGTGTCCTGGAACTC<br>CGGCGCTCTGACCTCCGGCGTGCACACCTTCCCTGCCG<br>TGCTGCAGTCCTCCGGCCTGTACTCCCTGTCCTCCGTCG<br>TGACCGTGCCTTCCTCCAGCCTGGGCACCCAGACCTAC<br>ATCTGCAACGTGAACCACAAGCCCTCCAACACCAAAGT<br>GGACAAGCGGGTGGAACCCAAGTCCTGCGACAAGACC<br>CACACCTGTCCTCCCTGCCCTGCCCCTGAGCTGCTGGG<br>AGGCCCTTCCGTGTTCCTGTTCCCTCCAAAGCCCAAGG<br>ACACCCTGATGATCTCCCGGACCCCTGAAGTGACCTGC<br>GTGGTGGTGGCCGTGTCCCACGAGGATCCCGAAGTGA<br>AGTTCAATTGGTACGTGGACGGCGTGGAAGTGCACAA<br>TGCCAAGACCAAGCCCAGAGAGGAACAGTACAACTCC<br>ACCTACCGGGTGGTGTCCGTGCTGACCGTGCTGCACCA<br>GGACTGGCTGAACGGCAAAGAGTACAAGTGCAAAGT<br>GTCCAACAAGGCCCTGGCCGCTCCCATCGAAAAGACC<br>ATCTCCAAGGCCAAGGGCCAGCCCAGAGAGCCCCAAG<br>TGTACACACTGCCTCCCAGCCGGGAAGAGATGACCAA<br>GAACCAAGTGTCCCTGACCTGCCTCGTGAAGGGCTTCT<br>ACCCCTGCGATATCGCCGTGGAGTGGGAGTCCAACGG<br>CCAGCCCGAGAACAACTACAAGACCACCCCTCCCGTGC<br>TGGACAGCGACGGCTCATTCTTCCTGTACTCCAAGCTG<br>ACCGTGGACAAGTCCCGGTGGCAGCAGGGCAACGTGT<br>TCTCCTGCTCCGTGATGCACGAGGCCCTGCACAACCAC<br>TACACCCAGAAGTCCCTGTCCCTGAGCCCCGGCAAG |
| SEQ ID NO: 17 | LCDR1<br>(Combined) | RASQDIGSSLN |
| SEQ ID NO: 18 | LCD R2<br>(Combined) | ATSSLDS |
| SEQ ID NO: 19 | LCD R3<br>(Combined) | LQYASSPPT |
| SEQ ID NO: 20 | LCDR1<br>(Kabat) | RASQDIGSSLN |
| SEQ ID NO: 21 | LCDR2<br>(Kabat) | ATSSLDS |
| SEQ ID NO: 22 | LCDR3<br>(Kabat) | LQYASSPPT |
| SEQ ID NO: 23 | LCDR1<br>(Chothia) | SQDIGSS |
| SEQ ID NO: 24 | LCDR2<br>(Chothia) | ATS |
| SEQ ID NO: 25 | LCDR3<br>(Chothia) | YASSPP |
| SEQ ID NO: 26 | LCDR1<br>(IMGT) | QDIGSS |
| SEQ ID NO: 27 | LCDR2<br>(IMGT) | ATS |
| SEQ ID NO: 28 | LCDR3<br>(IMGT) | LQYASSPPT |
| SEQ ID NO: 29 | VL | DIQMTQSPSSLSASVGDRVTLTCRASQDIGSSLNWLQQK<br>PGKAIKRLIYATSSLDSGVPSRFSGSRSGTDYTLTISSLQPE<br>DFVVYYCLQYASSPPTFGGGTKLEIK |
| SEQ ID NO: 30 | DNA VL | GACATCCAGATGACCCAGAGCCCCTCCAGCCTGTCCGC<br>CTCCGTGGGCGATAGAGTGACCCTGACCTGCCGGGCC<br>TCCCAGGACATCGGCTCCTCCCTGAACTGGCTGCAGCA<br>GAAGCCCGGCAAGGCCATCAAGCGGCTGATCTACGCC<br>ACCTCCTCCCTGGACTCCGGCGTGCCCTCCCGGTTCTCT<br>GGCTCCAGATCCGGCACCGACTACACCCTGACCATCTC<br>CAGCCTGCAGCCCGAGGACTTCGTGGTGTACTACTGCC<br>TGCAGTACGCCTCCAGCCCTCCCACCTTCGGCGGAGGC<br>ACCAAGCTGGAAATCAAG |
| SEQ ID NO: 31 | Light Chain | DIQMTQSPSSLSASVGDRVTLTCRASQDIGSSLNWLQQK<br>PGKAIKRLIYATSSLDSGVPSRFSGSRSGTDYTLTISSLQPE<br>DFVVYYCLQYASSPPTFGGGTKLEIKRTVAAPSVFIFPPSD<br>EQLKSGTASVVCLLNNFYPREAKVQWKVDNALQSGNSQ<br>ESVTEQDSKDSTYSLSSTLTLSKADYEKHKVYACEVTHQGL<br>SSPVTKSFNRGEC |
| SEQ ID NO: 32 | DNA Light<br>Chain | GACATCCAGATGACCCAGAGCCCCTCCAGCCTGTCCGC<br>CTCCGTGGGCGATAGAGTGACCCTGACCTGCCGGGCC<br>TCCCAGGACATCGGCTCCTCCCTGAACTGGCTGCAGCA |

TABLE 1-continued

Examples of Anti-CCR7 Antibodies of the Present Invention

```
GAAGCCCGGCAAGGCCATCAAGCGGCTGATCTACGCC
ACCTCCTCCCTGGACTCCGGCGTGCCCTCCCGGTTCTCT
GGCTCCAGATCCGGCACCGACTACACCCTGACCATCTC
CAGCCTGCAGCCCGAGGACTTCGTGGTGTACTACTGCC
TGCAGTACGCCTCCAGCCCTCCCACCTTCGGCGGAGGC
ACCAAGCTGGAAATCAAGCGTACGGTGGCCGCTCCCA
GCGTGTTCATCTTCCCCCCCAGCGACGAGCAGCTGAAG
AGCGGCACCGCCAGCGTGGTGTGCCTGCTGAACAACT
TCTACCCCCGGGAGGCCAAGGTGCAGTGGAAGGTGGA
CAACGCCCTGCAGAGCGGCAACAGCCAGGAGAGCGTC
ACCGAGCAGGACAGCAAGGACTCCACCTACAGCCTGA
GCAGCACCCTGACCCTGAGCAAGGCCGACTACGAGAA
GCATAAGGTGTACGCCTGCGAGGTGACCCACCAGGGC
CTGTCCAGCCCCGTGACCAAGAGCTTCAACAGGGGCG
AGTGC
```

121G12 (Humanized CysMab, DAPA)

| SEQ ID NO: 33 | HCDR1 (Combined) | GFTFSTYAMS |
| --- | --- | --- |
| SEQ ID NO: 34 | HCDR2 (Combined) | TISDAGSYSYYPDNVKG |
| SEQ ID NO: 35 | HCDR3 (Combined) | RGSRYEEYYVMDY |
| SEQ ID NO: 36 | HCDR1 (Kabat) | TYAMS |
| SEQ ID NO: 37 | HCDR2 (Kabat) | TISDAGSYSYYPDNVKG |
| SEQ ID NO: 38 | HCDR3 (Kabat) | RGSRYEEYYVMDY |
| SEQ ID NO: 39 | HCDR1 (Chothia) | GFTFSTY |
| SEQ ID NO: 40 | HCDR2 (Chothia) | SDAGSY |
| SEQ ID NO: 41 | HCDR3 (Chothia) | RGSRYEEYYVMDY |
| SEQ ID NO: 42 | HCDR1 (IMGT) | GFTFSTYA |
| SEQ ID NO: 43 | HCDR2 (IMGT) | ISDAGSYS |
| SEQ ID NO: 44 | HCDR3 (IMGT) | ARRGSRYEEYYVMDY |
| SEQ ID NO: 45 | VH | EVQLVESGGGLVKPGGSLRLSCAASGFTFSTYAMSWVRQ APGKGLEWVATISDAGSYSYYPDNVKGRFTISRDNAKNSL YLQMNSLRAEDTAVYYCARRGSRYEEYYVMDYWGQGT TVTVSS |
| SEQ ID NO: 46 | DNA VH | GAAGTGCAGCTGGTGGAATCTGGCGGCGGACTGGTCA AGCCTGGCGGCTCCCTGAGACTGTCTTGCGCCGCCTCC GGCTTCACCTTCTCCACCTACGCCATGTCCTGGGTCCGA CAGGCCCCTGGAAAGGGCCTGGAGTGGGTGGCCACCA TCTCCGACGCCGGCTCCTACTCCTACTACCCCGACAAC GTGAAGGGCCGGTTCACCATCTCCCGGGACAACGCCA AGAACTCCCTGTACCTGCAGATGAACTCCCTGCGGGCC GAGGACACCGCCGTGTACTACTGCGCCAGACGGGGCT CCAGATACGAAGAGTACTACGTGATGGACTACTGGGG CCAGGGCACAACCGTGACCGTGTCCTCC |
| SEQ ID NO: 47 | Heavy Chain (DAPA, CysMab mutations underlined) | EVQLVESGGGLVKPGGSLRLSCAASGFTFSTYAMSWVRQ APGKGLEWVATISDAGSYSYYPDNVKGRFTISRDNAKNSL YLQMNSLRAEDTAVYYCARRGSRYEEYYVMDYWGQGT TVTVSSASTKGPSVFPLAPSSKSTSGGTAALGCLVKDYFPC PVTVSWNSGALTSGVHTFPAVLQSSGLYSLSSVVTVPSSS LGTQTYICNVNHKPSNTKVDKRVEPKSCDKTHTCPPCPA PELLGGPSVFLFPPKPKDTLMISRTPEVTCVVVAVSHEDPE VKFNWYVDGVEVHNAKTKPREEQYNSTYRVVSVLTVLH QDWLNGKEYKCKVSNKALAAPIEKTISKAKGQPREPQVY TLPPSREEMTKNQVSLTCLVKGFYPCDIAVEWESNGQPE NNYKTTPPVLDSDGSFFLYSKLTVDKSRWQQGNVFSCSV MHEALHNHYTQKSLSLSPGK |
| SEQ ID NO: 48 | DNA Heavy Chain | GAAGTGCAGCTGGTGGAATCTGGCGGCGGACTGGTCA AGCCTGGCGGCTCCCTGAGACTGTCTTGCGCCGCCTCC GGCTTCACCTTCTCCACCTACGCCATGTCCTGGGTCCGA CAGGCCCCTGGAAAGGGCCTGGAGTGGGTGGCCACCA TCTCCGACGCCGGCTCCTACTCCTACTACCCCGACAAC GTGAAGGGCCGGTTCACCATCTCCCGGGACAACGCCA AGAACTCCCTGTACCTGCAGATGAACTCCCTGCGGGCC GAGGACACCGCCGTGTACTACTGCGCCAGACGGGGCT CCAGATACGAAGAGTACTACGTGATGGACTACTGGGG CCAGGGCACAACCGTGACCGTGTCCTCCGCCTCCACCA |

TABLE 1-continued

Examples of Anti-CCR7 Antibodies of the Present Invention

| | | |
|---|---|---|
| | | AGGGACCCTCCGTGTTCCCTCTGGCCCCTTCCAGCAAG |
| | | TCCACCTCTGGCGGCACCGCCGCTCTGGGCTGCCTGGT |
| | | CAAGGACTACTTCCCCTGCCCTGTGACAGTGTCCTGGA |
| | | ACTCCGGCGCTCTGACCTCCGGCGTGCACACCTTCCCT |
| | | GCCGTGCTGCAGTCCTCCGGCCTGTACTCCCTGTCCTCC |
| | | GTCGTGACCGTGCCTTCCTCCAGCCTGGGCACCCAGAC |
| | | CTACATCTGCAACGTGAACCACAAGCCCTCCAACACCA |
| | | AAGTGGACAAGCGGGTGGAACCCAAGTCCTGCGACAA |
| | | GACCCACACCTGTCCTCCCTGCCCTGCCCCTGAGCTGCT |
| | | GGGAGGCCCTTCCGTGTTCCTGTTCCCTCCAAAGCCCA |
| | | AGGACACCCTGATGATCTCCCGGACCCCTGAAGTGACC |
| | | TGCGTGGTGGTGGCCGTGTCCCACGAGGATCCCGAAG |
| | | TGAAGTTCAATTGGTACGTGGACGGCGTGGAAGTGCA |
| | | CAATGCCAAGACCAAGCCCAGAGAGGAACAGTACAAC |
| | | TCCACCTACCGGGTGGTGTCCGTGCTGACCGTGCTGCA |
| | | CCAGGACTGGCTGAACGGCAAAGAGTACAAGTGCAAA |
| | | GTGTCCAACAAGGCCCTGGCCGCTCCCATCGAAAAGA |
| | | CCATCTCCAAGGCCAAGGGCCAGCCCAGAGAGCCCCA |
| | | AGTGTACACACTGCCTCCCAGCCGGGAAGAGATGACC |
| | | AAGAACCAAGTGTCCCTGACCTGCCTCGTGAAGGGCTT |
| | | CTACCCCTGCGATATCGCCGTGGAGTGGGAGTCCAAC |
| | | GGCCAGCCCGAGAACAACTACAAGACCACCCCTCCCGT |
| | | GCTGGACTCCGACGGCTCATTCTTCCTGTACTCCAAGCT |
| | | GACCGTGGACAAGTCCCGGTGGCAGCAGGGCAACGT |
| | | GTTCTCCTGCTCCGTGATGCACGAGGCCCTGCACAACC |
| | | ACTACACCCAGAAGTCCCTGTCCCTGAGCCCCGGCAAG |
| SEQ ID NO: 49 | LCDR1 (Combined) | RASQSISNNLH |
| SEQ ID NO: 50 | LCDR2 (Combined) | YASQSIS |
| SEQ ID NO: 51 | LCDR3 (Combined) | QQSSSWLT |
| SEQ ID NO: 52 | LCDR1 (Kabat) | RASQSISNNLH |
| SEQ ID NO: 53 | LCDR2 (Kabat) | YASQSIS |
| SEQ ID NO: 54 | LCDR3 (Kabat) | QQSSSWLT |
| SEQ ID NO: 55 | LCDR1 (Chothia) | SQSISNN |
| SEQ ID NO: 56 | LCDR2 (Chothia) | YAS |
| SEQ ID NO: 57 | LCDR3 (Chothia) | SSSWL |
| SEQ ID NO: 58 | LCDR1 (IMGT) | QSISNN |
| SEQ ID NO: 59 | LCDR2 (IMGT) | YAS |
| SEQ ID NO: 60 | LCDR3 (IMGT) | QQSSSWLT |
| SEQ ID NO: 61 | VL | EIVLTQSPATLSVSPGERVTLSCRASQSISNNLHWYQQKP GQAPRLLIKYASQSISGIPARFSGSGSGTDFTLTISSVEPED FGVYFCQQSSSWLTFGQGTKLEIK |
| SEQ ID NO: 62 | DNA VL | GAGATCGTGCTGACACAGTCCCCTGCCACCCTGTCTGT GTCTCCCGGCGAGAGAGTGACCCTGTCCTGCCGGGCC TCCCAGTCCATCTCCAACAACCTGCACTGGTATCAGCA GAAGCCCGGCCAGGCCCCTCGGCTGCTGATTAAGTAC GCCTCCCAGAGCATCTCCGGCATCCCTGCCAGATTCTC CGGCTCCGGCAGCGGCACCGACTTCACCCTGACCATCT CCAGCGTGGAACCCGAGGACTTCGGCGTGTACTTCTGC CAGCAGTCCTCCTCCTGGCTGACCTTCGGCCAGGGCAC CAAGCTGGAAATCAAG |
| SEQ ID NO: 63 | Light Chain | EIVLTQSPATLSVSPGERVTLSCRASQSISNNLHWYQQKP GQAPRLLIKYASQSISGIPARFSGSGSGTDFTLTISSVEPED FGVYFCQQSSSWLTFGQGTKLEIKRTVAAPSVFIFPPSDE QLKSGTASVVCLLNNFYPREAKVQWKVDNALQSGNSQE SVTEQDSKDSTYSLSSTLTLSKADYEKHKVYACEVTHQGLS SPVTKSFNRGEC |
| SEQ ID NO: 64 | DNA Light Chain | GAGATCGTGCTGACACAGTCCCCTGCCACCCTGTCTGT GTCTCCCGGCGAGAGAGTGACCCTGTCCTGCCGGGCC TCCCAGTCCATCTCCAACAACCTGCACTGGTATCAGCA GAAGCCCGGCCAGGCCCCTCGGCTGCTGATTAAGTAC GCCTCCCAGAGCATCTCCGGCATCCCTGCCAGATTCTC CGGCTCCGGCAGCGGCACCGACTTCACCCTGACCATCT CCAGCGTGGAACCCGAGGACTTCGGCGTGTACTTCTGC CAGCAGTCCTCCTCCTGGCTGACCTTCGGCCAGGGCAC CAAGCTGGAAATCAAGCGTACGGTGGCCGCTCCCAGC GTGTTCATCTTCCCCCCCAGCGACGAGCAGCTGAAGAG |

TABLE 1-continued

Examples of Anti-CCR7 Antibodies of the Present Invention

```
CGGCACCGCCAGCGTGGTGTGCCTGCTGAACAACTTCT
ACCCCCGGGAGGCCAAGGTGCAGTGGAAGGTGGACA
ACGCCCTGCAGAGCGGCAACAGCCAGGAGAGCGTCAC
CGAGCAGGACAGCAAGGACTCCACCTACAGCCTGAGC
AGCACCCTGACCCTGAGCAAGGCCGACTACGAGAAGC
ATAAGGTGTACGCCTGCGAGGTGACCCACCAGGGCCT
GTCCAGCCCCGTGACCAAGAGCTTCAACAGGGGCGAG
TGC
```

674J13 (Humanized, CysMab DAPA)

| | | |
|---|---|---|
| SEQ ID NO: 65 | HCDR1 (Combined) | GYSITSGYSWH |
| SEQ ID NO: 66 | HCDR2 (Combined) | HIHSSGSTNYNPSLKS |
| SEQ ID NO: 67 | HCDR3 (Combined) | GGVQAFAY |
| SEQ ID NO: 68 | HCDR1 (Kabat) | SGYSWH |
| SEQ ID NO: 69 | HCDR2 (Kabat) | HIHSSGSTNYNPSLKS |
| SEQ ID NO: 70 | HCDR3 (Kabat) | GGVQAFAY |
| SEQ ID NO: 71 | HCDR1 (Chothia) | GYSITSGY |
| SEQ ID NO: 72 | HCDR2 (Chothia) | HSSGS |
| SEQ ID NO: 73 | HCDR3 (Chothia) | GGVQAFAY |
| SEQ ID NO: 74 | HCDR1 (IMGT) | GYSITSGYS |
| SEQ ID NO: 75 | HCDR2 (IMGT) | IHSSGST |
| SEQ ID NO: 76 | HCDR3 (IMGT) | ARGGVQAFAY |
| SEQ ID NO: 77 | VH | DVQLQESGPGLVKPSQTLSLTCTVSGYSITSGYSWHWIR QHPGKGLEWMAHIHSSGSTNYNPSLKSRITISRDTSKNQ FSLKLSSVTAADTAVYYCARGGVQAFAYWGQGTLVTVSS |
| SEQ ID NO: 78 | DNA VH | GACGTGCAGCTGCAGGAATCTGGCCCTGGCCTGGTCA AGCCCTCCCAGACCCTGTCCCTGACCTGCACCGTGTCC GGCTACTCTATCACCTCCGGCTACAGCTGGCACTGGAT CCGGCAGCACCCCGGCAAGGGCCTGGAATGGATGGCC CACATCCACTCCTCCGGCTCCACCAACTACAACCCCAGC CTGAAGTCCGGATCACCATCTCCCGGGACACCTCCAA GAACCAGTTCTCCCTGAAGCTGTCCTCCGTGACCGCCG CTGACACCGCCGTGTACTACTGTGCCAGAGGCGGCGT GCAGGCCTTCGCTTATTGGGGCCAGGGAACCCTGGTC ACCGTGTCCTCC |
| SEQ ID NO: 79 | Heavy Chain (DAPA, CysMab mutations underlined) | DVQLQESGPGLVKPSQTLSLTCTVSGYSITSGYSWHWIR QHPGKGLEWMAHIHSSGSTNYNPSLKSRITISRDTSKNQ FSLKLSSVTAADTAVYYCARGGVQAFAYWGQGTLVTVSS ASTKGPSVFPLAPSSKSTSGGTAALGCLVKDYFP<u>C</u>PVTVS WNSGALTSGVHTFPAVLQSSGLYSLSSVVTVPSSSLGTQT YICNVNHKPSNTKVDKRVEPKSCDKTHTCPPCPAPELLGG PSVFLFPPKPKDTLMISRTPEVTCVVV<u>A</u>VSHEDPEVKFNW YVDGVEVHNAKTKPREEQYNSTYRVVSVLTVLHQDWLN GKEYKCKVSNKAL<u>A</u>API EKTISKAKGQPREPQVYTLPPSRE EMTKNQVSLTCLVKGFYP<u>C</u>DIAVEWESNGQPENNYKTTP PVLDSDGSFFLYSKLTVDKSRWQQGNVFSCSVMHEALH NHYTQKSLSLSPGK |
| SEQ ID NO: 80 | DNA Heavy Chain | GACGTGCAGCTGCAGGAATCTGGCCCTGGCCTGGTCA AGCCCTCCCAGACCCTGTCCCTGACCTGCACCGTGTCC GGCTACTCTATCACCTCCGGCTACAGCTGGCACTGGAT CCGGCAGCACCCCGGCAAGGGCCTGGAATGGATGGCC CACATCCACTCCTCCGGCTCCACCAACTACAACCCCAGC CTGAAGTCCGGATCACCATCTCCCGGGACACCTCCAA GAACCAGTTCTCCCTGAAGCTGTCCTCCGTGACCGCCG CTGACACCGCCGTGTACTACTGTGCCAGAGGCGGCGT GCAGGCCTTCGCTTATTGGGGCCAGGGAACCCTGGTC ACCGTGTCCTCCGCCAGCACCAAGGGACCCTCCGTGTT CCCTCTGGCCCCTTCCAGCAAGTCCACCTCTGGCGGCA CCGCCGCTCTGGGCTGCCTCGTGAAGGACTACTTCCCC TGCCCCGTGACCGTGTCCTGGAACTCCGGCGCTCTGAC CTCCGGCGTGCACACCTTCCCTGCCGTGCTGCAGTCCT CCGGCCTGTACTCCCTGTCCAGCGTCGTGACCGTGCCC TCCAGCTCTCTGGGCACCCAGACCTACATCTGCAACGT GAACCACAAGCCCTCCAACACCAAAGTGGACAAGCGG GTGGAACCCAAGTCCTGCGACAAGACCCACACCTGTCC |

TABLE 1-continued

Examples of Anti-CCR7 Antibodies of the Present Invention

|  |  |  |
|---|---|---|
|  |  | TCCCTGCCCTGCCCCTGAGCTGCTGGGAGGCCCTTCCG<br>TGTTCCTGTTCCCTCCAAAGCCCAAGGACACCCTGATG<br>ATCTCCCGGACCCCTGAAGTGACCTGCGTGGTGGTGG<br>CCGTGTCCCACGAGGATCCCGAAGTGAAGTTCAATTG<br>GTACGTGGACGGCGTGGAAGTGCACAACGCCAAGACC<br>AAGCCCAGAGAGGAACAGTACAACTCCACCTACCGGG<br>TGGTGTCCGTGCTGACCGTGCTGCACCAGGACTGGCT<br>GAACGGCAAAGAGTACAAGTGCAAAGTGTCCAACAAG<br>GCCCTGGCCGCTCCCATCGAAAAGACCATCTCCAAGGC<br>CAAGGGCCAGCCCAGAGAGCCCCAAGTGTACACACTG<br>CCTCCCAGCCGGGAAGAGATGACCAAGAATCAAGTGT<br>CCCTGACCTGTCTGGTCAAGGGCTTCTACCCCTGCGAT<br>ATCGCCGTGGAGTGGGAGTCCAACGGCCAGCCCGAGA<br>ACAACTACAAGACCACCCCTCCCGTGCTGGACTCCGAC<br>GGCTCATTCTTCCTGTACTCCAAGCTGACCGTGGACAA<br>GTCCCGGTGGCAGCAGGGCAACGTGTTCTCCTGCTCCG<br>TGATGCACGAGGCCCTGCACAACCACTACACCCAGAA<br>GTCCCTGAGCCTGTCCCCTGGCAAG |
| SEQ ID NO: 81 | LCDR1<br>(Combined) | SASSSVIYMH |
| SEQ ID NO: 82 | LCDR2<br>(Combined) | DTSKLAS |
| SEQ ID NO: 83 | LCDR3<br>(Combined) | QQWSSNPLT |
| SEQ ID NO: 84 | LCDR1<br>(Kabat) | SASSSVIYMH |
| SEQ ID NO: 85 | LCDR2<br>(Kabat) | DTSKLAS |
| SEQ ID NO: 86 | LCDR3<br>(Kabat) | QQWSSNPLT |
| SEQ ID NO: 87 | LCDR1<br>(Chothia) | SSSVIY |
| SEQ ID NO: 88 | LCDR2<br>(Chothia) | DTS |
| SEQ ID NO: 89 | LCDR3<br>(Chothia) | WSSNPL |
| SEQ ID NO: 90 | LCDR1<br>(IMGT) | SSVIY |
| SEQ ID NO: 91 | LCDR2<br>(IMGT) | DTS |
| SEQ ID NO: 92 | LCDR3<br>(IMGT) | QQWSSNPLT |
| SEQ ID NO: 93 | VL | EIVLTQSPATLSASPGERVTMSCSASSSVIYMHWYQQKP<br>GQAPRRWIYDTSKLASGVPARFSGSGSGTDYTLTISSMEP<br>EDAAVYYCQQWSSNPLTFGQGTKLEIK |
| SEQ ID NO: 94 | DNA VL | GAGATCGTGCTGACACAGTCCCCTGCCACCCTGTCCGC<br>CTCTCCAGGCGAGCGCGTGACAATGTCCTGCTCCGCCT<br>CCTCCTCCGTGATCTACATGCACTGGTATCAGCAGAAG<br>CCCGGCCAGGCCCCTCGGCGGTGGATCTACGATACCTC<br>CAAGCTGGCCTCCGGCGTGCCCGCCAGATTCTCCGGCT<br>CTGGCTCTGGCACCGACTACACCCTGACCATCTCCAGC<br>ATGGAACCCGAGGACGCCGCCGTGTACTACTGCCAGC<br>AGTGGTCCTCCAACCCTCTGACCTTCGGCCAGGGCACC<br>AAGCTGGAAATCAAG |
| SEQ ID NO: 95 | Light Chain | EIVLTQSPATLSASPGERVTMSCSASSSVIYMHWYQQKP<br>GQAPRRWIYDTSKLASGVPARFSGSGSGTDYTLTISSMEP<br>EDAAVYYCQQWSSNPLTFGQGTKLEIKRTVAAPSVFIFPP<br>SDEQLKSGTASVVCLLNNFYPREAKVQWKVDNALQSGN<br>SQESVTEQDSKDSTYSLSSTLTLSKADYEKHKVYACEVTH<br>QGLSSPVTKSFNRGEC |
| SEQ ID NO: 96 | DNA Light<br>Chain | GAGATCGTGCTGACACAGTCCCCTGCCACCCTGTCCGC<br>CTCTCCAGGCGAGCGCGTGACAATGTCCTGCTCCGCCT<br>CCTCCTCCGTGATCTACATGCACTGGTATCAGCAGAAG<br>CCCGGCCAGGCCCCTCGGCGGTGGATCTACGATACCTC<br>CAAGCTGGCCTCCGGCGTGCCCGCCAGATTCTCCGGCT<br>CTGGCTCTGGCACCGACTACACCCTGACCATCTCCAGC<br>ATGGAACCCGAGGACGCCGCCGTGTACTACTGCCAGC<br>AGTGGTCCTCCAACCCTCTGACCTTCGGCCAGGGCACC<br>AAGCTGGAAATCAAGCGTACGGTGGCCGCTCCCAGCG<br>TGTTCATCTTCCCCCCCAGCGACGAGCAGCTGAAGAGC<br>GGCACCGCCAGCGTGGTGTGCCTGCTGAACAACTTCTA<br>CCCCCGGGAGGCCAAGGTGCAGTGGAAGGTGGACAA<br>CGCCCTGCAGAGCGGCAACAGCCAGGAGAGCGTCACC<br>GAGCAGGACAGCAAGGACTCCACCTACAGCCTGAGCA |

TABLE 1-continued

Examples of Anti-CCR7 Antibodies of the Present Invention

```
GCACCCTGACCCTGAGCAAGGCCGACTACGAGAAGCA
TAAGGTGTACGCCTGCGAGGTGACCCACCAGGGCCTG
TCCAGCCCCGTGACCAAGAGCTTCAACAGGGGCGAGT
GC
```

Other antibodies of the invention include those where the amino acids or nucleic acids encoding the amino acids have been mutated, yet have at least 60, 70, 80, 90 or 95 percent identity to the sequences described in Tables 1 and 4. In some embodiments, 1, 2, 3, 4 or 5 amino acids have been mutated in the variable regions when compared with the variable regions depicted in the sequence described in Tables 1 and 4, while retaining substantially the same therapeutic activity as the antibodies listed in Tables 1 and 4.

Since each of these antibodies can bind to CCR7, the VH, VL, full length light chain, and full length heavy chain sequences (amino acid sequences and the nucleotide sequences encoding the amino acid sequences) can be "mixed and matched" to create other CCR7-binding antibodies of the invention. Such "mixed and matched" CCR7-binding antibodies can be tested using the binding assays known in the art (e.g., ELISAs, and other assays described in the Example section). When these chains are mixed and matched, a VH sequence from a particular VH/VL pairing should be replaced with a structurally similar VH sequence. Likewise a full length heavy chain sequence from a particular full length heavy chain/full length light chain pairing should be replaced with a structurally similar full length heavy chain sequence. Likewise, a VL sequence from a particular VH/VL pairing should be replaced with a structurally similar VL sequence. Likewise a full length light chain sequence from a particular full length heavy chain/full length light chain pairing should be replaced with a structurally similar full length light chain sequence. Accordingly, in one aspect, the invention provides an isolated monoclonal antibody or antigen binding region thereof having: a heavy chain variable region comprising an amino acid sequence selected from the group consisting of SEQ ID NOs: 13, 45, 77 and 608; and a light chain variable region comprising an amino acid sequence selected from the group consisting of SEQ ID NOs: 29, 61, 93 and 624; wherein the antibody specifically binds to CCR7.

In another aspect, the invention provides (i) an isolated monoclonal antibody having: a full length heavy chain comprising an amino acid sequence that has been optimized for expression in the cell of a mammalian expression system selected from the group consisting of SEQ ID NOs: 15, 47, 79 and 610; and a full length light chain comprising an amino acid sequence that has been optimized for expression in the cell of a mammalian selected from the group consisting of SEQ ID NOs: 31, 63, 95 and 626; or (ii) a functional protein comprising an antigen binding portion thereof.

In another aspect, the present invention provides CCR7-binding antibodies that comprise the heavy chain and light chain CDR1s, CDR2s and CDR3s as described in Tables 1 and 4, or combinations thereof. The amino acid sequences of the VH CDR1s of the antibodies are shown, for example, in SEQ ID NOs: 1, 4, 7, 10, 33, 36, 39, 42, 65, 68, 71 and 74. The amino acid sequences of the VH CDR2s of the antibodies are and are shown, for example, in SEQ ID NOs: 2, 5, 8, 11, 34, 37, 40, 43, 66, 69, 72 and 75. The amino acid sequences of the VH CDR3s of the antibodies are shown, for example, in SEQ ID NOs: 3, 6, 9, 12, 35, 38, 41, 44, 67, 70, 73 and 76. The amino acid sequences of the VL CDR1s of the antibodies are shown, for example, in SEQ ID NOs: 17, 20, 23, 26, 49, 52, 55, 58, 81, 84, 87 and 90. The amino acid sequences of the VL CDR2s of the antibodies are shown, for example, in SEQ ID NOs: 18, 21, 24, 27, 50, 53, 56, 59, 82, 85, 88 and 91. The amino acid sequences of the VL CDR3s of the antibodies are shown, for example, in SEQ ID NOs: 19, 22, 25, 28, 51, 54, 57, 60, 83, 86, 89 and 92.

Given that each of these antibodies can bind to CCR7 and that antigen-binding specificity is provided primarily by the CDR1, 2 and 3 regions, the VH CDR1, CDR2 and CDR3 sequences and VL CDR1, CDR2 and CDR3 sequences can be "mixed and matched" (i.e., CDRs from different antibodies can be mixed and matched. Such "mixed and matched" CCR7-binding antibodies can be tested using the binding assays known in the art and those described in the Examples (e.g., ELISAs). When VH CDR sequences are mixed and matched, the CDR1, CDR2 and/or CDR3 sequence from a particular VH sequence should be replaced with a structurally similar CDR sequence(s). Likewise, when VL CDR sequences are mixed and matched, the CDR1, CDR2 and/or CDR3 sequence from a particular VL sequence should be replaced with a structurally similar CDR sequence(s). It will be readily apparent to the ordinarily skilled artisan that novel VH and VL sequences can be created by substituting one or more VH and/or VL CDR region sequences with structurally similar sequences from the CDR sequences shown herein for monoclonal antibodies of the present invention.

Accordingly, in some embodiments, the present invention provides an isolated monoclonal antibody or antigen binding region thereof comprising a heavy chain CDR1 comprising an amino acid sequence selected from the group consisting of SEQ ID NOs: 1, 4, 7, 10, 33, 36, 39, 42, 65, 68, 71, 74, 596, 599, 602 and 605; a heavy chain CDR2 comprising an amino acid sequence selected from the group consisting of SEQ ID NOs: 2, 5, 8, 11, 34, 37, 40, 43, 66, 69, 72, 75, 597, 600, 603 and 606; a heavy chain CDR3 comprising an amino acid sequence selected from the group consisting of SEQ ID NOs: 3, 6, 9, 12, 35, 38, 41, 44, 67, 70, 73, 76, 598, 601, 604 and 607; a light chain CDR1 comprising an amino acid sequence selected from the group consisting of SEQ ID NOs: 17, 20, 23, 26, 49, 52, 55, 58, 81, 84, 87, 90, 612, 615, 618 and 621; a light chain CDR2 comprising an amino acid sequence selected from the group consisting of SEQ ID NOs: 18, 21, 24, 27, 50, 53, 56, 59, 82, 85, 88, 91, 613, 616, 619 and 622; and a light chain CDR3 comprising an amino acid sequence selected from the group consisting of SEQ ID NOs: 19, 22, 25, 28, 51, 54, 57, 60, 83, 86, 89, 92, 614, 617, 620 and 623; wherein the antibody specifically binds CCR7.

In a specific embodiment, an antibody or antibody fragment (e.g., antigen binding fragments) that specifically binds to CCR7 comprises a heavy chain CDR1 of SEQ ID NO:1, a heavy chain CDR2 of SEQ ID NO:2; a heavy chain CDR3 of SEQ ID NO:3; a light chain CDR1 of SEQ ID NO:17; a light chain CDR2 of SEQ ID NO:18; and a light chain CDR3 of SEQ ID NO:19.

In a specific embodiment, an antibody or antibody fragment (e.g., antigen binding fragments) that specifically binds to CCR7 comprises a heavy chain CDR1 of SEQ ID NO:4, a heavy chain CDR2 of SEQ ID NO:5; a heavy chain CDR3 of SEQ ID NO:6; a light chain CDR1 of SEQ ID NO:20; a light chain CDR2 of SEQ ID NO:21; and a light chain CDR3 of SEQ ID NO:22.

In a specific embodiment, an antibody or antibody fragment (e.g., antigen binding fragments) that specifically binds to CCR7 comprises a heavy chain CDR1 of SEQ ID NO:7, a heavy chain CDR2 of SEQ ID NO:8; a heavy chain CDR3 of SEQ ID NO:9; a light chain CDR1 of SEQ ID NO:23; a light chain CDR2 of SEQ ID NO:24; and a light chain CDR3 of SEQ ID NO:25.

In a specific embodiment, an antibody or antibody fragment (e.g., antigen binding fragments) that specifically binds to CCR7 comprises a heavy chain CDR1 of SEQ ID NO:10, a heavy chain CDR2 of SEQ ID NO:11; a heavy chain CDR3 of SEQ ID NO:12; a light chain CDR1 of SEQ ID NO:26; a light chain CDR2 of SEQ ID NO:27; and a light chain CDR3 of SEQ ID NO:28.

In a specific embodiment, an antibody or antibody fragment (e.g., antigen binding fragments) that specifically binds to CCR7 comprises a heavy chain CDR1 of SEQ ID NO:33, a heavy chain CDR2 of SEQ ID NO:34; a heavy chain CDR3 of SEQ ID NO:35; a light chain CDR1 of SEQ ID NO:49; a light chain CDR2 of SEQ ID NO:50; and a light chain CDR3 of SEQ ID NO:51.

In a specific embodiment, an antibody or antibody fragment (e.g., antigen binding fragments) that specifically binds to CCR7 comprises a heavy chain CDR1 of SEQ ID NO:36, a heavy chain CDR2 of SEQ ID NO:37; a heavy chain CDR3 of SEQ ID NO:38; a light chain CDR1 of SEQ ID NO:52; a light chain CDR2 of SEQ ID NO:53; and a light chain CDR3 of SEQ ID NO:54.

In a specific embodiment, an antibody or antibody fragment (e.g., antigen binding fragments) that specifically binds to CCR7 comprises a heavy chain CDR1 of SEQ ID NO:39, a heavy chain CDR2 of SEQ ID NO:40; a heavy chain CDR3 of SEQ ID NO:41; a light chain CDR1 of SEQ ID NO:55; a light chain CDR2 of SEQ ID NO:56; and a light chain CDR3 of SEQ ID NO:57.

In a specific embodiment, an antibody or antibody fragment (e.g., antigen binding fragments) that specifically binds to CCR7 comprises a heavy chain CDR1 of SEQ ID NO:42, a heavy chain CDR2 of SEQ ID NO:43; a heavy chain CDR3 of SEQ ID NO:44; a light chain CDR1 of SEQ ID NO:58; a light chain CDR2 of SEQ ID NO:59; and a light chain CDR3 of SEQ ID NO:60.

In a specific embodiment, an antibody or antibody fragment (e.g., antigen binding fragments) that specifically binds to CCR7 comprises a heavy chain CDR1 of SEQ ID NO:65, a heavy chain CDR2 of SEQ ID NO:66; a heavy chain CDR3 of SEQ ID NO:67; a light chain CDR1 of SEQ ID NO:81; a light chain CDR2 of SEQ ID NO:82; and a light chain CDR3 of SEQ ID NO:83.

In a specific embodiment, an antibody or antibody fragment (e.g., antigen binding fragments) that specifically binds to CCR7 comprises a heavy chain CDR1 of SEQ ID NO:68, a heavy chain CDR2 of SEQ ID NO:69; a heavy chain CDR3 of SEQ ID NO:70; a light chain CDR1 of SEQ ID NO:84; a light chain CDR2 of SEQ ID NO:85; and a light chain CDR3 of SEQ ID NO:86.

In a specific embodiment, an antibody or antibody fragment (e.g., antigen binding fragments) that specifically binds to CCR7 comprises a heavy chain CDR1 of SEQ ID NO:71, a heavy chain CDR2 of SEQ ID NO:72; a heavy chain CDR3 of SEQ ID NO:73; a light chain CDR1 of SEQ ID NO:87; a light chain CDR2 of SEQ ID NO:88; and a light chain CDR3 of SEQ ID NO:89.

In a specific embodiment, an antibody or antibody fragment (e.g., antigen binding fragments) that specifically binds to CCR7 comprises a heavy chain CDR1 of SEQ ID NO:74, a heavy chain CDR2 of SEQ ID NO:75; a heavy chain CDR3 of SEQ ID NO:76; a light chain CDR1 of SEQ ID NO:90; a light chain CDR2 of SEQ ID NO:91; and a light chain CDR3 of SEQ ID NO:92.

In a specific embodiment, an antibody or antibody fragment (e.g., antigen binding fragments) that specifically binds to CCR7 comprises a heavy chain variable region that comprises an HCDR1 of SEQ ID NO:596, an HCDR2 of SEQ ID NO:597, and an HCDR3 of SEQ ID NO:598; and a light chain variable region that comprises an LCDR1 of SEQ ID NO:612, an LCDR2 of SEQ ID NO:613, and an LCDR3 of SEQ ID NO:614.

In a specific embodiment, an antibody or antibody fragment (e.g., antigen binding fragments) that specifically binds to CCR7 comprises a heavy chain variable region that comprises an HCDR1 of SEQ ID NO:599, an HCDR2 of SEQ ID NO:600, and an HCDR3 of SEQ ID NO:601; and a light chain variable region that comprises an LCDR1 of SEQ ID NO:615, an LCDR2 of SEQ ID NO:616, and an LCDR3 of SEQ ID NO:617.

In a specific embodiment, an antibody or antibody fragment (e.g., antigen binding fragments) that specifically binds to CCR7 comprises a heavy chain variable region that comprises an HCDR1 of SEQ ID NO:602, an HCDR2 of SEQ ID NO:603, and an HCDR3 of SEQ ID NO:604; and a light chain variable region that comprises an LCDR1 of SEQ ID NO:618, an LCDR2 of SEQ ID NO:619, and an LCDR3 of SEQ ID NO:620.

In a specific embodiment, an antibody or antibody fragment (e.g., antigen binding fragments) that specifically binds to CCR7 comprises a heavy chain variable region that comprises an HCDR1 of SEQ ID NO:605, an HCDR2 of SEQ ID NO:606, and an HCDR3 of SEQ ID NO:607; and a light chain variable region that comprises an LCDR1 of SEQ ID NO:621, an LCDR2 of SEQ ID NO:622, and an LCDR3 of SEQ ID NO:623.

In a specific embodiment, an antibody or antibody fragment (e.g., antigen binding fragments) that specifically binds to CCR7 comprises a heavy chain variable region (VH) comprising the amino acid sequence of SEQ ID NO:13, and a light chain variable region (VL) comprising the amino acid sequence of SEQ ID NO:29.

In a specific embodiment, an antibody or antibody fragment (e.g., antigen binding fragments) that specifically binds to CCR7 comprises a heavy chain variable region (VH) comprising the amino acid sequence of SEQ ID NO:45, and a light chain variable region (VL) comprising the amino acid sequence of SEQ ID NO:61.

In a specific embodiment, an antibody or antibody fragment (e.g., antigen binding fragments) that specifically binds to CCR7 comprises a heavy chain variable region (VH) comprising the amino acid sequence of SEQ ID NO:77, and a light chain variable region (VL) comprising the amino acid sequence of SEQ ID NO:93.

In a specific embodiment, an antibody or antibody fragment (e.g., antigen binding fragments) that specifically binds to CCR7 comprises a heavy chain variable region (VH) comprising the amino acid sequence of SEQ ID NO:608, and a light chain variable region (VL) comprising the amino acid sequence of SEQ ID NO:624.

In a specific embodiment, an antibody or antibody fragment (e.g., antigen binding fragments) that specifically binds to CCR7 comprises a heavy chain comprising the amino acid sequence of SEQ ID NO:15, and a light chain comprising the amino acid sequence of SEQ ID NO:31.

In a specific embodiment, an antibody or antibody fragment (e.g., antigen binding fragments) that specifically binds to CCR7 comprises a heavy chain comprising the amino acid sequence of SEQ ID NO:47, and a light chain comprising the amino acid sequence of SEQ ID NO:63.

In a specific embodiment, an antibody or antibody fragment (e.g., antigen binding fragments) that specifically binds to CCR7 comprises a heavy chain comprising the amino acid sequence of SEQ ID NO:79, and a light chain comprising the amino acid sequence of SEQ ID NO:95.

In a specific embodiment, an antibody or antibody fragment (e.g., antigen binding fragments) that specifically binds to CCR7 comprises a heavy chain comprising the amino acid sequence of SEQ ID NO:610, and a light chain comprising the amino acid sequence of SEQ ID NO:626

In certain embodiments, an antibody that specifically binds to CCR7 is an antibody or antibody fragment (e.g., antigen binding fragment) that is described in Tables 1 and 4.

1. Identification of Epitopes and Antibodies That Bind to the Same Epitope

The present invention also provides antibodies and antibody fragments (e.g., antigen binding fragments) that specifically bind to the same epitope as the anti-CCR7 antibodies described in Tables 1 and 4, or cross compete with the antibodies described in Tables 1 and 4. Additional antibodies and antibody fragments (e.g., antigen binding fragments) can therefore be identified based on their ability to cross-compete (e.g., to competitively inhibit the binding of, in a statistically significant manner) with other antibodies of the invention in CCR7 binding assays, for example, via BIA-CORE or assays known to persons skilled in the art for measuring binding. The ability of a test antibody to inhibit the binding of antibodies and antibody fragments (e.g., antigen binding fragments) of the present invention to a CCR7 (e.g., human CCR7) demonstrates that the test antibody can compete with that antibody or antibody fragment (e.g., antigen binding fragments) for binding to CCR7; such an antibody may, according to non-limiting theory, bind to the same or a related (e.g., a structurally similar or spatially proximal or overlapping) epitope on the CCR7 protein as the antibody or antibody fragment (e.g., antigen binding fragments) with which it competes. In certain embodiments, the antibodies that bind to the same epitope on CCR7 as the antibodies or antibody fragments (e.g., antigen binding fragments) described in Tables 1 and 4 are human or humanized monoclonal antibodies. Such human or humanized monoclonal antibodies can be prepared and isolated as described herein.

2. Further Alteration of the Framework of Fc Region

The immunoconjugates of the invention may comprise modified antibodies or antigen binding fragments thereof that further comprise modifications to framework residues within VH and/or VL, e.g. to improve the properties of the antibody. In some embodiments, the framework modifications are made to decrease the immunogenicity of the antibody. For example, one approach is to "back-mutate" one or more framework residues to the corresponding germline sequence. More specifically, an antibody that has undergone somatic mutation may contain framework residues that differ from the germline sequence from which the antibody is derived. Such residues can be identified by comparing the antibody framework sequences to the germline sequences from which the antibody is derived. To return the framework region sequences to their germline configuration, the somatic mutations can be "back-mutated" to the germline sequence by, for example, site-directed mutagenesis. Such "back-mutated" antibodies are also intended to be encompassed by the invention.

Another type of framework modification involves mutating one or more residues within the framework region, or even within one or more CDR regions, to remove T-cell epitopes to thereby reduce the potential immunogenicity of the antibody. This approach is also referred to as "deimmunization" and is described in further detail in U.S. Patent Publication No. 20030153043 by Carr et al.

In addition or in the alternative to modifications made within the framework or CDR regions, antibodies of the invention may be engineered to include modifications within the Fc region, typically to alter one or more functional properties of the antibody, such as serum half-life, complement fixation, Fc receptor binding, and/or antigen-dependent cellular cytotoxicity (ADCC). Furthermore, an antibody of the invention may be chemically modified (e.g., one or more chemical moieties can be attached to the antibody) or be modified to alter its glycosylation, again to alter one or more functional properties of the antibody. Each of these embodiments is described in further detail below.

In one embodiment, the hinge region of CH1 is modified such that the number of cysteine residues in the hinge region is altered, e.g., increased or decreased. This approach is described further in U.S. Pat. No. 5,677,425 by Bodmer et al. The number of cysteine residues in the hinge region of CH1 is altered to, for example, facilitate assembly of the light and heavy chains or to increase or decrease the stability of the antibody.

In some embodiments, the antibody or antibody fragment disclosed herein include modified or engineered amino acid residues, e.g., one or more cysteine residues, as sites for conjugation to a drug moiety (Junutula J R, et al., Nat Biotechnol 2008, 26:925-932). In one embodiment, the invention provides a modified antibody or antibody fragment comprising a substitution of one or more amino acids with cysteine at the positions described herein. Sites for cysteine substitution are in the constant regions of the antibody or antibody fragment and are thus applicable to a variety of antibody or antibody fragment, and the sites are selected to provide stable and homogeneous conjugates. A modified antibody or fragment can have one, two or more cysteine substitutions, and these substitutions can be used in combination with other modification and conjugation methods as described herein. Methods for inserting cysteine at specific locations of an antibody are known in the art, see, e.g., Lyons et A, (1990) Protein Eng., 3:703-708, WO 2011/005481, W02014/124316, WO 2015/138615. In certain embodiments, a modified antibody comprises a substitution of one or more amino acids with cysteine on its constant region selected from positions 117, 119, 121, 124, 139, 152, 153, 155, 157, 164, 169, 171, 174, 189, 191, 195, 197, 205, 207, 246, 258, 269, 274, 286, 288, 290, 292, 293, 320, 322, 326, 333, 334, 335, 337, 344, 355, 360, 375, 382, 390, 392, 398, 400 and 422 of a heavy chain of the antibody, and wherein the positions are numbered according to the EU system. In some embodiments a modified antibody or antibody fragment comprises a substitution of one or more amino acids with cysteine on its constant region selected from positions 107, 108, 109, 114, 129, 142, 143, 145, 152, 154, 156, 159, 161, 165, 168, 169, 170, 182, 183, 197, 199, and 203 of a light chain of the antibody or antibody fragment, wherein the positions are numbered according to the EU system, and wherein the light chain is a human kappa light chain. In certain embodiments a modified antibody or antibody fragment thereof comprises a combination of substitution of two or more amino acids with cysteine on its constant regions wherein the combinations comprise substitutions at positions 375 of an antibody heavy chain, position 152 of an antibody heavy chain, position 360 of an antibody heavy chain, or position 107 of an antibody light chain and wherein the positions are numbered according to the EU system. In certain embodiments a modified antibody or antibody fragment thereof comprises a substitution of one amino acid with cysteine on its constant regions wherein the substitution is position 375 of an antibody heavy chain, position 152 of an antibody heavy chain, position 360 of an antibody heavy chain, position 107 of an antibody light chain, position 165 of an antibody light chain or position 159 of an antibody light chain and wherein the positions are numbered according to the EU system, and wherein the light chain is a kappa chain. In particular embodiments a modified antibody or antibody fragment thereof comprises a combination of substitution of two amino acids with cysteine on its constant regions wherein the combinations comprise substitutions at positions 375 of an antibody heavy chain and position 152 of an antibody heavy chain, wherein the positions are numbered according to the EU system. In particular embodiments a modified antibody or antibody fragment thereof comprises a substitution of one amino acid with cysteine at position 360 of an antibody heavy chain, wherein the positions are numbered according to the EU system. In other particular embodiments a modified antibody or antibody fragment thereof comprises a substitution of one amino acid with cysteine at position 107 of an antibody light chain and wherein the positions are numbered according to the EU system, and wherein the light chain is a kappa chain.

In additional embodiments antibodies or antibody fragments (e.g., antigen binding fragment) useful in immunoconjugates of the invention include modified or engineered antibodies, such as an antibody modified to introduce one or more other reactive amino acid (other than cysteine), including Pcl, pyrrolysine, peptide tags (such as S6, A1 and ybbR tags), and non-natural amino acids, in place of at least one amino acid of the native sequence, thus providing a reactive site on the antibody or antigen binding fragment for conjugation to a drug moiety or a linker-drug moiety with complementary reactivity. For example, the antibodies or antibody fragments can be modified to incorporate Pc1 or pyrrolysine (W. Ou, et al., (2011) PNAS 108 (26), 10437-10442; WO2014124258) or unnatural amino acids (J. Y. Axup, et al., Proc Natl Acad Sci U.S.A., 109 (2012), pp. 16101-16106; for review, see C. C. Liu and P. G. Schultz (2010) Annu Rev Biochem 79, 413-444; C. H. Kim, et al., (2013) Curr Opin Chem Biol. 17, 412-419) as sites for conjugation to a drug. Similarly, peptide tags for enzymatic conjugation methods can be introduced into an antibody (Strop P., et al., Chem Biol. 2013, 20(2):161-7; Rabuka D., Curr Opin Chem Biol. 2010 December; 14(6):790-6; Rabuka D, et al., Nat Protoc. 2012, 7(6):1052-67). One other example is the use of 4'-phosphopantetheinyl transferases (PPTase) for the conjugation of Co-enzyme A analogs (WO2013184514), and (Grünewald et al., (2015) Bioconjugate Chem. 26 (12), 2554-62). Methods for conjugating such modified or engineered antibodies with payloads or linker-payload combinations are known in the art.

In another embodiment, the Fc hinge region of an antibody is mutated to decrease the biological half-life of the antibody. More specifically, one or more amino acid mutations are introduced into the CH2-CH3 domain interface region of the Fc-hinge fragment such that the antibody has impaired Staphylococcyl protein A (SpA) binding relative to native Fc-hinge domain SpA binding. This approach is described in further detail in U.S. Pat. No. 6,165,745 by Ward et al.

In yet other embodiments, the Fc region is altered by replacing at least one amino acid residue with a different amino acid residue to alter the effector functions of the antibody. For example, one or more amino acids can be replaced with a different amino acid residue such that the antibody has an altered affinity for an effector ligand but retains the antigen-binding ability of the parent antibody. The effector ligand to which affinity is altered can be, for example, an Fc receptor or the C1 component of complement. This approach is described in, e.g., U.S. Pat. Nos. 5,624,821 and 5,648,260, both by Winter et al.

In another embodiment, one or more amino acids selected from amino acid residues can be replaced with a different amino acid residue such that the antibody has altered C1q binding and/or reduced or abolished complement dependent cytotoxicity (CDC). This approach is described in, e.g., U.S. Pat. No. 6,194,551 by Idusogie et al.

In another embodiment, one or more amino acid residues are altered to thereby alter the ability of the antibody to fix complement. This approach is described in, e.g., the PCT Publication WO 94/29351 by Bodmer et al. Allotypic amino acid residues include, but are not limited to, constant region of a heavy chain of the IgG1, IgG2, and IgG3 subclasses as well as constant region of a light chain of the kappa isotype as described by Jefferis et al., MAbs. 1:332-338 (2009).

Antibody fusion protein complexes containing such mutations mediate reduced or no antibody-dependent cellular cytotoxicity (ADCC) or complement-dependent cytotoxicity (CDC). In some embodiments, amino acid residues L234 and L235 of the IgG1 constant region are substituted to A234 and A235. In some embodiments, amino acid residue N267 of the IgG1 constant region is substituted to A267. In some embodiments, amino acid residues D265 and P329 of the IgG1 constant region are substituted to A265 and A329. In certain embodiments an immunoglobulin heavy chain optionally comprises a mutation or combination of mutations conferring reduced effector function selected from any of D265A, P329A, P329G, N297A, D265A/P329A, D265A/N297A, L234/L235A, P329A/L234A/L235A, and P329G/L234A/L235A. In particular embodiments, an immunoconjugate comprises an immunoglobulin heavy chain comprising a mutation or combination of mutations conferring reduced effector function selected from any of D265A, P329A, P329G, N297A, D265A/P329A, D265A/N297A, L234/L235A, P329A/L234A/L235A, and P329G/L234A/L235A.

In another embodiment, one or more amino acid residues are altered to thereby alter the ability of the antibody to fix complement. This approach is described in, e.g., the PCT Publication WO 94/29351 by Bodmer et al. In a specific embodiment, one or more amino acids of an antibody or antigen binding fragment thereof of the present invention are replaced by one or more allotypic amino acid residues. Allotypic amino acid residues also include, but are not limited to, the constant region of the heavy chain of the IgG1, IgG2, and IgG3 subclasses as well as the constant region of the light chain of the kappa isotype as described by Jefferis et al., MAbs. 1:332-338 (2009).

In still another embodiment, the glycosylation of an antibody is modified. For example, an aglycosylated antibody can be made (i.e., the antibody lacks glycosylation). Glycosylation can be altered to, for example, increase the affinity of the antibody for "antigen." Such carbohydrate modifications can be accomplished by, for example, altering one or more sites of glycosylation within the antibody sequence. For example, one or more amino acid substitutions can be made that result in elimination of one or more variable region framework glycosylation sites to thereby eliminate glycosylation at that site. Such aglycosylation may increase the affinity of the antibody for antigen. Such an approach is described in, e.g., U.S. Pat. Nos. 5,714,350 and 6,350,861 by Co et al.

In another embodiment, the antibody is modified to increase its biological half-life. Various approaches are possible. For example, one or more of the following mutations can be introduced: T252L, T254S, T256F, as described in U.S. Pat. No. 6,277,375 to Ward. Alternatively, to increase the biological half-life, the antibody can be altered within the CH1 or CL region to contain a salvage receptor binding epitope taken from two loops of a CH2 domain of an Fc region of an IgG, as described in U.S. Pat. Nos. 5,869,046 and 6,121,022 by Presta et al.

3. Production of the CCR7 Antibodies

Anti-CCR7 antibodies and antibody fragments (e.g., antigen binding fragments) thereof can be produced by any means known in the art, including but not limited to, recombinant expression, chemical synthesis, and enzymatic digestion of antibody tetramers, whereas full-length monoclonal antibodies can be obtained by, e.g., hybridoma or recombinant production. Recombinant expression can be from any appropriate host cells known in the art, for example, mammalian host cells, bacterial host cells, yeast host cells, insect host cells, etc.

The invention further provides polynucleotides encoding the antibodies described herein, e.g., polynucleotides encoding heavy or light chain variable regions or segments comprising the complementarity determining regions as described herein. In some embodiments, the polynucleotide encoding the heavy chain variable regions has at least 85%, 89%, 90%, 91%, 92%, 93%, 94%, 95%, 96%, 97%, 98%, 99%, or 100% nucleic acid sequence identity with a polynucleotide selected from the group consisting of SEQ ID NOs: 14, 46, 78 and 609. In some embodiments, the polynucleotide encoding the light chain variable regions has at least 85%, 89%, 90%, 91%, 92%, 93%, 94%, 95%, 96%, 97%, 98%, 99%, or 100% nucleic acid sequence identity with a polynucleotide selected from the group consisting of SEQ ID NOs: 30, 62, 94 and 625.

In some embodiments, the polynucleotide encoding the heavy chain has at least 85%, 89%, 90%, 91%, 92%, 93%, 94%, 95%, 96%, 97%, 98%, 99%, or 100% nucleic acid sequence identity with a polynucleotide of SEQ ID NO: 16, 48, 80 or 611. In some embodiments, the polynucleotide encoding the light chain has at least 85%, 89%, 90%, 91%, 92%, 93%, 94%, 95%, 96%, 97%, 98%, 99%, or 100% nucleic acid sequence identity with a polynucleotide of SEQ ID NO: 32, 64, 96 or 627.

The polynucleotides of the invention can encode only the variable region sequence of an anti-CCR7 antibody. They can also encode both a variable region and a constant region of the antibody. Some of the polynucleotide sequences encode a polypeptide that comprises variable regions of both the heavy chain and the light chain of one of the exemplified mouse anti-CCR7 antibody. Some other polynucleotides encode two polypeptide segments that respectively are substantially identical to the variable regions of the heavy chain and the light chain of one of the mouse antibodies.

The polynucleotide sequences can be produced by de novo solid-phase DNA synthesis or by PCR mutagenesis of an existing sequence (e.g., sequences as described in the Examples below) encoding an anti-CCR7 antibody or its binding fragment. Direct chemical synthesis of nucleic acids can be accomplished by methods known in the art, such as the phosphotriester method of Narang et al., Meth. Enzymol. 68:90, 1979; the phosphodiester method of Brown et al., Meth. Enzymol. 68:109, 1979; the diethylphosphoramidite method of Beaucage et al., Tetra. Lett., 22:1859, 1981; and the solid support method of U.S. Pat. No. 4,458,066. Introducing mutations to a polynucleotide sequence by PCR can be performed as described in, e.g., PCR Technology: Principles and Applications for DNA Amplification, H. A. Erlich (Ed.), Freeman Press, NY, N.Y., 1992; PCR Protocols: A Guide to Methods and Applications, Innis et al. (Ed.), Academic Press, San Diego, Calif., 1990; Mattila et al., Nucleic Acids Res. 19:967, 1991; and Eckert et al., PCR Methods and Applications 1:17, 1991.

Also provided in the invention are expression vectors and host cells for producing the anti-CCR7 antibodies described above. Various expression vectors can be employed to express the polynucleotides encoding the anti-CCR7 antibody chains or binding fragments. Both viral-based and nonviral expression vectors can be used to produce the antibodies in a mammalian host cell. Nonviral vectors and systems include plasmids, episomal vectors, typically with an expression cassette for expressing a protein or RNA, and human artificial chromosomes (see, e.g., Harrington et al., Nat Genet 15:345, 1997). For example, nonviral vectors useful for expression of the anti-CCR7 polynucleotides and polypeptides in mammalian (e g., human) cells include pThioHis A, B & C, pcDNA™3.1/His, pEBVHis A, B & C (Invitrogen, San Diego, Calif.), MPSV vectors, and numerous other vectors known in the art for expressing other proteins. Useful viral vectors include vectors based on retroviruses, adenoviruses, adenoassociated viruses, herpes viruses, vectors based on SV40, papilloma virus, HBP Epstein Barr virus, vaccinia virus vectors and Semliki Forest virus (SFV). See Brent et al., supra; Smith, Annu. Rev. Microbiol. 49:807, 1995; and Rosenfeld et al., Cell 68:143, 1992.

The choice of expression vector depends on the intended host cells in which the vector is to be expressed. Typically, the expression vectors contain a promoter and other regulatory sequences (e.g., enhancers) that are operably linked to the polynucleotides encoding an anti-CCR7 antibody chain or fragment. In some embodiments, an inducible promoter is employed to prevent expression of inserted sequences except under inducing conditions. Inducible promoters include, e.g., arabinose, lacZ, metallothionein promoter or a heat shock promoter. Cultures of transformed organisms can be expanded under noninducing conditions without biasing the population for coding sequences whose expression products are better tolerated by the host cells. In addition to promoters, other regulatory elements may also be required or desired for efficient expression of an anti-CCR7 antibody chain or fragment. These elements typically include an ATG initiation codon and adjacent ribosome binding site or other sequences. In addition, the efficiency of expression may be enhanced by the inclusion of enhancers appropriate to the cell system in use (see, e.g., Scharf et al., Results Probl. Cell Differ. 20:125, 1994; and Bittner et al., Meth. Enzymol., 153:516, 1987). For example, the SV40 enhancer or CMV enhancer may be used to increase expression in mammalian host cells.

The expression vectors may also provide a secretion signal sequence position to form a fusion protein with polypeptides encoded by inserted anti-CCR7 antibody sequences. More often, the inserted anti-CCR7 antibody sequences are linked to a signal sequences before inclusion in the vector. Vectors to be used to receive sequences encoding anti-CCR7 antibody light and heavy chain variable domains sometimes also encode constant regions or parts thereof. Such vectors allow expression of the variable regions as fusion proteins with the constant regions thereby leading to production of intact antibodies or fragments thereof. Typically, such constant regions are human.

The host cells for harboring and expressing the anti-CCR7 antibody chains can be either prokaryotic or eukaryotic. E. coli is one prokaryotic host useful for cloning and expressing the polynucleotides of the present invention. Other microbial hosts suitable for use include bacilli, such as Bacillus subtilis, and other enterobacteriaceae, such as Salmonella, Serratia, and various Pseudomonas species. In these prokaryotic hosts, one can also make expression vectors, which typically contain expression control sequences compatible with the host cell (e.g., an origin of replication). In addition, any number of a variety of well-known promoters will be present, such as the lactose promoter system, a tryptophan (trp) promoter system, a beta-lactamase promoter system, or a promoter system from phage lambda. The promoters typically control expression, optionally with an operator sequence, and have ribosome binding site sequences and the like, for initiating and completing transcription and translation. Other microbes, such as yeast, can also be employed to express anti-CCR7 polypeptides of the invention. Insect cells in combination with baculovirus vectors can also be used.

In some preferred embodiments, mammalian host cells are used to express and produce the anti-CCR7 polypeptides of the present invention. For example, they can be either a hybridoma cell line expressing endogenous immunoglobulin genes (e.g., the myeloma hybridoma clones as described in the Examples) or a mammalian cell line harboring an exogenous expression vector (e.g., the SP2/0 myeloma cells exemplified below). These include any normal mortal or normal or abnormal immortal animal or human cell. For example, a number of suitable host cell lines capable of secreting intact immunoglobulins have been developed, including the CHO cell lines, various Cos cell lines, HeLa cells, myeloma cell lines, transformed B-cells and hybridomas. The use of mammalian tissue cell culture to express polypeptides is discussed generally in, e.g., Winnacker, From Genes to Clones, VCH Publishers, N.Y., N.Y., 1987. Expression vectors for mammalian host cells can include expression control sequences, such as an origin of replication, a promoter, and an enhancer (see, e.g., Queen et al., Immunol. Rev. 89:49-68, 1986), and necessary processing information sites, such as ribosome binding sites, RNA splice sites, polyadenylation sites, and transcriptional terminator sequences. These expression vectors usually contain promoters derived from mammalian genes or from mammalian viruses. Suitable promoters may be constitutive, cell type-specific, stage-specific, and/or modulatable or regulatable. Useful promoters include, but are not limited to, the metallothionein promoter, the constitutive adenovirus major late promoter, the dexamethasone-inducible MMTV promoter, the SV40 promoter, the MRP polIII promoter, the constitutive MPSV promoter, the tetracycline-inducible CMV promoter (such as the human immediate-early CMV promoter), the constitutive CMV promoter, and promoter-enhancer combinations known in the art.

Methods for introducing expression vectors containing the polynucleotide sequences of interest vary depending on the type of cellular host. For example, calcium chloride transfection is commonly utilized for prokaryotic cells, whereas calcium phosphate treatment or electroporation may be used for other cellular hosts (see generally Sambrook et al., Molecular Cloning: A Laboratory Manual, 4th ed.). Other methods include, e.g., electroporation, calcium phosphate treatment, liposome-mediated transformation, injection and microinjection, ballistic methods, virosomes, immunoliposomes, polycation:nucleic acid conjugates, naked DNA, artificial virions, fusion to the herpes virus structural protein VP22 (Elliot and O'Hare, Cell 88:223, 1997), agent-enhanced uptake of DNA, and ex vivo transduction. For long-term, high-yield production of recombinant proteins, stable expression will often be desired. For example, cell lines which stably express anti-CCR7 antibody chains or binding fragments can be prepared using expression vectors of the invention which contain viral origins of replication or endogenous expression elements and a selectable marker gene. Following introduction of the vector, cells may be allowed to grow for 1-2 days in an enriched media before they are switched to selective media. The purpose of the selectable marker is to confer resistance to selection, and its presence allows growth of cells which successfully express the introduced sequences in selective media. Resistant, stably transfected cells can be proliferated using tissue culture techniques appropriate to the cell type.

Therapeutic Uses

The antibodies, antibody fragments (e.g., antigen binding fragments), and antibody drug conjugates of the invention are useful in a variety of applications including, but not limited to, treatment or prevention of cancer, such as solid cancers or heme malignancies. In certain embodiments, the antibodies, antibody fragments (e.g., antigen binding fragments), and antibody drug conjugates of the invention are useful for inhibiting tumor growth, inducing differentiation, reducing tumor volume, and/or reducing the tumorigenicity of a tumor. The methods of use can be in vitro, ex vivo, or in vivo methods.

In one aspect, the antibodies, antibody fragments (e.g., antigen binding fragments), and antibody drug conjugates of the invention are useful for detecting the presence of CCR7 in a biological sample. The term "detecting" as used herein encompasses quantitative or qualitative detection. In certain embodiments, a biological sample comprises a cell or tissue. In certain embodiments, such tissues include normal and/or cancerous tissues that express CCR7 at higher levels relative to other tissues.

In one aspect, the invention provides a method of detecting the presence of CCR7 in a biological sample. In certain embodiments, the method comprises contacting the biological sample with an anti-CCR7 antibody under conditions permissive for binding of the antibody to the antigen, and detecting whether a complex is formed between the antibody and the antigen.

In one aspect, the invention provides a method of diagnosing a disorder associated with increased expression of CCR7. In certain embodiments, the method comprises contacting a test cell with an anti-CCR7 antibody; determining the level of expression (either quantitatively or qualitatively) of CCR7 on the test cell by detecting binding of the anti-CCR7 antibody to the CCR7 antigen; and comparing the level of expression of CCR7 in the test cell with the level of expression of CCR7 on a control cell (e.g., a normal cell of the same tissue origin as the test cell or a cell that expresses CCR7 at levels comparable to such a normal cell), wherein a higher level of expression of CCR7 on the test cell as compared to the control cell indicates the presence of a disorder associated with increased expression of CCR7. In certain embodiments, the test cell is obtained from an individual suspected of having a disorder associated with increased expression of CCR7. In certain embodiments, the disorder is a cell proliferative disorder, such as a cancer or a tumor. In certain embodiments, the method comprises measuring the copy number of the CCR7 gene in a test cell.

In certain embodiments, a method of diagnosis or detection, such as those described above, comprises detecting binding of an anti-CCR7 antibody to CCR7 expressed on the surface of a cell or in a membrane preparation obtained from a cell expressing CCR7 on its surface. An exemplary assay for detecting binding of an anti-CCR7 antibody to CCR7 expressed on the surface of a cell is a "FACS" assay.

Certain other methods can be used to detect binding of anti-CCR7 antibodies to CCR7. Such methods include, but are not limited to, antigen-binding assays that are well known in the art, such as Western blots, radioimmunoassays, ELISA (enzyme linked immunosorbent assay), "sandwich" immunoassays, immunoprecipitation assays, fluorescent immunoassays, protein A immunoassays, and immunohistochemistry (IHC).

In certain embodiments, anti-CCR7 antibodies are labeled. Labels include, but are not limited to, labels or moieties that are detected directly (such as fluorescent, chromophoric, electron-dense, chemiluminescent, and radioactive labels), as well as moieties, such as enzymes or ligands, that are detected indirectly, e.g., through an enzymatic reaction or molecular interaction.

In certain embodiments, anti-CCR7 antibodies are immobilized on an insoluble matrix Immobilization entails separating the anti-CCR7 antibody from any CCR7 protein that remains free in solution. This conventionally is accomplished by either insolubilizing the anti-CCR7 antibody before the assay procedure, as by adsorption to a water-insoluble matrix or surface (Bennich et al, U.S. Pat. No. 3,720,760), or by covalent coupling (for example, using glutaraldehyde cross-linking), or by insolubilizing the anti-CCR7 antibody after formation of a complex between the anti-CCR7 antibody and CCR7 protein, e.g., by immunoprecipitation.

Any of the above embodiments of diagnosis or detection can be carried out using an immunoconjugate of the invention in place of or in addition to an anti-CCR7 antibody.

In one embodiment, the invention provides a method of treating or preventing a disease comprising administering the antibodies, antibody fragments (e.g., antigen binding fragments), or antibody drug conjugates of the invention to a patient. The invention also provides use of the antibodies, antibody fragments (e.g., antigen binding fragments), or antibody drug conjugates of the invention to treat or prevent disease in a patient. In some embodiments, the invention provides antibodies, antibody fragments (e.g., antigen binding fragments), or antibody drug conjugates of the invention for use in the treatment or prevention of disease in a patient. In further embodiments, the invention provides use of the antibodies, antibody fragments (e.g., antigen binding fragments), or antibody drug conjugates of the invention in the manufacture of a medicament for treatment or prevention of disease in a patient.

In certain embodiments, the disease treated with the antibodies, antibody fragments (e.g., antigen binding fragments), and antibody drug conjugates of the invention is a cancer. In certain embodiments, the cancer is characterized by CCR7 expressing cells to which the antibodies, antibody fragments (e.g., antigen binding fragments), and antibody drug conjugates of the invention binds. In certain embodiments, the cancer is characterized by an increase in expression of CCR7 relative to a healthy patient. In some embodiments, the expression of CCR7 may be measured by an increase in CCR7 RNA. In other embodiments, the cancer is characterized by an increase in DNA copy number of CCR7. Other methods of measuring or determining levels of CCR7 expression are known to persons skilled in the art. Examples of diseases which can be treated and/or prevented include, but are not limited to, chronic lymphocytic leukemia (CLL), peripheral T cell lymphomas (PTCL) such as adult T-cell leukemia/lymphoma (ATLL) and anaplastic large-cell lymphoma (ALCL), Non-Hodgkin's lymphoma (NHL) such as mantle cell lymphoma (MCL), Burkitt's lymphoma and diffuse large B-cell lymphoma (DLBCL), gastric carcinoma, non-small cell lung cancer, small cell lung cancer, head and neck cancer, nasopharyngeal carcinoma (NPC), esophageal cancer, colorectal carcinoma, pancreatic cancer, thyroid cancer, breast cancer, renal cell cancer, and cervical cancer.

The present invention provides for methods of treating or preventing cancer comprising administering a therapeutically effective amount of the antibodies, antibody fragments (e.g., antigen binding fragments), or antibody drug conjugates of the invention. In certain embodiments, the cancer is a solid cancer. In certain embodiments, the subject is a human. In certain embodiments, the cancer is a resistant cancer and/or relapsed cancer. In certain aspects, for example, the resistant cancer is resistant to tyrosine kinase inhibitors, EGFR inhibitors, Her2 inhibitors, Her3 inhibitors, IGFR inhibitors and Met inhibitors.

In certain embodiments, the invention provides for methods of inhibiting tumor growth comprising administering to a subject a therapeutically effective amount of the antibodies, antibody fragments (e.g., antigen binding fragments), or antibody drug conjugates of the invention. In certain embodiments, the subject is a human. In certain embodiments, the subject has a tumor or has had a tumor removed. In certain embodiments, the tumor is resistant to other tyrosine kinase inhibitors, including but not limited to, EGFR inhibitors, Her2 inhibitors, Her3 inhibitors, IGFR inhibitors and Met inhibitors.

In certain embodiments, the tumor expresses the CCR7 to which the anti-CCR7 antibody binds. In certain embodiments, the tumor overexpresses the human CCR7. In certain embodiments, the tumor has an increase copy number of the CCR7 gene.

The present invention also provides for methods of selecting patients for treatment with antibodies, antibody fragments (e.g., antigen binding fragments), or antibody drug conjugates of the invention comprising administering a therapeutically effective amount of said antibodies, antibody fragments (e.g., antigen binding fragments), or antibody drug conjugates. In certain aspects the method comprises selecting patients with a tyrosine kinase inhibitor resistant cancer. In certain aspects it is contemplated that the tyrosine kinase inhibitor resistant cancer is resistant to EGFR inhibitors, Her2 inhibitors, Her3 inhibitors, IGFR inhibitors and/or Met inhibitors. In certain aspects it is contemplated that the resistant cancer is a Her2 resistant cancer. In certain aspects it is contemplated that the cancer is a de novo resistant cancer, and in still other aspects it is contemplated that the cancer is a relapsed cancer. In certain aspects of the invention the methods comprise selecting a patient with a de novo resistant or relapsed cancer and measuring for expression of CCR7. It is contemplated that in certain aspects the relapsed cancer or tumor was not initially a CCR7 expressing cancer or tumor, but becomes a CCR7 positive cancer that is a tyrosine kinase resistant or relapsed cancer or tumor after treatment with tyrosine kinase inhibitors.

For the treatment or prevention of the disease, the appropriate dosage of the antibodies, antibody fragments (e.g., antigen binding fragments), or antibody drug conjugates of the present invention depends on various factors, such as the type of disease to be treated, the severity and course of the disease, the responsiveness of the disease, previous therapy, patient's clinical history, and so on. The antibody or agent can be administered one time or over a series of treatments lasting from several days to several months, or until a cure is effected or a diminution of the disease state is achieved (e.g., reduction in tumor size). Optimal dosing schedules can be calculated from measurements of drug accumulation in the body of the patient and will vary depending on the relative potency of an individual antibody, antibody fragment (e.g., antigen binding fragment), or antibody drug conjugates. The treating physician can estimate repetition rates for dosing based on measured residence times and concentrations of the drug in bodily fluids or tissues.

Combination Therapy

In certain instances, an antibody, antibody fragment (e.g., antigen binding fragment), or antibody drug conjugate of the present invention is combined with other therapeutic agents, such as other anti-cancer agents, anti-allergic agents, anti-nausea agents (or anti-emetics), pain relievers, cytoprotective agents, and combinations thereof.

In one embodiment, an antibody, antibody fragment (e.g., antigen binding fragment), or antibody drug conjugate of the present invention is combined in a pharmaceutical combination formulation, or dosing regimen as combination therapy, with a second compound having anti-cancer properties. The second compound of the pharmaceutical combination formulation or dosing regimen can have complementary activities to the antibody or immunoconjugate of the combination such that they do not adversely affect each other. For example, an antibody, antibody fragment (e.g., antigen binding fragment), or antibody drug conjugate of the present invention can be administered in combination with, but not limited to, a chemotherapeutic agent, a tyrosine kinase inhibitor, a CCR7 downstream signaling pathway inhibitor, IAP inhibitors, Bcl2 inhibitors, Mcl1 inhibitors, and other CCR7 inhibitors.

The term "pharmaceutical combination" as used herein refers to either a fixed combination in one dosage unit form, or non-fixed combination or a kit of parts for the combined administration where two or more therapeutic agents may be administered independently at the same time or separately within time intervals, especially where these time intervals allow that the combination partners show a cooperative, e.g., synergistic effect.

The term "combination therapy" refers to the administration of two or more therapeutic agents to treat or prevent a therapeutic condition or disorder described in the present disclosure. Such administration encompasses co-administration of these therapeutic agents in a substantially simultaneous manner, such as in a single capsule having a fixed ratio of active ingredients. Alternatively, such administration encompasses co-administration in multiple, or in separate containers (e.g., capsules, powders, and liquids) for each active ingredient. Powders and/or liquids may be reconstituted or diluted to a desired dose prior to administration. In addition, such administration also encompasses use of each type of therapeutic agent in a sequential manner, either at approximately the same time or at different times. In either case, the treatment regimen will provide beneficial effects of the drug combination in treating or preventing the conditions or disorders described herein.

The combination therapy can provide "synergy" and prove "synergistic", i.e., the effect achieved when the active ingredients used together is greater than the sum of the effects that results from using the compounds separately. A synergistic effect can be attained when the active ingredients are: (1) co-formulated and administered or delivered simultaneously in a combined, unit dosage formulation; (2) delivered by alternation or in parallel as separate formulations; or (3) by some other regimen. When delivered in alternation therapy, a synergistic effect can be attained when the compounds are administered or delivered sequentially, e.g., by different injections in separate syringes. In general, during alternation therapy, an effective dosage of each active ingredient is administered sequentially, i.e., serially, whereas in combination therapy, effective dosages of two or more active ingredients are administered together.

General Chemotherapeutic agents considered for use in combination therapies include anastrozole (Arimidex®), bicalutamide (Casodex®), bleomycin sulfate (Blenoxane®), busulfan (Myleran®), busulfan injection (Busulfex), capecitabine (Xeloda), N4-pentoxycarbonyl-5-deoxy-5-fluorocytidine, carboplatin (Paraplatin®), carmustine (BiCNU®), chlorambucil (Leukeran®), cisplatin (Platinol®), cladribine (Leustatin®), cyclophosphamide (Cytoxan® or Neosar®), cytarabine, cytosine arabinoside (Cytosar-U®), cytarabine liposome injection (DepoCyt®), dacarbazine (DTIC-Dome®), dactinomycin (Actinomycin D, Cosmegan), daunorubicin hydrochloride (Cerubidine®), daunorubicin citrate liposome injection (DaunoXome), dexamethasone, docetaxel (Taxotere®), doxorubicin hydrochloride (Adriamycin®, Rubex®), etoposide (Vepesid®), fludarabine phosphate (Fludara®), 5-fluorouracil (Adrucil®, Efudex®), flutamide (Eulexin®), tezacitibine, Gemcitabine (difluorodeoxycitidine), hydroxyurea (Hydrea®), Idarubicin (Idamycin®), ifosfamide (IFEX®), irinotecan (Camptosar®), L-asparaginase (ELSPAR), leucovorin calcium, melphalan (Alkeran®), 6-mercaptopurine (Purinethol®), methotrexate (Folex®), mitoxantrone (Novantrone®), mylotarg, paclitaxel (Taxol®), phoenix (Yttrium90/MX-DTPA), pentostatin, polifeprosan 20 with carmustine implant (Gliadel®), tamoxifen citrate (Nolvadex®), teniposide (Vumon®), 6-thioguanine, thiotepa, tirapazamine (Tirazone®), topotecan hydrochloride for injection (Hycamptin®), vinblastine (Velban®), vincristine (Oncovin®), and vinorelbine (Navelbine®), and pemetrexed.

In one aspect, the present invention provides a method of treating or preventing cancer by administering to a subject in need thereof an antibody drug conjugate of the present invention in combination with one or more tyrosine kinase inhibitors, including but not limited to, BTK inhibitors, EGFR inhibitors, Her2 inhibitors, Her3 inhibitors, IGFR inhibitors, and Met inhibitors.

For example, tyrosine kinase inhibitors include but are not limited to, Ibrutinib (PCI-32765); Erlotinib hydrochloride (Tarceva®); Linifanib (N-[4-(3-amino-1H-indazol-4-yl) phenyl]-N'-(2-fluoro-5-methylphenyl)urea, also known as ABT 869, available from Genentech); Sunitinib malate (Sutent®); Bosutinib (4-[(2,4-dichloro-5-methoxyphenyl) amino]-6-methoxy-7-[3-(4-methylpiperazin-1-yl)propoxy] quinoline-3-carbonitrile, also known as SKI-606, and described in U.S. Pat. No. 6,780,996); Dasatinib (Sprycel®); Pazopanib (Votrient®); Sorafenib (Nexavar®); Zactima (ZD6474); and Imatinib or Imatinib mesylate (Gilvec® and Gleevec®).

Epidermal growth factor receptor (EGFR) inhibitors include but are not limited to, Erlotinib hydrochloride (Tarceva®), Gefitinib (Iressa®); N-[4-4-[(3-Chloro-4-fluorophenyl)amino]-7-[[(3"S")-tetrahydro-3-furanyl]oxy]-6-quinazolinyl]-4(dimethylamino)-2-butenamide, Tovok®); Vandetanib (Caprelsa®); Lapatinib (Tykerb®); (3R,4R)-4-Amino-1-((4-((3-methoxyphenyl)amino)pyrrolo[2,1-f][1,2,4]triazin-5-yl)methyl)piperidin-3-ol (BMS690514); Canertinib dihydrochloride (CI-1033); 6-[4-[(4-Ethyl-1-piperazinyl)methylπphenyl]-N-[(1R)-1-phenylethyl]-7H-Pyrrolo[2,3-d]pyrimidin-4-amine (AEE788, CAS 497839-62-0); Mubritinib (TAK165); Pelitinib (EKB569); Afatinib (BIBW2992); Neratinib (HKI-272); N-[4-[[1-R3-Fluorophenyemethyl]-1H-indazol-5-yl]amino]-5-methylpyrrolo[2,1-f][1,2,4]triazin-6-yl]-carbamic acid, (3S)-3-morpholinylmethyl ester (BMS599626); N-(3,4-Dichloro-2-fluorophenyl)-6-methoxy-7-[[(3aa,513,6aa)-octahydro-2-methylcyclopenta[c]pyrrol-5-yl]methoxy]-4-quinazolinamine (XL647, CAS 781613-23-8); and 4-[4-[[(1R)-1-Phenylethyl]amino]-7H-pyrrolo[2,3-d]pyrimidin-6-yl]-phenol (PM166, CAS 187724-61-4).

EGFR antibodies include but are not limited to, Cetuximab (Erbitux®); Panitumumab (Vectibix®); Matuzumab (EMD-72000); Nimotuzumab (hR3); Zalutumumab; TheraCIM h-R3; MDX0447 (CAS 339151-96-1); and ch806 (mAb-806, CAS 946414-09-1).

Human Epidermal Growth Factor Receptor 2 (Her2 receptor) (also known as Neu, ErbB-2, CD340, or p185) inhibitors include but are not limited to, Trastuzumab (Herceptin®); Pertuzumab (Omnitarg®); trastuzumab emtansine (Kadcyla®); Neratinib (HKI-272, (2E)-N-[4-[[3-chloro-4-[(pyridin-2-yl)methoxy]phenyl]amino]-3-cyano-7-ethoxyquinolin-6-yl]-4-(dimethylamino)but-2-enamide, and described PCT Publication No. WO 05/028443); Lapatinib or Lapatinib ditosylate (Tykerb®); (3R,4R)-4-amino-1-((4-(3-methoxyphenyeamino)pyrrolo[2,1-f][1,2,4]triazin-5-yl)methyl)piperidin-3-ol (BMS690514); (2E)-N-[4-[(3-Chloro-4-fluorophenyl)amino]-7-[[(3S)-tetrahydro-3-furanyl]oxy]-6-quinazolinyl]-4-(dimethylamino)-2-butenamide (BIBW-2992, CAS 850140-72-6); N-[4-[[1-[(3-Fluorophenyl)methyl]-1H-indazol-5-yl]amino]-5-methylpyrrolo[2,1-f][1,2,4]triazin-6-yl]-carbamic acid, (3S)-3-morpholinylmethyl ester (BMS 599626, CAS 714971-09-2); Canertinib dihydrochloride (PD183805 or CI-1033); and N-(3,4-Dichloro-2-fluorophenyl)-6-methoxy-7-[[(3aα,5β,6aα)-octahydro-2-methylcyclopenta[c]pyrrol-5-yl]methoxy]-4-quinazolinamine (XL647, CAS 781613-23-8).

Her3 inhibitors include but are not limited to, LJM716, MM-121, AMG-888, RG7116, REGN-1400, AV-203, MP-RM-1, MM-111, and MEHD-7945A.

MET inhibitors include but are not limited to, Cabozantinib (XL184, CAS 849217-68-1); Foretinib (GSK1363089, formerly XL880, CAS 849217-64-7); Tivantinib (ARQ197, CAS 1000873-98-2); 1-(2-Hydroxy-2-methylpropyl)-N-(5-(7-methoxyquinolin-4-yloxy)pyridin-2-yl)-5-methyl-3-oxo-2-phenyl-2,3-dihydro-1H-pyrazole-4-carboxamide (AMG 458); Cryzotinib (Xalkori®, PF-02341066); (3Z)-5-(2,3-Dihydro-1H-indol-1-ylsulfonyl)-3-({3,5-dimethyl-4-[(4-methylpiperazin-1-yl)carbonyl]-1H-pyrrol-2-yl}methylene)-1,3-dihydro-2H-indol-2-one (SU11271); (3Z)-N-(3-Chlorophenyl)-3-([3,5-dimethyl-4-[(4-methylpiperazin-1-yl)carbonyl]-1H-pyrrol-2-yl]methylene)-N-methyl-2-oxoindoline-5-sulfonamide (SU11274); (3Z)-N-(3-Chlorophenyl)-3-[3,5-dimethyl-4-(3-morpholin-4-ylpropyl)-1H-pyrrol-2-yl]methylene 1-N-methyl-2-oxoindoline-5-sulfonamide (SU11606); 6-[Difluoro[6-(1-methyl-1H-pyrazol-4-yl)-1,2,4-triazolo[4,3-b]pyridazin-3-yl]methyl]-quinoline (JNJ38877605, CAS 943540-75-8); 2-[4-[1-(Quinolin-6-ylmethyl)-1H-[1,2,3]triazolo[4,5-b]pyrazin-6-yl]-1H-pyrazol-1-yl]ethanol (PF04217903, CAS 956905-27-4); N-((2R)-1,4-Dioxan-2-ylmethyl)-N-methyl-N'-[3-(1-methyl-1H-pyrazol-4-yl)-5-oxo-5H-benzo[4,5]cyclohepta[1,2-b]pyridin-7-yl]sulfamide (MK2461, CAS 917879-39-1); 6-[[6-(1-Methyl-1H-pyrazol-4-yl)-1,2,4-triazolo[4,3-b]pyridazin-3-yl]thio]-quinoline (SGX523, CAS 1022150-57-7); and (3Z)-5-[[(2,6-Dichlorophenyl)methyl]sulfonyl]-3-[[3,5-dimethyl-4-[[(2R)-2-(1-pyrrolidinylmethyl)-1-pyrrolidinyl]carbonyl]-1H-pyrrol-2-yl]methylene]-1,3-dihydro-2H-indol-2-one (PHA665752, CAS 477575-56-7).

IGF1R inhibitors include but are not limited to, BMS-754807, XL-228, OSI-906, GSK0904529A, A-928605, AXL1717, KW-2450, MK0646, AMG479, IMCA12, MEDI-573, and BI836845. See e.g., Yee, JNCI, 104; 975 (2012) for review.

In another aspect, the present invention provides a method of treating or preventing cancer by administering to a subject in need thereof an antibody drug conjugate of the present invention in combination with one or more CCR7 downstream signaling pathway inhibitors, including but not limited to, β-arrestin inhibitors, GRK inhibitors, MAPK inhibitors, PI3K inhibitors, JAK inhibitors, etc.

For example, phosphoinositide 3-kinase (PI3K) inhibitors include but are not limited to, Idelalisib (Zydelig, GS-1101, Cal-101), 4-[2-(1H-Indazol-4-yl)-6-[[4-(methylsulfonyl)piperazin-1-yl]methyl]thieno[3,2-d]pyrimidin-4-yl]morpholine (also known as GDC 0941 and described in PCT Publication Nos. WO 09/036082 and WO 09/055730); 2-Methyl-2-[4-[3-methyl-2-oxo-8-(quinolin-3-yl)-2,3-dihydroimidazo[4,5-c]quinolin-1-yl]phenyl]propionitrile (also known as BEZ 235 or NVP-BEZ 235, and described in PCT Publication No. WO 06/122806); 4-(trifluoromethyl)-5-(2,6-dimorpholinopyrimidin-4-yl)pyridin-2-amine (also known as BKM120 or NVP-BKM120, and described in PCT Publication No. W02007/084786); Tozasertib (VX680 or MK-0457, CAS 639089-54-6); (5Z)-5-[[4-(4-Pyridinyl)-6-quinolinyl]methylene]-2,4-thiazolidinedione (GSK1059615, CAS 958852-01-2); (1E,4S,4aR,5R,6aS,9aR)-5-(Acetyloxy)-1-[(di-2-propenylamino)methylene]-4,4a,5,6,6a,8,9,9a-octahydro-11-hydroxy-4-(methoxymethyl)-4a,6a-dimethyl-cyclopenta[5,6]naphtho[1,2-c]pyran-2,7,10(1H)-trione (PX866, CAS 502632-66-8); and 8-Phenyl-2-(morpholin-4-yl)-chromen-4-one (LY294002, CAS 154447-36-6).

In yet another aspect, the present invention provides a method of treating or preventing cancer by administering to a subject in need thereof an antibody drug conjugate of the present invention in combination with one or more pro-apoptosis, including but not limited to, IAP inhibitors, Bc12 inhibitors, MC11 inhibitors, Trail agents, Chk inhibitors.

For examples, IAP inhibitors include but are not limited to, LCL161, GDC-0917, AEG-35156, AT406, and TL32711. Other examples of IAP inhibitors include but are not limited to those disclosed in WO04/005284, WO 04/007529, WO05/097791, WO 05/069894, WO 05/069888, WO 05/094818, US2006/0014700, US2006/0025347, WO 06/069063, WO 06/010118, WO 06/017295, and W008/134679, all of which are incorporated herein by reference.

BCL-2 inhibitors include but are not limited to, Venetoclax (also known as GDC-0199, ABT-199, RG7601); 4-[4-[[2-(4-Chlorophenyl)-5,5-dimethyl-1-cyclohexen-1-yl]methyl]-1-piperazinyl]-N-[[4-[[(1R)-3-(4-morpholinyl)-1-[(phenylthio)methyl]propyl]amino]-3-[(trifluoromethyl)sulfonyl]phenyl]sulfonyl]benzamide (also known as ABT-263 and described in PCT Publication No. WO 09/155386); Tetrocarcin A; Antimycin; Gossypol ((−)BL-193); Obatoclax; Ethyl-2-amino-6-cyclopentyl-4-(1-cyano-2-ethoxy-2-oxoethyl)-4Hchromone-3-carboxylate (HA14-1); Oblimersen (G3139, Genasense®); Bak BH3 peptide; (-)-Gossypol acetic acid (AT-101); 4-[4-[(4'-Chloro[1,1'-biphenyl]-2-yl)methyl]-1-piperazinyl]-N-[[4-[[(1R)-3-(dimethylamino)-1-[(phenylthio)methyl]propyl]amino]-3-nitrophenyl]sulfonyl]-benzamide (ABT-737, CAS 852808-04-9); and Navitoclax (ABT-263, CAS 923564-51-6).

Proapoptotic receptor agonists (PARAS) including DR4 (TRAILR1) and DR5 (TRAILR2), including but are not limited to, Dulanermin (AMG-951, RhApo2L/TRAIL); Mapatumumab (HRS-ETR1, CAS 658052-09-6); Lexatumumab (HGS-ETR2, CAS 845816-02-6); Apomab (Apomab®); Conatumumab (AMG655, CAS 896731-82-1); and Tigatuzumab (CS1008, CAS 946415-34-5, available from Daiichi Sankyo).

Checkpoint Kinase (CHK) inhibitors include but are not limited to, 7-Hydroxystaurosporine (UCN-01); 6-Bromo-3-(1-methyl-1H-pyrazol-4-yl)-5-(3R)-3-piperidinyl-pyrazolo[1,5-a]pyrimidin-7-amine (SCH900776, CAS 891494-63-6); 5-(3-Fluorophenyl)-3-ureidothiophene-2-carboxylic acid N-[(S)-piperidin-3-yl]amide (AZD7762, CAS 860352-01-8); 4-[((3S)-1-Azabicyclo[2.2.2]oct-3-yl)amino]-3-(1H-benzimidazol-2-yl)-6-chloroquinolin-2(1H)-one (CHIR 124, CAS 405168-58-3); 7-Aminodactinomycin (7-AAD), Isogranulatimide, debromohymenialdisine; N-[5-Bromo-4-methyl-2-[(2S)-2-morpholinylmethoxy]-phenyl]-N'-(5-methyl-2-pyrazinyl)urea (LY2603618, CAS 911222-45-2); Sulforaphane (CAS 4478-93-7, 4-Methylsulfinylbutyl isothiocyanate); 9,10,11,12-Tetrahydro-9,12-epoxy-1H-diindolo[1,2,3-fg:3',2',1'-kl]pyrrolo[3,4-i][1,6]benzodiazocine-1,3(2H)-dione (SB-218078, CAS 135897-06-2); and TAT-S216A (YGRKKRRQRRRLYRSPAMPENL (SEQ ID NO: 629)), and CBP501 ((d-Bpa)sws(d-Phe-F5)(d-Cha)rrrqrr).

In a further embodiment, the present invention provides a method of treating or preventing cancer by administering to a subject in need thereof an antibody drug conjugate of the present invention in combination with one or more immunomodulators (e.g., one or more of: an activator of a costimulatory molecule or an inhibitor of an immune checkpoint molecule).

In certain embodiments, the immunomodulator is an activator of a costimulatory molecule. In one embodiment, the agonist of the costimulatory molecule is chosen from an agonist (e.g., an agonistic antibody or antigen-binding fragment thereof, or a soluble fusion) of OX40, CD2, CD27, CDS, ICAM-1, LFA-1 (CD11a/CD18), ICOS (CD278), 4-1BB (CD137), GITR, CD30, CD40, BAFFR, HVEM, CD7, LIGHT, NKG2C, SLAMF7, NKp80, CD160, B7-H3, STING, or CD83 ligand.

In certain embodiments, the immunomodulator is an inhibitor of an immune checkpoint molecule. In one embodiment, the immunomodulator is an inhibitor of PD-1, PD-L1, PD-L2, CTLA4, TIM3, LAG3, VISTA, BTLA, TIGIT, LAIR1, CD160, 2B4 and/or TGFR beta. In one embodiment, the inhibitor of an immune checkpoint molecule inhibits PD-1, PD-L1, LAG-3, TIM-3 or CTLA4, or any combination thereof. The term "inhibition" or "inhibitor" includes a reduction in a certain parameter, e.g., an activity, of a given molecule, e.g., an immune checkpoint inhibitor. For example, inhibition of an activity, e.g., a PD-1 or PD-L1 activity, of at least 5%, 10%, 20%, 30%, 40%, 50% or more is included by this term. Thus, inhibition need not be 100%.

Inhibition of an inhibitory molecule can be performed at the DNA, RNA or protein level. In some embodiments, an inhibitory nucleic acid (e.g., a dsRNA, siRNA or shRNA), can be used to inhibit expression of an inhibitory molecule. In other embodiments, the inhibitor of an inhibitory signal is a polypeptide e.g., a soluble ligand (e.g., PD-1-Ig or CTLA-4 Ig), or an antibody or antigen-binding fragment thereof, that binds to the inhibitory molecule; e.g., an antibody or fragment thereof (also referred to herein as "an antibody molecule") that binds to PD-1, PD-L1, PD-L2, CTLA4, TIM3, LAG3, VISTA, BTLA, TIGIT, LAIR1, CD160, 2B4 and/or TGFR beta, or a combination thereof.

In one embodiment, the antibody molecule is a full antibody or fragment thereof (e.g., a Fab, F(ab')$_2$, Fv, or a single chain Fv fragment (scFv)). In yet other embodiments, the antibody molecule has a heavy chain constant region (Fc) chosen from, e.g., the heavy chain constant regions of IgG1, IgG2, IgG3, IgG4, IgM, IgA1, IgA2, IgD, and IgE; particularly, chosen from, e.g., the heavy chain constant regions of IgG1, IgG2, IgG3, and IgG4, more particularly, the heavy chain constant region of IgG1 or IgG4 (e.g., human IgG1 or IgG4). In one embodiment, the heavy chain constant region is human IgG1 or human IgG4. In one embodiment, the constant region is altered, e.g., mutated, to modify the properties of the antibody molecule (e.g., to increase or decrease one or more of: Fc receptor binding, antibody glycosylation, the number of cysteine residues, effector cell function, or complement function).

In certain embodiments, the antibody molecule is in the form of a bispecific or multispecific antibody molecule. In one embodiment, the bispecific antibody molecule has a first binding specificity to PD-1 or PD-L1 and a second binding specificity, e.g., a second binding specificity to TIM-3, LAG-3, or PD-L2. In one embodiment, the bispecific antibody molecule binds to PD-1 or PD-L1 and TIM-3. In another embodiment, the bispecific antibody molecule binds to PD-1 or PD-L1 and LAG-3. In another embodiment, the bispecific antibody molecule binds to PD-1 and PD-L1. In yet another embodiment, the bispecific antibody molecule binds to PD-1 and PD-L2. In another embodiment, the bispecific antibody molecule binds to TIM-3 and LAG-3. Any combination of the aforesaid molecules can be made in a multispecific antibody molecule, e.g., a trispecific antibody that includes a first binding specificity to PD-1 or PD-1, and a second and third binding specificities to two or more of: TIM-3, LAG-3, or PD-L2.

In certain embodiments, the immunomodulator is an inhibitor of PD-1, e.g., human PD-1. In another embodiment, the immunomodulator is an inhibitor of PD-L1, e.g., human PD-L1. In one embodiment, the inhibitor of PD-1 or PD-L1 is an antibody molecule to PD-1 or PD-L1. The PD-1 or PD-L1 inhibitor can be administered alone, or in combination with other immunomodulators, e.g., in combination with an inhibitor of LAG-3, TIM-3 or CTLA4. In an exemplary embodiment, the inhibitor of PD-1 or PD-L1, e.g., the anti-PD-1 or PD-L1 antibody molecule, is administered in combination with a LAG-3 inhibitor, e.g., an anti-LAG-3 antibody molecule. In another embodiment, the inhibitor of PD-1 or PD-L1, e.g., the anti-PD-1 or PD-L1 antibody molecule, is administered in combination with a TIM-3 inhibitor, e.g., an anti-TIM-3 antibody molecule. In yet other embodiments, the inhibitor of PD-1 or PD-L1, e.g., the anti-PD-1 antibody molecule, is administered in combination with a LAG-3 inhibitor, e.g., an anti-LAG-3 antibody molecule, and a TIM-3 inhibitor, e.g., an anti-TIM-3 antibody molecule. Other combinations of immunomodulators with a PD-1 inhibitor (e.g., one or more of PD-L2, CTLA4, TIM3, LAG3, VISTA, BTLA, TIGIT, LAIR1, CD160, 2B4 and/or TGFR) are also within the present invention. Any of the antibody molecules known in the art or disclosed herein can be used in the aforesaid combinations of inhibitors of checkpoint molecule.

In one embodiment, the PD-1 inhibitor is an anti-PD-1 antibody chosen from Nivolumab, Pembrolizumab or Pidilizumab. In some embodiments, the anti-PD-1 antibody is Nivolumab. Alternative names for Nivolumab include MDX-1106, MDX-1106-04, ONO-4538, or BMS-936558. In some embodiments, the anti-PD-1 antibody is Nivolumab (CAS Registry Number: 946414-94-4). Nivolumab is a fully human IgG4 monoclonal antibody which specifically blocks PD1. Nivolumab (clone 5C4) and other human monoclonal antibodies that specifically bind to PD1 are disclosed in U.S. Pat. No. 8,008,449 and PCT Publication No. WO2006/121168.

In other embodiments, the anti-PD-1 antibody is Pembrolizumab. Pembrolizumab (Trade name KEYTRUDA formerly Lambrolizumab,-also known as Merck 3745, MK-3475 or SCH-900475) is a humanized IgG4 monoclonal antibody that binds to PD1. Pembrolizumab is disclosed, e.g., in Hamid, O. et al. (2013) *New England Journal of Medicine* 369 (2): 134-44, PCT Publication No. WO2009/114335, and U.S. Pat. No. 8,354,509.

In some embodiments, the anti-PD-1 antibody is Pidilizumab. Pidilizumab (CT-011; Cure Tech) is a humanized IgGlk monoclonal antibody that binds to PD1. Pidilizumab and other humanized anti-PD-1 monoclonal antibodies are disclosed in PCT Publication No. WO2009/101611. Other anti-PD1 antibodies are disclosed in U.S. Pat. No. 8,609,089, US Publication No. 2010028330, and/or US Publication No. 20120114649. Other anti-PD1 antibodies include AMP 514 (Amplimmune).

In some embodiments, the PD-1 inhibitor is PDR001 or any other anti-PD-1 antibody disclosed in WO2015/112900.

In some embodiments, the PD-1 inhibitor is an immunoadhesin (e.g., an immunoadhesin comprising an extracellular or PD-1 binding portion of PD-L1 or PD-L2 fused to a constant region (e.g., an Fc region of an immunoglobulin sequence). In some embodiments, the PD-1 inhibitor is AMP-224.

In some embodiments, the PD-L1 inhibitor is anti-PD-L1 antibody. In some embodiments, the anti-PD-L1 inhibitor is chosen from YW243.55.570, MPDL3280A, MEDI-4736, or MDX-1105MSB-0010718C (also referred to as A09-246-2) disclosed in, e.g., WO 2013/0179174, and having a sequence disclosed herein (or a sequence substantially identical or similar thereto, e.g., a sequence at least 85%, 90%, 95% identical or higher to the sequence specified).

In one embodiment, the PD-L1 inhibitor is MDX-1105. MDX-1105, also known as BMS-936559, is an anti-PD-L1 antibody described in PCT Publication No. WO2007/005874.

In one embodiment, the PD-L1 inhibitor is YW243.55.S70. The YW243.55.S70 antibody is an anti-PD-L1 described in PCT Publication No. WO 2010/077634 (heavy and light chain variable region sequences shown in SEQ ID Nos. 20 and 21, respectively).

In one embodiment, the PD-L1 inhibitor is MDPL3280A (Genentech/Roche). MDPL3280A is a human Fc optimized IgG1 monoclonal antibody that binds to PD-L1. MDPL3280A and other human monoclonal antibodies to PD-L1 are disclosed in U.S. Pat. No. 7,943,743 and U.S Publication No.: 20120039906.

In other embodiments, the PD-L2 inhibitor is AMP-224. AMP-224 is a PD-L2 Fc fusion soluble receptor that blocks the interaction between PD1 and B7-H1 (B7-DCIg; Amplimmune; e.g., disclosed in PCT Publication Nos. WO2010/027827 and WO2011/066342).

In one embodiment, the LAG-3 inhibitor is an anti-LAG-3 antibody molecule. In one embodiment, the LAG-3 inhibitor is BMS-986016.

Pharmaceutical Compositions

To prepare pharmaceutical or sterile compositions including immunoconjugates, the immunoconjugates of the invention are mixed with a pharmaceutically acceptable carrier or excipient. The compositions can additionally contain one or more other therapeutic agents that are suitable for treating or preventing a CCR7 expressing cancer (including, but not limited to chronic lymphocytic leukemia (CLL), peripheral T cell lymphomas (PTCL) such as adult T-cell leukemia/lymphoma (ATLL) and anaplastic large-cell lymphoma (ALCL), Non-Hodgkin's lymphoma (NHL) such as mantle cell lymphoma (MCL), Burkitt's lymphoma and diffuse large B-cell lymphoma (DLBCL), gastric carcinoma, non-small cell lung cancer, small cell lung cancer, head and neck cancer, nasopharyngeal carcinoma (NPC), esophageal cancer, colorectal carcinoma, pancreatic cancer, thyroid cancer, breast cancer, renal cell cancer, and cervical cancer).

Formulations of therapeutic and diagnostic agents can be prepared by mixing with physiologically acceptable carriers, excipients, or stabilizers in the form of, e.g., lyophilized powders, slurries, aqueous solutions, lotions, or suspensions (see, e.g., Hardman et al., Goodman and Gilman's The Pharmacological Basis of Therapeutics, McGraw-Hill, New York, N.Y., 2001; Gennaro, Remington: The Science and Practice of Pharmacy, Lippincott, Williams, and Wilkins, New York, N.Y., 2000; Avis, et al. (eds.), Pharmaceutical Dosage Forms: Parenteral Medications, Marcel Dekker, N.Y., 1993; Lieberman, et al. (eds.), Pharmaceutical Dosage Forms: tablets, Marcel Dekker, N.Y., 1990; Lieberman, et al. (eds.) Pharmaceutical Dosage Forms: Disperse Systems, Marcel Dekker, N.Y., 1990; Weiner and Kotkoskie, Excipient Toxicity and Safety, Marcel Dekker, Inc., New York, N.Y., 2000).

Selecting an administration regimen for a therapeutic depends on several factors, including the serum or tissue turnover rate of the entity, the level of symptoms, the immunogenicity of the entity, and the accessibility of the target cells in the biological matrix. In certain embodiments, an administration regimen maximizes the amount of therapeutic delivered to the patient consistent with an acceptable level of side effects. Accordingly, the amount of biologic delivered depends in part on the particular entity and the severity of the condition being treated. Guidance in selecting appropriate doses of antibodies, cytokines, and small molecules are available (see, e.g., Wawrzynczak, Antibody Therapy, Bios Scientific Pub. Ltd, Oxfordshire, UK, 1996; Kresina (ed.), Monoclonal Antibodies, Cytokines and Arthritis, Marcel Dekker, New York, N.Y., 1991; Bach (ed.), Monoclonal Antibodies and Peptide Therapy in Autoimmune Diseases, Marcel Dekker, New York, N.Y., 1993; Baert et al., New Engl. J. Med. 348:601-608, 2003; Milgrom et al., New Engl. J. Med. 341:1966-1973, 1999; Slamon et al., New Engl. J. Med. 344:783-792, 2001; Beniaminovitz et al., New Engl. J. Med. 342:613-619, 2000; Ghosh et al., New Engl. J. Med. 348:24-32, 2003; Lipsky et al., New Engl. J. Med. 343:1594-1602, 2000).

Determination of the appropriate dose is made by the clinician, e.g., using parameters or factors known or suspected in the art to affect treatment or prevention or predicted to affect treatment or prevention. Generally, the dose begins with an amount somewhat less than the optimum dose and it is increased by small increments thereafter until the desired or optimum effect is achieved relative to any negative side effects. Important diagnostic measures include those of symptoms of, e.g., the inflammation or level of inflammatory cytokines produced.

Actual dosage levels of the active ingredients in the pharmaceutical compositions of the present invention may be varied so as to obtain an amount of the active ingredient which is effective to achieve the desired therapeutic response for a particular patient, composition, and mode of administration, without being toxic to the patient. The selected dosage level will depend upon a variety of pharmacokinetic factors including the activity of the particular compositions of the present invention employed, or the ester, salt or amide thereof, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors known in the medical arts.

Compositions comprising antibodies or fragments thereof of the invention can be provided by continuous infusion, or by doses at intervals of, e.g., one day, one week, or 1-7 times per week, once every other week, once every three weeks, once every four weeks, once every five weeks, once every six weeks, once every seven weeks, or once very eight weeks. Doses may be provided intravenously, subcutaneously, topically, orally, nasally, rectally, intramuscular, intracerebrally, or by inhalation. A specific dose protocol is one involving the maximal dose or dose frequency that avoids significant undesirable side effects.

For the immunoconjugates of the invention, the dosage administered to a patient may be 0.0001 mg/kg to 100 mg/kg of the patient's body weight. The dosage may be between 0.0001 mg/kg and 30 mg/kg, 0.0001 mg/kg and 20 mg/kg, 0.0001 mg/kg and 10 mg/kg, 0.0001 mg/kg and 5 mg/kg, 0.0001 and 2 mg/kg, 0.0001 and 1 mg/kg, 0.0001 mg/kg and 0.75 mg/kg, 0.0001 mg/kg and 0.5 mg/kg, 0.0001 mg/kg to 0.25 mg/kg, 0.0001 to 0.15 mg/kg, 0.0001 to 0.10 mg/kg, 0.001 to 0.5 mg/kg, 0.01 to 0.25 mg/kg or 0.01 to 0.10 mg/kg of the patient's body weight. The dosage of the antibodies or fragments thereof of the invention may be calculated using the patient's weight in kilograms (kg) multiplied by the dose to be administered in mg/kg.

Doses of the immunoconjugates the invention may be repeated and the administrations may be separated by less than 1 day, at least 1 day, 2 days, 3 days, 5 days, 10 days, 15 days, 30 days, 45 days, 2 months, 75 days, 3 months, 4 months, 5 months, or at least 6 months. In some embodiments, the immunoconjugates of the invention may be given twice weekly, once weekly, once every two weeks, once every three weeks, once every four weeks, or less frequently. In a specific embodiment, doses of the immunoconjugates of the invention are repeated every 2 weeks.

An effective amount for a particular patient may vary depending on factors such as the condition being treated, the overall health of the patient, the method, route and dose of administration and the severity of side effects (see, e.g., Maynard et al., A Handbook of SOPs for Good Clinical Practice, Interpharm Press, Boca Raton, Fla., 1996; Dent, Good Laboratory and Good Clinical Practice, Urch Publ., London, UK, 2001).

The route of administration may be by, e.g., topical or cutaneous application, injection or infusion by subcutaneous, intravenous, intraperitoneal, intracerebral, intramuscular, intraocular, intraarterial, intracerebrospinal, intralesional administration, or by sustained release systems or an implant (see, e.g., Sidman et al., Biopolymers 22:547-556, 1983; Langer et al., J. Biomed. Mater. Res. 15:167-277, 1981; Langer, Chem. Tech. 12:98-105, 1982; Epstein et al., Proc. Natl. Acad. Sci. USA 82:3688-3692, 1985; Hwang et al., Proc. Natl. Acad. Sci. USA 77:4030-4034, 1980; U.S. Pat. Nos. 6,350,466 and 6,316,024). Where necessary, the composition may also include a solubilizing agent or a local anesthetic such as lidocaine to ease pain at the site of the injection, or both. In addition, pulmonary administration can also be employed, e.g., by use of an inhaler or nebulizer, and formulation with an aerosolizing agent. See, e.g., U.S. Pat. Nos. 6,019,968, 5,985,320, 5,985,309, 5,934,272, 5,874,064, 5,855,913, 5,290,540, and 4,880,078; and PCT Publication Nos. WO 92/19244, WO 97/32572, WO 97/44013, WO 98/31346, and WO 99/66903, each of which is incorporated herein by reference their entirety.

A composition of the present invention may also be administered via one or more routes of administration using one or more of a variety of methods known in the art. As will be appreciated by the skilled artisan, the route and/or mode of administration will vary depending upon the desired results. Selected routes of administration for the immunoconjugates of the invention include intravenous, intramuscular, intradermal, intraperitoneal, subcutaneous, spinal or other parenteral routes of administration, for example by injection or infusion. Parenteral administration may represent modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion. Alternatively, a composition of the invention can be administered via a non-parenteral route, such as a topical, epidermal or mucosal route of administration, for example, intranasally, orally, vaginally, rectally, sublingually or topically. In one embodiment, the immunoconjugates of the invention is administered by infusion. In another embodiment, the immunoconjugates of the invention is administered subcutaneously.

If the immunoconjugates of the invention are administered in a controlled release or sustained release system, a pump may be used to achieve controlled or sustained release (see Langer, supra; Sefton, CRC Crit. Ref Biomed. Eng. 14:20, 1987; Buchwald et al., Surgery 88:507, 1980; Saudek et al., N. Engl. J. Med. 321:574, 1989). Polymeric materials can be used to achieve controlled or sustained release of the therapies of the invention (see, e.g., Medical Applications of Controlled Release, Langer and Wise (eds.), CRC Pres., Boca Raton, Fla., 1974; Controlled Drug Bioavailability, Drug Product Design and Performance, Smolen and Ball (eds.), Wiley, N.Y., 1984; Ranger and Peppas, J. Macromol. Sci. Rev. Macromol. Chem. 23:61, 1983; see also Levy et al., Science 228:190, 1985; During et al., Ann. Neurol. 25:351, 1989; Howard et al., J. Neurosurg. 7 1:105, 1989; U.S. Pat. Nos. 5,679,377; 5,916,597; 5,912,015; 5,989,463; 5,128,326; PCT Publication No. WO 99/15154; and PCT Publication No. WO 99/20253. Examples of polymers used in sustained release formulations include, but are not limited to, poly(2-hydroxy ethyl methacrylate), poly(methyl methacrylate), poly(acrylic acid), poly(ethylene-co-vinyl acetate), poly(methacrylic acid), polyglycolides (PLG), polyanhydrides, poly(N-vinyl pyrrolidone), poly(vinyl alcohol), polyacrylamide, poly(ethylene glycol), polylactides (PLA), poly(lactide-co-glycolides) (PLGA), and polyorthoesters. In one embodiment, the polymer used in a sustained release formulation is inert, free of leachable impurities, stable on storage, sterile, and biodegradable. A controlled or sustained release system can be placed in proximity of the prophylactic or therapeutic target, thus requiring only a fraction of the systemic dose (see, e.g., Goodson, in Medical Applications of Controlled Release, supra, vol. 2, pp. 115-138, 1984).

Controlled release systems are discussed in the review by Langer, Science 249:1527-1533, 1990). Any technique known to one of skill in the art can be used to produce sustained release formulations comprising one or more immunoconjugates of the invention. See, e.g., U.S. Pat. No. 4,526,938, PCT publication WO 91/05548, PCT publication WO 96/20698, Ning et al., Radiotherapy & Oncology 39:179-189, 1996; Song et al., PDA Journal of Pharmaceutical Science & Technology 50:372-397, 1995; Cleek et al., Pro. Int'l. Symp. Control. Rd. Bioact. Mater. 24:853-854, 1997; and Lam et al., Proc. Int'l. Symp. Control Rel. Bioact. Mater. 24:759-760, 1997, each of which is incorporated herein by reference in their entirety.

If the immunoconjugates of the invention are administered topically, they can be formulated in the form of an ointment, cream, transdermal patch, lotion, gel, spray, aerosol, solution, emulsion, or other form well-known to one of skill in the art. See, e.g., Remington's Pharmaceutical Sciences and Introduction to Pharmaceutical Dosage Forms, 19th ed., Mack Pub. Co., Easton, Pa. (1995). For non-sprayable topical dosage forms, viscous to semi-solid or solid forms comprising a carrier or one or more excipients compatible with topical application and having a dynamic viscosity, in some instances, greater than water are typically employed. Suitable formulations include, without limitation, solutions, suspensions, emulsions, creams, ointments, powders, liniments, salves, and the like, which are, if desired, sterilized or mixed with auxiliary agents (e.g., preservatives, stabilizers, wetting agents, buffers, or salts) for influencing various properties, such as, for example, osmotic pressure. Other suitable topical dosage forms include sprayable aerosol preparations wherein the active ingredient, in some instances, in combination with a solid or liquid inert carrier, is packaged in a mixture with a pressurized volatile (e.g., a gaseous propellant, such as freon) or in a squeeze bottle. Moisturizers or humectants can also be added to pharmaceutical compositions and dosage forms if desired. Examples of such additional ingredients are well-known in the art.

If the compositions comprising the immunoconjugates are administered intranasally, it can be formulated in an aerosol form, spray, mist or in the form of drops. In particular, prophylactic or therapeutic agents for use according to the present invention can be conveniently delivered in the form of an aerosol spray presentation from pressurized packs or a nebuliser, with the use of a suitable propellant (e.g., dichlorodifluoromethane, trichlorofluoromethane, dichlorotetrafluoroethane, carbon dioxide or other suitable gas). In the case of a pressurized aerosol the dosage unit may be determined by providing a valve to deliver a metered amount. Capsules and cartridges (composed of, e.g., gelatin) for use in an inhaler or insufflator may be formulated containing a powder mix of the compound and a suitable powder base such as lactose or starch.

Methods for co-administration or treatment with a second therapeutic agent, e.g., a cytokine, steroid, chemotherapeutic agent, antibiotic, or radiation, are known in the art (see, e.g., Hardman et al., (eds.) (2001) Goodman and Gilman's The Pharmacological Basis of Therapeutics, 10th ed., McGraw-Hill, New York, N.Y.; Poole and Peterson (eds.) (2001) Pharmacotherapeutics for Advanced Practice:A Practical Approach, Lippincott, Williams & Wilkins, Phila., Pa.; Chabner and Longo (eds.) (2001) Cancer Chemotherapy and Biotherapy, Lippincott, Williams & Wilkins, Phila., Pa.). An effective amount of therapeutic may decrease the symptoms by at least 10%; by at least 20%; at least about 30%; at least 40%, or at least 50%.

Additional therapies (e.g., prophylactic or therapeutic agents), which can be administered in combination with the immunoconjugates of the invention may be administered less than 5 minutes apart, less than 30 minutes apart, 1 hour apart, at about 1 hour apart, at about 1 to about 2 hours apart, at about 2 hours to about 3 hours apart, at about 3 hours to about 4 hours apart, at about 4 hours to about 5 hours apart, at about 5 hours to about 6 hours apart, at about 6 hours to about 7 hours apart, at about 7 hours to about 8 hours apart, at about 8 hours to about 9 hours apart, at about 9 hours to about 10 hours apart, at about 10 hours to about 11 hours apart, at about 11 hours to about 12 hours apart, at about 12 hours to 18 hours apart, 18 hours to 24 hours apart, 24 hours to 36 hours apart, 36 hours to 48 hours apart, 48 hours to 52 hours apart, 52 hours to 60 hours apart, 60 hours to 72 hours apart, 72 hours to 84 hours apart, 84 hours to 96 hours apart, or 96 hours to 120 hours apart from the immunoconjugates of the invention. The two or more therapies may be administered within one same patient visit.

In certain embodiments, the immunoconjugates of the invention can be formulated to ensure proper distribution in vivo. For example, the blood-brain barrier (BBB) excludes many highly hydrophilic compounds. To ensure that the therapeutic compounds of the invention cross the BBB (if desired), they can be formulated, for example, in liposomes. For methods of manufacturing liposomes, see, e.g., U.S. Pat. Nos. 4,522,811; 5,374,548; and 5,399,331. The liposomes may comprise one or more moieties which are selectively transported into specific cells or organs, thus enhance targeted drug delivery (see, e.g., Ranade, (1989) J. Clin. Pharmacol. 29:685). Exemplary targeting moieties include folate or biotin (see, e.g., U.S. Pat. No. 5,416,016 to Low et al.); mannosides (Umezawa et al., (1988) Biochem. Biophys. Res. Commun. 153:1038); antibodies (Bloeman et al., (1995) FEBS Lett. 357:140; Owais et al., (1995) Antimicrob. Agents Chemother. 39:180); surfactant protein A receptor (Briscoe et al., (1995) Am. J. Physiol. 1233:134); p 120 (Schreier et al., (1994) J. Biol. Chem. 269:9090); see also K. Keinanen; M. L. Laukkanen (1994) FEBS Lett. 346:123; J. J. Killion; I. J. Fidler (1994) Immunomethods 4:273.

The invention provides protocols for the administration of pharmaceutical composition comprising immunoconjugates of the invention alone or in combination with other therapies to a subject in need thereof. The therapies (e.g., prophylactic or therapeutic agents) of the combination therapies of the present invention can be administered concomitantly or sequentially to a subject. The therapy (e.g., prophylactic or therapeutic agents) of the combination therapies of the present invention can also be cyclically administered. Cycling therapy involves the administration of a first therapy (e.g., a first prophylactic or therapeutic agent) for a period of time, followed by the administration of a second therapy (e.g., a second prophylactic or therapeutic agent) for a period of time and repeating this sequential administration, i.e., the cycle, in order to reduce the development of resistance to one of the therapies (e.g., agents) to avoid or reduce the side effects of one of the therapies (e.g., agents), and/or to improve, the efficacy of the therapies.

The therapies (e.g., prophylactic or therapeutic agents) of the combination therapies of the invention can be administered to a subject concurrently.

The term "concurrently" is not limited to the administration of therapies (e.g., prophylactic or therapeutic agents) at exactly the same time, but rather it is meant that a pharmaceutical composition comprising antibodies or fragments thereof the invention are administered to a subject in a sequence and within a time interval such that the antibody drug conjugates of the invention can act together with the other therapy(ies) to provide an increased benefit than if they were administered otherwise. For example, each therapy may be administered to a subject at the same time or sequentially in any order at different points in time; however, if not administered at the same time, they should be administered sufficiently close in time so as to provide the desired therapeutic or prophylactic effect. Each therapy can be administered to a subject separately, in any appropriate form and by any suitable route. In various embodiments, the therapies (e.g., prophylactic or therapeutic agents) are administered to a subject less than 5 minutes apart, less than 15 minutes apart, less than 30 minutes apart, less than 1 hour apart, at about 1 hour apart, at about 1 hour to about 2 hours apart, at about 2 hours to about 3 hours apart, at about 3 hours to about 4 hours apart, at about 4 hours to about 5 hours apart, at about 5 hours to about 6 hours apart, at about 6 hours to about 7 hours apart, at about 7 hours to about 8 hours apart, at about 8 hours to about 9 hours apart, at about 9 hours to about 10 hours apart, at about 10 hours to about 11 hours apart, at about 11 hours to about 12 hours apart, 24 hours apart, 48 hours apart, 72 hours apart, or 1 week apart.

In other embodiments, two or more therapies (e.g., prophylactic or therapeutic agents) are administered to a within the same patient visit.

The prophylactic or therapeutic agents of the combination therapies can be administered to a subject in the same pharmaceutical composition. Alternatively, the prophylactic or therapeutic agents of the combination therapies can be administered concurrently to a subject in separate pharmaceutical compositions. The prophylactic or therapeutic agents may be administered to a subject by the same or different routes of administration. The prophylactic or therapeutic agents of the combination therapies can be administered to a subject in the same pharmaceutical composition. Alternatively, the prophylactic or therapeutic agents of the combination therapies can be administered concurrently to a subject in separate pharmaceutical compositions. The prophylactic or therapeutic agents may be administered to a subject by the same or different routes of administration.

EXAMPLES

Example 1: Generation of Anti-C CR7 Antibodies

Generation of Expression Constructs for Human, Rat, Mouse and Cynomolgus Monkey CCR7

Full length human, cyno and mouse CCR7 genes were synthesized based on amino acid sequences from the GenBank or Uniprot databases (SEQ ID NO: 97, SEQ ID NO: 99, SEQ ID NO: 101). The rat CCR7 cDNA template was gene synthesized based on amino acid sequence information generated using mRNA isolated from various rat tissues (SEQ ID NO: 103). All synthesized DNA fragments were cloned into appropriate expression vectors.

TABLE 2

| Amino Acid and Nucleotide Sequence Information for CCR7 |
|---|
| Human CCR7 |
| SEQ ID NO: 97 | MDLGKPMKSVLVVALLVIFQVCLCQDEVTDDYIGDNTTVDYTLFESLCSKKDVRNFK<br>AWFLPIMYSIICFVGLLGNGLVVLTYIYFKRLKTMTDTYLLNLAVADILFLLTLPFWAYS<br>AAKSWVFGVHFCKLIFAIYKMSFFSGMLLLLCISIDRYVAIVQAVSAHRHRARVLLISK<br>LSCVGIWILATVLSIPELLYSDLQRSSSEQAMRCSLITEHVEAFITIQVAQMVIGFLVPL<br>LAMSFCYLVIIRTLLQARNFERNKAIKVIIAVVVVFIVFQLPYNGVVLAQTVANFNITSS<br>TCELSKQLNIAYDVTYSLACVRCCVNPFLYAFIGVKFRNDLFKLFKDLGCLSQEQLRQ<br>WSSCRHIRRSSMSVEAETTTTFSP |
| SEQ ID NO: 98 | ATGGACCTGGGGAAACCAATGAAAAGCGTGCTGGTGGTGGCCTCTCCTTGTCATT<br>TTCCAGGTATGCCTGTCAAGATGAGGTCACGGACGATTACATCGGAGACAAC<br>ACCACAGTGGACTACACTTTGTTCGAGTCTTTGTGCTCCAAGAAGGACGTGCGG<br>AACTTTAAAGCCTGGTTCCTCCCTATCATGTACTCCATCATTTGTTTCGTGGGCCT<br>ACTGGGCAATGGGCTGGTCGTGTTGACCTATATCTATTTCAAGAGGCTCAAGAC<br>CATGACCGATACCTACCTGCTCAACCTGGCGGTGGCAGACATCCTCTTCCTCCTG<br>ACCCTTCCCTTCTGGGCCTACAGCGCGGCCAAGTCCTGGGTCTTCGGTGTCCACT<br>TTTGCAAGCTCATCTTTGCCATCTACAAGATGAGCTTCTTCAGTGGCATGCTCCTA<br>CTTCTTTGCATCAGCATTGACCGCTACGTGGCCATCGTCCAGGCTGTCTCAGCTC<br>ACCGCCACCGTGCCCGCGTCCTTCTCATCAGCAAGCTGTCCTGTGTGGGCATCTG<br>GATACTAGCCACAGTGCTCTCCATCCCAGAGCTCCTGTACAGTGACCTCCAGAGG<br>AGCAGCAGTGAGCAAGCGATGCGATGCTCTCTCATCACAGAGCATGTGGAGGC<br>CTTTATCACCATCCAGGTGGCCCAGATGGTGATCGGCTTTCTGGTCCCCCTGCTG<br>GCCATGAGCTTCTGTTACCTTGTCATCATCCGCACCCTGCTCCAGGCACGCAACT<br>TTGAGCGCAACAAGGCCATCAAGGTGATCATCGCTGTGGTCGTGGTCTTCATAG<br>TCTTCCAGCTGCCCTACAATGGGGTGGTCCTGGCCCAGACGGTGGCCAACTTCA<br>ACATCACCAGTAGCACCTGTGAGCTCAGTAAGCAACTCAACATCGCCTACGACG<br>TCACCTACAGCCTGGCCTGCGTCCGCTGCTGCGTCAACCCTTTCTTGTACGCCTTC<br>ATCGGCGTCAAGTTCCGCAACGATCTCTTCAAGCTCTTCAAGGACCTGGGCTGCC<br>TCAGCCAGGAGCAGCTCCGGCAGTGGTCTTCCTGTCGGCACATCCGGCGCTCCT<br>CCATGAGTGTGGAGGCCGAGACCACCACCACCTTCTCCCCA |
| Cyno CCR7 |
| SEQ ID NO: 99 | MDLGKPMKSVLVVALLVIFQVCLCQDEVTDDYIGDNTTVDYTLFESLCSKKDVRNFK<br>AWFLPIMYSIICFVGLLGNGLVVLTYIYFKRLKTMTDTYLLNLAVADILFLLTLPFWAYS<br>AAKSWVFGVHFCKLIFAIYKMSFFSGMLLLLCISIDRYVAIVQAVSAHRHRARVLLISK<br>LSCVGIWILATVLSIPELLYSGLQRSSSEQAMRCSLITEHVEAFITIQVAQMVIGFLVPL |

TABLE 2-continued

Amino Acid and Nucleotide Sequence Information for CCR7

LAMSFCYLVIIRTLLQARNFERNKAIKVIIAVVVFIVFQLPYNGVVLAQTVANFNITSS
              TCELSKQLNIAYDVTYSLACVRCCVNPFLYAFIGVKFRNDLFKLFKDLGCLSQEQLRQ
              WSSCRHIRRSSMSVEAETTTTFSP

SEQ ID NO: 100  ATGGACCTGGGGAAACCAATGAAAAGCGTGCTGGTGGTGGCTCTCCTTGTCATT
              TTCCAGGTATGCCTGTGTCAAGATGAGGTCACGGACGATTACATCGGAGACAAC
              ACCACAGTGGACTACACTTTGTTCGAGTCTTTGTGCTCCAAGAAGGACGTGCGG
              AACTTTAAAGCCTGGTTCCTCCCTATCATGTACTCCATCATTTGTTTCGTGGGCCT
              ACTGGGCAATGGGCTGGTCGTGTTGACCTATATCTATTTCAAGAGGCTCAAGAC
              CATGACCGATACCTACCTGCTCAACCTGGCGGTGGCAGACATCCTCTTCCTCCTG
              ACCCTTCCCTTCTGGGCCTACAGCGCGGCCAAGTCCTGGGTCTTCGGTGTCCACT
              TTTGCAAGCTCATCTTTGCCATCTACAAGATGAGCTTCTTCAGTGGCATGCTCCTA
              CTTCTTTGCATCAGCATTGACCGCTACGTGGCCATCGTCCAGGCTGTCTCAGCTC
              ACCGCCACCGTGCCCGCGTCCTTCTCATCAGCAAGCTGTCCTGTGTGGGCATCTG
              GATACTAGCCACAGTGCTCTCCATCCCAGAGCTCCTGTACAGTGGCCTCCAGAG
              GAGCAGCAGTGAGCAAGCGATGCGATGCTCTCTCATCACAGAGCATGTGAGG
              CCTTTATCACCATCCAGGTGGCCCAGATGGTGATCGGCTTTCTGGTCCCCCTGCT
              GGCCATGAGCTTCTGTTACCTTGTCATCATCCGCACCCTGCTCCAGGCACGCAAC
              TTTGAGCGCAACAAGGCCATCAAGGTGATCATCGCTGTGGTCGTGGTCTTCATA
              GTCTTCCAGCTGCCCTACAATGGGGTGGTCCTGGCCCAGACGGTGGCCAACTTC
              AACATCACCAGTAGCACCTGTGAGCTCAGTAAGCAACTCAACATCGCCTACGAC
              GTCACCTACAGCCTGGCCTGCGTCCGCTGCTGCGTCAACCCTTTCTTGTACGCCTT
              CATCGGCGTCAAGTTCCGCAACGATCTCTTCAAGCTCTTCAAGGACCTGGGCTGC
              CTCAGCCAGGAGCAGCTCCGGCAGTGGTCTTCCTGTCGGCACATCCGGCGCTCC
              TCCATGAGTGTGGAGGCCGAGACCACCACCACCTTCTCCCCA

Mouse CCR7

SEQ ID NO: 101  MDPGKPRKNVLVVALLVIFQVCFCQDEVTDDYIGENTTVDYTLYESVCFKKDVRNFK
              AWFLPLMYSVICFVGLLGNGLVILTYIYFKRLKTMTDTYLLNLAVADILFLLILPFWAYS
              EAKSWIFGVYLCKGIFGIYKLSFFSGMLLLLCISIDRYVAIVQAVSAHRHRARVLLISKLS
              CVGIWMLALFLSIPELLYSGLQKNSGEDTLRCSLVSAQVEALITIQVAQMVFGFLVP
              MLAMSFCYLIIRTLLQARNFERNKAIKVIIAVVVFIVFQLPYNGVVLAQTVANFNIT
              NSSCETSKQLNIAYDVTYSLASVRCCVNPFLYAFIGVKFRSDLFKLFKDLGCLSQERLR
              HWSSCRHVRNASVSMEAETTTTFSP

SEQ ID NO: 102  ATGGACCCAGGGAAACCCAGGAAAAACGTGCTGGTGGTGGCTCTCCTTGTCATT
              TTCCAGGTGTGCTTCTGCCAAGATGAGGTCACCGATGACTACATCGGCGAGAAT
              ACCACGGTGGACTACACCCTGTACGAGTCGGTGTGCTTCAAGAAGGATGTGCGG
              AACTTTAAGGCCTGGTTCCTGCCTCTCATGTATTCTGTCATCTGCTTCGTGGGCCT
              GCTCGGCAACGGGCTGGTGATACTGACGTACATCTATTTCAAGAGGCTCAAGAC
              CATGACGGATACCTACCTGCTCAACCTGGCCGTGGCAGACATCCTTTTCCTCCTG
              ATTCTTCCCTTCTGGGCCTACAGCGAAGCCAAGTCCTGGATCTTTGGCGTCTACC
              TGTGTAAGGGCATCTTTGGCATCTATAAGTTAAGCTTCTTCAGCGGGATGCTGCT
              GCTCCTATGCATCAGCATTGACCGCTACGTAGCCATCGTCCAGGCCGTGTCGGCT
              CATCGCCACCGCGCCCGCGTGCTTCTCATCAGCAAGCTGTCCTGTGTGGGCATCT
              GGATGCTGGCCCTCTTCCTCTCCATCCCGGAGCTGCTCTACAGCGGCCTCCAGAA
              GAACAGCGGCGAGGACACGCTGAGATGCTCACTGGTCAGTGCCCAAGTGGAGG
              CCTTGATCACCATCCAAGTGGCCCAGATGGTTTTTGGTTCCTAGTGCCTATGCT
              GGCTATGAGTTTCTGCTACCTCATTATCATCGTACCTTGCTCCAGGCACGCAACT
              TTGAGCGGAACAAGGCCATCAAGGTGATCATTGCCGTGGTGGTAGTCTTCATAG
              TCTTCCAGCTGCCCTACAATGGGGTGGTCCTGGCTCAGACGGTGGCCAACTTCA
              ACATCACCAATAGCAGCTGCGAAACCAGCAAGCAGCTCAACATTGCCTATGACG
              TCACCTACAGCCTGGCCTCCGTCCGCTGCTGCGTCAACCCTTTCTTGTATGCCTTC
              ATCGGCGTCAAGTTCCGCAGCGACCTCTTCAAGCTCTTCAAGGACTTGGGCTGTC
              TCAGCCAGGAACGGCTCCGGCACTGGTCTTCCTGCCGGCATGTACGAACGCGT
              CGGTGAGCATGGAGGCGGAGACCACCACAACCTTCTCCCCG

Rat CCR7

SEQ ID NO: 103  MDLGKPTKNVLVVALLVIFQVCFCQDEVTDDYIGENTTVDYTLYESVCFKKDVRNFK
              AWFLPLMYSVICFVGLLGNGLVVLTYIYFKRLKTMTDTYLLNLAVADILFLMILPFWA
              YSEAKSWIFGAYLCKSIFGIYKLSFFSGMLLLLCISIDRYVAIVQAVSAHRHRARVLLISK
              LSCIGIWTLAFFLSIPELLYSGLQKNSGEDTWRCSLVSAQVEALIAIQVAQMVVGFVL
              PMLAMSFCYLVIIRTLLQARNFERNKAIKVIIAVVVVFVVFQLPYNGVVLAQTVANFN
              ITNSSCEASKQLNIAYDVTYSLASVRCCVNPFLYAFIGVKFRSDLFKLFKDLGCLSQERL
              RQWSSCRHVRHTSVSMEAETTTTFSP

SEQ ID NO: 104  ATGGACCTGGGGAAGCCCACGAAAAACGTGCTGGTGGTGGCTCTCCTGGTCATT
              TTCCAGGTGTGCTTCTGCCAAGATGAGGTCACAGACGACTACATCGGCGAGAAC
              ACCACCGTGGACTACACCCTGTATGAGTCGGTGTGCTTCAAGAAGGATGTGCGG
              AACTTTAAGGCCTGGTTCCTCCCTCTCATGTACTCAGTCATTTGTTCGTGGGCCT
              GCTAGGCAATGGGCTGGTGGTGCTGACATACATCTATTTCAAGAGACTGAAGAC
              CATGACGGATACCTACCTGCTCAACCTGGCCGTGGCAGACATCCTCTTCCTCATG
              ATCCTTCCCTTCTGGGCCTACAGCGAAGCCAAGTCCTGGATCTTTGGTGCCTACC
              TGTGTAAGAGCATCTTTGGCATCTACAAGTTAAGCTTCTTCAGCGGGATGTTGCT
              GCTCCTGTGTATCAGCATTGACCGCTATGTGGCCATCGTCCAGGCCGTGTCAGCC
              CACCGGCACCGCGCCCGCGTGCTTCTCATCAGCAAGCTGTCCTGTATAGGCATCT
              GGACGCTGGCCTTTTTCCTTTCTATCCCTGAGCTGCTCTACAGCGGCCTCCAGAA
              GAACAGCGGCGAGGACACGTGGAGATGCTCCCTGGTCAGTGCCCAAGTGGAGG
              CCTTGATCGCCATCCAAGTGGCCCAGATGGTTGTGGGTTTGTACTGCCTATGCT

TABLE 2-continued

Amino Acid and Nucleotide Sequence Information for CCR7

```
GGCTATGAGTTTCTGCTACCTGGTTATCATCCGCACTCTGCTCCAGGCGCGAAAC
TTCGAGCGGAACAAGGCCATCAAGGTGATCATCGCTGTGGTCGTAGTGTTCGTC
GTCTTCCAGCTGCCCTACAATGGGGTGGTCCTGGCCCAGACCGTGGCCAATTTC
AACATCACCAATAGCAGCTGCGAAGCCAGCAAGCAGCTCAACATTGCCTATGAC
GTCACCTACAGCCTGGCCTCCGTCCGCTGCTGTGTCAACCCTTTCTTGTATGCCTT
CATCGGCGTCAAGTTCCGCAGCGACCTCTTCAAGCTCTTCAAGGACTTGGGCTGC
CTCAGCCAGGAACGGCTCCGGCAGTGGTCTTCCTGCCGCCATGTACGGCACACG
TCCGTGAGCATGGAGGCGGAGACTACCACCACCTTCTCCCCG
```

Generation of Cell Lines Stably Expressing CCR7

Stable CCR7-expressing cell lines were generated using retroviral transduction. 293T cells were co-transfected with a CCR7 retroviral expression vector and a pCL-Eco or pCL-10A1 packaging vector (Novus, USA, cat #NBP2-29540 or NBP2-2952) using Fugene 6 transfection reagent (Promega, USA, cat #E2692) following manufacturer's recommendation. Cells were incubated in a 37° C. humidified $CO_2$ incubator and viral supernatant was collected 48 hours post-transfection. NIH/3T3 and 300.19 cells were grown to near confluent monolayer. Growth media was removed from the cells and viral supernatant was added in the presence of 8 ug polybrene/ml (final concentration) (EMD Millipore, cat #TR-1003-G). Following incubation for 3-6 hours at 37° C., fresh media was added. Cells were then cultured under appropriate selection conditions to produce stable CCR7-expressing cell lines.

Generation, Expression and Purification of Viral-Like Particles (VLPs)

HEK293T or NIH/3T3 cells were maintained in DMEM with 10% FBS. To make VLPs, cells were exchanged into DMEM with 4% FBS, then co-transfected with a CCR7 expression plasmid and a retroviral Gag expression plasmid at a μg ratio of 3:2. Forty-eight hours post-transfection, cell supernatant was collected and clarified by centrifugation at 2500×g for 5 min in a benchtop centrifuge and kept on ice. VLPs were purified by ultracentrifugation in at 100,000×g through a 20% sucrose cushion in Beckman Ultra-Clear 38 ml centrifugation tubes (catalog #344058) in a Beckman Coulter SW 32 Ti rotor in a Sorvall RC 6+ ultracentrifuge. Resulting pellets were resuspended in 300 μl of cold sterile PBS and quantitated using a BCA Assay (Pierce catalog #23225).

Structure Derived Generation of CCR7 Immunogen Scaffold

Members of the G coupled protein receptor family are membrane proteins that contain seven transmembrane helixes (TM1 . . . TM7) each connected by linking sequences of varying length. The amino terminus of the protein is on the ecto side of the cell surface which indicates that 4 regions of the protein are potentially exposed on the surface of the cell, the amino terminus (N-term) and 3 extracellular loop regions (EC1, EC2 and EC3). These regions are thus available as antigens for antibodies.

It was envisioned that a combination of one or more of these 4 entries could be inserted into a soluble protein scaffold to structurally approximate the extracellularly exposed region of CCR7.

To determine the optimal extracellular regions of CCR7, a model was built using the crystal structure of the close homologue CXCR4 (Wu et al., "Structures of the CXCR4 chemokine GPCR with small-molecule and cyclic peptide antagonists." (2010) Science 330: 1066-1071) using a combination of CXCR4 structure with Protein Data bank Entries (3ODU, 3OE0, 3OE6, 3OE8, 3OE9) and modelling software Amino acids that were interstitial to the connecting transmembrane helices were inferred from the model to be exposed on the surface of the protein. These regions are identified in Table 3 below.

TABLE 3

Amino Acid and Nucleotide Sequence Information for CCR7 Immunogen Scaffold

| SEQ ID NO: | Description | | Comments |
|---|---|---|---|
| 105 | CCR7 (NP_001829.1\|C-C chemokine receptor type 7) | MDLGKPMKSVLVVALLVIFQVCLCQDEVTDD YIGDNTTVDYTLFESLCSKKDVRNFKAWFLPI MYSIICFVGLLGNGLVVLTYIYFKRLKTMTDTYL LNLAVADILFLLTLPFWAYSAAKSWVFGVHFC KLIFAIYKMSFFSGMLLLLCISIDRYVAIVQAVSA HRHRARVLLISKLSCVGIWILATVLSIPELLYSDL QRSSSEQAMRCSLITEHVEAFITIQVAQMVIG FLVPLLAMSFCYLVIIRTLLQARNFERNKAIKVII AVVVVFIVFQLPYNGVVLAQTVANFNITSSTCE LSKQLNIAYDVTYSLACVRCCVNPFLYAFIGVKF RNDLFKLFKDLGCLSQEQLRQWSSCRHIRRSS MSVEAETTTTFSP | CCR7, precursor. Extracellular regions are highlighted in bold. Insert regions or derivatives thereof are in bold and underlined. |
| 106 | N-term | QDEVTDDYIGDNTTVDYTLFESLCSKKDVR | CCR7 N-terminal extracellular sequence |
| 107 | EC1 | KSWVFGVH | CCR7 Extracellular loop 1 |

TABLE 3-continued

Amino Acid and Nucleotide Sequence Information for CCR7 Immunogen Scaffold

| SEQ ID NO: | Description | | Comments |
|---|---|---|---|
| 108 | EC2 | YSDLQRSSSEQAMRCSLIT | CCR7 Extracellular loop 2 |
| 109 | EC3 | FNITSST | CCR7 Extracellular loop 3 |
| 110 | EC2_C24S | YSDLQRSSSEQAMRSSLIT | |
| 111 | H_MGFTX1 | EVQLVESGGGLVKPGGSLKLSCAASGFTFSDY GMLWVRQAPEKGLEWIAYISSGSSTIYYADRV KGRFTISRDNAKNTLFLQMTSLRSEDTAMYYC STGTFAYWGQGTPVTVSSAKTTPPSVYPLAPG SAAQTNSMVTLGCLVKGYFPEPVTVTWNSGS LSSGVHTFPAVLQSDLYTLSSSVTVPSSTWPSE TVTCNVAHPASSTKVDKKIVPRDC | Heavy chain of mouse Fab scaffold |
| 112 | L_MGFTX1 | DVVMTQNPLSLPVSLGDQASISCRSSQSLIYNN GNTYLHWYRQKPGQSPKLLIYKVSNRFSGVPD RFSGSGSGTDFTLKISRVEAEDLGVYFCSQSTH VPFTFGSGTKLEIKRADAAPTVSIFPPSSEQLTS GGASVVCFLNNFYPKDINVKWKIDGSERQNG VLNSWTDQDSKDSTYSMSSTLTLTKDEYERHN SYTCEATHKTSTSPIVKSFNRNEC | Light chain of mouse Fab scaffold |
| 113 | H_FabCCR7M1 | QDEVTDDYIGDNTTVDYTLFESLCSKKDVREV QLVESGGGLVKPGGSLKLSCAASGFTFSDYGM LWVRQAPEKGLEWIAYISSGSSTIYYADRVKGR FTISRDNAKNTLFLQMTSLRSEDTAMYYCSTG TYSDLQRSSSEQAMRSSLITFAYWGQGTPVT VSSAKTTPPSVYPLAPGSAAQTNSMVTLGCLV KGYFPEPVTVTWNSGSLSSGVHTFPAVLQSDL YTLSSSVTVPSSTWPSETVTCNVAHPASSTKVD KKIVPRDC | Heavy chain of Fab with N-term and EC2 inserted. Inserted sequences underlined and in bold |
| 114 | H_FabCCR7M1 | CAAGATGAGGTCACGGACGATTACATCGGA GACAACACCACAGTGGACTACACTTTGTTCG AGTCTTTGTGCTCCAAGAAGGACGTGCGGga ggtgcagctggtggagtctggtggtggtctggtcaagcct ggaggttccctgaaactgagttgtgccgcatctgggtttac attctctgactacggaatgctgtgggtgaggcaggcacca gagaagggcctggaatggatcgcttatatttccagcggat ctagtactatctactatgcagacagggtcaagggccggtt caccattagcagagataacgccaaaaatacctgtttctg cagatgacatcactgaggtccgaggataccgctatgtatt attgctccacagggactTACAGTGACCTCCAGAGG AGCAGCAGTGAGCAAGCGATGCGATCCTCT CTCATCACAtttgcttactggggacaggggacacccgt gaccgtcagctcagccaagaccaccccccccagcgtgtac cctctggccctggctctgccgcccagaccaacagcatgg tgaccctgggctgcctggtgaagggctacttccccgagcc cgtgaccgtgacctggaacagcggcagcctgagcagcgg cgtgcacaccttccccgccgtgctgcagagcgacctgtac accctgagcagctctgtgaccgtgcccagcagcacctggc ccagcgagaccgtgacatgcaacgtggcccaccccgcca gctccaccaaggtggacaagaaaatcgtgccccgggact gc | DNA sequence of HFabCCR7M1 heavy chain. Inserted sequence in upper case |
| 115 | L_MGFTX1 | atgtcgtgatgactcagaatccactgtccctgcctgtgtcc ctgggcgatcaggcttccattagctgtcgtcctctcagtcc ctgatctacaacaatggtaacacctacctgcactggtata gacagaagcccggccagtcccctaagctgctgatctacaa agtgagtaataggttctcaggagtcccagaccggttttccg gcagcggatctgggaccgatttcacactgaaaatctctag ggtggaggccgaagacctgggcgtctacttttgtagtcag agcactcacgtcccccttcaccttcggcagcggaacaaaac tggaaatcaagcgcgctgatgccgcccctaccgtgagcat cttccccccagcagcgagcagctgaccagcggcggagc cagcgtggtgtgcttcctgaacaacttctaccccaaggac atcaacgtgaagtggaagatcgacggcagcgagcggca gaacggcgtgctgaacagctggaccgaccaggacagca | DNA sequence of L_MGFTX1 |

TABLE 3-continued

Amino Acid and Nucleotide Sequence Information for CCR7 Immunogen Scaffold

| SEQ ID NO: | Description | | Comments |
|---|---|---|---|
| | | aggactccacctacagcatgagcagcaccctgaccctga ccaaggacgagtacgagcggcacaacagctacacctgcg aggccacccacaagaccagcaccagcccatcgtgaaga gcttcaaccggaacgagtgc | |

The small size of loops EC1 and EC3 and the spatial separation of EC3 from the other three regions prioritized the use of N-term and EC2 loop as candidate epitopes.

Modelling the fusion of the N-term sequence into the crystal structure of a mouse Fab with the EC2 sequence inserted into various loop regions of the Fab such as in Framework 1, CDR-H3 or CDR3-H1, showed that if a degree of flexibility is assumed in the two sequences then these could be reasonable approximations to the structure of these regions in CCR7.

Immunogen Scaffold Generation for Mouse Immunization

Engrafted constructs for mouse immunization were generated by fusing the N-terminal sequence from Table 3 to the N-terminus of the heavy chain of a mouse Fab scaffold (designated MGFTX1) and engrafting a modified version of EC2 sequence with the cysteine residue at position 24 mutated to a serine (Table 3 and underlined +emboldened sequences of SEQ ID NO: 113), into CDR3 of the MGFTX1 scaffold, then both heavy and light chain immunoglobulin chains were produced to generate final protein constructs. The constructs, designated FabCCR7M1, thus contained a mouse framework which should be immune tolerant combined with human sequence to which the mouse immune response was directed.

The N-term sequence was directly fused with the heavy chain of the MGFTX1 scaffold. Insertion points for EC2 were selected to be the mid-point of the CDR loop based on available structural or homology model data. Fab engrafted proteins were produced using standard molecular biology methodology utilizing recombinant DNA encoding the relevant sequences.

For example, a variable region of each antibody containing EC2 was inserted into heavy chain CDR3 was synthesized. DNA encoding variable region was amplified via PCR and the resulting fragment was sub-cloned into vector containing either the light chain constant region or the heavy chain constant and Fc regions. In this manner FabCCR7M1 proteins were made corresponding to fusion of N-term and insertion of EC2 into H3. Resulting constructs are shown in Table 3. Transfections of the appropriate combination of heavy and light chain vectors results in the expression of a recombinant Fab containing one N-term and one EC2 molecules.

The selection of which CDR is chosen for engraftment is determined based on the parameters of exposure of the loop and proximity to the N-terminal. At this time, modelling software is only partially useful in predicting which CDR and which location within the CDR will provide the desired parameters, due to the flexibility of the loops after fusion and engraftment. The structure of the MGFTX1 scaffold in combination with the EC2_C24S (Table 3, SEQ ID NO: 110) showed the sequence to be exposed and flexible as judged by lack of electron density for the majority of the sequence.

In summary, the insertion point in the CDR was chosen on a structural basis, with the hypothesis that grafting into the CDR would provide some level of structural semblance to the native antigen.

Hybridoma Generation

Bcl-2 transgenic mice (C57BL/6-Tgn (bcl-2) 22 WEHI strain) were immunized with antigen using a procedure that calls for Repetitive Immunization at Multiple Sites (RIMMS) (McIntyre G D. Hybridoma 1997). Briefly, mice were injected with 1-3 μg of CCR7 immunogen at 8 specific sites proximal to peripheral lymph nodes (PLNs). This procedure was repeated 8 times over a 12 day period. On Day 12, a test bleed was collected and the serum antibody titer was analyzed by FACS. In some instances, BALB/c and/or C57B1/6 mice were immunized with NIH3T3 or 300.19 cells stably overexpressing human CCR7 (SEQ ID NO: 97) Animals were injected subcutaneously with $5\times10^6$ cells in PBS once a month for 3 months followed by an intravenous boost with 25 μg of human CCR7-expressing VLPs. Two days after the boost, a test bleed was collected and serum antibody titer was analyzed by FACS. Spleens and pooled PLNs were removed from high titer mice. To harvest lymphocytes, spleens and PLNs were washed twice with DMEM, and then dissociated by passage through a 70 micron screen (Falcon #352350). The resulting lymphocytes were washed 2 additional times prior to fusion in Cytofusion media (BTXpress Cytofusion® Electroporation Medium cat #47001).

For the fusion, F0 myeloma cells were mixed with lymphocytes at a 1:4 ratio. The cell mixture was centrifuged, suspended in Cytofusion media and subsequently added to an electrofusion chamber (Harvard Apparatus Coaxial chamber 9ML Part #470020). Electrofusion was carried out per manufacturer's instructions using the CEEF-50B Hybrimune/Hybridoma system (Cyto Pulse Sciences, Inc). Fused cells were allowed to recover 5 min in chamber, diluted 1/10 in Fusion media without HAT (DMEM+20% FBS, 1% Pen/Strep/Glu, 1× NEAA, 0.5× HFCS) and placed at 37° C. for one hour. 4× HAT media (DMEM+20% FBS, 1% Pen/Strep/Glu, 1× NEAA, 4× HAT, 0.5× HFCS) was added to make a 1× solution, and density was adjusted to $1.67\times10^4$ cells/ml. The cells were plated in 384-well plates at 60 μl/well.

FACS Screening

Ten days after fusion, hybridoma plates were screened for the presence of CCR7-specific antibodies using flow cytometry to confirm specific binding of candidate antibodies to cell lines stably overexpressing or endogenously expressing CCR7. Cells were rinsed thoroughly with PBS and treated with Accutase (Millipore #SCR005) to lift from growth plates and resuspended in cold PBS. Cells were biotinylated labeled with a fluorescent dye according to manufacdturer's directions (FluoReporter Cell-Surface Biotinylation Kit, Thermo Fisher Scientific Cat #F-20650; PE-Cy7 Steptavidin, ThermoFisher Scientific Cat #SA1012). Cells were resuspended at approximately 1×10⁶ cells/ml in FACS buffer (1× DPBS, 3% FBS, 5 mM EDTA, 0.1% Sodium Azide). In a 384-well plate, 20 μL of hybridoma supernatant was pre-seeded and 20 μL of cell suspension was added. Cells were incubated for 1 hour at 4° C., washed twice with cold FACS buffer and resuspended in 20 μL of 1:400 secondary antibody FACS buffer (Allophycocyanin conjugated F(ab')2 goat anti-human IgG, Fcγ specific; Jackson Immunoresearch, Cat #109-136-098). After additional incubation for 45 min at 4° C., cells were washed twice with FACS buffer and resuspended in 20 uL of FACS buffer+with 2 μg/ml propidium iodide (Sigma Aldrich Cat #P4864-10ML). Geometric mean fluorescence intensity was calculated on live single cells using FlowJo™ software.

Antibody Purification

Chimeric antibodies comprising murine variable regions and human constant regions were prepared. Additionally, chimeric versions comprising cysteine mutations (e.g., cysteines at position K360C, or positions E152C and S375C of the heavy chain) were designed for conjugation of drug moiety and preparation of ADCs as described in further detail herein. Variable region (VH and VL) DNA sequences of hybridomas were obtained for generation of optimized sequences (e.g., humanization, preferred characteristics) for each of selected hybridomas mAb121G12, mAb506E15, mAb674J13 and mAb684E12. Variable region DNA from murine monoclonal antibodies was amplified by RACE from RNA obtained from each selected hybridoma cell line using standard methods. Polypeptide sequences for each of the murine variable heavy/light chains are shown in SEQ ID NO: 128/SEQ ID NO: 144, SEQ ID NO: 160/SEQ ID NO: 176, SEQ ID NO: 192/SEQ ID NO: 208, and SEQ ID NO: 224/SEQ ID NO: 240 respectively for each of 674J13, 121G12, 506E15 and 684E12 hybridomas. Corresponding derived variable heavy/light nucleotide sequences for each of the hybridomas are shown in SEQ ID NO: 129/SEQ ID NO: 145, SEQ ID NO: 161/SEQ ID NO: 177, SEQ ID NO: 193/SEQ ID NO: 209, and SEQ ID NO: 225/SEQ ID NO: 241. For preparation of chimeric antibodies, DNA sequences coding for the hybridoma VL and VH domain were subcloned into expression vectors containing the respective human wild type or engineered Cys or D265A/P329A (DAPA) mutation heavy chain and human light chain constant region sequences (IgG1, kappa).

Humanization of Antibodies

Variable region constructs were designed for humanization and optimization of sequences (e.g., removal of post-translational modifications, non-preferred sites, etc.), to include cysteine mutations (e.g., cysteines at position K360C, or positions E152C and S375C of the heavy chain) for conjugation of drug moiety and preparation of ADCs as described in further detail herein; as well as for modification of Fc effector mutations (e.g., D265A/P329A mutations in the Fc region) to include constructs having reduced Fc effector function, and combinations thereof.

DNA sequences coding for humanized VL and VH domains were ordered at GeneArt (Life Technologies Inc. Regensburg, Germany), including codon optimization for Cricetulus griseus. Sequences coding for VL and VH domains were subcloned from the GeneArt derived vectors into expression vectors suitable for protein production in mammalian cells. Heavy and light chains were cloned into individual expression vectors to allow co-transfection.

Recombinant antibodies (IgG1, kappa) were produced by co-transfection of vectors into Freestyle™ 293 expression cells (Invitrogen, USA) using PEI (polyethylenimine, MW 25,000 linear, Polysciences, USA, cat #23966) as transfection reagent. The PEI stock was prepared by dissolving 1 g of PEI in 900 ml cell culture grade water at room temperature (RT). To facilitate dissolution of PEI, the solution was acidified by addition of HCl to pH 3-5, followed by neutralization with NaOH to a final pH of 7.05. Finally, the volume was adjusted to 1 L and the solution was filter sterilized through a 0.22 um filter, aliquoted and frozen at −80° C. until further use.

Freestyle™ 293 cells (Gibco™, ThermoFisher scientific, USA, cat #R79007) were cultivated in Freestyle™ 293 media (Gibco™, ThermoFisher scientific, USA, cat #12338018) in shake flasks (Corning, Tewksbury, Mass.) on an orbital shaker (100-120 rpm) in a 37° C. humidified incubator at 5% $CO_2$. For transient transfections, cells were grown to a density or approximately 3×10⁶ cells/ml, and then 1 ug of filter sterilized DNA/ml of culture (0.5 ug of heavy chain+0.5 ug of light chain) was added to 2 ug PEI/1 ug of DNA in OptiMem (ThermoFisher Scientific, USA, #11058021) solution and incubated at RT for 8 minutes. The mixture was the added to the Freestyle™ 293 cells dropwise with gently swirling. Following transfection, the cells were cultured for one to two weeks prior to antibody purification from supernatant. To generate stable cell lines for antibody production, vectors were co-transfected by nucleofection (Nucleofector™ 96-well Shuttle™; Lonza) into CHO cells using manufacturer's recommendations, and cultured under selection conditions for up to four weeks in shake flasks. Cells were harvested by centrifugation, and supernatant recovered for antibody purification. Antibody was purified using protein A, Protein G or MabSelect SuRe (GE Healthcare Life Sciences) columns. Prior to loading the supernatant, the resin was equilibrated with PBS. Following binding of the sample, the column was washed with PBS, and the antibody was eluted with Thermo (Pierce) IgG pH 2.8 (cat #21004). The eluate fractions were neutralized with sodium citrate tribasic dehydrate buffer, pH 8.5 (Sigma Aldrich cat #54641-1Kg) and then dialyzed overnight into PBS, pH 7.2.

Summary of Antibodies

Table 4 sets forth the relevant sequence information for parental and humanized anti-CCR7 antibodies derived from murine hybridomas. Throughout this application, when describing the antibodies, the terms "Hybridoma" and "Parental" are used interchangeably and refer to the Ab that is derived from the hybridoma.

TABLE 4

Amino Acid and Nucleotide Sequence Information for Hybridomas and Humanized Anti-CCR7 Antibodies Parental 674J13 hIgG1

| | | | |
|---|---|---|---|
| SEQ ID NO: 116 | HCDR1 (Combined) | GYSITSGYSWH | |
| SEQ ID NO: 117 | HCDR2 (Combined) | HIHSSGSTNYNPSLKS | |

TABLE 4-continued

Amino Acid and Nucleotide Sequence Information for Hybridomas and Humanized Anti-CCR7 Antibodies

| | | |
|---|---|---|
| SEQ ID NO: 118 | HCDR3 (Combined) | GGVQAFAY |
| SEQ ID NO: 119 | HCDR1 (Kabat) | SGYSWH |
| SEQ ID NO: 120 | HCDR2 (Kabat) | HIHSSGSTNYNPSLKS |
| SEQ ID NO: 121 | HCDR3 (Kabat) | GGVQAFAY |
| SEQ ID NO: 122 | HCDR1 (Chothia) | GYSITSGY |
| SEQ ID NO: 123 | HCDR2 (Chothia) | HSSGS |
| SEQ ID NO: 124 | HCDR3 (Chothia) | GGVQAFAY |
| SEQ ID NO: 125 | HCDR1 (IMGT) | GYSITSGYS |
| SEQ ID NO: 126 | HCDR2 (IMGT) | IHSSGST |
| SEQ ID NO: 127 | HCDR3 (IMGT) | ARGGVQAFAY |
| SEQ ID NO: 128 | VH | DVQLQESGPDLVKPSQSLSLTCTVTGYSITSGYSWHWIR QFPGNKLEWMAHIHSSGSTNYNPSLKSRISIIRDTSKNLFF LQLNSVTTEDTATYYCARGGVQAFAYWGQGTLVTVSA |
| SEQ ID NO: 129 | DNA VH | GATGTGCAGCTTCAGGAGTCAGGACCTGACCTGGTGA AACCTTCTCAGTCACTTTCACTCACCTGCACTGTCACTG GCTACTCCATCACCAGTGGTTATAGCTGGCACTGGATC CGGCAGTTTCCAGGAAACAAACTGGAGTGGATGGCCC ACATCCACTCCAGTGGTAGCACTAACTACAACCCATCT CTCAAAAGTCGCATCTCTATCATTCGAGACACATCCAA GAACCTGTTCTTCCTGCAGTTGAATTCTGTGACTACTGA GGACACAGCCACATATTACTGTGCAAGAGGGGGGGTA CAGGCCTTTGCTTACTGGGGCCAAGGGACTCTGGTCAC TGTCTCTGCA |
| SEQ ID NO: 130 | Heavy Chain (WT Fc) | DVQLQESGPDLVKPSQSLSLTCTVTGYSITSGYSWHWIRQFPG NKLEWMAHIHSSGSTNYNPSLKSRISIIRDTSKNLFFLQLNSVTT EDTATYYCARGGVQAFAYWGQGTLVTVSAASTKGPSVFPLAP SSKSTSGGTAALGCLVKDYFPEPVTVSWNSGALTSGVHTFPAV LQSSGLYSLSSVVTVPSSSLGTQTYICNVNHKPSNTKVDKRVEP KSCDKTHTCPPCPAPELLGGPSVFLFPPKPKDTLMISRTPEVTCV VVDVSHEDPEVKFNWYVDGVEVHNAKTKPREEQYNSTYRVV SVLTVLHQDWLNGKEYKCKVSNKALPAPIEKTISKAKGQPREP QVYTLPPSREEMTKNQVSLTCLVKGFYPSDIAVEWESNGQPEN NYKTTPPVLDSDGSFFLYSKLTVDKSRWQQGNVFSCSVMHEA LHNHYTQKSLSLSPGK |
| SEQ ID NO: 131 | DNA Heavy Chain | gatgtgcagcttcaggagtcaggacctgacctggtgaaaccttctcagtcactttcactcacctgcactgtcactggctactccatcaccagtggttatagctggcactggatccggcagtttccaggaaacaaactggagtggatggcccacatccactccagtggtagcactaactacaacccatctctcaaaagtcgcatctctatcattcgagacacatccaagaacctgttcttcctgcagttgaattctgtgactactgaggacacagccacatattactgtgcaagaggggggtacaggcctttgcttactggggccaagggactctggtcactgtctctgcaGCTAGCACCAAGGGCCCAAGT GTGTTTCCCCTGGCCCCCAGCAGCAAGTCTACTTCCGGCGG AACTGCTGCCCTGGGTTGCCTGGTGAAGGACTACTTCCCCG AGCCCGTGACAGTGTCCTGGAACTCTGGGGCTCTGACTTCC GGCGTGCACACCTTCCCCGCCGTGCTGCAGAGCAGCGGCCT GTACAGCCTGAGCAGCGTGGTGACAGTGCCCTCCAGCTCTC TGGGAACCCAGACCTATATCTGCAACGTGAACCACAAGCCC AGCAACACCAAGGTGGACAAGAGAGTGGAGCCCAAGAGCT GCGACAAGACCCACACCTGCCCCCCCTGCCCAGCTCCAGAA CTGCTGGGAGGGCCTTCCGTGTTCCTGTTCCCCCCCAAGCCC AAGGACACCCTGATGATCAGCAGGACCCCCGAGGTGACCT GCGTGGTGGTGGACGTGTCCCACGAGGACCCAGAGGTGAA GTTCAACTGGTACGTGGACGGCGTGGAGGTGCACAACGCC AAGACCAAGCCCAGAGAGGAGCAGTACAACAGCACCTACA GGGTGGTGTCCGTGCTGACCGTGCTGCACCAGGACTGGCTG AACGGCAAGAATACAAGTGCAAAGTCTCCAACAAGGCCCT GCCAGCCCCAATCGAAAAGACAATCAGCAAGGCCAAGGGC CAGCCACGGGAGCCCCAGGTGTACACCCTGCCCCCCAGCCG GGAGGAGATGACCAAGAACCAGGTGTCCCTGACCTGTCTG GTGAAGGGCTTCTACCCCAGCGATATCGCCGTGGAGTGGG AGAGCAACGGCCAGCCCGAGAACAACTACAAGACCACCCCC CCAGTGCTGGACAGCGACGGCAGCTTCTTCCTGTACAGCAA GCTGACCGTGGACAAGTCCAGGTGGCAGCAGGGCAACGTG TTCAGCTGCAGCGTGATGCACGAGGCCCTGCACAACCACTA CACCCAGAAGTCCCTGAGCCTGAGCCCCGGCAAG |

TABLE 4-continued

Amino Acid and Nucleotide Sequence Information for Hybridomas and Humanized Anti-CCR7 Antibodies

| | | |
|---|---|---|
| SEQ ID NO: 132 | LCDR1 (Combined) | SASSSVIYMH |
| SEQ ID NO: 133 | LCDR2 (Combined) | DTSKLAS |
| SEQ ID NO: 134 | LCDR3 (Combined) | QQWSSNPLT |
| SEQ ID NO: 135 | LCDR1 (Kabat) | SASSSVIYMH |
| SEQ ID NO: 136 | LCDR2 (Kabat) | DTSKLAS |
| SEQ ID NO: 137 | LCDR3 (Kabat) | QQWSSNPLT |
| SEQ ID NO: 138 | LCDR1 (Chothia) | SSSVIY |
| SEQ ID NO: 139 | LCDR2 (Chothia) | DTS |
| SEQ ID NO: 140 | LCDR3 (Chothia) | WSSNPL |
| SEQ ID NO: 141 | LCDR1 (IMGT) | SSVIY |
| SEQ ID NO: 142 | LCDR2 (IMGT) | DTS |
| SEQ ID NO: 143 | LCDR3 (IMGT) | QQWSSNPLT |
| SEQ ID NO: 144 | VL | QIVLTQSPAIMSASPGEKVTMTCSASSSVIYMHWYQQKS GTSPKRWIYDTSKLASGVPARFSGSGSGTSYSLTISSMEAE DAATYYCQQWSSNPLTFGAGTTLELK |
| SEQ ID NO: 145 | DNA VL | CAAATTGTCCTCACCCAGTCTCCAGCAATCATGTCTGCA TCTCCAGGGGAGAAGGTCACCATGACCTGCAGTGCCA GTTCAAGTGTAATTTACATGCACTGGTACCAGCAGAAG TCAGGCACCTCCCCCAAAAGATGGATTTATGACACATC CAAACTGGCTTCTGGAGTCCCTGCTCGCTTCAGTGGTA GTGGGTCTGGGACCTCTTACTCTCTCACAATCAGCAGC ATGGAGGCTGAAGATGCTGCCACTTATTACTGCCAGCA GTGGAGTAGTAACCCGCTCACGTTCGGTGCTGGGACC ACGTTGGAGCTGAAA |
| SEQ ID NO: 146 | Light Chain | QIVLTQSPAIMSASPGEKVTMTCSASSSVIYMHWYQQKS GTSPKRWIYDTSKLASGVPARFSGSGSGTSYSLTISSMEAE DAATYYCQQWSSNPLTFGAGTTLELKRTVAAPSVFIFPPS DEQLKSGTASVVCLLNNFYPREAKVQWKVDNALQSGNS QESVTEQDSKDSTYSLSSTLTLSKADYEKHKVYACEVTHQ GLSSPVTKSFNRGEC |
| SEQ ID NO: 147 | DNA Light Chain | CAAATTGTCCTCACCCAGTCTCCAGCAATCATGTCTGCA TCTCCAGGGGAGAAGGTCACCATGACCTGCAGTGCCA GTTCAAGTGTAATTTACATGCACTGGTACCAGCAGAAG TCAGGCACCTCCCCCAAAAGATGGATTTATGACACATC CAAACTGGCTTCTGGAGTCCCTGCTCGCTTCAGTGGTA GTGGGTCTGGGACCTCTTACTCTCTCACAATCAGCAGC ATGGAGGCTGAAGATGCTGCCACTTATTACTGCCAGCA GTGGAGTAGTAACCCGCTCACGTTCGGTGCTGGGACC ACGTTGGAGCTGAAACGTACGGTGGCCGCTCCCAGCG TGTTCATCTTCCCCCCCAGCGACGAGCAGCTGAAGAGT GGCACCGCCAGCGTGGTGTGCCTGCTGAACAACTTCTA CCCCCGGGAGGCCAAGGTGCAGTGGAAGGTGGACAA CGCCCTGCAGAGCGGCAACAGCCAGGAGAGCGTCACC GAGCAGGACAGCAAGGACTCCACCTACAGCCTGAGCA GCACCCTGACCCTGAGCAAGGCCGACTACGAGAAGCA TAAGGTGTACGCCTGCGAGGTGACCCACCAGGGCCTG TCCAGCCCCGTGACCAAGAGCTTCAACAGGGGCGAGT GC |

Parental 121G12 hIgG1

| | | |
|---|---|---|
| SEQ ID NO: 148 | HCDR1 (Combined) | GFTFSTYAMS |
| SEQ ID NO: 149 | HCDR2 (Combined) | TISDGGSYSYYPDNVKG |
| SEQ ID NO: 150 | HCDR3 (Combined) | RGSRYEEYYVMDY |
| SEQ ID NO: 151 | HCDR1 (Kabat) | TYAMS |
| SEQ ID NO: 152 | HCDR2 (Kabat) | TISDGGSYSYYPDNVKG |
| SEQ ID NO: 153 | HCDR3 (Kabat) | RGSRYEEYYVMDY |
| SEQ ID NO: 154 | HCDR1 (Chothia) | GFTFSTY |

TABLE 4-continued

Amino Acid and Nucleotide Sequence Information for Hybridomas and Humanized Anti-CCR7 Antibodies

| SEQ ID NO: 155 | HCDR2 (Chothia) | SDGGSY |
|---|---|---|
| SEQ ID NO: 156 | HCDR3 (Chothia) | RGSRYEEYYVMDY |
| SEQ ID NO: 157 | HCDR1 (IMGT) | GFTFSTYA |
| SEQ ID NO: 158 | HCDR2 (IMGT) | ISDGGSYS |
| SEQ ID NO: 159 | HCDR3 (IMGT) | ARRGSRYEEYYVMDY |
| SEQ ID NO: 160 | VH | EVQLVESGGGLVKPGGSLKLSCAASGFTFSTYAMSWVRQ TPEKRLEWVATISDGGSYSYYPDNVKGRFTISRDNAKNNL YLQMSHLKSEDTAMYYCARRGSRYEEYYVMDYWGQGT SVTVSS |
| SEQ ID NO: 161 | DNA VH | GAAGTGCAGCTGGTGGAGTCTGGGGGAGGCTTAGTG AAGCCTGGAGGGTCCCTGAAACTCTCCTGTGCAGCCTC TGGATTCACTTTCAGTACCTATGCCATGTCTTGGGTTCG CCAGACTCCGGAAAAGAGGCTGGAGTGGGTCGCAACC ATTAGTGATGGTGGTAGTTATTCGTACTATCCAGACAA TGTAAAGGGCCGATTCACCATCTCCAGAGACAATGCCA AGAACAACCTATACCTGCAAATGAGCCATCTGAAGTCT GAGGACACAGCCATGTATTACTGTGCAAGACGAGGTA GTAGGTACGAAGAGTACTATGTTATGGACTACTGGGG TCAAGGAACCTCAGTCACCGTCTCCTCA |
| SEQ ID NO: 162 | Heavy Chain (WT Fc) | EVQLVESGGGLVKPGGSLKLSCAASGFTFSTYAMSWVRQ TPEKRLEWVATISDGGSYSYYPDNVKGRFTISRDNAKNNL YLQMSHLKSEDTAMYYCARRGSRYEEYYVMDYWGQGT SVTVSSASTKGPSVFPLAPSSKSTSGGTAALGCLVKDYFPE PVTVSWNSGALTSGVHTFPAVLQSSGLYSLSSVVTVPSSS LGTQTYICNVNHKPSNTKVDKRVEPKSCDKTHTCPPCPA PELLGGPSVFLFPPKPKDTLMISRTPEVTCVVVDVSHEDP EVKFNWYVDGVEVHNAKTKPREEQYNSTYRVVSVLTVL HQDWLNGKEYKCKVSNKALPAPIEKTISKAKGQPREPQV YTLPPSREEMTKNQVSLTCLVKGFYPSDIAVEWESNGQP ENNYKTTPPVLDSDGSFFLYSKLTVDKSRWQQGNVFSCS VMHEALHNHYTQKSLSLSPGK |
| SEQ ID NO: 163 | DNA Heavy Chain | GAAGTGCAGCTGGTGGAGTCTGGGGGAGGCTTAGTG AAGCCTGGAGGGTCCCTGAAACTCTCCTGTGCAGCCTC TGGATTCACTTTCAGTACCTATGCCATGTCTTGGGTTCG CCAGACTCCGGAAAAGAGGCTGGAGTGGGTCGCAACC ATTAGTGATGGTGGTAGTTATTCGTACTATCCAGACAA TGTAAAGGGCCGATTCACCATCTCCAGAGACAATGCCA AGAACAACCTATACCTGCAAATGAGCCATCTGAAGTCT GAGGACACAGCCATGTATTACTGTGCAAGACGAGGTA GTAGGTACGAAGAGTACTATGTTATGGACTACTGGGG TCAAGGAACCTCAGTCACCGTCTCCTCAGCTAGCACCA AGGGCCCAAGTGTGTTTCCCCTGGCCCCCAGCAGCAA GTCTACTTCCGGCGGAACTGCTGCCCTGGGTTGCCTGG TGAAGGACTACTTCCCCGAGCCCGTGACAGTGTCCTGG AACTCTGGGGCTCTGACTTCCGGCGTGCACACCTTCCC CGCCGTGCTGCAGAGCAGCGGCCTGTACAGCCTGAGC AGCGTGGTGACAGTGCCCTCCAGCTCTCTGGGAACCCA GACCTATATCTGCAACGTGAACCACAAGCCCAGCAACA CCAAGGTGGACAAGAGAGTGGAGCCCAAGAGCTGCG ACAAGACCCACACCTGCCCCCCCTGCCCAGCTCCAGAA CTGCTGGGAGGGCCTTCCGTGTTCCTGTTCCCCCCCAA GCCCAAGGACACCCTGATGATCAGCAGGACCCCCGAG GTGACCTGCGTGGTGGTGGACGTGTCCCACGAGGACC CAGAGGTGAAGTTCAACTGGTACGTGGACGGCGTGGA GGTGCACAACGCCAAGACCAAGCCCAGAGAGGAGCA GTACAACAGCACCTACAGGGTGGTGTCCGTGCTGACC GTGCTGCACCAGGACTGGCTGAACGGCAAAGAATACA AGTGCAAAGTCTCCAACAAGGCCCTGCCAGCCCCAATC GAAAAGACAATCAGCAAGGCCAAGGGCCAGCCACGG GAGCCCCAGGTGTACACCCTGCCCCCCAGCCGGGAGG AGATGACCAAGAACCAGGTGTCCCTGACCTGTCTG GT GAAGGGCTTCTACCCCAGCGATATCGCCGTGGAGTGG GAGAGCAACGGCCAGCCCGAGAACAACTACAAGACCA CCCCCCCAGTGCTGGACAGCGACGGCAGCTTCTTCCTG TACAGCAAGCTGACCGTGGACAAGTCCAGGTGGCAGC AGGGCAACGTGTTCAGCTGCAGCGTGATGCACGAGGC CCTGCACAACCACTACACCCAGAAGTCCCTGAGCCTGA GCCCCGGCAAG |
| SEQ ID NO: 164 | LCDR1 (Combined) | RASQSISNNLH |
| SEQ ID NO: 165 | LCDR2 (Combined) | YASQSIS |

TABLE 4-continued

Amino Acid and Nucleotide Sequence Information for Hybridomas and Humanized Anti-CCR7 Antibodies

| | | |
|---|---|---|
| SEQ ID NO: 166 | LCDR3 (Combined) | QQSNSWLT |
| SEQ ID NO: 167 | LCDR1 (Kabat) | RASQSISNNLH |
| SEQ ID NO: 168 | LCDR2 (Kabat) | YASQSIS |
| SEQ ID NO: 169 | LCDR3 (Kabat) | QQSNSWLT |
| SEQ ID NO: 170 | LCDR1 (Chothia) | SQSISNN |
| SEQ ID NO: 171 | LCDR2 (Chothia) | YAS |
| SEQ ID NO: 172 | LCDR3 (Chothia) | SNSWL |
| SEQ ID NO: 173 | LCDR1 (IMGT) | QSISNN |
| SEQ ID NO: 174 | LCDR2 (IMGT) | YAS |
| SEQ ID NO: 175 | LCDR3 (IMGT) | QQSNSWLT |
| SEQ ID NO: 176 | VL | DIVLTQSPATLSVTPGDSVSLSCRASQSISNNLHWYQQKS HESPKLLIKYASQSISGIPSRFSGSGSGTDFTLSINSVETEDF GMYFCQQSNSWLTFGAGTKLGLK |
| SEQ ID NO: 177 | DNA VL | GATATTGTGCTAACTCAGTCTCCAGCCACCCTGTCTGTG ACTCCAGGAGATAGCGTCAGTCTTTCCTGCAGGGCCAG CCAAAGTATTAGCAACAACCTACACTGGTATCAACAGA AATCACATGAGTCTCCAAAACTTCTCATCAAGTATGCTT CCCAGTCCATCTCTGGGATCCCCTCCAGGTTCAGTGGC AGTGGATCAGGGACAGATTTCACTCTCAGTATCAACAG TGTGGAGACTGAAGATTTTGGAATGTATTTCTGTCAAC AGAGTAACAGCTGGCTCACGTTCGGTGCTGGGACCAA GCTGGGGCTGAAA |
| SEQ ID NO: 178 | Light Chain | DIVLTQSPATLSVTPGDSVSLSCRASQSISNNLHWYQQKS HESPKLLIKYASQSISGIPSRFSGSGSGTDFTLSINSVETEDF GMYFCQQSNSWLTFGAGTKLGLKRTVAAPSVFIFPPSDE QLKSGTASVVCLLNNFYPREAKVQWKVDNALQSGNSQE SVTEQDSKDSTYSLSSTLTLSKADYEKHKVYACEVTHQGLS SPVTKSFNRGEC |
| SEQ ID NO: 179 | DNA Light Chain | GATATTGTGCTAACTCAGTCTCCAGCCACCCTGTCTGTG ACTCCAGGAGATAGCGTCAGTCTTTCCTGCAGGGCCAG CCAAAGTATTAGCAACAACCTACACTGGTATCAACAGA AATCACATGAGTCTCCAAAACTTCTCATCAAGTATGCTT CCCAGTCCATCTCTGGGATCCCCTCCAGGTTCAGTGGC AGTGGATCAGGGACAGATTTCACTCTCAGTATCAACAG TGTGGAGACTGAAGATTTTGGAATGTATTTCTGTCAAC AGAGTAACAGCTGGCTCACGTTCGGTGCTGGGACCAA GCTGGGGCTGAAACGTACGGTGGCCGCTCCCAGCGTG TTCATCTTCCCCCCCAGCGACGAGCAGCTGAAGAGTGG CACCGCCAGCGTGGTGTGCCTGCTGAACAACTTCTACC CCCGGGAGGCCAAGGTGCAGTGGAAGGTGGACAACG CCCTGCAGAGCGGCAACAGCCAGGAGAGCGTCACCGA GCAGGACAGCAAGGACTCCACCTACAGCCTGAGCAGC ACCCTGACCCTGAGCAAGGCCGACTACGAGAAGCATA AGGTGTACGCCTGCGAGGTGACCCACCAGGGCCTGTC CAGCCCCGTGACCAAGAGCTTCAACAGGGGCGAGTGC |

Parental 506E15 hIgG1

| | | |
|---|---|---|
| SEQ ID NO: 180 | HCDR1 (Combined) | GFTFSSYAMS |
| SEQ ID NO: 181 | HCDR2 (Combined) | TISSGGSFTYYPDSVKG |
| SEQ ID NO: 182 | HCDR3 (Combined) | RASTVVGTDFDV |
| SEQ ID NO: 183 | HCDR1 (Kabat) | SYAMS |
| SEQ ID NO: 184 | HCDR2 (Kabat) | TISSGGSFTYYPDSVKG |
| SEQ ID NO: 185 | HCDR3 (Kabat) | RASTVVGTDFDV |
| SEQ ID NO: 186 | HCDR1 (Chothia) | GFTFSSY |
| SEQ ID NO: 187 | HCDR2 (Chothia) | SSGGSF |
| SEQ ID NO: 188 | HCDR3 (Chothia) | RASTVVGTDFDV |

TABLE 4-continued

Amino Acid and Nucleotide Sequence Information for Hybridomas and Humanized Anti-CCR7 Antibodies

| SEQ ID NO: 189 | HCDR1 (IMGT) | GFTFSSYA |
|---|---|---|
| SEQ ID NO: 190 | HCDR2 (IMGT) | ISSGGSFT |
| SEQ ID NO: 191 | HCDR3 (IMGT) | ARRASTVVGTDFDV |
| SEQ ID NO: 192 | VH | EVMLVESGGGLVKPGGSLKLSCAASGFTFSSYAMSWIRQ TPEKRLEWVATISSGGSFTYYPDSVKGRFTISRDNVKNTLY LQMSSLRSEDTAMYYCARRASTVVGTDFDVWGAGTTVT VSS |
| SEQ ID NO: 193 | DNA VH | GAAGTGATGCTGGTGGAGTCTGGGGGAGGCTTAGTG AAGCCTGGAGGGTCCCTGAAACTCTCCTGTGCAGCCTC TGGATTCACTTTCAGTAGCTATGCCATGTCTTGGATTCG CCAGACTCCGGAGAAGAGACTGGAGTGGGTCGCAACC ATCAGTAGTGGTGGTAGTTTCACCTACTATCCAGACAG TGTGAAGGGGCGATTCACCATTTCTAGAGACAATGTCA AGAACACCCTGTACCTGCAAATGAGCAGTCTGAGGTCT GAAGACACGGCCATGTATTACTGTGCAAGACGGGCTT CTACGGTAGTAGGTACGGACTTCGATGTCTGGGGCGC AGGGACCACGGTCACCGTCTCCTCA |
| SEQ ID NO: 194 | Heavy Chain (WT Fc) | EVMLVESGGGLVKPGGSLKLSCAASGFTFSSYAMSWIRQ TPEKRLEWVATISSGGSFTYYPDSVKGRFTISRDNVKNTLY LQMSSLRSEDTAMYYCARRASTVVGTDFDVWGAGTTVT VSSASTKGPSVFPLAPSSKSTSGGTAALGCLVKDYFPEPVT VSWNSGALTSGVHTFPAVLQSSGLYSLSSVVTVPSSSLGT QTYICNVNHKPSNTKVDKRVEPKSCDKTHTCPPCPAPELL GGPSVFLFPPKPKDTLMISRTPEVTCVVVDVSHEDPEVKF NWYVDGVEVHNAKTKPREEQYNSTYRVVSVLTVLHQD WLNGKEYKCKVSNKALPAPIEKTISKAKGQPREPQVYTLP PSREEMTKNQVSLTCLVKGFYPSDIAVEWESNGQPENNY KTTPPVLDSDGSFFLYSKLTVDKSRWQQGNVFSCSVMHE ALHNHYTQKSLSLSPGK |
| SEQ ID NO: 195 | DNA Heavy Chain | GAAGTGATGCTGGTGGAGTCTGGGGGAGGCTTAGTG AAGCCTGGAGGGTCCCTGAAACTCTCCTGTGCAGCCTC TGGATTCACTTTCAGTAGCTATGCCATGTCTTGGATTCG CCAGACTCCGGAGAAGAGACTGGAGTGGGTCGCAACC ATCAGTAGTGGTGGTAGTTTCACCTACTATCCAGACAG TGTGAAGGGGCGATTCACCATTTCTAGAGACAATGTCA AGAACACCCTGTACCTGCAAATGAGCAGTCTGAGGTCT GAAGACACGGCCATGTATTACTGTGCAAGACGGGCTT CTACGGTAGTAGGTACGGACTTCGATGTCTGGGGCGC AGGGACCACGGTCACCGTCTCCTCAGCTAGCACCAAG GGCCCAAGTGTGTTTCCCCTGGCCCCCAGCAGCAAGTC TACTTCCGGCGGAACTGCTGCCCTGGGTTGCCTGGTGA AGGACTACTTCCCCGAGCCCGTGACAGTGTCCTGGAAC TCTGGGGCTCTGACTTCCGGCGTGCACACCTTCCCCGC CGTGCTGCAGAGCAGCGGCCTGTACAGCCTGAGCAGC GTGGTGACAGTGCCCTCCAGCTCTCTGGGAACCCAGAC CTATATCTGCAACGTGAACCACAAGCCCAGCAACACCA AGGTGGACAAGAGAGTGGAGCCCAAGAGCTGCGACA AGACCCACACCTGCCCCCCCTGCCCAGCTCCAGAACTG CTGGGAGGGCCTTCCGTGTTCCTGTTCCCCCCCAAGCC CAAGGACACCCTGATGATCAGCAGGACCCCCGAGGTG ACCTGCGTGGTGGTGGACGTGTCCCACGAGGACCCAG AGGTGAAGTTCAACTGGTACGTGGACGGCGTGGAGGT GCACAACGCCAAGACCAAGCCCAGAGAGGAGCAGTAC AACAGCACCTACAGGGTGGTGTCCGTGCTGACCGTGC TGCACCAGGACTGGCTGAACGGCAAAGAATACAAGTG CAAAGTCTCCAACAAGGCCCTGCCAGCCCCCAATCGAA AGACAATCAGCAAGGCCAAGGGCCAGCCACGGGAGC CCCAGGTGTACACCCTGCCCCCCAGCCGGGAGGAGAT GACCAAGAACCAGGTGTCCCTGACCTGTCTGGTGAAG GGCTTCTACCCCAGCGATATCGCCGTGGAGTGGGAGA GCAACGGCCAGCCCGAGAACAACTACAAGACCACCCC CCCAGTGCTGGACAGCGACGGCAGCTTCTTCCTGTACA GCAAGCTGACCGTGGACAAGTCCAGGTGGCAGCAGG GCAACGTGTTCAGCTGCAGCGTGATGCACGAGGCCCT GCACAACCACTACACCCAGAAGTCCCTGAGCCTGAGCC CCGGCAAG |
| SEQ ID NO: 196 | LCDR1 (Combined) | RASQDIGSSLN |
| SEQ ID NO: 197 | LCDR2 (Combined) | ATSSLDS |
| SEQ ID NO: 198 | LCDR3 (Combined) | LQYASSPPT |
| SEQ ID NO: 199 | LCDR1 (Kabat) | RASQDIGSSLN |

TABLE 4-continued

Amino Acid and Nucleotide Sequence Information for Hybridomas and Humanized Anti-CCR7 Antibodies

| SEQ ID NO: 200 | LCDR2 (Kabat) | ATSSLDS |
|---|---|---|
| SEQ ID NO: 201 | LCDR3 (Kabat) | LQYASSPPT |
| SEQ ID NO: 202 | LCDR1 (Chothia) | SQDIGSS |
| SEQ ID NO: 203 | LCDR2 (Chothia) | ATS |
| SEQ ID NO: 204 | LCDR3 (Chothia) | YASSPP |
| SEQ ID NO: 205 | LCDR1 (IMGT) | QDIGSS |
| SEQ ID NO: 206 | LCDR2 (IMGT) | ATS |
| SEQ ID NO: 207 | LCDR3 (IMGT) | LQYASSPPT |
| SEQ ID NO: 208 | VL | DIQMTQSPSSLSASLGERVSLTCRASQDIGSSLNWLQQEP DGTIKRLIYATSSLDSGVPKRFSGSRSGSDYSLTISSLESEDF VVYYCLQYASSPPTFGGGTKLEIK |
| SEQ ID NO: 209 | DNA VL | GACATCCAGATGACCCAGTCTCCATCCTCCTTATCTGCC TCTCTGGGAGAAAGAGTCAGTCTCACTTGTCGGGCAA GTCAGGACATTGGTAGTAGCTTAAACTGGCTTCAGCAG GAACCAGATGGAACTATTAAACGCCTGATCTATGCCAC ATCCAGTTTAGATTCTGGTGTCCCCAAAAGGTTCAGTG GCAGTAGGTCTGGGTCAGATTATTCTCTCACCATCAGC AGCCTTGAGTCTGAAGATTTTGTAGTCTATTACTGTCTA CAATATGCTAGTTCGCCTCCGACGTTCGGTGGAGGCAC CAAGCTGGAAATCAAA |
| SEQ ID NO: 210 | Light Chain | DIQMTQSPSSLSASLGERVSLTCRASQDIGSSLNWLQQEP DGTIKRLIYATSSLDSGVPKRFSGSRSGSDYSLTISSLESEDF VVYYCLQYASSPPTFGGGTKLEIKRTVAAPSVFIFPPSDEQ LKSGTASVVCLLNNFYPREAKVQWKVDNALQSGNSQES VTEQDSKDSTYSLSSTLTLSKADYEKHKVYACEVTHQGLSS PVTKSFNRGEC |
| SEQ ID NO: 211 | DNA Light Chain | GACATCCAGATGACCCAGTCTCCATCCTCCTTATCTGCC TCTCTGGGAGAAAGAGTCAGTCTCACTTGTCGGGCAA GTCAGGACATTGGTAGTAGCTTAAACTGGCTTCAGCAG GAACCAGATGGAACTATTAAACGCCTGATCTATGCCAC ATCCAGTTTAGATTCTGGTGTCCCCAAAAGGTTCAGTG GCAGTAGGTCTGGGTCAGATTATTCTCTCACCATCAGC AGCCTTGAGTCTGAAGATTTTGTAGTCTATTACTGTCTA CAATATGCTAGTTCGCCTCCGACGTTCGGTGGAGGCAC CAAGCTGGAAATCAAACGTACGGTGGCCGCTCCCAGC GTGTTCATCTTCCCCCCCAGCGACGAGCAGCTGAAGAG TGGCACCGCCAGCGTGGTGTGCCTGCTGAACAACTTCT ACCCCCGGGAGGCCAAGGTGCAGTGGAAGGTGGACA ACGCCCTGCAGAGCGGCAACAGCCAGGAGAGCGTCAC CGAGCAGGACAGCAAGGACTCCACCTACAGCCTGAGC AGCACCCTGACCCTGAGCAAGGCCGACTACGAGAAGC ATAAGGTGTACGCCTGCGAGGTGACCCACCAGGGCCT GTCCAGCCCCGTGACCAAGAGCTTCAACAGGGGCGAG TGC |

Parental 684E12 hIgG1

| SEQ ID NO: 212 | HCDR1 (Combined) | GFTFSNFAMS |
|---|---|---|
| SEQ ID NO: 213 | HCDR2 (Combined) | TISTGGTYTYYPDSVKG |
| SEQ ID NO: 214 | HCDR3 (Combined) | RGYDGVDK |
| SEQ ID NO: 215 | HCDR1 (Kabat) | SNFAMS |
| SEQ ID NO: 216 | HCDR2 (Kabat) | TISTGGTYTYYPDSVKG |
| SEQ ID NO: 217 | HCDR3 (Kabat) | RGYDGVDK |
| SEQ ID NO: 218 | HCDR1 (Chothia) | GFTFSNF |
| SEQ ID NO: 219 | HCDR2 (Chothia) | STGGTY |
| SEQ ID NO: 220 | HCDR3 (Chothia) | RGYDGVDK |
| SEQ ID NO: 221 | HCDR1 (IMGT) | GFTFSNFA |
| SEQ ID NO: 222 | HCDR2 (IMGT) | ISTGGTYT |

TABLE 4-continued

Amino Acid and Nucleotide Sequence Information for Hybridomas and Humanized Anti-CCR7 Antibodies

| SEQ ID NO: 223 | HCDR3 (IMGT) | TRRGYDGVDK |
|---|---|---|
| SEQ ID NO: 224 | VH | EVHLVESGGGLVKPGGSLKLSCAASGFTFSNFAMSWVRQTPE KRLEWVATISTGGTYTYYPDSVKGRFTISRDNAKKTLYLQMSSL RSEDTAMYYCTRRGYDGVDKWGQGTTLTVSS |
| SEQ ID NO: 225 | DNA VH | gaagtgcatctggtggagtctggggggaggcttagtgaagcctggagggtccct gaaa ctctcctgtgcagcctctggattcactttcagtaactttgccatgtcttggg ttcgccagactccggagaagagactggagtgggtcgcaaccattagtactggt ggtacttacacctactatccagacagtgtgaagggtcgattcaccatctccaga gacaatgccaagaaaaccctgtacctgcaaatgagcagtctgaggtctgagg acacgccatgtattactgtacaagacgggggtacgacggcgtggacaaatg gggccaaggcaccactctcacagtctcctca |
| SEQ ID NO: 226 | Heavy Chain (WT Fc) | EVHLVESGGGLVKPGGSLKLSCAASGFTFSNFAMSWVRQTPE KRLEWVATISTGGTYTYYPDSVKGRFTISRDNAKKTLYLQMSSL RSEDTAMYYCTRRGYDGVDKWGQGTTLTVSSASTKGPSVFPL APSSKSTSGGTAALGCLVKDYFPEPVTVSWNSGALTSGVHTFP AVLQSSGLYSLSSVVTVPSSSLGTQTYICNVNHKPSNTKVDKRV EPKSCDKTHTCPPCPAPELLGGPSVFLFPPKPKDTLMISRTPEVT CVVVDVSHEDPEVKFNWYVDGVEVHNAKTKPREEQYNSTYR VVSVLTVLHQDWLNGKEYKCKVSNKALPAPIEKTISKAKGQPR EPQVYTLPPSREEMTKNQVSLTCLVKGFYPSDIAVEWESNGQP ENNYKTTPPVLDSDGSFFLYSKLTVDKSRWQQGNVFSCSVMH EALHNHYTQKSLSLSPGK |
| SEQ ID NO: 227 | DNA Heavy Chain | GAAGTGCATCTGGTGGAGTCTGGGGGAGGCTTAGTGAAGC CTGGAGGGTCCCTGAAACTCTCCTGTGCAGCCTCTGGATTCA CTTTCAGTAACTTTGCCATGTCTTGGGTTCGCCAGACTCCGG AGAAGAGACTGGAGTGGGTCGCAACCATTAGTACTGGTGG TACTTACACCTACTATCCAGACAGTGTGAAGGGTCGATTCAC CATCTCCAGAGACAATGCCAAGAAAACCCTGTACCTGCAAA TGAGCAGTCTGAGGTCTGAGGACACGGCCATGTATTACTGT ACAAGACGGGGGTACGACGGCGTGGACAAATGGGGCCAA GGCACCACTCTCACAGICTCCTCAgctagcaccaagggcccaagtgt gtttcccctggccccagcagcaagtctacttccggcggaactgctgccctggg ttgcctggtgaaggactacttccccgagcccgtgacagtgtcctggaactctgg ggctctgacttccggcgtgcacacctccccgcctgctgcagagcagcggcct gtacagcctgagcagcgtggtgacagtgccctccagctctctgggaacccaga cctatatctgcaacgtgaaccacaagcccagcaacaccaaggtggacaagag agtggagcccaagagctgcgacaagacccacacctgcccccctgcccagctc cagaactgctgggagggcctccgtgttcctgttcccccccaagcccaaggaca ccctgatgatcagcaggacccccgaggtgacctgcgtggtggtggacgtgtcc cacgaggacccagaggtgaagttcaactggtacgtggacggcgtggaggtgc acaacgccaagaccaagcccagagaggagcagtacaacagcacctacaggg tggtgtccgtgctgaccgtgctgcaccaggactggctgaacggcaaagaatac aagtgcaaagtctccaacaaggccctgccagccccaatcgaaaagacaatca gcaaggccaagggccagccacgggagccccaggtgtacaccctgcccccag ccgggaggagatgaccaagaaccaggtgtccctgacctgtctggtgaagggct tctaccccagcgatatcgccgtggagtgggagagcaacggccagcccgagaa caactacaagaccacccccagtgctggacagcgacggcagcttcttcctgta cagcaagctgaccgtggacaagtccaggtggcagcagggcaacgtgttcagct gcagcgtgatgcacgaggccctgcacaaccactacacccagaagtccctgagc ctgagcccggcaag |
| SEQ ID NO: 228 | LCDR1 (Combined) | KSGQSLLDSDGKTYLN |
| SEQ ID NO: 229 | LCDR2 (Combined) | LVSKLDS |
| SEQ ID NO: 230 | LCDR3 (Combined) | WQGTHFPQT |
| SEQ ID NO: 231 | LCDR1 (Kabat) | KSGQSLLDSDGKTYLN |
| SEQ ID NO: 232 | LCDR2 (Kabat) | LVSKLDS |
| SEQ ID NO: 233 | LCDR3 (Kabat) | WQGTHFPQT |
| SEQ ID NO: 234 | LCDR1 (Chothia) | GQSLLDSDGKTY |
| SEQ ID NO: 235 | LCDR2 (Chothia) | LVS |
| SEQ ID NO: 236 | LCDR3 (Chothia) | GTHFPQ |
| SEQ ID NO: 237 | LCDR1 (IMGT) | QSLLDSDGKTY |
| SEQ ID NO: 238 | LCDR2 (IMGT) | LVS |
| SEQ ID NO: 239 | LCDR3 (IMGT) | WQGTHFPQT |

TABLE 4-continued

Amino Acid and Nucleotide Sequence Information for Hybridomas and Humanized Anti-CCR7 Antibodies

| | | |
|---|---|---|
| SEQ ID NO: 240 | VL | DVVMTQTPLTLSVTIGQPASISCKSGQSLLDSDGKTYLNWFLQ RPGQSPKRLIYLVSKLDSGVPDRFTGSGSGTDFTLKISRVEAEDL GVYYCWQGTHFPQTFGGGTKLEIK |
| SEQ ID NO: 241 | DNA VL | gatgttgtgatgacccagactccactcactttgtcggttaccattggacaaccag cctccatctcttgcaagtcaggtcagagcctcttagatagtgatggaaagacat atttgaattggttttacagaggccaggccagtctccaaagcgcctaatctatct ggtgtctaaactggactctggagtccctgacaggttcactggcagtggatcagg gacagatttcacactgaaaatcagcagagtggaggctgaggatttgggagttt attattgctggcaaggtacacattttcctcagacgttcggtggaggcaccaagc tggaaatcaaa |
| SEQ ID NO: 242 | Light Chain | DVVMTQTPLTLSVTIGQPASISCKSGQSLLDSDGKTYLNWFLQ RPGQSPKRLIYLVSKLDSGVPDRFTGSGSGTDFTLKISRVEAEDL GVYYCWQGTHFPQTFGGGTKLEIKRTVAAPSVFIFPPSDEQLK SGTASVVCLLNNFYPREAKVQWKVDNALQSGNSQESVTEQDS KDSTYSLSSTLTLSKADYEKHKVYACEVTHQGLSSPVTKSFNRGE C |
| SEQ ID NO: 243 | DNA Light Chain | GATGTTGTGATGACCCAGACTCCACTCACTTTGTCGGTTACC ATTGGACAACCAGCCTCCATCTCTTGCAAGTCAGGTCAGAG CCTCTTAGATAGTGATGGAAAGACATATTTGAATTGGTTTTT ACAGAGGCCAGGCCAGTCTCCAAAGCGCCTAATCTATCTGG TGTCTAAACTGGACTCTGGAGTCCCTGACAGGTTCACTGGC AGTGGATCAGGGACAGATTTCACACTGAAAATCAGCAGAGT GGAGGCTGAGGATTTGGGAGTTTATTATTGCTGGCAAGGTA CACATTTTCCTCAGACGTTCGGTGGAGGCACCAAGCTGGAA ATCAAAcgtacggtggccgctcccagcgtgttcatcttccccccagcgacg agcagctgaaagagtggcaccgccagcgtggtgtgcctgctgaacaacttctac cccgggaggccaaggtgcagtggaaggtggacaacgccctgcagagcggc aacagccaggagagcgtcaccgagcaggacagcaaggactccacctacagc ctgagcagcaccctgaccctgagcaaggccgactacgagaagcataaggtgt acgcctgcgaggtgacccaccagggcctgtccagccccgtgaccaagagcttc aacaggggcgagtgc |

Parental 674J13 hIgG1 CysMab

| | | |
|---|---|---|
| SEQ ID NO: 244 | HCDR1 (Combined) | GYSITSGYSWH |
| SEQ ID NO: 245 | HCDR2 (Combined) | HIHSSGSTNYNPSLKS |
| SEQ ID NO: 246 | HCDR3 (Combined) | GGVQAFAY |
| SEQ ID NO: 247 | HCDR1 (Kabat) | SGYSWH |
| SEQ ID NO: 248 | HCDR2 (Kabat) | HIHSSGSTNYNPSLKS |
| SEQ ID NO: 249 | HCDR3 (Kabat) | GGVQAFAY |
| SEQ ID NO: 250 | HCDR1 (Chothia) | GYSITSGY |
| SEQ ID NO: 251 | HCDR2 (Chothia) | HSSGS |
| SEQ ID NO: 252 | HCDR3 (Chothia) | GGVQAFAY |
| SEQ ID NO: 253 | HCDR1 (IMGT) | GYSITSGYS |
| SEQ ID NO: 254 | HCDR2 (IMGT) | IHSSGST |
| SEQ ID NO: 255 | HCDR3 (IMGT) | ARGGVQAFAY |
| SEQ ID NO: 256 | VH | DVQLQESGPDLVKPSQSLSLTCTVTGYSITSGYSWHWIR QFPGNKLEWMAHIHSSGSTNYNPSLKSRISIIRDTSKNLFF LQLNSVTTEDTATYYCARGGVQAFAYWGQGTLVTVSA |
| SEQ ID NO: 257 | DNA VH | GATGTGCAGCTTCAGGAGTCAGGACCTGACCTGGTGA AACCTTCTCAGTCACTTTCACTCACCTGCACTGTCACTG GCTACTCCATCACCAGTGGTTATAGCTGGCACTGGATC CGGCAGTTTCCAGGAAACAAACTGGAGTGGATGGCCC ACATCCACTCCAGTGGTAGCACTAACTACAACCCATCT CTCAAAAGTCGCATCTCTATCATTCGAGACACATCCAA GAACCTGTTCTTCCTGCAGTTGAATTCTGTGACTACTGA GGACACAGCCACATATTACTGTGCAAGAGGGGGGGTA CAGGCCTTTGCTTACTGGGGCCAAGGGACTCTGGTCAC TGTCTCTGCA |
| SEQ ID NO: 258 | Heavy Chain (Cys Mab mutations underlined) | DVQLQESGPDLVKPSQSLSLTCTVTGYSITSGYSWHWIR QFPGNKLEWMAHIHSSGSTNYNPSLKSRISIIRDTSKNLFF LQLNSVTTEDTATYYCARGGVQAFAYWGQGTLVTVSAA STKGPSVFPLAPSSKSTSGGTAALGCLVKDYFPCPVTVSW NSGALTSGVHTFPAVLQSSGLYSLSSVVTVPSSSLGTQTYI CNVNHKPSNTKVDKRVEPKSCDKTHTCPPCPAPELLGGP |

TABLE 4-continued

Amino Acid and Nucleotide Sequence Information for Hybridomas and Humanized Anti-CCR7 Antibodies

| | | |
|---|---|---|
| | | SVFLFPPKPKDTLMISRTPEVTCVVVDVSHEDPEVKFNWY<br>VDGVEVHNAKTKPREEQYNSTYRVVSVLTVLHQDWLNG<br>KEYKCKVSNKALPAPIEKTISKAKGQPREPQVYTLPPSREE<br>MTKNQVSLTCLVKGFYP<u>C</u>DIAVEWESNGQPENNYKTTP<br>PVLDSDGSFFLYSKLTVDKSRWQQGNVFSCSVMHEALH<br>NHYTQKSLSLSPGK |
| SEQ ID NO: 259 | DNA Heavy Chain | GATGTGCAGCTTCAGGAGTCAGGACCTGACCTGGTGA<br>AACCTTCTCAGTCACTTTCACTCACCTGCACTGTCACTG<br>GCTACTCCATCACCAGTGGTTATAGCTGGCACTGGATC<br>CGGCAGTTTCCAGGAAACAAACTGGAGTGGATGGCCC<br>ACATCCACTCCAGTGGTAGCACTAACTACAACCCATCT<br>CTCAAAAGTCGCATCTCTATCATTCGAGACACATCCAA<br>GAACCTGTTCTTCCTGCAGTTGAATTCTGTGACTACTGA<br>GGACACAGCCACATATTACTGTGCAAGAGGGGGGGTA<br>CAGGCCTTTGCTTACTGGGGCCAAGGGACTCTGGTCAC<br>TGTCTCTGCAgctagcaccaagggcccaagtgtgttccctggccc<br>ccagcagcaagtctacttccggcggaactgctgccctgggttgcctggtg<br>aaggactacttcccctgtcccgtgacagtgtcctggaactctggggctct<br>gacttccggcgtgcacaccttccccgccgtgctgcagagcagcggcctg<br>tacagcctgagcagcgtggtgacagtgccctccagctctctgggaaccc<br>agacctatatctgcaacgtgaaccacaagcccagcaacaccaaggtgg<br>acaagagagtggagcccaagagctgcgacaagacccacacctgcccc<br>cctgcccagctccagaactgctgggagggcttccgtgttcctgttccc<br>ccccaagcccaaggacacccctgatgatcagcaggacccccgaggtgac<br>ctgcgtggtggtggacgtgtcccacgaggacccagaggtgaagttcaac<br>tggtacgtggacggcgtggaggtgcacaacgccaagaccaagcccag<br>agaggagcagtacaacagcacctacagggtggtgtccgtgctgaccgt<br>gctgcaccaggactggctgaacggcaaagaatacaagtgcaaagtctc<br>caacaaggccctgccagccccaatcgaaaagacaatcagcaaggcca<br>agggccagccacgggagccccaggtgtacaccctgccccccagccggg<br>aggagatgaccaagaaccaggtgtccctgacctgtctggtgaagggctt<br>ctaccctgtgatatcgccgtggagtgggagagcaacggccagcccga<br>gaacaactacaagaccacccccagtgctggacagcgacggcagctt<br>cttcctgtacagcaagctgaccgtggacaagtccaggtggcagcaggg<br>caacgtgttcagctgcagcgtgatgcacgaggccctgcacaaccactac<br>acccagaagtccctgagcctgagccccggcaag |
| SEQ ID NO: 260 | LCDR1 (Combined) | SASSSVIYMH |
| SEQ ID NO: 261 | LCDR2 (Combined) | DTSKLAS |
| SEQ ID NO: 262 | LCDR3 (Combined) | QQWSSNPLT |
| SEQ ID NO: 263 | LCDR1 (Kabat) | SASSSVIYMH |
| SEQ ID NO: 264 | LCDR2 (Kabat) | DTSKLAS |
| SEQ ID NO: 265 | LCDR3 (Kabat) | QQWSSNPLT |
| SEQ ID NO: 266 | LCDR1 (Chothia) | SSSVIY |
| SEQ ID NO: 267 | LCDR2 (Chothia) | DTS |
| SEQ ID NO: 268 | LCDR3 (Chothia) | WSSNPL |
| SEQ ID NO: 269 | LCDR1 (IMGT) | SSVIY |
| SEQ ID NO: 270 | LCDR2 (IMGT) | DTS |
| SEQ ID NO: 271 | LCDR3 (IMGT) | QQWSSNPLT |
| SEQ ID NO: 272 | VL | QIVLTQSPAIMSASPGEKVTMTCSASSSVIYMHWYQQKS<br>GTSPKRWIYDTSKLASGVPARFSGSGSGTSYSLTISSMEAE<br>DAATYYCQQWSSNPLTFGAGTTLELK |
| SEQ ID NO: 273 | DNA VL | CAAATTGTCCTCACCCAGTCTCCAGCAATCATGTCTGCA<br>TCTCCAGGGGAGAAGGTCACCATGACCTGCAGTGCCA<br>GTTCAAGTGTAATTTACATGCACTGGTACCAGCAGAAG<br>TCAGGCACCTCCCCCAAAAGATGGATTTATGACACATC<br>CAAACTGGCTTCTGGAGTCCCTGCTCGCTTCAGTG GTA<br>GTGGGTCTGGGACCTCTTACTCTCTCACAATCAGCAGC<br>ATGGAGGCTGAAGATGCTGCCACTTATTACTGCCAGCA<br>GTGGAGTAGTAACCCGCTCACGTTCGGTGCTGGGACC<br>ACGTTGGAGCTGAAA |
| SEQ ID NO: 274 | Light Chain | QIVLTQSPAIMSASPGEKVTMTCSASSSVIYMHWYQQKS<br>GTSPKRWIYDTSKLASGVPARFSGSGSGTSYSLTISSMEAE<br>DAATYYCQQWSSNPLTFGAGTTLELKRTVAAPSVFIFPPS |

TABLE 4-continued

Amino Acid and Nucleotide Sequence Information for Hybridomas and Humanized Anti-CCR7 Antibodies

| | | |
|---|---|---|
| | | DEQLKSGTASVVCLLNNFYPREAKVQWKVDNALQSGNS QESVTEQDSKDSTYSLSSTLTLSKADYEKHKVYACEVTHQ GLSSPVTKSFNRGEC |
| SEQ ID NO: 275 | DNA Light Chain | CAAATTGTCCTCACCCAGTCTCCAGCAATCATGTCTGCA TCTCCAGGGGAGAAGGTCACCATGACCTGCAGTGCCA GTTCAAGTGTAATTTACATGCACTGGTACCAGCAGAAG TCAGGCACCTCCCCCAAAAGATGGATTTATGACACATC CAAACTGGCTTCTGGAGTCCCTGCTCGCTTCAGTGGTA GTGGGTCTGGGACCTCTTACTCTCTCACAATCAGCAGC ATGGAGGCTGAAGATGCTGCCACTTATTACTGCCAGCA GTGGAGTAGTAACCCGCTCACGTTCGGTGCTGGGACC ACGTTGGAGCTGAAACGTACGGTGGCCGCTCCCAGCG TGTTCATCTTCCCCCCAGCGACGAGCAGCTGAAGAGT GGCACCGCCAGCGTGGTGTGCCTGCTGAACAACTTCTA CCCCCGGGAGGCCAAGGTGCAGTGGAAGGTGGACAA CGCCCTGCAGAGCGGCAACAGCCAGGAGAGCGTCACC GAGCAGGACAGCAAGGACTCCACCTACAGCCTGAGCA GCACCCTGACCCTGAGCAAGGCCGACTACGAGAAGCA TAAGGTGTACGCCTGCGAGGTGACCCACCAGGGCCTG TCCAGCCCCGTGACCAAGAGCTTCAACAGGGGCGAGT GC |

Parental 674J13 hIgG1 DAPA CysMab

| | | |
|---|---|---|
| SEQ ID NO: 276 | HCDR1 (Combined) | GYSITSGYSWH |
| SEQ ID NO: 277 | HCDR2 (Combined) | HIHSSGSTNYNPSLKS |
| SEQ ID NO: 278 | HCDR3 (Combined) | GGVQAFAY |
| SEQ ID NO: 279 | HCDR1 (Kabat) | SGYSWH |
| SEQ ID NO: 280 | HCDR2 (Kabat) | HIHSSGSTNYNPSLKS |
| SEQ ID NO: 281 | HCDR3 (Kabat) | GGVQAFAY |
| SEQ ID NO: 282 | HCDR1 (Chothia) | GYSITSGY |
| SEQ ID NO: 283 | HCDR2 (Chothia) | HSSGS |
| SEQ ID NO: 284 | HCDR3 (Chothia) | GGVQAFAY |
| SEQ ID NO: 285 | HCDR1 (IMGT) | GYSITSGYS |
| SEQ ID NO: 286 | HCDR2 (IMGT) | IHSSGST |
| SEQ ID NO: 287 | HCDR3 (IMGT) | ARGGVQAFAY |
| SEQ ID NO: 288 | VH | DVQLQESGPGLVKPSQTLSLTCTVSGYSITSGYSWHWIR QHPGKGLEWMAHIHSSGSTNYNPSLKSRITISRDTSKNQ FSLKLSSVTAADTAVYYCARGGVQAFAYWGQGTLVTVSS |
| SEQ ID NO: 289 | DNA VH | GACGTGCAGCTGCAGGAATCTGGCCCTGGCCTGGTGA AACCCTCCCAGACCCTGTCCCTGACCTGCACCGTGTCC GGCTACTCCATCACCTCCGGCTACAGCTGGCACTGGAT CCGGCAGCACCCCGGCAAGGGCCTGGAATGGATGGCC CACATCCACTCCTCCGGCTCCACCAACTACAACCCCAGC CTGAAGTCCAGAATCACCATCAGCCGGGACACCTCCAA GAACCAGTTCTCCCTGAAGCTGTCCTCCGTGACCGCCG CTGACACCGCCGTGTACTACTGTGCCAGAGGCGGCGT GCAGGCCTTCGCTTATTGGGGCCAGGGCACCCTGGTG ACAGTGTCCTCC |
| SEQ ID NO: 290 | Heavy Chain (DAPA, CysMab mutations underlined) | DVQLQESGPGLVKPSQTLSLTCTVSGYSITSGYSWHWIR QHPGKGLEWMAHIHSSGSTNYNPSLKSRITISRDTSKNQ FSLKLSSVTAADTAVYYCARGGVQAFAYWGQGTLVTVSS ASTKGPSVFPLAPSSKSTSGGTAALGCLVKDYFPCPVTVS WNSGALTSGVHTFPAVLQSSGLYSLSSVVTVPSSSLGTQT YICNVNHKPSNTKVDKRVEPKSCDKTHTCPPCPAPELLGG PSVFLFPPKPKDTLMISRTPEVTCVVVAVSHEDPEVKFNW YVDGVEVHNAKTKPREEQYNSTYRVVSVLTVLHQDWLN GKEYKCKVSNKALAAPIEKTISKAKGQPREPQVYTLPPSRE EMTKNQVSLTCLVKGFYPCDIAVEWESNGQPENNYKTTP PVLDSDGSFFLYSKLTVDKSRWQQGNVFSCSVMHEALH NHYTQKSLSLSPGK |
| SEQ ID NO: 291 | DNA Heavy Chain | GACGTGCAGCTGCAGGAATCTGGCCCTGGCCTGGTGA AACCCTCCCAGACCCTGTCCCTGACCTGCACCGTGTCC GGCTACTCCATCACCTCCGGCTACAGCTGGCACTGGAT CCGGCAGCACCCCGGCAAGGGCCTGGAATGGATGGCC |

TABLE 4-continued

Amino Acid and Nucleotide Sequence Information for Hybridomas and Humanized Anti-CCR7 Antibodies

| | | |
|---|---|---|
| | | CACATCCACTCCTCCGGCTCCACCAACTACAACCCCAGC<br>CTGAAGTCCAGAATCACCATCAGCCGGGACACCTCCAA<br>GAACCAGTTCTCCCTGAAGCTGTCCTCCGTGACCGCCG<br>CTGACACCGCCGTGTACTACTGTGCCAGAGGCGGCGT<br>GCAGGCCTTCGCTTATTGGGGCCAGGGCACCCTGGTG<br>ACAGTGTCCTCCGCTAGCACCAAGGGCCCAAGTGTGTT<br>CCCCCTGGCCCCCAGCAGCAAGTCTACTTCCGGCGGAA<br>CTGCTGCCCTGGGTTGCCTGGTGAAGGACTACTTCCCC<br>TGTCCCGTGACAGTGTCCTGGAACTCTGGGGCTCTGAC<br>TTCCGGCGTGCACACCTTCCCCGCCGTGCTGCAGAGCA<br>GCGGCCTGTACAGCCTGAGCAGCGTGGTGACAGTGCC<br>CTCCAGCTCTCTGGGAACCCAGACCTATATCTGCAACG<br>TGAACCACAAGCCCAGCAACACCAAGGTGGACAAGAG<br>AGTGGAGCCCAAGAGCTGCGACAAGACCCACACCTGC<br>CCCCCCTGCCCAGCTCCAGAACTGCTGGGAGGGCCTTC<br>CGTGTTCCTGTTCCCCCCCAAGCCCAAGGACACCCTGA<br>TGATCAGCAGGACCCCCGAGGTGACCTGCGTGGTGGT<br>GGCCGTGTCCCACGAGGACCCAGAGGTGAAGTTCAAC<br>TGGTACGTGGACGGCGTGGAGGTGCACAACGCCAAG<br>ACCAAGCCCAGAGAGGAGCAGTACAACAGCACCTACA<br>GGGTGGTGTCCGTGCTGACCGTGCTGCACCAGGACTG<br>GCTGAACGGCAAAGAATACAAGTGCAAAGTCTCCAAC<br>AAGGCCCTGGCTGCCCCAATCGAAAAGACAATCAGCA<br>AGGCCAAGGGCCAGCCACGGGAGCCCCAGGTGTACAC<br>CCTGCCCCCAGCCGGGAGGAGATGACCAAGAACCAG<br>GTGTCCCTGACCTGTCTGGTGAAGGGCTTCTACCCCTG<br>TGATATCGCCGTGGAGTGGGAGAGCAACGGCCAGCCC<br>GAGAACAACTACAAGACCACCCCCCCAGTGCTGGACA<br>GCGACGGCAGCTTCTTCCTGTACAGCAAGCTGACCGTG<br>GACAAGTCCAGGTGGCAGCAGGGCAACGTGTTCAGCT<br>GCAGCGTGATGCACGAGGCCCTGCACAACCACTACAC<br>CCAGAAGTCCCTGAGCCTGAGCCCCGGCAAG |
| SEQ ID NO: 292 | LCDR1 (Combined) | SASSSVIYMH |
| SEQ ID NO: 293 | LCDR2 (Combined) | DTSKLAS |
| SEQ ID NO: 294 | LCDR3 (Combined) | QQWSSNPLT |
| SEQ ID NO: 295 | LCDR1 (Kabat) | SASSSVIYMH |
| SEQ ID NO: 296 | LCDR2 (Kabat) | DTSKLAS |
| SEQ ID NO: 297 | LCDR3 (Kabat) | QQWSSNPLT |
| SEQ ID NO: 298 | LCDR1 (Chothia) | SSSVIY |
| SEQ ID NO: 299 | LCDR2 (Chothia) | DTS |
| SEQ ID NO: 300 | LCDR3 (Chothia) | WSSNPL |
| SEQ ID NO: 301 | LCDR1 (IMGT) | SSVIY |
| SEQ ID NO: 302 | LCDR2 (IMGT) | DTS |
| SEQ ID NO: 303 | LCDR3 (IMGT) | QQWSSNPLT |
| SEQ ID NO: 304 | VL | EIVLTQSPATLSASPGERVTMSCSASSSVIYMHWYQQKP<br>GQAPRRWIYDTSKLASGVPARFSGSGSGTDYTLTISSMEP<br>EDAAVYYCQQWSSNPLTFGQGTKLEIK |
| SEQ ID NO: 305 | DNA VL | GAGATCGTGCTGACCCAGTCCCCTGCCACCCTGTCTGC<br>TAGCCCTGGCGAGCGCGTGACAATGTCCTGCTCCGCCT<br>CCTCCTCCGTGATCTACATGCACTGGTATCAGCAGAAG<br>CCCGGCCAGGCCCCTCGGCGGTGGATCTACGATACCTC<br>CAAGCTGGCCTCCGGCGTGCCCGCCAGATTCTCCGGCT<br>CTGGCTCTGGCACCGACTACACCCTGACCATCTCCAGC<br>ATGGAACCCGAGGACGCCGCCGTGTACTACTGCCAGC<br>AGTGGTCCTCCAACCCCCTGACCTTCGGCCAGGGCACC<br>AAGCTGGAAATCAAG |
| SEQ ID NO: 306 | Light Chain | EIVLTQSPATLSASPGERVTMSCSASSSVIYMHWYQQKP<br>GQAPRRWIYDTSKLASGVPARFSGSGSGTDYTLTISSMEP<br>EDAAVYYCQQWSSNPLTFGQGTKLEIKRTVAAPSVFIFPP<br>SDEQLKSGTASVVCLLNNFYPREAKVQWKVDNALQSGN<br>SQESVTEQDSKDSTYSLSSTLTLSKADYEKHKVYACEVTH<br>QGLSSPVTKSFNRGEC |
| SEQ ID NO: 307 | DNA Light Chain | GAGATCGTGCTGACCCAGTCCCCTGCCACCCTGTCTGC<br>TAGCCCTGGCGAGCGCGTGACAATGTCCTGCTCCGCCT<br>CCTCCTCCGTGATCTACATGCACTGGTATCAGCAGAAG |

TABLE 4-continued

Amino Acid and Nucleotide Sequence Information for Hybridomas and Humanized Anti-CCR7 Antibodies

```
CCCGGCCAGGCCCCTCGGCGGTGGATCTACGATACCTC
CAAGCTGGCCTCCGGCGTGCCCGCCAGATTCTCCGGCT
CTGGCTCTGGCACCGACTACACCCTGACCATCTCCAGC
ATGGAACCCGAGGACGCCGCCGTGTACTACTGCCAGC
AGTGGTCCTCCAACCCCCTGACCTTCGGCCAGGGCACC
AAGCTGGAAATCAAGCGTACGGTGGCCGCTCCCAGCG
TGTTCATCTTCCCCCCCAGCGACGAGCAGCTGAAGAGT
GGCACCGCCAGCGTGGTGTGCCTGCTGAACAACTTCTA
CCCCCGGGAGGCCAAGGTGCAGTGGAAGGTGGACAA
CGCCCTGCAGAGCGGCAACAGCCAGGAGAGCGTCACC
GAGCAGGACAGCAAGGACTCCACCTACAGCCTGAGCA
GCACCCTGACCCTGAGCAAGGCCGACTACGAGAAGCA
TAAGGTGTACGCCTGCGAGGTGACCCACCAGGGCCTG
TCCAGCCCCGTGACCAAGAGCTTCAACAGGGGCGAGT
GC
```

Parental 121G12 hIgG1 CysMab

| | | |
|---|---|---|
| SEQ ID NO: 308 | HCDR1 (Combined) | GFTFSTYAMS |
| SEQ ID NO: 309 | HCDR2 (Combined) | TISDAGSYSYYPDNVKG |
| SEQ ID NO: 310 | HCDR3 (Combined) | RGSRYEEYYVMDY |
| SEQ ID NO: 311 | HCDR1 (Kabat) | TYAMS |
| SEQ ID NO: 312 | HCDR2 (Kabat) | TISDAGSYSYYPDNVKG |
| SEQ ID NO: 313 | HCDR3 (Kabat) | RGSRYEEYYVMDY |
| SEQ ID NO: 314 | HCDR1 (Chothia) | GFTFSTY |
| SEQ ID NO: 315 | HCDR2 (Chothia) | SDAGSY |
| SEQ ID NO: 316 | HCDR3 (Chothia) | RGSRYEEYYVMDY |
| SEQ ID NO: 317 | HCDR1 (IMGT) | GFTFSTYA |
| SEQ ID NO: 318 | HCDR2 (IMGT) | ISDAGSYS |
| SEQ ID NO: 319 | HCDR3 (IMGT) | ARRGSRYEEYYVMDY |
| SEQ ID NO: 320 | VH | EVQLVESGGGLVKPGGSLKLSCAASGFTFSTYAMSWVRQ TPEKRLEWVATISDGGSYSYYPDNVKGRFTISRDNAKNNL YLQMSHLKSEDTAMYYCARRGSRYEEYYVMDYWGQGT SVTVSS |
| SEQ ID NO: 321 | DNA VH (CysMab mutations underlined) | GAAGTGCAGCTGGTGGAGTCTGGGGGAGGCTTAGTG AAGCCTGGAGGGTCCCTGAAACTCTCCTGTGCAGCCTC TGGATTCACTTTCAGTACCTATGCCATGTCTTGGGTTCG CCAGACTCCGGAAAAGAGGCTGGAGTGGGTCGCAACC ATTAGTGATGGTGGTAGTTATTCGTACTATCCAGACAA TGTAAAGGGCCGATTCACCATCTCCAGAGACAATGCCA AGAACAACCTATACCTGCAAATGAGCCATCTGAAGTCT GAGGACACAGCCATGTATTACTGTGCAAGACGAGGTA GTAGGTACGAAGAGTACTATGTTATGGACTACTGGGG TCAAGGAACCTCAGTCACCGTCTCCTCA |
| SEQ ID NO: 322 | Heavy Chain (CysMab mutations underlined) | EVQLVESGGGLVKPGGSLKLSCAASGFTFSTYAMSWVRQTPE KRLEWVATISDGGSYSYYPDNVKGRFTISRDNAKNNLYLQMSH LKSEDTAMYYCARRGSRYEEYYVMDYWGQGTSVTVSSastkgp svfplapssksts ggtaalgclykdyfp<u>C</u>pvtvswnsgaltsgvhtfpavlqss glyslssvvtvpssslgtqtyicnvnhkpsntkvdkrvepkscdkthtcppcpa pellggpsvflfppkpkdtlmisrtpevtcvvvdvshedpevkfnwyvdgve vhnaktkpreeqynstyryysvltylhqdwlngkeykckvsnkalpapiekti skakgqprepqvytlppsreemtknqvsltclvkgfyp<u>C</u>diavewesngqp ennyktttppvldsdgsfflyskltvdksrwqqgnvfscsvmhealhnhytqk slslspgk |
| SEQ ID NO: 323 | DNA Heavy Chain | GAAGTGCAGCTGGTGGAGTCTGGGGGAGGCTTAGTG AAGCCTGGAGGGTCCCTGAAACTCTCCTGTGCAGCCTC TGGATTCACTTTCAGTACCTATGCCATGTCTTGGGTTCG CCAGACTCCGGAAAAGAGGCTGGAGTGGGTCGCAACC ATTAGTGATGGTGGTAGTTATTCGTACTATCCAGACAA TGTAAAGGGCCGATTCACCATCTCCAGAGACAATGCCA AGAACAACCTATACCTGCAAATGAGCCATCTGAAGTCT GAGGACACAGCCATGTATTACTGTGCAAGACGAGGTA GTAGGTACGAAGAGTACTATGTTATGGACTACTGGGG TCAAGGAACCTCAGTCACCGTCTCCTCAgctagcaccaagg gcccaagtgtgtttcccctggccccagcagcaagtctacttccggcgga |

TABLE 4-continued

Amino Acid and Nucleotide Sequence Information for Hybridomas and Humanized Anti-CCR7 Antibodies

|  |  |  |
|---|---|---|
|  |  | actgctgccctgggttgcctggtgaaggactacttcccctgtcccgtgac<br>agtgtcctggaactctggggctctgacttccggcgtgcacaccttccccg<br>ccgtgctgcagagcagcggcctgtacagcctgagcagcgtggtgacag<br>tgccctccagctctctgggaacccagacctatatctgcaacgtgaacca<br>caagcccagcaacaccaaggtggacaagagagtggagcccaagagct<br>gcgacaagacccacacctgccccccctgcccagctccagaactgctgg<br>gagggccttccgtgttcctgttccccccaagcccaaggacaccctgatg<br>atcagcaggacccccgaggtgacctgcgtggtggtggacgtgtcccacg<br>aggacccagaggtgaagttcaactggtacgtggacggcgtggaggtgc<br>acaacgccaagaccaagcccagagaggagcagtacaacagcacctac<br>agggtggtgtccgtgctgaccgtgctgcaccaggactggctgaacggca<br>agaatacaagtgcaaagtctccaacaaggccctgccagccccaatcg<br>aaaagacaatcagcaaggccaagggccagccacgggagcccaggtg<br>tacaccctgccccccagccgggaggagatgaccaagaaccaggtgtcc<br>ctgacctgtctggtgaagggcttctaccctgtgatatcgccgtggagtg<br>ggagagcaacggccagcccgagaacaactacaagaccacccccccag<br>tgctggacagcgacggcagcttcttcctgtacagcaagctgaccgtgga<br>caagtccaggtggcagcagggcaacgtgttcagctgcagcgtgatgca<br>cgaggccctgcacaaccactacacccagaagtccctgagcctgagccc<br>cggcaag |
| SEQ ID NO: 324 | LCDR1<br>(Combined) | RASQSISNNLH |
| SEQ ID NO: 325 | LCDR2<br>(Combined) | YASQSIS |
| SEQ ID NO: 326 | LCDR3<br>(Combined) | QQSSSWLT |
| SEQ ID NO: 327 | LCDR1<br>(Kabat) | RASQSISNNLH |
| SEQ ID NO: 328 | LCDR2<br>(Kabat) | YASQSIS |
| SEQ ID NO: 329 | LCDR3<br>(Kabat) | QQSSSWLT |
| SEQ ID NO: 330 | LCDR1<br>(Chothia) | SQSISNN |
| SEQ ID NO: 331 | LCDR2<br>(Chothia) | YAS |
| SEQ ID NO: 332 | LCDR3<br>(Chothia) | SSSWL |
| SEQ ID NO: 333 | LCDR1<br>(IMGT) | QSISNN |
| SEQ ID NO: 334 | LCDR2<br>(IMGT) | YAS |
| SEQ ID NO: 335 | LCDR3<br>(IMGT) | QQSSSWLT |
| SEQ ID NO: 336 | VL | DIVLTQSPATLSVTPGDSVSLSCRASQSISNNLHWYQQKS<br>HESPKLLIKYASQSISGIPSRFSGSGSGTDFTLSINSVETEDF<br>GMYFCQQSNSWLTFGAGTKLGLK |
| SEQ ID NO: 337 | DNA VL | GATATTGTGCTAACTCAGTCTCCAGCCACCCTGTCTGTG<br>ACTCCAGGAGATAGCGTCAGTCTTTCCTGCAGGGCCAG<br>CCAAAGTATTAGCAACAACCTACACTGGTATCAACAGA<br>AATCACATGAGTCTCCAAAACTTCTCATCAAGTATGCTT<br>CCCAGTCCATCTCTGGGATCCCCTCCAGGTTCAGTGGC<br>AGTGGATCAGGGACAGATTTCACTCTCAGTATCAACAG<br>TGTGGAGACTGAAGATTTTGGAATGTATTTCTGTCAAC<br>AGAGTAACAGCTGGCTCACGTTCGGTGCTGGGACCAA<br>GCTGGGGCTGAAA |
| SEQ ID NO: 338 | Light Chain | DIVLTQSPATLSVTPGDSVSLSCRASQSISNNLHWYQQKS<br>HESPKLLIKYASQSISGIPSRFSGSGSGTDFTLSINSVETEDF<br>GMYFCQQSNSWLTFGAGTKLGLKRTVAAPSVFIFPPSDE<br>QLKSGTASVVCLLNNFYPREAKVQWKVDNALQSGNSQE<br>SVTEQDSKDSTYSLSSTLTLSKADYEKHKVYACEVTHQGLS<br>SPVTKSFNRGEC |
| SEQ ID NO: 339 | DNA Light<br>Chain | GATATTGTGCTAACTCAGTCTCCAGCCACCCTGTCTGTG<br>ACTCCAGGAGATAGCGTCAGTCTTTCCTGCAGGGCCAG<br>CCAAAGTATTAGCAACAACCTACACTGGTATCAACAGA<br>AATCACATGAGTCTCCAAAACTTCTCATCAAGTATGCTT<br>CCCAGTCCATCTCTGGGATCCCCTCCAGGTTCAGTGGC<br>AGTGGATCAGGGACAGATTTCACTCTCAGTATCAACAG<br>TGTGGAGACTGAAGATTTTGGAATGTATTTCTGTCAAC<br>AGAGTAACAGCTGGCTCACGTTCGGTGCTGGGACCAA<br>GCTGGGGCTGAAACGTACGGTGGCCGCTCCCAGCGTG<br>TTCATCTTCCCCCCCAGCGACGAGCAGCTGAAGAGTGG<br>CACCGCCAGCGTGGTGTGCCTGCTGAACAACTTCTACC<br>CCCGGGAGGCCAAGGTGCAGTGGAAGGTGGACAACG<br>CCCTGCAGAGCGGCAACAGCCAGGAGAGCGTCACCGA<br>GCAGGACAGCAAGGACTCCACCTACAGCCTGAGCAGC<br>ACCCTGACCCTGAGCAAGGCCGACTACGAGAAGCATA |

TABLE 4-continued

Amino Acid and Nucleotide Sequence Information for Hybridomas and Humanized Anti-CCR7 Antibodies

```
                    AGGTGTACGCCTGCGAGGTGACCCACCAGGGCCTGTC
                    CAGCCCCGTGACCAAGAGCTTCAACAGGGGCGAGTGC
```

Parental 121G12 hIgG1 DAPA CysMab

| | | |
|---|---|---|
| SEQ ID NO: 340 | HCDR1 (Combined) | GFTFSTYAMS |
| SEQ ID NO: 341 | HCDR2 (Combined) | TISDAGSYSYYPDNVKG |
| SEQ ID NO: 342 | HCDR3 (Combined) | RGSRYEEYYVMDY |
| SEQ ID NO: 343 | HCDR1 (Kabat) | TYAMS |
| SEQ ID NO: 344 | HCDR2 (Kabat) | TISDAGSYSYYPDNVKG |
| SEQ ID NO: 345 | HCDR3 (Kabat) | RGSRYEEYYVMDY |
| SEQ ID NO: 346 | HCDR1 (Chothia) | GFTFSTY |
| SEQ ID NO: 347 | HCDR2 (Chothia) | SDAGSY |
| SEQ ID NO: 348 | HCDR3 (Chothia) | RGSRYEEYYVMDY |
| SEQ ID NO: 349 | HCDR1 (IMGT) | GFTFSTYA |
| SEQ ID NO: 350 | HCDR2 (IMGT) | ISDAGSYS |
| SEQ ID NO: 351 | HCDR3 (IMGT) | ARRGSRYEEYYVMDY |
| SEQ ID NO: 352 | VH | EVQLVESGGGLVKPGGSLRLSCAASGFTFSTYAMSWVRQ APGKGLEWVATISDAGSYSYYPDNVKGRFTISRDNAKNSL YLQMNSLRAEDTAVYYCARRGSRYEEYYVMDYWGQGT TVTVSS |
| SEQ ID NO: 353 | DNA VH | GAGGTGCAGCTGGTGGAATCTGGCGGAGGCCTGGTG AAACCCGGCGGATCCCTGAGACTGTCCTGCGCCGCCTC CGGCTTCACCTTCTCCACCTACGCCATGTCCTGGGTGC GGCAGGCTCCCGGCAAGGGCCTGGAATGGGTGGCCA CCATCTCCGACGCCGGCTCCTACTCCTACTACCCCGACA ACGTGAAGGGCAGATTCACCATCAGCCGGGACAACGC CAAGAACTCCCTGTACCTGCAGATGAACTCCCTGCGGG CCGAGGACACCGCCGTGTACTACTGTGCCAGACGGGG CTCCAGATACGAAGAGTACTACGTGATGGACTATTGG GGCCAGGGCACCACCGTGACAGTGTCCTCC |
| SEQ ID NO: 354 | Heavy Chain (DAPA, CysMab mutations underlined) | EVQLVESGGGLVKPGGSLRLSCAASGFTFSTYAMSWVRQ APGKGLEWVATISDAGSYSYYPDNVKGRFTISRDNAKNSL YLQMNSLRAEDTAVYYCARRGSRYEEYYVMDYWGQGT TVTVSSASTKGPSVFPLAPSSKSTSGGTAALGCLVKDYFPC PVTVSWNSGALTSGVHTFPAVLQSSGLYSLSSVVTVPSSS LGTQTYICNVNHKPSNTKVDKRVEPKSCDKTHTCPPCPA PELLGGPSVFLFPPKPKDTLMISRTPEVTCVVVAVSHEDPE VKFNWYVDGVEVHNAKTKPREEQYNSTYRVVSVLTVLH QDWLNGKEYKCKVSNKALAAPIEKTISKAKGQPREPQVY TLPPSREEMTKNQVSLTCLVKGFYPCDIAVEWESNGQPE NNYKTTPPVLDSDGSFFLYSKLTVDKSRWQQGNVFSCSV MHEALHNHYTQKSLSLSPGK |
| SEQ ID NO: 355 | DNA Heavy Chain | GAGGTGCAGCTGGTGGAATCTGGCGGAGGCCTGGTG AAACCCGGCGGATCCCTGAGACTGTCCTGCGCCGCCTC CGGCTTCACCTTCTCCACCTACGCCATGTCCTGGGTGC GGCAGGCTCCCGGCAAGGGCCTGGAATGGGTGGCCA CCATCTCCGACGCCGGCTCCTACTCCTACTACCCCGACA ACGTGAAGGGCAGATTCACCATCAGCCGGGACAACGC CAAGAACTCCCTGTACCTGCAGATGAACTCCCTGCGGG CCGAGGACACCGCCGTGTACTACTGTGCCAGACGGGG CTCCAGATACGAAGAGTACTACGTGATGGACTATTGG GGCCAGGGCACCACCGTGACAGTGTCCTCCGCTAGCA CCAAGGGCCCAAGTGTGTTTCCCCTGGCCCCCAGCAGC AAGTCTACTTCCGGCGGAACTGCTGCCCTGGGTTGCCT GGTGAAGGACTACTTCCCCTGTCCCGTGACAGTGTCCT GGAACTCTGGGGCTCTGACTTCCGGCGTGCACACCTTC CCCGCCGTGCTGCAGAGCAGCGGCCTGTACAGCCTGA GCAGCGTGGTGACAGTGCCCTCCAGCTCTCTGGGAAC CCAGACCTATATCTGCAACGTGAACCACAAGCCCAGCA ACACCAAGGTGGACAAGAGAGTGGAGCCCAAGAGCT GCGACAAGACCCACACCTGCCCCCCTGCCCAGCTCCA GAACTGCTGGGAGGGCCTTCCGTGTTCCTGTTCCCCCC CAAGCCCAAGGACACCCTGATGATCAGCAGGACCCCC GAGGTGACCTGCGTGGTGGTGGCCGTGTCCCACGAGG |

TABLE 4-continued

Amino Acid and Nucleotide Sequence Information for Hybridomas and Humanized Anti-CCR7 Antibodies

| | | |
|---|---|---|
| | | ACCCAGAGGTGAAGTTCAACTGGTACGTGGACGGCGT<br>GGAGGTGCACAACGCCAAGACCAAGCCCAGAGAGGA<br>GCAGTACAACAGCACCTACAGGGTGGTGTCCGTGCTG<br>ACCGTGCTGCACCAGGACTGGCTGAACGGCAAAGAAT<br>ACAAGTGCAAAGTCTCCAACAAGGCCCTGGCTGCCCCA<br>ATCGAAAAGACAATCAGCAAGGCCAAGGGCCAGCCAC<br>GGGAGCCCCAGGTGTACACCCTGCCCCCAGCCGGGA<br>GGAGATGACCAAGAACCAGGTGTCCCTGACCTGTCTG<br>GTGAAGGGCTTCTACCCCTGTGATATCGCCGTGGAGTG<br>GGAGAGCAACGGCCAGCCCGAGAACAACTACAAGACC<br>ACCCCCCCAGTGCTGGACAGCGACGGCAGCTTCTTCCT<br>GTACAGCAAGCTGACCGTGGACAAGTCCAGGTGGCAG<br>CAGGGCAACGTGTTCAGCTGCAGCGTGATGCACGAGG<br>CCCTGCACAACCACTACACCCAGAAGTCCCTGAGCCTG<br>AGCCCCGGCAAG |
| SEQ ID NO: 356 | LCDR1<br>(Combined) | RASQSISNNLH |
| SEQ ID NO: 357 | LCD R2<br>(Combined) | YASQSIS |
| SEQ ID NO: 358 | LCD R3<br>(Combined) | QQSSSWLT |
| SEQ ID NO: 359 | LCDR1<br>(Kabat) | RASQSISNNLH |
| SEQ ID NO: 360 | LCD R2<br>(Kabat) | YASQSIS |
| SEQ ID NO: 361 | LCD R3<br>(Kabat) | QQSSSWLT |
| SEQ ID NO: 362 | LCDR1<br>(Chothia) | SQSISNN |
| SEQ ID NO: 363 | LCD R2<br>(Chothia) | YAS |
| SEQ ID NO: 364 | LCD R3<br>(Chothia) | SSSWL |
| SEQ ID NO: 365 | LCDR1<br>(IMGT) | QSISNN |
| SEQ ID NO: 366 | LCD R2<br>(IMGT) | YAS |
| SEQ ID NO: 367 | LCD R3<br>(IMGT) | QQSSSWLT |
| SEQ ID NO: 368 | VL | EIVLTQSPATLSVSPGERVTLSCRASQSISNNLHWYQQKP<br>GQAPRLLIKYASQSISGIPARFSGSGSGTDFTLTISSVEPED<br>FGVYFCQQSSSWLTFGQGTKLEIK |
| SEQ ID NO: 369 | DNA VL | GAGATCGTGCTGACCCAGTCCCCTGCCACCCTGTCCGT<br>GTCTCCCGGCGAGAGAGTGACCCTGTCCTGCCGGGCC<br>TCCCAGTCCATCTCCAACAACCTGCACTGGTATCAGCA<br>GAAGCCCGGCCAGGCCCCTCGGCTGCTGATTAAGTAC<br>GCCTCCCAGAGCATCTCCGGCATCCCTGCCAGATTCTC<br>CGGCTCCGGCAGCGGCACCGACTTCACCCTGACCATCT<br>CCAGCGTGGAACCCGAGGACTTCGGCGTGTACTTCTGC<br>CAGCAGTCCTCATCCTGGCTGACCTTCGGCCAGGGCAC<br>CAAGCTGGAAATCAAG |
| SEQ ID NO: 370 | Light Chain | EIVLTQSPATLSVSPGERVTLSCRASQSISNNLHWYQQKP<br>GQAPRLLIKYASQSISGIPARFSGSGSGTDFTLTISSVEPED<br>FGVYFCQQSSSWLTFGQGTKLEIKRTVAAPSVFIFPPSDE<br>QLKSGTASVVCLLNNFYPREAKVQWKVDNALQSGNSQE<br>SVTEQDSKDSTYSLSSTLTLSKADYEKHKVYACEVTHQGLS<br>SPVTKSFNRGEC |
| SEQ ID NO: 371 | DNA Light<br>Chain | GAGATCGTGCTGACCCAGTCCCCTGCCACCCTGTCCGT<br>GTCTCCCGGCGAGAGAGTGACCCTGTCCTGCCGGGCC<br>TCCCAGTCCATCTCCAACAACCTGCACTGGTATCAGCA<br>GAAGCCCGGCCAGGCCCCTCGGCTGCTGATTAAGTAC<br>GCCTCCCAGAGCATCTCCGGCATCCCTGCCAGATTCTC<br>CGGCTCCGGCAGCGGCACCGACTTCACCCTGACCATCT<br>CCAGCGTGGAACCCGAGGACTTCGGCGTGTACTTCTGC<br>CAGCAGTCCTCATCCTGGCTGACCTTCGGCCAGGGCAC<br>CAAGCTGGAAATCAAGCGTACGGTGGCCGCTCCCAGC<br>GTGTTCATCTTCCCCCCCAGCGACGAGCAGCTGAAGAG<br>TGGCACCGCCAGCGTGGTGTGCCTGCTGAACAACTTCT<br>ACCCCCGGGAGGCCAAGGTGCAGTGGAAGGTGGACA<br>ACGCCCTGCAGAGCGGCAACAGCCAGGAGAGCGTCAC<br>CGAGCAGGACAGCAAGGACTCCACCTACAGCCTGAGC<br>AGCACCCTGACCCTGAGCAAGGCCGACTACGAGAAGC<br>ATAAGGTGTACGCCTGCGAGGTGACCCACCAGGGCCT<br>GTCCAGCCCCGTGACCAAGAGCTTCAACAGGGGCGAG<br>TGC |

TABLE 4-continued

Amino Acid and Nucleotide Sequence Information for Hybridomas and Humanized Anti-CCR7 Antibodies

Parental 506E15 hIgG1 CysMab

| | | |
|---|---|---|
| SEQ ID NO: 372 | HCDR1 (Combined) | GFTFSSYAMS |
| SEQ ID NO: 373 | HCDR2 (Combined) | TISSGGSFTYYPDSVKG |
| SEQ ID NO: 374 | HCDR3 (Combined) | RASTVVGTDFDV |
| SEQ ID NO: 375 | HCDR1 (Kabat) | SYAMS |
| SEQ ID NO: 376 | HCDR2 (Kabat) | TISSGGSFTYYPDSVKG |
| SEQ ID NO: 377 | HCDR3 (Kabat) | RASTVVGTDFDV |
| SEQ ID NO: 378 | HCDR1 (Chothia) | GFTFSSY |
| SEQ ID NO: 379 | HCDR2 (Chothia) | SSGGSF |
| SEQ ID NO: 380 | HCDR3 (Chothia) | RASTVVGTDFDV |
| SEQ ID NO: 381 | HCDR1 (IMGT) | GFTFSSYA |
| SEQ ID NO: 382 | HCDR2 (IMGT) | ISSGGSFT |
| SEQ ID NO: 383 | HCDR3 (IMGT) | ARRASTVVGTDFDV |
| SEQ ID NO: 384 | VH | EVMLVESGGGLVKPGGSLKLSCAASGFTFSSYAMSWIRQ TPEKRLEWVATISSGGSFTYYPDSVKGRFTISRDNVKNTLY LQMSSLRSEDTAMYYCARRASTVVGTDFDVWGAGTTVT VSS |
| SEQ ID NO: 385 | DNA VH | GAAGTGATGCTGGTGGAGTCTGGGGGAGGCTTAGTG AAGCCTGGAGGGTCCCTGAAACTCTCCTGTGCAGCCTC TGGATTCACTTTCAGTAGCTATGCCATGTCTTGGATTCG CCAGACTCCGGAGAAGAGACTGGAGTGGGTCGCAACC ATCAGTAGTGGTGGTAGTTTCACCTACTATCCAGACAG TGTGAAGGGGCGATTCACCATTTCTAGAGACAATGTCA AGAACACCCTGTACCTGCAAATGAGCAGTCTGAGGTCT GAAGACACGGCCATGTATTACTGTGCAAGACGGGCTT CTACGGTAGTAGGTACGGACTTCGATGTCTGGGGCGC AGGGACCACGGTCACCGTCTCCTCA |
| SEQ ID NO: 386 | Heavy Chain (CysMab mutations underlined) | EVMLVESGGGLVKPGGSLKLSCAASGFTFSSYAMSWIRQTPEK RLEWVATISSGGSFTYYPDSVKGRFTISRDNVKNTLYLQMSSLR SEDTAMYYCARRASTVVGTDFDVWGAGTTVTVSSastkgpsvfp lapsskstsggtaalgclvkdyfpCpvtvswnsgaltsgvhtfpavlqssglysl ssvvtvpssslgtqtyicnvnhkpsntkvdkrvepkscdkthtcppcpapell ggpsvflfppkpkdtlmisrtpevtcvvvdvshedpevkfnwyvdgvevhn aktkpreeqynstyrvvsvltvlhqdwlngkeykckvsnkalpapiektiska kgqprepqvytlppsreemtknqvsltclvkgfypCdiavewesngqpen nyktppvldsdgsffylyskltvdksrwqqgnvfscsvmhealhnhytqksls lspgk |
| SEQ ID NO: 387 | DNA Heavy Chain | GAAGTGATGCTGGTGGAGTCTGGGGGAGGCTTAGTG AAGCCTGGAGGGTCCCTGAAACTCTCCTGTGCAGCCTC TGGATTCACTTTCAGTAGCTATGCCATGTCTTGGATTCG CCAGACTCCGGAGAAGAGACTGGAGTGGGTCGCAACC ATCAGTAGTGGTGGTAGTTTCACCTACTATCCAGACAG TGTGAAGGGGCGATTCACCATTTCTAGAGACAATGTCA AGAACACCCTGTACCTGCAAATGAGCAGTCTGAGGTCT GAAGACACGGCCATGTATTACTGTGCAAGACGGGCTT CTACGGTAGTAGGTACGGACTTCGATGTCTGGGGCGC AGGGACCACGGTCACCGTCTCCTCAgctagcaccaagggcc caagtgtgtttcccctggcccccagcagcaagtctacttccggcggaact gctgccctgggttgctggtgaaggactacttccctgtcccgtgacagt gtcctggaactctggggctctgacttccggcgtgcacaccttcccgccg tgctgcagagcagcggcctgtacagcctgagcagcgtggtgacagtgc cctccagctctctgggaacccagacctatatctgcaacgtgaaccacaa gcccagcaacaccaaggtggacaagagagtggagcccaagagctgcg acaagacccacacctgcccccccctgcccagctccagaactgctgggag ggcttccgtgttcctgttccccccaagcccaaggacaccctgatgatc agcaggaccccgaggtgacctgcgtggtggtggacgtgtcccacgag gacccagaggtgaagttcaactggtacgtggacggcgtggaggtgcac aacgccaagacaagcccagagaggagcagtacaacagcacctacag ggtggtgtccgtgctgaccgtgctgcaccaggactggctgaacggcaaa gaatacaagtgcaaagtctccaacaaggccctgccagcccaatcgaa aagacaatcagcaaggccaagggccagccacgggagccccaggtgta caccctgccccccagccgggaggagatgaccaagaaccaggtgtccct gacctgtctggtgaagggcttctaccctgtgatatcgccgtggagtggg |

TABLE 4-continued

Amino Acid and Nucleotide Sequence Information for Hybridomas and Humanized Anti-CCR7 Antibodies

|  |  |  |
|---|---|---|
| | | agagcaacggccagcccgagaacaactacaagaccacccccccagtg<br>ctggacagcgacggcagcttcttcctgtacagcaagctgaccgtggaca<br>agtccaggtggcagcagggcaacgtgttcagctgcagcgtgatgcacg<br>aggccctgcacaaccactacacccagaagtccctgagcctgagccccg<br>gcaag |
| SEQ ID NO: 388 | LCDR1 (Combined) | RASQDIGSSLN |
| SEQ ID NO: 389 | LCDR2 (Combined) | ATSSLDS |
| SEQ ID NO: 390 | LCDR3 (Combined) | LQYASSPPT |
| SEQ ID NO: 391 | LCDR1 (Kabat) | RASQDIGSSLN |
| SEQ ID NO: 392 | LCDR2 (Kabat) | ATSSLDS |
| SEQ ID NO: 393 | LCDR3 (Kabat) | LQYASSPPT |
| SEQ ID NO: 394 | LCDR1 (Chothia) | SQDIGSS |
| SEQ ID NO: 395 | LCDR2 (Chothia) | ATS |
| SEQ ID NO: 396 | LCDR3 (Chothia) | YASSPP |
| SEQ ID NO: 397 | LCDR1 (IMGT) | QDIGSS |
| SEQ ID NO: 398 | LCDR2 (IMGT) | ATS |
| SEQ ID NO: 399 | LCDR3 (IMGT) | LQYASSPPT |
| SEQ ID NO: 400 | VL | DIQMTQSPSSLSASLGERVSLTCRASQDIGSSLNWLQQEP<br>DGTIKRLIYATSSLDSGVPKRFSGSRSGSDYSLTISSLESEDF<br>VVYYCLQYASSPPTFGGGTKLEIK |
| SEQ ID NO: 401 | DNA VL | GACATCCAGATGACCCAGTCTCCATCCTCCTTATCTGCC<br>TCTCTGGGAGAAAGAGTCAGTCTCACTTGTCGGGCAA<br>GTCAGGACATTGGTAGTAGCTTAAACTGGCTTCAGCAG<br>GAACCAGATGGAACTATTAAACGCCTGATCTATGCCAC<br>ATCCAGTTTAGATTCTGGTGTCCCCAAAAGGTTCAGTG<br>GCAGTAGGTCTGGGTCAGATTATTCTCTCACCATCAGC<br>AGCCTTGAGTCTGAAGATTTTGTAGTCTATTACTGTCTA<br>CAATATGCTAGTTCGCCTCCGACGTTCGGTGGAGGCAC<br>CAAGCTGGAAATCAAA |
| SEQ ID NO: 402 | Light Chain | DIQMTQSPSSLSASLGERVSLTCRASQDIGSSLNWLQQEP<br>DGTIKRLIYATSSLDSGVPKRFSGSRSGSDYSLTISSLESEDF<br>VVYYCLQYASSPPTFGGGTKLEIKRTVAAPSVFIFPPSDEQ<br>LKSGTASVVCLLNNFYPREAKVQWKVDNALQSGNSQES<br>VTEQDSKDSTYSLSSTLTLSKADYEKHKVYACEVTHQGLSS<br>PVTKSFNRGEC |
| SEQ ID NO: 403 | DNA Light Chain | GACATCCAGATGACCCAGTCTCCATCCTCCTTATCTGCC<br>TCTCTGGGAGAAAGAGTCAGTCTCACTTGTCGGGCAA<br>GTCAGGACATTGGTAGTAGCTTAAACTGGCTTCAGCAG<br>GAACCAGATGGAACTATTAAACGCCTGATCTATGCCAC<br>ATCCAGTTTAGATTCTGGTGTCCCCAAAAGGTTCAGTG<br>GCAGTAGGTCTGGGTCAGATTATTCTCTCACCATCAGC<br>AGCCTTGAGTCTGAAGATTTTGTAGTCTATTACTGTCTA<br>CAATATGCTAGTTCGCCTCCGACGTTCGGTGGAGGCAC<br>CAAGCTGGAAATCAAACGTACGGTGGCCGCTCCCAGC<br>GTGTTCATCTTCCCCCCCAGCGACGAGCAGCTGAAGAG<br>TGGCACCGCCAGCGTGGTGTGCCTGCTGAACAACTTCT<br>ACCCCCGGGAGGCCAAGGTGCAGTGGAAGGTGGACA<br>ACGCCCTGCAGAGCGGCAACAGCCAGGAGAGCGTCAC<br>CGAGCAGGACAGCAAGGACTCCACCTACAGCCTGAGC<br>AGCACCCTGACCCTGAGCAAGGCCGACTACGAGAAGC<br>ATAAGGTGTACGCCTGCGAGGTGACCCACCAGGGCCT<br>GTCCAGCCCCGTGACCAAGAGCTTCAACAGGGGCGAG<br>TGC |

Parental 506E15 hIgG1 DAPA CysMab

| SEQ ID NO: 404 | HCDR1 (Combined) | GFTFSSYAMS |
| SEQ ID NO: 405 | HCDR2 (Combined) | TISSGGSFTYYPDSVKG |
| SEQ ID NO: 406 | HCDR3 (Combined) | RASTVVGTDFDV |
| SEQ ID NO: 407 | HCDR1 (Kabat) | SYAMS |

TABLE 4-continued

Amino Acid and Nucleotide Sequence Information for Hybridomas and Humanized Anti-CCR7 Antibodies

| | | |
|---|---|---|
| SEQ ID NO: 408 | HCDR2 (Kabat) | TISSGGSFTYYPDSVKG |
| SEQ ID NO: 409 | HCDR3 (Kabat) | RASTVVGTDFDV |
| SEQ ID NO: 410 | HCDR1 (Chothia) | GFTFSSY |
| SEQ ID NO: 411 | HCDR2 (Chothia) | SSGGSF |
| SEQ ID NO: 412 | HCDR3 (Chothia) | RASTVVGTDFDV |
| SEQ ID NO: 413 | HCDR1 (IMGT) | GFTFSSYA |
| SEQ ID NO: 414 | HCDR2 (IMGT) | ISSGGSFT |
| SEQ ID NO: 415 | HCDR3 (IMGT) | ARRASTVVGTDFDV |
| SEQ ID NO: 416 | VH | EVQLVESGGGLVKPGGSLRLSCAASGFTFSSYAMSWIRQ APGKGLEWVATISSGGSFTYYPDSVKGRFTISRDNAKNSL YLQMNSLRAEDTAVYYCARRASTVVGTDFDVWGQGTT VTVSS |
| SEQ ID NO: 417 | DNA VH | GAGGTGCAGCTGGTGGAATCTGGCGGAGGCCTGGTG AAACCCGGCGGATCCCTGAGACTGTCCTGCGCCGCCTC CGGCTTCACCTTCTCCAGCTACGCCATGTCCTGGATCCG GCAGGCTCCCGGCAAGGGCCTGGAATGGGTGGCCACC ATCTCCTCCGGCGGCAGCTTCACCTACTACCCCGACAG CGTGAAGGGCAGATTCACCATCAGCCGGGACAACGCC AAGAACTCCCTGTACCTGCAGATGAACTCCCTGCGGGC CGAGGACACCGCCGTGTACTACTGTGCCAGACGGGCC TCCACCGTCGTGGGAACCGACTTCGATGTGGGGCC AGGGCACCACCGTGACAGTGTCCTCC |
| SEQ ID NO: 418 | Heavy Chain (DAPA, CysMab mutations underlined) | EVQLVESGGGLVKPGGSLRLSCAASGFTFSSYAMSWIRQ APGKGLEWVATISSGGSFTYYPDSVKGRFTISRDNAKNSL YLQMNSLRAEDTAVYYCARRASTVVGTDFDVWGQGTT VTVSSASTKGPSVFPLAPSSKSTSGGTAALGCLVKDYFP<u>C</u>P VTVSWNSGALTSGVHTFPAVLQSSGLYSLSSVVTVPSSSL GTQTYICNVNHKPSNTKVDKRVEPKSCDKTHTCPPCPAP ELLGGPSVFLFPPKPKDTLMISRTPEVTCVVV<u>A</u>VSHEDPE VKFNWYVDGVEVHNAKTKPREEQYNSTYRVVSVLTVLH QDWLNGKEYKCKVSNKAL<u>A</u>APIEKTISKAKGQPREPQVY TLPPSREEMTKNQVSLTCLVKGFYP<u>C</u>DIAVEWESNGQPE NNYKTTPPVLDSDGSFFLYSKLTVDKSRWQQGNVFSCSV MHEALHNHYTQKSLSLSPGK |
| SEQ ID NO: 419 | DNA Heavy Chain | GAGGTGCAGCTGGTGGAATCTGGCGGAGGCCTGGTG AAACCCGGCGGATCCCTGAGACTGTCCTGCGCCGCCTC CGGCTTCACCTTCTCCAGCTACGCCATGTCCTGGATCCG GCAGGCTCCCGGCAAGGGCCTGGAATGGGTGGCCACC ATCTCCTCCGGCGGCAGCTTCACCTACTACCCCGACAG CGTGAAGGGCAGATTCACCATCAGCCGGGACAACGCC AAGAACTCCCTGTACCTGCAGATGAACTCCCTGCGGGC CGAGGACACCGCCGTGTACTACTGTGCCAGACGGGCC TCCACCGTCGTGGGAACCGACTTCGATGTGGGGCC AGGGCACCACCGTGACAGTGTCCTCCGCTAGCACCAA GGGCCCAAGTGTGTTTCCCCTGGCCCCCAGCAGCAAGT CTACTTCCGGCGGAACTGCTGCCCTGGGTTGCCTGGTG AAGGACTACTTCCCCTGTCCCGTGACAGTGTCCTGGAA CTCTGGGGCTCTGACTTCCGGCGTGCACACCTTCCCCG CCGTGCTGCAGAGCAGCGGCCTGTACAGCCTGAGCAG CGTGGTGACAGTGCCCTCCAGCTCTCTGGGAACCCAGA CCTATATCTGCAACGTGAACCACAAGCCCAGCAACACC AAGGTGGACAAGAGAGTGGAGCCCAAGAGCTGCGAC AAGACCCACACCTGCCCCCCCTGCCCAGCTCCAGAACT GCTGGGAGGGCCTTCCGTGTTCCTGTTCCCCCCCAAGC CCAAGGACACCCTGATGATCAGCAGGACCCCCGAGGT GACCTGCGTGGTGGTGGCCGTGTCCCACGAGGACCCA GAGGTGAAGTTCAACTGGTACGTGGACGGCGTGGAG GTGCACAACGCCAAGACCAAGCCCAGAGAGGAGCAGT ACAACAGCACCTACAGGGTGGTGTCCGTGCTGACCGT GCTGCACCAGGACTGGCTGAACGGCAAAGAATACAAG TGCAAAGTCTCCAACAAGGCCCTGGCTGCCCCAATCGA AAAGACAATCAGCAAGGCCAAGGGCCAGCCACGGGA GCCCCAGGTGTACACCCTGCCCCCCAGCCGGGAGGAG ATGACCAAGAACCAGGTGTCCCTGACCTGTCTGGTGAA GGGCTTCTACCCCTGTGATATCGCCGTGGAGTGGGAG AGCAACGGCCAGCCCGAGAACAACTACAAGACCACCC CCCCAGTGCTGGACAGCGACGGCAGCTTCTTCCTGTAC AGCAAGCTGACCGTGGACAAGTCCAGGTGGCAGCAG GGCAACGTGTTCAGCTGCAGCGTGATGCACGAGGCCC |

TABLE 4-continued

Amino Acid and Nucleotide Sequence Information for Hybridomas and Humanized Anti-CCR7 Antibodies

| | | |
|---|---|---|
| | | TGCACAACCACTACACCCAGAAGTCCCTGAGCCTGAGC CCCGGCAAG |
| SEQ ID NO: 420 | LCDR1 (Combined) | RASQDIGSSLN |
| SEQ ID NO: 421 | LCDR2 (Combined) | ATSSLDS |
| SEQ ID NO: 422 | LCDR3 (Combined) | LQYASSPPT |
| SEQ ID NO: 423 | LCDR1 (Kabat) | RASQDIGSSLN |
| SEQ ID NO: 424 | LCDR2 (Kabat) | ATSSLDS |
| SEQ ID NO: 425 | LCDR3 (Kabat) | LQYASSPPT |
| SEQ ID NO: 426 | LCDR1 (Chothia) | SQDIGSS |
| SEQ ID NO: 427 | LCDR2 (Chothia) | ATS |
| SEQ ID NO: 428 | LCDR3 (Chothia) | YASSPP |
| SEQ ID NO: 429 | LCDR1 (IMGT) | QDIGSS |
| SEQ ID NO: 430 | LCDR2 (IMGT) | ATS |
| SEQ ID NO: 431 | LCDR3 (IMGT) | LQYASSPPT |
| SEQ ID NO: 432 | VL | DIQMTQSPSSLSASVGDRVTLTCRASQDIGSSLNWLQQK PGKAIKRLIYATSSLDSGVPSRFSGSRSGTDYTLTISSLQPE DFVVYYCLQYASSPPTFGGGTKLEIK |
| SEQ ID NO: 433 | DNA VL | GACATCCAGATGACCCAGTCCCCCTCCAGCCTGTCCGC CTCCGTGGGCGATAGAGTGACCCTGACCTGCCGGGCC TCCCAGGACATCGGCTCCTCCCTGAACTGGCTGCAGCA GAAGCCCGGCAAGGCCATCAAGCGGCTGATCTACGCC ACCTCCTCCCTGGACTCCGGCGTGCCCTCCCGGTTCTCC GGCTCTAGATCCGGCACCGACTACACCCTGACCATCTC CAGCCTGCAGCCCGAGGACTTCGTGGTGTACTACTGCC TGCAGTACGCCTCCAGCCCCCCCACCTTTGGCGGAGGC ACCAAGCTGGAAATCAAG |
| SEQ ID NO: 434 | Light Chain | DIQMTQSPSSLSASVGDRVTLTCRASQDIGSSLNWLQQK PGKAIKRLIYATSSLDSGVPSRFSGSRSGTDYTLTISSLQPE DFVVYYCLQYASSPPTFGGGTKLEIKRTVAAPSVFIFPPSD EQLKSGTASVVCLLNNFYPREAKVQWKVDNALQSGNSQ ESVTEQDSKDSTYSLSSTLTLSKADYEKHKVYACEVTHQGL SSPVTKSFNRGEC |
| SEQ ID NO: 435 | DNA Light Chain | GACATCCAGATGACCCAGTCCCCCTCCAGCCTGTCCGC CTCCGTGGGCGATAGAGTGACCCTGACCTGCCGGGCC TCCCAGGACATCGGCTCCTCCCTGAACTGGCTGCAGCA GAAGCCCGGCAAGGCCATCAAGCGGCTGATCTACGCC ACCTCCTCCCTGGACTCCGGCGTGCCCTCCCGGTTCTCC GGCTCTAGATCCGGCACCGACTACACCCTGACCATCTC CAGCCTGCAGCCCGAGGACTTCGTGGTGTACTACTGCC TGCAGTACGCCTCCAGCCCCCCCACCTTTGGCGGAGGC ACCAAGCTGGAAATCAAGCGTACGGTGGCCGCTCCCA GCGTGTTCATCTTCCCCCCCAGCGACGAGCAGCTGAAG AGTGGCACCGCCAGCGTGGTGTGCCTGCTGAACAACT TCTACCCCCGGGAGGCCAAGGTGCAGTGGAAGGTGGA CAACGCCCTGCAGAGCGGCAACAGCCAGGAGAGCGTC ACCGAGCAGGACAGCAAGGACTCCACCTACAGCCTGA GCAGCACCCTGACCCTGAGCAAGGCCGACTACGAGAA GCATAAGGTGTACGCCTGCGAGGTGACCCACCAGGGC CTGTCCAGCCCCGTGACCAAGAGCTTCAACAGGGGCG AGTGC |

Parental 684E12 hIgG1 CysMab

| | | |
|---|---|---|
| SEQ ID NO: 436 | HCDR1 (Combined) | GFTFSNFAMS |
| SEQ ID NO: 437 | HCDR2 (Combined) | TISTGGTYTYYPDSVKG |
| SEQ ID NO: 438 | HCDR3 (Combined) | RGYDGVDK |
| SEQ ID NO: 439 | HCDR1 (Kabat) | SNFAMS |
| SEQ ID NO: 440 | HCDR2 (Kabat) | TISTGGTYTYYPDSVKG |
| SEQ ID NO: 441 | HCDR3 (Kabat) | RGYDGVDK |

TABLE 4-continued

Amino Acid and Nucleotide Sequence Information for Hybridomas and Humanized Anti-CCR7 Antibodies

| | | |
|---|---|---|
| SEQ ID NO: 442 | HCDR1 (Chothia) | GFTFSNF |
| SEQ ID NO: 443 | HCDR2 (Chothia) | STGGTY |
| SEQ ID NO: 444 | HCDR3 (Chothia) | RGYDGVDK |
| SEQ ID NO: 445 | HCDR1 (IMGT) | GFTFSNFA |
| SEQ ID NO: 446 | HCDR2 (IMGT) | ISTGGTYT |
| SEQ ID NO: 447 | HCDR3 (IMGT) | TRRGYDGVDK |
| SEQ ID NO: 448 | VH | EVHLVESGGGLVKPGGSLKLSCAASGFTFSNFAMSWVRQTPE KRLEWVATISTGGTYTYYPDSVKGRFTISRDNAKKTLYLQMSSL RSEDTAMYYCTRRGYDGVDKWGQGTTLTVSS |
| SEQ ID NO: 449 | DNA VH | GAAGTGCATCTGGTGGAGTCTGGGGGAGGCTTAGTGAAGC CTGGAGGGTCCCTGAAACTCTCCTGTGCAGCCTCTGGATTCA CTTTCAGTAACTTTGCCATGTCTTGGGTTCGCCAGACTCCGG AGAAGAGACTGGAGTGGGTCGCAACCATTAGTACTGGTGG TACTTACACCTACTATCCAGACAGTGTGAAGGGTCGATTCAC CATCTCCAGAGACAATGCCAAGAAAACCCTGTACCTGCAAA TGAGCAGTCTGAGGTCTGAGGACACGGCCATGTATTACTGT ACAAGACGGGGTACGACGGCGTGGACAAATGGGGCCAA GGCACCACTCTCACAGTCTCCTCA |
| SEQ ID NO: 450 | Heavy Chain (CysMab mutations underlined) | EVHLVESGGGLVKPGGSLKLSCAASGFTFSNFAMSWVRQTPE KRLEWVATISTGGTYTYYPDSVKGRFTISRDNAKKTLYLQMSSL RSEDTAMYYCTRRGYDGVDKWGQGTTLIVSSastkgpsvfplap sskstsggtaalgclvkdyfpCpvtvswnsgaltsgvhtfpavlqssglyslssv vtvpssslgtqtyicnvnhkpsntkvdkrvepkscdkthtcppcpapellggp svflfppkpkdtlmisrtpevtcvvvdvshedpevkfnwyvdgvevhnakt kpreeqynstyrvvsvltvlhqdwlngkeykckvsnkalpapiektiskakgq prepqvytlppsreemtknqvsltclvkgfypCdiavewesngqpennykt tppvldsdgsfflysklvdksrwqqgnvfscsvmhealhnhytqkslslspg k |
| SEQ ID NO: 451 | DNA Heavy Chain (CysMab mutations underlined) | GAAGTGCATCTGGTGGAGTCTGGGGGAGGCTTAGTGAAGC CTGGAGGGTCCCTGAAACTCTCCTGTGCAGCCTCTGGATTCA CTTTCAGTAACTTTGCCATGTCTTGGGTTCGCCAGACTCCGG AGAAGAGACTGGAGTGGGTCGCAACCATTAGTACTGGTGG TACTTACACCTACTATCCAGACAGTGTGAAGGGTCGATTCAC CATCTCCAGAGACAATGCCAAGAAAACCCTGTACCTGCAAA TGAGCAGTCTGAGGTCTGAGGACACGGCCATGTATTACTGT ACAAGACGGGGTACGACGGCGTGGACAAATGGGGCCAA GGCACCACTCTCACAGTCTCCTCAgctagcaccaagggcccaagt gtgtttcccctggccccagcagcaagtctacttccggcggaactgctgc cctgggttgcctggtgaaggactactttcccctgtcccgtgacagtgtcct ggaactctggggctctgacttccggcgtgcacaccttcccgccgctg cagagcagcggcctgtacagcctgagcagcgtggtgacagtgccctcc agctctctgggaacccagacctatatctgcaacgtgaaccacaagccca gcaacaccaaggtggacaagagagtggagcccaagagctgcgacaag acccacacctgccccccctgcccagctccagaactgctgggaggccctt ccgtgttcctgttccccccaagcccaaggaccctgatgatcagcag gacccccgaggtgacctgcgtggtggtggacgtgtcccacgaggaccc agaggtgaagttcaactggtacgtggacggcgtggaggtgcacaacgc caagaccaagcccagagaggagcagtacaacagcacctacagggtgg tgtccgtgctgaccgtgctgcaccaggactggctgaacggcaaagaata caagtgcaaagtctccaacaaggccctgccagccccaatcgaaaagac aatcagcaaggccaagggccagccacgggagccccaggtgtacaccct gcccccagccgggaggagatgaccaagaaccaggtgtccctgacctg tctggtgaagggcttctaccctgtgatatcgccgtggagtgggagagc aacggccagcccgagaacaactacaagaccacccccccagtgctggac agcgacggcagcttcttcctgtacagcaagctgaccgtggacaagtcca ggtggcagcagggcaacgtgttcagctgcagcgtgatgcacgaggccc tgcacaaccactacacccagaagtccctgagcctgagccccggcaag |
| SEQ ID NO: 452 | LCDR1 (Combined) | KSGQSLLDSDGKTYLN |
| SEQ ID NO: 453 | LCDR2 (Combined) | LVSKLDS |
| SEQ ID NO: 454 | LCDR3 (Combined) | WQGTHFPQT |
| SEQ ID NO: 455 | LCDR1 (Kabat) | KSGQSLLDSDGKTYLN |
| SEQ ID NO: 456 | LCDR2 (Kabat) | LVSKLDS |
| SEQ ID NO: 457 | LCDR3 (Kabat) | WQGTHFPQT |
| SEQ ID NO: 458 | LCDR1 (Chothia) | GQSLLDSDGKTY |

TABLE 4-continued

Amino Acid and Nucleotide Sequence Information for Hybridomas and Humanized Anti-CCR7 Antibodies

| SEQ ID NO: 459 | LCDR2 (Chothia) | LVS |
|---|---|---|
| SEQ ID NO: 460 | LCDR3 (Chothia) | GTHFPQ |
| SEQ ID NO: 461 | LCDR1 (IMGT) | QSLLDSDGKTY |
| SEQ ID NO: 462 | LCDR2 (IMGT) | LVS |
| SEQ ID NO: 463 | LCDR3 (IMGT) | WQGTHFPQT |
| SEQ ID NO: 464 | VL | DVVMTQTPLTLSVTIGQPASISCKSGQSLLDSDGKTYLNWFLQ RPGQSPKRLIYLVSKLDSGVPDRFTGSGSGTDFTLKISRVEAEDL GVYYCWQGTHFPQTFGGGTKLEIK |
| SEQ ID NO: 465 | DNA VL | gatgttgtgatgacccagactccactcactttgtcggttaccattggacaaccag cctccatctcttgcaagtcaggtcagagcctcttagatagtgatggaaagacat atttgaattggttttacagaggccaggccagtctccaaagcgcctaatctatct ggtgtctaaactggactctggagtccctgacaggttcactggcagtggatcagg gacagatttcacactgaaaatcagcagagtggaggctgaggatttgggagttt attattgctggcaaggtacacattttcctcagacgttcggtggaggcaccaagc tggaaatcaaa |
| SEQ ID NO: 466 | Light Chain | DVVMTQTPLTLSVTIGQPASISCKSGQSLLDSDGKTYLNWFLQ RPGQSPKRLIYLVSKLDSGVPDRFTGSGSGTDFTLKISRVEAEDL GVYYCWQGTHFPQTFGGGTKLEIKRTVAAPSVFIFPPSDEQLK SGTASVVCLLNNFYPREAKVQWKVDNALQSGNSQESVTEQDS KDSTYSLSSTLTLSKADYEKHKVYACEVTHQGLSSPVTKSFNRGE C |
| SEQ ID NO: 467 | DNA Light Chain | GATGTTGTGATGACCCAGACTCCACTCACTTTGTCGGTTACC ATTGGACAACCAGCCTCCATCTCTTGCAAGTCAGGTCAGAG CCTCTTAGATAGTGATGGAAAGACATATTTGAATTGGTTTTT ACAGAGGCCAGGCCAGTCTCCAAAGCGCCTAATCTATCTGG TGTCTAAACTGGACTCTGGAGTCCCTGACAGGTTCACTGGC AGTGGATCAGGGACAGATTTCACACTGAAAATCAGCAGAGT GGAGGCTGAGGATTTGGGAGTTTATTATTGCTGGCAAGGTA CACATTTTCCTCAGACGTTCGGTGGAGGCACCAAGCTGGAA ATCAAAcgtacggtggccgctcccagcgtgttcatcttccccccccagcgacg agcagctgaagagtggcaccgccagcgtggtgtgcctgctgaacaacttctac cccgggaggccaaggtgcagtggaaggtggacaacgccctgcagagcggc aacagccaggagagcgtcaccgagcaggacagcaaggactccacctacagc ctgagcagcaccctgaccctgagcaaggccgactacgagaagcataaggtgt acgcctgcgaggtgacccaccagggcctgtccagccccgtgaccaagagcttc aacaggggcgagtgc |

Parental 684E12 hIgG1 DAPA CysMab

| SEQ ID NO: 468 | HCDR1 (Combined) | GFTFSNFAMS |
|---|---|---|
| SEQ ID NO: 469 | HCDR2 (Combined) | TISTGGTYTYYPDSVKG |
| SEQ ID NO: 470 | HCDR3 (Combined) | RGYDGVDK |
| SEQ ID NO: 471 | HCDR1 (Kabat) | SNFAMS |
| SEQ ID NO: 472 | HCDR2 (Kabat) | TISTGGTYTYYPDSVKG |
| SEQ ID NO: 473 | HCDR3 (Kabat) | RGYDGVDK |
| SEQ ID NO: 474 | HCDR1 (Chothia) | GFTFSNF |
| SEQ ID NO: 475 | HCDR2 (Chothia) | STGGTY |
| SEQ ID NO: 476 | HCDR3 (Chothia) | RGYDGVDK |
| SEQ ID NO: 477 | HCDR1 (IMGT) | GFTFSNFA |
| SEQ ID NO: 478 | HCDR2 (IMGT) | ISTGGTYT |
| SEQ ID NO: 479 | HCDR3 (IMGT) | TRRGYDGVDK |
| SEQ ID NO: 480 | VH | EVHLVESGGGLVKPGGSLKLSCAASGFTFSNFAMSWVRQTPE KRLEWVATISTGGTYTYYPDSVKGRFTISRDNAKKTLYLQMSSL RSEDTAMYYCTRRGYDGVDKWGQGTTLTVSS |
| SEQ ID NO: 481 | DNA VH | GAAGTGCATCTGGTGGAGTCTGGGGGAGGCTTAGTGAAGC CTGGAGGGTCCCTGAAACTCTCCTGTGCAGCCTCTGGATTCA CTTTCAGTAACTTTGCCATGTCTTGGGTTCGCCAGACTCCGG AGAAGAGACTGGAGTGGGTCGCAACCATTAGTACTGGTGG TACTTACACCTACTATCCAGACAGTGTGAAGGGTCGATTCAC CATCTCCAGAGACAATGCCAAGAAAACCCTGTACCTGCAAA |

TABLE 4-continued

Amino Acid and Nucleotide Sequence Information for Hybridomas and Humanized Anti-CCR7 Antibodies

| | | |
|---|---|---|
| | | TGAGCAGTCTGAGGTCTGAGGACACGGCCATGTATTACTGT<br>ACAAGACGGGGTACGACGGCGTGGACAAATGGGGCCAA<br>GGCACCACTCTCACAGTCTCCTCA |
| SEQ ID NO: 482 | Heavy<br>Chain<br>(DAPA,<br>CysMab<br>mutations<br>underlined) | EVHLVESGGGLVKPGGSLKLSCAASGFTFSNFAMSWVRQTPE<br>KRLEWVATISTGGTYTYYPDSVKGRFTISRDNAKKTLYLQMSSL<br>RSEDTAMYYCTRRGYDGVDKWGQGTTLTVSSASTKGPSVFPL<br>APSSKSTSGGTAALGCLVKDYFPCPVTVSWNSGALTSGVHTFP<br>AVLQSSGLYSLSSVVTVPSSSLGTQTYICNVNHKPSNTKVDKRV<br>EPKSCDKTHTCPPCPAPELLGGPSVFLFPPKPKDTLMISRTPEVT<br>CVVVAVSHEDPEVKFNWYVDGVEVHNAKTKPREEQYNSTYR<br>VVSVLTVLHQDWLNGKEYKCKVSNKALAAPIEKTISKAKGQPR<br>EPQVYTLPPSREEMTKNQVSLTCLVKGFYPCDIAVEWESNGQP<br>ENNYKTTPPVLDSDGSFFLYSKLTVDKSRWQQGNVFSCSVMH<br>EALHNHYTQKSLSLSPGK |
| SEQ ID NO: 483 | DNA Heavy<br>Chain | GAAGTGCATCTGGTGGAGTCTGGGGGAGGCTTAGTGAAGC<br>CTGGAGGGTCCCTGAAACTCTCCTGTGCAGCCTCTGGATTCA<br>CTTTCAGTAACTTTGCCATGTCTTGGGTTCGCCAGACTCCGG<br>AGAAGAGACTGGAGTGGGTCGCAACCATTAGTACTGGTGG<br>TACTTACACCTACTATCCAGACAGTGTGAAGGGTCGATTCAC<br>CATCTCCAGAGACAATGCCAAGAAAACCCTGTACCTGCAAA<br>TGAGCAGTCTGAGGTCTGAGGACACGGCCATGTATTACTGT<br>ACAAGACGGGGTACGACGGCGTGGACAAATGGGGCCAA<br>GGCACCACTCTCACAGTCTCCTCAgctagcaccaagggcccaagt<br>gtgtttcccctggccccccagcagcaagtctacttccggcggaactgctgc<br>cctgggttgcctggtgaaggactacttccccgtcccgtgacagtgtcct<br>ggaactctggggctctgacttccggcgtgcacaccttccccgccgtgctg<br>cagagcagcggcctgtacagcctgagcagcgtggtgacagtgccctcc<br>agctctctgggaacccagacctatatctgcaacgtgaaccacaagccca<br>gcaacaccaaggtggacaagagagtggagcccaagagctgcgacaag<br>acccacacctgccccccctgcccagctccagaactgctggagggccttc<br>cgtgttcctgttcccccccaagcccaaggaccctgatgatcagcag<br>gaccccgaggtgacctgcgtggtggtggccgtgtcccacgaggaccc<br>agaggtgaagttcaactggtacgtggacggcgtggaggtgcacaacgc<br>caagaccaagcccagagaggagcagtacaacagcacctacagggtgg<br>tgtccgtgctgaccgtgctgcaccaggactggctgaacggcaaagaata<br>caagtgcaaagtctccaacaaggccctggctgccccaatcgaaaagac<br>aatcagcaaggccaagggccagccacgggagccccaggtgtacaccct<br>gcccccagccgggaggagatgaccaagaaccaggtgtccctgacctg<br>tctggtgaagggcttctacccctgtgatatcgccgtggagtgggagagc<br>aacggccagcccgagaacaactacaagaccacccccccagtgctggac<br>agcgacggcagcttcttcctgtacagcaagctgaccgtggacaagtcca<br>ggtggcagcagggcaacgtgttcagctgcagcgtgatgcacgaggcc<br>ctgcacaaccactacacccagaagtccctgagcctgagccccggcaag |
| SEQ ID NO: 484 | LCDR1<br>(Combined) | KSGQSLLDSDGKTYLN |
| SEQ ID NO: 485 | LCDR2<br>(Combined) | LVSKLDS |
| SEQ ID NO: 486 | LCDR3<br>(Combined) | WQGTHFPQT |
| SEQ ID NO: 487 | LCDR1<br>(Kabat) | KSGQSLLDSDGKTYLN |
| SEQ ID NO: 488 | LCDR2<br>(Kabat) | LVSKLDS |
| SEQ ID NO: 489 | LCDR3<br>(Kabat) | WQGTHFPQT |
| SEQ ID NO: 490 | LCDR1<br>(Chothia) | GQSLLDSDGKTY |
| SEQ ID NO: 491 | LCDR2<br>(Chothia) | LVS |
| SEQ ID NO: 492 | LCDR3<br>(Chothia) | GTHFPQ |
| SEQ ID NO: 493 | LCDR1<br>(IMGT) | QSLLDSDGKTY |
| SEQ ID NO: 494 | LCDR2<br>(IMGT) | LVS |
| SEQ ID NO: 495 | LCDR3<br>(IMGT) | WQGTHFPQT |
| SEQ ID NO: 496 | VL | DVVMTQTPLTLSVTIGQPASISCKSGQSLLDSDGKTYLNWFLQ<br>RPGQSPKRLIYLVSKLDSGVPDRFTGSGSGTDFTLKISRVEAEDL<br>GVYYCWQGTHFPQTFGGGTKLEIK |
| SEQ ID NO: 497 | DNA VL | gatgttgtgatgacccagactccactcactttgtcggttaccattggacaaccag<br>cctccatctcttgcaagtcaggtcagagcctcttagatagtgatggaaagacat<br>atttgaattggttttacagaggccaggccagtctccaaagcgcctaatctatct<br>ggtgtctaaactggactctggagtccctgacaggttcactggcagtggatcagg<br>gacagatttcacactgaaaatcagcagagtggaggctgaggatttggagttt<br>attattgctggcaaggtacacattttcctcagacgttcggtggaggcaccaagc<br>tggaaatcaaa |

TABLE 4-continued

Amino Acid and Nucleotide Sequence Information for Hybridomas and Humanized Anti-CCR7 Antibodies

| | | |
|---|---|---|
| SEQ ID NO: 498 | Light Chain | DVVMTQTPLTLSVTIGQPASISCKSGQSLLDSDGKTYLNWFLQ<br>RPGQSPKRLIYLVSKLDSGVPDRFTGSGSGTDFTLKISRVEAEDL<br>GVYYCWQGTHFPQTFGGGTKLEIKRTVAAPSVFIFPPSDEQLK<br>SGTASVVCLLNNFYPREAKVQWKVDNALQSGNSQESVTEQDS<br>KDSTYSLSSTLTLSKADYEKHKVYACEVTHQGLSSPVTKSFNRGE<br>C |
| SEQ ID NO: 499 | DNA Light Chain | GATGTTGTGATGACCCAGACTCCACTCACTTTGTCGGTTACC<br>ATTGGACAACCAGCCTCCATCTCTTGCAAGTCAGGTCAGAG<br>CCTCTTAGATAGTGATGGAAAGACATATTTGAATTGGTTTTT<br>ACAGAGGCCAGGCCAGTCTCCAAAGCGCCTAATCTATCTGG<br>TGTCTAAACTGGACTCTGGAGTCCCTGACAGGTTCACTGGC<br>AGTGGGATCAGGGACAGATTTCACACTGAAAATCAGCAGAGT<br>GGAGGCTGAGGATTTGGGAGTTTATTATTGCTGGCAAGGTA<br>CACATTTTCCTCAGACGTTCGGTGGAGGCACCAAGCTGGAA<br>ATCAAAcgtacggtggccgctcccagcgtgttcatcttcccccccagcgacg<br>agcagctgaagagtggcaccgccagcgtggtgtgcctgctgaacaacttctac<br>ccccgggaggccaaggtgcagtggaaggtggacaacgccctgcagagcggc<br>aacagccaggagagcgtcaccgagcaggacagcaaggactccacctacagc<br>ctgagcagcaccctgaccctgagcaaggccgactacgagaagcataaggtgt<br>acgcctgcgaggtgacccaccagggcctgtccagcccgtgaccaagagcttc<br>aacaggggcgagtgc |

Humanized 674J13 higG1 DAPA

| | | |
|---|---|---|
| SEQ ID NO: 500 | HCDR1 (Combined) | GYSITSGYSWH |
| SEQ ID NO: 501 | HCDR2 (Combined) | HIHSSGSTNYNPSLKS |
| SEQ ID NO: 502 | HCDR3 (Combined) | GGVQAFAY |
| SEQ ID NO: 503 | HCDR1 (Kabat) | SGYSWH |
| SEQ ID NO: 504 | HCDR2 (Kabat) | HIHSSGSTNYNPSLKS |
| SEQ ID NO: 505 | HCDR3 (Kabat) | GGVQAFAY |
| SEQ ID NO: 506 | HCDR1 (Chothia) | GYSITSGY |
| SEQ ID NO: 507 | HCDR2 (Chothia) | HSSGS |
| SEQ ID NO: 508 | HCDR3 (Chothia) | GGVQAFAY |
| SEQ ID NO: 509 | HCDR1 (IMGT) | GYSITSGYS |
| SEQ ID NO: 510 | HCDR2 (IMGT) | IHSSGST |
| SEQ ID NO: 511 | HCDR3 (IMGT) | ARGGVQAFAY |
| SEQ ID NO: 512 | VH | DVQLQESGPGLVKPSQTLSLTCTVSGYSITSGYSWHWIR<br>QHPGKGLEWMAHIHSSGSTNYNPSLKSRITISRDTSKNQ<br>FSLKLSSVTAADTAVYYCARGGVQAFAYWGQGTLVTVSS |
| SEQ ID NO: 513 | DNA VH | GACGTGCAGCTGCAGGAATCGGCCCTGGCCTGGTGA<br>AACCCTCCCAGACCCTGTCCCTGACCTGCACCGTGTCC<br>GGCTACTCCATCACCTCCGGCTACAGCTGGCACTGGAT<br>CCGGCAGCACCCCGGCAAGGGCCTGGAATGGATGGCC<br>CACATCCACTCCTCCGGCTCCACCAACTACAACCCCAGC<br>CTGAAGTCCAGAATCACCATCAGCCGGGACACCTCCAA<br>GAACCAGTTCTCCCTGAAGCTGTCCTCCGTGACCGCCG<br>CTGACACCGCCGTGTACTACTGTGCCAGAGGCGGCGT<br>GCAGGCCTTCGCTTATTGGGGCCAGGGCACCCTGGTG<br>ACAGTGTCCTCC |
| SEQ ID NO: 514 | Heavy Chain (DAPA mutations underlined) | DVQLQESGPGLVKPSQTLSLTCTVSGYSITSGYSWHWIR<br>QHPGKGLEWMAHIHSSGSTNYNPSLKSRITISRDTSKNQ<br>FSLKLSSVTAADTAVYYCARGGVQAFAYWGQGTLVTVSS<br>ASTKGPSVFPLAPSSKSTSGGTAALGCLVKDYFPEPVTVS<br>WNSGALTSGVHTFPAVLQSSGLYSLSSVVTVPSSSLGTQT<br>YICNVNHKPSNTKVDKRVEPKSCDKTHTCPPCPAPELLGG<br>PSVFLFPPKPKDTLMISRTPEVTCVVVaVSHEDPEVKFNW<br>YVDGVEVHNAKTKPREEQYNSTYRVVSVLTVLHQDWLN<br>GKEYKCKVSNKALaAPIEKTISKAKGQPREPQVYTLPPSRE<br>EMTKNQVSLTCLVKGFYPSDIAVEWESNGQPENNYKTTP<br>PVLDSDGSFFLYSKLTVDKSRWQQGNVFSCSVMHEALH<br>NHYTQKSLSLSPGK |
| SEQ ID NO: 515 | DNA Heavy Chain | GACGTGCAGCTGCAGGAATCGGCCCTGGCCTGGTGA<br>AACCCTCCCAGACCCTGTCCCTGACCTGCACCGTGTCC<br>GGCTACTCCATCACCTCCGGCTACAGCTGGCACTGGAT<br>CCGGCAGCACCCCGGCAAGGGCCTGGAATGGATGGCC |

TABLE 4-continued

Amino Acid and Nucleotide Sequence Information for Hybridomas and Humanized Anti-CCR7 Antibodies

|  |  |  |
|---|---|---|
|  |  | CACATCCACTCCTCCGGCTCCACCAACTACAACCCCAGC
CTGAAGTCCAGAATCACCATCAGCCGGGACACCTCCAA
GAACCAGTTCTCCCTGAAGCTGTCCTCCGTGACCGCCG
CTGACACCGCCGTGTACTACTGTGCCAGAGGCGGCGT
GCAGGCCTTCGCTTATTGGGGCCAGGGCACCCTGGTG
ACAGTGTCCTCCGCTAGCACCAAGGGCCCAAGTGTGTT
TCCCCTGGCCCCCAGCAGCAAGTCTACTTCCGGCGGAA
CTGCTGCCCTGGGTTGCCTGGTGAAGGACTACTTCCCC
GAGCCCGTGACAGTGTCCTGGAACTCTGGGGCTCTGA
CTTCCGGCGTGCACACCTTCCCCGCCGTGCTGCAGAGC
AGCGGCCTGTACAGCCTGAGCAGCGTGGTGACAGTGC
CCTCCAGCTCTCTGGGAACCCAGACCTATATCTGCAAC
GTGAACCACAAGCCCAGCAACACCAAGGTGGACAAGA
GAGTGGAGCCCAAGAGCTGCGACAAGACCCACACCTG
CCCCCCCTGCCCAGCTCCAGAACTGCTGGGAGGGCCTT
CCGTGTTCCTGTTCCCCCCCAAGCCCAAGGACACCCTG
ATGATCAGCAGGACCCCCGAGGTGACCTGCGTGGTGG
TGGCCGTGTCCCACGAGGACCCAGAGGTGAAGTTCAA
CTGGTACGTGGACGGCGTGGAGGTGCACAACGCCAAG
ACCAAGCCCAGAGAGGAGCAGTACAACAGCACCTACA
GGGTGGTGTCCGTGCTGACCGTGCTGCACCAGGACTG
GCTGAACGGCAAGGAATACAAGTGCAAAGTCTCCAAC
AAGGCCCTGGCTGCCCCAATCGAAAAGACAATCAGCA
AGGCCAAGGGCCAGCCACGGGAGCCCCAGGTGTACAC
CCTGCCCCCAGCCGGGAGGAGATGACCAAGAACCAG
GTGTCCCTGACCTGTCTGGTGAAGGGCTTCTACCCCAG
CGATATCGCCGTGGAGTGGGAGAGCAACGGCCAGCCC
GAGAACAACTACAAGACCACCCCCCCAGTGCTGGACA
GCGACGGCAGCTTCTTCCTGTACAGCAAGCTGACCGTG
GACAAGTCCAGGTGGCAGCAGGGCAACGTGTTCAGCT
GCAGCGTGATGCACGAGGCCCTGCACAACCACTACAC
CCAGAAGTCCCTGAGCCTGAGCCCCGGCAAG |
| SEQ ID NO: 516 | LCDR1 (Combined) | SASSSVIYMH |
| SEQ ID NO: 517 | LCDR2 (Combined) | DTSKLAS |
| SEQ ID NO: 518 | LCDR3 (Combined) | QQWSSNPLT |
| SEQ ID NO: 519 | LCDR1 (Kabat) | SASSSVIYMH |
| SEQ ID NO: 520 | LCDR2 (Kabat) | DTSKLAS |
| SEQ ID NO: 521 | LCDR3 (Kabat) | QQWSSNPLT |
| SEQ ID NO: 522 | LCDR1 (Chothia) | SSSVIY |
| SEQ ID NO: 523 | LCDR2 (Chothia) | DTS |
| SEQ ID NO: 524 | LCDR3 (Chothia) | WSSNPL |
| SEQ ID NO: 525 | LCDR1 (IMGT) | SSVIY |
| SEQ ID NO: 526 | LCDR2 (IMGT) | DTS |
| SEQ ID NO: 527 | LCDR3 (IMGT) | QQWSSNPLT |
| SEQ ID NO: 528 | VL | EIVLTQSPATLSASPGERVTMSCSASSSVIYMHWYQQKP
GQAPRRWIYDTSKLASGVPARFSGSGSGTDYTLTISSMEP
EDAAVYYCQQWSSNPLTFGQGTKLEIK |
| SEQ ID NO: 529 | DNA VL | GAGATCGTGCTGACCCAGTCCCCTGCCACCCTGTCTGC
TAGCCCTGGCGAGCGCGTGACAATGTCCTGCTCCGCCT
CCTCCTCCGTGATCTACATGCACTGGTATCAGCAGAAG
CCCGGCCAGGCCCCTCGGCGGTGGATCTACGATACCTC
CAAGCTGGCCTCCGGCGTGCCCGCCAGATTCTCCGGCT
CTGGCTCTGGCACCGACTACACCCTGACCATCTCCAGC
ATGGAACCCGAGGACGCCGCCGTGTACTACTGCCAGC
AGTGGTCCTCCAACCCCCTGACCTTCGGCCAGGGCACC
AAGCTGGAAATCAAG |
| SEQ ID NO: 530 | Light Chain | EIVLTQSPATLSASPGERVTMSCSASSSVIYMHWYQQKP
GQAPRRWIYDTSKLASGVPARFSGSGSGTDYTLTISSMEP
EDAAVYYCQQWSSNPLTFGQGTKLEIKRTVAAPSVFIFPP
SDEQLKSGTASVVCLLNNFYPREAKVQWKVDNALQSGN
SQESVTEQDSKDSTYSLSSTLTLSKADYEKHKVYACEVTH
QGLSSPVTKSFNRGEC |
| SEQ ID NO: 531 | DNA Light Chain | GAGATCGTGCTGACCCAGTCCCCTGCCACCCTGTCTGC
TAGCCCTGGCGAGCGCGTGACAATGTCCTGCTCCGCCT
CCTCCTCCGTGATCTACATGCACTGGTATCAGCAGAAG |

TABLE 4-continued

Amino Acid and Nucleotide Sequence Information for Hybridomas and Humanized Anti-CCR7 Antibodies

```
CCCGGCCAGGCCCCTCGGCGGTGGATCTACGATACCTC
CAAGCTGGCCTCCGGCGTGCCCGCCAGATTCTCCGGCT
CTGGCTCTGGCACCGACTACACCCTGACCATCTCCAGC
ATGGAACCCGAGGACGCCGCCGTGTACTACTGCCAGC
AGTGGTCCTCCAACCCCCTGACCTTCGGCCAGGGCACC
AAGCTGGAAATCAAGCGTACGGTGGCCGCTCCCAGCG
TGTTCATCTTCCCCCCCAGCGACGAGCAGCTGAAGAGT
GGCACCGCCAGCGTGGTGTGCCTGCTGAACAACTTCTA
CCCCCGGGAGGCCAAGGTGCAGTGGAAGGTGGACAA
CGCCCTGCAGAGCGGCAACAGCCAGGAGAGCGTCACC
GAGCAGGACAGCAAGGACTCCACCTACAGCCTGAGCA
GCACCCTGACCCTGAGCAAGGCCGACTACGAGAAGCA
TAAGGTGTACGCCTGCGAGGTGACCCACCAGGGCCTG
TCCAGCCCCGTGACCAAGAGCTTCAACAGGGGCGAGT
GC
```

Humanized 121G12 higG1 DAPA

| SEQ ID NO: 532 | HCDR1 (Combined) | GFTFSTYAMS |
| SEQ ID NO: 533 | HCDR2 (Combined) | TISDAGSYSYYPDNVKG |
| SEQ ID NO: 534 | HCDR3 (Combined) | RGSRYEEYYVMDY |
| SEQ ID NO: 535 | HCDR1 (Kabat) | TYAMS |
| SEQ ID NO: 536 | HCDR2 (Kabat) | TISDAGSYSYYPDNVKG |
| SEQ ID NO: 537 | HCDR3 (Kabat) | RGSRYEEYYVMDY |
| SEQ ID NO: 538 | HCDR1 (Chothia) | GFTFSTY |
| SEQ ID NO: 539 | HCDR2 (Chothia) | SDAGSY |
| SEQ ID NO: 540 | HCDR3 (Chothia) | RGSRYEEYYVMDY |
| SEQ ID NO: 541 | HCDR1 (IMGT) | GFTFSTYA |
| SEQ ID NO: 542 | HCDR2 (IMGT) | ISDAGSYS |
| SEQ ID NO: 543 | HCDR3 (IMGT) | ARRGSRYEEYYVMDY |
| SEQ ID NO: 544 | VH | EVQLVESGGGLVKPGGSLRLSCAASGFTFSTYAMSWVRQ APGKGLEWVATISDAGSYSYYPDNVKGRFTISRDNAKNSL YLQMNSLRAEDTAVYYCARRGSRYEEYYVMDYWGQGT TVTVSS |
| SEQ ID NO: 545 | DNA VH | GAGGTGCAGCTGGTGGAATCTGGCGGAGGCCTGGTG AAACCCGGCGGATCCCTGAGACTGTCCTGCGCCGCCTC CGGCTTCACCTTCTCCACCTACGCCATGTCCTGGGTGC GGCAGGCTCCCGGCAAGGGCCTGGAATGGGTGGCCA CCATCTCCGACGCCGGCTCCTACTCCTACTACCCCGACA ACGTGAAGGGCAGATTCACCATCAGCCGGGACAACGC CAAGAACTCCCTGTACCTGCAGATGAACTCCCTGCGGG CCGAGGACACCGCCGTGTACTACTGTGCCAGACGGGG CTCCAGATACGAAGAGTACTACGTGATGGACTATTGG GGCCAGGGCACCACCGTGACAGTGTCCTCC |
| SEQ ID NO: 546 | Heavy Chain (DAPA mutations underlined) | EVQLVESGGGLVKPGGSLRLSCAASGFTFSTYAMSWVRQ APGKGLEWVATISDAGSYSYYPDNVKGRFTISRDNAKNSL YLQMNSLRAEDTAVYYCARRGSRYEEYYVMDYWGQGT TVTVSSASTKGPSVFPLAPSSKSTSGGTAALGCLVKDYFPE PVTVSWNSGALTSGVHTFPAVLQSSGLYSLSSVVTVPSSS LGTQTYICNVNHKPSNTKVDKRVEPKSCDKTHTCPPCPA PELLGGPSVFLFPPKPKDTLMISRTPEVTCVVVaVSHEDPE VKFNWYVDGVEVHNAKTKPREEQYNSTYRVVSVLTVLH QDWLNGKEYKCKVSNKALaAPIEKTISKAKGQPREPQVY TLPPSREEMTKNQVSLTCLVKGFYPSDIAVEWESNGQPE NNYKTTPPVLDSDGSFFLYSKLTVDKSRWQQGNVFSCSV MHEALHNHYTQKSLSLSPGK |
| SEQ ID NO: 547 | DNA Heavy Chain | GAGGTGCAGCTGGTGGAATCTGGCGGAGGCCTGGTG AAACCCGGCGGATCCCTGAGACTGTCCTGCGCCGCCTC CGGCTTCACCTTCTCCACCTACGCCATGTCCTGGGTGC GGCAGGCTCCCGGCAAGGGCCTGGAATGGGTGGCCA CCATCTCCGACGCCGGCTCCTACTCCTACTACCCCGACA ACGTGAAGGGCAGATTCACCATCAGCCGGGACAACGC CAAGAACTCCCTGTACCTGCAGATGAACTCCCTGCGGG CCGAGGACACCGCCGTGTACTACTGTGCCAGACGGGG CTCCAGATACGAAGAGTACTACGTGATGGACTATTGG |

TABLE 4-continued

Amino Acid and Nucleotide Sequence Information for Hybridomas and Humanized Anti-CCR7 Antibodies

|  |  |  |
|---|---|---|
|  |  | GGCCAGGGCACCACCGTGACAGTGTCCTCCGCTAGCA<br>CCAAGGGCCCAAGTGTGTTTCCCCTGGCCCCCAGCAGC<br>AAGTCTACTTCCGGCGGAACTGCTGCCCTGGGTTGCCT<br>GGTGAAGGACTACTTCCCCGAGCCCGTGACAGTGTCCT<br>GGAACTCTGGGGCTCTGACTTCCGGCGTGCACACCTTC<br>CCCGCCGTGCTGCAGAGCAGCGGCCTGTACAGCCTGA<br>GCAGCGTGGTGACAGTGCCCTCCAGCTCTCTGGGAAC<br>CCAGACCTATATCTGCAACGTGAACCACAAGCCCAGCA<br>ACACCAAGGTGGACAAGAGAGTGGAGCCCAAGAGCT<br>GCGACAAGACCCACACCTGCCCCCCCTGCCCAGCTCCA<br>GAACTGCTGGGAGGGCCTTCCGTGTTCCTGTTCCCCCC<br>CAAGCCCAAGGACACCCTGATGATCAGCAGGACCCCC<br>GAGGTGACCTGCGTGGTGGTGGCCGTGTCCCACGAGG<br>ACCCAGAGGTGAAGTTCAACTGGTACGTGGACGGCGT<br>GGAGGTGCACAACGCCAAGACCAAGCCCAGAGAGGA<br>GCAGTACAACAGCACCTACAGGGTGGTGTCCGTGCTG<br>ACCGTGCTGCACCAGGACTGGCTGAACGGCAAAGAAT<br>ACAAGTGCAAAGTCTCCAACAAGGCCCTGGCTGCCCCA<br>ATCGAAAAGACAATCAGCAAGGCCAAGGGCCAGCCAC<br>GGGAGCCCCAGGTGTACACCCTGCCCCCCAGCCGGGA<br>GGAGATGACCAAGAACCAGGTGTCCCTGACCTGTCTG<br>GTGAAGGGCTTCTACCCCAGCGATATCGCCGTGGAGT<br>GGGAGAGCAACGGCCAGCCCGAGAACAACTACAAGA<br>CCACCCCCCCAGTGCTGGACAGCGACGGCAGCTTCTTC<br>CTGTACAGCAAGCTGACCGTGGACAAGTCCAGGTG GC<br>AGCAGGGCAACGTGTTCAGCTGCAGCGTGATGCACGA<br>GGCCCTGCACAACCACTACACCCAGAAGTCCCTGAGCC<br>TGAGCCCCGGCAAG |
| SEQ ID NO: 548 | LCDR1<br>(Combined) | RASQSISNNLH |
| SEQ ID NO: 549 | LCDR2<br>(Combined) | YASQSIS |
| SEQ ID NO: 550 | LCDR3<br>(Combined) | QQSSSWLT |
| SEQ ID NO: 551 | LCDR1<br>(Kabat) | RASQSISNNLH |
| SEQ ID NO: 552 | LCDR2<br>(Kabat) | YASQSIS |
| SEQ ID NO: 553 | LCDR3<br>(Kabat) | QQSSSWLT |
| SEQ ID NO: 554 | LCDR1<br>(Chothia) | SQSISNN |
| SEQ ID NO: 555 | LCDR2<br>(Chothia) | YAS |
| SEQ ID NO: 556 | LCDR3<br>(Chothia) | SSSWL |
| SEQ ID NO: 557 | LCDR1<br>(IMGT) | QSISNN |
| SEQ ID NO: 558 | LCDR2<br>(IMGT) | YAS |
| SEQ ID NO: 559 | LCDR3<br>(IMGT) | QQSSSWLT |
| SEQ ID NO: 560 | VL | EIVLTQSPATLSVSPGERVTLSCRASQSISNNLHWYQQKP<br>GQAPRLLIKYASQSISGIPARFSGSGSGTDFTLTISSVEPED<br>FGVYFCQQSSSWLTFGQGTKLEIK |
| SEQ ID NO: 561 | DNA VL | GAGATCGTGCTGACCCAGTCCCCTGCCACCCTGTCCGT<br>GTCTCCCGGCGAGAGAGTGACCCTGTCCTGCCGGGCC<br>TCCCAGTCCATCTCCAACAACCTGCACTGGTATCAGCA<br>GAAGCCCGGCCAGGCCCCTCGGCTGCTGATTAAGTAC<br>GCCTCCCAGAGCATCTCCGGCATCCCTGCCAGATTCTC<br>CGGCTCCGGCAGCGGCACCGACTTCACCCTGACCATCT<br>CCAGCGTGGAACCCGAGGACTTCGGCGTGTACTTCTGC<br>CAGCAGTCCTCATCCTGGCTGACCTTCGGCCAGGGCAC<br>CAAGCTGGAAATCAAG |
| SEQ ID NO: 562 | Light Chain | EIVLTQSPATLSVSPGERVTLSCRASQSISNNLHWYQQKP<br>GQAPRLLIKYASQSISGIPARFSGSGSGTDFTLTISSVEPED<br>FGVYFCQQSSSWLTFGQGTKLEIKRTVAAPSVFIFPPSDE<br>QLKSGTASVVCLLNNFYPREAKVQWKVDNALQSGNSQE<br>SVTEQDSKDSTYSLSSTLTLSKADYEKHKVYACEVTHQGLS<br>SPVTKSFNRGEC |
| SEQ ID NO: 563 | DNA Light<br>Chain | GAGATCGTGCTGACCCAGTCCCCTGCCACCCTGTCCGT<br>GTCTCCCGGCGAGAGAGTGACCCTGTCCTGCCGGGCC<br>TCCCAGTCCATCTCCAACAACCTGCACTGGTATCAGCA<br>GAAGCCCGGCCAGGCCCCTCGGCTGCTGATTAAGTAC<br>GCCTCCCAGAGCATCTCCGGCATCCCTGCCAGATTCTC<br>CGGCTCCGGCAGCGGCACCGACTTCACCCTGACCATCT<br>CCAGCGTGGAACCCGAGGACTTCGGCGTGTACTTCTGC |

TABLE 4-continued

Amino Acid and Nucleotide Sequence Information for Hybridomas and Humanized Anti-CCR7 Antibodies

|  |  |  |
|---|---|---|
|  |  | CAGCAGTCCTCATCCTGGCTGACCTTCGGCCAGGGCAC<br>CAAGCTGGAAATCAAGCGTACGGTGGCCGCTCCCAGC<br>GTGTTCATCTTCCCCCCCAGCGACGAGCAGCTGAAGAG<br>TGGCACCGCCAGCGTGGTGTGCCTGCTGAACAACTTCT<br>ACCCCCGGGAGGCCAAGGTGCAGTGGAAGGTGGACA<br>ACGCCCTGCAGAGCGGCAACAGCCAGGAGAGCGTCAC<br>CGAGCAGGACAGCAAGGACTCCACCTACAGCCTGAGC<br>AGCACCCTGACCCTGAGCAAGGCCGACTACGAGAAGC<br>ATAAGGTGTACGCCTGCGAGGTGACCCACCAGGGCCT<br>GTCCAGCCCCGTGACCAAGAGCTTCAACAGGGGCGAG<br>TGC |

Humanized 506E15 hIgG1 DAPA

| SEQ ID NO: 564 | HCDR1 (Combined) | GFTFSSYAMS |
|---|---|---|
| SEQ ID NO: 565 | HCDR2 (Combined) | TISSGGSFTYYPDSVKG |
| SEQ ID NO: 566 | HCDR3 (Combined) | RASTVVGTDFDV |
| SEQ ID NO: 567 | HCDR1 (Kabat) | SYAMS |
| SEQ ID NO: 568 | HCDR2 (Kabat) | TISSGGSFTYYPDSVKG |
| SEQ ID NO: 569 | HCDR3 (Kabat) | RASTVVGTDFDV |
| SEQ ID NO: 570 | HCDR1 (Chothia) | GFTFSSY |
| SEQ ID NO: 571 | HCDR2 (Chothia) | SSGGSF |
| SEQ ID NO: 572 | HCDR3 (Chothia) | RASTVVGTDFDV |
| SEQ ID NO: 573 | HCDR1 (IMGT) | GFTFSSYA |
| SEQ ID NO: 574 | HCDR2 (IMGT) | ISSGGSFT |
| SEQ ID NO: 575 | HCDR3 (IMGT) | ARRASTVVGTDFDV |
| SEQ ID NO: 576 | VH | EVQLVESGGGLVKPGGSLRLSCAASGFTFSSYAMSWIRQ<br>APGKGLEWVATISSGGSFTYYPDSVKGRFTISRDNAKNSL<br>YLQMNSLRAEDTAVYYCARRASTVVGTDFDVWGQGTT<br>VTVSS |
| SEQ ID NO: 577 | DNA VH | GAGGTGCAGCTGGTGGAATCTGGCGGAGGCCTGGTG<br>AAACCCGGCGGATCCCTGAGACTGTCCTGCGCCGCCTC<br>CGGCTTCACCTTCTCCAGCTACGCCATGTCCTGGATCCG<br>GCAGGCTCCCGGCAAGGGCCTGGAATGGGTGGCCACC<br>ATCTCCTCCGGCGGCAGCTTCACCTACTACCCCGACAG<br>CGTGAAGGGCAGATTCACCATCAGCCGGGACAACGCC<br>AAGAACTCCCTGTACCTGCAGATGAACTCCCTGCGGGC<br>CGAGGACACCGCCGTGTACTACTGTGCCAGACGGGCC<br>TCCACCGTCGTGGGAACCGACTTCGATGTGTGGGGCC<br>AGGGCACCACCGTGACAGTGTCCTCC |
| SEQ ID NO: 578 | Heavy Chain (DAPA mutations underlined) | EVQLVESGGGLVKPGGSLRLSCAASGFTFSSYAMSWIRQ<br>APGKGLEWVATISSGGSFTYYPDSVKGRFTISRDNAKNSL<br>YLQMNSLRAEDTAVYYCARRASTVVGTDFDVWGQGTT<br>VTVSSASTKGPSVFPLAPSSKSTSGGTAALGCLVKDYFPEP<br>VTVSWNSGALTSGVHTFPAVLQSSGLYSLSSVVTVPSSSL<br>GTQTYICNVNHKPSNTKVDKRVEPKSCDKTHTCPPCPAP<br>ELLGGPSVFLFPPKPKDTLMISRTPEVTCVVV<u>a</u>VSHEDPEV<br>KFNWYVDGVEVHNAKTKPREEQYNSTYRVVSVLTVLHQ<br>DWLNGKEYKCKVSNKAL<u>a</u>APIEKTISKAKGQPREPQVYTL<br>PPSREEMTKNQVSLTCLVKGFYPSDIAVEWESNGQPENN<br>YKTTPPVLDSDGSFFLYSKLTVDKSRWQQGNVFSCSVMH<br>EALHNHYTQKSLSLSPGK |
| SEQ ID NO: 579 | DNA Heavy Chain | GAGGTGCAGCTGGTGGAATCTGGCGGAGGCCTGGTG<br>AAACCCGGCGGATCCCTGAGACTGTCCTGCGCCGCCTC<br>CGGCTTCACCTTCTCCAGCTACGCCATGTCCTGGATCCG<br>GCAGGCTCCCGGCAAGGGCCTGGAATGGGTGGCCACC<br>ATCTCCTCCGGCGGCAGCTTCACCTACTACCCCGACAG<br>CGTGAAGGGCAGATTCACCATCAGCCGGGACAACGCC<br>AAGAACTCCCTGTACCTGCAGATGAACTCCCTGCGGGC<br>CGAGGACACCGCCGTGTACTACTGTGCCAGACGGGCC<br>TCCACCGTCGTGGGAACCGACTTCGATGTGTGGGGCC<br>AGGGCACCACCGTGACAGTGTCCTCCGCTAGCACCAA<br>GGGCCCAAGTGTGTTTCCCCTGGCCCCCAGCAGCAAGT<br>CTACTTCCGGCGGAACTGCTGCCCTGGGTTGCCTGGTG<br>AAGGACTACTTCCCCGAGCCCGTGACAGTGTCCTGGAA |

TABLE 4-continued

Amino Acid and Nucleotide Sequence Information for Hybridomas and Humanized Anti-CCR7 Antibodies

|  |  |  |
|---|---|---|
|  |  | CTCTGGGGCTCTGACTTCCGGCGTGCACACCTTCCCCG |
|  |  | CCGTGCTGCAGAGCAGCGGCCTGTACAGCCTGAGCAG |
|  |  | CGTGGTGACAGTGCCCTCCAGCTCTCTGGGAACCCAGA |
|  |  | CCTATATCTGCAACGTGAACCACAAGCCCAGCAACACC |
|  |  | AAGGTGGACAAGAGAGTGGAGCCCAAGAGCTGCGAC |
|  |  | AAGACCCACACCTGCCCCCCCTGCCCAGCTCCAGAACT |
|  |  | GCTGGGAGGGCCTTCCGTGTTCCTGTTCCCCCCCAAGC |
|  |  | CCAAGGACACCCTGATGATCAGCAGGACCCCCGAGGT |
|  |  | GACCTGCGTGGTGGTGGCCGTGTCCCACGAGGACCCA |
|  |  | GAGGTGAAGTTCAACTGGTACGTGGACGGCGTGGAG |
|  |  | GTGCACAACGCCAAGACCAAGCCCAGAGAGGAGCAGT |
|  |  | ACAACAGCACCTACAGGGTGGTGTCCGTGCTGACCGT |
|  |  | GCTGCACCAGGACTGGCTGAACGGCAAAGAATACAAG |
|  |  | TGCAAAGTCTCCAACAAGGCCCTGGCTGCCCCAATCGA |
|  |  | AAAGACAATCAGCAAGGCCAAGGGCCAGCCACGGGA |
|  |  | GCCCCAGGTGTACACCCTGCCCCCCAGCCGGGAGGAG |
|  |  | ATGACCAAGAACCAGGTGTCCCTGACCTGTCTGGTGAA |
|  |  | GGGCTTCTACCCCAGCGATATCGCCGTGGAGTGGGAG |
|  |  | AGCAACGGCCAGCCCGAGAACAACTACAAGACCACCC |
|  |  | CCCCAGTGCTGGACAGCGACGGCAGCTTCTTCCTGTAC |
|  |  | AGCAAGCTGACCGTGGACAAGTCCAGGTGGCAGCAG |
|  |  | GGCAACGTGTTCAGCTGCAGCGTGATGCACGAGGCCC |
|  |  | TGCACAACCACTACACCCAGAAGTCCCTGAGCCTGAGC |
|  |  | CCCGGCAAG |
| SEQ ID NO: 580 | LCDR1 (Combined) | RASQDIGSSLN |
| SEQ ID NO: 581 | LCD R2 (Combined) | ATSSLDS |
| SEQ ID NO: 582 | LCD R3 (Combined) | LQYASSPPT |
| SEQ ID NO: 583 | LCDR1 (Kabat) | RASQDIGSSLN |
| SEQ ID NO: 584 | LCD R2 (Kabat) | ATSSLDS |
| SEQ ID NO: 585 | LCD R3 (Kabat) | LQYASSPPT |
| SEQ ID NO: 586 | LCDR1 (Chothia) | SQDIGSS |
| SEQ ID NO: 587 | LCD R2 (Chothia) | ATS |
| SEQ ID NO: 588 | LCD R3 (Chothia) | YASSPP |
| SEQ ID NO: 589 | LCDR1 (IMGT) | QDIGSS |
| SEQ ID NO: 590 | LCD R2 (IMGT) | ATS |
| SEQ ID NO: 591 | LCD R3 (IMGT) | LQYASSPPT |
| SEQ ID NO: 592 | VL | DIQMTQSPSSLSASVGDRVTLTCRASQDIGSSLNWLQQK PGKAIKRLIYATSSLDSGVPSRFSGSRSGTDYTLTISSLQPE DFVVYYCLQYASSPPTFGGGTKLEIK |
| SEQ ID NO: 593 | DNA VL | GACATCCAGATGACCCAGTCCCCCTCCAGCCTGTCCGC CTCCGTGGGCGATAGAGTGACCCTGACCTGCCGGGCC TCCCAGGACATCGGCTCCTCCCTGAACTGGCTGCAGCA GAAGCCCGGCAAGGCCATCAAGCGGCTGATCTACGCC ACCTCCTCCCTGGACTCCGGCGTGCCCTCCCGGTTCTCC GGCTCTAGATCCGGCACCGACTACACCCTGACCATCTC CAGCCTGCAGCCCGAGGACTTCGTGGTGTACTACTGCC TGCAGTACGCCTCCAGCCCCCCCACCTTTGGCGGAGGC ACCAAGCTGGAAATCAAG |
| SEQ ID NO: 594 | Light Chain | DIQMTQSPSSLSASVGDRVTLTCRASQDIGSSLNWLQQK PGKAIKRLIYATSSLDSGVPSRFSGSRSGTDYTLTISSLQPE DFVVYYCLQYASSPPTFGGGTKLEIKRTVAAPSVFIFPPSD EQLKSGTASVVCLLNNFYPREAKVQWKVDNALQSGNSQ ESVTEQDSKDSTYSLSSTLTLSKADYEKHKVYACEVTHQGL SSPVTKSFNRGEC |
| SEQ ID NO: 595 | DNA Light Chain | GACATCCAGATGACCCAGTCCCCCTCCAGCCTGTCCGC CTCCGTGGGCGATAGAGTGACCCTGACCTGCCGGGCC TCCCAGGACATCGGCTCCTCCCTGAACTGGCTGCAGCA GAAGCCCGGCAAGGCCATCAAGCGGCTGATCTACGCC ACCTCCTCCCTGGACTCCGGCGTGCCCTCCCGGTTCTCC GGCTCTAGATCCGGCACCGACTACACCCTGACCATCTC CAGCCTGCAGCCCGAGGACTTCGTGGTGTACTACTGCC TGCAGTACGCCTCCAGCCCCCCCACCTTTGGCGGAGGC ACCAAGCTGGAAATCAAGCGTACGGTGGCCGCTCCCA GCGTGTTCATCTTCCCCCCCAGCGACGAGAGCAGCTGAAG AGTGGCACCGCCAGCGTGGTGTGCCTGCTGAACAACT |

TABLE 4-continued

Amino Acid and Nucleotide Sequence Information for Hybridomas and Humanized Anti-CCR7 Antibodies

```
                      TCTACCCCCGGGAGGCCAAGGTGCAGTGGAAGGTGGA
                      CAACGCCCTGCAGAGCGGCAACAGCCAGGAGAGCGTC
                      ACCGAGCAGGACAGCAAGGACTCCACCTACAGCCTGA
                      GCAGCACCCTGACCCTGAGCAAGGCCGACTACGAGAA
                      GCATAAGGTGTACGCCTGCGAGGTGACCCACCAGGGC
                      CTGTCCAGCCCCGTGACCAAGAGCTTCAACAGGGGCG
                      AGTGC
```

Humanized 684E12 hIgG1 DAPA CysMab

| SEQ ID NO: 596 | HCDR1 (Combined) | GFTFSNFAMS |
| --- | --- | --- |
| SEQ ID NO: 597 | HCDR2 (Combined) | TISTGGTYTYYPDSVKG |
| SEQ ID NO: 598 | HCDR3 (Combined) | RGYSGVDK |
| SEQ ID NO: 599 | HCDR1 (Kabat) | SNFAMS |
| SEQ ID NO: 600 | HCDR2 (Kabat) | TISTGGTYTYYPDSVKG |
| SEQ ID NO: 601 | HCDR3 (Kabat) | RGYSGVDK |
| SEQ ID NO: 602 | HCDR1 (Chothia) | GFTFSNF |
| SEQ ID NO: 603 | HCDR2 (Chothia) | STGGTY |
| SEQ ID NO: 604 | HCDR3 (Chothia) | RGYSGVDK |
| SEQ ID NO: 605 | HCDR1 (IMGT) | GFTFSNFA |
| SEQ ID NO: 606 | HCDR2 (IMGT) | ISTGGTYT |
| SEQ ID NO: 607 | HCDR3 (IMGT) | TRRGYSGVDK |
| SEQ ID NO: 608 | VH | EVQLVESGGGLVKPGGSLRLSCAASGFTFSNFAMSWVRQAPG KGLEWVSTISTGGTYTYYPDSVKGRFTISRDNAKNSLYLQMNSL RAEDTAVYYCARRGYSGVDKWGQGTTVTVSS |
| SEQ ID NO: 609 | DNA VH | GAGGTGCAGCTGGTGGAATCTGGCGGAGGCCTGGTGAAAC CCGGCGGATCCCTGAGACTGTCCTGCGCCGCCTCCGGCTTC ACCTTCTCCAACTTCGCCATGTCCTGGGTGCGGCAGGCTCCC GGCAAGGGCCTGGAATGGGTGTCCACCATCTCCACCGGCG GCACCTACACCTACTACCCCGACAGCGTGAAGGGCAGATTC ACCATCAGCCGGGACAACGCCAAGAACTCCCTGTACCTGCA GATGAACTCCCTGCGGGCCGAGGACACCGCCGTGTACTACT GTGCCAGACGGGGCTACTCAGGCGTGGACAAATGGGGCCA GGGCACCACCGTGACAGTGTCCTCC |
| SEQ ID NO: 610 | Heavy Chain (DAPA, CysMab mutations underlined) | EVQLVESGGGLVKPGGSLRLSCAASGFTFSNFAMSWVRQAPG KGLEWVSTISTGGTYTYYPDSVKGRFTISRDNAKNSLYLQMNSL RAEDTAVYYCARRGYSGVDKWGQGTTVTVSSASTKGPSVFPL APSSKSTSGGTAALGCLVKDYFPCPVTVSWNSGALTSGVHTFP AVLQSSGLYSLSSVVTVPSSSLGTQTYICNVNHKPSNTKVDKRV EPKSCDKTHTCPPCPAPELLGGPSVFLFPPKPKDTLMISRTPEVT CVVVAVSHEDPEVKFNWYVDGVEVHNAKTKPREEQYNSTYR VVSVLTVLHQDWLNGKEYKCKVSNKALAAPIEKTISKAKGQPR EPQVYTLPPSREEMTKNQVSLTCLVKGFYPCDIAVEWESNGQP ENNYKTTPPVLDSDGSFFLYSKLTVDKSRWQQGNVFSCSVMH EALHNHYTQKSLSLSPGK |
| SEQ ID NO: 611 | DNA Heavy Chain | GAGGTGCAGCTGGTGGAATCTGGCGGAGGCCTGGTG AAACCCGGCGGATCCCTGAGACTGTCCTGCGCCGCCTC CGGCTTCACCTTCTCCAACTTCGCCATGTCCTGGGTGCG GCAGGCTCCCGGCAAGGGCCTGGAATGGGTGTCCACC ATCTCCACCGGCGGCACCTACACCTACTACCCCGACAG CGTGAAGGGCAGATTCACCATCAGCCGGGACAACGCC AAGAACTCCCTGTACCTGCAGATGAACTCCCTGCGGGC CGAGGACACCGCCGTGTACTACTGTGCCAGACGGGGC TACTCAGGCGTGGACAAATGGGGCCAGGGCACCACCG TGACAGTGTCCTCCgctagcaccaagggcccaagtgtgtttcccct ggccccagcagcaagtctacttccggcggaactgctgccctgggttgc ctggtgaaggactacttcccctgtcccgtgacagtgtcctggaactctgg ggctctgacttccggcgtgcacacctttccccgccgtgctgcagagcagc ggcctgtacagcctgagcagcgtggtgacagtgccctccagctctctgg gaacccagacctatatctgcaacgtgaaccacaagcccagcaacacca aggtggacaagagagtggagcccaagagctgcgacaagacccacacc tgcccccctgcccagctccagaactgctgggagggccttccgtgttcct gttccccccaagcccaaggacaccctgatgatcagcaggaccccga ggtgacctgcgtggtggtggccgtgtcccacgaggacccagaggtgaa gttcaactggtacgtggacggcgtggaggtgcacaacgccaagaccaa |

TABLE 4-continued

Amino Acid and Nucleotide Sequence Information for Hybridomas and Humanized Anti-CCR7 Antibodies

|  |  |  |
|---|---|---|
|  |  | gcccagagaggagcagtacaacagcacctacagggtggtgtccgtgct<br>gaccgtgctgcaccaggactggctgaacggcaaagaatacaagtgcaa<br>agtctccaacaaggccctggctgcccaatcgaaaagacaatcagcaa<br>ggccaagggccagccacgggagccccaggtgtacaccctgccccag<br>ccgggaggagatgaccaagaaccaggtgtccctgacctgtctggtgaa<br>gggcttctaccctgtgatatcgccgtggagtgggagcaacggccag<br>cccgagaacaactacaagaccaccccccagtgctggacagcgacggc<br>agcttcttcctgtacagcaagctgaccgtggacaagtccaggtggcagc<br>agggcaacgtgttcagctgcagcgtgatgcacgaggccctgcacaacc<br>actacacccagaagtccctgagcctgagccccggcaag |
| SEQ ID NO: 612 | LCDR1<br>(Combined) | KSGQSLLDSTGKTYLN |
| SEQ ID NO: 613 | LCDR2<br>(Combined) | LVSKLDS |
| SEQ ID NO: 614 | LCDR3<br>(Combined) | WQGTHFPQT |
| SEQ ID NO: 615 | LCDR1<br>(Kabat) | KSGQSLLDSTGKTYLN |
| SEQ ID NO: 616 | LCDR2<br>(Kabat) | LVSKLDS |
| SEQ ID NO: 617 | LCDR3<br>(Kabat) | WQGTHFPQT |
| SEQ ID NO: 618 | LCDR1<br>(Chothia) | GQSLLDSTGKTY |
| SEQ ID NO: 619 | LCDR2<br>(Chothia) | LVS |
| SEQ ID NO: 620 | LCDR3<br>(Chothia) | GTHFPQ |
| SEQ ID NO: 621 | LCDR1<br>(IMGT) | QSLLDSTGKTY |
| SEQ ID NO: 622 | LCDR2<br>(IMGT) | LVS |
| SEQ ID NO: 623 | LCDR3<br>(IMGT) | WQGTHFPQT |
| SEQ ID NO: 624 | VL | DVVMTQSPLSLPVTLGQPASISCKSGQSLLDSTGKTYLNWFLQ<br>RPGQSPRRLIYLVSKLDSGVPDRFSGSGSGTDFTLKISRVEAEDV<br>GVYYCWQGTHFPQTFGGGTKLEIK |
| SEQ ID NO: 625 | DNA VL | GACGTGGTGATGACCCAGTCCCCCCTGTCCCTGCCTGTGACC<br>CTGGGCCAGCCTGCCTCCATCTCCTGCAAGTCCGGCCAGTCC<br>CTGCTGGACTCCACTGGCAAGACCTACCTGAACTGGTTCCTG<br>CAGCGGCCTGGCCAGTCCCCTCGGCGGCTGATCTACCTGGT<br>GTCCAAGCTGGACAGCGGCGTGCCCGACAGATTCTCCGGCT<br>CTGGCTCCGGCACCGACTTCACCCTGAAGATCTCCCGGGTG<br>GAAGCCGAGGACGTGGGCGTGTACTACTGCTGGCAGGGCA<br>CCCACTTCCCCCAGACCTTCGGCGGAGGCACCAAGCTGGAA<br>ATCAAG |
| SEQ ID NO: 626 | Light Chain | DVVMTQSPLSLPVTLGQPASISCKSGQSLLDSTGKTYLNWFLQ<br>RPGQSPRRLIYLVSKLDSGVPDRFSGSGSGTDFTLKISRVEAEDV<br>GVYYCWQGTHFPQTFGGGTKLEIKRTVAAPSVFIFPPSDEQLK<br>SGTASVVCLLNNFYPREAKVQWKVDNALQSGNSQESVTEQDS<br>KDSTYSLSSTLTLSKADYEKHKVYACEVTHQGLSSPVTKSFNRGE<br>C |
| SEQ ID NO: 627 | DNA Light<br>Chain | GACGTGGTGATGACCCAGTCCCCCCTGTCCCTGCCTGTGACC<br>CTGGGCCAGCCTGCCTCCATCTCCTGCAAGTCCGGCCAGTCC<br>CTGCTGGACTCCACTGGCAAGACCTACCTGAACTGGTTCCTG<br>CAGCGGCCTGGCCAGTCCCCTCGGCGGCTGATCTACCTGGT<br>GTCCAAGCTGGACAGCGGCGTGCCCGACAGATTCTCCGGCT<br>CTGGCTCCGGCACCGACTTCACCCTGAAGATCTCCCGGGTG<br>GAAGCCGAGGACGTGGGCGTGTACTACTGCTGGCAGGGCA<br>CCCACTTCCCCCAGACCTTCGGCGGAGGCACCAAGCTGGAA<br>ATCAAGcgtacggtggccgctcccagcgtgttcatcttcccccccagcgacg<br>agcagctgaagagtggcaccgccagcgtggtgtgcctgctgaacaacttctac<br>ccccgggaggccaaggtgcagtggaaggtggacaacgccctgcagagcggc<br>aacagccaggagagcgtcacccgagcaggacagcaaggactccacctacagc<br>ctgagcagcaccctgaccctgagcaaggccgactacgagaagcataaggtgt<br>acgcctgcgaggtgacccaccagggcctgtccagcccgtgaccaagagcttc<br>aacaggggcgagtgc |

Example 2: In Vitro Assessment of Antibody Induced ADCC Activity

Capacity of candidate antibodies to mediate ADCC was assessed using a surrogate ADCC reporter assay. CCR7 and CD20 expressing JVM2 cells were used as target cells. JVM2 cells were washed and re-suspended at $8 \times 10^4$ cells/ml. Effector cells in this assay were a Jurkat cell line stably expressing CD16V158 and an NFAT dependent luciferase reporter (Jurkat-V158); expression of luciferase is a surrogate for canonical ADCC signaling through CD16. Briefly, Jurkat-V158 cells grown in suspension were spun down to remove spent media, the pellet was resuspended in assay media and adjusted to $1.6 \times 10^6$ cells/ml cells/mL. Mix equal volumes of effector and target cells to make a master mix of cells yielding a target to effector cell ratio of 1:5 or 1:20. A titration of antibody was diluted in assay media with a final top concentration of 50 ug/mL in the assay well. 12.5 uL of Ab solution was added to a 384 well round bottom plate and then 12.5 ul of the master cell mix was added. Antibody and cells were mixed well by pipetting and incubated for 4 hours at 37° C. in 5% $CO_2$. Following incubation, 15 uL of Bright Glo substrate (Promega #G7572) was added to each well and shaken for 5 min at RT at 1050 rpm. Luminescent signal was read on the Envision plate reader (Perkin Elmer).

A CD20-targeting antibody was included as a positive control, and showed substantial NFAT signaling, as measured by luciferase activity. Similarly the candidate anti-CCR7 antibodies induced significant ADCC activity (FIG. 1).

The table below summarizes representative results for the various antibody formats run in the ADCC assay using JVM2 and Jurkat-V158 cells.

TABLE 5

ADCC activity of non-humanized and humanized anti-CCR7 antibodies

|  | ADCC activity; IC50 (nM) |
|---|---|
| 121G12 non-humanized CysMab | 0.077 |
| 506E15 non-humanized CysMab | 0.131 |
| 674J13 non-humanized CysMab | 1.09 |
| 684E12 non-humanized CysMab | 2.63 |
| 121G12 humanized CysMab | Yes, but insufficient curve fitting |
| 506E15 humanized CysMab | 0.054 |
| 674J13 humanized CysMab | Yes, but insufficient curve fitting |
| CD20 control ADC | 0.132 |

The ADCC assay was run with non-humanized 506E15 antibody as a representative ADCC-capable anti-CCR7 antibody across various cell lines with a range of CCR7 receptor numbers to determine the minimal receptor density needed for ADCC activity and if there is a sufficient safety margin over normal CCR7+ T cells. The table below summarizes some of the data.

TABLE 6

ADCC activity of non-humanized 506E15 antibody

| Cell line | CCR7 receptor # | 506E15 IC50 (nM) | 506E15 (max RLU) |
|---|---|---|---|
| JVM2 | 66,500 | 0.046 | 5840 |
| MOTN-1 | 64,600 | 0.077 | 5387 |
| DEL | 62,000 | 0.074 | 6480 |
| CMLT-1 | 29,000 | 0.011 | 4400 |
| SR786 | 27,800 | 0.011 | 4067 |
| PEER | 8,700 | 0.038 | 3360 |
| ALL-SIL | 6,200 | 0.008 | 3720 |
| Jurkat V158 | 3,400 | 0.004 | 3267 |
| DND-41 | 1,700 | 0.002 | 3733 |
| Normal T cells | <1.5K | depletion in vivo | n.a. |

The data show that even very low CCR7 receptor levels comparable to CCR7 receptor levels on normal T cells were sufficient to enable significant ADCC activity. ADCC was also assessed using a co-culture viability assay of NK cells with CCR7+ cancer cells and similar findings were collected (not discussed here).

This fits the observation described below that T cell depletion was seen in vivo and found to be ADCC-mechanism based. These findings demonstrate that the ADCC modality is not suitable for CCR7 from a safety perspective. As a consequence all candidates were switched to the Fc silent (DAPA) format to improve overall on-target safety.

Figure 2:
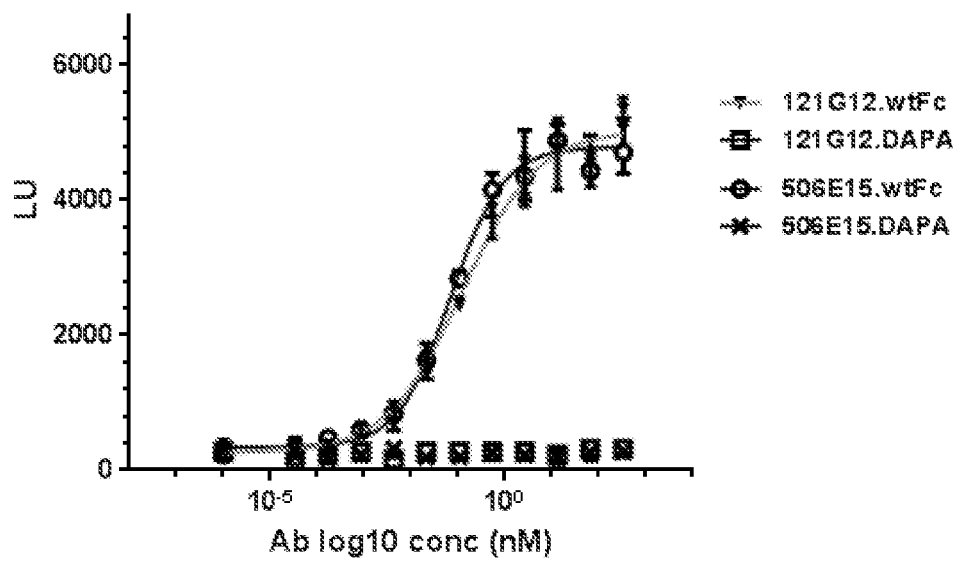
FIG. 2 depicts experimental data on in vitro ADCC activity of DAPA Fc-mutated versions of non-humanized anti-CCR7 antibodies using a surrogate ADCC reporter assay.

The ADCC in vitro reporter assay was repeated and confirmed lack of ADCC activity for the DAPA Fc-mutated versions of the non-humanized anti-CCR7 antibodies (FIG. 2).

Example 3: Biochemical Characterization of Antibodies

Affinities of Anti-CCR7 Antibodies to CCR7

The affinity of various antibodies and ADCs to CCR7 and its species orthologues was determined using FACS. Purified IgGs were titrated to determine EC50 values for binding to cell surface expressed CCR7.

For this purpose, CCR7 positive cells were harvested (adherent cells were detached with Accutase), washed twice with FACS buffer (PBS/ 3% FCS/0.02% sodium azide) and diluted to approximately $2 \times 10^6$ cells/ml in FACS buffer. All subsequent steps were done on ice to prevent internalization of the receptor. 100 µl cell suspension/well were transferred into 96-well U-bottom plates (Falcon). $2 \times 10^5$ cells/well were incubated with a serial dilution of antibody concentrations of the anti-CCR7 antibody-of-interest ranging across several logs, starting at a high of 100 nM for 60 minutes at 4° C., gently shaking. Following incubation, cells were spun down (1200 rpm, 2 min, 4° C.) and washed three times with FACS buffer. A fluorophore-conjugated anti-hFc gamma-APC (Jackson ImmunoResearch) detection antibody was added at 1:400 and samples were incubated for 1 h on ice in the dark, gently shaken. After a final wash, cells were resuspended in 100 µl of FACS buffer containing 0.2 µg/ml DAPI followed by readout on the flow cytometry machine (BD LSRFortessa Cell Analyzer; Cat #647177). Mean fluorescence intensity (MFI) of live, single cells was calculated in Flowjo 10.0.8 and exported into Graphpad Prism6 for EC50 determination.

Selectivity was assessed by measuring apparent binding affinities to isogenic cell pairs engineered to overexpress CCR7 as well as cell lines expressing CCR7 paralogs, e.g., CCR9, CCR6, CXCR4 and CCR8. All anti-CCR7 antibodies bind in a specific manner to CCR7 expressing cells only, as shown in Table 7 below.

TABLE 7

Binding of Various Anti-CCR7 Antibodies to CCR7 Expressing Cells

| Humanized CysMab (Fc Wild Type) antibody | Apparent FACS binding (at 5 ug/ml) | | | |
|---|---|---|---|---|
| | 121G12 | 506E15 | 674J13 | 684E12 |
| NIH3T3 cells | No binding | No binding | No binding | No binding |
| NIH3T3.hCCR7 | Binding | Binding | Binding | Binding |
| PF382 cells (CCR7−/CCR9+/CCR6+) | No binding | No binding | No binding | No binding |
| HEK293-CXCR4 | No binding | No binding | No binding | No binding |
| CHO-CCR8 | No binding | No binding | No binding | No binding |

In a similar experiment the antibodies were tested for cross-reactivity using engineered isogenic matched cell line sets (NIH3T3 series) and CD4+ T cells, which were purified from several PBMC batches from healthy donors as well as cynomolgus monkeys, Wistar rats and CD-1 mice. All antibodies were found to specifically bind human and cynomolgus monkey CCR7 at similar apparent affinities, as shown in Tables 8 & 9 below. Only the non-humanized 121G12 antibody is rodent cross-reactive.

TABLE 8

Cross-Reactivity of Various Non-Humanized Anti-CCR7 Antibodies

| Non-humanized CysMab antibody | Apparent FACS Affinity; EC50 (nM) | | | |
|---|---|---|---|---|
| | 121G12 | 506E15 | 674J13 | 684E12 |
| Human CD4+ T cells | 22-30 | 4.6-9.7 | 0.39-1.4 | n.d. |
| Cyno CD4+ T cells | 5.8-12 | 6.6 | 0.45 | n.d. |
| Mouse CD4+ T cells | 48-51 | No binding | No binding | n.d. |
| Rat CD4+ T cells | 18-31 | No binding | No binding | n.d. |
| NIH3T3.human CCR7 | 1.3 | n.d. | 3.6 | >30 |
| NIH3T3.cyno CCR7 | 1.3 | n.d. | n.d. | Binding |
| NIH3T3.mouse CCR7 | 2.5 | No binding | No binding | No binding |
| NIH3T3.rat CCR7 | 2.4 | No binding | No binding | No binding |
| Jeko-1 cancer cells (CCR7+) | 1.5 | n.d. | n.d. | 12 |

TABLE 9

Cross-Reactivity of Various Humanized Anti-CCR7 Antibodies

| Humanized CysMab antibody | Apparent FACS Affinity; EC50 (nM) | | | |
|---|---|---|---|---|
| | 121G12 | 506E15 | 674J13 | 684E12 |
| Human CD4+ T cells | 30-34 | 7.8-11 | 0.87-2.7 | 6.7 |
| Cyno CD4+ T cells | 12 | 7 | 0.5 | n.d. |
| NIH3T3.human CCR7 | 1 | n.d. | n.d. | n.d. |
| NIH3T3.cyno CCR7 | 0.9 | n.d. | n.d. | n.d. |

In order to determine receptor density impact on apparent affinity, and therefore the contribution avidity makes to cellular binding of antibody, FACS titration experiments were run on human CCR7 expressing cancer cell lines with varied expression levels and normal CCR7-positive PBMC-derived T cells. Receptor quantification was performed via FACS using microspheres from Bangs Laboratories as count standards and following the manufacturer's instructions. Exemplary results are shown in Table 10 below.

TABLE 10

Contribution of Avidity to Apparent Affinity in Correlation with Receptor Density

| Humanized CysMab.DAPA antibody | CCR7 Receptor density | Apparent FACS Affinity; EC50 (nM) | | | |
|---|---|---|---|---|---|
| | | 121G12 | 506E15 | 674J13 | 684E12 |
| NIH3T3.hCCR7 cells | >1,000,000 | 2.5 | 1.8 | 0.64 | n.d. |
| DEL cancer cells | ~100,000 | 1.78 | 3.09 | 0.47 | n.d. |
| Human CD4+ T cells | <2,000 | ~30 | ~10 | ~2 | ~7 |

All anti-CCR7 antibodies show substantial contribution of avidity to apparent affinity and the strength of binding decreased in correlation with receptor density. Especially 121G12 shows significantly weaker binding on low CCR7 expressing cells as represented by normal CD4+ T cells compared to indication-representative DEL cancer cells.

The relatively weak affinity of especially 121G12, which shows the strongest avidity effect among the anti-CCR7 antibodies, is optimal to utilize the receptor density difference between normal and cancer cells as a way to bias antibody binding to cancer cells.

Binding to Recombinant hCCR7 in ELISA

Binding and affinity was also assessed in an ELISA-based assay using recombinant CCR7 (Origene #TP306614). Maxisorp™ 384-well plates (Thermo Nunc) were coated with 3.5 µg/ml of recombinant CCR7 diluted in PBS. After blocking with 3% BSA (bovine serum albumin) in PBS for 1 hr at room temperature, washing plates 3× with PBS-T (0.01% Tween 20 in PBS), primary antibodies were added in a serial dilution and incubated for 1 hr at room temperature. Plates were washed again and bound antibodies were detected by incubation with 1:5000 anti-hFc gamma conjugated to horseradish peroxidase (HRP; Jackson ImmunoResearch, Cat #115-035-098) for 1 hr at room temperature followed by washing with PBS-T and afterwards addition of SureBlue Peroxidase substrate (KPL, #52-00-03) substrate. After 15 min, absorbance at 650 nM was recorded and analyzed in GraphPad Prism6.

Figure 3:
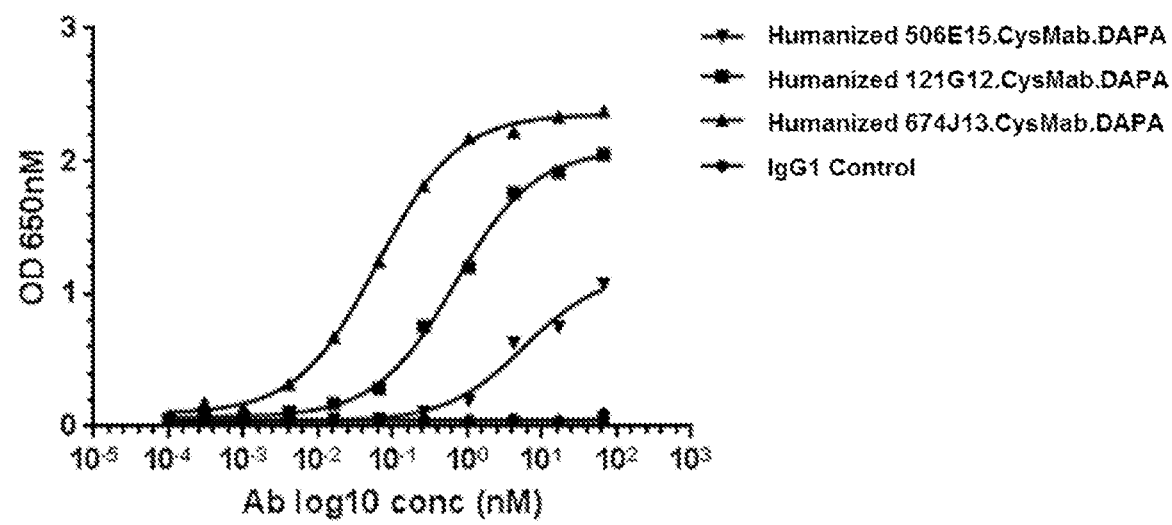
FIG. 3 depicts experimental data on binding to recombinant hCCR7 by anti-CCR7 antibodies in CysMab.DAPA format using an ELISA-based assay.

All tested anti-CCR7 antibodies are capable of binding recombinant hCCR7 (Table 11; FIG. 3).

TABLE 11

Binding Affinity of Humanized Anti-CCR7 Antibodies to Recombinant hCCR7

| Humanized CysMab antibody | Affinity, Kd (nM) |
|---|---|
| 121G12.DAPA | 0.677 |
| 506E15.DAPA | 5.731 |
| 674J13.DAPA | 0.006 |

Binding to Dual FabGraft

A FabGraft ELISA was performed to assess binding to a minimal epitope space, which comprises the N-terminus and EC2 of CCR7. In short, Maxisorp™ 384-well plates (Thermo Nunc) were coated with 5 µg/ml of FabGraft. Otherwise the generic ELISA protocol instructions as described above were followed. All anti-CCR7 antibodies are capable of binding the dual FabGraft as shown in Table 12 below.

TABLE 12

Binding Affinity of Humanized Anti-CCR7 Antibodies to FabGraft

| Humanized CysMab antibody | ELISA; Kd (nM) |
|---|---|
| 121G12.DAPA | 0.023 |
| 506E15.DAPA | 0.025 |
| 674J13.DAPA | 0.023 | pH Dependency ELISA with VLPs

It is known that CCR7-bound CCL19 internalizes the receptor-ligand complex. However, while CCR7 recycles back to the cell surface, CCL19 is sorted to the lysososme for degradation, showing opposite fate for endocytosed CCR7 and its ligand (Otero et al., J Immunol 2006; 177: 2314-2323). For a successful anti-CCR7 ADC it is preferable that the antibody behaves similar to the ligand, e.g., internalizes rapidly, but does not recycle back out with CCR7. In order to accomplish this, we made sure to select ph-dependent antibodies, which would display weaker binding to CCR7 under low pH conditions.

To assess pH-dependency of the anti-CCR7 antibodies, an ELISA was performed using CCR7-expressing virus-like particles (VLPs). In short, Maxisorp™ 384-well plates (Thermo Nunc) were coated with 25 µg/ml of VLPs. Primary antibodies were incubated either in pH5.8 (1:1; dH2O: 0.1M Citrate buffer, 150 mM NaCl) or pH7.4 buffer. Otherwise the generic ELISA protocol instructions as described above were followed.

Among a number of humanization variants for each candidates, comparison of antibody binding at neutral (7.4) and acidic (5.8) pH showed that all CCR7 candidate antibodies have improved affinity at pH 7.4 (Table 13). The entities below were chosen based on their superior ph-dependency among other features.

TABLE 13 pH Dependency of Humanized Anti-CCR7 Antibodies to CCR7-Expressing VLPs

| Humanized CysMab antibody | ELISA; Kd (nM) | | |
|---|---|---|---|
| | pH 7.4 buffer | pH 5.8 buffer | fold change (pH 5.8/7.4) |
| 121G12 | 0.1411 | 0.5207 | 4 |
| 506E15 | 0.0571 | 0.4942 | 9 |
| 674J13 | 0.0162 | 0.1657 | 10 |
| 684E12 | 0.0374 | 0.5041 | 13 | bArrestin Assay

To determine functionality of the anti-CCR7 antibodies, the β-Arrestin assay was performed using the PathHunter Flash Detection Kit from DiscoverX (#93-0247) either in agonistic mode for assessment of agonistic function or antagonistic mode for assessment of antagonistic function.

In the agonistic mode, CHO-flpin-hCCR7 (cell line made by DiscoverX expressing hCCR7 tagged with ProLink, β-arrestin-EA) were seeded at $8\times10^4$ cell/well in 20 µl/well in growth medium (Ham's F-12/Glutamax medium; Invitrogen+10% FBS+0.5 mg/ml G418+0.2 mg/ml hygromycinB; Invitrogen+5 µg/ml Blasticidin; Gibco) with Dox 100 ng/ml in 384-well plates, covered with metal lids, incubated at 37° C. 5% $CO_2$ overnight. The next day, a serial dilution of a 5x working solution in 1x assay buffer (20 mM HEPES/0.1% BSA/1x HBSS pH7.4) was made with test antibodies or positive control, using the ligand hCCL19 (R&D, 361/MI-025/CF). 5 µl of the 5x working solution of antibodies or ligand were added to each well, briefly spun down, and incubated at 37° C./5% $CO_2$ for 2 h. Following incubation, 25 µl of detection reagent were added to each well, incubated at room temperature in the dark while shaking for 20 min. Then, the luminescence signal for enzyme activity was measured on the Envision machine. Finally, enzyme activity was analyzed using Excel.

In the antagonistic mode, CHO-flpin-hCCR7 cells were seeded as described above. The next day, a 6x working solution (0.5 µMx6=3.0 µM) in 1x assay buffer was made for each test antibody or positive control MAB197 (R&D reference antibody; ligand antagonist) or negative control hIgG. 5 µl of the 6x working solution of antibodies or controls were added to each well, briefly spun down, and incubated at 37° C./5% $CO_2$ for 30 min. During incubation, serial dilutions of a 6x working solution in 1x assay buffer were made for hCCL19. Following incubation, 5 µl of the 6x working solution of hCCL19 were added to each well, briefly spun down, and incubated at 37° C./5% $CO_2$ for 90 min. Following incubation, 25 µl of detection reagent were added to each well, incubated at room temperature in the dark while shaking for 20 min. Then, the luminescence signal for enzyme activity was measured on the Envision machine and analyzed in Excel.

Figure 4A:
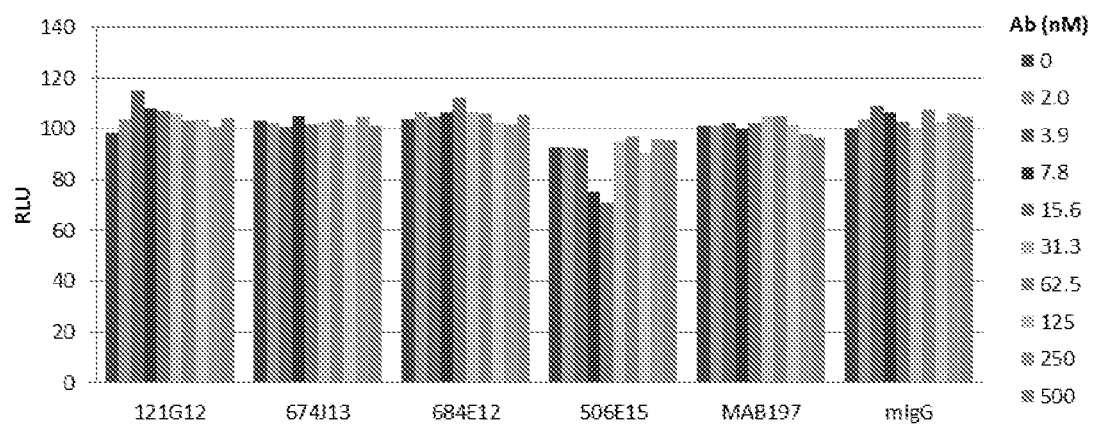
FIG. 4A-C depicts experimental data on functionality of parental anti-CCR7 antibodies using a β-Arrestin assay in agonistic mode (FIG. 4A) and antagonist mode (FIG. 4B, FIG. 4C).
Figure 4B:
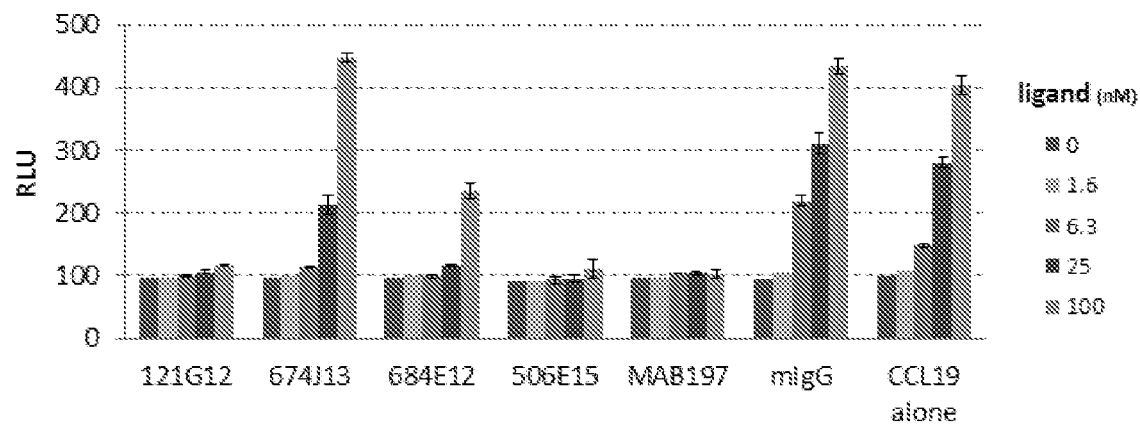
Figure 4C:
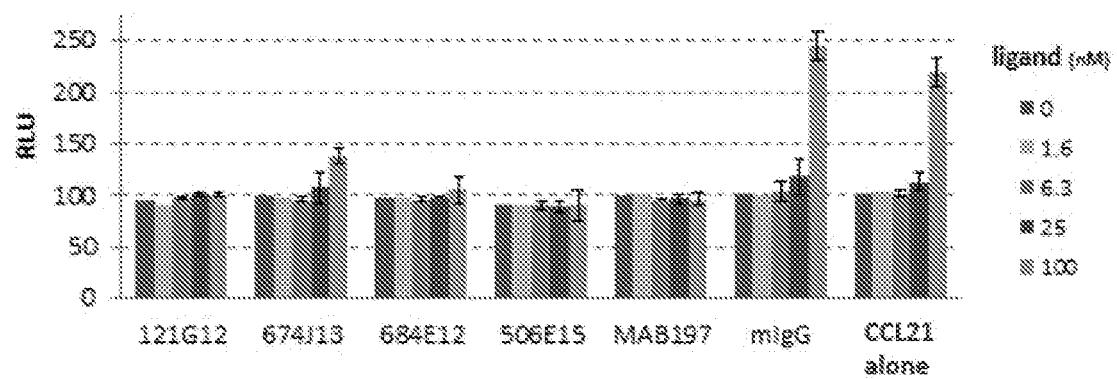

None of the parental anti-CCR7 antibodies showed activity in the agonistic model (FIG. 4A). However, when run in antagonistic format, 506E15 and 121G12 were identified as strong antagonists, e.g., ligand blocking antibodies (FIGS. 4B, 4C). 674J12 is a neutral, non-ligand blocking antibody. 684E12 is a weak antagonist.

FACS Competition Assay with Ligand

To confirm antibody competition with the CCR7 ligand, the FACS assay was run in presence of excess ligand concentration. The FACS assay was performed as described above. Some changes were made to the protocol, e.g., CCL19 was kept at a constant concentration of 1 µM, while the primary antibody was simultaneously applied to DEL cells ranging across several logs, starting at a high of 100 nM. After an incubation time of 30 min in ice-cold FACS buffer, cells were washed, secondary anti-hFc.PE antibody was applied for 15 min and MFI was determined as described above.

Figure 5:
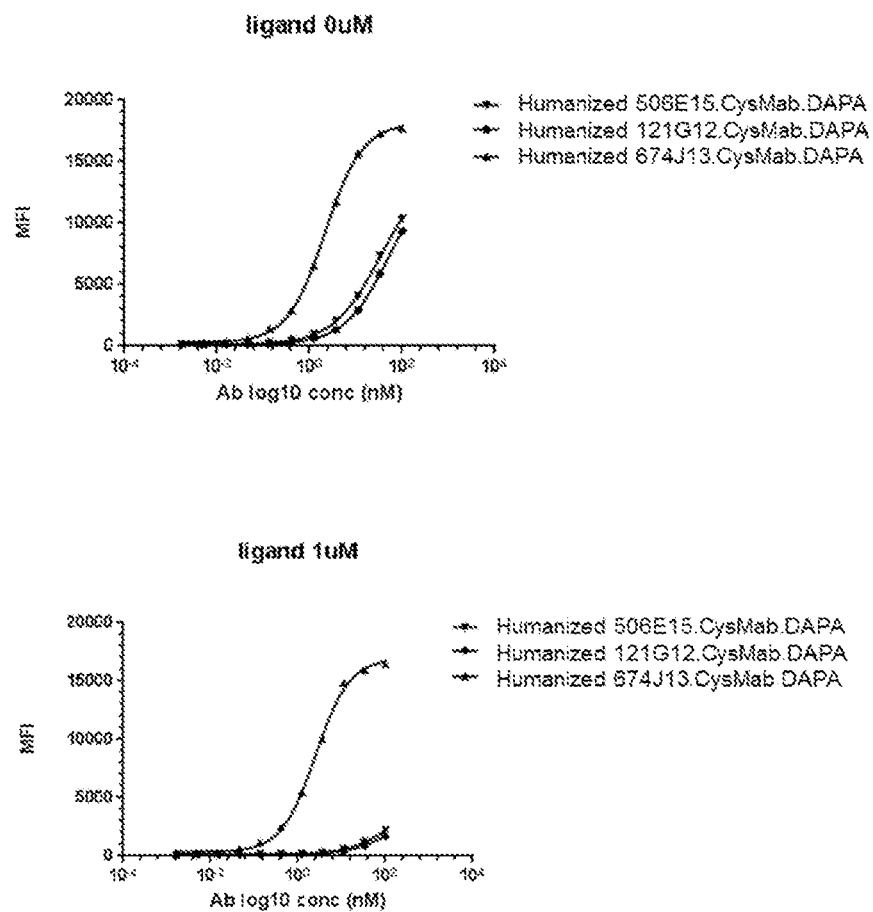
FIG. 5 depicts experimental data on competition with the CCR7 ligand by anti-CCR7 antibodies in CysMab.DAPA format using a FACS assay.

FIG. 5 shows that humanized CysMab.DAPA 674J13 is not impacted by the presence of excess CCL19, confirming its neutral functionality. Humanized CysMab.DAPA 121G12 and 506E15 are indeed strongly impacted in their binding affinity by the presence of excess ligand.

Internalization Capabilities Across Cell Lines with a Range of Receptor Densities Another aspect of a successful anti-CCR7 ADC is to ensure optimal usage of the differential expression distribution of CCR7. As a representative of normal CCR7 expressing cells, CD4+ T cells were isolated from healthy donor PBMCs. In addition, a number of CCR7-positive cancer cell lines were chosen displaying a range of receptor densities. We had purposely chosen antibodies with weaker apparent FACS binding affinities on CCR7+ T cells than CCR7+ cancer cells. In addition, the here described pHrodo assay utilizes a low pH-activated fluorophore-label on the anti-CCR7 antibodies to assess, if antibody uptake into cells as measured by fluorescence, correlates to receptor density. It is preferable to minimize antibody uptake to normal cells to maximize the therapeutic window.

Briefly, labeling of the anti-CCR7 antibodies in CysMab format with maleimide-pHrodo (ThermoFisher) was performed following the manufacturer's instructions yielding DAR=4 (drug, e.g., fluorophore to antibody ratio) entities. The FACS assay was performed as described above. Some changes were made to the protocol, e.g., to allow for internalization, the primary antibody was incubated at 5 µg/ml with cells at 37° C. in culture medium for 6 h, then washed with ice-cold FACS buffer containing sodium azide to stop the reaction.

Table 14 below summarizes the internalization capabilities of three antibodies across a panel of cell lines. A non-targeting pHrodo-labeled antibody was used as control and it was found that up to 400 MFI constitutes background noise of signal, e.g., non-target mediated antibody-conjugate uptake. The data show that all three anti-CCR7 antibodies require CCR7 receptor levels in the range that is typical for most CCR7+cancer lines, e.g., above 20,000 receptors, to efficiently internalize and accumulate conjugated matter, while sparing normal CD4+ T cells.

TABLE 14

Internalization Capabilities of Various Anti-CCR7 Antibodies

| | | pHrodo (6 h MFI) | | |
| --- | --- | --- | --- | --- |
| Cell Line | Receptor numbers | Humanized 121G12.CysMab. DAPA | Humanized 506E15.CysMab. DAPA | Humanized 617J13.CysMab. DAPA |
| CD4+ T cells | 2000 | 278 | 429 | 402 |
| JVM3 | 8717 | 148 | 238 | 146 |
| CMLT1 | 19583 | 301 | 465 | 561 |
| Jeko-1 | 28852 | 450 | 908 | 1389 |
| Mec2 | 50840 | 1340 | 3089 | 3004 |
| L1236 | 61602 | 1237 | 3126 | 5824 |
| MOTN1 | 84200 | 1026 | 2899 | 2539 |
| DEL | 110685 | 1913 | 3058 | 3777 |

TABLE 14-continued

Internalization Capabilities of Various Anti-CCR7 Antibodies

| | | pHrodo (6 h MFI) | | |
|---|---|---|---|---|
| Cell Line | Receptor numbers | Humanized 121G12.CysMab. DAPA | Humanized 506E15.CysMab. DAPA | Humanized 617J13.CysMab. DAPA |
| MJ | 111121 | 1649 | 3870 | 3259 |
| KE97 | 152093 | 1567 | 2723 | 4416 |
| L540 | 167549 | 6836 | 16117 | 11800 |

Epitope Binning Using Octet Red96 System

Epitope binning of anti-hCCR7 parental antibodies was performed using the Octet Red96 system (ForteBio, USA) that measures biolayer interferometry (BLI). The CCR7 immunogen scaffold was biotinylated via an AviTag™ utilizing BirA biotin ligase according to Manufacturer's recommendations (Avidity, LLC, USA cat #BirA500). The biotinylated immunogen scaffold was loaded at 1.5 µg/ml onto pre-equilibrated streptavidin sensors (ForteBio, USA). The sensors were then transferred to a solution containing 100 nM antibody A in 1× kinetics buffer (ForteBio, USA). Sensors were briefly washed in 1× kinetics buffer and transferred to a second solution containing 100 nM of competitor antibody. Binding kinetics was determined from raw data using the Octet Red96 system analysis software (Version 6.3, ForteBio, USA). Antibodies were tested in all pairwise combinations, as both Antibody A and as competitor antibody.

TABLE 15

Antibody Binning Results

| Bin | Antibody |
|---|---|
| 1 | 684E12; MAB197 |
| 2 | 674J13 |
| 3 | 506E15 |
| 4 | 121G12 |

Epitope Mapping Using CCR7 Mutations

Additional epitope mapping was carried out utilizing mutant CCR7 cell lines. NIH/3T3 cell lines expressing mutated variants of human CCR7 were generated. Mutations were introduced at specific positions to exchange the human CCR7 residue into the corresponding murine CCR7 residue. Mutations generated included D35E, F44Y, L47V, S49F, D198G, R201K, S202N, S204G, Q206D, A207T, M208L, I213V, T214S, E215A, and H216Q. The mutant CCR7 plasmid constructs were generated by site-directed mutagenesis and introduced into NIH/3T3 cells to produce stable-expressing cell lines. Specific binding of candidate antibodies to each mutant CCR7 cell line was assessed by flow cytometry. Cells were rinsed thoroughly with PBS and treated with Accutase (Millipore #SCR005) to lift from growth plates and resuspended at approximately $1*10^5$ cells/90 µL in 1× FACS buffer (2% FBS+0.1% NaN3 in PBS). In a 96-well U-bottom plate, 10 µL of 10× antibody solution in FACS buffer was pre-seeded and 90 µL of cell suspension was added. Cell were incubated for 30 minutes at 4° C., washed 1× with cold PBS and resuspended in 100 µL of 1:500 secondary antibody 1× FACS buffer (Allophycocyanin conjugated F(ab')2 goat anti-human IgG, Fcγ specific; Jackson Immunoresearch, Cat #109-136-098). After additional incubation for 15 min at 4° C., cells were washed twice with PBS and resuspended in 100 µL of 1×FACS buffer +4 µg/mL propidium iodide (Life Technologies, Cat #P3566). Geometric mean fluorescence intensity was calculated on live single cells using FlowJo and plotted as % of WT CCR7 Geometric mean fluorescence intensity.

Figure 6:
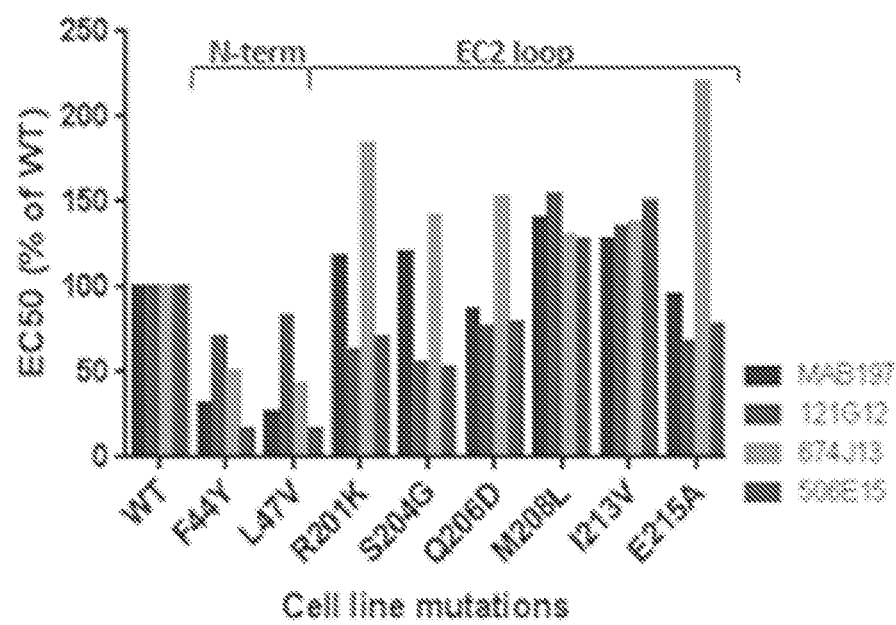
FIG. 6 depicts experimental data on epitope mapping of parental anti-CCR7 antibodies using mutated CCR7 proteins.

EC50-based affinities to point mutated CCR7 show that all tested antibodies have different binding profiles, implying different utilization of a conformational epitope (FIG. 6). Out of all shown antibodies, 506E15 has the most similar binding pattern to MAB197, e.g., both show a significant drop in binding affinity when residues F44 or L47 in the N-terminus of CCR7 are mutated, but not, when M208 or I213 in the EC2 loop are mutated. 121G12 and 674J13 seem to utilize a different set of crucial contact points within the conformational epitope space, as they differ from MAB197 in at least 4 of the 8 tested point mutations.

Example 4: Generation and Characterization of CCR7 Antibody Drug Conjugates In the Section Below, uL and μL are Used Interchangeably to Refer to Microliter. Similarly, uM and μM are Used Interchangeably to Refer to MicroMolar; and um is Used to Refer to Micrometer Example 4A: Preparation of Antibody Drug Conjugate 121G12.CysMab.DAPA.MPET.DM4

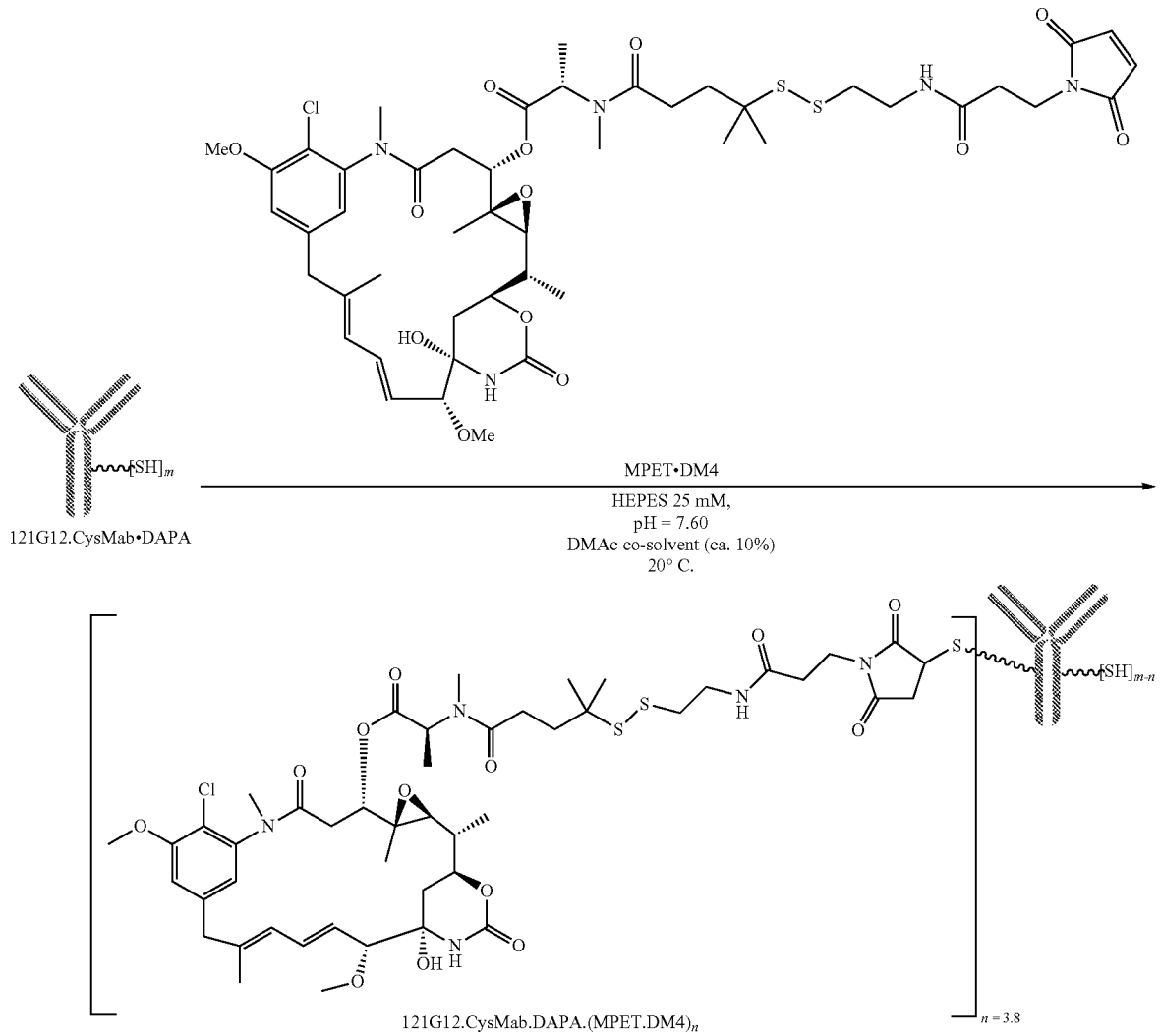

Conjugation of Purified 121G12.CysMab.DAPA and MPET.DM4:

Starting material was 121G12.CysMab.DAPA antibody at 127 mg/ml (OD280 with an extinction coefficient of 13.7 for a 10 mg/ml IgG solution) in 10 mM histidine hydrochloride buffer. To 7.9 ml of antibody (1003 mg) was added 16 ml of 0.5M sodium phosphate pH 8 (Teknova S1280), pH was verified as >7, then antibody was absorbed to 100.3 ml of RMP Protein A resin (GE Healthcare 1-223BPO/I) for 25 minutes with gentle swirling at room temperature. The resin, loaded at 10 mg Ab/ml bed was washed with 15 bed volumes of 1×PBS buffer (Hyclone SH30256.02) by vacuum filtration through a bottletop 0.2 um filter unit (Nalgene 567-0020), then re-suspended in 100.3 ml of 1×PBS to yield a 50% slurry.

To the slurry was added 4329 ul of 0.5M cysteine (Sigma G121-03) formulated in 0.5 M phosphate pH 8 to which NaOH (Alfa Aesar A16037) had been added at ratio of 13.6 g/L. Slurry was occasionally swirled at room temperature for 30 minutes, then washed by vacuum filtration through a bottletop 0.2 um filter unit with 50 bed volumes of 1×PBS in at least 10 cycles of filtration and addition. The washed resin was re-suspended in 100.3 ml of 1×PBS (50% slurry) and 1003 ul of 100 uM $CuCl_2$ (Aldrich 751944) was added (net 500 nM $Cu^{2+}$) to initiate reoxidation. The reoxidation of the antibody was tested by removing a 30 ul aliquot of slurry, adding 1 ul of a 20 mM stock of a reference maleimide (Example 3, page 110 of WO2015/095301), which is known to shift the antibody peak by RPLC, mixing for 1 minute, spinning 7,000×g for 10 seconds, removing supernatant, adding 60 ul of Thermo IgG elution buffer (Thermo Scientific 21009), spinning 14,000×g for 10 seconds, sampling supernatant and analyzing products by RPLC as follows: 2 ul sample was injected onto a heated (80° C.) 4.6×50 mm Agilent PLRP-S column (5 μm particles, 4000 Å pore size) equilibrated to 0.1% trifluoroacetic acid in 29.5% $CH_3CN$/water (Millipore TX1280P-1, Burdick and Jackson 407-4) running at 1.5 ml/min. The column was eluted with a 5 minute gradient to 44.5% $CH_3CN$/water which was maintained for 1.9 minutes and peaks were detected at 280 nm. The optimal time for conjugation is defined as that time in which the main product peak is maximal, later-eluting peaks are minimized and earlier eluting peaks are not yet increasing.

When RPLC assay indicated reoxidation was optimal (in this case 60 minutes), 3010 ul of a 20 mM stock of MPET.DM4 in DMSO was added and slurry was occasionally gently swirled at room temperature for 30 minutes. The slurry was then washed with 20 bed volumes of 1×PBS in at least 10 cycles of filtration and addition.

The slurry was then transferred to a fritted column (Pierce 7375021), pre-eluted with 0.5 bed volumes of Thermo IgG elution buffer (discarded), then eluted with 2 bed volumes of the same buffer. The entire eluate (201 ml) was neutralized with 20.1 ml of 0.5M sodium phosphate pH 8, then concentrated to 60 ml using spin concentrators (Amicon UFC905024) at 3,000×g. The concentrate was then applied to 24×PD-10 buffer exchange columns (GE Healthcare 17-0851-01) equilibrated to 1×PBS, loading 2.5 ml of concentrate and eluting with 3.5 ml of 1×PBS as per manufacturer.

For stability studies, material was pooled with an identically prepared batch to provide 2 grams of starting material. The pooled material was dialyzed extensively (Slidealyzer flask, Thermo Scientific 87762) against 10 mM histidine chloride buffer pH 5 (histidine from JTBaker 2080-05), concentrated to ~30 mg/ml, then sucrose (Millipore 1.00892.1003) and Tween 20 (JTBaker 4116-04) were added to 240 mM and 0.02% (v/v) respectively. Material in excess to that required for stability studies was back-exchanged to 1×PBS. Samples were aliquotted and flash-frozen with liquid nitrogen and stored at −80° C. Final concentrations were 23.9 mg/ml for the material formulated for stability testing and 18.9 mg/ml for the material formulated in 1×PBS.

Analytics on the Resultant Samples are as Follows:

| Parameter | Stability sample | 1xPBS sample |
|---|---|---|
| Concentration (mg/ml) | 23.9 | 18.9 |
| Pyrogen (EU/ml) | 0.1 | 0.05 |
| % aggregate | <1 | <1 |
| DAR | 3.79 | 3.79 |

Analytics Methods: Concentration was determined by OD280 with an extinction coefficient of 13.7 for a 10 mg/ml IgG solution. Pyrogen was determined using Kinetic QCL assay (Lonza Walkersville 50-650H) read on a TECAN Safire plate reader. Percent aggregate was determined by analytical size exclusion chromatography on a Shodex KW-G guard (Thomson Instrument Company Cat #6960955) and KW-803 column (TIC Cat #6960940) equilibrated with mobile phase [20 mM Tris ~pH7.65 (prepped w/10 mM Tris pH7.4, 10 mM Tris pH8), 200 mM NaCl, 0.02% sodium azide], with data acquisition at 280 nm. An aliquot of the sample was prepared for DAR determination was prepareded by diluting the sample to 2 mg/ml in 1×PBS, deglycosylating the sample with PNGaseF (in-house) for 10 minutes at 50° C., removing the PNGaseF by binding to protein A, washing with 1×PBS, and eluting with 1% formic acid. Sample was then injected onto an 2.1×50 mm PLRP-S column (8 μm particles, 1000 Å poresize), equilibrated to 0.1% formic acid in 20% $CH_3CN$/ water (Invitrogen) running at 0.5 ml/min. The column was washed at 20% $CH_3CN$/water for 3 minutes then eluted with a 0.1 minute gradient to 0.1% formic acid 90% $CH_3CN$/water which was maintained for 1.9 minutes. Mass spectral data was taken on an Agilent 1260 instrument and deconvoluted with MassHunter Qualitative Analysis B.05.00 in a range 110-180 kDa. Peak areas corresponding to various calculated DAR states were weighted according to DAR of each peak, then summed and weighted area of the DAR4 peak was divided by the sum of all weighted peaks to obtain the DAR value.

Preparation of the Linker Payload MPET.DM4:

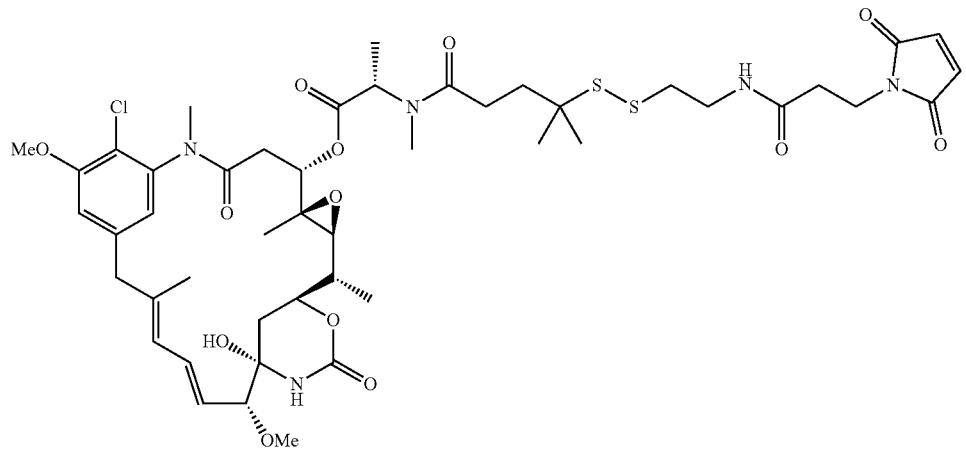 [SMILES: COc1cc2cc(c1Cl)N(C)C(=O)C[C@H](OC(=O)[C@H](C)N(C)C(=O)CCC(C)(C)SSCCNC(=O)CCN1C(=O)C=CC1=O)[C@]1(C)O[C@H]1[C@H](C)[C@@H]1C[C@@](O)(NC(=O)O1)[C@H](OC)/C=C/C=C(\C)C2]

Analytical Methods

Unless otherwise indicated, the following HPLC and HPLC/MS methods were used in the preparation of Intermediates and Examples.

LC/MS analysis was performed on an Agilent 1200sl/6140 system.

Column: Waters Acquity HSS T3 C18, 50×2.0, 1.8 um

Mobile Phase: A) H$_2$O+0.05% TFA; B: acetonitrile+0.035% TFA

Pump Method:

| Time | A % | B % | Flow (mL/min) |
|------|-----|-----|---------------|
| 0    | 90  | 10  | 0.9           |
| 1.35 | 0   | 100 | 0.9           |
| 1.36 | 0   | 100 | 0.9           |
| 1.95 | 0   | 100 | 0.9           |
| 1.96 | 90  | 10  | 0.9           |
| 2.0  | 90  | 10  | 0.9           |

Detection: UV Diode Array at 190 nm-400 nm

MS Scan: 200-1350 amu

ELSD: 60° C.

MS Parameters:

| Polarity | Positive |
|----------|----------|
| Drying Gas | 12 |
| Nebulizer Pressure | 50 |
| Drying Gas Temperature | 350 |
| Capillary Voltage | 3000 |

(14S,16S,32S,33S,2R,4S,10E,12E,14R)-86-chloro-14-hydroxy-85,14-dimethoxy-33,2,7,10-tetramethyl-12,6-dioxo-7-aza-1(6,4)-oxazinana-3(2,3)-oxirana-8(1,3)-benzena-cyclotetradecaphane-10,12-dien-4-yl N-(4-((2-(3-(2,5-dioxo-2,5-dihydro-1H-pyrrol-1-yl)propanamido)ethyl)disulfanyl)-4-methylpentanoyl)-N-methyl-L-alaninate

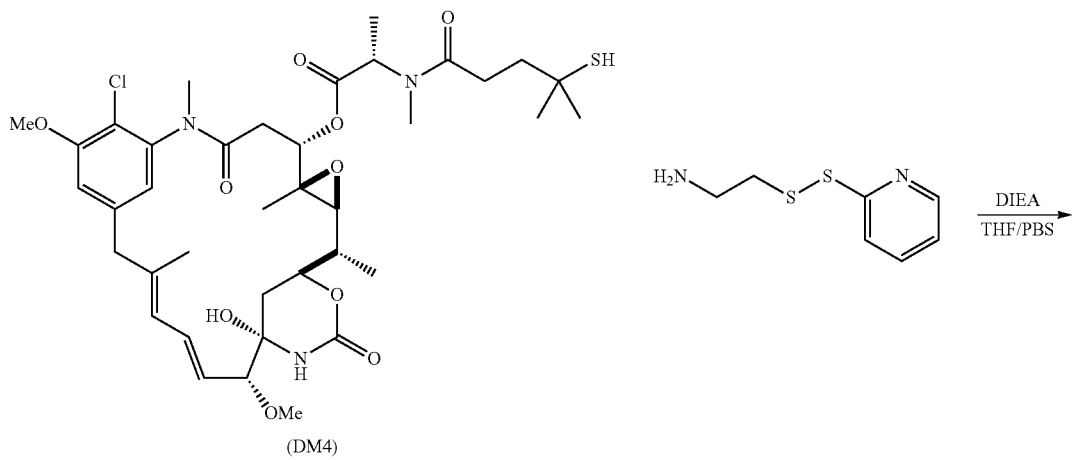

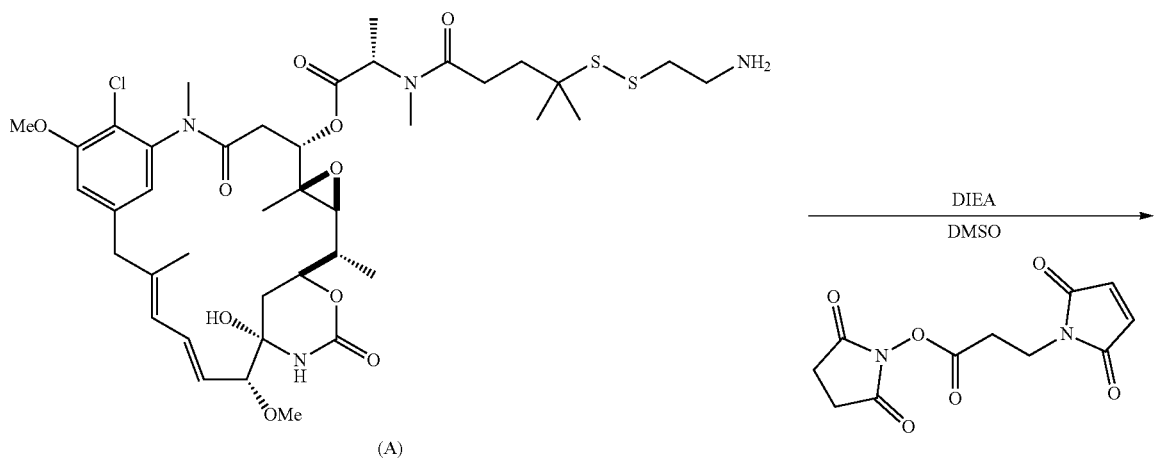

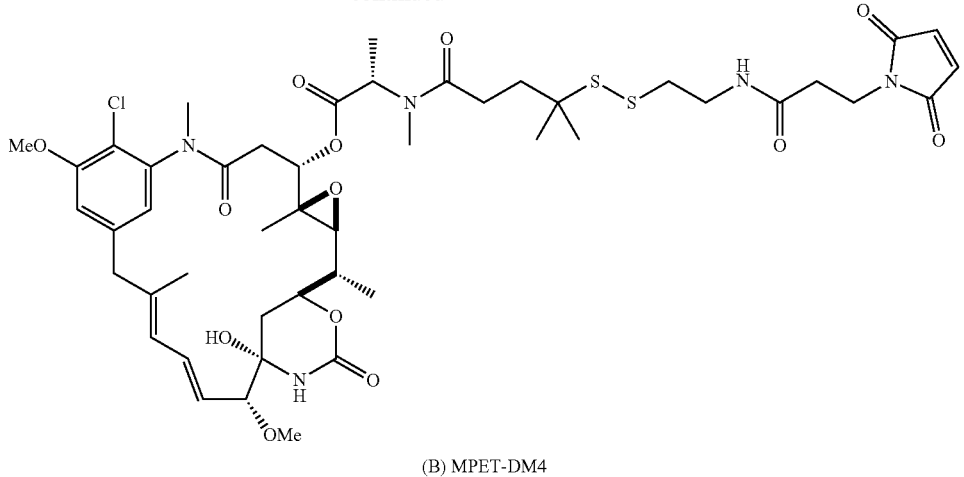

(B) MPET-DM4

Step 1: Preparation of (14S,16S,32S,33S,2R,4S,10E,12E,14R)-86-chloro-14-hydroxy-85,14-dimethoxy-33,2,7,10-tetramethyl-12,6-dioxo-7-aza-1(6,4)-oxazinana-3(2,3)-oxirana-8(1,3)-benzenacyclotetradecaphane-10,12-dien-4-yl N-(4-((2-aminoethyl)disulfanyl)-4-methylpentanoyl)-N-methyl-L-alaninate To DM4 (480 mg, 0.62 mmol) dissolved in PBS buffer (10.5 mL) and anhydrous THF (21 mL) were added 2-(pyridin-2-yldisulfanyl)ethan-1-amine (151 mg, 0.68 mmol) and DIEA (0.27 mL, 1.54 mmol) at room temperature. The reaction mixture was stirred at room temperature for 30 min and concentrated in vacuo. The aqueous residue was diluted with CH$_3$CN (1 mL) and H$_2$O (2 mL) and purified by reverse phase ISCO, eluted with 10-60% acetonitrile-H$_2$O containing 0.05% TFA. Fractions containing desired product were lyophilized to obtain desired product (555 mg, 93% yield). $^1$H NMR (400 MHz, MeOD-d$_4$) δ ppm 0.83 (s, 3 H) 1.21 (d, J=5.0 Hz, 3 H) 1.25 (s, 3 H) 1.28 (s, 3 H) 1.30 (d, J=5.0 Hz, 3 H) 1.45-1.55 (m, 3 H) 1.67 (s, 3 H) 1.84-1.88 (m, 1 H) 1.95-2.01 (m, 1 H) 2.14 (dd, J=5.0 and 15.0 Hz, 1 H) 2.37-2.43 (m, 1 H) 2.53-2.59 (m, 1 H) 2.64 (dd, J=10.0 and 15.0 Hz, 1 H) 2.82-2.89 (m, 5 H) 2.91 (d, J=10.0 Hz, 1 H) 3.16 (dd, J=5.0 and 10.0 Hz, 2 H) 3.20 (s, 3 H) 3.23 (d, J=10.0 Hz, 1 H) 3.35 (s, 3 H) 3.55 (d, J=5.0 Hz, 1 H) 3.58 (d, J=10.0 Hz, 1 H) 4.15-4.20 (m, 1 H) 4.64 (dd, J=5.0 and 10.0 Hz, 1 H) 5.43 (q, J=5.0 Hz, 2 H) 5.66 (dd, J=10.0 and 15.0 Hz, 1 H)) 6.58 (dd, J=10.0 and 15.0 Hz, 1 H) 6.65 (d, J=10.0 Hz, 1 H) 6.66 (s, 1 H) 7.11 (bs, 1H) 7.28 (bs, 1H); MS m/z 855.3 (M+H), Retention time 0.988 minutes.

Step 2: Preparation of (14S,16S,32S,33S,2R,4S,10E,12E,14R)-86-chloro-14-hydroxy-85,14-dimethoxy-33,2,7,10-tetramethyl-12,6-dioxo-7-aza-1(6,4)-oxazinana-3(2,3)-oxirana-8(1,3)-benzenacyclotetradecaphane-10,12-dien-4-yl N-(4-((2-(3-(2,5-dioxo-2,5-dihydro-1H-pyrrol-1-yl)propanamido)ethyl)disulfanyl)-4-methylpentanoyl)-N-methyl-L-alaninate To (14S,16S,32S,33S,2R,4S,10E,12E,14R)-86-chloro-14-hydroxy-85,14-dimethoxy-33,2,7,10-tetramethyl-12,6-dioxo-7-aza-1(6,4)-oxazinana-3(2,3)-oxirana-8(1,3)-benzenacyclotetradecaphane-10,12-dien-4-yl N-(4-((2-aminoethyl)disulfanyl)-4-methylpentanoyl)-N-methyl-L-alaninate (555 mg, 0.57 mmol)dissolved in anhydrous DMSO (7 mL) were added 2,5-dioxopyrrolidin-1-yl 3-(2,5-dioxo-2,5-dihydro-1H-pyrrol-1-yl)propanoate (171 mg, 0.63 mmol) and DIEA (249 mL, 1.43 mmol) at room temperature. The reaction mixture was stirred at room temperature for 15 min and neutralized using TFA. The mixture was cooled to 0° C. with iced bath, followed by addition of CH$_3$CN (2 mL) and H$_2$O (7 mL), and then purified by reverse phase ISCO, eluted with 10-70% acetonitrile-H2O containing 0.05% TFA. Fractions containing desired product were lyophilized to obtain desired product (430 mg, 66% yield).). $^1$H NMR (400 MHz, CDCl$_3$) δ ppm 0.81 (s, 3 H) 1.23 (s, 3 H) 1.24 (s, 3 H) 1.25 (s, 1 H) 1.28 (d, J=5.0 Hz, 3 H) 1.31 (d, J=5.0 Hz, 3 H) 1.43-1.49 (m, 1 H) 1.61 (d, J=15.0 Hz, 1 H) 1.64 (s, 3 H) 1.81-1.87 (m, 1 H) 1.94-2.01 (m, 1 H) 2.19 (dd, J=5.0 and 15.0 Hz, 1 H) 2.30-2.36 (m, 1 H) 2.54 (t, J=5.0 Hz, 2 H) 2.61 (dd, J=10.0 and 15.0 Hz, 1 H) 2.70 (t, J=5.0 Hz, 2 H) 2.88 (s, 3 H) 3.00 (d, J=10.0 Hz, 1 H) 3.13 (d, J=10.0 Hz, 1 H) 3.21 (s, 3 H) 3.55 (s, 3 H) 3.45 (q, J=5.0 Hz, 2 H) 3.49 (d, J=5.0 Hz, 1 H) 3.62 (d, J=10.0 Hz, 1 H) 3.83 (t, J=5.0 Hz, 1 H) 3.98 (s, 3 H) 4.32 (m, 1 H) 4.80 (dd, J=5.0 and 10.0 Hz, 1 H) 5.28 (d, J=5.0 Hz, 1 H) 5.66 (dd, J=10.0 and 15.0 Hz, 1 H)) 6.22 (bs, 1 H) 6.42 (dd, J=10.0 and 15.0 Hz, 1 H) 6.50 (s, 1 H) 6.63 (s, 1 H) 6.66 (d, J=10.0 Hz, 1 H) 6.70 (s, 2H) 6.83(s, 1H); MS m/z 988.3 (M+H-H20), Retention time 1.145 minutes.

Example 4B: Preparation of Antibody Drug Conjugate 121G12.DAPA.sSPDB.DM4

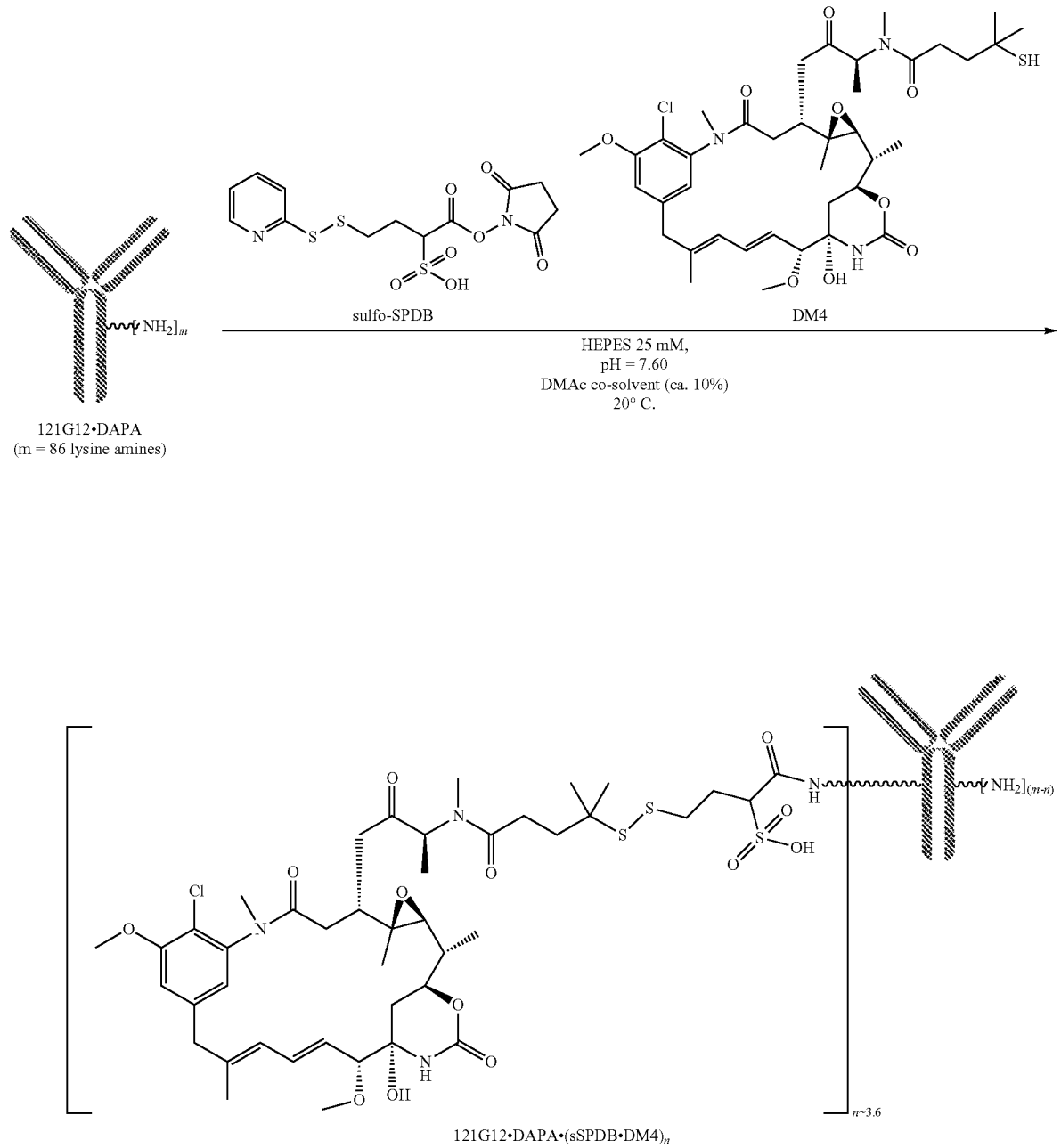

To a stirred solution of 25 mM HEPES buffer pH 7.6 (3 ml; sterile) and dimethylacetamid (DMAc; 0.12 ml) at 22° C. a solution (1.695 ml) of 121G12.DAPA; MW-145546 g/mol; 62 mg (0.426 µmol)) in potassium phosphate buffer (10 mM, pH6; sterile) was added. Maytansinoid DM4 (2.42 mg (3.101 µmol) dissolved in 0.242 ml DMAc was added. Linker sulfoSPDB (0.970 mg (2.386 µmol, corrected for assay) dissolved in 0.970 ml DMAc was added. After 18 h the reaction mixture was analyzed for reaction completeness by SEC-UV and HPLC.

The reaction mixture was purified from small molecule by-products and buffer-exchanged by filtration over Amicon membrane cells; cut-off 30 kDa using 10 mM PBS-pH7.4 buffer (sterile) for washing. The obtained Amicon-retentate was combined and diluted to 10 mg/ml (UV) to give 2.9 ml solution of the antibody drug conjugate 121G12.DAPA.sSPDB-DM4 in 10 mM PBS-pH7.4 buffer (49% protein recovery).

By SEC-UV the drug antibody ratio was determined to be n=3.6 and the monomeric purity to be 98.7%. The Endotoxin-level was 0.14 EU/mg (BET Endosafe-test).

Example 4C: Preparation of Antibody Drug Conjugate 684E12.SMCC.DM1

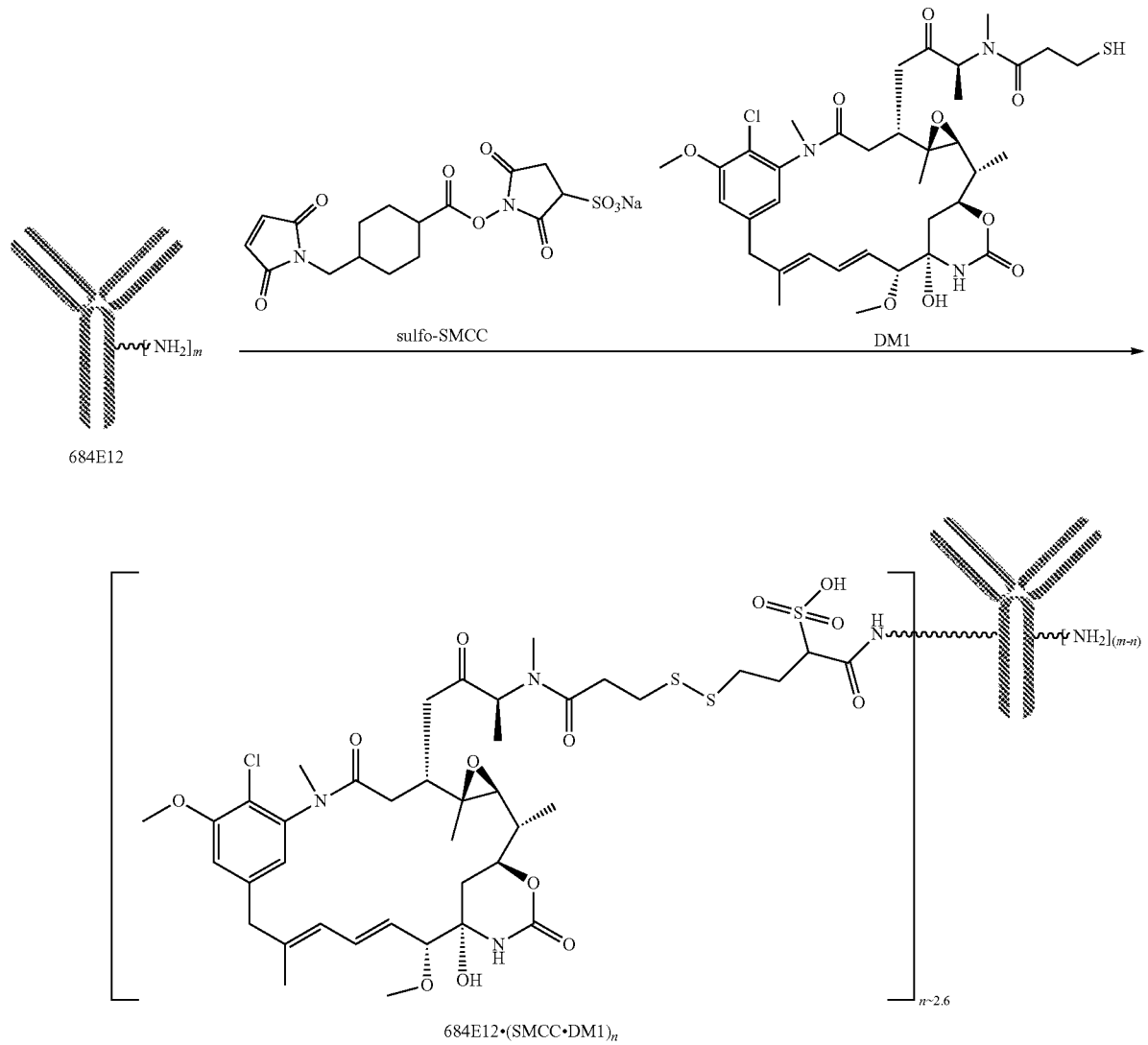

684E12•(SMCC•DM1)$_n$

To the antibody (parental 684E12) solution (7.1 mg/mL, 3.4 mL, ca 47 µM, PBS, pH 7.4) 100 µL of 2 mM DM1 (0.17 mg) in DMA and 50 µL of 4 mM sulfo-SMCC (0.15 mg) in DMA were added and the mixture was incubated and gently stirred at 4° C. overnight. After incubation the reaction mixture was purified via desalting on a HiPrep 26/10 Desalting column (GE Healthcare) using PBS, pH 7.4 as the running buffer and sterile filtered. The purified conjugate was analyzed by MALDI-MS and the DAR estimated to be 2.6. Analytical SEC showed 3.7% aggregation (or 96.3% monomer) present in the sample and LAL testing (PTS, Charles River Laboratories) determined the endotoxin value to be 0.36 EU/mg.

Example 4D: Preparation of Antibody Drug Conjugate 506E15.AURIX1

Starting material was 506E15.CysMab (WT Fc) antibody at 18.8 mg/ml (0D280 with an extinction coefficient of 13.7 for a 10 mg/ml IgG solution) in 1× phosphate buffered saline (1×PBS). 1.76 ml of antibody was absorbed to 3 ml of RMP Protein A resin (GE Healthcare 1-223BPO/I) and to resultant slurry was added 240 ul of 0.5M cysteine (Sigma G121-03) formulated in 0.5 M phosphate pH 8 to which NaOH (Alfa Aesar A16037) had been added at ratio of 13.6 g/L. Slurry was occasionally swirled at room temperature for 30 minutes, then washed by vacuum filtration through a bottletop 0.2 um filter unit with 50 bed volumes of 1×PBS in at least 10 cycles of filtration and addition. The washed resin was resuspended in 2 ml of 1×PBS (50% slurry) and 60 ul of 100 uM CuCl2 (Aldrich 751944) was added (net 100 nM Cu$^{2+}$) to initiate reoxidation. After 420 minutes, and additional 90 ul of 100 uM CuCl2 was added to further accelerate the reoxidation. The reoxidation of the antibody was tested by removing a 30 ul aliquot of slurry, adding 1 ul of a 20 mM stock of a reference maleimide: (Example 3, page 110 of WO2015/095301), which is known to shift the antibody peak by RPLC, mixing for 1 minute, spinning 7,000×g for 10 seconds, removing supernatant, adding 60 ul of Thermo IgG elution buffer (Thermo Scientific 21009), spinning 14,000×g for 10 seconds, sampling supernatant and analyzing products by RPLC as follows: 2 ul sample was injected onto a heated (80° C.) 4.6×50 mm Agilent PLRP-S column (5 µm particles, 4000 Å poresize) equilibrated to 0.1% trifluoroacetic acid in 29.5% $CH_3CN$/water (Millipore TX1280P-1, Burdick and Jackson 407-4) running at 1.5 ml/min. The column was eluted with a 5 minute gradient to 44.5% $CH_3CN$/water which was maintained for 1.9 minutes and peaks were detected at 280 nm. The optimal time for conjugation is defined as that time in which the main product peak is maximal, later-eluting peaks are minimized and earlier eluting peaks are not yet increasing.

When RPLC assay indicated reoxidation was optimal (in this case 565 minutes), 220 ul of a 20 mM stock of AURIX1 in DMSO was added and slurry was occasionally gently swirled at room temperature for 70 minutes. The slurry was then washed with 20 bed volumes of 1×PBS in at least 10 cycles of filtration and addition.

The slurry was then transferred to a fritted column (Pierce 7375021), pre-eluted with 0.5 bed volumes of Thermo IgG elution buffer (discarded), then eluted with 2 bed volumes of the same buffer. The entire eluate (6 ml) was neutralized with 0.6 ml of 0.5M sodium phosphate pH 8, concentrated to 2.5 ml using a spin concentrator (Amicon UFC905024) at 3,000×g, applied to a PD-10 buffer exchange column (GE Healthcare 17-0851-01) equilibrated to 1×PBS, loading 2.5 ml of concentrate and eluting with 3.5 ml of 1×PBS as per manufacturer. Yield was 22 mg (66%).

Example 4E: Preparation of Antibody Drug Conjugate 506E15.CysMab.DAPA.AURIX2

Starting material was 506E15.CysMab.DAPA antibody at 10 mg/ml (OD280 with an extinction coefficient of 13.7 for a 10 mg/ml IgG solution) in 1× phosphate buffered saline (1×PBS). 2.0 ml of antibody was absorbed to 2 ml of RMP Protein A resin (GE Healthcare 1-223BPO/I) and to resultant slurry was added 160 ul of 0.5M cysteine (Sigma G121-03) formulated in 0.5 M phosphate pH 8 to which NaOH (Alfa Aesar A16037) had been added at ratio of 13.6 g/L. Slurry was occasionally swirled at room temperature for 30 minutes, then washed by vacuum filtration through a bottletop 0.2 um filter unit with 50 bed volumes of 1×PBS in at least 10 cycles of filtration and addition. The washed resin was re-suspended in 2 ml of 1×PBS (50% slurry) and 10 ul of 100 uM CuCl2 (Aldrich 751944) was added (net 250 nM $Cu^{2+}$) to initiate reoxidation. The reoxidation of the antibody was tested by removing a 30 ul aliquot of slurry, adding 1 ul of a 20 mM stock of a reference maleimide (Example 3, page 110 of WO2015/095301), which is known to shift the antibody peak by RPLC, mixing for 1 minute, spinning 7,000×g for 10 seconds, removing supernatant, adding 60 ul of Thermo IgG elution buffer (Thermo Scientific 21009), spinning 14,000×g for 10 seconds, sampling supernatant and analyzing products by RPLC as follows: 2 ul sample was injected onto a heated (80° C.) 4.6×50 mm Agilent PLRP-S column (5 µm particles, 4000 Å pore size) equilibrated to 0.1% trifluoroacetic acid in 29.5% $CH_3CN$/ water (Millipore TX1280P-1, Burdick and Jackson 407-4) running at 1.5 ml/min. The column was eluted with a 5 minute gradient to 44.5% $CH_3CN$/water which was maintained for 1.9 minutes and peaks were detected at 280 nm. The optimal time for conjugation is defined as that time in which the main product peak is maximal, later-eluting peaks are minimized and earlier eluting peaks are not yet increasing.

When RPLC assay indicated reoxidation was optimal (in this case 295 minutes), 80 ul of a 20 mM stock of AURIX2 in DMSO was added and slurry was occasionally gently swirled at room temperature for 85 minutes. The slurry was then washed with 20 bed volumes of 1×PBS in at least 10 cycles of filtration and addition.

The slurry was then transferred to a fritted column (Pierce 7375021), pre-eluted with 0.5 bed volumes of Thermo IgG elution buffer (discarded), then eluted with 2 bed volumes of the same buffer. The entire eluate (4 ml) was neutralized with 0.4 ml of 0.5M sodium phosphate pH 8, applied to 2×PD-10 buffer exchange columns (GE Healthcare 17-0851-01) equilibrated to 1×PBS, loading 2.5 ml of eluate and eluting with 3.5 ml of 1×PBS as per manufacturer. Yield was 13.3 mg (67%).

Example 4F: Preparation of Antibody Drug Conjugate 674J13.CysMab.AURIX1

Starting material was 674J13.CysMab (WT Fc) antibody at 9 mg/ml (OD280 with an extinction coefficient of 13.7 for a 10 mg/ml IgG solution) in 1× phosphate buffered saline (1×PBS). To 57.6 ml of antibody was added DTT to 200 mM (Invitrogen 15508-013) and solution was incubated 75 minutes to strongly reduce the Ab. The reduced Abs were then applied to PD-10 buffer exchange columns (GE Healthcare 17-0851-01) equilibrated to 1×PBS, loading 2.5 ml of concentrate and eluting with 3.5 ml of 1×PBS as per manufacturer. The eluate from the PD10s was pooled then reapplied to fresh PD10 columns to more completely remove the DTT. Note that in separate experiments, PD10 columns are more effective at removal of DTT than would be seen just through size exclusion mechanism, provided the columns are used only once.

The reoxidation of the antibody was tested by removing a 30 ul aliquot of slurry, adding 1 ul of a 20 mM stock of AURIX1 known to shift the antibody peak by RPLC, mixing for 1 minute, spinning 7,000×g for 10 seconds, removing supernatant, adding 60 ul of Thermo IgG elution buffer (Thermo Scientific 21009), spinning 14,000×g for 10 seconds, sampling supernatant and analyzing products by RPLC as follows: 2 ul sample was injected onto a heated (80° C.) 4.6×50 mm Agilent PLRP-S column (5 µm particles, 4000 Å poresize) equilibrated to 0.1% trifluoroacetic acid in 29.5% $CH_3CN$/ water (Millipore TX1280P-1, Burdick and Jackson 407-4) running at 1.5 ml/min. The column was eluted with a 5 minute gradient to 44.5% $CH_3CN$/water which was maintained for 1.9 minutes and peaks were detected at 280 nm. The optimal time for conjugation is defined as that time in which the main product peak is maximal, later-eluting peaks are minimized and earlier eluting peaks are not yet increasing.

When RPLC assay indicated reoxidation was optimal (in this case 180 minutes), 290 ul of a 20 mM stock of AURIX1 in DMSO was added along with 6 ml of RMP Protein A resin (GE Healthcare 1-223BPO/I) resin. The slurry was occasionally gently swirled at room temperature for 40 minutes. The slurry was then washed with 20 bed volumes of 1×PBS in at least 10 cycles of filtration and addition.

The slurry was then transferred to a fritted column (Pierce 7375021), pre-eluted with 0.5 bed volumes of Thermo IgG elution buffer (discarded), then eluted with 2 bed volumes of the same buffer. The entire eluate (11.5 ml) was neutralized with 1.2 ml of 0.5M sodium phosphate pH 8, concentrated to 2.5 ml using a spin concentrator (Amicon UFC905024) at 3,000×g, applied to a PD-10 buffer exchange column (GE Healthcare 17-0851-01) equilibrated to 1×PBS, loading 2.5 ml of concentrate and eluting with 3.5 ml of 1×PBS as per manufacturer. Yield was 26 mg (41%)

Example 4G: Preparation of Antibody Drug Conjugate 674J13.CysMab.DAPA.AURIX2

Starting material was 674J13.CysMab.DAR4.DAPA antibody at 31.7 mg/ml (OD280 with an extinction coefficient of 13.7 for a 10 mg/ml IgG solution) in 1 × phosphatebuffered saline (1×PBS). 9.5 ml of antibody was absorbed to 30.1 ml of RMP Protein A resin (GE Healthcare 1-223BPO/I) and to resultant slurry was added 1800 mg of DTT (Invitrogen 15508-013) to strongly reduce the Ab (net 200 mM DTT). Slurry was swirled at room temperature for 20 minutes, then washed by vacuum filtration through a bottletop 0.2 um filter unit with 50 bed volumes of 1×PBS in at least 10 cycles of filtration and addition. The washed resin was resuspended in 2 ml of 1×PBS and swirled at room temperature—no copper was added (this accelerated the reoxidation too severely). The reoxidation of the antibody was tested by removing a 30 ul aliquot of slurry, adding 1 ul of a 20 mM stock of a reference maleimide (Example 3, page 110 of WO2015/095301), which is known to shift the antibody peak by RPLC, mixing for 1 minute, spinning 7,000×g for 10 seconds, removing supernatant, adding 60 ul of Thermo IgG elution buffer (Thermo Scientific 21009), spinning 14,000×g for 10 seconds, sampling supernatant and analyzing products by RPLC as follows: 2 ul sample was injected onto a heated (80° C.) 4.6×50 mm Agilent PLRP-S column (5 μm particles, 4000 Å poresize) equilibrated to 0.1% trifluoroacetic acid in 29.5% $CH_3CN$/water (Millipore TX1280P-1, Burdick and Jackson 407-4) running at 1.5 ml/min. The column was eluted with a 5 minute gradient to 44.5% $CH_3CN$/water which was maintained for 1.9 minutes and peaks were detected at 280 nm. The optimal time for conjugation is defined as that time in which the main product peak is maximal, later-eluting peaks are minimized and earlier eluting peaks are not yet increasing.

When RPLC assay indicated reoxidation was optimal (in this case 80 minutes), 903 ul of a 20 mM stock of AURIX2 in DMSO was added and slurry was occasionally gently swirled at room temperature for 50 minutes. The slurry was then washed with 20 bed volumes of 1×PBS in at least 10 cycles of filtration and addition.

The slurry was then transferred to a fritted column (Pierce 7375021), pre-eluted with 0.5 bed volumes of Thermo IgG elution buffer (discarded), then eluted with 2 bed volumes of the same buffer. The entire eluate (60.2 ml) was neutralized with 6.0 ml of 0.5M sodium phosphate pH 8, concentrated to 17.5 ml using a spin concentrator (Amicon UFC905024) at 3,000×g, applied to 7 PD-10 buffer exchange columns (GE Healthcare 17-0851-01) equilibrated to 1×PBS, loading 2.5 ml of concentrate and eluting with 3.5 ml of 1×PBS as per manufacturer. Yield was 243 mg (81%)

Example 4H: Preparation of Antibody Drug Conjugate 121G12.CysMab.DAPA.AURIX1

Starting material was 121G12.CysMab.DAPA antibody at 16.7 mg/ml (OD280 with an extinction coefficient of 13.7 for a 10 mg/ml IgG solution) in 1× phosphatebuffered saline (1×PBS). 3.6 ml of antibody was absorbed to 6 ml of RMP Protein A resin (GE Healthcare 1-223BPO/I) and resultant slurry was swirled at room temperature for 125 minutes then added 544 ul of 0.5M cysteine (Sigma G121-03) formulated in 0.5 M phosphate pH 8 to which NaOH (Alfa Aesar A16037) had been added at ratio of 13.6 g/L. Slurry was occasionally swirled at room temperature for 60 minutes, then washed by vacuum filtration through a bottletop 0.2 um filter unit with 50 bed volumes of 1×PBS in at least 10 cycles of filtration and addition. The washed resin was resuspended in 2 ml of 1×PBS (50% slurry) and 16 ul of 100 uM CuCl2 (Aldrich 751944) was added (net 250 nM $Cu^{2+}$) to initiate reoxidation. The reoxidation of the antibody was tested by removing a 30 ul aliquot of slurry, adding 1 ul of a 20 mM stock of AURIX1 known to shift the antibody peak by RPLC, mixing for 1 minute, spinning 7,000 xg for 10 seconds, removing supernatant, adding 60 ul of Thermo IgG elution buffer (Thermo Scientific 21009), spinning 14,000×g for 10 seconds, sampling supernatant and analyzing products by RPLC as follows: 2 ul sample was injected onto a heated (80° C.) 4.6×50 mm Agilent PLRP-S column (5 μm particles, 4000 Å poresize) equilibrated to 0.1% trifluoroacetic acid in 29.5% $CH_3CN$/ water (Millipore TX1280P-1, Burdick and Jackson 407-4) running at 1.5 ml/min. The column was eluted with a 5 minute gradient to 44.5% $CH_3CN$/water which was maintained for 1.9 minutes and peaks were detected at 280 nm. The optimal time for conjugation is defined as that time in which the main product peak is maximal, later-eluting peaks are minimized and earlier eluting peaks are not yet increasing.

When RPLC assay indicated reoxidation was optimal (in this case 170 minutes), 67 ul of a 20 mM stock of AURIX1 in DMSO was added and slurry was occasionally gently swirled at room temperature for 120 minutes. The slurry was then washed with 20 bed volumes of 1xPBS in at least 10 cycles of filtration and addition.

The slurry was then transferred to a fritted column (Pierce 7375021), pre-eluted with 0.5 bed volumes of Thermo IgG elution buffer (discarded), then eluted with 2 bed volumes of the same buffer. The entire eluate (15 ml) was neutralized with 1.5 ml of 0.5M sodium phosphate pH 8, concentrated to 5 ml using a spin concentrator (Amicon UFC905024) at 3,000×g, applied to 2×PD-10 buffer exchange columns (GE Healthcare 17-0851-01) equilibrated to 1×PBS, loading 2.5 ml of eluate and eluting with 3.5 ml of 1×PBS as per manufacturer. Yield was 54 mg (92%).

Example 4I: Preparation of Antibody Drug Conjugate 121G12.CysMab.AURIX1

Starting material was 121G12.CysMab (Fc WT) antibody at 12.5 mg/ml (OD280 with an extinction coefficient of 13.7 for a 10 mg/ml IgG solution) in 1× phosphatebuffered saline (1×PBS). 4.8 ml of antibody was absorbed to 6 ml of RMP Protein A resin (GE Healthcare 1-223BPO/I) and resultant slurry was swirled at room temperature for 125 minutes then added 592 ul of 0.5M cysteine (Sigma G121-03) formulated in 0.5 M phosphate pH 8 to which NaOH (Alfa Aesar A16037) had been added at ratio of 13.6 g/L. Slurry was occasionally swirled at room temperature for 60 minutes, then washed by vacuum filtration through a bottletop 0.2 um filter unit with 50 bed volumes of 1×PBS in at least 10 cycles of filtration and addition. The washed resin was resuspended in 2 ml of 1×PBS (50% slurry) and 16 ul of 100 uM CuCl2 (Aldrich 751944) was added (net 250 nM $Cu^{2+}$) to initiate reoxidation. The reoxidation of the antibody was tested by removing a 30 ul aliquot of slurry, adding 1 ul of a 20 mM stock of AURIX1 known to shift the antibody peak by RPLC, mixing for 1 minute, spinning 7,000×g for 10 seconds, removing supernatant, adding 60 ul of Thermo IgG elution buffer (Thermo Scientific 21009), spinning 14,000×g for 10 seconds, sampling supernatant and analyzing products by RPLC as follows: 2 ul sample was injected onto a heated (80° C.) 4.6×50 mm Agilent PLRP-S column (5 µm particles, 4000 Å poresize) equilibrated to 0.1% trifluoroacetic acid in 29.5% CH₃CN/water (Millipore TX1280P-1, Burdick and Jackson 407-4) running at 1.5 ml/min. The column was eluted with a 5 minute gradient to 44.5% CH3CN/ water which was maintained for 1.9 minutes and peaks were detected at 280 nm. The optimal time for conjugation is defined as that time in which the main product peak is maximal, later-eluting peaks are minimized and earlier eluting peaks are not yet increasing.

When RPLC assay indicated reoxidation was optimal (in this case 160 minutes), 67 ul of a 20 mM stock of AURIX1 in DMSO was added and slurry was occasionally gently swirled at room temperature for 120 minutes. The slurry was then washed with 20 bed volumes of 1×PBS in at least 10 cycles of filtration and addition.

The slurry was then transferred to a fritted column (Pierce 7375021), pre-eluted with 0.5 bed volumes of Thermo IgG elution buffer (discarded), then eluted with 2 bed volumes of the same buffer. The entire eluate (15 ml) was neutralized with 1.5 ml of 0.5M sodium phosphate pH 8, concentrated to 5 ml using a spin concentrator (Amicon UFC905024) at 3,000×g, applied to 2×PD-10 buffer exchange columns (GE Healthcare 17-0851-01) equilibrated to 1×PBS, loading 2.5 ml of eluate and eluting with 3.5 ml of 1×PBS as per manufacturer. Yield was 52 mg (89%).

Analytics Methods: Concentration was determined by OD280 with an extinction coefficient of 13.7 for a 10 mg/ml IgG solution. Pyrogen was determined using Kinetic QCL assay (Lonza Walkersville 50-650H) read on a TECAN Safire plate reader. Percent aggregate was determined by analytical size exclusion chromatography on a Shodex KW-G guard (Thomson Instrument Company Cat #6960955) and KW-803 column (TIC Cat #6960940) equilibrated with mobile phase [20 mM Tris ~pH7.65 (prepped w/10 mM Tris pH7.4, 10 mM Tris pH8), 200 mM NaCl, 0.02% sodium azide], with data acquisition at 280 nm. An aliquot of the sample was prepared for DAR determination by diluting the sample to 2 mg/ml in 1×PBS, deglycosylating the sample with PNGaseF (in-house) for 10 minutes at 50° C., removing the PNGaseF by binding to protein A, washing with 1×PBS, and eluting with 1% formic acid. Sample was reduced by adding ¼ volume of 5M ammonium acetate pH 5.0 containing 0.5M TCEP and incubating at room temperature for 30 minutes. Sample was then injected onto an 2.1×50 mm PLRP-S column (8 µm particles, 1000 Å poresize), equilibrated to 0.1% formic acid in 20% CH₃CN/water (Invitrogen) running at 0.5 ml/min. The column was washed at 20% CH₃CN/ water for 3 minutes then eluted with a 0.1 minute gradient to 0.1% formic acid 90% CH₃CN/ water which was maintained for 1.9 minutes. Mass spectral data was taken on an Agilent 1260 instrument and deconvoluted with MassHunter Qualitative Analysis B.05.00 in a range 15-60 kDa. Peak areas corresponding to various calculated DAR states were weighted according to DAR of each peak, then summed and weighted area of the DAR4 peak was divided by the sum of all weighted peaks to obtain the DAR value.

Analytics on the Resultant Sample is as Follows:

| Parameter | 506E15.DAPA.AURIX2 | 506E15.AURIX1 | 674J13.DAPA.AURIX2 | 674J13.AURIX1 | 121G12.AURIX1 | 121G12.DAPA AURIX1 |
|---|---|---|---|---|---|---|
| Concentration (mg/ml) | 1.9 | 6.7 | 9 | 8.4 | 7.5 | 7.8 |
| Pyrogen (EU/ml) | 0.05 | 0.42 | 0.05 | <0.5 | 0.05 | 0.05 |
| % aggregate | <1 | <1 | 2.8 | <1 | 1.2 | 1.9 |
| DAR | 3.80 | 3.78 | HC 3.93 LC 0.03 | HC 3.8 | 3.80 | 3.80 |

Example 4J: Preparation of Additional Conjugates Using Other CysMab Antibodies

The methods described in Example 4A are also used to produce MPET.DM4 conjugates with other cysteine engineered antibodies.

The methods are used to product anti-P-cadherin Ab.CysMab.MPET.DM4 conjugates using antibodies NOV169N31Q(E152C-S375C), NEG0012(E152C-S375C), NEG0013(E152C-S375C), NEG0016(E152C-S375C), NEG0064(E152C-S375C), NEG0067(E152C-S375C), NOV169N31Q(K360C(HC)-K107C(LC)), NEG0012 (K360C(HC)-K107C(LC)), NEG0013(K360C(HC)-K107C (LC)), NEG0016(K360C(HC)-K107C(LC)), NEG0064 (K360C(HC)-K107C(LC)), and NEG0067(K360C(HC)-K107C(LC)) disclosed in PCT Publication No. WO2016/203432.

Example 5: In Vitro ADC Characterization

Antibody drug conjugates (ADCs) were characterized by various functional and analytical methods. ADCs retained binding to target CCR7 protein on cells as assessed by FACS. For all ADCs, the geometric mean fluorescence intensity in FACS binding assay was within 20% of the value for the unconjugated antibody. By analytical SEC, ADCs were shown to be >95% material at desired molecular weight; in cases where this was not observed for initial reaction products, use of preparative SEC attained the necessary specification. Drug antibody ratio (DAR) was assessed by LCMS of the deglycosylated reduced antibody sample, summing the abundances of various DAR species and weighting by the number of drug molecules on each DAR species (e.g., a single DAR2 ion counts as 2, a single DAR1 ion counts as 1). Conjugates comprising constant regions containing two cysteine mutations were at least at or above DAR 3.4 and most commonly at or above DAR 3.8. This was consistent across reported conjugates.

Example 6: Inhibition of Cell Proliferation/Cellular Viability Assay

Above we showed that fluorophore-conjugated versions of all three anti-CCR7 antibodies can internalize CCR7 and effectively accumulate the conjugated fluorophore in the low-pH departments of cells across a panel of cell lines. Here we show the antibody's capability to internalize and accumulate conjugated matter intracellularly in a setting where the conjugated matter is a toxic payload.

In a piggyback ADC (pgADC) setting, cytotoxic effects of anti-CCR7 antibodies complexed with a payload-conjugated secondary antibody fragment were studied by assessing cell viability after four days of treatment. Three fold dilutions of the CCR7-specific IgGs were prepared and mixed with a constant amount of payload-coupled Fab fragment. The final concentration of payload-coupled Fab fragment was 0.5 µg/ml. The Fab reagent is an anti-mouseFc directed Fab conjugated either to MMAF or to Saporin (Advanced Targeting Systems, Fab-Zap). After pre-incubation for 30 min at room temperature, 10 µl/well of the antibody-payload complex was added to 384-well bottom white plates in triplicates. Respective CCR7(+) cells were seeded such that their density was less than $1\times10^6$/ml for suspension cells and 80% confluency was reached for adherent cells. Cells were harvested (adherent cells were detached with Accutase) and resuspended to approximately $2\times10^4$ cells/ml. Cells were added to 384-well plates on top of the antibody-payload complex (20 µl/well). The plate was incubated for four days at 37° C. and 5% $CO_2$. Subsequently, 20 µl/well of CellTiter-Glo solution (CellTiter-Glo® Luminescent Cell Viability Assay; Promega, #G7571) were prepared and added to the cells. Only viable cells are producing ATP, which is needed for the luciferase reaction (provided by CellTiter-Glo) resulting in luminescence. According to this, the cell viability was determined by the luminescence signal, which was measured after 10 min of incubation at 22° C. and 400 rpm with the Envision 2104 Multilabel reader. IC50 values were calculated using the Graphpad Prism software.

Figure 7A:
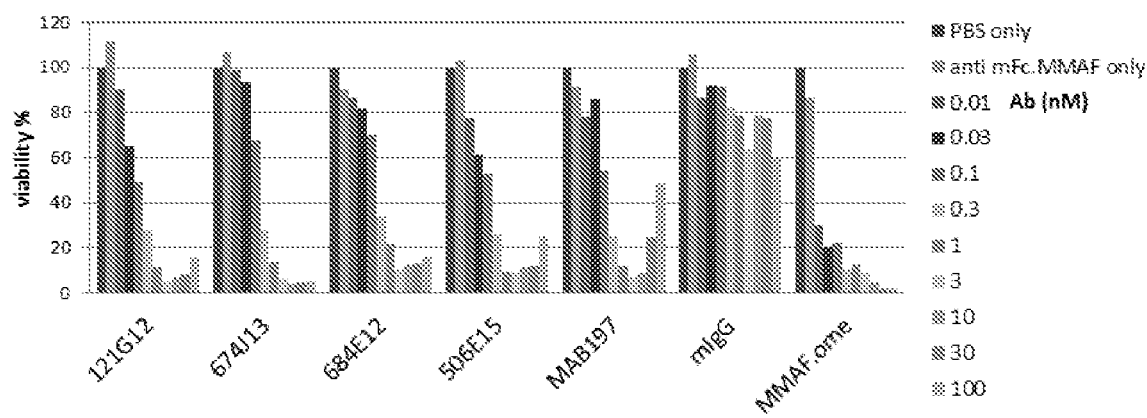
FIG. 7A-B depicts experimental data on piggyback ADC (pgADC) assays of parental anti-CCR7 antibodies complexed with a payload-conjugated secondary antibody fragment.
Figure 7B:
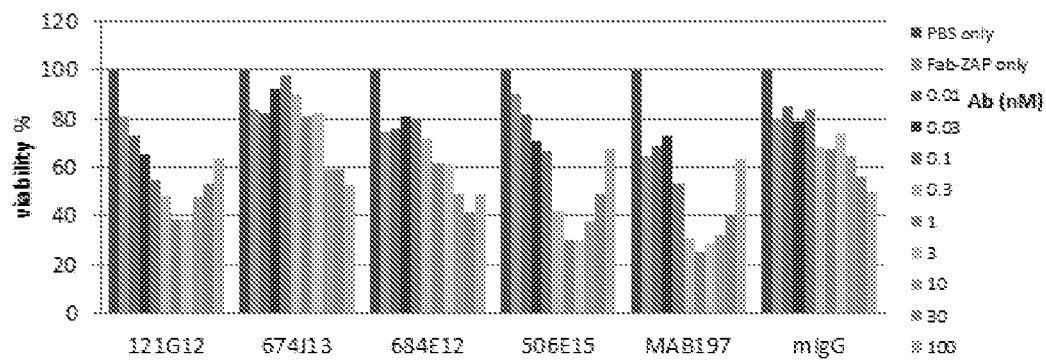

FIG. 7A and FIG. 7B shows that all four anti-CCR7 antibodies are capable of concentration-dependent cell killing of CCR7+KE97 cells in the piggyback assay format using the MMAF-conjugated reagent. The table below summarizes results from experiments using MMAF or Saporin as tool piggy-back payloads.

TABLE 16

IC50 and AMAX of anti-CCR7 antibodies in pgADC cytotoxic assay

|  | Anti-mFc.MMAF | | Fab-ZAP | |
| --- | --- | --- | --- | --- |
|  | IC50 (nM) | AMAX (%) | IC50 (nM) | AMAX (%) |
| 121G12 Parental | 0.055 | 104 | 0.064 | 43 |
| 506E15 Parental | 0.070 | 95 | 0.135 | 60 |
| 674J13 Parental | 0.137 | 102 | 6.12 | 31 |
| 684E12 Parental | 0.214 | 80 | 2.60 | 33 |
| MAB197 (R&D) | 0.142 | 85 | 0.155 | 40 |

Figure 8:
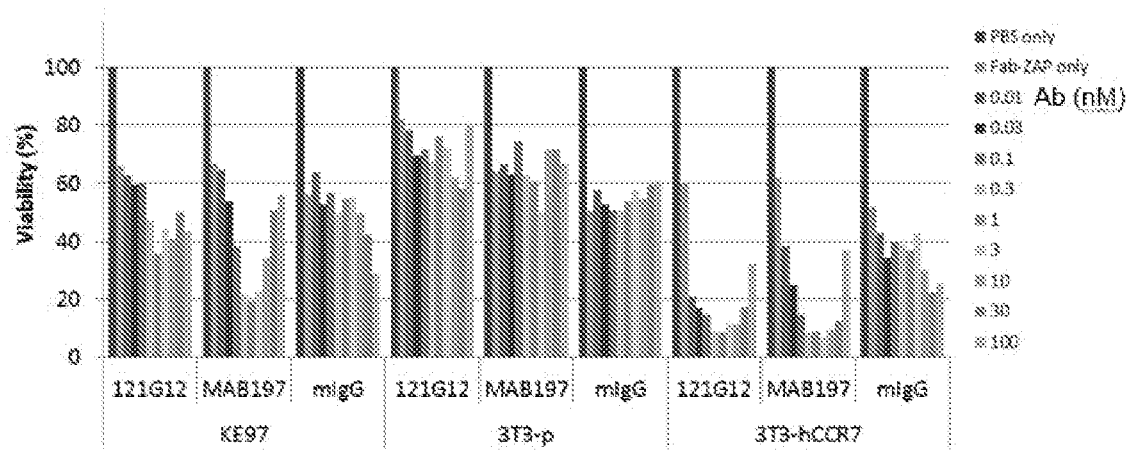
FIG. 8 depicts experimental data on piggyback ADC (pgADC) killing assay of cytotoxic effects of 121G12 parental Ab complexed with a payload-conjugated secondary antibody fragment using target negative cell lines.

Specificity of pgADC killing was assessed using target negative cell lines. An example is shown in FIG. 8 using the FabZap reagent. Specific CCR7-dependent increase in 121G12 pgADC activity is seen in KE97 and NIH3T3.hCCR7 cells in contrast to CCR7 negative NIH3T3 parental cells or mIgG control antibody.

Example 7: Impact of Mouse-Cross-Reactive Unconjugated or AURIX1 Conjugated Anti-CCR7 Antibodies on Normal Mouse Hematopoietic Cells In Vivo Normal tissue expression across species is restricted to cells of hematopoietic origin, including CD4+ and CD8+ T cells in blood and lymphoid organs, presenting a potential safety liability for CCR7 targeting ADC, especially in a wild type Fc format that could lead to ADCC and lymphoid cell depletion.

To determine impact of targeting CCR7 with an ADC on normal hematopoietic cells in vivo, a mouse cross-reactive 121G12 parental Ab either unconjugated or conjugated to AURIX1 was evaluated in healthy female 6-8 week-old CD-1 mice either in a wild type or silenced (DAPA) Fc format. Mice received a single IV treatment of 121G12 parental.Cys-Mab.wild type Fc.hIgG1 (121G12.wt.Fc), 121G12 parental.Cys-Mab .DAPA.hIgG1 (121G12.DAPA.Fc), 121G12 parental.Cys-Mab.wild type Fc.hIgG1.AURIX1 (121G12.wt.Fc.AURIX1) or 121G12.parental.Cys-Mab .DAPA.hIgG1.AURIX1 (121G12.DAPA.Fc.AURIX1) at a final dose of 10 mg/kg. All doses were adjusted to individual mouse body weights.

On day 25 post treatment spleens were extracted and dissociated into single cell suspensions using the gentleMACS Dissociator (Miltenyi Biotec Inc, San Diego, Calif.). 1 million cells for each sample were then stained with a cocktail of Abs, that included BUV737 Rat Anti-Mouse CD8a Antibody, clone 53-6.7 (1:100) (BD Biosciences, San Jose, Calif., Cat #564297) and BV510 Rat Anti-Mouse CD4, clone RM4-5 (1:200) (BD Biosciences, San Jose, Calif., Cat #563106) to determine impact of the individual treatments on CD4+ and CD8a+ T cells. Samples were incubated at 4° C. for 30 min, washed in ice-cold HyClone Phosphate Buffered Saline (Hyclone Laboratories, Logan, Utah) and evaluated on the BD LSRFortessa™ cell analyzer (BD Biosciences, San Jose, Calif.). Total splenocyte cell counts were used to determine CD4+ or CD8a+ T-cell depletion. T-Test was used to determine significance between groups.

Figure 9:
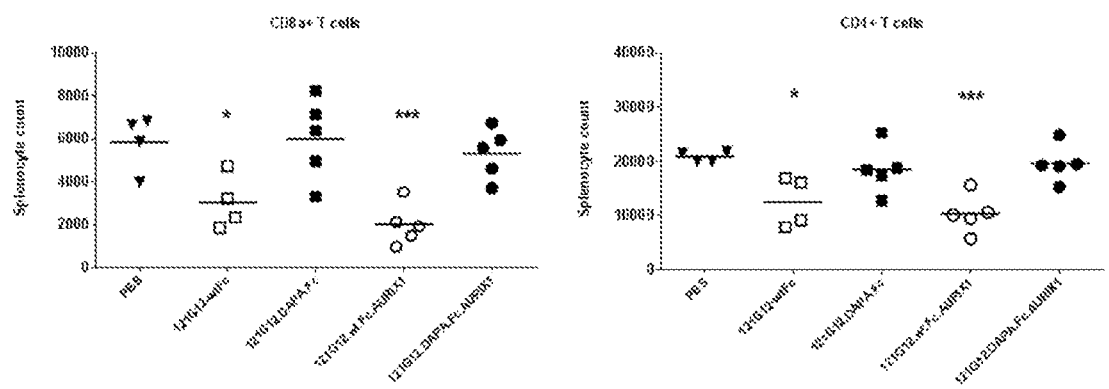
FIG. 9 depicts graphs illustrating CD4+ and CD8a+ T cell depletion with a mouse CCR7 cross-reactive 121G12 parental Ab in a CysMab wild type Fc format, either as an antibody alone or conjugated to an auristatin cytotoxin, the effects of which are rescued by switching to a DAPA silenced Fc format.

As shown in Table 17 and FIG. 9, a strong reduction of CD4+ (FC 0.5-0.6) and CD8a+ T cells (FC 0.3-0.5) in the spleen was observed by Day 3 of treatment with either 121G12.wt.FC or 121G12.wt.Fc.AURIX1 Abs at 10 mg/kg, suggesting T cell depletion impact was independent of presence of AURIX1 payload. These effects were rescued by silencing the Fc through the introduction of DAPA mutations. Both 121G12.DAPA.Fc and 121G12.DAPA.Fc.AURIX1 failed to impact the T cell populations relative to No Treatment group. These data indicate that anti-CCR7 ADCs may have a T cell depletion safety liability that can be rescued through DAPA silencing of the Fc.

TABLE 17

Impact of 121G12 Antibody on CD4+ and CD8a+ T cell populations in CD-1 mice

|  | No Treatment | 121G12-wtFc | 121G12.DAPA. Fc | 121G12.wt.Fc. AURIX1 | 121G12.DAPA. Fc.AURIX1 |
| --- | --- | --- | --- | --- | --- |
| | CD8+ T cells | | | | |
| Mean | 5833 | 3041 | 6003 | 2013 | 5317 |
| SE | 650 | 629 | 860 | 426 | 526 |
| Fold Change |  | 0.5 | 1.0 | 0.3 | 0.9 |
| p value |  | <0.05 | NS | <0.001 | NS |

TABLE 17-continued

Impact of 121G12 Antibody on CD4+ and CD8a+ T cell populations in CD-1 mice

| | No Treatment | 121G12-wtFc | 121G12.DAPA.Fc | 121G12.wt.Fc.AURIX1 | 121G12.DAPA.Fc.AURIX1 |
|---|---|---|---|---|---|
| | | | CD4+ T cells | | |
| Mean | 20896 | 12512 | 18547 | 10324 | 19633 |
| SE | 480 | 2326 | 2004 | 1602 | 1520 |
| Fold Change | | 0.6 | 0.9 | 0.5 | 0.9 |
| p value | | <0.05 | NS | <0.001 | NS |

The experiment was evaluated on treatment Day 25. Fold change (FC)=Mean Splenocyte counts on Day 25 for indicated Treatment Group/Mean Splenocyte Counts for No Treatment Control Group on Day 3. T-Test was used to determine significance vs. No Treatment group (*p<0.05, * * * p<0.001; NS=not significant).

Example 8: Anti-CCR7 ADC Activity of Direct Conjugates

Cytotoxic effects after binding of directly conjugated antibodies (ADCs) with various payloads and their internalization into CCR7(+) cells were studied by assessing cell viability after four days of treatment. Three fold dilutions of the ADCs were added to 384-well bottom white plates in triplicates (10 μl/ml). Respective CCR7(+) cells were seeded such that their density was less than $1 \times 10^6$/ml for suspension cells and 80% confluency was reached for adherent cells. Cells were harvested (adherent cells were detached with Accutase) and resuspended to approximately $2 \times 10^4$ cells/ml. Cells were added to 384-well plates on top of the antibody (20 μl/well). The plates were incubated for four days at 37° C. and 5% $CO_2$. Subsequently, 20 μl/well of CellTiter-Glo solution (CellTiter-Glo® Luminescent Cell Viability Assay; Promega, #G7571) was prepared and added to the cells. Cell viability was determined by the luminescence signal, which was measured after 10 min of incubation at 22° C. and 400 rpm with the Envision reader. IC50 values were calculated using the Graphpad Prism software.

The table below shows examples of cell viability effects measured with anti-CCR7 CysMab antibodies in either wild type Fc or silenced (DAPA) Fc format conjugated to AURIX1 or AURIX2.

TABLE 18

IC50 of Anti-CCR7 ADCs in Cytotoxic Assay

| | | ADC activity in cell viability assay; IC50 (nM) | | | |
|---|---|---|---|---|---|
| Cell line | Cancer type | 506E15.CysMab.AURIX1 | 674J13.CysMab.AURIX1 | 506E15.CysMab.DAPA.AURIX2 | 674J13.CysMab.DAPA.AURIX2 |
| DEL | ALCL | 0.0029 | 0.0741 | 0.0084 | 0.1167 |
| KE97 | Multiple myeloma | 0.0031 | 0.03 | 0.0131 | 0.0658 |

To assess the ADCs for target-specificity and receptor-level dependency, ADC activity was tested across cell lines with different CCR7 receptor levels. The table below shows an example for the humanized 674J13 antibody in CysMab.DAPA format and conjugated to AURIX2. Cell lines were chosen based on similar sensitivity to payload.

TABLE 19

IC50 of the humanized 674J13 antibody in DAPA format and conjugated to AURIX2

| Cell line | Cancer type | CCR7 receptor levels | ADC activity in cell viability assay; IC50 (nM) 674J13.CysMab.DAPA.AURIX2 |
|---|---|---|---|
| DEL | ALCL | ~100,000 | 0.2417 (>95% AMAX) |
| KE97 | Multiple Myeloma | ~100,000 | 0.1018 (>95% AMAX) |
| SR786 | Anaplastic large T cell lymphoma | ~28,000 | 2.737 (90% AMAX) |
| CML-T1 | T cell leukemia | ~29,000 | 3.779 (60% AMAX) |
| DND-41 | T cell leukemia | 1,700 | <20% AMAX |
| NCI-H82 | Small cell lung cancer | 0 | No killing |

As seen in the pHrodo experiment, ADC activity requires a higher degree of receptor numbers than the ADCC modality. The exact receptor cut-off depends on various parameters (e.g., antibody avidity, payload potency), but the data shown here describe the general concept. Using an avidity-dependent anti-CCR7 antibody in DAPA-format, biases ADC activity towards cancer cells over normal CCR7+ PBMCs, which are here represented by cancer cell lines with less than 2,000 CCR7 receptors.

Example 9: Introduction of a Site-Specific MPET.DM4 ADC

DM4 conjugated ADCs are well established in the ADC field. Here we describe the generation and use of a site-specifically conjugated MPET.DM4 using the CysMab version of the antibodies, which has the advantage of yielding a reproducibly homogeneous, DAR-controlled ADC batch, where the DAR (drug to antibody ratio) is about 4. Non-site specific conjugates have been described to often contain significant populations with high DAR, which have been linked to unfavorable biophysical features including increased hydrophobicity, and consequentially more rapid clearance, poor PK profile and increased toxicity. Below we show various in vitro and in vivo assessments of an MPET.DM4 based anti-CCR7 ADC in comparison to its sSPDB.DM4 counterpart.

Example 10: FACS Binding Affinity of MPET.DM4 Versus sSPDB.DM4 ADCs

Another potential improvement of site-specific conjugation over non site-specific conjugation could be a potential interference of Lysine-conjugation sites that are structurally in the vicinity of essential CSD residues. Payload conjugation to such Lysine sites may be expected to impact binding affinity of the ADC. To test binding affinities of ADCs using the here described CysMab conjugated MPET.DM4 versus endogenous Lysine conjugated sSPDB.DM4, binding affinity was determined by FACS as described above. The table below summarizes some representative affinity data, which show a mild decrease in binding affinity of the sSPDB.DM4 ADC versus the MPET.DM4 ADC.

TABLE 20

Binding affinity of anti-CCR7 ADCs

| Cell line | CCR7 receptor levels | 121G12.CysMab.DAR4 unconjugated | 121G12.CysMab.DAPA.MPET.DM4 (DAR 3.8) | 121G12.DAPA.sSPDB.DM4 (DAR3.9) |
|---|---|---|---|---|
| | | ADC affinity in FACS; EC50 (nM) | | |
| DEL | ≥100,000 | 5.24 | 5.61 | 8.42 |

Example 11: In Vitro Activity of MPET.DM4 Versus sSPDB.DM4 ADCs

Cytotoxic effects of the ADCs 121G12.CysMab.DAPA.MPET.DM4 and 121G12.DAPA.sSPDB.DM4 (DAR3.9) were assessed in an in vitro viability assay as described above. The table below shows similar, slightly improved activity of the MPET.DM4 conjugate compared to sSPDB.DM4. This may be the consequence of better conserved affinity or other factors.

TABLE 21

In vitro cytotoxic activity of anti-CCR7 ADCs

| Cell line | 121G12.CysMab.DAPA.MPET.DM4 | 121G12.DAPA.sSPDB.DM4 (DAR3.9) |
|---|---|---|
| | ADC activity in cell viability assay; IC50 (nM) | |
| L540 | 2.944 | 3.905 |
| DEL | 2.286 | 2.983 |
| KE97 | 2.171 | 3.177 |

The 121G12.CysMab.DAPA.MPET.DM4 ADC was further tested in a variety of cancer cell lines covering various indication settings, where it achieved substantial cell killing that correlates to receptor densities.

TABLE 22

In Vitro Cytotoxic Activity of Anti-CCR7 ADCs in Cell Lines

| Cell line | Cancer type | Relative receptor density (%) | 121G12.CysMab.DAPA.MPET.DM4 IC50 (nM) |
| --- | --- | --- | --- |
| SUPHD1 | Hodgkin's Lymphoma | 310 | 1.69 |
| L540 | Hodgkin's Lymphoma | 175 | 4.90 |
| KE97 | Multiple Myeloma | 100 | 2.24 |
| JVM2 | MCL | 79 | 4.62 |
| MOTN1 | CLL | 67 | 4.24 |
| DEL | ALCL | 67 | 2.28 |
| OCI-Ly3 | ABC-DLBCL | 43 | 6.42 |
| Toledo | DLBCL | 20 | n.d. |
| Mec-2 | CLL | 15 | >20 |
| PEER | T-ALL | 2 | >20 |

Example 12: Dose Dependent In Vivo Efficacy of 121G12.CysMab.DAPA.MPET.DM4 and 121G12.DAPA.sSPDB.DM4 Against KE97 Multiple Myeloma Xenograft Model in SCID-Beige Mice To demonstrate targeted anti-tumor activity of 121G12.CysMab.DAPA.MPET.DM4 and 121G12.DAPA.sSPDB.DM4 in vivo, KE97 xenograft model was established in female SCID-beige mice by subcutaneous injection of $3 \times 10^6$ cells into the right flank of each mouse. Once tumors reached approximately 135 mm³, mice were randomized according to tumor volume into treatment groups (n=8 per group). Mice received an IV treatment of either 121G12.CysMab.DAPA.MPET.DM4 (DAR4) at a final dose of 0.5, 2 or 5 mg/kg, 121G12.DAPA.sSPDB.DM4 (DAR 3.9) at 0.5, 2 or 5 mg/kg, or a non-specific isotype control IgG1.CysMab.DAPA.MPET.DM4 at 5 mg/kg. All doses were adjusted to individual mouse body weights.

All test agents were tolerated on study and no overt clinical symptoms of toxicities or body weight loss were observed in any of the treatment groups (Table 23).

TABLE 23

Anti-CCR7 ADC dose response efficacy in KE97 xenograft model

| Treatment | Dose, schedule | Tumor Response ΔT/ΔC (%) | Tumor Response Regression (%) | Host Response Δ body weight (%) | Host Response Survival (alive/total) |
| --- | --- | --- | --- | --- | --- |
| No treatment | None | 100 | — | 2.09 | 8/8 |
| IgG1.CysMab.DAPA.MPET.DM4 | 5 mg/kg Single dose | 92.94 | — | 3.02 | 8/8 |
| 121G12.CysMab.DAPA.MPET.DM4 | 0.5 mg/kg Single dose | 78.62 | — | 1.05 | 8/8 |
| 121G12.CysMab.DAPA.MPET.DM4 | 2 mg/kg Single dose | — | 33.07* | 2.74 | 8/8 |
| 121G12.CysMab.DAPA.MPET.DM4 | 5 mg/kg Single dose | — | 53.66* | 0.46 | 8/8 |
| 121G12.DAPA.sSPDB.DM4 | 0.5 mg/kg Single dose | 85.38 | — | 1.84 | 8/8 |

TABLE 23-continued

Anti-CCR7 ADC dose response efficacy in KE97 xenograft model

|  |  | Tumor Response | | Host Response | |
|---|---|---|---|---|---|
|  |  |  |  | Δ body | Survival |
| Treatment | Dose, schedule | ΔT/ΔC (%) | Regression (%) | weight (%) | (alive/total) |
| 121G12.DAPA.sSPDB.DM4 | 2 mg/kg Single dose | 13.77* | — | 0.59 | 8/8 |
| 121G12.DAPA.sSPDB.DM4 | 5 mg/kg Single dose | — | 32.63* | 3.63 | 8/8 |

The experiment was evaluated on treatment Day 9 (Day 23 post implant),
*p < 0.001 versus control No Treatment group (One-Way ANOVA/Tukey's Multiple Comparisons Test). % ΔT/ΔC = 100 ΔT/ΔC where: ΔT = mean tumor volume of the drug treated group on D 23 of study − mean tumor volume of the drug treated group on initial day of dosing; ΔC = mean tumor volume of the control group on D 23 of study − mean tumor volume of the control group on initial day of dosing D 14. % Regression = (1 − T final/T initial) x 100, where T final is mean tumor volume D 23 and T initial is defined as tumor volume on D 14 post implant.
Δ body weight (%) = (Mean body weight D 23 − mean body weight D 14) *100/Mean body weight D 14 of treatment.

Figure 10:
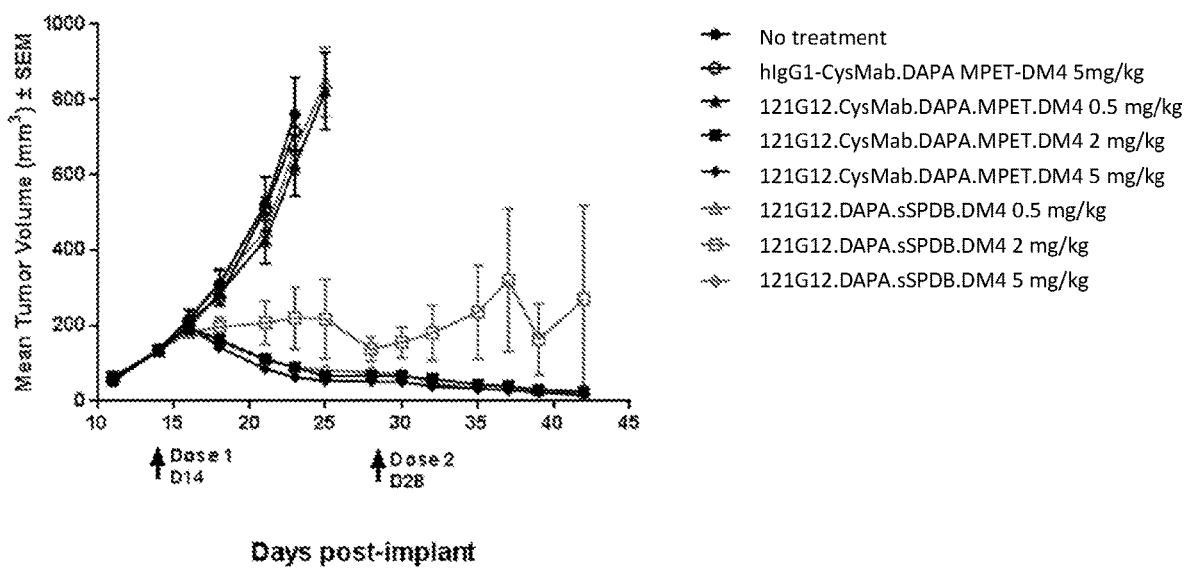
FIG. 10 depicts a graph illustrating dose response efficacy of antibody drug conjugates 121G12.CysMab.DAPA.MPET.DM4 and 121G12.DAPA.sSPDB.DM4 in a KE97 multiple myeloma xenograft model.

No significant anti-tumor efficacy was observed after treatment with the non-specific isotype control IgG1.CysMab.DAPA.MPET.DM4 at 5 mg/kg. 121G12.CysMab.DAPA.MPET.DM4 treatment resulted in dose-dependent anti-tumor efficacy, with ΔT/ΔC value of 78.62% (0.5 mg/kg), while doses of 2 and 5 mg/kg resulted in mean regression of 33% and 54% respectively by D9 post first dose (D23 post implant). 121G12.DAPA.sSPDB.DM4 treatment also demonstrated dose-dependent anti-tumor efficacy with AT/AC values of 85.38% (0.5 mg/kg) and 13.77% (2 mg/kg), while the 5 mg/kg dose resulted in mean regression of 33% by D9 post first dose (D23 post implant). By D23-D25 post implant, control groups and 0.5 mg/kg treatment groups were euthanized, and remaining groups received a second dose on D28 post implant of either 121G12.CysMab.DAPA.MPET.DM4 at 2 or 5 mg/kg or 121G12.DAPA.sSPDB.DM4 at 2 or 5 mg/kg. Sustained tumor regression was observed with 121G12.CysMab.DAPA.MPET.DM4 at 2 and 5 mg/kg, as well as with 121G12.DAPA.sSPDB.DM4 at 5 mg/kg through to the end of study on D42 post implant. At 2 mg/kg with 121G12.DAPA.sSPDB.DM4 the response was more heterogeneous, with approximately 25% of the mice displaying sustained tumor regression, while the rest of the group showing either stable disease or tumor progression (FIG. 10, Table 23).

Example 13: Efficacy Assessment of 121G12.CysMab.DAPA.MPET.DM4 vs 121G12.DAPA.sSPDB.DM4 in the KE97 Multiple Myeloma Model at Larger Starting Tumor Volumes A higher bar in vivo model was set up using the KE97 multiple myeloma cell line to further differentiate the anti-tumor efficacy of the different cleavable linkers comparing efficacy of 121G12.CysMab.DAPA.MPET.DM4 121G12.DAPA.sSPDB.DM4 (DAR3.9) in tumors with larger starting tumor volumes at first dose. KE97 xenograft model was established in female SCID-beige mice by subcutaneous injection of 3×10$^6$ cells into the right flank of each mouse. Once tumors reached approximately 450 mm$^3$, mice were randomized according to tumor volume into two treatment groups (n=8). Mice received an IV treatment of 2 mg/kg of either 121G12.CysMab.DAPA.MPET.DM4 or 121G12.DAPA.sSPDB.DM4.

Figure 11:
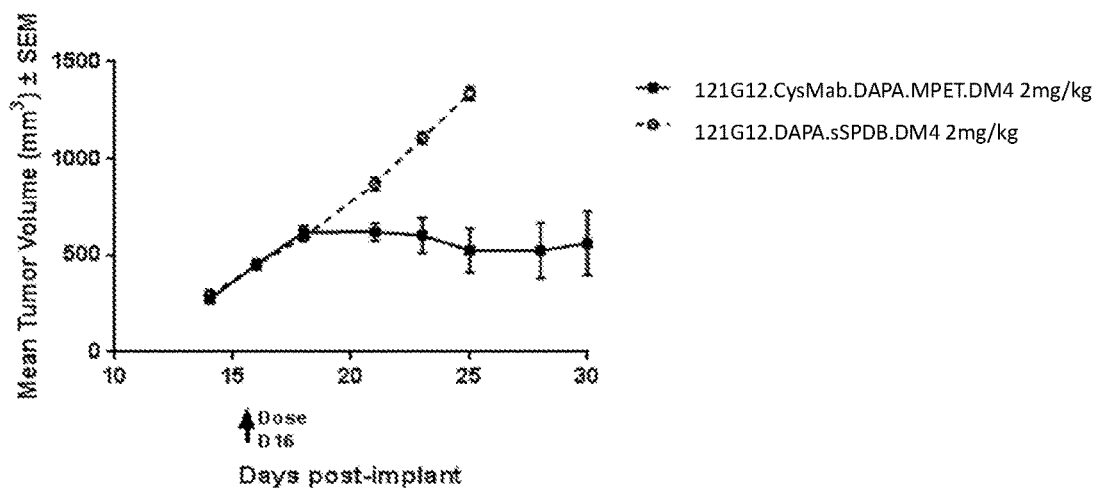
FIG. 11 depicts a graph illustrating activity of antibody drug conjugates 121G12.CysMab.DAPA.MPET.DM4 and 121G12.sSPDB.DM4 in a KE97 multiple myeloma model with dosing initiated at a larger starting tumor burden than FIG. 10.

No significant anti-tumor efficacy was observed after treatment with the 121G12.DAPA.sSPDB.DM4 at 2 mg/kg. 121G12.CysMab.DAPA.MPET.DM4 treatment resulted in partial regression/prolonged stasis in 75% (6 of 8) of the mice with a single dose treatment (FIG. 11). 121G12.CysMab.DAPA.MPET.DM4 strongly out-performed 121G12.DAPA.sSPDB.DM4 in this model (D25 Mean Tumor Volume 524.83±143.20 vs 1337.13±35.13 respectively, p<0.001; unpaired T-Test).

Example 14: In Vivo Efficacy of 121G12.CysMab.DAPA.MPET.DM4 Against Primary Patient Derived Non-Small Cell Lung Cancer HLUX1934 Tumor Model Anti-tumor activity of 121G12.CysMab.DAPA.MPET.DM4 was evaluated in the CCR7 expressing HLUX1934 primary non-small cell lung cancer xenograft model. Female athymic nude mice were implanted subcutaneously with tumor fragments into the right flank of each mouse. Once tumors reached approximately 100 mm$^3$, mice were randomized according to tumor volume into treatment groups (n=8). Mice received an IV treatment of either 121G12.CysMab.DAPA.MPET.DM4 (DAR4) at 10 mg/kg, or a non-specific isotype control IgG1.CysMab.DAPA.MPET.DM4 at 10 mg/kg. A second dose of each antibody was delivered 2 weeks later. All doses were adjusted to individual mouse body weights.

Figure 12:
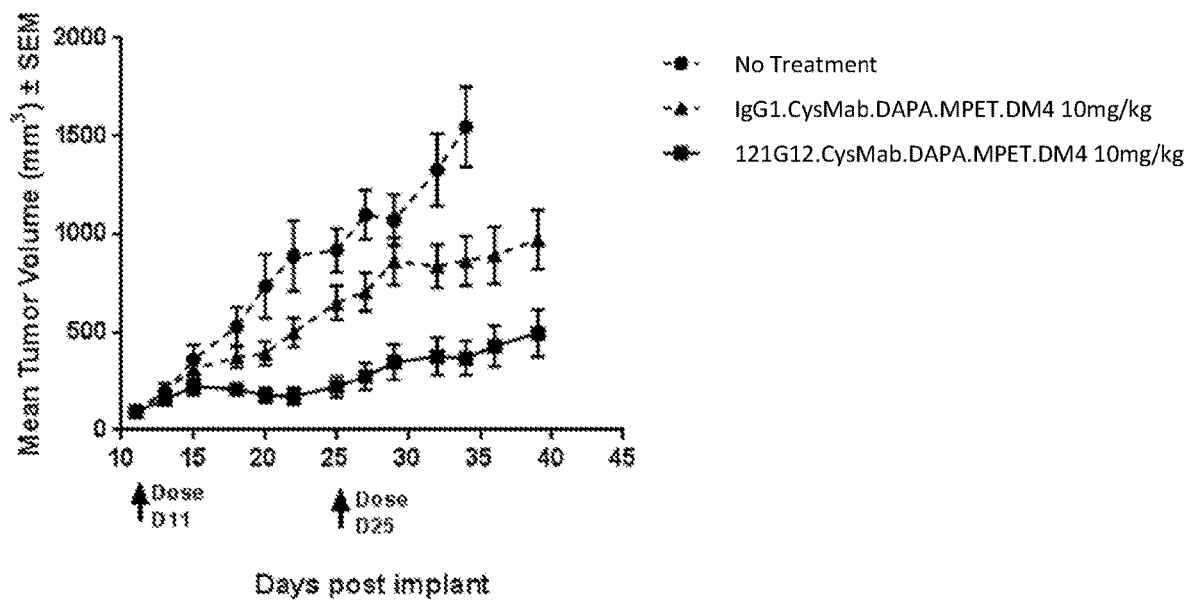
FIG. 12 depicts a graph illustrating in vivo activity of conjugate 121G12.CysMab.DAPA.MPET.DM4 in a primary non-small cell lung tumor model HLUX1934.

Non-specific isotype control IgG1.CysMab.DAPA.MPET.DM4 at 10 mg/kg appeared to slightly delay tumor growth relative to the No Treatment group (ΔT/ΔC value 53.07%) potentially due to non-specific binding of the antibody to an off-target in the HLUX1934 model. 121G12.CysMab.DAPA.MPET.DM4 treatment resulted in more pronounced efficacy that was sustained with the administration of the second dose. The 10 mg/kg dose of 121G12.CysMab.DAPA.MPET.DM4 treatment was well tolerated with no apparent body weight loss and AT/AC value of 18.83% on D34 post implant. (FIG. 12, Table 24).

TABLE 24

121G12.CysMab.DAPA.MPET.DM4 efficacy in the HLUX1934 NSCLC patient derived model. The experiment was evaluated on Day 34 post implant (D 23 post treatment).

| Treatment | Dose | Tumor Response ΔT/ΔC (%) | Host Response Δ body weight (%) | Survival (alive/total) |
|---|---|---|---|---|
| No treatment | None | 100 | 5.12 | 5/8** |
| IgG1.CysMab.DAPA.MPET.DM4 | 10 mg/kg | 53.07 | 2.81 | 8/8 |
| 121G12.CysMab.DAPA.MPET.DM4 | 10 mg/kg | 18.83* | 0.61 | 8/8 |

*p < 0.001 versus control No Treatment group (One-Way ANOVA/Tukey's Multiple Comparisons Test). % ΔT/ΔC = 100 ΔT/ΔC where: ΔT = mean tumor volume of the drug treated group on D 34 of study − mean tumor volume of the drug treated group on initial day of dosing; ΔC = mean tumor volume of the control group on D 34 of study − mean tumor volume of the control group on initial day of dosing. Δ body weight (%) = (Mean body weight D 34 − mean body weight D 11) *100/Mean body weight D 11 of treatment.
**Mice euthanized in the No Treatment group due to excessive tumor burden D 25-D 27 post treatment.

Example 15: In Vivo Efficacy of 684E12.SMCC.DM1 Against KE97 Multiple Myeloma Xenograft Model in SCID-Beige Mice To demonstrate targeted anti-tumor activity of 684E12.SMCC.DM1 in vivo, KE97 xenograft model was established in female SCID-beige mice by subcutaneous injection of $3 \times 10^6$ cells into the right flank of each mouse. Once tumors reached approximately 200 mm$^3$, mice were randomized according to tumor volume into treatment groups (n=8 per group). Mice received an IV treatment of either parental 684E12.SMCC.DM1 (DAR2.6) at a final dose of 2 or 6 mg/kg or a non-specific isotype control IgG1.SMCC.DM1 at 6 mg/kg. All doses were adjusted to individual mouse body weights.

Figure 13:
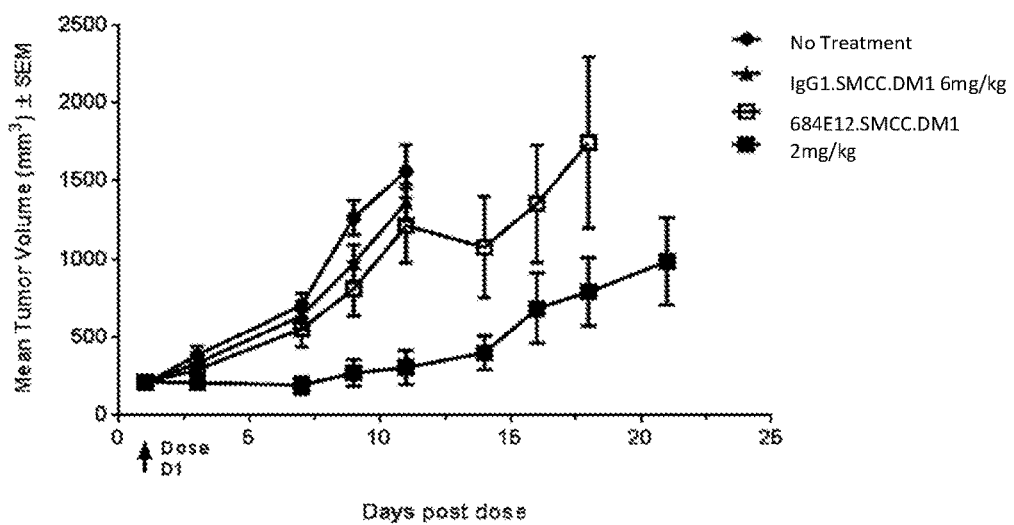
FIG. 13 depicts a graph illustrating activity of conjugated parental 684E12.SMCC.DM1 in a KE97 multiple myeloma xenograft model.

All test agents were tolerated on study and no overt clinical symptoms of toxicities or body weight loss were observed in any of the treatment groups. No significant anti-tumor efficacy was observed after treatment with the non-specific isotype control IgG1.SMCC.DM1 or parental 684E12.SMCC.DM1 at 2 mg/kg. Parental 684E12.SMCC.DM1 6 mg/kg treatment resulted in AT/AC value 6.72% on D11 post dose (p<0.0001, One-Way ANOVA/Tukey's Multiple Comparisons Test) (FIG. 13).

Example 16: In Vivo On-Target Pharmacodynamic Marker Modulation by 121G12.CysMab.DAPA.MPET.DM4 in the KE97 Tumor Model Accumulation of the phospho-histone H3 marker positive tumor cells post treatment with 121G12.CysMab.DAPA.MPET.DM4 was used to assess the ability of anti-CCR7 ADC to induce G2/M arrest in vivo.

A study was conducted where KE97 xenograft model was established in female SCID-beige mice by subcutaneous injection of $3 \times 10^6$ cells into the right flank of each mouse. Once tumors reached approximately 140 mm$^3$, mice were randomized according to tumor volume into treatment groups (n=3 per group). Mice received a single IV treatment of either 121G12.CysMab.DAPA.MPET.DM4 at a final dose of 2, 5 or 10 mg/kg, or a non-specific isotype control IgG1.CysMab.DAPA.MPET.DM4 at 10 mg/kg. All doses were adjusted to individual mouse body weights. 48 hr post treatment tumors were collected for assessment of phospho-histone H3 levels by immunohistochemical staining described below.

To measure accumulation of phospho-Histone H3 positive nuclei by immunohistochemistry a rabbit polyclonal antibody targeting residues surrounding phosphorylated Serine 10 of human histone H3 was obtained from Ventana Medical Systems (Tuscon, Ariz., Cat #760-4591). The IHC protocol included heat and mild exposure (32 min) to Ventana Discovery Cell Conditioner 1 antigen retrieval reagent. The samples were incubated for 60 min at room temperature with the primary antibody (pre-diluted by manufacturer). Subsequently incubation with OmniMap anti-rabbit HRP secondary Ab (Ventana, Tuscon, Ariz., Cat #760-4311) was performed for 12 min (pre-diluted by manufacturer).

Figure 14A:
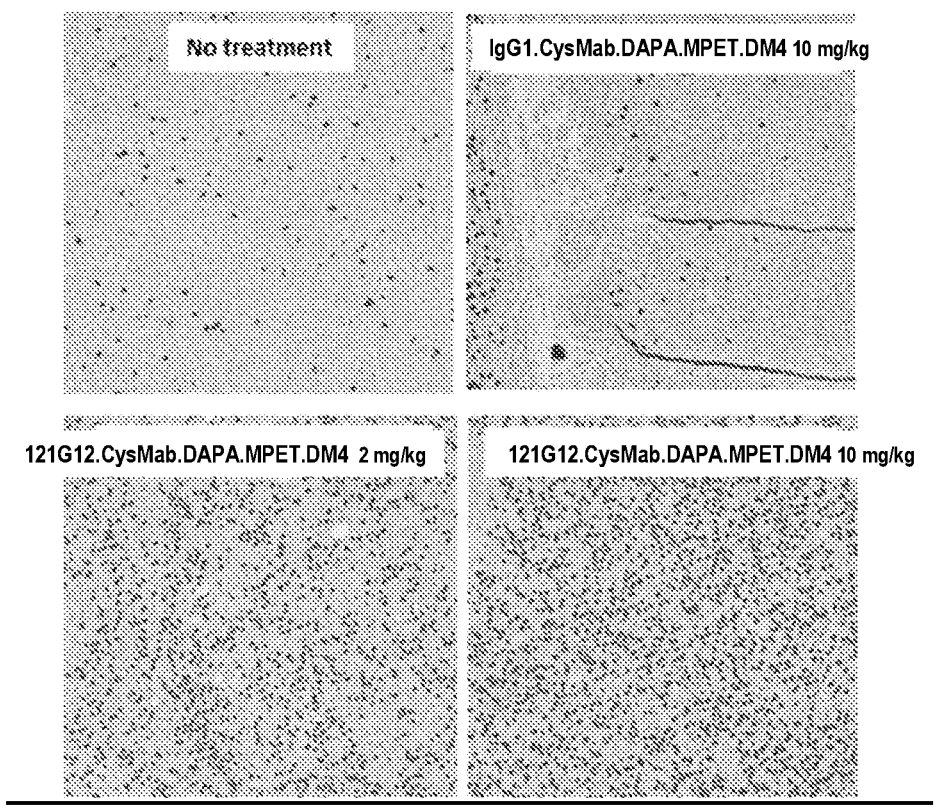
FIG. 14A-B depicts phospho-Histone H3 IHC images (FIG. 14A) and quantified phospho-Histone H3 signal (FIG. 14B) across KE97 tumors at 48 hr post treatment of single dose of either 121G12.CysMab.DAPA.MPET.DM4 at 2, 5, or 10 mg/kg or isotype control IgG 1.CysMab.DAPA.MPET.DM4 at 10 mg/kg, demonstrating induction of mitotic arrest (phospho-histone H3) after treatment with anti-CCR7 ADC.
Figure 14B:
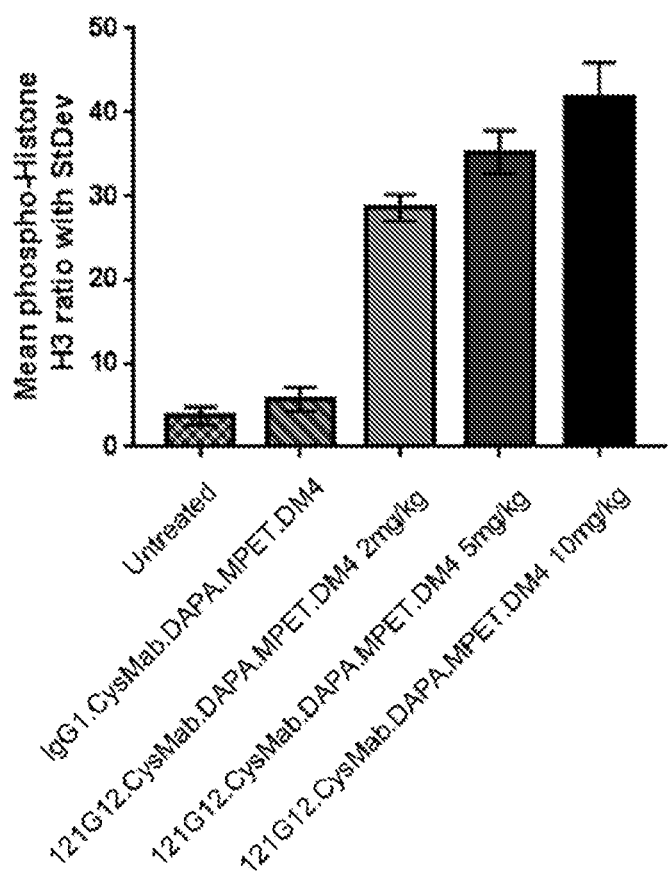

In FIG. 14A although the representative No Treatment and isotype control IgG1.CysMab.DAPA.MPET.DM4 show occasional tumor cells positive for phopho-histone H3, a robust dose-dependent increase in phopho-histone H3 immunostaining is detected 48 hr post administration of 121G12.CysMab.DAPA.MPET.DM4. Quantification of signal was done using MatLab (MathWorks, Natick Mass.) where total area of phospho-Histone H3 signal ($\mu m^2$) was normalized by total area of nuclei ($\mu m^2$), generating phospho-Histone H3 ratio (%) values shown below for each of the treatment groups. These data in FIG. 14B indicate that 121G12.CysMab.DAPA.MPET.DM4 is capable of eliciting a strong G2/M arrest in the tumor xenografts, consistent with the expected mechanism of action of the payload.

Example 17: Process for the Production of 121G12.CysMab.DAPA Antibody

This example describes a process for producing the CCR7 antibody 121G12.CysMab.DAPA from a cell culture, wherein the Ab is expressed from a vector that encodes the Ab. Once the Ab is expressed in the cell culture, the Ab is purified from the cell culture as follows:

The first step in the purification process of 121G12.CysMab.DAPA antibody drug substance intermediate consists of cell removal by inline depth filtration, followed by a 0.2 μm filtration.

The second step consists of a Protein A affinity liquid chromatography step. Depending on total amount of the bulk product, this step is performed in several runs. Each run allows a maximal loading of approximately 20 g/L column volume. The elution is performed with 50 mM acetic acid at approximately pH 3.0. The operation temperature is 18-28° C. All eluates are pooled and stored at 2-8° C. before the virus inactivation step.

Step three is a "low pH treatment" virus inactivation. The intermediate solution of step 2 is adjusted to 18-28° C. and an adjustment of the pH to 3.5 (range 3.4-3.6). The product intermediate solution is then held for virus inactivation for 70 minutes (range 60-90 minutes). After the holding time, the solution is adjusted to pH 6.0 (range 5.8-6.2). At the end of the step the solution is depth filtered in line with a 0.2 μm filtration and stored at 2-8° C.

The fourth step is a cation exchange chromatography in bind/elute mode which includes an integrated on-column reduction. Depending on the titer, this step is performed in several runs. Each run allows a loading of approximately 30 g/L column volume. The column is equilibrated with buffer A containing 20 mM sodium succinate, pH 6.0. On-column reduction is performed using 20 mM sodium phosphate, 1 mM EDTA, 7 mM L-cysteine, pH 7.1 as reduction buffer. The reduction buffer is removed with buffer A and the elution is performed with a linear gradient from 10% to 90% with buffer A and buffer B containing 10 mM sodium succinate, 300 mM sodium chloride, pH 6.0. Eluates and pools may be stored at 2-8° C. before the multimodal anion exchange chromatography step.

The fifth step of the process is an anion exchange chromatography in flow-through mode. Depending on the titer, this step is performed in several runs. Each run allows a maximal loading of approximately 350 g/L column volume. The operation temperature is 18-28° C. The equilibrium is performed with 20 mM sodium succinate, 119 mM sodium chloride, pH 6.0. The final percolate is stored at 2-8° C. before the virus removal step.

The virus filtration, step six, consists of a pre-filtration with a 0.1 μm filter followed by a virus filtration with a Planova 20N nanofilter. The temperature of the intermediate solution from Step 5 is adjusted to 18-28° C. before the virus filtration. The operation temperature is 18-28° C. After the nanofiltration the intermediate is stored at 2-8° C. or 18-28° C.

The seventh step, Ultrafiltration/Diafiltration, consists of an up-concentration step to approximately 70 g/L followed by a Pt diafiltration step with 10 mM potassium phosphate, pH 6.0. A diafiltration exchange factor of at least 7 is targeted followed by a dilution to approximately 50 g/L. The final drug substance intermediate is 0.2 μm filtered and stored at 2-8° C.

In the eighth and last step final bulk drug substance intermediate is filled in aliquots into suitable containers, and stored at below −60° C. after freezing.

TABLE 25

Flow diagram of the purification and reduction process

| Step | Operation |
|---|---|
| Step 1 | Harvesting, cell removal and filtration |
| Step 2 | Affinity Chromatography (MabSelect SuRE) |
| Step 3 | Virus inactivation at pH 3.5 |
| Step 4 | Cation Exchange Chromatography and On-column reduction (Fractogel EMD SO3 (M)) |
| Step 5 | Multimodal Anion Exchange Chromatography (Capto adhere) |
| Step 6 | Virus removal by nanofiltration (Planova 20N) |
| Step 7 | Ultrafiltration/Diafiltration and final filtration |
| Step 8 | Filling and deep-freezing |

Example 18: Dose Dependent In Vivo Efficacy of 121G12.CysMab.DAPA.MPET.DM4 Against OCI-LY3 ABC-DLBCL Xenograft Model in NSG Mice To demonstrate targeted anti-tumor activity of 121G12.CysMab.DAPA.MPET.DM4 in vivo in an ABC-DLBCL model, OCI-LY3 xenograft model was established in female NSG mice by subcutaneous injection of $10 \times 10^6$ cells into the right flank of each mouse. Once tumors reached approximately 140 mm$^3$, mice were randomized according to tumor volume into treatment groups (n=6 per group). Mice received an IV treatment of either 121G12.CysMab.DAPA.MPET.DM4 (DAR4) at a final dose of 0.5, 1 or 2 mg/kg or a non-specific isotype control hIgG1.CysMab.DAPA.MPET.DM4 at 2 mg/kg on day 1 and day 15 of study. All doses were adjusted to individual mouse body weights. All test agents were tolerated on study and no overt clinical symptoms of toxicities or body weight loss were observed in any of the treatment groups (Table 26).

Figure 15:
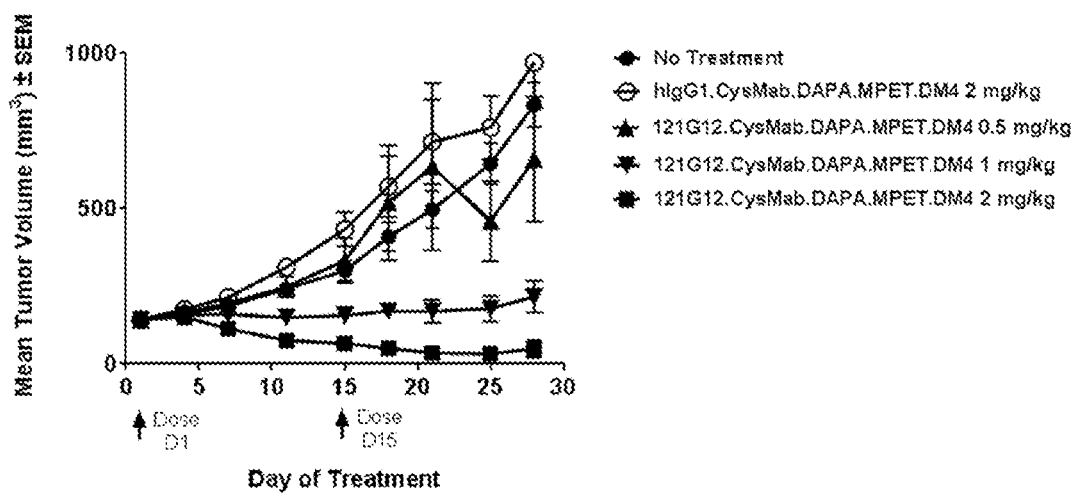
FIG. 15 depicts a graph illustrating dose response efficacy of 121G12.CysMab.DAPA.MPET.DM4 against OCI-LY3 ABC-DLBCL xenograft model.

No significant anti-tumor efficacy was observed after treatment with the non-specific isotype control hIgG1.CysMab.DAPA.MPET.DM4 at 2 mg/kg. 121G12.CysMab.DAPA.MPET.DM4 treatment resulted in dose-dependent anti-tumor efficacy with ΔT/ΔC value of 74.6% (0.5 mg/kg) and 10.7% (1 mg/kg), while the 2 mg/kg dose led to mean regression of 65.9% by day 28 of study. 3 of 6 mice in 121G12.CysMab.DAPA.MPET.DM4 2 mg/kg group displayed complete regression (FIG. 15).

TABLE 26

Anti-CCR7 ADC dose response efficacy in OCI-LY3 xenograft model on Day 28 of treatment.

| | | Tumor Response | | Host Response | |
|---|---|---|---|---|---|
| Treatment | Dose, schedule | ΔT/ΔC (%) | Regression (%) | Δ body weight (%) | Survival (alive/total) |
| No treatment | None | 100.0 | — | 5.6 | 6/6 |
| hIgG1.CysMab.DAPA.MPET.DM4 | 2 mg/kg dosed D 1 and D 15 | 119.7 | — | 1.8 | 5/6 |
| 121G12.CysMab.DAPA.MPET.DM4 | 0.5 mg/kg dosed D 1 and D 15 | 74.6 | — | 3.5 | 5/6 |
| 121G12.CysMab.DAPA.MPET.DM4 | 1 mg/kg dosed D 1 and D 15 | 10.7** | | 2.9 | 6/6 |

TABLE 26-continued

Anti-CCR7 ADC dose response efficacy in OCI-LY3 xenograft model on Day 28 of treatment.

| Treatment | Dose, schedule | Tumor Response ΔT/ΔC (%) | Regression (%) | Host Response Δ body weight (%) | Survival (alive/total) |
|---|---|---|---|---|---|
| 121G12.CysMab.DAPA.MPET.DM4 | 2 mg/kg dosed D 1 and D 15 | — | 65.9** | −0.8 | 6/6 |

The experiment was evaluated on treatment Day 28,

**p < 0.005 versus control No Treatment group (One-Way ANOVA/Tukey's Multiple Comparisons Test). % ΔT/ΔC = 100 ΔT/ΔC where: ΔT = mean tumor volume of the drug treated group on D 28 of study − mean tumor volume of the drug treated group on initial day of dosing; ΔC = mean tumor volume of the control group on D 28 of study − mean tumor volume of the control group on initial day of dosing D 1. % Regression = (1 − $T_{final}/T_{initial}$) × 100 was calculated if ΔT < 0, where $T_{final}$ is mean tumor volume D 28 and $T_{initial}$ is defined as tumor volume on D 1 of treatment. Δ body weight (%) = (Mean body weight D 28 − mean body weight D 1) *100/Mean body weight D 1 of treatment.

Example 19: Dose Dependent In Vivo Efficacy of 121G12.CysMab.DAPA.MPET.DM4 Against Toledo GCB-DLBCL Xenograft Model in SCID-bg Mice To demonstrate targeted anti-tumor activity of 121G12.CysMab.DAPA.MPET.DM4 in vivo in a GCB-DLBCL model, Toledo xenograft model was established in female Scid-bg mice by subcutaneous injection of 3×10$^6$ cells into the right flank of each mouse. Once tumors reached approximately 100 mm$^3$, mice were randomized according to tumor volume into treatment groups (n=4 per group). Mice received an IV treatment of either 121G12.CysMab.DAPA.MPET.DM4 (DAR4) at a final dose of 2 or 5 mg/kg or a non-specific isotype control hIgG1.CysMab.DAPA.MPET.DM4 at 5 mg/kg on day 1 and day 15 of study. All doses were adjusted to individual mouse body weights. All test agents were tolerated on study and no overt clinical symptoms of toxicities or body weight loss were observed in any of the treatment groups (Table 27).

Figure 16:
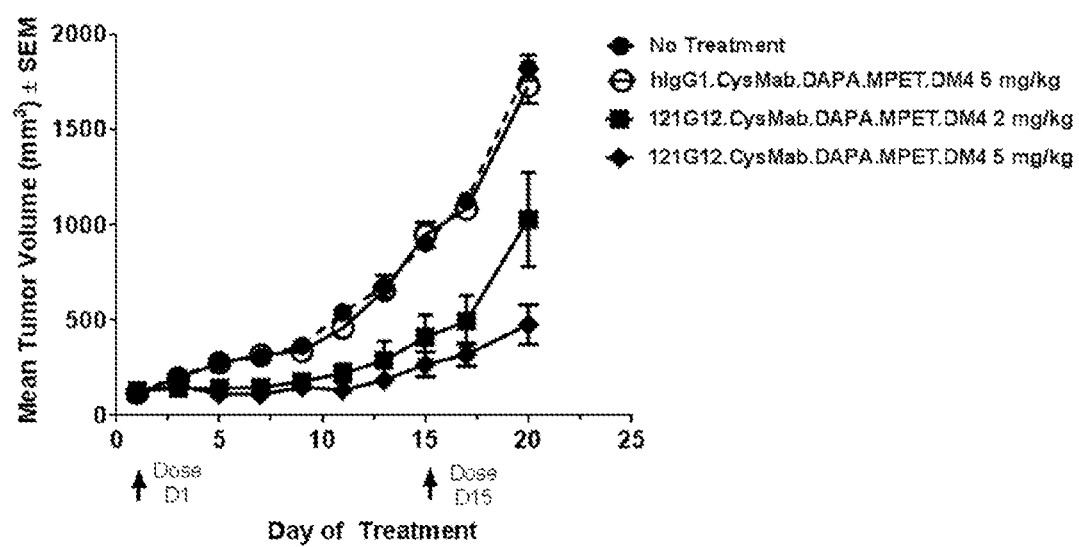
FIG. 16 depicts a graph illustrating dose response efficacy of 121G12.CysMab.DAPA.MPET.DM4 against Toledo GCB-DLBCL xenograft model.

No significant anti-tumor efficacy was observed after treatment with the non-specific isotype control hIgG1.CysMab.DAPA.MPET.DM4 at 5 mg/kg. 121G12.CysMab.DAPA.MPET.DM4 treatment resulted in dose-dependent anti-tumor efficacy, with ΔT/ΔC value of 52.7% (2 mg/kg) and 20.6% (5 mg/kg) (FIG. 16, Table 27).

TABLE 27

Anti-CCR7 ADC dose response efficacy in Toledo xenograft model on Day 20 of treatment.

| Treatment | Dose, schedule | Tumor Response ΔT/ΔC (%) | Host Response Δ body weight (%) | Survival (alive/total) |
|---|---|---|---|---|
| No treatment | None | 100.0 | 4.9 | 3/6 |
| hIgG1.CysMab.DAPA.MPET.DM4 | 5 mg/kg dosed D 1 and D 15 | 94.5 | 1.0 | 3/6 |
| 121G12.CysMab.DAPA.MPET.DM4 | 2 mg/kg dosed D 1 and D 15 | 52.7* | 3.2 | 4/6 |
| 121G12.CysMab.DAPA.MPET.DM4 | 5 mg/kg dosed D 1 and D 15 | 20.6 ** | 0.1 | 4/6 |

The experiment was evaluated on treatment Day 20,

*p < 0.05,

**p < 0.005 versus control No Treatment group (One-Way ANOVA/Tukey's Multiple Comparisons Test). % ΔT/ΔC = 100 ΔT/ΔC where: ΔT = mean tumor volume of the drug treated group on D 20 of study − mean tumor volume of the drug treated group on initial day of dosing; ΔC = mean tumor volume of the control group on D 20 of study − mean tumor volume of the control group on initial day of dosing D 1. Δ body weight (%) = (Mean body weight D 20 − mean body weight D 1) *100/Mean body weight D 1 of treatment.

Example 20: In Vivo Efficacy of 121G12.CysMab.DAPA.MPET.DM4 Against DEL ALCL Xenograft Model in SCID-bg Mice To demonstrate targeted anti-tumor activity of 121G12.CysMab.DAPA.MPET.DM4 in vivo in a CCR7 positive ALCL model, DEL xenograft model was established in female Scid-bg mice by subcutaneous injection of $3 \times 10^6$ cells into the right flank of each mouse. Once tumors reached approximately 100 mm$^3$, mice were randomized according to tumor volume into treatment groups (n=4 per group). Mice received an IV treatment of either 121G12.CysMab.DAPA.MPET.DM4 (DAR4) at a final dose of 2 mg/kg or a non-specific isotype control isotype.MPET.DM4 at 2 mg/kg on day 1 and day 15 of study. All doses were adjusted to individual mouse body weights.

Figure 17:
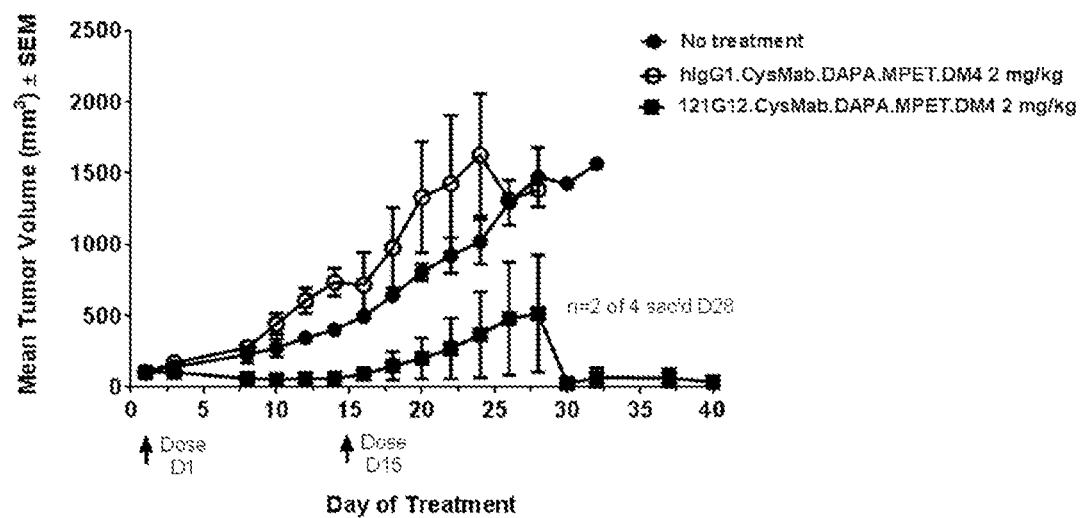
FIG. 17 depicts a graph illustrating efficacy of 121G12.CysMab.DAPA.MPET.DM4 against DEL ALCL xenograft model.

No significant anti-tumor efficacy was observed after treatment with the non-specific isotype control hIgG1.CysMab.DAPA.MPET.DM4 at 2 mg/kg. Treatment with 121G12.CysMab.DAPA.MPET.DM4 2 mg/kg resulted in mean regression of 40.2% by day 14 of study after a single dose (p<0.01). Mice received a second dose on day 15 and were monitored for three more weeks. One outlier animal failed to respond to a second dose of treatment and had to be euthanized by day 28 due to tumor burden. One additional animal showed slow disease progression and was also taken down on day 28 for target expression follow-up. Two of the four mice continued to display a sustained impact on tumor growth (FIG. 17). All treatments were well tolerated with no apparent body weight loss.

Example 21: In Vivo Efficacy of 121G12.CysMab.DAPA.MPET.DM4 Against Primary Patient Derived Non-Small Cell Lung Cancer HLUX1787 Tumor Model Anti-tumor activity of 121G12.CysMab.DAPA.MPET.DM4 was evaluated in the CCR7 expressing HLUX1787 primary non-small cell lung cancer xenograft model. Female NSG mice were implanted subcutaneously with tumor fragments into the right flank of each mouse. Once tumors reached approximately 150 mm$^3$, mice were randomized according to tumor volume into treatment groups (n=6 per group). Mice received an IV treatment of either 121G12.CysMab.DAPA.MPET.DM4 (DAR4) at 0.5, 2 or 5 mg/kg on day 1 and a second dose was delivered 2 weeks later on day 15. All doses were adjusted to individual mouse body weights.

Figure 18:
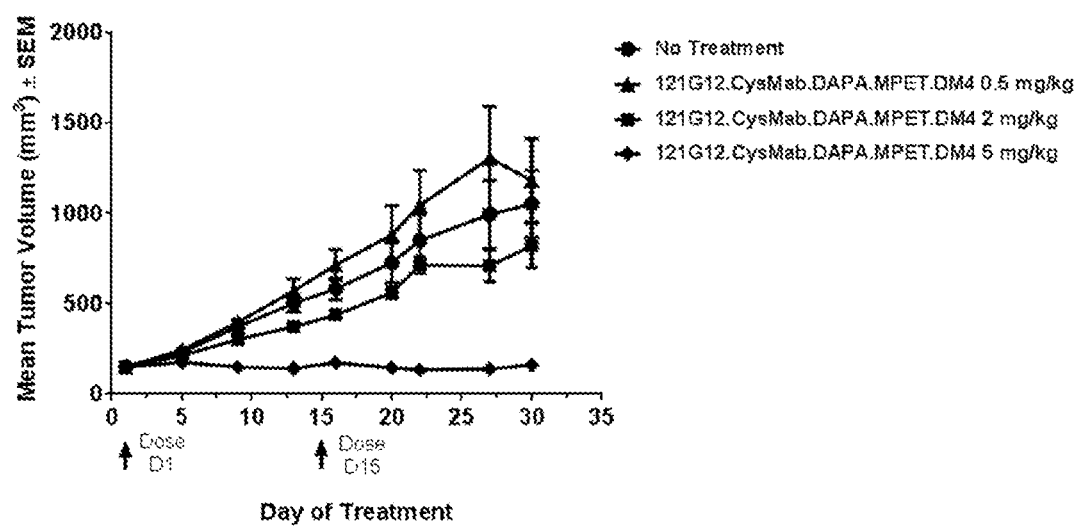
FIG. 18 depicts a graph illustrating dose response efficacy of 121G12.CysMab.DAPA.MPET.DM4 against HLUX1787 NSCLC patient derived xenograft model.

No significant anti-tumor efficacy was observed with the lower doses of the conjugated Ab, however partial regressions or stable disease were observed with 121G12.CysMab.DAPA.MPET.DM4 treatment at 5 mg/kg. Sustained tumor efficacy was observed two weeks after the second dose, resulting in AT/AC value of 1.3% on D30 of treatment (p<0.001; One-Way ANOVA/Tukey's Multiple Comparisons Test) (FIG. 18). All treatments were well tolerated with no apparent body weight loss.

---

We claim:

1. An antibody or antigen binding fragment thereof comprising:
   a. a heavy chain variable region that comprises an HCDR1 (Heavy Chain Complementarity Determining Region 1) of SEQ ID NO:1, an HCDR2 (Heavy Chain Complementarity Determining Region 2) of SEQ ID NO:2, and an HCDR3 (Heavy Chain Complementarity Determining Region 3) of SEQ ID NO:3; and a light chain variable region that comprises an LCDR1 (Light Chain Complementarity Determining Region 1) of SEQ ID NO:17, an LCDR2 (Light Chain Complementarity Determining Region 2) of SEQ ID NO:18, and an LCDR3 (Light Chain Complementarity Determining Region 3) of SEQ ID NO:19;
   b. a heavy chain variable region that comprises an HCDR1 of SEQ ID NO:4, an HCDR2 of SEQ ID NO:5, and an HCDR3 of SEQ ID NO:6; and a light chain variable region that comprises an LCDR1 of SEQ ID NO:20, an LCDR2 of SEQ ID NO:21, and an LCDR3 of SEQ ID NO:22;
   c. a heavy chain variable region that comprises an HCDR1 of SEQ ID NO:7, an HCDR2 of SEQ ID NO:8, and an HCDR3 of SEQ ID NO:9; and a light chain variable region that comprises an LCDR1 of SEQ ID NO:23, an LCDR2 of SEQ ID NO:24, and an LCDR3 of SEQ ID NO:25;
   d. a heavy chain variable region that comprises an HCDR1 of SEQ ID NO:10, an HCDR2 of SEQ ID NO:11, and an HCDR3 of SEQ ID NO:12; and a light chain variable region that comprises an LCDR1 of SEQ ID NO:26, an LCDR2 of SEQ ID NO:27, and an LCDR3 of SEQ ID NO:28;
   e. a heavy chain variable region that comprises an HCDR1 of SEQ ID NO:33, an HCDR2 of SEQ ID NO:34, and an HCDR3 of SEQ ID NO:35; and a light chain variable region that comprises an LCDR1 of SEQ ID NO:49, an LCDR2 of SEQ ID NO:50, and an LCDR3 of SEQ ID NO:51;
   f. a heavy chain variable region that comprises an HCDR1 of SEQ ID NO:36, an HCDR2 of SEQ ID NO:37, and an HCDR3 of SEQ ID NO:38; and a light chain variable region that comprises an LCDR1 of SEQ ID NO:52, an LCDR2 of SEQ ID NO:53, and an LCDR3 of SEQ ID NO:54;
   g. a heavy chain variable region that comprises an HCDR1 of SEQ ID NO:39, an HCDR2 of SEQ ID NO:40, and an HCDR3 of SEQ ID NO:41; and a light chain variable region that comprises an LCDR1 of SEQ ID NO:55, an LCDR2 of SEQ ID NO:56, and an LCDR3 of SEQ ID NO:57;
   h. a heavy chain variable region that comprises an HCDR1 of SEQ ID NO:42, an HCDR2 of SEQ ID NO:43, and an HCDR3 of SEQ ID NO:44; and a light chain variable region that comprises an LCDR1 of SEQ ID NO:58, an LCDR2 of SEQ ID NO:59, and an LCDR3 of SEQ ID NO:60;
   i. a heavy chain variable region that comprises an HCDR1 of SEQ ID NO:65, an HCDR2 of SEQ ID NO:66, and an HCDR3 of SEQ ID NO:67; and a light chain variable region that comprises an LCDR1 of SEQ ID NO:81, an LCDR2 of SEQ ID NO:82, and an LCDR3 of SEQ ID NO:83;
   j. a heavy chain variable region that comprises an HCDR1 of SEQ ID NO:68, an HCDR2 of SEQ ID NO:69, and an HCDR3 of SEQ ID NO:70; and a light chain variable region that comprises an LCDR1 of SEQ ID NO:84, an LCDR2 of SEQ ID NO:85, and an LCDR3 of SEQ ID NO:86;
k. a heavy chain variable region that comprises an HCDR1 of SEQ ID NO:71, an HCDR2 of SEQ ID NO:72, and an HCDR3 of SEQ ID NO:73; and a light chain variable region that comprises an LCDR1 of SEQ ID NO:87, an LCDR2 of SEQ ID NO:88, and an LCDR3 of SEQ ID NO:89;
l. a heavy chain variable region that comprises an HCDR1 of SEQ ID NO:74, an HCDR2 of SEQ ID NO:75, and an HCDR3 of SEQ ID NO:76; and a light chain variable region that comprises an LCDR1 of SEQ ID NO:90, an LCDR2 of SEQ ID NO:91, and an LCDR3 of SEQ ID NO:92;
m. a heavy chain variable region that comprises an HCDR1 of SEQ ID NO:596, an HCDR2 of SEQ ID NO:597, and an HCDR3 of SEQ ID NO:598; and a light chain variable region that comprises an LCDR1 of SEQ ID NO:612, an LCDR2 of SEQ ID NO:613, and an LCDR3 of SEQ ID NO:614;
n. a heavy chain variable region that comprises an HCDR1 of SEQ ID NO:599, an HCDR2 of SEQ ID NO:600, and an HCDR3 of SEQ ID NO:601; and a light chain variable region that comprises an LCDR1 of SEQ ID NO:615, an LCDR2 of SEQ ID NO:616, and an LCDR3 of SEQ ID NO:617;
o. a heavy chain variable region that comprises an HCDR1 of SEQ ID NO:602, an HCDR2 of SEQ ID NO:603, and an HCDR3 of SEQ ID NO:604; and a light chain variable region that comprises an LCDR1 of SEQ ID NO:618, an LCDR2 of SEQ ID NO:619, and an LCDR3 of SEQ ID NO:620; or
p. a heavy chain variable region that comprises an HCDR1 of SEQ ID NO:605, an HCDR2 of SEQ ID NO:606, and an HCDR3 of SEQ ID NO:607; and a light chain variable region that comprises an LCDR1 of SEQ ID NO:621, an LCDR2 of SEQ ID NO:622, and an LCDR3 of SEQ ID NO:623.

2. The antibody or antigen binding fragment thereof of claim 1 comprising:
   a. A heavy chain variable region (VH) comprising the amino acid sequence of SEQ ID NO:13, and a light chain variable region (VL) comprising the amino acid sequence of SEQ ID NO:29;
   b. A heavy chain variable region (VH) comprising the amino acid sequence of SEQ ID NO:45, and a light chain variable region (VL) comprising the amino acid sequence of SEQ ID NO:61;
   c. A heavy chain variable region (VH) comprising the amino acid sequence of SEQ ID NO:77, and a light chain variable region (VL) comprising the amino acid sequence of SEQ ID NO:93; or
   d. A heavy chain variable region (VH) comprising the amino acid sequence of SEQ ID NO:608, and a light chain variable region (VL) comprising the amino acid sequence of SEQ ID NO:624.

3. The antibody or antigen binding fragment thereof of claim 1 comprising:
   a. A heavy chain comprising the amino acid sequence of SEQ ID NO:15, and a light chain comprising the amino acid sequence of SEQ ID NO:31;
   b. A heavy chain comprising the amino acid sequence of SEQ ID NO:47, and a light chain comprising the amino acid sequence of SEQ ID NO:63;
   c. A heavy chain comprising the amino acid sequence of SEQ ID NO:79, and a light chain comprising the amino acid sequence of SEQ ID NO:95; or
   d. A heavy chain comprising the amino acid sequence of SEQ ID NO:610, and a light chain comprising the amino acid sequence of SEQ ID NO:626.

4. An antibody drug conjugate comprising the formula $$Ab\text{-}(L\text{-}(D)_m)_n$$

or a pharmaceutically acceptable salt thereof; wherein

Ab is an antibody or antigen binding fragment thereof according to claim 1;

L is a linker;

D is a drug moiety;

m is an integer from 1 to 8; and n is an integer from 1 to 12.

5. The antibody drug conjugate of claim 4, wherein said m is 1.

6. The antibody drug conjugate of claim 4, wherein said n is about 3 to about 4.

7. The antibody drug conjugate of claim 4, wherein the linker is derived from a cross-linking reagent selected from the group consisting of N-succinimidyl-3-(2-pyridyldithio) propionate (SPDP), N-succinimidyl 4-(2-pyridyldithio)pentanoate (SPP), N-succinimidyl 4-(2-pyridyldithio)butanoate (SPDB), N-succinimidyl-4-(2-pyridyldithio)-2-sulfo-butanoate (sulfo-SPDB), N-succinimidyl iodoacetate (SIA), N-succinimidyl(4-iodoacetyl)aminobenzoate (SIAB), maleimide PEG NHS, N-succinimidyl 4-(maleimidomethyl) cyclohexanecarboxylate (SMCC), N-sulfosuccinimidyl 4-(maleimidomethyl) cyclohexanecarboxylate (sulfo-SMCC), and 2,5-dioxopyrrolidin-1-yl 17-(2,5-dioxo-2,5-dihydro-1H-pyrrol-1-yl)-5,8,11,14-tetraoxo-4,7,10,13-tetraazaheptadecan-l-oate (CX1-1).

8. The antibody drug conjugate of claim 4, wherein said linker has the following Formula (IIA):

$$\text{*} \diagdown \text{N-L}^1\text{-X-L}^2\text{-S} \diagup \text{**} \quad (IIA)$$

wherein * is linked to the thiol functionality on the antibody or antigen binding fragment thereof, and ** is linked to the thiol functionality of the drug moiety; and wherein:

$L^1$ is a $C_{1\text{-}6}$alkylene wherein one of the methylene groups may be replaced with oxygen;

$L^2$ is a $C_{1\text{-}6}$alkylene or is $-(CH_2CH_2O)_y-CH_2-CH_2-$ wherein y is 1 to 11;

X is $-C(O)-NH-$, $-NHC(O)-$ or a triazole; and alkylene is linear or branched.

9. The antibody drug conjugate of claim 8, wherein said linker is selected from the following:

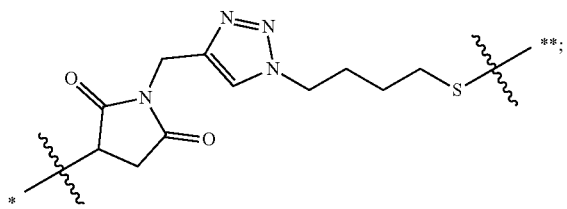

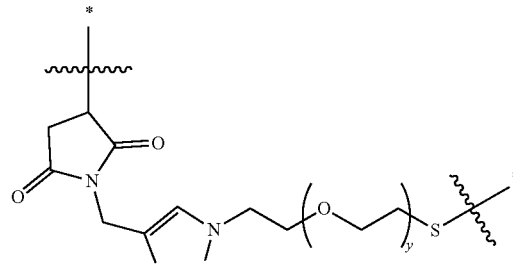

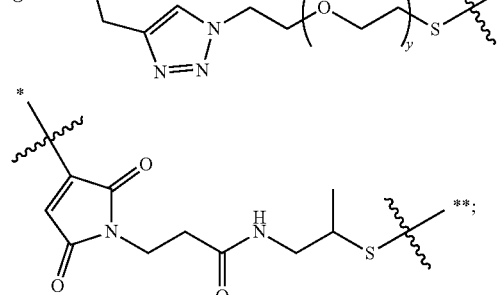

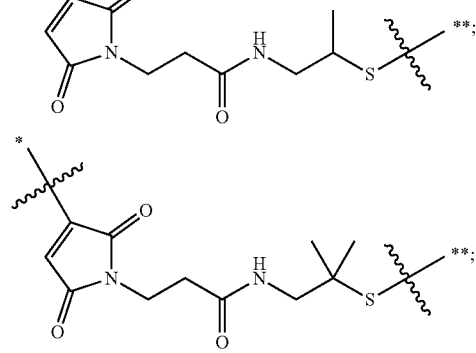

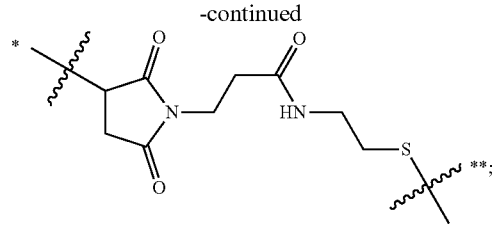

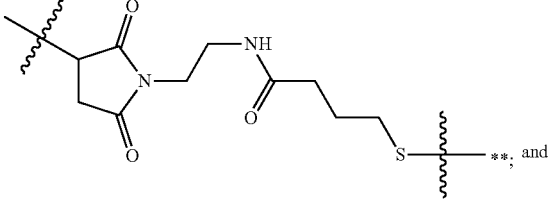

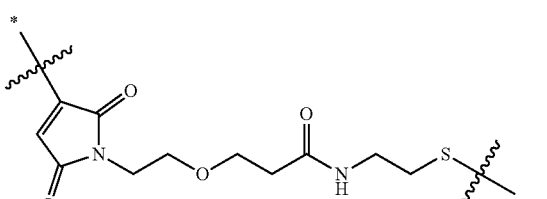

wherein y is 1 to 11; * is linked to the thiol functionality on the antibody, and ** is linked to the thiol functionality of the drug moiety.

10. The antibody drug conjugate of claim 4, wherein the drug moiety cytotoxic agent is a maytansinoid.

11. The antibody drug conjugate of claim 10, wherein the maytansinoid is N(2')-deacetyl-N(2')-(3-mercapto-1-oxopropyl)-maytansine (DM1), N(2')-deacetyl-N(2')-(4-mercapto-1-oxopentyl)-maytansine (DM3) or N(2')-deacetyl-N2-(4-mercapto-4-methyl-1-oxopentyl)-maytansine (DM4).

12. The antibody drug conjugate of claim 4 having the following formula (VIII):

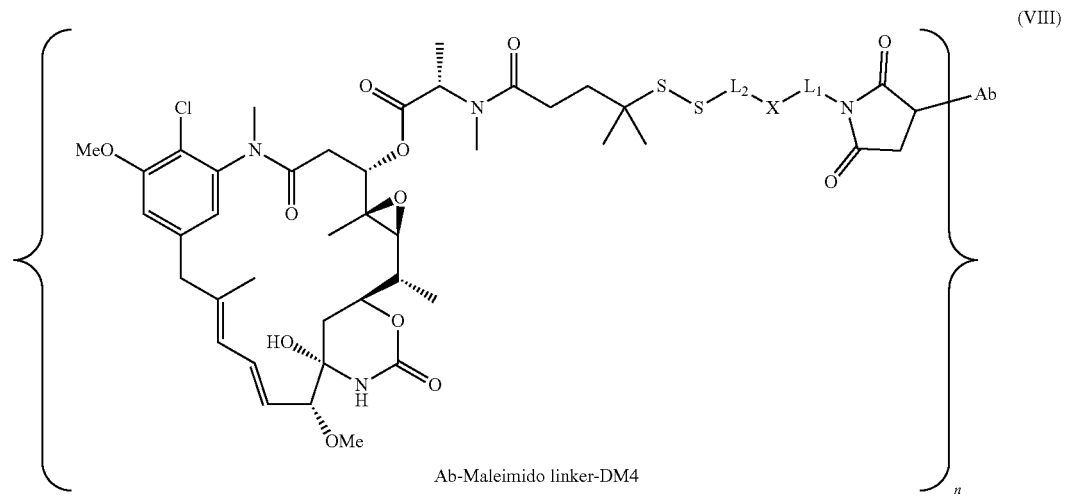

Ab-Maleimido linker-DM4 wherein L¹ is a $C_{1-6}$alkylene wherein one of the methylene groups may be replaced with oxygen;
L² is a $C_{1-6}$alkylene or is —$(CH_2CH_2O)_y$—$CH_2$—$CH_2$— wherein y is 1 to 11;
X is —C(O)—NH—, —NHC(O)— or a triazole; and alkylene is linear or branched; and wherein n is about 3 to about 4; or a pharmaceutically acceptable salt thereof.

13. An antibody drug conjugate having the following formula:

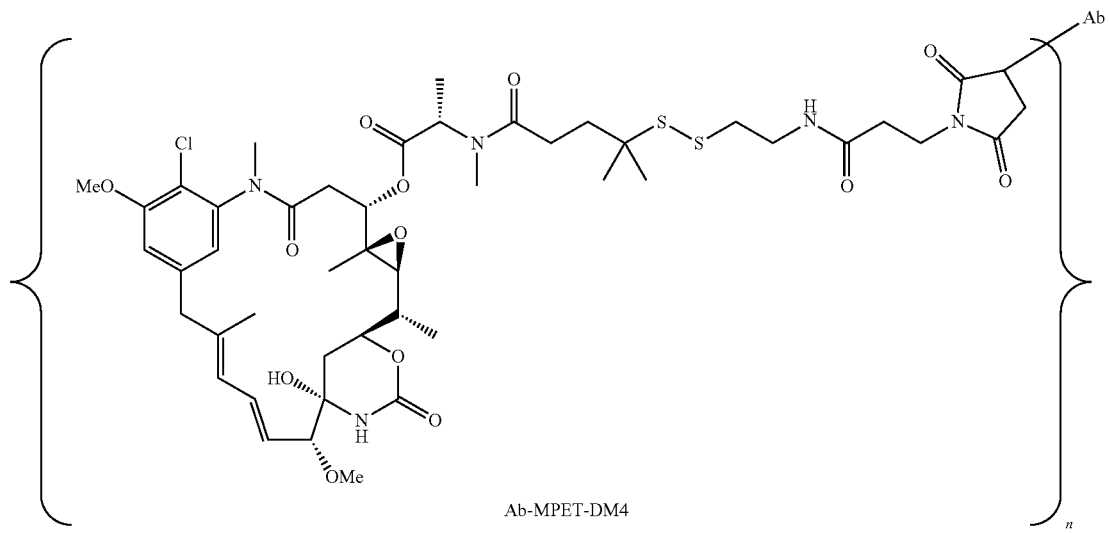

Ab-MPET-DM4 wherein n is about 3 to about 4, and Ab is an antibody comprising a heavy chain comprising the amino acid sequence of SEQ ID NO:47, and a light chain comprising the amino acid sequence of SEQ ID NO:63; or a pharmaceutically acceptable salt thereof.

14. A pharmaceutical composition comprising the antibody drug conjugate of claim 4 and a pharmaceutically acceptable carrier.

15. A method of treating or preventing cancer in a patient in need thereof, comprising administering to said patient the antibody drug conjugate of claim 4, wherein the cancer expresses CCR7.

16. The method of claim 15, wherein the antibody drug conjugate is administered to the patient in combination with one or more additional therapeutic compounds.

17. The method of claim 16, wherein the one or more additional therapeutic compounds is selected from a standard of care chemotherapeutic, a costimulatory molecule, and a checkpoint inhibitor.

18. The method of claim 17, wherein the costimulatory molecule is selected from an agonist of OX40, CD2, CD27, CDS, ICAM-1, LFA-1 (CD11a/CD18), ICOS (CD278), 4-1BB (CD137), GITR, CD30, CD40, BAFFR, HVEM, CD7, LIGHT, NKG2C, SLAMF7, NKp80, CD160, B7-H3, STING, and CD83 ligand.

19. The method of claim 17, wherein the checkpoint inhibitor is selected from an inhibitor of PD-1, PD-L1, PD-L2, CTLA4, TIM3, LAG3, VISTA, BTLA, TIGIT, LAIR1, CD160, 2B4 and/or TGFR beta.

20. The method of claim 15, wherein the cancer is selected from the group consisting of chronic lymphocytic leukemia (CLL), peripheral T cell lymphomas (PTCL), Non-Hodgkin's lymphoma (NHL), gastric carcinoma, non-small cell lung cancer, small cell lung cancer, head and neck cancer, nasopharyngeal carcinoma (NPC), esophageal cancer, colorectal carcinoma, pancreatic cancer, thyroid cancer, breast cancer, renal cell cancer, and cervical cancer.

21. The method of claim 15, wherein the cancer is selected from the group consisting of adult T-cell leukemia/lymphoma (ATLL), anaplastic large-cell lymphoma (ALCL), mantle cell lymphoma (MCL), Burkitt's lymphoma and diffuse large B-cell lymphoma (DLBCL).

22. A pharmaceutical composition comprising the antibody drug conjugate of claim 13 and a pharmaceutically acceptable carrier.

23. A method of treating cancer in a patient in need thereof, comprising administering to said patient the antibody drug conjugate of claim 13, wherein the cancer expresses CCR7.

24. The method of claim 23, wherein the cancer is chronic lymphocytic leukemia (CLL).

25. The method of claim 23, wherein the cancer is Non-Hodgkin's lymphoma (NHL).

26. The method of claim 23, wherein the cancer is diffuse large B-cell lymphoma (DLBCL).

* * * * *

SEQUENCE LISTING

```
<160> NUMBER OF SEQ ID NOS: 629

<210> SEQ ID NO 1
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 1

Gly Phe Thr Phe Ser Ser Tyr Ala Met Ser
1               5                   10

<210> SEQ ID NO 2
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 2

Thr Ile Ser Ser Gly Gly Ser Phe Thr Tyr Tyr Pro Asp Ser Val Lys
1               5                   10                  15

Gly

<210> SEQ ID NO 3
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
```

-continued

Synthetic peptide"

<400> SEQUENCE: 3

Arg Ala Ser Thr Val Val Gly Thr Asp Phe Asp Val
1               5                   10

<210> SEQ ID NO 4
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 4

Ser Tyr Ala Met Ser
1               5

<210> SEQ ID NO 5
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 5

Thr Ile Ser Ser Gly Gly Ser Phe Thr Tyr Tyr Pro Asp Ser Val Lys
1               5                   10                  15

Gly

<210> SEQ ID NO 6
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 6

Arg Ala Ser Thr Val Val Gly Thr Asp Phe Asp Val
1               5                   10

<210> SEQ ID NO 7
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 7

Gly Phe Thr Phe Ser Ser Tyr
1               5

<210> SEQ ID NO 8
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

```
<400> SEQUENCE: 8

Ser Ser Gly Gly Ser Phe
1               5

<210> SEQ ID NO 9
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 9

Arg Ala Ser Thr Val Val Gly Thr Asp Phe Asp Val
1               5                   10

<210> SEQ ID NO 10
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 10

Gly Phe Thr Phe Ser Ser Tyr Ala
1               5

<210> SEQ ID NO 11
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 11

Ile Ser Ser Gly Gly Ser Phe Thr
1               5

<210> SEQ ID NO 12
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 12

Ala Arg Arg Ala Ser Thr Val Val Gly Thr Asp Phe Asp Val
1               5                   10

<210> SEQ ID NO 13
<211> LENGTH: 121
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 13

Glu Val Gln Leu Val Glu Ser Gly Gly Gly Leu Val Lys Pro Gly Gly
1               5                   10                  15
```

Ser Leu Arg Leu Ser Cys Ala Ala Ser Gly Phe Thr Phe Ser Ser Tyr
            20                  25                  30

Ala Met Ser Trp Ile Arg Gln Ala Pro Gly Lys Gly Leu Glu Trp Val
        35                  40                  45

Ala Thr Ile Ser Ser Gly Gly Ser Phe Thr Tyr Tyr Pro Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Arg Ala Ser Thr Val Val Gly Thr Asp Phe Asp Val Trp Gly
            100                 105                 110

Gln Gly Thr Thr Val Thr Val Ser Ser
        115                 120

<210> SEQ ID NO 14
<211> LENGTH: 363
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 14
gaagtgcagc tggtggaatc tggcggcgga ctggtcaagc ctggcggctc cctgagactg    60
tcttgcgccg cctccggctt caccttctcc agctacgcca tgtcctggat ccggcaggcc   120
cctggcaagg gactggagtg ggtggccacc atctcctccg gcggcagctt cacctactac   180
cccgactccg tgaagggccg gttcaccatc tcccgggaca acgccaagaa ctccctgtac   240
ctgcagatga actccctgcg ggccgaggac accgccgtgt actactgtgc cagacgggcc   300
tccaccgtcg tgggcaccga tttcgatgtg tggggccagg gcacaaccgt gaccgtgtcc   360
tcc                                                                363

<210> SEQ ID NO 15
<211> LENGTH: 451
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 15

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Ile Arg Gln Ala Pro Gly Lys Gly Leu Glu Trp Val
        35                  40                  45

Ala Thr Ile Ser Ser Gly Gly Ser Phe Thr Tyr Tyr Pro Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Arg Ala Ser Thr Val Val Gly Thr Asp Phe Asp Val Trp Gly 100                 105                 110
Gln Gly Thr Thr Val Thr Val Ser Ser Ala Ser Thr Lys Gly Pro Ser
                115                 120                 125

Val Phe Pro Leu Ala Pro Ser Ser Lys Ser Thr Ser Gly Gly Thr Ala
130                 135                 140

Ala Leu Gly Cys Leu Val Lys Asp Tyr Phe Pro Cys Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
                180                 185                 190

Pro Ser Ser Ser Leu Gly Thr Gln Thr Tyr Ile Cys Asn Val Asn His
                195                 200                 205

Lys Pro Ser Asn Thr Lys Val Asp Lys Arg Val Glu Pro Lys Ser Cys
210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Ala Val Ser His
                260                 265                 270

Glu Asp Pro Glu Val Lys Phe Asn Trp Tyr Val Asp Gly Val Glu Val
                275                 280                 285

His Asn Ala Lys Thr Lys Pro Arg Glu Glu Gln Tyr Asn Ser Thr Tyr
                290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Ala Ala Pro Ile
                325                 330                 335

Glu Lys Thr Ile Ser Lys Ala Lys Gly Gln Pro Arg Glu Pro Gln Val
                340                 345                 350

Tyr Thr Leu Pro Pro Ser Arg Glu Glu Met Thr Lys Asn Gln Val Ser
                355                 360                 365

Leu Thr Cys Leu Val Lys Gly Phe Tyr Pro Cys Asp Ile Ala Val Glu
                370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
                420                 425                 430

His Glu Ala Leu His Asn His Tyr Thr Gln Lys Ser Leu Ser Leu Ser
                435                 440                 445

Pro Gly Lys
    450

<210> SEQ ID NO 16
<211> LENGTH: 1353
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 16

```
gaagtgcagc tggtggaatc tggcggcgga ctggtcaagc ctggcggctc cctgagactg      60
tcttgcgccg cctccggctt caccttctcc agctacgcca tgtcctggat ccggcaggcc     120
cctggcaagg gactggagtg ggtggccacc atctcctccg gcggcagctt cacctactac     180
cccgactccg tgaagggccg gttcaccatc tcccgggaca cgccaagaa ctccctgtac      240
ctgcagatga actccctgcg ggccgaggac accgccgtgt actactgtgc agacgggcc      300
tccaccgtcg tgggcaccga tttcgatgtg tggggccagg gcacaaccgt gaccgtgtcc     360
tccgcctcca ccaagggacc ctccgtgttc cctctggccc cttccagcaa gtccacctct     420
ggcggcaccg ccgctctggg ctgcctggtc aaggactact ccccctgccc tgtgacagtg     480
tcctggaact ccggcgctct gacctccggc gtgcacacct ccctgccgt gctgcagtcc      540
tccggcctgt actccctgtc ctccgtcgtg accgtgcctt cctccagcct gggcacccag     600
acctacatct gcaacgtgaa ccacaagccc tccaacacca agtggacaa gcgggtggaa      660
cccaagtcct gcgacaagac ccacacctgt cctccctgcc ctgcccctga gctgctggga     720
ggcccttccg tgttcctgtt ccctccaaag cccaaggaca ccctgatgat ctcccggacc     780
cctgaagtga cctgcgtggt ggtggccgtg tcccacgagg atcccgaagt gaagttcaat     840
tggtacgtgg acggcgtgga agtgcacaat gccaagacca gcccagaga ggaacagtac      900
aactccacct accgggtggt gtccgtgctg accgtgctgc accaggactg gctgaacggc     960
aaagagtaca agtgcaaagt gtccaacaag gccctggccg ctcccatcga aagaccatc     1020
tccaaggcca agggccagcc cagagagccc aagtgtaca cactgcctcc cagccgggaa     1080
gagatgacca gaaccaagt gtccctgacc tgcctcgtga agggcttcta cccctgcgat     1140
atcgccgtgg agtgggagtc caacggccag cccgagaaca actacaagac caccctcccc     1200
gtgctggaca gcgacggctc cttcttcctg tactccaagc tgaccgtgga caagtcccgg     1260
tggcagcagg gcaacgtgtt ctcctgctcc gtgatgcacg aggccctgca caaccactac     1320
acccagaagt ccctgtccct gagccccggc aag                                  1353
```

<210> SEQ ID NO 17
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 17

Arg Ala Ser Gln Asp Ile Gly Ser Ser Leu Asn
1               5                   10

<210> SEQ ID NO 18
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 18

Ala Thr Ser Ser Leu Asp Ser
1               5

<210> SEQ ID NO 19

```
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 19

Leu Gln Tyr Ala Ser Ser Pro Pro Thr
1               5

<210> SEQ ID NO 20
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 20

Arg Ala Ser Gln Asp Ile Gly Ser Ser Leu Asn
1               5                   10

<210> SEQ ID NO 21
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 21

Ala Thr Ser Ser Leu Asp Ser
1               5

<210> SEQ ID NO 22
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 22

Leu Gln Tyr Ala Ser Ser Pro Pro Thr
1               5

<210> SEQ ID NO 23
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 23

Ser Gln Asp Ile Gly Ser Ser
1               5

<210> SEQ ID NO 24
<211> LENGTH: 3
<212> TYPE: PRT
<213> ORGANISM: Artificial Sequence
<220> FEATURE:
```

```
<221> NAME/KEY: source
<223> OTHER INFORMATION: /note="Description of Artificial Sequence:
      Synthetic peptide"

<400> SEQUENCE: 24

Ala Thr Ser
1

<210> SEQ ID NO 25
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 25

Tyr Ala Ser Ser Pro Pro
1               5

<210> SEQ ID NO 26
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 26

Gln Asp Ile Gly Ser Ser
1               5

<210> SEQ ID NO 27
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 27

Ala Thr Ser
1

<210> SEQ ID NO 28
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 28

Leu Gln Tyr Ala Ser Ser Pro Pro Thr
1               5

<210> SEQ ID NO 29
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
```

<400> SEQUENCE: 29

Asp Ile Gln Met Thr Gln Ser Pro Ser Ser Leu Ser Ala Ser Val Gly
1               5                   10                  15

Asp Arg Val Thr Leu Thr Cys Arg Ala Ser Gln Asp Ile Gly Ser Ser
                20                  25                  30

Leu Asn Trp Leu Gln Gln Lys Pro Gly Lys Ala Ile Lys Arg Leu Ile
            35                  40                  45

Tyr Ala Thr Ser Ser Leu Asp Ser Gly Val Pro Ser Arg Phe Ser Gly
    50                  55                  60

Ser Arg Ser Gly Thr Asp Tyr Thr Leu Thr Ile Ser Ser Leu Gln Pro
65                  70                  75                  80

Glu Asp Phe Val Val Tyr Tyr Cys Leu Gln Tyr Ala Ser Ser Pro Pro
                85                  90                  95

Thr Phe Gly Gly Gly Thr Lys Leu Glu Ile Lys
            100                 105

<210> SEQ ID NO 30
<211> LENGTH: 321
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 30
gacatccaga tgacccagag cccctccagc ctgtccgcct ccgtgggcga tagagtgacc      60
ctgacctgcc gggcctccca ggacatcggc tcctccctga actggctgca gcagaagccc     120
ggcaaggcca tcaagcggct gatctacgcc acctcctccc tggactccgg cgtgccctcc     180
cggttctctg gctccagatc cggcaccgac tacaccctga ccatctccag cctgcagccc     240
gaggacttcg tggtgtacta ctgcctgcag tacgcctcca gccctccac  cttcggcgga     300 ggcaccaagc tggaaatcaa g                                               321

<210> SEQ ID NO 31
<211> LENGTH: 214
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 31

Asp Ile Gln Met Thr Gln Ser Pro Ser Ser Leu Ser Ala Ser Val Gly
1               5                   10                  15

Asp Arg Val Thr Leu Thr Cys Arg Ala Ser Gln Asp Ile Gly Ser Ser
                20                  25                  30

Leu Asn Trp Leu Gln Gln Lys Pro Gly Lys Ala Ile Lys Arg Leu Ile
            35                  40                  45

Tyr Ala Thr Ser Ser Leu Asp Ser Gly Val Pro Ser Arg Phe Ser Gly
    50                  55                  60

Ser Arg Ser Gly Thr Asp Tyr Thr Leu Thr Ile Ser Ser Leu Gln Pro
65                  70                  75                  80

Glu Asp Phe Val Val Tyr Tyr Cys Leu Gln Tyr Ala Ser Ser Pro Pro
                85                  90                  95

Thr Phe Gly Gly Gly Thr Lys Leu Glu Ile Lys Arg Thr Val Ala Ala
            100                 105                 110

```
Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 32
<211> LENGTH: 642
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 32

```
gacatccaga tgacccagag ccccccagc ctgtccgcct ccgtgggcga tagagtgacc      60
ctgacctgcc gggcctccca ggacatcggc tcctccctga actggctgca gcagaagccc    120
ggcaaggcca tcaagcggct gatctacgcc acctcctccc tggactccgg cgtgccctcc    180
cggttctctg gctccagatc cggcaccgac tacaccctga ccatctccag cctgcagccc    240
gaggacttcg tggtgtacta ctgcctgcag tacgcctcca cccctccac cttcggcgga    300
ggcaccaagc tggaaatcaa gcgtacggtg gccgctccca gcgtgttcat cttcccccc    360
agcgacgagc agctgaagag cggcaccgcc agcgtggtgt gcctgctgaa caacttctac    420
ccccgggagg ccaaggtgca gtggaaggtg gacaacgccc tgcagagcgg caacagccag    480
gagagcgtca ccgagcagga cagcaaggac tccacctaca gcctgagcag caccctgacc    540
ctgagcaagg ccgactacga gaagcataag gtgtacgcct gcgaggtgac ccaccagggc    600
ctgtccagcc ccgtgaccaa gagcttcaac aggggcgagt gc                       642
```

<210> SEQ ID NO 33
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 33

```
Gly Phe Thr Phe Ser Thr Tyr Ala Met Ser
1               5                   10
```

<210> SEQ ID NO 34
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:

Synthetic peptide"

<400> SEQUENCE: 34

Thr Ile Ser Asp Ala Gly Ser Tyr Ser Tyr Tyr Pro Asp Asn Val Lys
1               5                   10                  15

Gly

<210> SEQ ID NO 35
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 35

Arg Gly Ser Arg Tyr Glu Glu Tyr Tyr Val Met Asp Tyr
1               5                   10

<210> SEQ ID NO 36
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 36

Thr Tyr Ala Met Ser
1               5

<210> SEQ ID NO 37
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 37

Thr Ile Ser Asp Ala Gly Ser Tyr Ser Tyr Tyr Pro Asp Asn Val Lys
1               5                   10                  15

Gly

<210> SEQ ID NO 38
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 38

Arg Gly Ser Arg Tyr Glu Glu Tyr Tyr Val Met Asp Tyr
1               5                   10

<210> SEQ ID NO 39
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:

```
          Synthetic peptide"

<400> SEQUENCE: 39

Gly Phe Thr Phe Ser Thr Tyr
1               5

<210> SEQ ID NO 40
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 40

Ser Asp Ala Gly Ser Tyr
1               5

<210> SEQ ID NO 41
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 41

Arg Gly Ser Arg Tyr Glu Glu Tyr Tyr Val Met Asp Tyr
1               5                   10

<210> SEQ ID NO 42
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 42

Gly Phe Thr Phe Ser Thr Tyr Ala
1               5

<210> SEQ ID NO 43
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 43

Ile Ser Asp Ala Gly Ser Tyr Ser
1               5

<210> SEQ ID NO 44
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 44
```

Ala Arg Arg Gly Ser Arg Tyr Glu Glu Tyr Tyr Val Met Asp Tyr
1               5                   10                  15

<210> SEQ ID NO 45
<211> LENGTH: 122
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 45

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Thr Tyr
            20                  25                  30

Ala Met Ser Trp Val Arg Gln Ala Pro Gly Lys Gly Leu Glu Trp Val
        35                  40                  45

Ala Thr Ile Ser Asp Ala Gly Ser Tyr Ser Tyr Tyr Pro Asp Asn Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Arg Gly Ser Arg Tyr Glu Glu Tyr Tyr Val Met Asp Tyr Trp
            100                 105                 110

Gly Gln Gly Thr Thr Val Thr Val Ser Ser
        115                 120

<210> SEQ ID NO 46
<211> LENGTH: 366
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 46
gaagtgcagc tggtggaatc tggcggcgga ctggtcaagc ctggcggctc cctgagactg      60
tcttgcgccg cctccggctt cacctcctcc acctacgcca tgtcctgggt ccgacaggcc     120
cctggaaagg gcctggagtg ggtggccacc atctccgacg ccggctccta ctcctactac     180
cccgacaacg tgaagggccg gttcaccatc tcccgggaca acgccaagaa ctccctgtac     240
ctgcagatga actccctgcg ggccgaggac accgccgtgt actactgcgc cagacggggc     300
tccagatacg aagagtacta cgtgatggac tactggggcc agggcacaac cgtgaccgtg     360
tcctcc                                                                366

<210> SEQ ID NO 47
<211> LENGTH: 452
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 47

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Thr Tyr
            20                  25                  30

Ala Met Ser Trp Val Arg Gln Ala Pro Gly Lys Gly Leu Glu Trp Val
            35                  40                  45

Ala Thr Ile Ser Asp Ala Gly Ser Tyr Ser Tyr Tyr Pro Asp Asn Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Arg Gly Ser Arg Tyr Glu Glu Tyr Tyr Val Met Asp Tyr Trp
            100                 105                 110

Gly Gln Gly Thr Thr Val Thr Val Ser Ser Ala Ser Thr Lys Gly Pro
            115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Cys Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
    195                 200                 205

His Lys Pro Ser Asn Thr Lys Val Asp Lys Arg Val Glu Pro Lys Ser
210                 215                 220

Cys Asp Lys Thr His Thr Cys Pro Pro Cys Pro Ala Pro Glu Leu Leu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Ala Val Ser
            260                 265                 270

His Glu Asp Pro Glu Val Lys Phe Asn Trp Tyr Val Asp Gly Val Glu
    275                 280                 285

Val His Asn Ala Lys Thr Lys Pro Arg Glu Glu Gln Tyr Asn Ser Thr
290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Ala Ala Pro
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Arg Glu Glu Met Thr Lys Asn Gln Val
    355                 360                 365

Ser Leu Thr Cys Leu Val Lys Gly Phe Tyr Pro Cys Asp Ile Ala Val
370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
                405                 410                 415

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
           435                 440                 445
Ser Pro Gly Lys
    450

<210> SEQ ID NO 48
<211> LENGTH: 1356
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 48
gaagtgcagc tggtggaatc tggcggcgga ctggtcaagc ctggcggctc cctgagactg      60
tcttgcgccg cctccggctt caccttctcc acctacgcca tgtcctgggt ccgacaggcc     120
cctggaaagg gcctggagtg gtggccacc atctccgacg ccggctccta ctcctactac      180
cccgacaacg tgaagggccg gttcaccatc tcccgggaca cgccaagaa ctccctgtac      240 ctgcagatga actccctgcg ggccgaggac accgccgtgt actactgcgc cagacggggc     300
tccagatacg aagagtacta cgtgatggac tactggggcc agggcacaac cgtgaccgtg     360
tcctccgcct ccaccaaggg accctccgtg ttccctctgg ccccttccag caagtccacc     420
tctggcggca ccgccgctct gggctgcctg gtcaaggact acttccctg ccctgtgaca      480 gtgtcctgga actccggcgc tctgacctcc ggcgtgcaca ccttccctgc cgtgctgcag     540
tcctccggcc tgtactccct gtcctccgtc gtgaccgtgc cttcctccag cctgggcacc     600
cagacctaca tctgcaacgt gaaccacaag ccctccaaca ccaaagtgga caagcgggtg     660
gaacccaagt cctgcgacaa gacccacacc tgtcctccct gccctgcccc tgagctgctg     720
ggaggccctt ccgtgttcct gttccctcca aagcccaagg acaccctgat gatctcccgg     780 accctgaag tgacctgcgt ggtggtggcc gtgtcccacg aggatcccga agtgaagttc      840
aattggtacg tggacggcgt ggaagtgcac aatgccaaga ccaagcccag agaggaacag     900
tacaactcca cctaccgggt ggtgtccgtg ctgaccgtgc tgcaccagga ctggctgaac     960
ggcaaagagt acaagtgcaa agtgtccaac aaggccctgg ccgctcccat cgaaaagacc    1020
atctccaagg ccaagggcca gcccagagag ccccaagtgt acacactgcc tccagccgg    1080 gaagagatga ccaagaacca agtgtccctg acctgcctcg tgaagggctt ctaccctgc    1140 gatatcgccg tggagtggga gtccaacggc cagcccgaga caactacaa gaccacccct   1200 cccgtgctgg actccgacgg ctcattcttc ctgtactcca gctgaccgt ggacaagtcc    1260 cggtggcagc agggcaacgt gttctcctgc tccgtgatgc acgaggccct gcacaaccac    1320
tacacccaga gtccctgtc cctgagcccc ggcaag                              1356

<210> SEQ ID NO 49
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 49

Arg Ala Ser Gln Ser Ile Ser Asn Asn Leu His
1               5                   10

```
<210> SEQ ID NO 50
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 50

Tyr Ala Ser Gln Ser Ile Ser
1               5

<210> SEQ ID NO 51
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 51

Gln Gln Ser Ser Ser Trp Leu Thr
1               5

<210> SEQ ID NO 52
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 52

Arg Ala Ser Gln Ser Ile Ser Asn Asn Leu His
1               5                   10

<210> SEQ ID NO 53
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 53

Tyr Ala Ser Gln Ser Ile Ser
1               5

<210> SEQ ID NO 54
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 54

Gln Gln Ser Ser Ser Trp Leu Thr
1               5

<210> SEQ ID NO 55
<211> LENGTH: 7
<212> TYPE: PRT
```

<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 55

Ser Gln Ser Ile Ser Asn Asn
1               5

<210> SEQ ID NO 56
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 56

Tyr Ala Ser
1

<210> SEQ ID NO 57
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 57

Ser Ser Ser Trp Leu
1               5

<210> SEQ ID NO 58
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 58

Gln Ser Ile Ser Asn Asn
1               5

<210> SEQ ID NO 59
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 59

Tyr Ala Ser
1

<210> SEQ ID NO 60
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:

Synthetic peptide"

<400> SEQUENCE: 60

Gln Gln Ser Ser Ser Trp Leu Thr
1               5

<210> SEQ ID NO 61
<211> LENGTH: 106
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 61

Glu Ile Val Leu Thr Gln Ser Pro Ala Thr Leu Ser Val Ser Pro Gly
1               5                   10                  15

Glu Arg Val Thr Leu Ser Cys Arg Ala Ser Gln Ser Ile Ser Asn Asn
                20                  25                  30

Leu His Trp Tyr Gln Gln Lys Pro Gly Gln Ala Pro Arg Leu Leu Ile
            35                  40                  45

Lys Tyr Ala Ser Gln Ser Ile Ser Gly Ile Pro Ala Arg Phe Ser Gly
    50                  55                  60

Ser Gly Ser Gly Thr Asp Phe Thr Leu Thr Ile Ser Ser Val Glu Pro
65                  70                  75                  80

Glu Asp Phe Gly Val Tyr Phe Cys Gln Gln Ser Ser Ser Trp Leu Thr
                85                  90                  95

Phe Gly Gln Gly Thr Lys Leu Glu Ile Lys
            100                 105

<210> SEQ ID NO 62
<211> LENGTH: 318
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 62
gagatcgtgc tgacacagtc ccctgccacc ctgtctgtgt ctcccggcga gagagtgacc        60
ctgtcctgcc gggcctccca gtccatctcc aacaacctgc actggtatca gcagaagccc       120
ggccaggccc ctcggctgct gattaagtac gcctcccaga gcatctccgg catccctgcc       180
agattctccg gctccggcag cggcaccgac ttcaccctga ccatctccag cgtggaaccc       240
gaggacttcg gcgtgtactt ctgccagcag tcctcctcct ggctgacctt cggccagggc       300
accaagctgg aaatcaag                                                     318

<210> SEQ ID NO 63
<211> LENGTH: 213
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 63

Glu Ile Val Leu Thr Gln Ser Pro Ala Thr Leu Ser Val Ser Pro Gly
1               5                   10                  15

Glu Arg Val Thr Leu Ser Cys Arg Ala Ser Gln Ser Ile Ser Asn Asn
                20                  25                  30

Leu His Trp Tyr Gln Gln Lys Pro Gly Gln Ala Pro Arg Leu Leu Ile
     35                  40                  45

Lys Tyr Ala Ser Gln Ser Ile Ser Gly Ile Pro Ala Arg Phe Ser Gly
 50                  55                  60

Ser Gly Ser Gly Thr Asp Phe Thr Leu Thr Ile Ser Ser Val Glu Pro
 65                  70                  75                  80

Glu Asp Phe Gly Val Tyr Phe Cys Gln Gln Ser Ser Ser Trp Leu Thr
                85                  90                  95

Phe Gly Gln Gly Thr Lys Leu Glu Ile Lys Arg Thr Val Ala Ala Pro
                100                 105                 110

Ser Val Phe Ile Phe Pro Pro Ser Asp Glu Gln Leu Lys Ser Gly Thr
            115                 120                 125

Ala Ser Val Val Cys Leu Leu Asn Asn Phe Tyr Pro Arg Glu Ala Lys
        130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210

<210> SEQ ID NO 64
<211> LENGTH: 639
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 64
gagatcgtgc tgacacagtc ccctgccacc ctgtctgtgt ctcccggcga gagagtgacc    60
ctgtcctgcc gggcctccca gtccatctcc aacaacctgc actggtatca gcagaagccc   120
ggccaggccc ctcggctgct gattaagtac gcctcccaga gcatctccgg catccctgcc   180
agattctccg gctccggcag cggcaccgac ttcaccctga ccatctccag cgtggaaccc   240
gaggacttcg gcgtgtactt ctgccagcag tcctcctcct ggctgacctt cggccagggc   300
accaagctga aaatcaagcg tacggtggcc gctcccagcg tgttcatctt cccccccagc   360
gacgagcagc tgaagagcgg caccgccagc gtggtgtgcc tgctgaacaa cttctacccc   420
cgggaggcca aggtgcagtg gaaggtggac aacgccctgc agagcggcaa cagccaggag   480
agcgtcaccg agcaggacag caaggactcc acctacagcc tgagcagcac cctgaccctg   540
agcaaggccg actacgagaa gcataaggtg tacgcctgcg aggtgaccca ccagggcctg   600
tccagccccg tgaccaagag cttcaacagg ggcgagtgc                          639

<210> SEQ ID NO 65
<211> LENGTH: 11
<212> TYPE: PRT
<213> ORGANISM: Artificial Sequence
<220> FEATURE:

```
<221> NAME/KEY: source
<223> OTHER INFORMATION: /note="Description of Artificial Sequence:
      Synthetic peptide"

<400> SEQUENCE: 65

Gly Tyr Ser Ile Thr Ser Gly Tyr Ser Trp His
1               5                   10

<210> SEQ ID NO 66
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 66

His Ile His Ser Ser Gly Ser Thr Asn Tyr Asn Pro Ser Leu Lys Ser
1               5                   10                  15

<210> SEQ ID NO 67
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 67

Gly Gly Val Gln Ala Phe Ala Tyr
1               5

<210> SEQ ID NO 68
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 68

Ser Gly Tyr Ser Trp His
1               5

<210> SEQ ID NO 69
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 69

His Ile His Ser Ser Gly Ser Thr Asn Tyr Asn Pro Ser Leu Lys Ser
1               5                   10                  15

<210> SEQ ID NO 70
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
```

```
<400> SEQUENCE: 70

Gly Gly Val Gln Ala Phe Ala Tyr
1               5

<210> SEQ ID NO 71
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 71

Gly Tyr Ser Ile Thr Ser Gly Tyr
1               5

<210> SEQ ID NO 72
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 72

His Ser Ser Gly Ser
1               5

<210> SEQ ID NO 73
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 73

Gly Gly Val Gln Ala Phe Ala Tyr
1               5

<210> SEQ ID NO 74
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 74

Gly Tyr Ser Ile Thr Ser Gly Tyr Ser
1               5

<210> SEQ ID NO 75
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 75

Ile His Ser Ser Gly Ser Thr
1               5
```

<210> SEQ ID NO 76
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 76

Ala Arg Gly Gly Val Gln Ala Phe Ala Tyr
1               5                   10

<210> SEQ ID NO 77
<211> LENGTH: 117
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 77

Asp Val Gln Leu Gln Glu Ser Gly Pro Gly Leu Val Lys Pro Ser Gln
1               5                   10                  15

Thr Leu Ser Leu Thr Cys Thr Val Ser Gly Tyr Ser Ile Thr Ser Gly
            20                  25                  30

Tyr Ser Trp His Trp Ile Arg Gln His Pro Gly Lys Gly Leu Glu Trp
        35                  40                  45

Met Ala His Ile His Ser Ser Gly Ser Thr Asn Tyr Asn Pro Ser Leu
    50                  55                  60

Lys Ser Arg Ile Thr Ile Ser Arg Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Gly Gly Val Gln Ala Phe Ala Tyr Trp Gly Gln Gly Thr Leu
            100                 105                 110

Val Thr Val Ser Ser
        115

<210> SEQ ID NO 78
<211> LENGTH: 351
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 78
gacgtgcagc tgcaggaatc tggccctggc ctggtcaagc cctcccagac cctgtccctg      60
acctgcaccg tgtccggcta ctctatcacc tccggctaca gctggcactg gatccggcag     120
caccccggca agggcctgga atggatggcc cacatccact cctccggctc caccaactac     180
aaccccagcc tgaagtcccg gatcaccatc tccggaca cctccaagaa ccagttctcc     240
ctgaagctgt cctccgtgac cgccgctgac accgccgtgt actactgtgc cagaggcggc     300
gtgcaggcct cgcttattg gggccaggga accctggtca ccgtgtcctc c             351

<210> SEQ ID NO 79
<211> LENGTH: 447

```
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 79
```

Asp Val Gln Leu Gln Glu Ser Gly Pro Gly Leu Val Lys Pro Ser Gln
1               5                   10                  15

Thr Leu Ser Leu Thr Cys Thr Val Ser Gly Tyr Ser Ile Thr Ser Gly
            20                  25                  30

Tyr Ser Trp His Trp Ile Arg Gln His Pro Gly Lys Gly Leu Glu Trp
        35                  40                  45

Met Ala His Ile His Ser Ser Gly Ser Thr Asn Tyr Asn Pro Ser Leu
    50                  55                  60

Lys Ser Arg Ile Thr Ile Ser Arg Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Gly Gly Val Gln Ala Phe Ala Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Cys Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Arg Val Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Ala Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Ala Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
        355                 360                 365

Val Lys Gly Phe Tyr Pro Cys Asp Ile Ala Val Glu Trp Glu Ser Asn

```
                    370                375                380
Gly Gln Pro Glu Asn Asn Tyr Lys Thr Thr Pro Pro Val Leu Asp Ser
385                 390                395                400

Asp Gly Ser Phe Phe Leu Tyr Ser Lys Leu Thr Val Asp Lys Ser Arg
                405                410                415

Trp Gln Gln Gly Asn Val Phe Ser Cys Ser Val Met His Glu Ala Leu
            420                425                430

His Asn His Tyr Thr Gln Lys Ser Leu Ser Leu Ser Pro Gly Lys
        435                440                445

<210> SEQ ID NO 80
<211> LENGTH: 1341
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 80
gacgtgcagc tgcaggaatc tggccctggc ctggtcaagc cctcccagac cctgtccctg      60
acctgcaccg tgtccggcta ctctatcacc tccggctaca gctggcactg gatccggcag     120
caccccggca agggcctgga atggatggcc cacatccact cctccggctc caccaactac    180
aaccccagcc tgaagtcccg gatcaccatc tcccgggaca cctccaagaa ccagttctcc    240
ctgaagctgt cctccgtgac cgccgctgac accgccgtgt actactgtgc cagaggcggc    300
gtgcaggcct tcgcttattg gggccaggga accctggtca ccgtgtcctc cgccagcacc    360
aagggaccct ccgtgttccc tctggccct tccagcaagt ccacctctgg cggcaccgcc     420
gctctgggct gcctcgtgaa ggactacttc cctgccccg tgaccgtgtc ctggaactcc     480
ggcgctctga cctccggcgt gcacaccttc cctgccgtgc tgcagtcctc cggcctgtac    540
tccctgtcca gcgtcgtgac cgtgccctcc agctctctgg gcacccagac ctacatctgc    600
aacgtgaacc acaagccctc caacaccaaa gtggacaagc gggtggaacc caagtcctgc    660
gacaagaccc acacctgtcc tcctgccct gcccctgagc tgctgggagg cccttccgtg     720
ttcctgttcc ctccaaagcc caaggacacc ctgatgatct cccggacccc tgaagtgacc    780
tgcgtggtgg tggccgtgtc ccacgaggat cccgaagtga agttcaattg gtacgtggac    840
ggcgtggaag tgcacaacgc caagaccaag cccagagagg aacagtacaa ctccacctac    900
cgggtggtgt ccgtgctgac cgtgctgcac caggactggc tgaacggcaa agagtacaag    960
tgcaaagtgt ccaacaaggc cctggccgct cccatcgaaa agaccatctc caaggccaag   1020
ggccagccca gagagcccca agtgtacaca ctgcctccca gccgggaaga tgaccaag     1080 aatcaagtgt ccctgacctg tctggtcaag ggcttctacc cctgcgatat cgccgtggag   1140
tgggagtcca acggccagcc cgagaacaac tacaagacca cccctcccgt gctggactcc   1200
gacggctcat tcttcctgta ctccaagctg accgtggaca gtcccggtg cagcagggc     1260 aacgtgttct cctgctccgt gatgcacgag gccctgcaca accactacac ccagaagtcc   1320
ctgagcctgt ccctggcaa g                                                1341

<210> SEQ ID NO 81
<211> LENGTH: 10
<212> TYPE: PRT
<213> ORGANISM: Artificial Sequence
<220> FEATURE:
<221> NAME/KEY: source
```

```
<223> OTHER INFORMATION: /note="Description of Artificial Sequence:
      Synthetic peptide"

<400> SEQUENCE: 81

Ser Ala Ser Ser Ser Val Ile Tyr Met His
1               5                   10

<210> SEQ ID NO 82
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 82

Asp Thr Ser Lys Leu Ala Ser
1               5

<210> SEQ ID NO 83
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 83

Gln Gln Trp Ser Ser Asn Pro Leu Thr
1               5

<210> SEQ ID NO 84
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 84

Ser Ala Ser Ser Ser Val Ile Tyr Met His
1               5                   10

<210> SEQ ID NO 85
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 85

Asp Thr Ser Lys Leu Ala Ser
1               5

<210> SEQ ID NO 86
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 86
```

```
Gln Gln Trp Ser Ser Asn Pro Leu Thr
1               5

<210> SEQ ID NO 87
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 87

Ser Ser Ser Val Ile Tyr
1               5

<210> SEQ ID NO 88
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 88

Asp Thr Ser
1

<210> SEQ ID NO 89
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 89

Trp Ser Ser Asn Pro Leu
1               5

<210> SEQ ID NO 90
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 90

Ser Ser Val Ile Tyr
1               5

<210> SEQ ID NO 91
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 91

Asp Thr Ser
1
```

<210> SEQ ID NO 92
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 92

Gln Gln Trp Ser Ser Asn Pro Leu Thr
1               5

<210> SEQ ID NO 93
<211> LENGTH: 106
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 93

Glu Ile Val Leu Thr Gln Ser Pro Ala Thr Leu Ser Ala Ser Pro Gly
1               5                   10                  15

Glu Arg Val Thr Met Ser Cys Ser Ala Ser Ser Val Ile Tyr Met
            20                  25                  30

His Trp Tyr Gln Gln Lys Pro Gly Gln Ala Pro Arg Trp Ile Tyr
        35                  40                  45

Asp Thr Ser Lys Leu Ala Ser Gly Val Pro Ala Arg Phe Ser Gly Ser
50                  55                  60

Gly Ser Gly Thr Asp Tyr Thr Leu Thr Ile Ser Ser Met Glu Pro Glu
65                  70                  75                  80

Asp Ala Ala Val Tyr Tyr Cys Gln Gln Trp Ser Ser Asn Pro Leu Thr
                85                  90                  95

Phe Gly Gln Gly Thr Lys Leu Glu Ile Lys
            100                 105

<210> SEQ ID NO 94
<211> LENGTH: 318
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 94
gagatcgtgc tgacacagtc ccctgccacc ctgtccgcct ctccaggcga gcgcgtgaca     60
atgtcctgct ccgcctcctc ctccgtgatc tacatgcact ggtatcagca aaagcccggc    120
caggcccctc ggcggtggat ctacgatacc tccaagctgg cctccggcgt gcccgccaga    180
ttctccggct ctggctctgg caccgactac accctgacca tctccagcat ggaacccgag    240
gacgccgccg tgtactactg ccagcagtgg tcctccaacc ctctgacctt cggccagggc    300
accaagctgg aaatcaag                                                  318

<210> SEQ ID NO 95
<211> LENGTH: 213
<212> TYPE: PRT
<213> ORGANISM: Artificial Sequence
<220> FEATURE:
<221> NAME/KEY: source
<223> OTHER INFORMATION: /note="Description of Artificial Sequence:
       Synthetic polypeptide"

<400> SEQUENCE: 95

Glu Ile Val Leu Thr Gln Ser Pro Ala Thr Leu Ser Ala Ser Pro Gly
1               5                   10                  15

Glu Arg Val Thr Met Ser Cys Ser Ala Ser Ser Val Ile Tyr Met
            20                  25                  30

His Trp Tyr Gln Gln Lys Pro Gly Gln Ala Pro Arg Arg Trp Ile Tyr
        35                  40                  45

Asp Thr Ser Lys Leu Ala Ser Gly Val Pro Ala Arg Phe Ser Gly Ser
    50                  55                  60

Gly Ser Gly Thr Asp Tyr Thr Leu Thr Ile Ser Ser Met Glu Pro Glu
65                  70                  75                  80

Asp Ala Ala Val Tyr Tyr Cys Gln Gln Trp Ser Ser Asn Pro Leu Thr
                85                  90                  95

Phe Gly Gln Gly Thr Lys Leu Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210

<210> SEQ ID NO 96
<211> LENGTH: 639
<212> TYPE: DNA
<213> ORGANISM: Artificial Sequence
<220> FEATURE:
<221> NAME/KEY: source
<223> OTHER INFORMATION: /note="Description of Artificial Sequence:
       Synthetic polynucleotide"

<400> SEQUENCE: 96
gagatcgtgc tgacacagtc ccctgccacc ctgtccgcct ctccaggcga gcgcgtgaca     60
atgtcctgct ccgcctcctc ctccgtgatc tacatgcact ggtatcagca gaagcccggc    120
caggcccctc ggcggtggat ctacgatacc tccaagctgg cctccggcgt gcccgccaga    180
ttctccggct ctggctctgg caccgactac accctgacca tctccagcat ggaacccgag    240
gacgccgccg tgtactactg ccagcagtgg tcctccaacc ctctgacctt cggccagggc    300
accaagctgg aaatcaagcg tacggtggcc gctcccagcg tgttcatctt cccccccagc    360
gacgagcagc tgaagagcgg caccgccagc gtggtgtgcc tgctgaacaa cttctacccc    420
cgggaggcca aggtgcagtg gaaggtggac aacgccctgc agagcggcaa cagccaggag    480
agcgtcaccg agcaggacag caaggactcc acctacagcc tgagcagcac cctgaccctg    540
agcaaggccg actacgagaa gcataaggtg tacgcctgcg aggtgaccca ccagggcctg    600
tccagccccg tgaccaagag cttcaacagg ggcgagtgc 639

<210> SEQ ID NO 97
<211> LENGTH: 378
<212> TYPE: PRT
<213> ORGANISM: Homo sapiens

<400> SEQUENCE: 97

Met Asp Leu Gly Lys Pro Met Lys Ser Val Leu Val Val Ala Leu Leu
1               5                   10                  15

Val Ile Phe Gln Val Cys Leu Cys Gln Asp Glu Val Thr Asp Asp Tyr
            20                  25                  30

Ile Gly Asp Asn Thr Thr Val Asp Tyr Thr Leu Phe Glu Ser Leu Cys
        35                  40                  45

Ser Lys Lys Asp Val Arg Asn Phe Lys Ala Trp Phe Leu Pro Ile Met
    50                  55                  60

Tyr Ser Ile Ile Cys Phe Val Gly Leu Leu Gly Asn Gly Leu Val Val
65                  70                  75                  80

Leu Thr Tyr Ile Tyr Phe Lys Arg Leu Lys Thr Met Thr Asp Thr Tyr
                85                  90                  95

Leu Leu Asn Leu Ala Val Ala Asp Ile Leu Phe Leu Leu Thr Leu Pro
            100                 105                 110

Phe Trp Ala Tyr Ser Ala Ala Lys Ser Trp Val Phe Gly Val His Phe
        115                 120                 125

Cys Lys Leu Ile Phe Ala Ile Tyr Lys Met Ser Phe Phe Ser Gly Met
    130                 135                 140

Leu Leu Leu Leu Cys Ile Ser Ile Asp Arg Tyr Val Ala Ile Val Gln
145                 150                 155                 160

Ala Val Ser Ala His Arg His Arg Ala Arg Val Leu Leu Ile Ser Lys
                165                 170                 175

Leu Ser Cys Val Gly Ile Trp Ile Leu Ala Thr Val Leu Ser Ile Pro
            180                 185                 190

Glu Leu Leu Tyr Ser Asp Leu Gln Arg Ser Ser Glu Gln Ala Met
        195                 200                 205

Arg Cys Ser Leu Ile Thr Glu His Val Glu Ala Phe Ile Thr Ile Gln
    210                 215                 220

Val Ala Gln Met Val Ile Gly Phe Leu Val Pro Leu Leu Ala Met Ser
225                 230                 235                 240

Phe Cys Tyr Leu Val Ile Ile Arg Thr Leu Leu Gln Ala Arg Asn Phe
                245                 250                 255

Glu Arg Asn Lys Ala Ile Lys Val Ile Ala Val Val Val Val Phe
            260                 265                 270

Ile Val Phe Gln Leu Pro Tyr Asn Gly Val Val Leu Ala Gln Thr Val
        275                 280                 285

Ala Asn Phe Asn Ile Thr Ser Ser Thr Cys Glu Leu Ser Lys Gln Leu
    290                 295                 300

Asn Ile Ala Tyr Asp Val Thr Tyr Ser Leu Ala Cys Val Arg Cys Cys
305                 310                 315                 320

Val Asn Pro Phe Leu Tyr Ala Phe Ile Gly Val Lys Phe Arg Asn Asp
                325                 330                 335

Leu Phe Lys Leu Phe Lys Asp Leu Gly Cys Leu Ser Gln Glu Gln Leu
            340                 345                 350

Arg Gln Trp Ser Ser Cys Arg His Ile Arg Arg Ser Ser Met Ser Val
        355                 360                 365

Glu Ala Glu Thr Thr Thr Thr Phe Ser Pro
    370                 375

<210> SEQ ID NO 98
<211> LENGTH: 1134
<212> TYPE: DNA
<213> ORGANISM: Homo sapiens

<400> SEQUENCE: 98

| | |
|---|---:|
| atggacctgg ggaaaccaat gaaaagcgtg ctggtggtgg ctctccttgt cattttccag | 60 |
| gtatgcctgt gtcaagatga ggtcacggac gattacatcg agacaacac cacagtggac | 120 |
| tacactttgt tcgagtcttt gtgctccaag aaggacgtgc ggaactttaa agcctggttc | 180 |
| ctccctatca tgtactccat catttgtttc gtgggcctac tgggcaatgg gctggtcgtg | 240 |
| ttgacctata tctatttcaa gaggctcaag accatgaccg ataccaccct gctcaacctg | 300 |
| gcggtggcag acatcctctt cctcctgacc cttcccttct gggcctacag cgcggccaag | 360 |
| tcctgggtct tcggtgtcca cttttgcaag ctcatctttg ccatctacaa gatgagcttc | 420 |
| ttcagtggca tgctcctact tctttgcatc agcattgacc gctacgtggc catcgtccag | 480 |
| gctgtctcag ctcaccgcca ccgtgcccgc gtccttctca tcagcaagct gtcctgtgtg | 540 |
| ggcatctgga tactagccac agtgctctcc atcccagagc tcctgtacag tgacctccag | 600 |
| aggagcagca gtgagcaagc gatgcgatgc tctctcatca cagagcatgt ggaggccttt | 660 |
| atcaccatcc aggtggccca gatggtgatc ggctttctgg tccccctgct ggccatgagc | 720 |
| ttctgttacc ttgtcatcat ccgcacctg ctccaggcac gcaactttga gcgcaacaag | 780 |
| gccatcaagg tgatcatcgc tgtggtcgtg gtcttcatag tcttccagct gcctacaat | 840 |
| ggggtggtcc tggcccagac ggtggccaac ttcaacatca ccagtagcac ctgtgagctc | 900 |
| agtaagcaac tcaacatcgc ctacgacgtc acctacagcc tggcctgcgt ccgctgctgc | 960 |
| gtcaacccttt tcttgtacgc cttcatcggc gtcaagttcc gcaacgatct cttcaagctc | 1020 |
| ttcaaggacc tgggctgcct cagccaggag cagctccggc agtggtcttc ctgtcggcac | 1080 |
| atccggcgct cctccatgag tgtggaggcc gagaccacca ccaccttctc ccca | 1134 |

<210> SEQ ID NO 99
<211> LENGTH: 378
<212> TYPE: PRT
<213> ORGANISM: Macaca fascicularis

<400> SEQUENCE: 99

Met Asp Leu Gly Lys Pro Met Lys Ser Val Leu Val Val Ala Leu Leu
1               5                   10                  15

Val Ile Phe Gln Val Cys Leu Cys Gln Asp Glu Val Thr Asp Asp Tyr
            20                  25                  30

Ile Gly Asp Asn Thr Thr Val Asp Tyr Thr Leu Phe Glu Ser Leu Cys
        35                  40                  45

Ser Lys Lys Asp Val Arg Asn Phe Lys Ala Trp Phe Leu Pro Ile Met
    50                  55                  60

Tyr Ser Ile Ile Cys Phe Val Gly Leu Leu Gly Asn Gly Leu Val Val
65                  70                  75                  80

Leu Thr Tyr Ile Tyr Phe Lys Arg Leu Lys Thr Met Thr Asp Thr Tyr
                85                  90                  95

Leu Leu Asn Leu Ala Val Ala Asp Ile Leu Phe Leu Leu Thr Leu Pro
            100                 105                 110

Phe Trp Ala Tyr Ser Ala Ala Lys Ser Trp Val Phe Gly Val His Phe

```
            115                 120                 125
Cys Lys Leu Ile Phe Ala Ile Tyr Lys Met Ser Phe Phe Ser Gly Met
        130                 135                 140

Leu Leu Leu Leu Cys Ile Ser Ile Asp Arg Tyr Val Ala Ile Val Gln
145                 150                 155                 160

Ala Val Ser Ala His Arg His Arg Ala Arg Val Leu Leu Ile Ser Lys
                165                 170                 175

Leu Ser Cys Val Gly Ile Trp Ile Leu Ala Thr Val Leu Ser Ile Pro
            180                 185                 190

Glu Leu Leu Tyr Ser Gly Leu Gln Arg Ser Ser Glu Gln Ala Met
            195                 200                 205

Arg Cys Ser Leu Ile Thr Glu His Val Glu Ala Phe Ile Thr Ile Gln
        210                 215                 220

Val Ala Gln Met Val Ile Gly Phe Leu Val Pro Leu Leu Ala Met Ser
225                 230                 235                 240

Phe Cys Tyr Leu Val Ile Ile Arg Thr Leu Leu Gln Ala Arg Asn Phe
                245                 250                 255

Glu Arg Asn Lys Ala Ile Lys Val Ile Ala Val Val Val Val Phe
            260                 265                 270

Ile Val Phe Gln Leu Pro Tyr Asn Gly Val Val Leu Ala Gln Thr Val
        275                 280                 285

Ala Asn Phe Asn Ile Thr Ser Ser Thr Cys Glu Leu Ser Lys Gln Leu
290                 295                 300

Asn Ile Ala Tyr Asp Val Thr Tyr Ser Leu Ala Cys Val Arg Cys Cys
305                 310                 315                 320

Val Asn Pro Phe Leu Tyr Ala Phe Ile Gly Val Lys Phe Arg Asn Asp
                325                 330                 335

Leu Phe Lys Leu Phe Lys Asp Leu Gly Cys Leu Ser Gln Glu Gln Leu
            340                 345                 350

Arg Gln Trp Ser Ser Cys Arg His Ile Arg Arg Ser Ser Met Ser Val
        355                 360                 365

Glu Ala Glu Thr Thr Thr Thr Phe Ser Pro
    370                 375

<210> SEQ ID NO 100
<211> LENGTH: 1134
<212> TYPE: DNA
<213> ORGANISM: Macaca fascicularis

<400> SEQUENCE: 100
atggacctgg ggaaaccaat gaaaagcgtg ctggtggtgg ctctccttgt cattttccag     60
gtatgcctgt gtcaagatga ggtcacggac gattacatcg agacaacaca cacagtggac    120
tacactttgt tcgagtcttt gtgctccaag aaggacgtgc ggaactttaa agcctggttc    180
ctccctatca tgtactccat catttgtttc gtgggcctac tgggcaatgg gctggtcgtg    240
ttgacctata tctatttcaa gaggctcaag accatgaccg ataccacct gctcaacctg    300 gcggtggcag acatcctctt cctcctgacc cttcccttct gggcctacag cgcggccaag    360
tcctgggtct tcggtgtcca cttttgcaag ctcatctttg ccatctacaa gatgagcttc    420
ttcagtggca tgctcctact tctttgcatc agcattgacc gctacgtggc catcgtccag    480
gctgtctcag ctcaccgcca ccgtgcccgc gtccttctca tcagcaagct gtcctgtgtg    540
ggcatctgga tactagccac agtgctctcc atcccagagc tcctgtacag tggcctccag    600
aggagcagca gtgagcaagc gatgcgatgc tctctcatca gagcatgt ggaggccttt    660
```

```
atcaccatcc aggtggccca gatggtgatc ggctttctgg tcccccctgct ggccatgagc   720 ttctgttacc ttgtcatcat ccgcaccctg ctccaggcac gcaactttga gcgcaacaag   780
gccatcaagg tgatcatcgc tgtggtcgtg gtcttcatag tcttccagct gccctacaat   840
ggggtggtcc tggcccagac ggtggccaac ttcaacatca ccagtagcac ctgtgagctc   900
agtaagcaac tcaacatcgc ctacgacgtc acctacagcc tggcctgcgt ccgctgctgc   960 gtcaacccctt tcttgtacgc cttcatcggc gtcaagttcc gcaacgatct cttcaagctc  1020
ttcaaggacc tgggctgcct cagccaggag cagctccggc agtggtcttc ctgtcggcac  1080
atccggcgct cctccatgag tgtggaggcc gagaccacca ccaccttctc ccca          1134
```

<210> SEQ ID NO 101
<211> LENGTH: 378
<212> TYPE: PRT
<213> ORGANISM: Mus sp.

<400> SEQUENCE: 101

```
Met Asp Pro Gly Lys Pro Arg Lys Asn Val Leu Val Ala Leu Leu
1               5                   10                  15

Val Ile Phe Gln Val Cys Phe Cys Gln Asp Glu Val Thr Asp Asp Tyr
            20                  25                  30

Ile Gly Glu Asn Thr Thr Val Asp Tyr Thr Leu Tyr Glu Ser Val Cys
        35                  40                  45

Phe Lys Lys Asp Val Arg Asn Phe Lys Ala Trp Phe Leu Pro Leu Met
    50                  55                  60

Tyr Ser Val Ile Cys Phe Val Gly Leu Leu Asn Gly Leu Val Ile
65                  70                  75                  80

Leu Thr Tyr Ile Tyr Phe Lys Arg Leu Lys Thr Met Thr Asp Thr Tyr
                85                  90                  95

Leu Leu Asn Leu Ala Val Ala Asp Ile Leu Phe Leu Leu Ile Leu Pro
            100                 105                 110

Phe Trp Ala Tyr Ser Glu Ala Lys Ser Trp Ile Phe Gly Val Tyr Leu
        115                 120                 125

Cys Lys Gly Ile Phe Gly Ile Tyr Lys Leu Ser Phe Phe Ser Gly Met
    130                 135                 140

Leu Leu Leu Leu Cys Ile Ser Ile Asp Arg Tyr Val Ala Ile Val Gln
145                 150                 155                 160

Ala Val Ser Ala His Arg His Arg Ala Arg Val Leu Leu Ile Ser Lys
                165                 170                 175

Leu Ser Cys Val Gly Ile Trp Met Leu Ala Leu Phe Leu Ser Ile Pro
            180                 185                 190

Glu Leu Leu Tyr Ser Gly Leu Gln Lys Asn Ser Gly Glu Asp Thr Leu
        195                 200                 205

Arg Cys Ser Leu Val Ser Ala Gln Val Glu Ala Leu Ile Thr Ile Gln
    210                 215                 220

Val Ala Gln Met Val Phe Gly Phe Leu Val Pro Met Leu Ala Met Ser
225                 230                 235                 240

Phe Cys Tyr Leu Ile Ile Ile Arg Thr Leu Leu Gln Ala Arg Asn Phe
                245                 250                 255

Glu Arg Asn Lys Ala Ile Lys Val Ile Ile Ala Val Val Val Val Phe
            260                 265                 270

Ile Val Phe Gln Leu Pro Tyr Asn Gly Val Val Leu Ala Gln Thr Val
        275                 280                 285
```

Ala Asn Phe Asn Ile Thr Asn Ser Ser Cys Glu Thr Ser Lys Gln Leu
            290                 295                 300

Asn Ile Ala Tyr Asp Val Thr Tyr Ser Leu Ala Ser Val Arg Cys Cys
305                 310                 315                 320

Val Asn Pro Phe Leu Tyr Ala Phe Ile Gly Val Lys Phe Arg Ser Asp
                325                 330                 335

Leu Phe Lys Leu Phe Lys Asp Leu Gly Cys Leu Ser Gln Glu Arg Leu
            340                 345                 350

Arg His Trp Ser Ser Cys Arg His Val Arg Asn Ala Ser Val Ser Met
            355                 360                 365

Glu Ala Glu Thr Thr Thr Thr Phe Ser Pro
        370                 375

<210> SEQ ID NO 102
<211> LENGTH: 1134
<212> TYPE: DNA
<213> ORGANISM: Mus sp.

<400> SEQUENCE: 102

```
atggacccag ggaaacccag gaaaaacgtg ctggtggtgg ctctccttgt catttttccag     60
gtgtgcttct gccaagatga ggtcaccgat gactacatcg gcgagaatac cacggtggac    120
tacaccctgt acgagtcggt gtgcttcaag aaggatgtgc ggaactttaa ggcctggttc    180
ctgcctctca tgtattctgt catctgcttc gtgggcctgc tcggcaacgg gctggtgata    240
ctgacgtaca tctatttcaa gaggctcaag accatgacgg ataccacct gctcaacctg    300
gccgtggcag acatcctttt cctcctgatt cttcccttct gggcctacag cgaagccaag    360
tcctggatct ttggcgtcta cctgtgtaag ggcatctttg catctataa gttaagcttc    420
ttcagcggga tgctgctgct cctatgcatc agcattgacc gctacgtagc catcgtccag    480
gccgtgtcgg ctcatcgcca ccgcgcccgc gtgcttctca tcagcaagct gtcctgtgtg    540
ggcatctgga tgctggccct cttcctctcc atcccggagc tgctctacag cggcctccag    600
aagaacagcg gcgaggacac gctgagatgc tcactggtca gtgcccaagt ggaggccttg    660
atcaccatcc aagtggccca gatggttttt gggttcctag tgcctatgct ggctatgagt    720
ttctgctacc tcattatcat ccgtaccttg ctccaggcac gcaactttga gcggaacaag    780
gccatcaagg tgatcattgc cgtggtggta gtcttcatag tcttccagct gcccta caat    840
ggggtggtcc tggctcagac ggtggccaac ttcaacatca ccaatagcag ctgcgaaacc    900
agcaagcagc tcaacattgc ctatgacgtc acctacagcc tggcctccgt ccgctgctgc    960
gtcaaccctt tcttgtatgc cttcatcggc gtcaagttcc gcagcgacct cttcaagctc   1020
ttcaaggact gggctgtct cagccaggaa cggctccggc actggtcttc ctgccggcat   1080
gtacggaacg cgtcggtgag catggaggcg agaccacca caaccttctc cccg          1134
```

<210> SEQ ID NO 103
<211> LENGTH: 378
<212> TYPE: PRT
<213> ORGANISM: Rattus sp.

<400> SEQUENCE: 103

Met Asp Leu Gly Lys Pro Thr Lys Asn Val Leu Val Val Ala Leu Leu
1               5                   10                  15

Val Ile Phe Gln Val Cys Phe Cys Gln Asp Glu Val Thr Asp Asp Tyr
            20                  25                  30

Ile Gly Glu Asn Thr Thr Val Asp Tyr Thr Leu Tyr Glu Ser Val Cys

|    |    |    |    | 35  |     |     |     |     | 40  |     |     |     |     | 45  |     |
|----|----|----|----|-----|-----|-----|-----|-----|-----|-----|-----|-----|-----|-----|-----|

Phe Lys Lys Asp Val Arg Asn Phe Lys Ala Trp Phe Leu Pro Leu Met
 50                  55                  60

Tyr Ser Val Ile Cys Phe Val Gly Leu Leu Gly Asn Gly Leu Val Val
 65                  70                  75                  80

Leu Thr Tyr Ile Tyr Phe Lys Arg Leu Lys Thr Met Thr Asp Thr Tyr
                     85                  90                  95

Leu Leu Asn Leu Ala Val Ala Asp Ile Leu Phe Leu Met Ile Leu Pro
                100                 105                 110

Phe Trp Ala Tyr Ser Glu Ala Lys Ser Trp Ile Phe Gly Ala Tyr Leu
                115                 120                 125

Cys Lys Ser Ile Phe Gly Ile Tyr Lys Leu Ser Phe Phe Ser Gly Met
            130                 135                 140

Leu Leu Leu Leu Cys Ile Ser Ile Asp Arg Tyr Val Ala Ile Val Gln
145                 150                 155                 160

Ala Val Ser Ala His Arg His Arg Ala Arg Val Leu Leu Ile Ser Lys
                165                 170                 175

Leu Ser Cys Ile Gly Ile Trp Thr Leu Ala Phe Phe Leu Ser Ile Pro
                180                 185                 190

Glu Leu Leu Tyr Ser Gly Leu Gln Lys Asn Ser Gly Glu Asp Thr Trp
                195                 200                 205

Arg Cys Ser Leu Val Ser Ala Gln Val Glu Ala Leu Ile Ala Ile Gln
210                 215                 220

Val Ala Gln Met Val Val Gly Phe Val Leu Pro Met Leu Ala Met Ser
225                 230                 235                 240

Phe Cys Tyr Leu Val Ile Ile Arg Thr Leu Leu Gln Ala Arg Asn Phe
                245                 250                 255

Glu Arg Asn Lys Ala Ile Lys Val Ile Ala Val Val Val Val Val Phe
                260                 265                 270

Val Val Phe Gln Leu Pro Tyr Asn Gly Val Val Leu Ala Gln Thr Val
            275                 280                 285

Ala Asn Phe Asn Ile Thr Asn Ser Ser Cys Glu Ala Ser Lys Gln Leu
290                 295                 300

Asn Ile Ala Tyr Asp Val Thr Tyr Ser Leu Ala Ser Val Arg Cys Cys
305                 310                 315                 320

Val Asn Pro Phe Leu Tyr Ala Phe Ile Gly Val Lys Phe Arg Ser Asp
                325                 330                 335

Leu Phe Lys Leu Phe Lys Asp Leu Gly Cys Leu Ser Gln Glu Arg Leu
                340                 345                 350

Arg Gln Trp Ser Ser Cys Arg His Val Arg His Thr Ser Val Ser Met
            355                 360                 365

Glu Ala Glu Thr Thr Thr Thr Phe Ser Pro
370                 375

<210> SEQ ID NO 104
<211> LENGTH: 1134
<212> TYPE: DNA
<213> ORGANISM: Rattus sp.

<400> SEQUENCE: 104
atggacctgg ggaagcccac gaaaaacgtg ctggtggtgg ctctcctggt catttttccag    60 gtgtgcttct gccaagatga ggtcacagac gactacatcg gcgagaacac caccgtggac    120
tacaccctgt atgagtcggt gtgcttcaag aaggatgtgc ggaactttaa ggcctggttc    180

```
ctccctctca tgtactcagt catttgcttc gtgggcctgc taggcaatgg gctggtggtg      240
ctgacataca tctatttcaa gagactgaag accatgacgg atacctacct gctcaacctg      300
gccgtggcag acatcctctt cctcatgatc cttcccttct gggcctacag cgaagccaag      360
tcctggatct ttggtgccta cctgtgtaag agcatctttg catctacaa gttaagcttc       420
ttcagcggga tgttgctgct cctgtgtatc agcattgacc gctatgtggc catcgtccag      480
gccgtgtcag cccaccggca ccgcgcccgc gtgcttctca tcagcaagct gtcctgtata      540
ggcatctgga cgctggcctt tttccttct atccctgagc tgctctacag cggcctccag       600
aagaacagcg gcgaggacac gtggagatgc tccctggtca gtgcccaagt ggaggccttg      660
atcgccatcc aagtggccca gatggttgtt gggtttgtac tgcctatgct ggctatgagt      720
ttctgctacc tggttatcat ccgcactctg ctccaggcgc gaaacttcga gcggaacaag      780
gccatcaagg tgatcatcgc tgtggtcgta gtgttcgtcg tcttccagct gccctacaat      840
ggggtggtcc tggcccagac cgtggccaat ttcaacatca ccaatagcag ctgcgaagcc      900
agcaagcagc tcaacattgc ctatgacgtc acctacagcc tggcctccgt ccgctgctgt      960
gtcaacccctt tcttgtatgc cttcatcggc gtcaagttcc gcagcgacct cttcaagctc     1020
ttcaaggact tgggctgcct cagccaggaa cggctccggc agtggtcttc ctgccgccat      1080
gtacggcaca cgtccgtgag catggaggcg agactacca ccaccttctc cccg             1134
```

<210> SEQ ID NO 105
<211> LENGTH: 378
<212> TYPE: PRT
<213> ORGANISM: Homo sapiens

<400> SEQUENCE: 105

```
Met Asp Leu Gly Lys Pro Met Lys Ser Val Leu Val Val Ala Leu Leu
1               5                   10                  15

Val Ile Phe Gln Val Cys Leu Cys Gln Asp Glu Val Thr Asp Asp Tyr
            20                  25                  30

Ile Gly Asp Asn Thr Thr Val Asp Tyr Thr Leu Phe Glu Ser Leu Cys
        35                  40                  45

Ser Lys Lys Asp Val Arg Asn Phe Lys Ala Trp Phe Leu Pro Ile Met
    50                  55                  60

Tyr Ser Ile Ile Cys Phe Val Gly Leu Leu Gly Asn Gly Leu Val Val
65                  70                  75                  80

Leu Thr Tyr Ile Tyr Phe Lys Arg Leu Lys Thr Met Thr Asp Thr Tyr
                85                  90                  95

Leu Leu Asn Leu Ala Val Ala Asp Ile Leu Phe Leu Leu Thr Leu Pro
            100                 105                 110

Phe Trp Ala Tyr Ser Ala Ala Lys Ser Trp Val Phe Gly Val His Phe
        115                 120                 125

Cys Lys Leu Ile Phe Ala Ile Tyr Lys Met Ser Phe Phe Ser Gly Met
    130                 135                 140

Leu Leu Leu Leu Cys Ile Ser Ile Asp Arg Tyr Val Ala Ile Val Gln
145                 150                 155                 160

Ala Val Ser Ala His Arg His Arg Ala Arg Val Leu Leu Ile Ser Lys
                165                 170                 175

Leu Ser Cys Val Gly Ile Trp Ile Leu Ala Thr Val Leu Ser Ile Pro
            180                 185                 190

Glu Leu Leu Tyr Ser Asp Leu Gln Arg Ser Ser Ser Glu Gln Ala Met
        195                 200                 205
```

Arg Cys Ser Leu Ile Thr Glu His Val Glu Ala Phe Ile Thr Ile Gln
    210                 215                 220

Val Ala Gln Met Val Ile Gly Phe Leu Val Pro Leu Leu Ala Met Ser
225                 230                 235                 240

Phe Cys Tyr Leu Val Ile Ile Arg Thr Leu Leu Gln Ala Arg Asn Phe
                245                 250                 255

Glu Arg Asn Lys Ala Ile Lys Val Ile Ile Ala Val Val Val Val Phe
                260                 265                 270

Ile Val Phe Gln Leu Pro Tyr Asn Gly Val Val Leu Ala Gln Thr Val
                275                 280                 285

Ala Asn Phe Asn Ile Thr Ser Ser Thr Cys Glu Leu Ser Lys Gln Leu
    290                 295                 300

Asn Ile Ala Tyr Asp Val Thr Tyr Ser Leu Ala Cys Val Arg Cys Cys
305                 310                 315                 320

Val Asn Pro Phe Leu Tyr Ala Phe Ile Gly Val Lys Phe Arg Asn Asp
                325                 330                 335

Leu Phe Lys Leu Phe Lys Asp Leu Gly Cys Leu Ser Gln Glu Gln Leu
                340                 345                 350

Arg Gln Trp Ser Ser Cys Arg His Ile Arg Arg Ser Ser Met Ser Val
                355                 360                 365

Glu Ala Glu Thr Thr Thr Thr Phe Ser Pro
    370                 375

<210> SEQ ID NO 106
<211> LENGTH: 30
<212> TYPE: PRT
<213> ORGANISM: Homo sapiens

<400> SEQUENCE: 106

Gln Asp Glu Val Thr Asp Tyr Ile Gly Asp Asn Thr Thr Val Asp
1               5                   10                  15

Tyr Thr Leu Phe Glu Ser Leu Cys Ser Lys Lys Asp Val Arg
                20                  25                  30

<210> SEQ ID NO 107
<211> LENGTH: 8
<212> TYPE: PRT
<213> ORGANISM: Homo sapiens

<400> SEQUENCE: 107

Lys Ser Trp Val Phe Gly Val His
1               5

<210> SEQ ID NO 108
<211> LENGTH: 19
<212> TYPE: PRT
<213> ORGANISM: Homo sapiens

<400> SEQUENCE: 108

Tyr Ser Asp Leu Gln Arg Ser Ser Glu Gln Ala Met Arg Cys Ser
1               5                   10                  15

Leu Ile Thr

<210> SEQ ID NO 109
<211> LENGTH: 7
<212> TYPE: PRT
<213> ORGANISM: Homo sapiens

<400> SEQUENCE: 109

Phe Asn Ile Thr Ser Ser Thr
1               5

<210> SEQ ID NO 110
<211> LENGTH: 19
<212> TYPE: PRT
<213> ORGANISM: Homo sapiens

<400> SEQUENCE: 110

Tyr Ser Asp Leu Gln Arg Ser Ser Glu Gln Ala Met Arg Ser Ser
1               5                   10                  15

Leu Ile Thr

<210> SEQ ID NO 111
<211> LENGTH: 216
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 111

Glu Val Gln Leu Val Glu Ser Gly Gly Gly Leu Val Lys Pro Gly Gly
1               5                   10                  15

Ser Leu Lys Leu Ser Cys Ala Ala Ser Gly Phe Thr Phe Ser Asp Tyr
            20                  25                  30

Gly Met Leu Trp Val Arg Gln Ala Pro Glu Lys Gly Leu Glu Trp Ile
        35                  40                  45

Ala Tyr Ile Ser Ser Gly Ser Ser Thr Ile Tyr Tyr Ala Asp Arg Val
    50                  55                  60

Lys Gly Arg Phe Thr Ile Ser Arg Asp Asn Ala Lys Asn Thr Leu Phe
65                  70                  75                  80

Leu Gln Met Thr Ser Leu Arg Ser Glu Asp Thr Ala Met Tyr Tyr Cys
                85                  90                  95

Ser Thr Gly Thr Phe Ala Tyr Trp Gly Gln Gly Thr Pro Val Thr Val
            100                 105                 110

Ser Ser Ala Lys Thr Thr Pro Pro Ser Val Tyr Pro Leu Ala Pro Gly
        115                 120                 125

Ser Ala Ala Gln Thr Asn Ser Met Val Thr Leu Gly Cys Leu Val Lys
    130                 135                 140

Gly Tyr Phe Pro Glu Pro Val Thr Val Thr Trp Asn Ser Gly Ser Leu
145                 150                 155                 160

Ser Ser Gly Val His Thr Phe Pro Ala Val Leu Gln Ser Asp Leu Tyr
                165                 170                 175

Thr Leu Ser Ser Ser Val Thr Val Pro Ser Ser Thr Trp Pro Ser Glu
            180                 185                 190

Thr Val Thr Cys Asn Val Ala His Pro Ala Ser Ser Thr Lys Val Asp
        195                 200                 205

Lys Lys Ile Val Pro Arg Asp Cys
    210                 215

<210> SEQ ID NO 112
<211> LENGTH: 219
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 112

```
Asp Val Val Met Thr Gln Asn Pro Leu Ser Leu Pro Val Ser Leu Gly
1               5                   10                  15
Asp Gln Ala Ser Ile Ser Cys Arg Ser Ser Gln Ser Leu Ile Tyr Asn
            20                  25                  30
Asn Gly Asn Thr Tyr Leu His Trp Tyr Arg Gln Lys Pro Gly Gln Ser
        35                  40                  45
Pro Lys Leu Leu Ile Tyr Lys Val Ser Asn Arg Phe Ser Gly Val Pro
    50                  55                  60
Asp Arg Phe Ser Gly Ser Gly Ser Gly Thr Asp Phe Thr Leu Lys Ile
65                  70                  75                  80
Ser Arg Val Glu Ala Glu Asp Leu Gly Val Tyr Phe Cys Ser Gln Ser
                85                  90                  95
Thr His Val Pro Phe Thr Phe Gly Ser Gly Thr Lys Leu Glu Ile Lys
            100                 105                 110
Arg Ala Asp Ala Ala Pro Thr Val Ser Ile Phe Pro Pro Ser Ser Glu
        115                 120                 125
Gln Leu Thr Ser Gly Gly Ala Ser Val Val Cys Phe Leu Asn Asn Phe
    130                 135                 140
Tyr Pro Lys Asp Ile Asn Val Lys Trp Lys Ile Asp Gly Ser Glu Arg
145                 150                 155                 160
Gln Asn Gly Val Leu Asn Ser Trp Thr Asp Gln Asp Ser Lys Asp Ser
                165                 170                 175
Thr Tyr Ser Met Ser Ser Thr Leu Thr Leu Thr Lys Asp Glu Tyr Glu
            180                 185                 190
Arg His Asn Ser Tyr Thr Cys Glu Ala Thr His Lys Thr Ser Thr Ser
        195                 200                 205
Pro Ile Val Lys Ser Phe Asn Arg Asn Glu Cys
    210                 215
```

<210> SEQ ID NO 113
<211> LENGTH: 265
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 113

```
Gln Asp Glu Val Thr Asp Asp Tyr Ile Gly Asp Asn Thr Thr Val Asp
1               5                   10                  15
Tyr Thr Leu Phe Glu Ser Leu Cys Ser Lys Lys Asp Val Arg Glu Val
            20                  25                  30
Gln Leu Val Glu Ser Gly Gly Gly Leu Val Lys Pro Gly Gly Ser Leu
        35                  40                  45
Lys Leu Ser Cys Ala Ala Ser Gly Phe Thr Phe Ser Asp Tyr Gly Met
    50                  55                  60
Leu Trp Val Arg Gln Ala Pro Glu Lys Gly Leu Glu Trp Ile Ala Tyr
65                  70                  75                  80
Ile Ser Ser Gly Ser Ser Thr Ile Tyr Tyr Ala Asp Arg Val Lys Gly
                85                  90                  95
Arg Phe Thr Ile Ser Arg Asp Asn Ala Lys Asn Thr Leu Phe Leu Gln
            100                 105                 110
Met Thr Ser Leu Arg Ser Glu Asp Thr Ala Met Tyr Tyr Cys Ser Thr
```

```
            115                 120                 125
Gly Thr Tyr Ser Asp Leu Gln Arg Ser Ser Glu Gln Ala Met Arg
        130                 135                 140

Ser Ser Leu Ile Thr Phe Ala Tyr Trp Gly Gln Gly Thr Pro Val Thr
145                 150                 155                 160

Val Ser Ser Ala Lys Thr Thr Pro Pro Ser Val Tyr Pro Leu Ala Pro
                165                 170                 175

Gly Ser Ala Ala Gln Thr Asn Ser Met Val Thr Leu Gly Cys Leu Val
                180                 185                 190

Lys Gly Tyr Phe Pro Glu Pro Val Thr Val Thr Trp Asn Ser Gly Ser
                195                 200                 205

Leu Ser Ser Gly Val His Thr Phe Pro Ala Val Leu Gln Ser Asp Leu
        210                 215                 220

Tyr Thr Leu Ser Ser Ser Val Thr Val Pro Ser Ser Thr Trp Pro Ser
225                 230                 235                 240

Glu Thr Val Thr Cys Asn Val Ala His Pro Ala Ser Ser Thr Lys Val
                245                 250                 255

Asp Lys Lys Ile Val Pro Arg Asp Cys
                260                 265

<210> SEQ ID NO 114
<211> LENGTH: 795
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 114
caagatgagg tcacggacga ttacatcgga gacaacacca cagtggacta cactttgttc        60
gagtctttgt gctccaagaa ggacgtgcgg gaggtgcagc tggtggagtc tggtggtggt       120
ctggtcaagc ctggaggttc cctgaaactg agttgtgccg catctgggtt tacattctct       180
gactacggaa tgctgtgggt gaggcaggca ccagagaagg gcctggaatg gatcgcttat       240
atttccagcg gatctagtac tatctactat gcagacaggg tcaagggccg gttcaccatt       300
agcagagata cgccaaaaaa tacgctgttt ctgcagatga catcactgag gtccgaggat       360
accgctatgt attattgctc cacagggact tacagtgacc tccagaggag cagcagtgag       420
caagcgatgc gatcctctct catcacattt gcttactggg gacaggggac acccgtgacc       480
gtcagctcag ccaagaccac cccccccagc gtgtaccctc tggcccctgg ctctgccgcc       540
cagaccaaca gcatggtgac cctgggctgc ctggtgaagg gctacttccc cgagcccgtg       600
accgtgacct ggaacagcgg cagcctgagc agcggcgtgc acaccttccc cgccgtgctg       660
cagagcgacc tgtacaccct gagcagctct gtgaccgtgc ccagcagcac ctggcccagc       720
gagaccgtga catgcaacgt ggcccacccc gccagctcca ccaaggtgga caagaaaatc       780
gtgccccggg actgc                                                        795

<210> SEQ ID NO 115
<211> LENGTH: 656
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"
```

```
<400> SEQUENCE: 115
atgtcgtgat gactcagaat ccactgtccc tgcctgtgtc cctgggcgat caggcttcca    60
ttagctgtcg ttcctctcag tccctgatct acaacaatgg taacacctac ctgcactggt   120
atagacagaa gcccggccag tcccctaagc tgctgatcta caaagtgagt aataggttct   180
caggagtccc agaccggttt tccggcagcg atctgggac cgatttcaca ctgaaaatct    240
ctagggtgga ggccgaagac ctgggcgtct acttttgtag tcagagcact cacgtccct    300 tcaccttcgg cagcggaaca aaactggaaa tcaagcgcgc tgatgccgcc cctaccgtga   360
gcatcttccc ccccagcagc gagcagctga ccagcggcgg agccagcgtg gtgtgcttcc   420
tgaacaactt ctaccccaag gacatcaacg tgaagtggaa gatcgacggc agcgagcggc   480
agaacggcgt gctgaacagc tggaccgacc aggacagcaa ggactccacc tacagcatga   540
gcagcaccct gaccctgacc aaggacgagt acgagcggca caacagctac acctgcgagg   600
ccacccacaa gaccagcacc agccccatcg tgaagagctt caaccggaac gagtgc       656

<210> SEQ ID NO 116
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 116

Gly Tyr Ser Ile Thr Ser Gly Tyr Ser Trp His
1               5                   10

<210> SEQ ID NO 117
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 117

His Ile His Ser Ser Gly Ser Thr Asn Tyr Asn Pro Ser Leu Lys Ser
1               5                   10                  15

<210> SEQ ID NO 118
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 118

Gly Gly Val Gln Ala Phe Ala Tyr
1               5

<210> SEQ ID NO 119
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
```

```
<400> SEQUENCE: 119

Ser Gly Tyr Ser Trp His
1               5

<210> SEQ ID NO 120
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 120

His Ile His Ser Ser Gly Ser Thr Asn Tyr Asn Pro Ser Leu Lys Ser
1               5                   10                  15

<210> SEQ ID NO 121
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 121

Gly Gly Val Gln Ala Phe Ala Tyr
1               5

<210> SEQ ID NO 122
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 122

Gly Tyr Ser Ile Thr Ser Gly Tyr
1               5

<210> SEQ ID NO 123
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 123

His Ser Ser Gly Ser
1               5

<210> SEQ ID NO 124
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 124

Gly Gly Val Gln Ala Phe Ala Tyr
1               5
```

<210> SEQ ID NO 125
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 125

Gly Tyr Ser Ile Thr Ser Gly Tyr Ser
1               5

<210> SEQ ID NO 126
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 126

Ile His Ser Ser Gly Ser Thr
1               5

<210> SEQ ID NO 127
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 127

Ala Arg Gly Gly Val Gln Ala Phe Ala Tyr
1               5                   10

<210> SEQ ID NO 128
<211> LENGTH: 117
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 128

Asp Val Gln Leu Gln Glu Ser Gly Pro Asp Leu Val Lys Pro Ser Gln
1               5                   10                  15

Ser Leu Ser Leu Thr Cys Thr Val Thr Gly Tyr Ser Ile Thr Ser Gly
            20                  25                  30

Tyr Ser Trp His Trp Ile Arg Gln Phe Pro Gly Asn Lys Leu Glu Trp
        35                  40                  45

Met Ala His Ile His Ser Ser Gly Ser Thr Asn Tyr Asn Pro Ser Leu
    50                  55                  60

Lys Ser Arg Ile Ser Ile Ile Arg Asp Thr Ser Lys Asn Leu Phe Phe
65                  70                  75                  80

Leu Gln Leu Asn Ser Val Thr Thr Glu Asp Thr Ala Thr Tyr Tyr Cys
                85                  90                  95

Ala Arg Gly Gly Val Gln Ala Phe Ala Tyr Trp Gly Gln Gly Thr Leu
            100                 105                 110

Val Thr Val Ser Ala
        115

<210> SEQ ID NO 129
<211> LENGTH: 351
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 129
gatgtgcagc ttcaggagtc aggacctgac ctggtgaaac cttctcagtc actttcactc    60
acctgcactg tcactggcta ctccatcacc agtggttata ctggcactg gatccggcag    120 tttccaggaa acaaactgga gtggatggcc cacatccact ccagtggtag cactaactac    180
aacccatctc tcaaaagtcg catctctatc attcgagaca catccaagaa cctgttcttc    240
ctgcagttga attctgtgac tactgaggac acagccacat attactgtgc aagagggggg    300
gtacaggcct ttgcttactg gggccaaggg actctggtca ctgtctctgc a            351

<210> SEQ ID NO 130
<211> LENGTH: 447
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 130

Asp Val Gln Leu Gln Glu Ser Gly Pro Asp Leu Val Lys Pro Ser Gln
1               5                   10                  15

Ser Leu Ser Leu Thr Cys Thr Val Thr Gly Tyr Ser Ile Thr Ser Gly
            20                  25                  30

Tyr Ser Trp His Trp Ile Arg Gln Phe Pro Gly Asn Lys Leu Glu Trp
        35                  40                  45

Met Ala His Ile His Ser Ser Gly Ser Thr Asn Tyr Asn Pro Ser Leu
    50                  55                  60

Lys Ser Arg Ile Ser Ile Ile Arg Asp Thr Ser Lys Asn Leu Phe Phe
65                  70                  75                  80

Leu Gln Leu Asn Ser Val Thr Thr Glu Asp Thr Ala Thr Tyr Tyr Cys
                85                  90                  95

Ala Arg Gly Gly Val Gln Ala Phe Ala Tyr Trp Gly Gln Gly Thr Leu
            100                 105                 110

Val Thr Val Ser Ala Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Arg Val Glu Pro Lys Ser Cys Asp Lys Thr His

| | | | | | | | | | | | |
|---|---|---|---|---|---|---|---|---|---|---|---|
| | | 210 | | | 215 | | | 220 | | | |
| Thr | Cys | Pro | Pro | Cys | Pro | Ala | Pro | Glu | Leu | Leu | Gly | Gly | Pro | Ser | Val |
| 225 | | | | 230 | | | | 235 | | | | 240 |

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
            245                 250                 255

Pro Glu Val Thr Cys Val Val Val Asp Val Ser His Glu Asp Pro Glu
                260                 265                 270

Val Lys Phe Asn Trp Tyr Val Asp Gly Val Glu Val His Asn Ala Lys
            275                 280                 285

Thr Lys Pro Arg Glu Glu Gln Tyr Asn Ser Thr Tyr Arg Val Val Ser
290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
            355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
            435                 440                 445

```
<210> SEQ ID NO 131
<211> LENGTH: 1341
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 131
gatgtgcagc ttcaggagtc aggacctgac ctggtgaaac cttctcagtc actttcactc      60
acctgcactg tcactggcta ctccatcacc agtggttata gctggcactg gatccggcag     120
tttccaggaa acaaactgga gtggatggcc cacatccact ccagtggtag cactaactac     180
aacccatctc tcaaaagtcg catctctatc attcgagaca catccaagaa cctgttcttc     240
ctgcagttga attctgtgac tactgaggac acagccacat attactgtgc aagagggggg     300
gtacaggcct ttgcttactg gggccaaggg actctggtca ctgtctctgc agctagcacc     360
aagggcccaa gtgtgtttcc cctggccccc agcagcaagt ctacttccgg cggaactgct     420
gccctgggtt gcctggtgaa ggactacttc cccgagcccg tgacagtgtc ctggaactct     480
ggggctctga cttccggcgt gcacaccttc cccgccgtgc tgcagagcag cggcctgtac     540
agcctgagca gcgtggtgac agtgccctcc agctctctgg gaacccagac ctatatctgc     600
aacgtgaacc acaagcccag caacaccaag gtggacaaga gagtggagcc caagagctgc     660
gacaagaccc acacctgccc ccctgcccca gctccagaac tgctgggagg ccttccgtg     720
```

```
ttcctgttcc cccccaagcc caaggacacc ctgatgatca gcaggacccc cgaggtgacc    780
tgcgtggtgg tggacgtgtc ccacgaggac ccagaggtga agttcaactg gtacgtggac    840
ggcgtggagg tgcacaacgc caagaccaag cccagagagg agcagtacaa cagcacctac    900
agggtggtgt ccgtgctgac cgtgctgcac caggactggc tgaacggcaa agaatacaag    960
tgcaaagtct ccaacaaggc cctgccagcc ccaatcgaaa agacaatcag caaggccaag   1020
ggccagccac gggagcccca ggtgtacacc ctgccccca gccggagga gatgaccaag     1080 aaccaggtgt ccctgacctg tctggtgaag ggcttctacc ccagcgatat cgccgtggag   1140
tgggagagca acggccagcc cgagaacaac tacaagacca cccccccagt gctggacagc   1200
gacggcagct tcttcctgta cagcaagctg accgtggaca agtccaggtg gcagcagggc   1260
aacgtgttca gctgcagcgt gatgcacgag gccctgcaca accactacac ccagaagtcc   1320
ctgagcctga gccccggcaa g                                            1341
```

<210> SEQ ID NO 132
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 132

```
Ser Ala Ser Ser Ser Val Ile Tyr Met His
1               5                   10
```

<210> SEQ ID NO 133
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 133

```
Asp Thr Ser Lys Leu Ala Ser
1               5
```

<210> SEQ ID NO 134
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 134

```
Gln Gln Trp Ser Ser Asn Pro Leu Thr
1               5
```

<210> SEQ ID NO 135
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 135

```
Ser Ala Ser Ser Ser Val Ile Tyr Met His
1               5                   10
```

<210> SEQ ID NO 136
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 136

```
Asp Thr Ser Lys Leu Ala Ser
1               5
```

<210> SEQ ID NO 137
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 137

```
Gln Gln Trp Ser Ser Asn Pro Leu Thr
1               5
```

<210> SEQ ID NO 138
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 138

```
Ser Ser Ser Val Ile Tyr
1               5
```

<210> SEQ ID NO 139
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 139

```
Asp Thr Ser
1
```

<210> SEQ ID NO 140
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 140

```
Trp Ser Ser Asn Pro Leu
1               5
```

```
<210> SEQ ID NO 141
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 141

Ser Ser Val Ile Tyr
1               5

<210> SEQ ID NO 142
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 142

Asp Thr Ser
1

<210> SEQ ID NO 143
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 143

Gln Gln Trp Ser Ser Asn Pro Leu Thr
1               5

<210> SEQ ID NO 144
<211> LENGTH: 106
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 144

Gln Ile Val Leu Thr Gln Ser Pro Ala Ile Met Ser Ala Ser Pro Gly
1               5                   10                  15

Glu Lys Val Thr Met Thr Cys Ser Ala Ser Ser Ser Val Ile Tyr Met
            20                  25                  30

His Trp Tyr Gln Gln Lys Ser Gly Thr Ser Pro Lys Arg Trp Ile Tyr
        35                  40                  45

Asp Thr Ser Lys Leu Ala Ser Gly Val Pro Ala Arg Phe Ser Gly Ser
    50                  55                  60

Gly Ser Gly Thr Ser Tyr Ser Leu Thr Ile Ser Ser Met Glu Ala Glu
65                  70                  75                  80

Asp Ala Ala Thr Tyr Tyr Cys Gln Gln Trp Ser Ser Asn Pro Leu Thr
                85                  90                  95

Phe Gly Ala Gly Thr Thr Leu Glu Leu Lys
            100                 105
```

<210> SEQ ID NO 145
<211> LENGTH: 318
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 145

```
caaattgtcc tcacccagtc tccagcaatc atgtctgcat ctccagggga gaaggtcacc      60
atgacctgca gtgccagttc aagtgtaatt tacatgcact ggtaccagca gaagtcaggc     120
acctccccca aaagatggat ttatgacaca tccaaactgg cttctggagt ccctgctcgc     180
ttcagtggta gtgggtctgg gacctcttac tctctcacaa tcagcagcat ggaggctgaa     240
gatgctgcca cttattactg ccagcagtgg agtagtaacc cgctcacgtt cggtgctggg     300
accacgttgg agctgaaa                                                   318
```

<210> SEQ ID NO 146
<211> LENGTH: 213
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 146

```
Gln Ile Val Leu Thr Gln Ser Pro Ala Ile Met Ser Ala Ser Pro Gly
1               5                   10                  15

Glu Lys Val Thr Met Thr Cys Ser Ala Ser Ser Ser Val Ile Tyr Met
            20                  25                  30

His Trp Tyr Gln Gln Lys Ser Gly Thr Ser Pro Lys Arg Trp Ile Tyr
        35                  40                  45

Asp Thr Ser Lys Leu Ala Ser Gly Val Pro Ala Arg Phe Ser Gly Ser
    50                  55                  60

Gly Ser Gly Thr Ser Tyr Ser Leu Thr Ile Ser Ser Met Glu Ala Glu
65                  70                  75                  80

Asp Ala Ala Thr Tyr Tyr Cys Gln Gln Trp Ser Ser Asn Pro Leu Thr
                85                  90                  95

Phe Gly Ala Gly Thr Thr Leu Glu Leu Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210
```

<210> SEQ ID NO 147

<211> LENGTH: 639
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 147

```
caaattgtcc tcacccagtc tccagcaatc atgtctgcat ctccagggga gaaggtcacc      60
atgacctgca gtgccagttc aagtgtaatt tacatgcact ggtaccagca gaagtcaggc     120
acctccccca aaagatggat ttatgacaca tccaaactgg cttctggagt ccctgctcgc     180
ttcagtggta gtgggtctgg gacctcttac tctctcacaa tcagcagcat ggaggctgaa     240
gatgctgcca cttattactg ccagcagtgg agtagtaacc cgctcacgtt cggtgctggg     300
accacgttgg agctgaaacg tacggtggcc gctcccagcg tgttcatctt ccccccagc      360
gacgagcagc tgaagagtgg caccgccagc gtggtgtgcc tgctgaacaa cttctacccc     420
cgggaggcca aggtgcagtg gaaggtggac aacgccctgc agagcggcaa cagccaggag     480
agcgtcaccg agcaggacag caaggactcc acctacagcc tgagcagcac cctgaccctg     540
agcaaggcca ctacgagaaa gcataaggtg tacgcctgcg aggtgaccca ccagggcctg     600
tccagccccg tgaccaagag cttcaacagg ggcgagtgc                            639
```

<210> SEQ ID NO 148
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 148

Gly Phe Thr Phe Ser Thr Tyr Ala Met Ser
1               5                   10

<210> SEQ ID NO 149
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 149

Thr Ile Ser Asp Gly Gly Ser Tyr Ser Tyr Tyr Pro Asp Asn Val Lys
1               5                   10                  15
Gly

<210> SEQ ID NO 150
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 150

Arg Gly Ser Arg Tyr Glu Glu Tyr Tyr Val Met Asp Tyr
1               5                   10

<210> SEQ ID NO 151
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 151

Thr Tyr Ala Met Ser
1               5

<210> SEQ ID NO 152
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 152

Thr Ile Ser Asp Gly Gly Ser Tyr Ser Tyr Tyr Pro Asp Asn Val Lys
1               5                   10                  15

Gly

<210> SEQ ID NO 153
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 153

Arg Gly Ser Arg Tyr Glu Glu Tyr Tyr Val Met Asp Tyr
1               5                   10

<210> SEQ ID NO 154
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 154

Gly Phe Thr Phe Ser Thr Tyr
1               5

<210> SEQ ID NO 155
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 155

Ser Asp Gly Gly Ser Tyr
1               5

<210> SEQ ID NO 156

```
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 156

Arg Gly Ser Arg Tyr Glu Glu Tyr Tyr Val Met Asp Tyr
1               5                   10

<210> SEQ ID NO 157
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 157

Gly Phe Thr Phe Ser Thr Tyr Ala
1               5

<210> SEQ ID NO 158
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 158

Ile Ser Asp Gly Gly Ser Tyr Ser
1               5

<210> SEQ ID NO 159
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 159

Ala Arg Arg Gly Ser Arg Tyr Glu Glu Tyr Tyr Val Met Asp Tyr
1               5                   10                  15

<210> SEQ ID NO 160
<211> LENGTH: 122
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 160

Glu Val Gln Leu Val Glu Ser Gly Gly Gly Leu Val Lys Pro Gly Gly
1               5                   10                  15

Ser Leu Lys Leu Ser Cys Ala Ala Ser Gly Phe Thr Phe Ser Thr Tyr
            20                  25                  30

Ala Met Ser Trp Val Arg Gln Thr Pro Glu Lys Arg Leu Glu Trp Val
        35                  40                  45
```

Ala Thr Ile Ser Asp Gly Gly Ser Tyr Ser Tyr Tyr Pro Asp Asn Val
    50                  55                  60

Lys Gly Arg Phe Thr Ile Ser Arg Asp Asn Ala Lys Asn Asn Leu Tyr
 65                  70                  75                  80

Leu Gln Met Ser His Leu Lys Ser Glu Asp Thr Ala Met Tyr Tyr Cys
                 85                  90                  95

Ala Arg Arg Gly Ser Arg Tyr Glu Glu Tyr Tyr Val Met Asp Tyr Trp
                100                 105                 110

Gly Gln Gly Thr Ser Val Thr Val Ser Ser
            115                 120

<210> SEQ ID NO 161
<211> LENGTH: 366
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 161
gaagtgcagc tggtggagtc tgggggaggc ttagtgaagc ctggagggtc cctgaaactc       60
tcctgtgcag cctctggatt cactttcagt acctatgcca tgtcttgggt tcgccagact      120
ccggaaaaga ggctggagtg ggtcgcaacc attagtgatg gtggtagtta ttcgtactat      180
ccagacaatg taaagggccg attcaccatc tccagagaca atgccaagaa caacctatac      240
ctgcaaatga gccatctgaa gtctgaggac acagccatgt attactgtgc aagacgaggt      300
agtaggtacg aagagtacta tgttatggac tactggggtc aaggaacctc agtcaccgtc      360
tcctca                                                                 366

<210> SEQ ID NO 162
<211> LENGTH: 452
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 162

Glu Val Gln Leu Val Glu Ser Gly Gly Gly Leu Val Lys Pro Gly Gly
 1               5                  10                  15

Ser Leu Lys Leu Ser Cys Ala Ala Ser Gly Phe Thr Phe Ser Thr Tyr
                20                  25                  30

Ala Met Ser Trp Val Arg Gln Thr Pro Glu Lys Arg Leu Glu Trp Val
            35                  40                  45

Ala Thr Ile Ser Asp Gly Gly Ser Tyr Ser Tyr Tyr Pro Asp Asn Val
    50                  55                  60

Lys Gly Arg Phe Thr Ile Ser Arg Asp Asn Ala Lys Asn Asn Leu Tyr
 65                  70                  75                  80

Leu Gln Met Ser His Leu Lys Ser Glu Asp Thr Ala Met Tyr Tyr Cys
                 85                  90                  95

Ala Arg Arg Gly Ser Arg Tyr Glu Glu Tyr Tyr Val Met Asp Tyr Trp
                100                 105                 110

Gly Gln Gly Thr Ser Val Thr Val Ser Ser Ala Ser Thr Lys Gly Pro
            115                 120                 125

Ser Val Phe Pro Leu Ala Pro Ser Ser Lys Ser Thr Ser Gly Gly Thr
        130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
            165                 170                 175

Ala Val Leu Gln Ser Ser Gly Leu Tyr Ser Leu Ser Ser Val Val Thr
        180                 185                 190

Val Pro Ser Ser Leu Gly Thr Gln Thr Tyr Ile Cys Asn Val Asn
    195                 200                 205

His Lys Pro Ser Asn Thr Lys Val Asp Lys Arg Val Glu Pro Lys Ser
210                 215                 220

Cys Asp Lys Thr His Thr Cys Pro Pro Cys Pro Ala Pro Glu Leu Leu
225                 230                 235                 240

Gly Gly Pro Ser Val Phe Leu Phe Pro Pro Lys Pro Lys Asp Thr Leu
            245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
        275                 280                 285

Val His Asn Ala Lys Thr Lys Pro Arg Glu Glu Gln Tyr Asn Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
            325                 330                 335

Ile Glu Lys Thr Ile Ser Lys Ala Lys Gly Gln Pro Arg Glu Pro Gln
            340                 345                 350

Val Tyr Thr Leu Pro Pro Ser Arg Glu Glu Met Thr Lys Asn Gln Val
        355                 360                 365

Ser Leu Thr Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
            405                 410                 415

Val Asp Lys Ser Arg Trp Gln Gln Gly Asn Val Phe Ser Cys Ser Val
        420                 425                 430

Met His Glu Ala Leu His Asn His Tyr Thr Gln Lys Ser Leu Ser Leu
    435                 440                 445

Ser Pro Gly Lys
    450

<210> SEQ ID NO 163
<211> LENGTH: 1356
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 163
gaagtgcagc tggtggagtc tgggggaggc ttagtgaagc ctggagggtc cctgaaactc      60
tcctgtgcag cctctggatt cactttcagt acctatgcca tgtcttgggt tcgccagact     120
ccggaaaaga ggctggagtg ggtcgcaacc attagtgatg gtggtagtta ttcgtactat     180

```
ccagacaatg taaagggccg attcaccatc tccagagaca atgccaagaa caacctatac    240
ctgcaaatga gccatctgaa gtctgaggac acagccatgt attactgtgc aagacgaggt    300
agtaggtacg aagagtacta tgttatggac tactggggtc aaggaacctc agtcaccgtc    360
tcctcagcta gcaccaaggg cccaagtgtg tttcccctgg cccccagcag caagtctact    420
tccggcggaa ctgctgccct gggttgcctg gtgaaggact acttccccga gcccgtgaca    480
gtgtcctgga actctggggc tctgacttcc ggcgtgcaca ccttcccgc cgtgctgcag    540 agcagcggcc tgtacagcct gagcagcgtg gtgacagtgc cctccagctc tctgggaacc    600
cagacctata tctgcaacgt gaaccacaag cccagcaaca ccaaggtgga caagagagtg    660
gagcccaaga gctgcgacaa gacccacacc tgccccccct gcccagctcc agaactgctg    720
ggagggcctt ccgtgttcct gttcccccc aagcccaagg acaccctgat gatcagcagg    780 accccgagg tgacctgcgt ggtggtggac gtgtcccacg aggacccaga ggtgaagttc    840
aactggtacg tggacggcgt ggaggtgcac aacgccaaga ccaagccag agaggagcag    900 tacaacagca cctacagggt ggtgtccgtg ctgaccgtgc tgcaccagga ctggctgaac    960
ggcaaagaat acaagtgcaa agtctccaac aaggccctgc cagccccaat cgaaaagaca   1020
atcagcaagg ccaagggcca gccacgggag ccccaggtgt acaccctgcc ccccagccgg   1080
gaggagatga ccaagaacca ggtgtccctg acctgtctgg tgaagggctt ctaccccagc   1140
gatatcgccg tggagtggga gagcaacggc cagcccgaga caactacaa gaccacccc   1200 ccagtgctgg acagcgacgg cagcttcttc ctgtacagca agctgaccgt ggacaagtcc   1260
aggtggcagc agggcaacgt gttcagctgc agcgtgatgc acgaggccct gcacaaccac   1320
tacacccaga agtccctgag cctgagcccc ggcaag                             1356
```

<210> SEQ ID NO 164
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 164

Arg Ala Ser Gln Ser Ile Ser Asn Asn Leu His
1               5                   10

<210> SEQ ID NO 165
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 165

Tyr Ala Ser Gln Ser Ile Ser
1               5

<210> SEQ ID NO 166
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 166

Gln Gln Ser Asn Ser Trp Leu Thr
1               5

<210> SEQ ID NO 167
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 167

Arg Ala Ser Gln Ser Ile Ser Asn Asn Leu His
1               5                   10

<210> SEQ ID NO 168
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 168

Tyr Ala Ser Gln Ser Ile Ser
1               5

<210> SEQ ID NO 169
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 169

Gln Gln Ser Asn Ser Trp Leu Thr
1               5

<210> SEQ ID NO 170
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 170

Ser Gln Ser Ile Ser Asn Asn
1               5

<210> SEQ ID NO 171
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 171

Tyr Ala Ser
1

<210> SEQ ID NO 172
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 172

Ser Asn Ser Trp Leu
1               5

<210> SEQ ID NO 173
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 173

Gln Ser Ile Ser Asn Asn
1               5

<210> SEQ ID NO 174
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 174

Tyr Ala Ser
1

<210> SEQ ID NO 175
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 175

Gln Gln Ser Asn Ser Trp Leu Thr
1               5

<210> SEQ ID NO 176
<211> LENGTH: 106
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 176

Asp Ile Val Leu Thr Gln Ser Pro Ala Thr Leu Ser Val Thr Pro Gly
1               5                   10                  15

Asp Ser Val Ser Leu Ser Cys Arg Ala Ser Gln Ser Ile Ser Asn Asn
            20                  25                  30

```
Leu His Trp Tyr Gln Gln Lys Ser His Glu Ser Pro Lys Leu Leu Ile
        35                  40                  45

Lys Tyr Ala Ser Gln Ser Ile Ser Gly Ile Pro Ser Arg Phe Ser Gly
    50                  55                  60

Ser Gly Ser Gly Thr Asp Phe Thr Leu Ser Ile Asn Ser Val Glu Thr
65                  70                  75                  80

Glu Asp Phe Gly Met Tyr Phe Cys Gln Gln Ser Asn Ser Trp Leu Thr
                85                  90                  95

Phe Gly Ala Gly Thr Lys Leu Gly Leu Lys
                100                 105

<210> SEQ ID NO 177
<211> LENGTH: 318
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 177
gatattgtgc taactcagtc tccagccacc ctgtctgtga ctccaggaga tagcgtcagt      60
ctttcctgca gggccagcca agtattagc aacaacctac actggtatca acagaaatca     120
catgagtctc caaaacttct catcaagtat gcttcccagt ccatctctgg atcccctcc     180 aggttcagtg gcagtggatc agggacagat ttcactctca gtatcaacag tgtggagact     240
gaagattttg gaatgtattt ctgtcaacag agtaacagct ggctcacgtt cggtgctggg     300
accaagctgg ggctgaaa                                                   318

<210> SEQ ID NO 178
<211> LENGTH: 213
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 178

Asp Ile Val Leu Thr Gln Ser Pro Ala Thr Leu Ser Val Thr Pro Gly
1               5                   10                  15

Asp Ser Val Ser Leu Ser Cys Arg Ala Ser Gln Ser Ile Ser Asn Asn
                20                  25                  30

Leu His Trp Tyr Gln Gln Lys Ser His Glu Ser Pro Lys Leu Leu Ile
        35                  40                  45

Lys Tyr Ala Ser Gln Ser Ile Ser Gly Ile Pro Ser Arg Phe Ser Gly
    50                  55                  60

Ser Gly Ser Gly Thr Asp Phe Thr Leu Ser Ile Asn Ser Val Glu Thr
65                  70                  75                  80

Glu Asp Phe Gly Met Tyr Phe Cys Gln Gln Ser Asn Ser Trp Leu Thr
                85                  90                  95

Phe Gly Ala Gly Thr Lys Leu Gly Leu Lys Arg Thr Val Ala Ala Pro
                100                 105                 110

Ser Val Phe Ile Phe Pro Pro Ser Asp Glu Gln Leu Lys Ser Gly Thr
            115                 120                 125

Ala Ser Val Val Cys Leu Leu Asn Asn Phe Tyr Pro Arg Glu Ala Lys
        130                 135                 140
```

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210

<210> SEQ ID NO 179
<211> LENGTH: 639
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic polynucleotide"

<400> SEQUENCE: 179

```
gatattgtgc taactcagtc tccagccacc ctgtctgtga ctccaggaga tagcgtcagt      60
ctttcctgca gggccagcca agtattagc aacaacctac actggtatca acagaaatca     120
catgagtctc caaaacttct catcaagtat gcttcccagt ccatctctgg gatcccctcc    180
aggttcagtg gcagtggatc agggacagat ttcactctca gtatcaacag tgtggagact    240
gaagattttg gaatgtattt ctgtcaacag agtaacagct ggctcacgtt cggtgctggg    300
accaagctgg ggctgaaacg tacggtggcc gctcccagcg tgttcatctt ccccccagc    360
gacgagcagc tgaagagtgg caccgccagc gtggtgtgcc tgctgaacaa cttctacccc    420
cgggaggcca aggtgcagtg gaaggtggac aacgccctgc agagcggcaa cagccaggag    480
agcgtcaccg agcaggacag caaggactcc acctacagcc tgagcagcac cctgaccctg    540
agcaaggccg actacgagaa gcataaggtg tacgcctgcg aggtgaccca ccagggcctg    600
tccagccccg tgaccaagag cttcaacagg ggcgagtgc                            639
```

<210> SEQ ID NO 180
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
    Synthetic peptide"

<400> SEQUENCE: 180

Gly Phe Thr Phe Ser Ser Tyr Ala Met Ser
1               5                   10

<210> SEQ ID NO 181
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
    Synthetic peptide"

<400> SEQUENCE: 181

Thr Ile Ser Ser Gly Gly Ser Phe Thr Tyr Tyr Pro Asp Ser Val Lys
1               5                   10                  15

Gly

<210> SEQ ID NO 182
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 182

Arg Ala Ser Thr Val Val Gly Thr Asp Phe Asp Val
1               5                   10

<210> SEQ ID NO 183
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 183

Ser Tyr Ala Met Ser
1               5

<210> SEQ ID NO 184
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 184

Thr Ile Ser Ser Gly Gly Ser Phe Thr Tyr Tyr Pro Asp Ser Val Lys
1               5                   10                  15

Gly

<210> SEQ ID NO 185
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 185

Arg Ala Ser Thr Val Val Gly Thr Asp Phe Asp Val
1               5                   10

<210> SEQ ID NO 186
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 186

Gly Phe Thr Phe Ser Ser Tyr
1               5

<210> SEQ ID NO 187
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 187

Ser Ser Gly Gly Ser Phe
1               5

<210> SEQ ID NO 188
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 188

Arg Ala Ser Thr Val Val Gly Thr Asp Phe Asp Val
1               5                   10

<210> SEQ ID NO 189
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 189

Gly Phe Thr Phe Ser Ser Tyr Ala
1               5

<210> SEQ ID NO 190
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 190

Ile Ser Ser Gly Gly Ser Phe Thr
1               5

<210> SEQ ID NO 191
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 191

Ala Arg Arg Ala Ser Thr Val Val Gly Thr Asp Phe Asp Val
1               5                   10

<210> SEQ ID NO 192
<211> LENGTH: 121
<212> TYPE: PRT

<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 192

```
Glu Val Met Leu Val Glu Ser Gly Gly Gly Leu Val Lys Pro Gly
1               5                   10                  15
Ser Leu Lys Leu Ser Cys Ala Ala Ser Gly Phe Thr Phe Ser Ser Tyr
            20                  25                  30
Ala Met Ser Trp Ile Arg Gln Thr Pro Glu Lys Arg Leu Glu Trp Val
        35                  40                  45
Ala Thr Ile Ser Ser Gly Gly Ser Phe Thr Tyr Tyr Pro Asp Ser Val
    50                  55                  60
Lys Gly Arg Phe Thr Ile Ser Arg Asp Asn Val Lys Asn Thr Leu Tyr
65                  70                  75                  80
Leu Gln Met Ser Ser Leu Arg Ser Glu Asp Thr Ala Met Tyr Tyr Cys
                85                  90                  95
Ala Arg Arg Ala Ser Thr Val Val Gly Thr Asp Phe Asp Val Trp Gly
            100                 105                 110
Ala Gly Thr Thr Val Thr Val Ser Ser
        115                 120
```

<210> SEQ ID NO 193
<211> LENGTH: 363
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 193

```
gaagtgatgc tggtggagtc tgggggaggc ttagtgaagc ctggagggtc cctgaaactc    60
tcctgtgcag cctctggatt cactttcagt agctatgcca tgtcttggat tcgccagact   120
ccggagaaga gactggagtg ggtcgcaacc atcagtagtg gtggtagttt cacctactat   180
ccagacagtg tgaaggggcg attcaccatt tctagagaca atgtcaagaa caccctgtac   240
ctgcaaatga gcagtctgag gtctgaagac acggccatgt attactgtgc aagacgggct   300
tctacggtag taggtacgga cttcgatgtc tggggcgcag gaccacggt caccgtctcc   360
tca                                                                363
```

<210> SEQ ID NO 194
<211> LENGTH: 451
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 194

```
Glu Val Met Leu Val Glu Ser Gly Gly Gly Leu Val Lys Pro Gly Gly
1               5                   10                  15
Ser Leu Lys Leu Ser Cys Ala Ala Ser Gly Phe Thr Phe Ser Ser Tyr
            20                  25                  30
Ala Met Ser Trp Ile Arg Gln Thr Pro Glu Lys Arg Leu Glu Trp Val
        35                  40                  45
```

-continued

Ala Thr Ile Ser Ser Gly Gly Ser Phe Thr Tyr Tyr Pro Asp Ser Val
    50                  55                  60

Lys Gly Arg Phe Thr Ile Ser Arg Asp Asn Val Lys Asn Thr Leu Tyr
 65              70                  75                      80

Leu Gln Met Ser Ser Leu Arg Ser Glu Asp Thr Ala Met Tyr Tyr Cys
                85                  90                  95

Ala Arg Arg Ala Ser Thr Val Val Gly Thr Asp Phe Asp Val Trp Gly
            100                 105                 110

Ala Gly Thr Thr Val Thr Val Ser Ala Ser Thr Lys Gly Pro Ser
            115                 120                 125

Val Phe Pro Leu Ala Pro Ser Ser Lys Ser Thr Ser Gly Gly Thr Ala
130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
                180                 185                 190

Pro Ser Ser Ser Leu Gly Thr Gln Thr Tyr Ile Cys Asn Val Asn His
            195                 200                 205

Lys Pro Ser Asn Thr Lys Val Asp Lys Arg Val Glu Pro Lys Ser Cys
210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
                260                 265                 270

Glu Asp Pro Glu Val Lys Phe Asn Trp Tyr Val Asp Gly Val Glu Val
            275                 280                 285

His Asn Ala Lys Thr Lys Pro Arg Glu Glu Gln Tyr Asn Ser Thr Tyr
            290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser
            355                 360                 365

Leu Thr Cys Leu Val Lys Gly Phe Tyr Pro Ser Asp Ile Ala Val Glu
370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
            435                 440                 445

Pro Gly Lys
450

<210> SEQ ID NO 195
<211> LENGTH: 1353
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 195

```
gaagtgatgc tggtggagtc tgggggaggc ttagtgaagc ctggagggtc cctgaaactc      60
tcctgtgcag cctctggatt cactttcagt agctatgcca tgtcttggat tcgccagact     120
ccggagaaga gactggagtg ggtcgcaacc atcagtagtg gtggtagttt cacctactat     180
ccagacagtg tgaaggggcg attcaccatt tctagagaca atgtcaagaa caccctgtac     240
ctgcaaatga gcagtctgag gtctgaagac acggccatgt attactgtgc aagacgggct     300
tctacggtag taggtacgga cttcgatgtc tggggcgcag ggaccacggt caccgtctcc     360
tcagctagca ccaagggccc aagtgtgttt cccctggccc cagcagcaa gtctacttcc      420
ggcggaactg ctgccctggg ttgcctggtg aaggactact ccccgagcc cgtgacagtg      480
tcctggaact ctggggctct gacttccggc gtgcacacct tcccgccgt gctgcagagc      540
agcggcctgt acagcctgag cagcgtggtg acagtgccct ccagctctct gggaacccag     600
acctatatct gcaacgtgaa ccacaagccc agcaacacca aggtggacaa gagagtggag     660
cccaagagct gcgacaagac ccacacctgc cccccctgcc cagctccaga actgctggga     720
gggccttccg tgttcctgtt ccccccaag cccaaggaca ccctgatgat cagcaggacc      780
cccgaggtga cctgcgtggt ggtggacgtg tcccacgagg acccagaggt gaagttcaac     840
tggtacgtgg acggcgtgga ggtgcacaac gccaagacca gcccagaga ggagcagtac      900
aacagcacct acagggtggt gtccgtgctg accgtgctgc accaggactg gctgaacggc     960
aaagaataca agtgcaaagt ctccaacaag gccctgccag ccccaatcga aaagacaatc    1020
agcaaggcca agggccagcc acgggagccc caggtgtaca ccctgccccc cagccgggag    1080
gagatgacca gaaccaggt gtccctgacc tgtctggtga agggcttcta ccccagcgat     1140
atcgccgtgg agtgggagag caacggccag cccgagaaca actacaagac cacccccca     1200
gtgctggaca gcgacggcag cttcttcctg tacagcaagc tgaccgtgga caagtccagg    1260
tggcagcagg gcaacgtgtt cagctgcagc gtgatgcacg aggccctgca caaccactac    1320
acccagaagt ccctgagcct gagccccggc aag                                 1353
```

<210> SEQ ID NO 196
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 196

Arg Ala Ser Gln Asp Ile Gly Ser Ser Leu Asn
1               5                   10

<210> SEQ ID NO 197
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 197

Ala Thr Ser Ser Leu Asp Ser
1               5

<210> SEQ ID NO 198
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 198

Leu Gln Tyr Ala Ser Ser Pro Pro Thr
1               5

<210> SEQ ID NO 199
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 199

Arg Ala Ser Gln Asp Ile Gly Ser Ser Leu Asn
1               5                   10

<210> SEQ ID NO 200
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 200

Ala Thr Ser Ser Leu Asp Ser
1               5

<210> SEQ ID NO 201
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 201

Leu Gln Tyr Ala Ser Ser Pro Pro Thr
1               5

<210> SEQ ID NO 202
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 202

```
Ser Gln Asp Ile Gly Ser Ser
1               5
```

<210> SEQ ID NO 203
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 203

```
Ala Thr Ser
1
```

<210> SEQ ID NO 204
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 204

```
Tyr Ala Ser Ser Pro Pro
1               5
```

<210> SEQ ID NO 205
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 205

```
Gln Asp Ile Gly Ser Ser
1               5
```

<210> SEQ ID NO 206
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 206

```
Ala Thr Ser
1
```

<210> SEQ ID NO 207
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 207

```
Leu Gln Tyr Ala Ser Ser Pro Pro Thr
1               5
```

<210> SEQ ID NO 208
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 208

Asp Ile Gln Met Thr Gln Ser Pro Ser Ser Leu Ser Ala Ser Leu Gly
1               5                   10                  15

Glu Arg Val Ser Leu Thr Cys Arg Ala Ser Gln Asp Ile Gly Ser Ser
            20                  25                  30

Leu Asn Trp Leu Gln Gln Glu Pro Asp Gly Thr Ile Lys Arg Leu Ile
        35                  40                  45

Tyr Ala Thr Ser Ser Leu Asp Ser Gly Val Pro Lys Arg Phe Ser Gly
    50                  55                  60

Ser Arg Ser Gly Ser Asp Tyr Ser Leu Thr Ile Ser Ser Leu Glu Ser
65                  70                  75                  80

Glu Asp Phe Val Val Tyr Tyr Cys Leu Gln Tyr Ala Ser Ser Pro Pro
                85                  90                  95

Thr Phe Gly Gly Gly Thr Lys Leu Glu Ile Lys
            100                 105

<210> SEQ ID NO 209
<211> LENGTH: 321
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 209
gacatccaga tgacccagtc tccatcctcc ttatctgcct ctctgggaga aagagtcagt      60
ctcacttgtc gggcaagtca ggacattggt agtagcttaa actggcttca gcaggaacca     120
gatggaacta ttaaacgcct gatctatgcc acatccagtt tagattctgg tgtccccaaa     180
aggttcagtg gcagtaggtc tgggtcagat tattctctca ccatcagcag ccttgagtct     240
gaagattttg tagtctatta ctgtctacaa tatgctagtt cgcctccgac gttcggtgga     300
ggcaccaagc tggaaatcaa a                                               321

<210> SEQ ID NO 210
<211> LENGTH: 214
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 210

Asp Ile Gln Met Thr Gln Ser Pro Ser Ser Leu Ser Ala Ser Leu Gly
1               5                   10                  15

Glu Arg Val Ser Leu Thr Cys Arg Ala Ser Gln Asp Ile Gly Ser Ser
            20                  25                  30

Leu Asn Trp Leu Gln Gln Glu Pro Asp Gly Thr Ile Lys Arg Leu Ile
        35                  40                  45

Tyr Ala Thr Ser Ser Leu Asp Ser Gly Val Pro Lys Arg Phe Ser Gly

```
                50              55                60
Ser Arg Ser Gly Ser Asp Tyr Ser Leu Thr Ile Ser Ser Leu Glu Ser
 65                  70                  75                  80

Glu Asp Phe Val Val Tyr Tyr Cys Leu Gln Tyr Ala Ser Ser Pro Pro
                     85                  90                  95

Thr Phe Gly Gly Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
            130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                    165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205

Phe Asn Arg Gly Glu Cys
    210
```

<210> SEQ ID NO 211
<211> LENGTH: 642
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 211

```
gacatccaga tgacccagtc tccatcctcc ttatctgcct ctctgggaga aagagtcagt      60
ctcacttgtc gggcaagtca ggacattggt agtagcttaa actggcttca gcaggaacca     120
gatggaacta ttaaacgcct gatctatgcc acatccagtt tagattctgg tgtcccccaaa    180 aggttcagtg gcagtaggtc tgggtcagat tattctctca ccatcagcag ccttgagtct     240
gaagattttg tagtctatta ctgtctacaa tatgctagtt cgcctccgac gttcggtgga     300
ggcaccaagc tggaaatcaa acgtacggtg gccgctccca gcgtgttcat cttcccccc     360 agcgacgagc agctgaagag tggcaccgcc agcgtggtgt gcctgctgaa caacttctac     420 ccccggagg ccaaggtgca gtggaaggtg gacaacgccc tgcagagcgg caacagccag      480
gagagcgtca ccgagcagga cagcaaggac tccacctaca gcctgagcag caccctgacc     540
ctgagcaagg ccgactacga aagcataag gtgtacgcct gcgaggtgac ccaccagggc      600
ctgtccagcc ccgtgaccaa gagcttcaac aggggcgagt gc                        642
```

<210> SEQ ID NO 212
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 212

Gly Phe Thr Phe Ser Asn Phe Ala Met Ser

```
<210> SEQ ID NO 213
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 213

Thr Ile Ser Thr Gly Gly Thr Tyr Thr Tyr Tyr Pro Asp Ser Val Lys
1               5                   10                  15

Gly

<210> SEQ ID NO 214
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 214

Arg Gly Tyr Asp Gly Val Asp Lys
1               5

<210> SEQ ID NO 215
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 215

Ser Asn Phe Ala Met Ser
1               5

<210> SEQ ID NO 216
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 216

Thr Ile Ser Thr Gly Gly Thr Tyr Thr Tyr Tyr Pro Asp Ser Val Lys
1               5                   10                  15

Gly

<210> SEQ ID NO 217
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 217

Arg Gly Tyr Asp Gly Val Asp Lys
1               5
```

```
<210> SEQ ID NO 218
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 218

Gly Phe Thr Phe Ser Asn Phe
1               5

<210> SEQ ID NO 219
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 219

Ser Thr Gly Gly Thr Tyr
1               5

<210> SEQ ID NO 220
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 220

Arg Gly Tyr Asp Gly Val Asp Lys
1               5

<210> SEQ ID NO 221
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 221

Gly Phe Thr Phe Ser Asn Phe Ala
1               5

<210> SEQ ID NO 222
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 222

Ile Ser Thr Gly Gly Thr Tyr Thr
1               5

<210> SEQ ID NO 223
```

```
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 223

Thr Arg Arg Gly Tyr Asp Gly Val Asp Lys
1               5                   10

<210> SEQ ID NO 224
<211> LENGTH: 117
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 224

Glu Val His Leu Val Glu Ser Gly Gly Gly Leu Val Lys Pro Gly Gly
1               5                   10                  15

Ser Leu Lys Leu Ser Cys Ala Ala Ser Gly Phe Thr Phe Ser Asn Phe
            20                  25                  30

Ala Met Ser Trp Val Arg Gln Thr Pro Glu Lys Arg Leu Glu Trp Val
        35                  40                  45

Ala Thr Ile Ser Thr Gly Gly Thr Tyr Thr Tyr Tyr Pro Asp Ser Val
    50                  55                  60

Lys Gly Arg Phe Thr Ile Ser Arg Asp Asn Ala Lys Lys Thr Leu Tyr
65                  70                  75                  80

Leu Gln Met Ser Ser Leu Arg Ser Glu Asp Thr Ala Met Tyr Tyr Cys
                85                  90                  95

Thr Arg Arg Gly Tyr Asp Gly Val Asp Lys Trp Gly Gln Gly Thr Thr
            100                 105                 110

Leu Thr Val Ser Ser
        115

<210> SEQ ID NO 225
<211> LENGTH: 351
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 225
gaagtgcatc tggtggagtc tgggggaggc ttagtgaagc ctggagggtc cctgaaactc      60
tcctgtgcag cctctggatt cactttcagt aactttgcca tgtcttgggt tcgccagact     120
ccggagaaga gactggagtg ggtcgcaacc attagtactg gtggtactta cacctactat     180
ccagacagtg tgaagggtcg attcaccatc tccagagaca atgccaagaa aaccctgtac     240
ctgcaaatga gcagtctgag gtctgaggac acggccatgt attactgtac aagacggggg     300
tacgacggcg tggacaaatg gggccaaggc accactctca cagtctcctc a              351

<210> SEQ ID NO 226
<211> LENGTH: 447
<212> TYPE: PRT
<213> ORGANISM: Artificial Sequence
<220> FEATURE:
```

```
<221> NAME/KEY: source
<223> OTHER INFORMATION: /note="Description of Artificial Sequence:
      Synthetic polypeptide"

<400> SEQUENCE: 226
```

| | | | | | | | | | | | | | | | |
|---|---|---|---|---|---|---|---|---|---|---|---|---|---|---|---|
| Glu | Val | His | Leu | Val | Glu | Ser | Gly | Gly | Gly | Leu | Val | Lys | Pro | Gly | Gly |
| 1 | | | | 5 | | | | | 10 | | | | | 15 | |
| Ser | Leu | Lys | Leu | Ser | Cys | Ala | Ala | Ser | Gly | Phe | Thr | Phe | Ser | Asn | Phe |
| | | | 20 | | | | | 25 | | | | | 30 | | |
| Ala | Met | Ser | Trp | Val | Arg | Gln | Thr | Pro | Glu | Lys | Arg | Leu | Glu | Trp | Val |
| | | 35 | | | | | 40 | | | | | 45 | | | |
| Ala | Thr | Ile | Ser | Thr | Gly | Gly | Thr | Tyr | Thr | Tyr | Tyr | Pro | Asp | Ser | Val |
| | 50 | | | | | 55 | | | | | 60 | | | | |
| Lys | Gly | Arg | Phe | Thr | Ile | Ser | Arg | Asp | Asn | Ala | Lys | Lys | Thr | Leu | Tyr |
| 65 | | | | | 70 | | | | | 75 | | | | | 80 |
| Leu | Gln | Met | Ser | Ser | Leu | Arg | Ser | Glu | Asp | Thr | Ala | Met | Tyr | Tyr | Cys |
| | | | | 85 | | | | | 90 | | | | | 95 | |
| Thr | Arg | Arg | Gly | Tyr | Asp | Gly | Val | Asp | Lys | Trp | Gly | Gln | Gly | Thr | Thr |
| | | | 100 | | | | | 105 | | | | | 110 | | |
| Leu | Thr | Val | Ser | Ser | Ala | Ser | Thr | Lys | Gly | Pro | Ser | Val | Phe | Pro | Leu |
| | | 115 | | | | | 120 | | | | | 125 | | | |
| Ala | Pro | Ser | Ser | Lys | Ser | Thr | Ser | Gly | Gly | Thr | Ala | Ala | Leu | Gly | Cys |
| | 130 | | | | | 135 | | | | | 140 | | | | |
| Leu | Val | Lys | Asp | Tyr | Phe | Pro | Glu | Pro | Val | Thr | Val | Ser | Trp | Asn | Ser |
| 145 | | | | | 150 | | | | | 155 | | | | | 160 |
| Gly | Ala | Leu | Thr | Ser | Gly | Val | His | Thr | Phe | Pro | Ala | Val | Leu | Gln | Ser |
| | | | | 165 | | | | | 170 | | | | | 175 | |
| Ser | Gly | Leu | Tyr | Ser | Leu | Ser | Ser | Val | Val | Thr | Val | Pro | Ser | Ser | Ser |
| | | | 180 | | | | | 185 | | | | | 190 | | |
| Leu | Gly | Thr | Gln | Thr | Tyr | Ile | Cys | Asn | Val | Asn | His | Lys | Pro | Ser | Asn |
| | | 195 | | | | | 200 | | | | | 205 | | | |
| Thr | Lys | Val | Asp | Lys | Arg | Val | Glu | Pro | Lys | Ser | Cys | Asp | Lys | Thr | His |
| | 210 | | | | | 215 | | | | | 220 | | | | |
| Thr | Cys | Pro | Pro | Cys | Pro | Ala | Pro | Glu | Leu | Leu | Gly | Gly | Pro | Ser | Val |
| 225 | | | | | 230 | | | | | 235 | | | | | 240 |
| Phe | Leu | Phe | Pro | Pro | Lys | Pro | Lys | Asp | Thr | Leu | Met | Ile | Ser | Arg | Thr |
| | | | | 245 | | | | | 250 | | | | | 255 | |
| Pro | Glu | Val | Thr | Cys | Val | Val | Val | Asp | Val | Ser | His | Glu | Asp | Pro | Glu |
| | | | 260 | | | | | 265 | | | | | 270 | | |
| Val | Lys | Phe | Asn | Trp | Tyr | Val | Asp | Gly | Val | Glu | Val | His | Asn | Ala | Lys |
| | | 275 | | | | | 280 | | | | | 285 | | | |
| Thr | Lys | Pro | Arg | Glu | Glu | Gln | Tyr | Asn | Ser | Thr | Tyr | Arg | Val | Val | Ser |
| | 290 | | | | | 295 | | | | | 300 | | | | |
| Val | Leu | Thr | Val | Leu | His | Gln | Asp | Trp | Leu | Asn | Gly | Lys | Glu | Tyr | Lys |
| 305 | | | | | 310 | | | | | 315 | | | | | 320 |
| Cys | Lys | Val | Ser | Asn | Lys | Ala | Leu | Pro | Ala | Pro | Ile | Glu | Lys | Thr | Ile |
| | | | | 325 | | | | | 330 | | | | | 335 | |
| Ser | Lys | Ala | Lys | Gly | Gln | Pro | Arg | Glu | Pro | Gln | Val | Tyr | Thr | Leu | Pro |
| | | | 340 | | | | | 345 | | | | | 350 | | |
| Pro | Ser | Arg | Glu | Glu | Met | Thr | Lys | Asn | Gln | Val | Ser | Leu | Thr | Cys | Leu |
| | | 355 | | | | | 360 | | | | | 365 | | | |
| Val | Lys | Gly | Phe | Tyr | Pro | Ser | Asp | Ile | Ala | Val | Glu | Trp | Glu | Ser | Asn |
| | 370 | | | | | 375 | | | | | 380 | | | | |
| Gly | Gln | Pro | Glu | Asn | Asn | Tyr | Lys | Thr | Thr | Pro | Pro | Val | Leu | Asp | Ser |

```
                385                 390                 395                 400
Asp Gly Ser Phe Phe Leu Tyr Ser Lys Leu Thr Val Asp Lys Ser Arg
                        405                 410                 415

Trp Gln Gln Gly Asn Val Phe Ser Cys Ser Val Met His Glu Ala Leu
                420                 425                 430

His Asn His Tyr Thr Gln Lys Ser Leu Ser Leu Ser Pro Gly Lys
                    435                 440                 445
```

<210> SEQ ID NO 227
<211> LENGTH: 1341
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 227

| | | | | | |
|---|---|---|---|---|---|
| gaagtgcatc | tggtggagtc | tgggggaggc | ttagtgaagc | ctggagggtc | cctgaaactc | 60 |
| tcctgtgcag | cctctggatt | cactttcagt | aactttgcca | tgtcttgggt | tcgccagact | 120 |
| ccggagaaga | gactggagtg | ggtcgcaacc | attagtactg | gtggtactta | cacctactat | 180 |
| ccagacagtg | tgaagggtcg | attcaccatc | tccagagaca | atgccaagaa | aaccctgtac | 240 |
| ctgcaaatga | gcagtctgag | gtctgaggac | acggccatgt | attactgtac | aagacggggg | 300 |
| tacgacggcg | tggacaaatg | gggccaaggc | accactctca | cagtctcctc | agctagcacc | 360 |
| aagggcccaa | gtgtgtttcc | cctggccccc | agcagcaagt | ctacttccgg | cggaactgct | 420 |
| gccctgggtt | gcctggtgaa | ggactacttc | cccgagcccg | tgacagtgtc | ctggaactct | 480 |
| ggggctctga | cttccggcgt | gcacaccttc | ccgccgtgc | tgcagagcag | cggcctgtac | 540 |
| agcctgagca | gcgtggtgac | agtgccctcc | agctctctgg | gaacccagac | ctatatctgc | 600 |
| aacgtgaacc | acaagcccag | caacaccaag | gtggacaaga | gagtggagcc | caagagctgc | 660 |
| gacaagaccc | acacctgccc | ccctgccca | gctccagaac | tgctgggagg | gccttccgtg | 720 |
| ttcctgttcc | cccccaagcc | caaggacacc | ctgatgatca | gcaggacccc | cgaggtgacc | 780 |
| tgcgtggtgg | tggacgtgtc | ccacgaggac | ccagaggtga | agttcaactg | gtacgtggac | 840 |
| ggcgtggagg | tgcacaacgc | caagaccaag | cccagagagg | agcagtacaa | cagcacctac | 900 |
| agggtggtgt | ccgtgctgac | cgtgctgcac | caggactggc | tgaacggcaa | agaatacaag | 960 |
| tgcaaagtct | ccaacaaggc | cctgccagcc | ccaatcgaaa | agacaatcag | caaggccaag | 1020 |
| ggccagccac | gggagcccca | ggtgtacacc | ctgcccccca | gccgggagga | gatgaccaag | 1080 |
| aaccaggtgt | ccctgacctg | tctggtgaag | ggcttctacc | ccagcgatat | cgccgtggag | 1140 |
| tgggagagca | acggccagcc | cgagaacaac | tacaagacca | cccccccagt | gctggacagc | 1200 |
| gacggcagct | tcttcctgta | cagcaagctg | accgtggaca | agtccaggtg | gcagcagggc | 1260 |
| aacgtgttca | gctgcagcgt | gatgcacgag | gccctgcaca | accactacac | ccagaagtcc | 1320 |
| ctgagcctga | gccccggcaa | g | | | | 1341 |

<210> SEQ ID NO 228
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

```
<400> SEQUENCE: 228

Lys Ser Gly Gln Ser Leu Leu Asp Ser Asp Gly Lys Thr Tyr Leu Asn
1               5                   10                  15

<210> SEQ ID NO 229
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 229

Leu Val Ser Lys Leu Asp Ser
1               5

<210> SEQ ID NO 230
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 230

Trp Gln Gly Thr His Phe Pro Gln Thr
1               5

<210> SEQ ID NO 231
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 231

Lys Ser Gly Gln Ser Leu Leu Asp Ser Asp Gly Lys Thr Tyr Leu Asn
1               5                   10                  15

<210> SEQ ID NO 232
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 232

Leu Val Ser Lys Leu Asp Ser
1               5

<210> SEQ ID NO 233
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 233

Trp Gln Gly Thr His Phe Pro Gln Thr
1               5
```

```
<210> SEQ ID NO 234
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 234

Gly Gln Ser Leu Leu Asp Ser Asp Gly Lys Thr Tyr
1               5                   10

<210> SEQ ID NO 235
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 235

Leu Val Ser
1

<210> SEQ ID NO 236
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 236

Gly Thr His Phe Pro Gln
1               5

<210> SEQ ID NO 237
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 237

Gln Ser Leu Leu Asp Ser Asp Gly Lys Thr Tyr
1               5                   10

<210> SEQ ID NO 238
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 238

Leu Val Ser
1

<210> SEQ ID NO 239
<211> LENGTH: 9
```

<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 239

Trp Gln Gly Thr His Phe Pro Gln Thr
1               5

<210> SEQ ID NO 240
<211> LENGTH: 112
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 240

Asp Val Val Met Thr Gln Thr Pro Leu Thr Leu Ser Val Thr Ile Gly
1               5                   10                  15

Gln Pro Ala Ser Ile Ser Cys Lys Ser Gly Gln Ser Leu Leu Asp Ser
            20                  25                  30

Asp Gly Lys Thr Tyr Leu Asn Trp Phe Leu Gln Arg Pro Gly Gln Ser
        35                  40                  45

Pro Lys Arg Leu Ile Tyr Leu Val Ser Lys Leu Asp Ser Gly Val Pro
    50                  55                  60

Asp Arg Phe Thr Gly Ser Gly Ser Gly Thr Asp Phe Thr Leu Lys Ile
65                  70                  75                  80

Ser Arg Val Glu Ala Glu Asp Leu Gly Val Tyr Tyr Cys Trp Gln Gly
                85                  90                  95

Thr His Phe Pro Gln Thr Phe Gly Gly Gly Thr Lys Leu Glu Ile Lys
            100                 105                 110

<210> SEQ ID NO 241
<211> LENGTH: 336
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 241
gatgttgtga tgacccagac tccactcact ttgtcggtta ccattggaca accagcctcc     60
atctcttgca gtcaggtca gagcctctta gatagtgatg gaaagacata tttgaattgg    120
tttttacaga ggccaggcca gtctccaaag cgcctaatct atctggtgtc taaactggac    180
tctggagtcc ctgacaggtt cactggcagt ggatcaggga cagatttcac actgaaaatc    240
agcagagtgg aggctgagga tttgggagtt tattattgct ggcaaggtac acattttcct    300
cagacgttcg gtggaggcac caagctggaa atcaaa                              336

<210> SEQ ID NO 242
<211> LENGTH: 219
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 242

Asp Val Val Met Thr Gln Thr Pro Leu Thr Leu Ser Val Thr Ile Gly
1               5                   10                  15

Gln Pro Ala Ser Ile Ser Cys Lys Ser Gly Gln Ser Leu Leu Asp Ser
            20                  25                  30

Asp Gly Lys Thr Tyr Leu Asn Trp Phe Leu Gln Arg Pro Gly Gln Ser
        35                  40                  45

Pro Lys Arg Leu Ile Tyr Leu Val Ser Lys Leu Asp Ser Gly Val Pro
    50                  55                  60

Asp Arg Phe Thr Gly Ser Gly Ser Gly Thr Asp Phe Thr Leu Lys Ile
65                  70                  75                  80

Ser Arg Val Glu Ala Glu Asp Leu Gly Val Tyr Tyr Cys Trp Gln Gly
                85                  90                  95

Thr His Phe Pro Gln Thr Phe Gly Gly Gly Thr Lys Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 243
<211> LENGTH: 657
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 243
gatgttgtga tgacccagac tccactcact ttgtcggtta ccattggaca accagcctcc      60
atctcttgca agtcaggtca gagcctctta gatagtgatg gaaagacata tttgaattgg     120
tttttacaga ggccaggcca gtctccaaag cgcctaatct atctggtgtc taaactggac     180
tctggagtcc ctgacaggtt cactggcagt ggatcaggga cagatttcac actgaaaatc     240
agcagagtgg aggctgagga tttgggagtt tattattgct ggcaaggtac acatttcct     300 cagacgttcg gtggaggcac caagctggaa atcaaacgta cggtggccgc tcccagcgtg     360
ttcatcttcc cccccagcga cgagcagctg aagagtggca ccgccagcgt ggtgtgcctg     420
ctgaacaact ctaccccccg ggaggccaag gtgcagtgga aggtggacaa cgccctgcag     480
agcggcaaca gccaggagag cgtcaccgag caggacagca aggactccac ctacagcctg     540
agcagcaccc tgaccctgag caaggccgac tacgagaagc ataaggtgta cgcctgcgag     600
gtgacccacc agggcctgtc cagccccgtg accaagagct caacagggg cgagtgc       657

```
<210> SEQ ID NO 244
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 244

Gly Tyr Ser Ile Thr Ser Gly Tyr Ser Trp His
1               5                   10

<210> SEQ ID NO 245
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 245

His Ile His Ser Ser Gly Ser Thr Asn Tyr Asn Pro Ser Leu Lys Ser
1               5                   10                  15

<210> SEQ ID NO 246
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 246

Gly Gly Val Gln Ala Phe Ala Tyr
1               5

<210> SEQ ID NO 247
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 247

Ser Gly Tyr Ser Trp His
1               5

<210> SEQ ID NO 248
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 248

His Ile His Ser Ser Gly Ser Thr Asn Tyr Asn Pro Ser Leu Lys Ser
1               5                   10                  15

<210> SEQ ID NO 249
<211> LENGTH: 8
<212> TYPE: PRT
<213> ORGANISM: Artificial Sequence
```

```
<220> FEATURE:
<221> NAME/KEY: source
<223> OTHER INFORMATION: /note="Description of Artificial Sequence:
      Synthetic peptide"

<400> SEQUENCE: 249

Gly Gly Val Gln Ala Phe Ala Tyr
1               5

<210> SEQ ID NO 250
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 250

Gly Tyr Ser Ile Thr Ser Gly Tyr
1               5

<210> SEQ ID NO 251
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 251

His Ser Ser Gly Ser
1               5

<210> SEQ ID NO 252
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 252

Gly Gly Val Gln Ala Phe Ala Tyr
1               5

<210> SEQ ID NO 253
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 253

Gly Tyr Ser Ile Thr Ser Gly Tyr Ser
1               5

<210> SEQ ID NO 254
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
```

<400> SEQUENCE: 254

Ile His Ser Ser Gly Ser Thr
1               5

<210> SEQ ID NO 255
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 255

Ala Arg Gly Gly Val Gln Ala Phe Ala Tyr
1               5                   10

<210> SEQ ID NO 256
<211> LENGTH: 117
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 256

Asp Val Gln Leu Gln Glu Ser Gly Pro Asp Leu Val Lys Pro Ser Gln
1               5                   10                  15

Ser Leu Ser Leu Thr Cys Thr Val Thr Gly Tyr Ser Ile Thr Ser Gly
            20                  25                  30

Tyr Ser Trp His Trp Ile Arg Gln Phe Pro Gly Asn Lys Leu Glu Trp
        35                  40                  45

Met Ala His Ile His Ser Ser Gly Ser Thr Asn Tyr Asn Pro Ser Leu
    50                  55                  60

Lys Ser Arg Ile Ser Ile Ile Arg Asp Thr Ser Lys Asn Leu Phe Phe
65                  70                  75                  80

Leu Gln Leu Asn Ser Val Thr Thr Glu Asp Thr Ala Thr Tyr Tyr Cys
                85                  90                  95

Ala Arg Gly Gly Val Gln Ala Phe Ala Tyr Trp Gly Gln Gly Thr Leu
            100                 105                 110

Val Thr Val Ser Ala
        115

<210> SEQ ID NO 257
<211> LENGTH: 351
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 257
gatgtgcagc ttcaggagtc aggacctgac ctggtgaaac cttctcagtc actttcactc      60
acctgcactg tcactggcta ctccatcacc agtggttata gctggcactg gatccggcag     120
tttccaggaa acaaactgga gtggatggcc cacatccact ccagtggtag cactaactac     180
aacccatctc tcaaaagtcg catctctatc attcgagaca catccaagaa cctgttcttc     240
ctgcagttga attctgtgac tactgaggac acagccacat attactgtgc aagagggggg     300

```
gtacaggcct tgcttactg gggccaaggg actctggtca ctgtctctgc a           351
```

<210> SEQ ID NO 258
<211> LENGTH: 447
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 258

```
Asp Val Gln Leu Gln Glu Ser Gly Pro Asp Leu Val Lys Pro Ser Gln
1               5                   10                  15

Ser Leu Ser Leu Thr Cys Thr Val Thr Gly Tyr Ser Ile Thr Ser Gly
            20                  25                  30

Tyr Ser Trp His Trp Ile Arg Gln Phe Pro Gly Asn Lys Leu Glu Trp
        35                  40                  45

Met Ala His Ile His Ser Ser Gly Ser Thr Asn Tyr Asn Pro Ser Leu
    50                  55                  60

Lys Ser Arg Ile Ser Ile Ile Arg Asp Thr Ser Lys Asn Leu Phe Phe
65                  70                  75                  80

Leu Gln Leu Asn Ser Val Thr Thr Glu Asp Thr Ala Thr Tyr Tyr Cys
                85                  90                  95

Ala Arg Gly Gly Val Gln Ala Phe Ala Tyr Trp Gly Gln Gly Thr Leu
            100                 105                 110

Val Thr Val Ser Ala Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Cys Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Arg Val Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350
```

```
Pro Ser Arg Glu Glu Met Thr Lys Asn Gln Val Ser Leu Thr Cys Leu
        355                 360                 365

Val Lys Gly Phe Tyr Pro Cys Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
        435                 440                 445

<210> SEQ ID NO 259
<211> LENGTH: 1341
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 259
gatgtgcagc ttcaggagtc aggacctgac ctggtgaaac cttctcagtc actttcactc      60
acctgcactg tcactggcta ctccatcacc agtggttata gctggcactg gatccggcag     120
tttccaggaa acaaactgga gtggatggcc cacatccact ccagtggtag cactaactac     180
aacccatctc tcaaaagtcg catctctatc attcgagaca catccaagaa cctgttcttc     240
ctgcagttga attctgtgac tactgaggac acagccacat attactgtgc aagaggggg     300 gtacaggcct ttgcttactg gggccaaggg actctggtca ctgtctctgc agctagcacc     360
aagggcccaa gtgtgtttcc cctggccccc agcagcaagt ctacttccgg cggaactgct     420
gccctgggtt gcctggtgaa ggactacttc cctgtcccg tgacagtgtc ctggaactct     480
ggggctctga cttccggcgt gcacaccttc cccgccgtgc tgcagagcag cggcctgtac     540
agcctgagca gcgtggtgac agtgccctcc agctctctgg aacccagac ctatatctgc     600 aacgtgaacc acaagcccag caacaccaag gtggacaaga gagtggagcc caagagctgc     660
gacaagaccc acacctgccc ccctgccca gctccagaaa ctgctgggag gccttccgtg     720
ttcctgttcc cccccaagcc caaggacacc ctgatgatca gcaggacccc cgaggtgacc     780
tgcgtggtgg tggacgtgtc ccacgaggac ccagaggtga agttcaactg gtacgtggac     840
ggcgtggagg tgcacaacgc caagaccaag cccagagagg agcagtacaa cagcacctac     900
agggtggtgt ccgtgctgac cgtgctgcac caggactggc tgaacggcaa agaatacaag     960
tgcaaagtct ccaacaaggc cctgccagcc ccaatcgaaa agacaatcag caaggccaag    1020
ggccagccac gggagcccca ggtgtacacc ctgcccccca gccggagga gatgaccaag    1080 aaccaggtgt ccctgacctg tctggtgaag ggcttctacc cctgtgatat cgccgtggag    1140
tgggagagca acggccagcc cgagaacaac tacaagacca ccccccccagt gctggacagc    1200 gacggcagct tcttcctgta cagcaagctg accgtggaca gtccaggtg cagcagggc    1260 aacgtgttca gctgcagcgt gatgcacgag gccctgcaca accactacac ccagaagtcc    1320
ctgagcctga gccccggcaa g                                              1341

<210> SEQ ID NO 260
```

```
-continued

<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 260

Ser Ala Ser Ser Ser Val Ile Tyr Met His
1               5                   10

<210> SEQ ID NO 261
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 261

Asp Thr Ser Lys Leu Ala Ser
1               5

<210> SEQ ID NO 262
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 262

Gln Gln Trp Ser Ser Asn Pro Leu Thr
1               5

<210> SEQ ID NO 263
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 263

Ser Ala Ser Ser Ser Val Ile Tyr Met His
1               5                   10

<210> SEQ ID NO 264
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 264

Asp Thr Ser Lys Leu Ala Ser
1               5

<210> SEQ ID NO 265
<211> LENGTH: 9
<212> TYPE: PRT
<213> ORGANISM: Artificial Sequence
<220> FEATURE:
```

```
<221> NAME/KEY: source
<223> OTHER INFORMATION: /note="Description of Artificial Sequence:
      Synthetic peptide"

<400> SEQUENCE: 265

Gln Gln Trp Ser Ser Asn Pro Leu Thr
1               5

<210> SEQ ID NO 266
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 266

Ser Ser Ser Val Ile Tyr
1               5

<210> SEQ ID NO 267
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 267

Asp Thr Ser
1

<210> SEQ ID NO 268
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 268

Trp Ser Ser Asn Pro Leu
1               5

<210> SEQ ID NO 269
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 269

Ser Ser Val Ile Tyr
1               5

<210> SEQ ID NO 270
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
```

<400> SEQUENCE: 270

Asp Thr Ser
1

<210> SEQ ID NO 271
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 271

Gln Gln Trp Ser Ser Asn Pro Leu Thr
1               5

<210> SEQ ID NO 272
<211> LENGTH: 106
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 272

Gln Ile Val Leu Thr Gln Ser Pro Ala Ile Met Ser Ala Ser Pro Gly
1               5                   10                  15

Glu Lys Val Thr Met Thr Cys Ser Ala Ser Ser Ser Val Ile Tyr Met
                20                  25                  30

His Trp Tyr Gln Gln Lys Ser Gly Thr Ser Pro Lys Arg Trp Ile Tyr
            35                  40                  45

Asp Thr Ser Lys Leu Ala Ser Gly Val Pro Ala Arg Phe Ser Gly Ser
        50                  55                  60

Gly Ser Gly Thr Ser Tyr Ser Leu Thr Ile Ser Ser Met Glu Ala Glu
65                  70                  75                  80

Asp Ala Ala Thr Tyr Tyr Cys Gln Gln Trp Ser Ser Asn Pro Leu Thr
                85                  90                  95

Phe Gly Ala Gly Thr Thr Leu Glu Leu Lys
                100                 105

<210> SEQ ID NO 273
<211> LENGTH: 318
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 273
caaattgtcc tcacccagtc tccagcaatc atgtctgcat ctccagggga gaaggtcacc    60
atgacctgca gtgccagttc aagtgtaatt tacatgcact ggtaccagca gaagtcaggc   120
acctccccca aaagatggat ttatgacaca tccaaactgg cttctggagt ccctgctcgc   180
ttcagtggta gtgggtctgg gacctcttac tctctcacaa tcagcagcat ggaggctgaa   240
gatgctgcca cttattactg ccagcagtgg agtagtaacc cgctcacgtt cggtgctggg   300
accacgttgg agctgaaa                                                  318

<210> SEQ ID NO 274

```
<211> LENGTH: 213
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 274
```

Gln Ile Val Leu Thr Gln Ser Pro Ala Ile Met Ser Ala Ser Pro Gly
1               5                   10                  15

Glu Lys Val Thr Met Thr Cys Ser Ala Ser Ser Ser Val Ile Tyr Met
            20                  25                  30

His Trp Tyr Gln Gln Lys Ser Gly Thr Ser Pro Lys Arg Trp Ile Tyr
        35                  40                  45

Asp Thr Ser Lys Leu Ala Ser Gly Val Pro Ala Arg Phe Ser Gly Ser
    50                  55                  60

Gly Ser Gly Thr Ser Tyr Ser Leu Thr Ile Ser Ser Met Glu Ala Glu
65                  70                  75                  80

Asp Ala Ala Thr Tyr Tyr Cys Gln Gln Trp Ser Ser Asn Pro Leu Thr
                85                  90                  95

Phe Gly Ala Gly Thr Thr Leu Glu Leu Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210

```
<210> SEQ ID NO 275
<211> LENGTH: 639
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 275
caaattgtcc tcacccagtc tccagcaatc atgtctgcat ctccagggga gaaggtcacc        60
atgacctgca gtgccagttc aagtgtaatt tacatgcact ggtaccagca gaagtcaggc       120
acctccccca aaagatggat ttatgacaca tccaaactgg cttctggagt ccctgctcgc       180
ttcagtggta gtgggtctgg gacctcttac tctctcacaa tcagcagcat ggaggctgaa       240
gatgctgcca cttattactg ccagcagtgg agtagtaacc cgctcacgtt cggtgctggg       300
accacgttgg agctgaaacg tacggtggcg gctcccagcg tgttcatctt ccccccagc        360 gacgagcagt tgaagagtgg caccgccagc gtggtgtgcc tgctgaacaa cttctacccc       420
cgggaggcca aggtgcagtg gaaggtggac aacgccctgc agagcggcaa cagccaggag       480
```

```
agcgtcaccg agcaggacag caaggactcc acctacagcc tgagcagcac cctgaccctg    540
agcaaggccg actacgagaa gcataaggtg tacgcctgcg aggtgaccca ccagggcctg    600
tccagccccg tgaccaagag cttcaacagg ggcgagtgc                          639
```

<210> SEQ ID NO 276
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 276

```
Gly Tyr Ser Ile Thr Ser Gly Tyr Ser Trp His
1               5                   10
```

<210> SEQ ID NO 277
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 277

```
His Ile His Ser Ser Gly Ser Thr Asn Tyr Asn Pro Ser Leu Lys Ser
1               5                   10                  15
```

<210> SEQ ID NO 278
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 278

```
Gly Gly Val Gln Ala Phe Ala Tyr
1               5
```

<210> SEQ ID NO 279
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 279

```
Ser Gly Tyr Ser Trp His
1               5
```

<210> SEQ ID NO 280
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 280

His Ile His Ser Ser Gly Ser Thr Asn Tyr Asn Pro Ser Leu Lys Ser
1               5                   10                  15

<210> SEQ ID NO 281
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 281

Gly Gly Val Gln Ala Phe Ala Tyr
1               5

<210> SEQ ID NO 282
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 282

Gly Tyr Ser Ile Thr Ser Gly Tyr
1               5

<210> SEQ ID NO 283
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 283

His Ser Ser Gly Ser
1               5

<210> SEQ ID NO 284
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 284

Gly Gly Val Gln Ala Phe Ala Tyr
1               5

<210> SEQ ID NO 285
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 285

Gly Tyr Ser Ile Thr Ser Gly Tyr Ser
1               5

```
<210> SEQ ID NO 286
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 286

Ile His Ser Ser Gly Ser Thr
1               5

<210> SEQ ID NO 287
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 287

Ala Arg Gly Gly Val Gln Ala Phe Ala Tyr
1               5                   10

<210> SEQ ID NO 288
<211> LENGTH: 117
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 288

Asp Val Gln Leu Gln Glu Ser Gly Pro Gly Leu Val Lys Pro Ser Gln
1               5                   10                  15

Thr Leu Ser Leu Thr Cys Thr Val Ser Gly Tyr Ser Ile Thr Ser Gly
            20                  25                  30

Tyr Ser Trp His Trp Ile Arg Gln His Pro Gly Lys Gly Leu Glu Trp
        35                  40                  45

Met Ala His Ile His Ser Ser Gly Ser Thr Asn Tyr Asn Pro Ser Leu
    50                  55                  60

Lys Ser Arg Ile Thr Ile Ser Arg Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Gly Gly Val Gln Ala Phe Ala Tyr Trp Gly Gln Gly Thr Leu
            100                 105                 110

Val Thr Val Ser Ser
        115

<210> SEQ ID NO 289
<211> LENGTH: 351
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 289
gacgtgcagc tgcaggaatc tggccctggc ctggtgaaac cctcccagac cctgtccctg    60
```

-continued

```
acctgcaccg tgtccggcta ctccatcacc tccggctaca gctggcactg gatccggcag    120
caccccggca agggcctgga atggatggcc cacatccact cctccggctc caccaactac    180
aaccccagcc tgaagtccag aatcaccatc agccgggaca cctccaagaa ccagttctcc    240
ctgaagctgt cctccgtgac cgccgctgac accgccgtgt actactgtgc cagaggcggc    300
gtgcaggcct tcgcttattg gggccagggc accctggtga cagtgtcctc c            351
```

<210> SEQ ID NO 290
<211> LENGTH: 447
<212> TYPE: PRT
<213> ORGANISM: Artificial Sequence
<220> FEATURE:
<221> NAME/KEY: source
<223> OTHER INFORMATION: /note="Description of Artificial Sequence:
    Synthetic polypeptide"

<400> SEQUENCE: 290

```
Asp Val Gln Leu Gln Glu Ser Gly Pro Gly Leu Val Lys Pro Ser Gln
1               5                   10                  15

Thr Leu Ser Leu Thr Cys Thr Val Ser Gly Tyr Ser Ile Thr Ser Gly
            20                  25                  30

Tyr Ser Trp His Trp Ile Arg Gln His Pro Gly Lys Gly Leu Glu Trp
        35                  40                  45

Met Ala His Ile His Ser Ser Gly Ser Thr Asn Tyr Asn Pro Ser Leu
    50                  55                  60

Lys Ser Arg Ile Thr Ile Ser Arg Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Gly Gly Val Gln Ala Phe Ala Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Cys Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Arg Val Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Ala Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300
```

```
Val Leu Thr Val Leu His Gln Asp Trp Leu Asn Gly Lys Glu Tyr Lys
305                 310                 315                 320

Cys Lys Val Ser Asn Lys Ala Leu Ala Ala Pro Ile Glu Lys Thr Ile
            325                 330                 335

Ser Lys Ala Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
            355                 360                 365

Val Lys Gly Phe Tyr Pro Cys Asp Ile Ala Val Glu Trp Glu Ser Asn
370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
            435                 440                 445

<210> SEQ ID NO 291
<211> LENGTH: 1341
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 291
gacgtgcagc tgcaggaatc tggccctggc ctggtgaaac cctcccagac cctgtccctg      60
acctgcaccg tgtccggcta ctccatcacc tccggctaca gctggcactg gatccggcag     120
caccccggca agggcctgga atggatggcc acatccact cctccggctc caccaactac      180
aaccccagcc tgaagtccag aatcaccatc agccgggaca cctccaagaa ccagttctcc     240
ctgaagctgt cctccgtgac cgccgctgac accgccgtgt actactgtgc cagaggcggc     300
gtgcaggcct tcgcttattg gggccagggc accctggtga cagtgtcctc cgctagcacc     360
aagggcccaa gtgtgtttcc cctggccccc agcagcaagt ctacttccgg cggaactgct     420
gccctgggtt gcctggtgaa ggactacttc cctgtcccg tgacagtgtc ctggaactct      480
ggggctctga cttccggcgt gcacaccttc ccgccgtgc tgcagagcag cggcctgtac      540
agcctgagca gcgtggtgac agtgccctcc agctctctgg aacccagac ctatatctgc      600 aacgtgaacc acaagcccag caacaccaag gtggacaaga gagtggagcc caagagctgc     660
gacaagaccc acacctgccc ccctgccca gctccagaac tgctgggagg gccttccgtg      720
ttcctgttcc cccccaagcc caaggacacc ctgatgatca gcaggacccc cgaggtgacc     780
tgcgtggtgg tggccgtgtc ccacgaggac ccagaggtga agttcaactg gtacgtggac     840
ggcgtggagg tgcacaacgc caagaccaag cccagagagg agcagtacaa cagcacctac     900
agggtggtgt ccgtgctgac cgtgctgcac caggactggc tgaacggcaa agaatacaag     960
tgcaaagtct ccaacaaggc cctggctgcc ccaatcgaaa agacaatcag caaggccaag    1020
ggccagccac gggagcccca ggtgtacacc ctgcccccca gccgggagga gatgaccaag    1080
aaccaggtgt ccctgacctg tctggtgaag ggcttctacc cctgtgatat cgccgtggag    1140
tgggagagca acggccagcc cgagaacaac tacaagacca ccccccccagt gctggacagc    1200
```

```
gacggcagct tcttcctgta cagcaagctg accgtggaca agtccaggtg gcagcagggc    1260
aacgtgttca gctgcagcgt gatgcacgag gccctgcaca accactacac ccagaagtcc    1320
ctgagcctga gccccggcaa g                                              1341
```

<210> SEQ ID NO 292
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 292

Ser Ala Ser Ser Ser Val Ile Tyr Met His
1               5                   10

<210> SEQ ID NO 293
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 293

Asp Thr Ser Lys Leu Ala Ser
1               5

<210> SEQ ID NO 294
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 294

Gln Gln Trp Ser Ser Asn Pro Leu Thr
1               5

<210> SEQ ID NO 295
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 295

Ser Ala Ser Ser Ser Val Ile Tyr Met His
1               5                   10

<210> SEQ ID NO 296
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 296

Asp Thr Ser Lys Leu Ala Ser

```
1               5
```

<210> SEQ ID NO 297
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 297

```
Gln Gln Trp Ser Ser Asn Pro Leu Thr
1               5
```

<210> SEQ ID NO 298
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 298

```
Ser Ser Ser Val Ile Tyr
1               5
```

<210> SEQ ID NO 299
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 299

```
Asp Thr Ser
1
```

<210> SEQ ID NO 300
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 300

```
Trp Ser Ser Asn Pro Leu
1               5
```

<210> SEQ ID NO 301
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 301

```
Ser Ser Val Ile Tyr
1               5
```

<210> SEQ ID NO 302

<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 302

Asp Thr Ser
1

<210> SEQ ID NO 303
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 303

Gln Gln Trp Ser Ser Asn Pro Leu Thr
1               5

<210> SEQ ID NO 304
<211> LENGTH: 106
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 304

Glu Ile Val Leu Thr Gln Ser Pro Ala Thr Leu Ser Ala Ser Pro Gly
1               5                   10                  15

Glu Arg Val Thr Met Ser Cys Ser Ala Ser Ser Ser Val Ile Tyr Met
                20                  25                  30

His Trp Tyr Gln Gln Lys Pro Gly Gln Ala Pro Arg Arg Trp Ile Tyr
            35                  40                  45

Asp Thr Ser Lys Leu Ala Ser Gly Val Pro Ala Arg Phe Ser Gly Ser
        50                  55                  60

Gly Ser Gly Thr Asp Tyr Thr Leu Thr Ile Ser Ser Met Glu Pro Glu
65                  70                  75                  80

Asp Ala Ala Val Tyr Tyr Cys Gln Gln Trp Ser Ser Asn Pro Leu Thr
                85                  90                  95

Phe Gly Gln Gly Thr Lys Leu Glu Ile Lys
            100                 105

<210> SEQ ID NO 305
<211> LENGTH: 318
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 305
gagatcgtgc tgacccagtc ccctgccacc ctgtctgcta gccctggcga gcgcgtgaca    60
atgtcctgct ccgcctcctc ctccgtgatc tacatgcact ggtatcagca gaagcccggc   120
caggcccctc ggcggtggat ctacgatacc tccaagctgg cctccggcgt gcccgccaga   180

```
ttctccggct ctggctctgg caccgactac accctgacca tctccagcat ggaacccgag      240
gacgccgccg tgtactactg ccagcagtgg tcctccaacc ccctgacctt cggccagggc      300
accaagctgg aaatcaag                                                    318
```

<210> SEQ ID NO 306
<211> LENGTH: 213
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 306

```
Glu Ile Val Leu Thr Gln Ser Pro Ala Thr Leu Ser Ala Ser Pro Gly
1               5                   10                  15

Glu Arg Val Thr Met Ser Cys Ser Ala Ser Ser Ser Val Ile Tyr Met
            20                  25                  30

His Trp Tyr Gln Gln Lys Pro Gly Gln Ala Pro Arg Arg Trp Ile Tyr
        35                  40                  45

Asp Thr Ser Lys Leu Ala Ser Gly Val Pro Ala Arg Phe Ser Gly Ser
    50                  55                  60

Gly Ser Gly Thr Asp Tyr Thr Leu Thr Ile Ser Ser Met Glu Pro Glu
65                  70                  75                  80

Asp Ala Ala Val Tyr Tyr Cys Gln Gln Trp Ser Ser Asn Pro Leu Thr
                85                  90                  95

Phe Gly Gln Gly Thr Lys Leu Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210
```

<210> SEQ ID NO 307
<211> LENGTH: 639
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 307

```
gagatcgtgc tgacccagtc ccctgccacc ctgtctgcta gccctggcga gcgcgtgaca      60
atgtcctgct ccgcctcctc ctccgtgatc tacatgcact ggtatcagca gaagcccggc     120
caggcccctc ggcggtggat ctacgatacc tccaagctgg cctccggcgt gcccgccaga     180
ttctccggct ctggctctgg caccgactac accctgacca tctccagcat ggaacccgag     240
```

```
gacgccgccg tgtactactg ccagcagtgg tcctccaacc ccctgacctt cggccagggc    300
accaagctgg aaatcaagcg tacggtggcc gctcccagcg tgttcatctt cccccccagc    360
gacgagcagc tgaagagtgg caccgccagc gtggtgtgcc tgctgaacaa cttctacccc    420
cgggaggcca aggtgcagtg gaaggtggac aacgccctgc agagcggcaa cagccaggag    480
agcgtcaccg agcaggacag caaggactcc acctacagcc tgagcagcac cctgaccctg    540
agcaaggccg actacgagaa gcataaggtg tacgcctgcg aggtgaccca ccagggcctg    600
tccagccccg tgaccaagag cttcaacagg ggcgagtgc                           639
```

```
<210> SEQ ID NO 308
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 308

Gly Phe Thr Phe Ser Thr Tyr Ala Met Ser
1               5                   10
```

```
<210> SEQ ID NO 309
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 309

Thr Ile Ser Asp Ala Gly Ser Tyr Ser Tyr Tyr Pro Asp Asn Val Lys
1               5                   10                  15
Gly
```

```
<210> SEQ ID NO 310
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 310

Arg Gly Ser Arg Tyr Glu Glu Tyr Tyr Val Met Asp Tyr
1               5                   10
```

```
<210> SEQ ID NO 311
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 311

Thr Tyr Ala Met Ser
1               5
```

```
<210> SEQ ID NO 312
```

```
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 312

Thr Ile Ser Asp Ala Gly Ser Tyr Ser Tyr Tyr Pro Asp Asn Val Lys
1               5                   10                  15
Gly

<210> SEQ ID NO 313
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 313

Arg Gly Ser Arg Tyr Glu Glu Tyr Tyr Val Met Asp Tyr
1               5                   10

<210> SEQ ID NO 314
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 314

Gly Phe Thr Phe Ser Thr Tyr
1               5

<210> SEQ ID NO 315
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 315

Ser Asp Ala Gly Ser Tyr
1               5

<210> SEQ ID NO 316
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 316

Arg Gly Ser Arg Tyr Glu Glu Tyr Tyr Val Met Asp Tyr
1               5                   10

<210> SEQ ID NO 317
<211> LENGTH: 8
<212> TYPE: PRT
```

<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 317

Gly Phe Thr Phe Ser Thr Tyr Ala
1               5

<210> SEQ ID NO 318
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 318

Ile Ser Asp Ala Gly Ser Tyr Ser
1               5

<210> SEQ ID NO 319
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 319

Ala Arg Arg Gly Ser Arg Tyr Glu Glu Tyr Tyr Val Met Asp Tyr
1               5                   10                  15

<210> SEQ ID NO 320
<211> LENGTH: 122
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 320

Glu Val Gln Leu Val Glu Ser Gly Gly Gly Leu Val Lys Pro Gly Gly
1               5                   10                  15

Ser Leu Lys Leu Ser Cys Ala Ala Ser Gly Phe Thr Phe Ser Thr Tyr
            20                  25                  30

Ala Met Ser Trp Val Arg Gln Thr Pro Glu Lys Arg Leu Glu Trp Val
        35                  40                  45

Ala Thr Ile Ser Asp Gly Gly Ser Tyr Ser Tyr Tyr Pro Asp Asn Val
    50                  55                  60

Lys Gly Arg Phe Thr Ile Ser Arg Asp Asn Ala Lys Asn Asn Leu Tyr
65                  70                  75                  80

Leu Gln Met Ser His Leu Lys Ser Glu Asp Thr Ala Met Tyr Tyr Cys
                85                  90                  95

Ala Arg Arg Gly Ser Arg Tyr Glu Glu Tyr Tyr Val Met Asp Tyr Trp
            100                 105                 110

Gly Gln Gly Thr Ser Val Thr Val Ser Ser
        115                 120

<210> SEQ ID NO 321

```
<211> LENGTH: 366
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 321
gaagtgcagc tggtggagtc tgggggaggc ttagtgaagc ctggagggtc cctgaaactc      60
tcctgtgcag cctctggatt cactttcagt acctatgcca tgtcttgggt tcgccagact     120
ccggaaaaga ggctggagtg ggtcgcaacc attagtgatg gtggtagtta ttcgtactat     180
ccagacaatg taaagggccg attcaccatc tccagagaca atgccaagaa caacctatac     240
ctgcaaatga gccatctgaa gtctgaggac acagccatgt attactgtgc aagacgaggt     300
agtaggtacg aagagtacta tgttatggac tactggggtc aaggaacctc agtcaccgtc     360
tcctca                                                                 366

<210> SEQ ID NO 322
<211> LENGTH: 452
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 322
```

Glu Val Gln Leu Val Glu Ser Gly Gly Gly Leu Val Lys Pro Gly Gly
1               5                   10                  15

Ser Leu Lys Leu Ser Cys Ala Ala Ser Gly Phe Thr Phe Ser Thr Tyr
            20                  25                  30

Ala Met Ser Trp Val Arg Gln Thr Pro Glu Lys Arg Leu Glu Trp Val
        35                  40                  45

Ala Thr Ile Ser Asp Gly Gly Ser Tyr Ser Tyr Tyr Pro Asp Asn Val
    50                  55                  60

Lys Gly Arg Phe Thr Ile Ser Arg Asp Asn Ala Lys Asn Asn Leu Tyr
65                  70                  75                  80

Leu Gln Met Ser His Leu Lys Ser Glu Asp Thr Ala Met Tyr Tyr Cys
                85                  90                  95

Ala Arg Arg Gly Ser Arg Tyr Glu Glu Tyr Tyr Val Met Asp Tyr Trp
            100                 105                 110

Gly Gln Gly Thr Ser Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Cys Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Arg Val Glu Pro Lys Ser
    210                 215                 220

Cys Asp Lys Thr His Thr Cys Pro Pro Cys Pro Ala Pro Glu Leu Leu

```
            225                 230                 235                 240
Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
                260                 265                 270

His Glu Asp Pro Glu Val Lys Phe Asn Trp Tyr Val Asp Gly Val Glu
            275                 280                 285

Val His Asn Ala Lys Thr Lys Pro Arg Glu Glu Gln Tyr Asn Ser Thr
        290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Arg Glu Glu Met Thr Lys Asn Gln Val
        355                 360                 365

Ser Leu Thr Cys Leu Val Lys Gly Phe Tyr Pro Ser Asp Ile Ala Val
370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
                405                 410                 415

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
        435                 440                 445

Ser Pro Gly Lys
    450

<210> SEQ ID NO 323
<211> LENGTH: 1356
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 323
gaagtgcagc tggtggagtc tgggggaggc ttagtgaagc ctggagggtc cctgaaactc      60
tcctgtgcag cctctggatt cactttcagt acctatgcca tgtcttgggt tcgccagact     120
ccggaaaaga ggctggagtg ggtcgcaacc attagtgatg gtggtagtta ttcgtactat     180
ccagacaatg taaagggccg attcaccatc tccagagaca atgccaagaa caacctatac     240
ctgcaaatga gccatctgaa gtctgaggac acagccatgt attactgtgc aagacgaggt     300
agtaggtacg aagagtacta tgttatggac tactggggtc aaggaacctc agtcaccgtc     360
tcctcagcta gcaccaaggg cccaagtgtg tttcccctgg ccccagcag caagtctact     420 tccggcggaa ctgctgccct gggttgcctg gtgaaggact acttccctg tcccgtgaca     480 gtgtcctgga actctggggc tctgacttcc ggcgtgcaca ccttcccgc cgtgctgcag     540 agcagcggcc tgtacagcct gagcagcgtg gtgacagtgc cctccagctc tctgggaacc     600
cagacctata tctgcaacgt gaaccacaag cccagcaaca ccaaggtgga caagagagtg     660
gagcccaaga gctgcgacaa gacccacacc tgccccccct gcccagctcc agaactgctg     720
```

```
ggagggcctt ccgtgttcct gttccccccc aagcccaagg acaccctgat gatcagcagg    780
acccccgagg tgacctgcgt ggtggtggac gtgtcccacg aggacccaga ggtgaagttc    840
aactggtacg tggacggcgt ggaggtgcac aacgccaaga ccaagcccag agaggagcag    900
tacaacagca cctacagggt ggtgtccgtg ctgaccgtgc tgcaccagga ctggctgaac    960
ggcaaagaat acaagtgcaa agtctccaac aaggccctgc cagccccaat cgaaaagaca   1020
atcagcaagg ccaagggcca gccacgggag ccccaggtgt acaccctgcc ccccagccgg   1080
gaggagatga ccaagaacca ggtgtccctg acctgtctgg tgaagggctt ctaccctgt    1140 gatatcgccg tggagtggga gagcaacggc cagcccgaga caactacaa gaccaccccc    1200 ccagtgctgg acagcgacgg cagcttcttc ctgtacagca gctgaccgt ggacaagtcc    1260 aggtggcagc agggcaacgt gttcagctgc agcgtgatgc acgaggccct gcacaaccac   1320
tacacccaga agtccctgag cctgagcccc ggcaag                              1356
```

<210> SEQ ID NO 324
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 324

Arg Ala Ser Gln Ser Ile Ser Asn Asn Leu His
1               5                   10

<210> SEQ ID NO 325
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 325

Tyr Ala Ser Gln Ser Ile Ser
1               5

<210> SEQ ID NO 326
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 326

Gln Gln Ser Ser Ser Trp Leu Thr
1               5

<210> SEQ ID NO 327
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 327

Arg Ala Ser Gln Ser Ile Ser Asn Asn Leu His
1               5                   10

<210> SEQ ID NO 328
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 328

Tyr Ala Ser Gln Ser Ile Ser
1               5

<210> SEQ ID NO 329
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 329

Gln Gln Ser Ser Ser Trp Leu Thr
1               5

<210> SEQ ID NO 330
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 330

Ser Gln Ser Ile Ser Asn Asn
1               5

<210> SEQ ID NO 331
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 331

Tyr Ala Ser
1

<210> SEQ ID NO 332
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 332

Ser Ser Ser Trp Leu
1               5

<210> SEQ ID NO 333
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 333

Gln Ser Ile Ser Asn Asn
1               5

<210> SEQ ID NO 334
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 334

Tyr Ala Ser
1

<210> SEQ ID NO 335
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 335

Gln Gln Ser Ser Ser Trp Leu Thr
1               5

<210> SEQ ID NO 336
<211> LENGTH: 106
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 336

Asp Ile Val Leu Thr Gln Ser Pro Ala Thr Leu Ser Val Thr Pro Gly
1               5                   10                  15

Asp Ser Val Ser Leu Ser Cys Arg Ala Ser Gln Ser Ile Ser Asn Asn
            20                  25                  30

Leu His Trp Tyr Gln Gln Lys Ser His Glu Ser Pro Lys Leu Leu Ile
        35                  40                  45

Lys Tyr Ala Ser Gln Ser Ile Ser Gly Ile Pro Ser Arg Phe Ser Gly
    50                  55                  60

Ser Gly Ser Gly Thr Asp Phe Thr Leu Ser Ile Asn Ser Val Glu Thr
65                  70                  75                  80

Glu Asp Phe Gly Met Tyr Phe Cys Gln Gln Ser Asn Ser Trp Leu Thr
                85                  90                  95

Phe Gly Ala Gly Thr Lys Leu Gly Leu Lys
            100                 105

<210> SEQ ID NO 337
<211> LENGTH: 318
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 337

```
gatattgtgc taactcagtc tccagccacc ctgtctgtga ctccaggaga tagcgtcagt    60
ctttcctgca gggccagcca agtattagc aacaacctac actggtatca acagaaatca   120
catgagtctc caaaacttct catcaagtat gcttcccagt ccatctctgg gatcccctcc   180
aggttcagtg gcagtggatc agggacagat ttcactctca gtatcaacag tgtggagact   240
gaagattttg gaatgtattt ctgtcaacag agtaacagct ggctcacgtt cggtgctggg   300
accaagctgg ggctgaaa                                                 318
```

<210> SEQ ID NO 338
<211> LENGTH: 213
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 338

```
Asp Ile Val Leu Thr Gln Ser Pro Ala Thr Leu Ser Val Thr Pro Gly
1               5                   10                  15
Asp Ser Val Ser Leu Ser Cys Arg Ala Ser Gln Ser Ile Ser Asn Asn
            20                  25                  30
Leu His Trp Tyr Gln Gln Lys Ser His Glu Ser Pro Lys Leu Leu Ile
        35                  40                  45
Lys Tyr Ala Ser Gln Ser Ile Ser Gly Ile Pro Ser Arg Phe Ser Gly
    50                  55                  60
Ser Gly Ser Gly Thr Asp Phe Thr Leu Ser Ile Asn Ser Val Glu Thr
65                  70                  75                  80
Glu Asp Phe Gly Met Tyr Phe Cys Gln Gln Ser Asn Ser Trp Leu Thr
                85                  90                  95
Phe Gly Ala Gly Thr Lys Leu Gly Leu Lys Arg Thr Val Ala Ala Pro
            100                 105                 110
Ser Val Phe Ile Phe Pro Pro Ser Asp Glu Gln Leu Lys Ser Gly Thr
        115                 120                 125
Ala Ser Val Val Cys Leu Leu Asn Asn Phe Tyr Pro Arg Glu Ala Lys
    130                 135                 140
Val Gln Trp Lys Val Asp Asn Ala Leu Gln Ser Gly Asn Ser Gln Glu
145                 150                 155                 160
Ser Val Thr Glu Gln Asp Ser Lys Asp Ser Thr Tyr Ser Leu Ser Ser
                165                 170                 175
Thr Leu Thr Leu Ser Lys Ala Asp Tyr Glu Lys His Lys Val Tyr Ala
            180                 185                 190
Cys Glu Val Thr His Gln Gly Leu Ser Ser Pro Val Thr Lys Ser Phe
        195                 200                 205
Asn Arg Gly Glu Cys
    210
```

<210> SEQ ID NO 339

<211> LENGTH: 639
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 339

```
gatattgtgc taactcagtc tccagccacc ctgtctgtga ctccaggaga tagcgtcagt    60
ctttcctgca gggccagcca agtattagc aacaacctac actggtatca acagaaatca   120
catgagtctc caaaacttct catcaagtat gcttcccagt ccatctctgg gatcccctcc   180
aggttcagtg gcagtggatc agggacagat ttcactctca gtatcaacag tgtggagact   240
gaagattttg gaatgtattt ctgtcaacag agtaacagct ggctcacgtt cggtgctggg   300
accaagctgg ggctgaaacg tacggtggcc gctcccagcg tgttcatctt ccccccagc   360
gacgagcagc tgaagagtgg caccgccagc gtggtgtgcc tgctgaacaa cttctacccc   420
cgggaggcca aggtgcagtg gaaggtggac aacgccctgc agagcggcaa cagccaggag   480
agcgtcaccg agcaggacag caaggactcc acctacagcc tgagcagcac cctgaccctg   540
agcaaggcca ctacgagaa gcataaggtg tacgcctgcg aggtgaccca ccagggcctg   600
tccagccccg tgaccaagag cttcaacagg ggcgagtgc                          639
```

<210> SEQ ID NO 340
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 340

Gly Phe Thr Phe Ser Thr Tyr Ala Met Ser
1               5                   10

<210> SEQ ID NO 341
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 341

Thr Ile Ser Asp Ala Gly Ser Tyr Ser Tyr Tyr Pro Asp Asn Val Lys
1               5                   10                  15

Gly

<210> SEQ ID NO 342
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 342

Arg Gly Ser Arg Tyr Glu Glu Tyr Tyr Val Met Asp Tyr
1               5                   10

```
<210> SEQ ID NO 343
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 343

Thr Tyr Ala Met Ser
1               5

<210> SEQ ID NO 344
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 344

Thr Ile Ser Asp Ala Gly Ser Tyr Ser Tyr Tyr Pro Asp Asn Val Lys
1               5                   10                  15

Gly

<210> SEQ ID NO 345
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 345

Arg Gly Ser Arg Tyr Glu Glu Tyr Tyr Val Met Asp Tyr
1               5                   10

<210> SEQ ID NO 346
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 346

Gly Phe Thr Phe Ser Thr Tyr
1               5

<210> SEQ ID NO 347
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 347

Ser Asp Ala Gly Ser Tyr
1               5

<210> SEQ ID NO 348
```

<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 348

Arg Gly Ser Arg Tyr Glu Glu Tyr Tyr Val Met Asp Tyr
1               5                   10

<210> SEQ ID NO 349
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 349

Gly Phe Thr Phe Ser Thr Tyr Ala
1               5

<210> SEQ ID NO 350
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 350

Ile Ser Asp Ala Gly Ser Tyr Ser
1               5

<210> SEQ ID NO 351
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 351

Ala Arg Arg Gly Ser Arg Tyr Glu Glu Tyr Tyr Val Met Asp Tyr
1               5                   10                  15

<210> SEQ ID NO 352
<211> LENGTH: 122
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 352

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Thr Tyr
            20                  25                  30

Ala Met Ser Trp Val Arg Gln Ala Pro Gly Lys Gly Leu Glu Trp Val
        35                  40                  45

Ala Thr Ile Ser Asp Ala Gly Ser Tyr Ser Tyr Tyr Pro Asp Asn Val
    50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Arg Arg Gly Ser Arg Tyr Glu Glu Tyr Tyr Val Met Asp Tyr Trp
            100                 105                 110

Gly Gln Gly Thr Thr Val Thr Val Ser Ser
            115                 120

<210> SEQ ID NO 353
<211> LENGTH: 366
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 353
gaggtgcagc tggtggaatc tggcggaggc ctggtgaaac cggcggatc cctgagactg    60 tcctgcgccg cctccggctt caccttctcc acctacgcca tgtcctgggt gcggcaggct   120
cccggcaagg gcctggaatg ggtggccacc atctccgacg ccggctccta ctcctactac   180
cccgacaacg tgaagggcag attcaccatc agccgggaca acgccaagaa ctccctgtac   240
ctgcagatga actccctgcg ggccgaggac accgccgtgt actactgtgc cagacggggc   300
tccagatacg aagagtacta cgtgatggac tattggggcc agggcaccac cgtgacagtg   360
tcctcc                                                              366

<210> SEQ ID NO 354
<211> LENGTH: 452
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 354

Glu Val Gln Leu Val Glu Ser Gly Gly Gly Leu Val Lys Pro Gly Gly
 1               5                  10                  15

Ser Leu Arg Leu Ser Cys Ala Ala Ser Gly Phe Thr Phe Ser Thr Tyr
                20                  25                  30

Ala Met Ser Trp Val Arg Gln Ala Pro Gly Lys Gly Leu Glu Trp Val
            35                  40                  45

Ala Thr Ile Ser Asp Ala Gly Ser Tyr Ser Tyr Tyr Pro Asp Asn Val
    50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Arg Arg Gly Ser Arg Tyr Glu Glu Tyr Tyr Val Met Asp Tyr Trp
            100                 105                 110

Gly Gln Gly Thr Thr Val Thr Val Ser Ser Ala Ser Thr Lys Gly Pro
            115                 120                 125

Ser Val Phe Pro Leu Ala Pro Ser Ser Lys Ser Thr Ser Gly Gly Thr
        130                 135                 140

Ala Ala Leu Gly Cys Leu Val Lys Asp Tyr Phe Pro Cys Pro Val Thr
145                 150                 155                 160

Val Ser Trp Asn Ser Gly Ala Leu Thr Ser Gly Val His Thr Phe Pro
            165                 170                 175

Ala Val Leu Gln Ser Ser Gly Leu Tyr Ser Leu Ser Val Val Thr
        180                 185                 190

Val Pro Ser Ser Leu Gly Thr Gln Thr Tyr Ile Cys Asn Val Asn
    195                 200                 205

His Lys Pro Ser Asn Thr Lys Val Asp Lys Arg Val Glu Pro Lys Ser
    210                 215                 220

Cys Asp Lys Thr His Thr Cys Pro Pro Cys Pro Ala Pro Glu Leu Leu
225                 230                 235                 240

Gly Gly Pro Ser Val Phe Leu Phe Pro Pro Lys Pro Lys Asp Thr Leu
            245                 250                 255

Met Ile Ser Arg Thr Pro Glu Val Thr Cys Val Val Val Ala Val Ser
            260                 265                 270

His Glu Asp Pro Glu Val Lys Phe Asn Trp Tyr Val Asp Gly Val Glu
        275                 280                 285

Val His Asn Ala Lys Thr Lys Pro Arg Glu Glu Gln Tyr Asn Ser Thr
290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Ala Ala Pro
            325                 330                 335

Ile Glu Lys Thr Ile Ser Lys Ala Lys Gly Gln Pro Arg Glu Pro Gln
            340                 345                 350

Val Tyr Thr Leu Pro Pro Ser Arg Glu Glu Met Thr Lys Asn Gln Val
        355                 360                 365

Ser Leu Thr Cys Leu Val Lys Gly Phe Tyr Pro Cys Asp Ile Ala Val
    370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
            405                 410                 415

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
        435                 440                 445

Ser Pro Gly Lys
        450

<210> SEQ ID NO 355
<211> LENGTH: 1356
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic polynucleotide"

<400> SEQUENCE: 355
gaggtgcagc tggtggaatc tggcggaggc ctggtgaaac ccggcggatc cctgagactg      60
tcctgcgccg cctccggctt caccttctcc acctacgcca tgtcctgggt gcggcaggct     120
cccggcaagg gcctggaatg ggtggccacc atctccgacg ccggctccta ctcctactac     180

```
cccgacaacg tgaagggcag attcaccatc agccgggaca cgccaagaa ctccctgtac    240 ctgcagatga actccctgcg ggccgaggac accgccgtgt actactgtgc agacggggc    300 tccagatacg aagagtacta cgtgatggac tattggggcc agggcaccac cgtgacagtg    360
tcctccgcta gcaccaaggg cccaagtgtg tttcccctgg ccccagcag caagtctact    420 tccggcggaa ctgctgccct gggttgcctg gtgaaggact acttcccctg tcccgtgaca    480
gtgtcctgga actctggggc tctgacttcc ggcgtgcaca ccttccccgc cgtgctgcag    540
agcagcggcc tgtacagcct gagcagcgtg gtgacagtgc cctccagctc tctgggaacc    600
cagacctata tctgcaacgt gaaccacaag cccagcaaca ccaaggtgga caagagagtg    660
gagcccaaga gctgcgacaa gacccacacc tgcccccct gcccagctcc agaactgctg    720
ggagggcctt ccgtgttcct gttcccccc aagcccaagg acaccctgat gatcagcagg    780 accccgagg tgacctgcgt ggtggtggcc gtgtcccacg aggacccaga ggtgaagttc    840
aactggtacg tggacggcgt ggaggtgcac aacgccaaga ccaagccag agaggagcag    900 tacaacagca cctacagggt ggtgtccgtg ctgaccgtgc tgcaccagga ctggctgaac    960
ggcaaagaat acaagtgcaa agtctccaac aaggccctgg ctgccccaat cgaaaagaca   1020
atcagcaagg ccaagggcca gccacggag ccccaggtgt acaccctgcc ccccagccgg   1080
gaggagatga ccaagaacca ggtgtccctg acctgtctgg tgaagggctt ctaccctgt   1140 gatatcgccg tggagtggga gagcaacggc cagcccgaga caactacaa gaccaccccc   1200 ccagtgctgg acagcgacgg cagcttcttc ctgtacagca agctgaccgt ggacaagtcc   1260
aggtggcagc agggcaacgt gttcagctgc agcgtgatgc acgaggccct gcacaaccac   1320
tacacccaga agtccctgag cctgagcccc ggcaag                             1356
```

<210> SEQ ID NO 356
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 356

Arg Ala Ser Gln Ser Ile Ser Asn Asn Leu His
1               5                   10

<210> SEQ ID NO 357
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 357

Tyr Ala Ser Gln Ser Ile Ser
1               5

<210> SEQ ID NO 358
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

```
<400> SEQUENCE: 358

Gln Gln Ser Ser Ser Trp Leu Thr
1               5

<210> SEQ ID NO 359
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 359

Arg Ala Ser Gln Ser Ile Ser Asn Asn Leu His
1               5                   10

<210> SEQ ID NO 360
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 360

Tyr Ala Ser Gln Ser Ile Ser
1               5

<210> SEQ ID NO 361
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 361

Gln Gln Ser Ser Ser Trp Leu Thr
1               5

<210> SEQ ID NO 362
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 362

Ser Gln Ser Ile Ser Asn Asn
1               5

<210> SEQ ID NO 363
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 363

Tyr Ala Ser
```

<210> SEQ ID NO 364
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 364

Ser Ser Ser Trp Leu
1               5

<210> SEQ ID NO 365
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 365

Gln Ser Ile Ser Asn Asn
1               5

<210> SEQ ID NO 366
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 366

Tyr Ala Ser
1

<210> SEQ ID NO 367
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 367

Gln Gln Ser Ser Ser Trp Leu Thr
1               5

<210> SEQ ID NO 368
<211> LENGTH: 106
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 368

Glu Ile Val Leu Thr Gln Ser Pro Ala Thr Leu Ser Val Ser Pro Gly
1               5                   10                  15

Glu Arg Val Thr Leu Ser Cys Arg Ala Ser Gln Ser Ile Ser Asn Asn
            20                  25                  30

Leu His Trp Tyr Gln Gln Lys Pro Gly Gln Ala Pro Arg Leu Leu Ile
            35                  40                  45

Lys Tyr Ala Ser Gln Ser Ile Ser Gly Ile Pro Ala Arg Phe Ser Gly
         50                  55                  60

Ser Gly Ser Gly Thr Asp Phe Thr Leu Thr Ile Ser Ser Val Glu Pro
 65                  70                  75                  80

Glu Asp Phe Gly Val Tyr Phe Cys Gln Gln Ser Ser Ser Trp Leu Thr
                 85                  90                  95

Phe Gly Gln Gly Thr Lys Leu Glu Ile Lys
            100                 105

<210> SEQ ID NO 369
<211> LENGTH: 318
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 369
gagatcgtgc tgacccagtc ccctgccacc ctgtccgtgt ctcccggcga gagagtgacc        60
ctgtcctgcc gggcctccca gtccatctcc aacaacctgc actggtatca gcagaagccc       120
ggccaggccc ctcggctgct gattaagtac gcctcccaga gcatctccgg catccctgcc       180
agattctccg gctccggcag cggcaccgac ttcaccctga ccatctccag cgtggaaccc       240
gaggacttcg gcgtgtactt ctgccagcag tcctcatcct ggctgacctt cggccagggc       300
accaagctgg aaatcaag                                                    318

<210> SEQ ID NO 370
<211> LENGTH: 213
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 370

Glu Ile Val Leu Thr Gln Ser Pro Ala Thr Leu Ser Val Ser Pro Gly
 1               5                  10                  15

Glu Arg Val Thr Leu Ser Cys Arg Ala Ser Gln Ser Ile Ser Asn Asn
             20                  25                  30

Leu His Trp Tyr Gln Gln Lys Pro Gly Gln Ala Pro Arg Leu Leu Ile
            35                  40                  45

Lys Tyr Ala Ser Gln Ser Ile Ser Gly Ile Pro Ala Arg Phe Ser Gly
         50                  55                  60

Ser Gly Ser Gly Thr Asp Phe Thr Leu Thr Ile Ser Ser Val Glu Pro
 65                  70                  75                  80

Glu Asp Phe Gly Val Tyr Phe Cys Gln Gln Ser Ser Ser Trp Leu Thr
                 85                  90                  95

Phe Gly Gln Gly Thr Lys Leu Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
            165                 170                 175

Thr Leu Thr Leu Ser Lys Ala Asp Tyr Glu Lys His Lys Val Tyr Ala
        180                 185                 190

Cys Glu Val Thr His Gln Gly Leu Ser Ser Pro Val Thr Lys Ser Phe
        195                 200                 205

Asn Arg Gly Glu Cys
    210

<210> SEQ ID NO 371
<211> LENGTH: 639
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 371
gagatcgtgc tgacccagtc ccctgccacc ctgtccgtgt ctcccggcga gagagtgacc    60
ctgtcctgcc gggcctccca gtccatctcc aacaacctgc actggtatca gcagaagccc   120
ggccaggccc ctcggctgct gattaagtac gcctcccaga gcatctccgg catccctgcc   180
agattctccg gctccggcag cggcaccgac ttcaccctga ccatctccag cgtggaaccc   240
gaggacttcg cgtgtacttt ctgccagcag tcctcatcct ggctgacctt cggccagggc   300
accaagctgg aaatcaagcg tacggtggcc gctcccagcg tgttcatctt ccccccagc    360 gacgagcagc tgaagagtgg caccgccagc gtggtgtgcc tgctgaacaa cttctacccc   420
cgggaggcca aggtgcagtg gaaggtggac aacgccctgc agagcggcaa cagccaggag   480
agcgtcaccg agcaggacag caaggactcc acctacagcc tgagcagcac cctgaccctg   540
agcaaggccg actacgagaa gcataaggtg tacgcctgcg aggtgaccca ccagggcctg   600
tccagccccg tgaccaagag cttcaacagg ggcgagtgc                          639

<210> SEQ ID NO 372
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 372

Gly Phe Thr Phe Ser Ser Tyr Ala Met Ser
1               5                   10

<210> SEQ ID NO 373
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 373

Thr Ile Ser Ser Gly Gly Ser Phe Thr Tyr Tyr Pro Asp Ser Val Lys
1               5                   10                  15

Gly

<210> SEQ ID NO 374
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 374

Arg Ala Ser Thr Val Val Gly Thr Asp Phe Asp Val
1               5                   10

<210> SEQ ID NO 375
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 375

Ser Tyr Ala Met Ser
1               5

<210> SEQ ID NO 376
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 376

Thr Ile Ser Ser Gly Gly Ser Phe Thr Tyr Tyr Pro Asp Ser Val Lys
1               5                   10                  15

Gly

<210> SEQ ID NO 377
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 377

Arg Ala Ser Thr Val Val Gly Thr Asp Phe Asp Val
1               5                   10

<210> SEQ ID NO 378
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 378

Gly Phe Thr Phe Ser Ser Tyr
1               5

```
<210> SEQ ID NO 379
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 379

Ser Ser Gly Gly Ser Phe
1               5

<210> SEQ ID NO 380
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 380

Arg Ala Ser Thr Val Val Gly Thr Asp Phe Asp Val
1               5                   10

<210> SEQ ID NO 381
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 381

Gly Phe Thr Phe Ser Ser Tyr Ala
1               5

<210> SEQ ID NO 382
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 382

Ile Ser Ser Gly Gly Ser Phe Thr
1               5

<210> SEQ ID NO 383
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 383

Ala Arg Arg Ala Ser Thr Val Val Gly Thr Asp Phe Asp Val
1               5                   10

<210> SEQ ID NO 384
<211> LENGTH: 121
<212> TYPE: PRT
```

<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 384

```
Glu Val Met Leu Val Glu Ser Gly Gly Gly Leu Val Lys Pro Gly
1               5                   10                  15

Ser Leu Lys Leu Ser Cys Ala Ala Ser Gly Phe Thr Phe Ser Ser Tyr
            20                  25                  30

Ala Met Ser Trp Ile Arg Gln Thr Pro Glu Lys Arg Leu Glu Trp Val
        35                  40                  45

Ala Thr Ile Ser Ser Gly Gly Ser Phe Thr Tyr Tyr Pro Asp Ser Val
    50                  55                  60

Lys Gly Arg Phe Thr Ile Ser Arg Asp Asn Val Lys Asn Thr Leu Tyr
65                  70                  75                  80

Leu Gln Met Ser Ser Leu Arg Ser Glu Asp Thr Ala Met Tyr Tyr Cys
                85                  90                  95

Ala Arg Arg Ala Ser Thr Val Val Gly Thr Asp Phe Asp Val Trp Gly
            100                 105                 110

Ala Gly Thr Thr Val Thr Val Ser Ser
        115                 120
```

<210> SEQ ID NO 385
<211> LENGTH: 363
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 385

```
gaagtgatgc tggtggagtc tgggggaggc ttagtgaagc ctggagggtc cctgaaactc    60
tcctgtgcag cctctggatt cactttcagt agctatgcca tgtcttggat tcgccagact   120
ccggagaaga gactggagtg ggtcgcaacc atcagtagtg gtggtagttt cacctactat   180
ccagacagtg tgaaggggcg attcaccatt tctagagaca atgtcaagaa caccctgtac   240
ctgcaaatga gcagtctgag gtctgaagac acggccatgt attactgtgc aagacgggct   300
tctacggtag taggtacgga cttcgatgtc tggggcgcag gaccacggt caccgtctcc   360
tca                                                                 363
```

<210> SEQ ID NO 386
<211> LENGTH: 451
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 386

```
Glu Val Met Leu Val Glu Ser Gly Gly Gly Leu Val Lys Pro Gly Gly
1               5                   10                  15

Ser Leu Lys Leu Ser Cys Ala Ala Ser Gly Phe Thr Phe Ser Ser Tyr
            20                  25                  30

Ala Met Ser Trp Ile Arg Gln Thr Pro Glu Lys Arg Leu Glu Trp Val
        35                  40                  45
```

```
Ala Thr Ile Ser Ser Gly Gly Ser Phe Thr Tyr Tyr Pro Asp Ser Val
 50              55                  60
Lys Gly Arg Phe Thr Ile Ser Arg Asp Asn Val Lys Asn Thr Leu Tyr
 65              70                  75                  80
Leu Gln Met Ser Ser Leu Arg Ser Glu Asp Thr Ala Met Tyr Tyr Cys
                 85                  90                  95
Ala Arg Arg Ala Ser Thr Val Val Gly Thr Asp Phe Asp Val Trp Gly
                100             105                 110
Ala Gly Thr Thr Val Thr Val Ser Ala Ser Thr Lys Gly Pro Ser
                115             120             125
Val Phe Pro Leu Ala Pro Ser Ser Lys Ser Thr Ser Gly Gly Thr Ala
130             135                 140
Ala Leu Gly Cys Leu Val Lys Asp Tyr Phe Pro Cys Pro Val Thr Val
145             150                 155                 160
Ser Trp Asn Ser Gly Ala Leu Thr Ser Gly Val His Thr Phe Pro Ala
                165             170                 175
Val Leu Gln Ser Ser Gly Leu Tyr Ser Leu Ser Ser Val Val Thr Val
                180             185                 190
Pro Ser Ser Ser Leu Gly Thr Gln Thr Tyr Ile Cys Asn Val Asn His
                195             200                 205
Lys Pro Ser Asn Thr Lys Val Asp Lys Arg Val Glu Pro Lys Ser Cys
210             215                 220
Asp Lys Thr His Thr Cys Pro Pro Cys Pro Ala Pro Glu Leu Leu Gly
225             230                 235                 240
Gly Pro Ser Val Phe Leu Phe Pro Pro Lys Pro Lys Asp Thr Leu Met
                245             250                 255
Ile Ser Arg Thr Pro Glu Val Thr Cys Val Val Val Asp Val Ser His
                260             265                 270
Glu Asp Pro Glu Val Lys Phe Asn Trp Tyr Val Asp Gly Val Glu Val
                275             280                 285
His Asn Ala Lys Thr Lys Pro Arg Glu Glu Gln Tyr Asn Ser Thr Tyr
                290             295                 300
Arg Val Val Ser Val Leu Thr Val Leu His Gln Asp Trp Leu Asn Gly
305             310                 315                 320
Lys Glu Tyr Lys Cys Lys Val Ser Asn Lys Ala Leu Pro Ala Pro Ile
                325             330                 335
Glu Lys Thr Ile Ser Lys Ala Lys Gly Gln Pro Arg Glu Pro Gln Val
                340             345                 350
Tyr Thr Leu Pro Pro Ser Arg Glu Glu Met Thr Lys Asn Gln Val Ser
                355             360                 365
Leu Thr Cys Leu Val Lys Gly Phe Tyr Pro Cys Asp Ile Ala Val Glu
                370             375                 380
Trp Glu Ser Asn Gly Gln Pro Glu Asn Asn Tyr Lys Thr Thr Pro Pro
385             390                 395                 400
Val Leu Asp Ser Asp Gly Ser Phe Phe Leu Tyr Ser Lys Leu Thr Val
                405             410                 415
Asp Lys Ser Arg Trp Gln Gln Gly Asn Val Phe Ser Cys Ser Val Met
                420             425                 430
His Glu Ala Leu His Asn His Tyr Thr Gln Lys Ser Leu Ser Leu Ser
                435             440                 445
Pro Gly Lys
450
```

```
<210> SEQ ID NO 387
<211> LENGTH: 1353
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 387
gaagtgatgc tggtggagtc tgggggaggc ttagtgaagc ctggagggtc cctgaaactc      60
tcctgtgcag cctctggatt cactttcagt agctatgcca tgtcttggat tcgccagact     120
ccggagaaga gactggagtg ggtcgcaacc atcagtagtg gtggtagttt cacctactat     180
ccagacagtg tgaaggggcg attcaccatt tctagagaca atgtcaagaa caccctgtac     240
ctgcaaatga gcagtctgag gtctgaagac acggccatgt attactgtgc aagacgggct     300
tctacggtag taggtacgga cttcgatgtc tggggcgcag ggaccacggt caccgtctcc     360
tcagctagca ccaagggccc aagtgtgttt cccctggccc cagcagcaa gtctacttcc      420 ggcggaactg ctgccctggg ttgcctggtg aaggactact cccctgtcc cgtgacagtg      480 tcctggaact ctggggctct gacttccggc gtgcacacct tccccgccgt gctgcagagc     540
agcggcctgt acagcctgag cagcgtggtg acagtgccct ccagctctct gggaacccag     600
acctatatct gcaacgtgaa ccacaagccc agcaacacca aggtggacaa gagagtggag     660
cccaagagct gcgacaagac ccacacctgc ccccctgcc cagctccaga actgctggga      720
gggccttccg tgttcctgtt ccccccaag cccaaggaca ccctgatgat cagcaggacc      780
cccgaggtga cctgcgtggt ggtggacgtg tcccacgagg acccagaggt gaagttcaac     840
tggtacgtgg acggcgtgga ggtgcacaac gccaagacca gcccagaga ggagcagtac      900 aacagcacct acagggtggt gtccgtgctg accgtgctgc accaggactg gctgaacggc     960
aaagaataca agtgcaaagt ctccaacaag gccctgccag ccccaatcga aaagacaatc    1020
agcaaggcca agggccagcc acgggagccc caggtgtaca ccctgccccc agccgggag     1080 gagatgacca gaaccaggt gtccctgacc tgtctggtga agggcttcta ccctgtgat      1140 atcgccgtgg agtgggagag caacggccag cccgagaaca actacaagac ccccccca      1200 gtgctggaca gcgacggcag cttcttcctg tacagcaagc tgaccgtgga caagtccagg    1260
tggcagcagg gcaacgtgtt cagctgcagc gtgatgcacg aggccctgca caaccactac    1320
acccagaagt ccctgagcct gagccccggc aag                                 1353

<210> SEQ ID NO 388
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 388

Arg Ala Ser Gln Asp Ile Gly Ser Ser Leu Asn
1               5                   10

<210> SEQ ID NO 389
<211> LENGTH: 7
<212> TYPE: PRT
<213> ORGANISM: Artificial Sequence
<220> FEATURE:
<221> NAME/KEY: source
```

<223> OTHER INFORMATION: /note="Description of Artificial Sequence:
      Synthetic peptide"

<400> SEQUENCE: 389

Ala Thr Ser Ser Leu Asp Ser
1               5

<210> SEQ ID NO 390
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 390

Leu Gln Tyr Ala Ser Ser Pro Pro Thr
1               5

<210> SEQ ID NO 391
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 391

Arg Ala Ser Gln Asp Ile Gly Ser Ser Leu Asn
1               5                   10

<210> SEQ ID NO 392
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 392

Ala Thr Ser Ser Leu Asp Ser
1               5

<210> SEQ ID NO 393
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 393

Leu Gln Tyr Ala Ser Ser Pro Pro Thr
1               5

<210> SEQ ID NO 394
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 394

```
Ser Gln Asp Ile Gly Ser Ser
1               5
```

<210> SEQ ID NO 395
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 395

```
Ala Thr Ser
1
```

<210> SEQ ID NO 396
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 396

```
Tyr Ala Ser Ser Pro Pro
1               5
```

<210> SEQ ID NO 397
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 397

```
Gln Asp Ile Gly Ser Ser
1               5
```

<210> SEQ ID NO 398
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 398

```
Ala Thr Ser
1
```

<210> SEQ ID NO 399
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 399

```
Leu Gln Tyr Ala Ser Ser Pro Pro Thr
1               5
```

<210> SEQ ID NO 400
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 400

```
Asp Ile Gln Met Thr Gln Ser Pro Ser Ser Leu Ser Ala Ser Leu Gly
1               5                   10                  15

Glu Arg Val Ser Leu Thr Cys Arg Ala Ser Gln Asp Ile Gly Ser Ser
            20                  25                  30

Leu Asn Trp Leu Gln Gln Glu Pro Asp Gly Thr Ile Lys Arg Leu Ile
        35                  40                  45

Tyr Ala Thr Ser Ser Leu Asp Ser Gly Val Pro Lys Arg Phe Ser Gly
    50                  55                  60

Ser Arg Ser Gly Ser Asp Tyr Ser Leu Thr Ile Ser Ser Leu Glu Ser
65                  70                  75                  80

Glu Asp Phe Val Val Tyr Tyr Cys Leu Gln Tyr Ala Ser Ser Pro Pro
                85                  90                  95

Thr Phe Gly Gly Gly Thr Lys Leu Glu Ile Lys
            100                 105
```

<210> SEQ ID NO 401
<211> LENGTH: 321
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 401

```
gacatccaga tgacccagtc tccatcctcc ttatctgcct ctctgggaga aagagtcagt      60
ctcacttgtc gggcaagtca ggacattggt agtagcttaa actggcttca gcaggaacca    120
gatggaacta ttaaacgcct gatctatgcc acatccagtt tagattctgg tgtcccaaa     180
aggttcagtg gcagtaggtc tgggtcagat tattctctca ccatcagcag ccttgagtct    240
gaagattttg tagtctatta ctgtctacaa tatgctagtt cgcctccgac gttcggtgga    300
ggcaccaagc tggaaatcaa a                                              321
```

<210> SEQ ID NO 402
<211> LENGTH: 214
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 402

```
Asp Ile Gln Met Thr Gln Ser Pro Ser Ser Leu Ser Ala Ser Leu Gly
1               5                   10                  15

Glu Arg Val Ser Leu Thr Cys Arg Ala Ser Gln Asp Ile Gly Ser Ser
            20                  25                  30

Leu Asn Trp Leu Gln Gln Glu Pro Asp Gly Thr Ile Lys Arg Leu Ile
        35                  40                  45

Tyr Ala Thr Ser Ser Leu Asp Ser Gly Val Pro Lys Arg Phe Ser Gly
```

```
                50                  55                  60
Ser Arg Ser Gly Ser Asp Tyr Ser Leu Thr Ile Ser Ser Leu Glu Ser
 65                  70                  75                  80

Glu Asp Phe Val Val Tyr Tyr Cys Leu Gln Tyr Ala Ser Ser Pro Pro
                 85                  90                  95

Thr Phe Gly Gly Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 403
<211> LENGTH: 642
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 403

```
gacatccaga tgacccagtc tccatcctcc ttatctgcct ctctgggaga aagagtcagt    60
ctcacttgtc gggcaagtca ggacattggt agtagcttaa actggcttca gcaggaacca   120
gatggaacta ttaaacgcct gatctatgcc acatccagtt tagattctgg tgtcccaaa   180
aggttcagtg gcagtaggtc tgggtcagat tattctctca ccatcagcag ccttgagtct   240
gaagattttg tagtctatta ctgtctacaa tatgctagtt cgcctccgac gttcggtgga   300
ggcaccaagc tggaaatcaa acgtacggtg gccgctccca gcgtgttcat cttccccccc   360
agcgacgagc agctgaagag tggcaccgcc agcgtggtgt gcctgctgaa caacttctac   420
cccggggagg ccaaggtgca gtggaaggtg gacaacgccc tgcagagcgg caacagccag   480
gagagcgtca ccgagcagga cagcaaggac tccacctaca gcctgagcag caccctgacc   540
ctgagcaagg ccgactacga aagcataag gtgtacgcct gcgaggtgac ccaccagggc   600
ctgtccagcc ccgtgaccaa gagcttcaac aggggcgagt gc                     642
```

<210> SEQ ID NO 404
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 404

Gly Phe Thr Phe Ser Ser Tyr Ala Met Ser

```
1               5                  10
```

<210> SEQ ID NO 405
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 405

```
Thr Ile Ser Ser Gly Gly Ser Phe Thr Tyr Tyr Pro Asp Ser Val Lys
1               5                  10                  15

Gly
```

<210> SEQ ID NO 406
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 406

```
Arg Ala Ser Thr Val Val Gly Thr Asp Phe Asp Val
1               5                  10
```

<210> SEQ ID NO 407
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 407

```
Ser Tyr Ala Met Ser
1               5
```

<210> SEQ ID NO 408
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 408

```
Thr Ile Ser Ser Gly Gly Ser Phe Thr Tyr Tyr Pro Asp Ser Val Lys
1               5                  10                  15

Gly
```

<210> SEQ ID NO 409
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 409

```
Arg Ala Ser Thr Val Val Gly Thr Asp Phe Asp Val
```

-continued

```
1               5                   10

<210> SEQ ID NO 410
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 410

Gly Phe Thr Phe Ser Ser Tyr
1               5

<210> SEQ ID NO 411
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 411

Ser Ser Gly Gly Ser Phe
1               5

<210> SEQ ID NO 412
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 412

Arg Ala Ser Thr Val Val Gly Thr Asp Phe Asp Val
1               5                   10

<210> SEQ ID NO 413
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 413

Gly Phe Thr Phe Ser Ser Tyr Ala
1               5

<210> SEQ ID NO 414
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 414

Ile Ser Ser Gly Gly Ser Phe Thr
1               5

<210> SEQ ID NO 415
```

```
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 415

Ala Arg Arg Ala Ser Thr Val Val Gly Thr Asp Phe Asp Val
1               5                   10

<210> SEQ ID NO 416
<211> LENGTH: 121
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 416

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Ile Arg Gln Ala Pro Gly Lys Gly Leu Glu Trp Val
        35                  40                  45

Ala Thr Ile Ser Ser Gly Gly Ser Phe Thr Tyr Tyr Pro Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Arg Ala Ser Thr Val Val Gly Thr Asp Phe Asp Val Trp Gly
            100                 105                 110

Gln Gly Thr Thr Val Thr Val Ser Ser
        115                 120

<210> SEQ ID NO 417
<211> LENGTH: 363
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 417
gaggtgcagc tggtggaatc tggcggaggc ctggtgaaac cggcggatc cctgagactg      60 tcctgcgccg cctccggctt caccttctcc agctacgcca tgtcctggat ccggcaggct    120
cccggcaagg gcctggaatg gtggccacc atctcctccg gcggcagctt cacctactac    180
cccgacagcg tgaagggcag attcaccatc agccgggaca cgccaagaa ctccctgtac    240 ctgcagatga actccctgcg ggccgaggac accgccgtgt actactgtgc cagacgggcc    300
tccaccgtcg tgggaaccga cttcgatgtg tggggccagg gcaccaccgt gacagtgtcc    360
tcc                                                                   363

<210> SEQ ID NO 418
<211> LENGTH: 451
<212> TYPE: PRT
```

<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 418

```
Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Ile Arg Gln Ala Pro Gly Lys Gly Leu Glu Trp Val
        35                  40                  45

Ala Thr Ile Ser Ser Gly Gly Ser Phe Thr Tyr Tyr Pro Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Arg Ala Ser Thr Val Val Gly Thr Asp Phe Asp Val Trp Gly
            100                 105                 110

Gln Gly Thr Thr Val Thr Val Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Cys Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Arg Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Ala Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Ala Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser
        355                 360                 365

Leu Thr Cys Leu Val Lys Gly Phe Tyr Pro Cys Asp Ile Ala Val Glu
    370                 375                 380
```

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
            405                 410                 415

Asp Lys Ser Arg Trp Gln Gln Gly Asn Val Phe Ser Cys Ser Val Met
        420                 425                 430

His Glu Ala Leu His Asn His Tyr Thr Gln Lys Ser Leu Ser Leu Ser
    435                 440                 445

Pro Gly Lys
    450

<210> SEQ ID NO 419
<211> LENGTH: 1353
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 419

| | | | | | |
|---|---|---|---|---|---|
| gaggtgcagc | tggtggaatc | tggcggaggc | ctggtgaaac | cggcggatc | cctgagactg | 60 |
| tcctgcgccg | cctccggctt | caccttctcc | agctacgcca | tgtcctggat | ccggcaggct | 120 |
| cccggcaagg | gcctggaatg | ggtggccacc | atctcctccg | gcggcagctt | cacctactac | 180 |
| cccgacagcg | tgaagggcag | attcaccatc | agccgggaca | acgccaagaa | ctccctgtac | 240 |
| ctgcagatga | actccctgcg | ggccgaggac | accgccgtgt | actactgtgc | cagacggggc | 300 |
| tccaccgtcg | tgggaaccga | cttcgatgtg | tggggccagg | gcaccaccgt | gacagtgtcc | 360 |
| tccgctagca | ccaagggccc | aagtgtgttt | cccctggccc | cagcagcaa | gtctacttcc | 420 |
| ggcggaactg | ctgccctggg | ttgcctggtg | aaggactact | cccctgtcc | cgtgacagtg | 480 |
| tcctggaact | ctggggctct | gacttccggc | gtgcacacct | ccccgccgt | gctgcagagc | 540 |
| agcggcctgt | acagcctgag | cagcgtggtg | acagtgccct | ccagctctct | gggaacccag | 600 |
| acctatatct | gcaacgtgaa | ccacaagccc | agcaacacca | aggtggacaa | gagagtggag | 660 |
| cccaagagct | gcgacaagac | ccacacctgc | cccccctgcc | cagctccaga | actgctggga | 720 |
| gggccttccg | tgttcctgtt | cccccccaag | cccaaggaca | ccctgatgat | cagcaggacc | 780 |
| cccgaggtga | cctgcgtggt | ggtggccgtg | tcccacgagg | acccagaggt | gaagttcaac | 840 |
| tggtacgtgg | acggcgtgga | ggtgcacaac | gccaagacca | agcccagaga | ggagcagtac | 900 |
| aacagcacct | acagggtggt | gtccgtgctg | accgtgctgc | accaggactg | gctgaacggc | 960 |
| aaagaataca | agtgcaaagt | ctccaacaag | gccctggctg | ccccaatcga | aaagacaatc | 1020 |
| agcaaggcca | agggccagcc | acgggagccc | caggtgtaca | ccctgccccc | cagccgggag | 1080 |
| gagatgacca | agaaccaggt | gtccctgacc | tgtctggtga | agggcttcta | cccctgtgat | 1140 |
| atcgccgtgg | agtgggagag | caacggccag | cccgagaaca | actacaagac | cacccccca | 1200 |
| gtgctggaca | gcgacggcag | cttcttcctg | tacagcaagc | tgaccgtgga | caagtccagg | 1260 |
| tggcagcagg | gcaacgtgtt | cagctgcagc | gtgatgcacg | aggccctgca | caaccactac | 1320 |
| acccagaagt | ccctgagcct | gagccccggc | aag | | | 1353 |

<210> SEQ ID NO 420
<211> LENGTH: 11
<212> TYPE: PRT
<213> ORGANISM: Artificial Sequence

```
<220> FEATURE:
<221> NAME/KEY: source
<223> OTHER INFORMATION: /note="Description of Artificial Sequence:
      Synthetic peptide"

<400> SEQUENCE: 420

Arg Ala Ser Gln Asp Ile Gly Ser Ser Leu Asn
1               5                   10

<210> SEQ ID NO 421
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 421

Ala Thr Ser Ser Leu Asp Ser
1               5

<210> SEQ ID NO 422
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 422

Leu Gln Tyr Ala Ser Ser Pro Pro Thr
1               5

<210> SEQ ID NO 423
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 423

Arg Ala Ser Gln Asp Ile Gly Ser Ser Leu Asn
1               5                   10

<210> SEQ ID NO 424
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 424

Ala Thr Ser Ser Leu Asp Ser
1               5

<210> SEQ ID NO 425
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
```

```
<400> SEQUENCE: 425

Leu Gln Tyr Ala Ser Ser Pro Pro Thr
1               5

<210> SEQ ID NO 426
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 426

Ser Gln Asp Ile Gly Ser Ser
1               5

<210> SEQ ID NO 427
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 427

Ala Thr Ser
1

<210> SEQ ID NO 428
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 428

Tyr Ala Ser Ser Pro Pro
1               5

<210> SEQ ID NO 429
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 429

Gln Asp Ile Gly Ser Ser
1               5

<210> SEQ ID NO 430
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 430

Ala Thr Ser
```

-continued

<210> SEQ ID NO 431
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 431

Leu Gln Tyr Ala Ser Ser Pro Pro Thr
1               5

<210> SEQ ID NO 432
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 432

Asp Ile Gln Met Thr Gln Ser Pro Ser Ser Leu Ser Ala Ser Val Gly
1               5                   10                  15

Asp Arg Val Thr Leu Thr Cys Arg Ala Ser Gln Asp Ile Gly Ser Ser
            20                  25                  30

Leu Asn Trp Leu Gln Gln Lys Pro Gly Lys Ala Ile Lys Arg Leu Ile
        35                  40                  45

Tyr Ala Thr Ser Ser Leu Asp Ser Gly Val Pro Ser Arg Phe Ser Gly
    50                  55                  60

Ser Arg Ser Gly Thr Asp Tyr Thr Leu Thr Ile Ser Ser Leu Gln Pro
65                  70                  75                  80

Glu Asp Phe Val Val Tyr Tyr Cys Leu Gln Tyr Ala Ser Ser Pro Pro
                85                  90                  95

Thr Phe Gly Gly Gly Thr Lys Leu Glu Ile Lys
            100                 105

<210> SEQ ID NO 433
<211> LENGTH: 321
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 433
gacatccaga tgacccagtc ccctccagc ctgtccgcct ccgtgggcga tagagtgacc      60
ctgacctgcc gggcctccca ggacatcggc tcctccctga actggctgca gcagaagccc    120
ggcaaggcca tcaagcggct gatctacgcc acctcctccc tggactccgg cgtgccctcc    180
cggttctccg gctctagatc cggcaccgac tacaccctga ccatctccag cctgcagccc    240
gaggacttcg tggtgtacta ctgcctgcag tacgcctcca gccccccac ctttggcgga    300 ggcaccaagc tggaaatcaa g                                              321

<210> SEQ ID NO 434
<211> LENGTH: 214
<212> TYPE: PRT
<213> ORGANISM: Artificial Sequence
<220> FEATURE:
<221> NAME/KEY: source
<223> OTHER INFORMATION: /note="Description of Artificial Sequence:
    Synthetic polypeptide"

<400> SEQUENCE: 434

Asp Ile Gln Met Thr Gln Ser Pro Ser Ser Leu Ser Ala Ser Val Gly
1               5                   10                  15

Asp Arg Val Thr Leu Thr Cys Arg Ala Ser Gln Asp Ile Gly Ser Ser
            20                  25                  30

Leu Asn Trp Leu Gln Gln Lys Pro Gly Lys Ala Ile Lys Arg Leu Ile
        35                  40                  45

Tyr Ala Thr Ser Ser Leu Asp Ser Gly Val Pro Ser Arg Phe Ser Gly
    50                  55                  60

Ser Arg Ser Gly Thr Asp Tyr Thr Leu Thr Ile Ser Ser Leu Gln Pro
65                  70                  75                  80

Glu Asp Phe Val Val Tyr Tyr Cys Leu Gln Tyr Ala Ser Ser Pro Pro
                85                  90                  95

Thr Phe Gly Gly Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 435
<211> LENGTH: 642
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic polynucleotide"

<400> SEQUENCE: 435
gacatccaga tgacccagtc cccctccagc ctgtccgcct ccgtgggcga tagagtgacc    60
ctgacctgcc gggcctccca ggacatcggc tcctccctga actggctgca gcagaagccc   120
ggcaaggcca tcaagcggct gatctacgcc acctcctccc tggactccgg cgtgccctcc   180
cggttctccg gctctagatc cggcaccgac tacaccctga ccatctccag cctgcagccc   240
gaggacttcg tggtgtacta ctgcctgcag tacgcctcca gccccccac ctttggcgga    300 ggcaccaagc tggaaatcaa gcgtacggtg gccgctccca gcgtgttcat cttcccccc    360 agcgacgagc agctgaagag tggcaccgcc agcgtggtgt gcctgctgaa caacttctac   420
ccccgggagg ccaaggtgca gtggaaggtg gacaacgccc tgcagagcgg caacagccag   480
gagagcgtca ccgagcagga cagcaaggac tccacctaca gcctgagcag caccctgacc   540

```
ctgagcaagg ccgactacga gaagcataag gtgtacgcct gcgaggtgac ccaccagggc    600
ctgtccagcc ccgtgaccaa gagcttcaac aggggcgagt gc                      642
```

<210> SEQ ID NO 436
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 436

```
Gly Phe Thr Phe Ser Asn Phe Ala Met Ser
1               5                   10
```

<210> SEQ ID NO 437
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 437

```
Thr Ile Ser Thr Gly Gly Thr Tyr Thr Tyr Tyr Pro Asp Ser Val Lys
1               5                   10                  15

Gly
```

<210> SEQ ID NO 438
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 438

```
Arg Gly Tyr Asp Gly Val Asp Lys
1               5
```

<210> SEQ ID NO 439
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 439

```
Ser Asn Phe Ala Met Ser
1               5
```

<210> SEQ ID NO 440
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 440

```
Thr Ile Ser Thr Gly Gly Thr Tyr Thr Tyr Tyr Pro Asp Ser Val Lys
```

```
1               5                   10                  15

Gly

<210> SEQ ID NO 441
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 441

Arg Gly Tyr Asp Gly Val Asp Lys
1               5

<210> SEQ ID NO 442
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 442

Gly Phe Thr Phe Ser Asn Phe
1               5

<210> SEQ ID NO 443
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 443

Ser Thr Gly Gly Thr Tyr
1               5

<210> SEQ ID NO 444
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 444

Arg Gly Tyr Asp Gly Val Asp Lys
1               5

<210> SEQ ID NO 445
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 445

Gly Phe Thr Phe Ser Asn Phe Ala
1               5
```

<210> SEQ ID NO 446
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 446

Ile Ser Thr Gly Gly Thr Tyr Thr
1               5

<210> SEQ ID NO 447
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 447

Thr Arg Arg Gly Tyr Asp Gly Val Asp Lys
1               5                   10

<210> SEQ ID NO 448
<211> LENGTH: 117
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 448

Glu Val His Leu Val Glu Ser Gly Gly Gly Leu Val Lys Pro Gly Gly
1               5                   10                  15

Ser Leu Lys Leu Ser Cys Ala Ala Ser Gly Phe Thr Phe Ser Asn Phe
                20                  25                  30

Ala Met Ser Trp Val Arg Gln Thr Pro Glu Lys Arg Leu Glu Trp Val
            35                  40                  45

Ala Thr Ile Ser Thr Gly Gly Thr Tyr Thr Tyr Pro Asp Ser Val
        50                  55                  60

Lys Gly Arg Phe Thr Ile Ser Arg Asp Asn Ala Lys Lys Thr Leu Tyr
65                  70                  75                  80

Leu Gln Met Ser Ser Leu Arg Ser Glu Asp Thr Ala Met Tyr Tyr Cys
                85                  90                  95

Thr Arg Arg Gly Tyr Asp Gly Val Asp Lys Trp Gly Gln Gly Thr Thr
            100                 105                 110

Leu Thr Val Ser Ser
        115

<210> SEQ ID NO 449
<211> LENGTH: 351
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 449
gaagtgcatc tggtggagtc tgggggaggc ttagtgaagc ctggagggtc cctgaaactc      60

```
tcctgtgcag cctctggatt cactttcagt aactttgcca tgtcttgggt tcgccagact      120
ccggagaaga gactggagtg ggtcgcaacc attagtactg gtggtactta cacctactat      180
ccagacagtg tgaagggtcg attcaccatc tccagagaca atgccaagaa aaccctgtac      240
ctgcaaatga gcagtctgag gtctgaggac acggccatgt attactgtac aagacggggg      300
tacgacggcg tggacaaatg gggccaaggc accactctca cagtctcctc a               351
```

<210> SEQ ID NO 450
<211> LENGTH: 447
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 450

```
Glu Val His Leu Val Glu Ser Gly Gly Gly Leu Val Lys Pro Gly Gly
1               5                   10                  15

Ser Leu Lys Leu Ser Cys Ala Ala Ser Gly Phe Thr Phe Ser Asn Phe
            20                  25                  30

Ala Met Ser Trp Val Arg Gln Thr Pro Glu Lys Arg Leu Glu Trp Val
        35                  40                  45

Ala Thr Ile Ser Thr Gly Gly Thr Tyr Thr Tyr Tyr Pro Asp Ser Val
    50                  55                  60

Lys Gly Arg Phe Thr Ile Ser Arg Asp Asn Ala Lys Lys Thr Leu Tyr
65                  70                  75                  80

Leu Gln Met Ser Ser Leu Arg Ser Glu Asp Thr Ala Met Tyr Tyr Cys
                85                  90                  95

Thr Arg Arg Gly Tyr Asp Gly Val Asp Lys Trp Gly Gln Gly Thr Thr
            100                 105                 110

Leu Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Cys Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Arg Val Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300
```

```
Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
            325                 330                 335

Ser Lys Ala Lys Gly Gln Pro Arg Glu Pro Gln Val Tyr Thr Leu Pro
        340                 345                 350

Pro Ser Arg Glu Glu Met Thr Lys Asn Gln Val Ser Leu Thr Cys Leu
    355                 360                 365

Val Lys Gly Phe Tyr Pro Cys Asp Ile Ala Val Glu Trp Glu Ser Asn
370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
            405                 410                 415

Trp Gln Gln Gly Asn Val Phe Ser Cys Ser Val Met His Glu Ala Leu
        420                 425                 430

His Asn His Tyr Thr Gln Lys Ser Leu Ser Leu Ser Pro Gly Lys
    435                 440                 445
```

<210> SEQ ID NO 451
<211> LENGTH: 1341
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 451

```
gaagtgcatc tggtggagtc tgggggaggc ttagtgaagc ctggagggtc cctgaaactc      60
tcctgtgcag cctctggatt cactttcagt aactttgcca tgtcttgggt tcgccagact     120
ccggagaaga gactggagtg ggtcgcaacc attagtactg gtggtactta cacctactat     180
ccagacagtg tgaagggtcg attcaccatc tccagagaca atgccaagaa aaccctgtac     240
ctgcaaatga gcagtctgag gtctgaggac acggccatgt attactgtac aagacggggg     300
tacgacggcg tggacaaatg gggccaaggc accactctca cagtctcctc agctagcacc     360
aagggcccaa gtgtgtttcc cctggccccc agcagcaagt ctacttccgg cggaactgct     420
gccctgggtt gcctggtgaa ggactacttc cctgtcccg tgacagtgtc ctggaactct     480
ggggctctga cttccggcgt gcacaccttc ccgccgtgc tgcagagcag cggcctgtac     540
agcctgagca gcgtggtgac agtgccctcc agctctctgg aacccagac ctatatctgc     600
aacgtgaacc acaagcccag caacaccaag gtggacaaga gagtggagcc caagagctgc     660
gacaagaccc acacctgccc ccctgccca gctccagaac tgctgggagg gccttccgtg     720
ttcctgttcc ccccaagcc caaggacacc ctgatgatca gcaggacccc cgaggtgacc     780
tgcgtggtgg tggacgtgtc ccacgaggac ccagaggtga agttcaactg gtacgtggac     840
ggcgtggagg tgcacaacgc caagaccaag cccagagagg agcagtacaa cagcacctac     900
agggtggtgt ccgtgctgac cgtgctgcac caggactggc tgaacggcaa agaatacaag     960
tgcaaagtct ccaacaaggc cctgccagcc ccaatcgaaa agacaatcag caaggccaag    1020
ggccagccac gggagcccca ggtgtacacc ctgcccccca gccggagga gatgaccaag    1080
aaccaggtgt ccctgacctg tctggtgaag ggcttctacc ctgtgatat cgccgtggag    1140
tgggagagca acggccagcc cgagaacaac tacaagacca cccccccagt gctggacagc    1200
```

```
gacggcagct tcttcctgta cagcaagctg accgtggaca agtccaggtg gcagcagggc    1260
aacgtgttca gctgcagcgt gatgcacgag gccctgcaca accactacac ccagaagtcc    1320
ctgagcctga gccccggcaa g                                              1341
```

<210> SEQ ID NO 452
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 452

```
Lys Ser Gly Gln Ser Leu Leu Asp Ser Asp Gly Lys Thr Tyr Leu Asn
1               5                   10                  15
```

<210> SEQ ID NO 453
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 453

```
Leu Val Ser Lys Leu Asp Ser
1               5
```

<210> SEQ ID NO 454
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 454

```
Trp Gln Gly Thr His Phe Pro Gln Thr
1               5
```

<210> SEQ ID NO 455
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 455

```
Lys Ser Gly Gln Ser Leu Leu Asp Ser Asp Gly Lys Thr Tyr Leu Asn
1               5                   10                  15
```

<210> SEQ ID NO 456
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 456

```
Leu Val Ser Lys Leu Asp Ser
1               5
```

<210> SEQ ID NO 457
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 457

```
Trp Gln Gly Thr His Phe Pro Gln Thr
1               5
```

<210> SEQ ID NO 458
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 458

```
Gly Gln Ser Leu Leu Asp Ser Asp Gly Lys Thr Tyr
1               5                   10
```

<210> SEQ ID NO 459
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 459

```
Leu Val Ser
1
```

<210> SEQ ID NO 460
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 460

```
Gly Thr His Phe Pro Gln
1               5
```

<210> SEQ ID NO 461
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 461

```
Gln Ser Leu Leu Asp Ser Asp Gly Lys Thr Tyr
1               5                   10
```

```
<210> SEQ ID NO 462
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 462

Leu Val Ser
1

<210> SEQ ID NO 463
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 463

Trp Gln Gly Thr His Phe Pro Gln Thr
1               5

<210> SEQ ID NO 464
<211> LENGTH: 112
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 464

Asp Val Val Met Thr Gln Thr Pro Leu Thr Leu Ser Val Thr Ile Gly
1               5                   10                  15

Gln Pro Ala Ser Ile Ser Cys Lys Ser Gly Gln Ser Leu Leu Asp Ser
            20                  25                  30

Asp Gly Lys Thr Tyr Leu Asn Trp Phe Leu Gln Arg Pro Gly Gln Ser
        35                  40                  45

Pro Lys Arg Leu Ile Tyr Leu Val Ser Lys Leu Asp Ser Gly Val Pro
    50                  55                  60

Asp Arg Phe Thr Gly Ser Gly Ser Gly Thr Asp Phe Thr Leu Lys Ile
65                  70                  75                  80

Ser Arg Val Glu Ala Glu Asp Leu Gly Val Tyr Tyr Cys Trp Gln Gly
                85                  90                  95

Thr His Phe Pro Gln Thr Phe Gly Gly Gly Thr Lys Leu Glu Ile Lys
            100                 105                 110

<210> SEQ ID NO 465
<211> LENGTH: 336
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 465
gatgttgtga tgacccagac tccactcact ttgtcggtta ccattggaca accagcctcc      60
atctcttgca agtcaggtca gagcctctta gatagtgatg gaaagacata tttgaattgg     120
tttttacaga ggccaggcca gtctccaaag cgcctaatct atctggtgtc taaactggac     180
```

```
tctggagtcc ctgacaggtt cactggcagt ggatcaggga cagatttcac actgaaaatc    240
agcagagtgg aggctgagga tttgggagtt tattattgct ggcaaggtac acatttcct     300 cagacgttcg gtggaggcac caagctggaa atcaaa                              336
```

<210> SEQ ID NO 466
<211> LENGTH: 219
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 466

```
Asp Val Val Met Thr Gln Thr Pro Leu Thr Leu Ser Val Thr Ile Gly
1               5                   10                  15

Gln Pro Ala Ser Ile Ser Cys Lys Ser Gly Gln Ser Leu Leu Asp Ser
            20                  25                  30

Asp Gly Lys Thr Tyr Leu Asn Trp Phe Leu Gln Arg Pro Gly Gln Ser
        35                  40                  45

Pro Lys Arg Leu Ile Tyr Leu Val Ser Lys Leu Asp Ser Gly Val Pro
    50                  55                  60

Asp Arg Phe Thr Gly Ser Gly Ser Gly Thr Asp Phe Thr Leu Lys Ile
65                  70                  75                  80

Ser Arg Val Glu Ala Glu Asp Leu Gly Val Tyr Tyr Cys Trp Gln Gly
                85                  90                  95

Thr His Phe Pro Gln Thr Phe Gly Gly Gly Thr Lys Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215
```

<210> SEQ ID NO 467
<211> LENGTH: 657
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 467

```
gatgttgtga tgacccagac tccactcact ttgtcggtta ccattggaca accagcctcc    60
atctcttgca agtcaggtca gagcctctta gatagtgatg gaaagacata tttgaattgg    120
tttttacaga ggccaggcca gtctccaaag cgcctaatct atctggtgtc taaactggac    180
```

```
tctggagtcc ctgacaggtt cactggcagt ggatcaggga cagatttcac actgaaaatc    240
agcagagtgg aggctgagga tttgggagtt tattattgct ggcaaggtac acatttcct     300 cagacgttcg gtggaggcac caagctggaa atcaaacgta cggtggccgc tcccagcgtg    360
ttcatcttcc cccccagcga cgagcagctg aagagtggca ccgccagcgt ggtgtgcctg    420
ctgaacaact tctaccccg ggaggccaag gtgcagtgga aggtggacaa cgccctgcag     480
agcggcaaca gccaggagag cgtcaccgag caggacagca aggactccac ctacagcctg    540
agcagcaccc tgaccctgag caaggccgac tacgagaagc ataaggtgta cgcctgcgag    600
gtgacccacc agggcctgtc cagccccgtg accaagagct caacaggggg cgagtgc      657
```

<210> SEQ ID NO 468
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 468

Gly Phe Thr Phe Ser Asn Phe Ala Met Ser
1               5                   10

<210> SEQ ID NO 469
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 469

Thr Ile Ser Thr Gly Gly Thr Tyr Thr Tyr Tyr Pro Asp Ser Val Lys
1               5                   10                  15

Gly

<210> SEQ ID NO 470
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 470

Arg Gly Tyr Asp Gly Val Asp Lys
1               5

<210> SEQ ID NO 471
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 471

Ser Asn Phe Ala Met Ser
1               5

```
<210> SEQ ID NO 472
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 472

Thr Ile Ser Thr Gly Gly Thr Tyr Thr Tyr Tyr Pro Asp Ser Val Lys
1               5                   10                  15

Gly

<210> SEQ ID NO 473
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 473

Arg Gly Tyr Asp Gly Val Asp Lys
1               5

<210> SEQ ID NO 474
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 474

Gly Phe Thr Phe Ser Asn Phe
1               5

<210> SEQ ID NO 475
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 475

Ser Thr Gly Gly Thr Tyr
1               5

<210> SEQ ID NO 476
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 476

Arg Gly Tyr Asp Gly Val Asp Lys
1               5

<210> SEQ ID NO 477
<211> LENGTH: 8
```

-continued

```
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 477

Gly Phe Thr Phe Ser Asn Phe Ala
1               5

<210> SEQ ID NO 478
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 478

Ile Ser Thr Gly Gly Thr Tyr Thr
1               5

<210> SEQ ID NO 479
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 479

Thr Arg Arg Gly Tyr Asp Gly Val Asp Lys
1               5                   10

<210> SEQ ID NO 480
<211> LENGTH: 117
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 480

Glu Val His Leu Val Glu Ser Gly Gly Gly Leu Val Lys Pro Gly Gly
1               5                   10                  15

Ser Leu Lys Leu Ser Cys Ala Ala Ser Gly Phe Thr Phe Ser Asn Phe
            20                  25                  30

Ala Met Ser Trp Val Arg Gln Thr Pro Glu Lys Arg Leu Glu Trp Val
        35                  40                  45

Ala Thr Ile Ser Thr Gly Gly Thr Tyr Thr Tyr Pro Asp Ser Val
    50                  55                  60

Lys Gly Arg Phe Thr Ile Ser Arg Asp Asn Ala Lys Lys Thr Leu Tyr
65                  70                  75                  80

Leu Gln Met Ser Ser Leu Arg Ser Glu Asp Thr Ala Met Tyr Tyr Cys
                85                  90                  95

Thr Arg Arg Gly Tyr Asp Gly Val Asp Lys Trp Gly Gln Gly Thr Thr
            100                 105                 110

Leu Thr Val Ser Ser
        115
```

<210> SEQ ID NO 481
<211> LENGTH: 351
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 481

```
gaagtgcatc tggtggagtc tgggggaggc ttagtgaagc ctggagggtc cctgaaactc      60
tcctgtgcag cctctggatt cactttcagt aactttgcca tgtcttgggt tcgccagact     120
ccggagaaga gactggagtg gtcgcaacc attagtactg gtggtactta cacctactat      180
ccagacagtg tgaagggtcg attcaccatc tccagagaca atgccaagaa aaccctgtac     240
ctgcaaatga gcagtctgag gtctgaggac acggccatgt attactgtac aagacggggg     300
tacgacggcg tggacaaatg gggccaaggc accactctca cagtctcctc a              351
```

<210> SEQ ID NO 482
<211> LENGTH: 447
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 482

```
Glu Val His Leu Val Glu Ser Gly Gly Gly Leu Val Lys Pro Gly Gly
1               5                   10                  15

Ser Leu Lys Leu Ser Cys Ala Ala Ser Gly Phe Thr Phe Ser Asn Phe
            20                  25                  30

Ala Met Ser Trp Val Arg Gln Thr Pro Glu Lys Arg Leu Glu Trp Val
        35                  40                  45

Ala Thr Ile Ser Thr Gly Gly Thr Tyr Thr Tyr Tyr Pro Asp Ser Val
    50                  55                  60

Lys Gly Arg Phe Thr Ile Ser Arg Asp Asn Ala Lys Lys Thr Leu Tyr
65                  70                  75                  80

Leu Gln Met Ser Ser Leu Arg Ser Glu Asp Thr Ala Met Tyr Tyr Cys
                85                  90                  95

Thr Arg Arg Gly Tyr Asp Gly Val Asp Lys Trp Gly Gln Gly Thr Thr
            100                 105                 110

Leu Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Cys Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Arg Val Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240
```

```
Phe Leu Phe Pro Pro Lys Pro Lys Asp Thr Leu Met Ile Ser Arg Thr
                245                 250                 255

Pro Glu Val Thr Cys Val Val Val Ala Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Ala Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
        355                 360                 365

Val Lys Gly Phe Tyr Pro Cys Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
        435                 440                 445
```

<210> SEQ ID NO 483
<211> LENGTH: 1341
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 483

```
gaagtgcatc tggtggagtc tgggggaggc ttagtgaagc ctggagggtc cctgaaactc      60
tcctgtgcag cctctggatt cactttcagt aactttgcca tgtcttgggt tcgccagact     120
ccggagaaga gactggagtg ggtcgcaacc attagtactg gtggtactta cacctactat     180
ccagacagtg tgaagggtcg attcaccatc tccagagaca atgccaagaa aaccctgtac     240
ctgcaaatga gcagtctgag gtctgaggac acggccatgt attactgtac aagacggggg     300
tacgacggcg tggacaaatg gggccaaggc accactctca cagtctcctc agctagcacc     360
aagggcccaa gtgtgtttcc cctggccccc agcagcaagt ctacttccgg cggaactgct     420
gccctgggtt gcctggtgaa ggactacttc cctgtcccg tgacagtgtc ctggaactct     480
ggggctctga cttccggcgt gcacaccttc ccgccgtgc tgcagagcag cggcctgtac     540
agcctgagca gcgtggtgac agtgccctcc agctctctgg aacccagac ctatatctgc     600 aacgtgaacc acaagcccag caacaccaag gtggacaaga gagtggagcc caagagctgc     660
gacaagaccc acacctgccc ccctgccca gctccagaac tgctgggagg gccttccgtg     720
ttcctgttcc cccccaagcc caaggacacc ctgatgatca gcaggacccc cgaggtgacc     780
tgcgtggtgg tggccgtgtc ccacgaggac ccagaggtga agttcaactg gtacgtggac     840
```

-continued

```
ggcgtggagg tgcacaacgc aagaccaag cccagagagg agcagtacaa cagcacctac    900
agggtggtgt ccgtgctgac cgtgctgcac caggactggc tgaacggcaa agaatacaag    960
tgcaaagtct ccaacaaggc cctggctgcc ccaatcgaaa agacaatcag caaggccaag   1020
ggccagccac gggagcccca ggtgtacacc ctgcccccca gccgggagga gatgaccaag   1080
aaccaggtgt ccctgacctg tctggtgaag ggcttctacc cctgtgatat cgccgtggag   1140
tgggagagca acggccagcc cgagaacaac tacaagacca cccccccagt gctggacagc   1200
gacggcagct tcttcctgta cagcaagctg accgtggaca agtccaggtg gcagcagggc   1260
aacgtgttca gctgcagcgt gatgcacgag gccctgcaca accactacac ccagaagtcc   1320
ctgagcctga gccccggcaa g                                            1341
```

<210> SEQ ID NO 484
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 484

Lys Ser Gly Gln Ser Leu Leu Asp Ser Asp Gly Lys Thr Tyr Leu Asn
1               5                   10                  15

<210> SEQ ID NO 485
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 485

Leu Val Ser Lys Leu Asp Ser
1               5

<210> SEQ ID NO 486
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 486

Trp Gln Gly Thr His Phe Pro Gln Thr
1               5

<210> SEQ ID NO 487
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 487

Lys Ser Gly Gln Ser Leu Leu Asp Ser Asp Gly Lys Thr Tyr Leu Asn
1               5                   10                  15

-continued

```
<210> SEQ ID NO 488
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 488

Leu Val Ser Lys Leu Asp Ser
1               5

<210> SEQ ID NO 489
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 489

Trp Gln Gly Thr His Phe Pro Gln Thr
1               5

<210> SEQ ID NO 490
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 490

Gly Gln Ser Leu Leu Asp Ser Asp Gly Lys Thr Tyr
1               5                   10

<210> SEQ ID NO 491
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 491

Leu Val Ser
1

<210> SEQ ID NO 492
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 492

Gly Thr His Phe Pro Gln
1               5

<210> SEQ ID NO 493
<211> LENGTH: 11
<212> TYPE: PRT
```

```
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 493

Gln Ser Leu Leu Asp Ser Asp Gly Lys Thr Tyr
1               5                   10

<210> SEQ ID NO 494
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 494

Leu Val Ser
1

<210> SEQ ID NO 495
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 495

Trp Gln Gly Thr His Phe Pro Gln Thr
1               5

<210> SEQ ID NO 496
<211> LENGTH: 112
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 496

Asp Val Val Met Thr Gln Thr Pro Leu Thr Leu Ser Val Thr Ile Gly
1               5                   10                  15

Gln Pro Ala Ser Ile Ser Cys Lys Ser Gly Gln Ser Leu Leu Asp Ser
            20                  25                  30

Asp Gly Lys Thr Tyr Leu Asn Trp Phe Leu Gln Arg Pro Gly Gln Ser
        35                  40                  45

Pro Lys Arg Leu Ile Tyr Leu Val Ser Lys Leu Asp Ser Gly Val Pro
    50                  55                  60

Asp Arg Phe Thr Gly Ser Gly Ser Gly Thr Asp Phe Thr Leu Lys Ile
65                  70                  75                  80

Ser Arg Val Glu Ala Glu Asp Leu Gly Val Tyr Tyr Cys Trp Gln Gly
                85                  90                  95

Thr His Phe Pro Gln Thr Phe Gly Gly Gly Thr Lys Leu Glu Ile Lys
            100                 105                 110

<210> SEQ ID NO 497
<211> LENGTH: 336
<212> TYPE: DNA
<213> ORGANISM: Artificial Sequence
```

<220> FEATURE:
<221> NAME/KEY: source
<223> OTHER INFORMATION: /note="Description of Artificial Sequence:
      Synthetic polynucleotide"

<400> SEQUENCE: 497

```
gatgttgtga tgacccagac tccactcact ttgtcggtta ccattggaca accagcctcc    60
atctcttgca agtcaggtca gagcctctta gatagtgatg gaaagacata tttgaattgg   120
tttttacaga ggccaggcca gtctccaaag cgcctaatct atctggtgtc taaactggac   180
tctggagtcc ctgacaggtt cactggcagt ggatcaggga cagatttcac actgaaaatc   240
agcagagtgg aggctgagga tttgggagtt tattattgct ggcaaggtac acatttcct    300 cagacgttcg gtggaggcac caagctggaa atcaaa                             336
```

<210> SEQ ID NO 498
<211> LENGTH: 219
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 498

```
Asp Val Val Met Thr Gln Thr Pro Leu Thr Leu Ser Val Thr Ile Gly
1               5                   10                  15

Gln Pro Ala Ser Ile Ser Cys Lys Ser Gly Gln Ser Leu Leu Asp Ser
            20                  25                  30

Asp Gly Lys Thr Tyr Leu Asn Trp Phe Leu Gln Arg Pro Gly Gln Ser
        35                  40                  45

Pro Lys Arg Leu Ile Tyr Leu Val Ser Lys Leu Asp Ser Gly Val Pro
    50                  55                  60

Asp Arg Phe Thr Gly Ser Gly Ser Gly Thr Asp Phe Thr Leu Lys Ile
65                  70                  75                  80

Ser Arg Val Glu Ala Glu Asp Leu Gly Val Tyr Tyr Cys Trp Gln Gly
                85                  90                  95

Thr His Phe Pro Gln Thr Phe Gly Gly Gly Thr Lys Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215
```

<210> SEQ ID NO 499
<211> LENGTH: 657
<212> TYPE: DNA
<213> ORGANISM: Artificial Sequence
<220> FEATURE:

<221> NAME/KEY: source
<223> OTHER INFORMATION: /note="Description of Artificial Sequence: Synthetic polynucleotide"

<400> SEQUENCE: 499

```
gatgttgtga tgacccagac tccactcact ttgtcggtta ccattggaca accagcctcc    60
atctcttgca agtcaggtca gagcctctta gatagtgatg gaaagacata tttgaattgg   120
tttttacaga ggccaggcca gtctccaaag cgcctaatct atctggtgtc taaactggac   180
tctggagtcc ctgacaggtt cactggcagt ggatcaggga cagatttcac actgaaaatc   240
agcagagtgg aggctgagga tttgggagtt tattattgct ggcaaggtac acattttcct   300
cagacgttcg gtggaggcac caagctggaa atcaaacgta cggtggccgc tcccagcgtg   360
ttcatcttcc cccccagcga cgagcagctg aagagtggca ccgccagcgt ggtgtgcctg   420
ctgaacaact ctaccccccg ggaggccaag gtgcagtgga aggtggacaa cgccctgcag   480
agcggcaaca gccaggagag cgtcaccgag caggacagca aggactccac ctacagcctg   540
agcagcaccc tgaccctgag caaggccgac tacgagaagc ataaggtgta cgcctgcgag   600
gtgacccacc agggcctgtc cagccccgtg accaagagct tcaacagggg cgagtgc     657
```

<210> SEQ ID NO 500
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 500

Gly Tyr Ser Ile Thr Ser Gly Tyr Ser Trp His
1               5                   10

<210> SEQ ID NO 501
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 501

His Ile His Ser Ser Gly Ser Thr Asn Tyr Asn Pro Ser Leu Lys Ser
1               5                   10                  15

<210> SEQ ID NO 502
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 502

Gly Gly Val Gln Ala Phe Ala Tyr
1               5

<210> SEQ ID NO 503
<211> LENGTH: 6
<212> TYPE: PRT
<213> ORGANISM: Artificial Sequence
<220> FEATURE:

-continued

```
<221> NAME/KEY: source
<223> OTHER INFORMATION: /note="Description of Artificial Sequence:
      Synthetic peptide"

<400> SEQUENCE: 503

Ser Gly Tyr Ser Trp His
1               5

<210> SEQ ID NO 504
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 504

His Ile His Ser Ser Gly Ser Thr Asn Tyr Asn Pro Ser Leu Lys Ser
1               5                   10                  15

<210> SEQ ID NO 505
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 505

Gly Gly Val Gln Ala Phe Ala Tyr
1               5

<210> SEQ ID NO 506
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 506

Gly Tyr Ser Ile Thr Ser Gly Tyr
1               5

<210> SEQ ID NO 507
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 507

His Ser Ser Gly Ser
1               5

<210> SEQ ID NO 508
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
```

-continued

```
<400> SEQUENCE: 508

Gly Gly Val Gln Ala Phe Ala Tyr
1               5

<210> SEQ ID NO 509
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 509

Gly Tyr Ser Ile Thr Ser Gly Tyr Ser
1               5

<210> SEQ ID NO 510
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 510

Ile His Ser Ser Gly Ser Thr
1               5

<210> SEQ ID NO 511
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 511

Ala Arg Gly Gly Val Gln Ala Phe Ala Tyr
1               5                   10

<210> SEQ ID NO 512
<211> LENGTH: 117
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 512

Asp Val Gln Leu Gln Glu Ser Gly Pro Gly Leu Val Lys Pro Ser Gln
1               5                   10                  15

Thr Leu Ser Leu Thr Cys Thr Val Ser Gly Tyr Ser Ile Thr Ser Gly
            20                  25                  30

Tyr Ser Trp His Trp Ile Arg Gln His Pro Gly Lys Gly Leu Glu Trp
        35                  40                  45

Met Ala His Ile His Ser Ser Gly Ser Thr Asn Tyr Asn Pro Ser Leu
    50                  55                  60

Lys Ser Arg Ile Thr Ile Ser Arg Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95
```

```
Ala Arg Gly Gly Val Gln Ala Phe Ala Tyr Trp Gly Gln Gly Thr Leu
            100                 105                 110

Val Thr Val Ser Ser
        115
```

<210> SEQ ID NO 513
<211> LENGTH: 351
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 513

```
gacgtgcagc tgcaggaatc tggccctggc ctggtgaaac cctcccagac cctgtccctg      60
acctgcaccg tgtccggcta ctccatcacc tccggctaca gctggcactg gatccggcag     120
caccccggca agggcctgga atggatggcc cacatccact cctccggctc caccaactac     180
aaccccagcc tgaagtccag aatcaccatc agccgggaca cctccaagaa ccagttctcc     240
ctgaagctgt cctccgtgac cgccgctgac accgccgtgt actactgtgc cagaggcggc     300
gtgcaggcct tcgcttattg gggccagggc accctggtga cagtgtcctc c              351
```

<210> SEQ ID NO 514
<211> LENGTH: 447
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 514

```
Asp Val Gln Leu Gln Glu Ser Gly Pro Gly Leu Val Lys Pro Ser Gln
1               5                   10                  15

Thr Leu Ser Leu Thr Cys Thr Val Ser Gly Tyr Ser Ile Thr Ser Gly
            20                  25                  30

Tyr Ser Trp His Trp Ile Arg Gln His Pro Gly Lys Gly Leu Glu Trp
        35                  40                  45

Met Ala His Ile His Ser Ser Gly Ser Thr Asn Tyr Asn Pro Ser Leu
    50                  55                  60

Lys Ser Arg Ile Thr Ile Ser Arg Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Gly Gly Val Gln Ala Phe Ala Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190
```

Leu Gly Thr Gln Thr Tyr Ile Cys Asn Val Asn His Lys Pro Ser Asn
        195                 200                 205

Thr Lys Val Asp Lys Arg Val Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Ala Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Ala Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
        435                 440                 445

<210> SEQ ID NO 515
<211> LENGTH: 1341
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 515
gacgtgcagc tgcaggaatc tggccctggc ctggtgaaac cctcccagac cctgtccctg    60
acctgcaccg tgtccggcta ctccatcacc tccggctaca gctggcactg gatccggcag   120
cacccgggca agggcctgga atggatggcc cacatccact cctccggctc caccaactac   180
aaccccagcc tgaagtccag aatcaccatc agccgggaca cctccaagaa ccagttctcc   240
ctgaagctgt cctccgtgac cgccgctgac accgccgtgt actactgtgc cagaggcggc   300
gtgcaggcct cgcttattg gggccagggc accctggtga cagtgtcctc cgctagcacc   360
aagggcccaa gtgtgtttcc cctggccccc agcagcaagt ctacttccgg cggaactgct   420
gccctgggtt gcctggtgaa ggactacttc cccgagcccg tgacagtgtc ctggaactct   480
ggggctctga cttccggcgt gcacaccttc cccgccgtgc tgcagagcag cggcctgtac   540
agcctgagca gcgtggtgac agtgccctcc agctctctgg gaacccagac ctatatctgc   600

```
aacgtgaacc acaagcccag caacaccaag gtggacaaga gagtggagcc caagagctgc    660
gacaagaccc acacctgccc ccctgccca gctccagaac tgctgggagg ccttccgtg      720 ttcctgttcc cccccaagcc caaggacacc ctgatgatca gcaggacccc cgaggtgacc    780
tgcgtggtgg tggccgtgtc ccacgaggac ccagaggtga agttcaactg gtacgtggac    840
ggcgtggagg tgcacaacgc caagaccaag cccagagagg agcagtacaa cagcacctac    900
agggtggtgt ccgtgctgac cgtgctgcac caggactggc tgaacggcaa agaatacaag    960
tgcaaagtct ccaacaaggc cctggctgcc ccaatcgaaa agacaatcag caaggccaag   1020
ggccagccac gggagcccca ggtgtacacc ctgccccca gccggaggga gatgaccaag    1080
aaccaggtgt ccctgacctg tctggtgaag ggcttctacc ccagcgatat cgccgtggag   1140
tgggagagca acggccagcc cgagaacaac tacaagacca cccccccagt gctggacagc   1200
gacggcagct tcttcctgta cagcaagctg accgtggaca agtccaggtg gcagcagggc   1260
aacgtgttca gctgcagcgt gatgcacgag gccctgcaca accactacac ccagaagtcc   1320
ctgagcctga gccccggcaa g                                             1341
```

<210> SEQ ID NO 516
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 516

Ser Ala Ser Ser Ser Val Ile Tyr Met His
1               5                   10

<210> SEQ ID NO 517
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 517

Asp Thr Ser Lys Leu Ala Ser
1               5

<210> SEQ ID NO 518
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 518

Gln Gln Trp Ser Ser Asn Pro Leu Thr
1               5

<210> SEQ ID NO 519
<211> LENGTH: 10
<212> TYPE: PRT
<213> ORGANISM: Artificial Sequence
<220> FEATURE:
<221> NAME/KEY: source

```
<223> OTHER INFORMATION: /note="Description of Artificial Sequence:
      Synthetic peptide"

<400> SEQUENCE: 519

Ser Ala Ser Ser Ser Val Ile Tyr Met His
1               5                   10

<210> SEQ ID NO 520
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 520

Asp Thr Ser Lys Leu Ala Ser
1               5

<210> SEQ ID NO 521
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 521

Gln Gln Trp Ser Ser Asn Pro Leu Thr
1               5

<210> SEQ ID NO 522
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 522

Ser Ser Ser Val Ile Tyr
1               5

<210> SEQ ID NO 523
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 523

Asp Thr Ser
1

<210> SEQ ID NO 524
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 524
```

```
Trp Ser Ser Asn Pro Leu
1               5

<210> SEQ ID NO 525
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 525

Ser Ser Val Ile Tyr
1               5

<210> SEQ ID NO 526
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 526

Asp Thr Ser
1

<210> SEQ ID NO 527
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 527

Gln Gln Trp Ser Ser Asn Pro Leu Thr
1               5

<210> SEQ ID NO 528
<211> LENGTH: 106
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 528

Glu Ile Val Leu Thr Gln Ser Pro Ala Thr Leu Ser Ala Ser Pro Gly
1               5                   10                  15

Glu Arg Val Thr Met Ser Cys Ser Ala Ser Ser Val Ile Tyr Met
            20                  25                  30

His Trp Tyr Gln Gln Lys Pro Gly Gln Ala Pro Arg Arg Trp Ile Tyr
                35                  40                  45

Asp Thr Ser Lys Leu Ala Ser Gly Val Pro Ala Arg Phe Ser Gly Ser
        50                  55                  60

Gly Ser Gly Thr Asp Tyr Thr Leu Thr Ile Ser Ser Met Glu Pro Glu
65                  70                  75                  80

Asp Ala Ala Val Tyr Tyr Cys Gln Gln Trp Ser Ser Asn Pro Leu Thr
                85                  90                  95
```

Phe Gly Gln Gly Thr Lys Leu Glu Ile Lys
            100                 105

<210> SEQ ID NO 529
<211> LENGTH: 318
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 529
gagatcgtgc tgacccagtc ccctgccacc ctgtctgcta gccctggcga gcgcgtgaca      60
atgtcctgct ccgcctcctc ctccgtgatc tacatgcact ggtatcagca gaagcccggc     120
caggcccctc ggcggtggat ctacgatacc tccaagctgg cctccggcgt gcccgccaga     180
ttctccggct ctggctctgg caccgactac accctgacca tctccagcat ggaacccgag     240
gacgccgccg tgtactactg ccagcagtgg tcctccaacc ccctgacctt cggccagggc     300
accaagctgg aaatcaag                                                    318

<210> SEQ ID NO 530
<211> LENGTH: 213
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 530

Glu Ile Val Leu Thr Gln Ser Pro Ala Thr Leu Ser Ala Ser Pro Gly
1               5                   10                  15

Glu Arg Val Thr Met Ser Cys Ser Ala Ser Ser Ser Val Ile Tyr Met
            20                  25                  30

His Trp Tyr Gln Gln Lys Pro Gly Gln Ala Pro Arg Arg Trp Ile Tyr
        35                  40                  45

Asp Thr Ser Lys Leu Ala Ser Gly Val Pro Ala Arg Phe Ser Gly Ser
    50                  55                  60

Gly Ser Gly Thr Asp Tyr Thr Leu Thr Ile Ser Ser Met Glu Pro Glu
65                  70                  75                  80

Asp Ala Ala Val Tyr Tyr Cys Gln Gln Trp Ser Ser Asn Pro Leu Thr
                85                  90                  95

Phe Gly Gln Gly Thr Lys Leu Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys

<210> SEQ ID NO 531
<211> LENGTH: 639
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 531

```
gagatcgtgc tgacccagtc ccctgccacc ctgtctgcta gccctggcga gcgcgtgaca    60
atgtcctgct ccgcctcctc ctccgtgatc tacatgcact ggtatcagca gaagcccggc   120
caggcccctc ggcggtggat ctacgatacc tccaagctgg cctccggcgt gcccgccaga   180
ttctccggct ctggctctgg caccgactac accctgacca tctccagcat ggaacccgag   240
gacgccgccg tgtactactg ccagcagtgg tcctccaacc ccctgacctt cggccagggc   300
accaagctgg aaatcaagcg tacggtggcc gctcccagcg tgttcatctt cccccccagc   360
gacgagcagc tgaagagtgg caccgccagc gtggtgtgcc tgctgaacaa cttctacccc   420
cgggaggcca aggtgcagtg gaaggtggac aacgccctgc agagcggcaa cagccaggag   480
agcgtcaccg agcaggacag caaggactcc acctacagcc tgagcagcac cctgaccctg   540
agcaaggcca actacgagaa gcataaggtg tacgcctgcg aggtgaccca ccagggcctg   600
tccagccccg tgaccaagag cttcaacagg ggcgagtgc                          639
```

<210> SEQ ID NO 532
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 532

Gly Phe Thr Phe Ser Thr Tyr Ala Met Ser
1               5                   10

<210> SEQ ID NO 533
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 533

Thr Ile Ser Asp Ala Gly Ser Tyr Ser Tyr Tyr Pro Asp Asn Val Lys
1               5                   10                  15

Gly

<210> SEQ ID NO 534
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 534

```
Arg Gly Ser Arg Tyr Glu Glu Tyr Tyr Val Met Asp Tyr
1               5                   10
```

<210> SEQ ID NO 535
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 535

```
Thr Tyr Ala Met Ser
1               5
```

<210> SEQ ID NO 536
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 536

```
Thr Ile Ser Asp Ala Gly Ser Tyr Ser Tyr Tyr Pro Asp Asn Val Lys
1               5                   10                  15

Gly
```

<210> SEQ ID NO 537
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 537

```
Arg Gly Ser Arg Tyr Glu Glu Tyr Tyr Val Met Asp Tyr
1               5                   10
```

<210> SEQ ID NO 538
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 538

```
Gly Phe Thr Phe Ser Thr Tyr
1               5
```

<210> SEQ ID NO 539
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 539

```
Ser Asp Ala Gly Ser Tyr
```

```
<210> SEQ ID NO 540
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 540

Arg Gly Ser Arg Tyr Glu Glu Tyr Tyr Val Met Asp Tyr
1               5                   10

<210> SEQ ID NO 541
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 541

Gly Phe Thr Phe Ser Thr Tyr Ala
1               5

<210> SEQ ID NO 542
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 542

Ile Ser Asp Ala Gly Ser Tyr Ser
1               5

<210> SEQ ID NO 543
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 543

Ala Arg Arg Gly Ser Arg Tyr Glu Glu Tyr Tyr Val Met Asp Tyr
1               5                   10                  15

<210> SEQ ID NO 544
<211> LENGTH: 122
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 544

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Thr Tyr
            20                  25                  30
```

Ala Met Ser Trp Val Arg Gln Ala Pro Gly Lys Gly Leu Glu Trp Val
         35                  40                  45

Ala Thr Ile Ser Asp Ala Gly Ser Tyr Ser Tyr Tyr Pro Asp Asn Val
     50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Arg Arg Gly Ser Arg Tyr Glu Tyr Tyr Val Met Asp Tyr Trp
             100                 105                 110

Gly Gln Gly Thr Thr Val Thr Val Ser Ser
            115                 120

<210> SEQ ID NO 545
<211> LENGTH: 366
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 545
gaggtgcagc tggtggaatc tggcggaggc ctggtgaaac cggcggatc cctgagactg      60 tcctgcgccg cctccggctt caccttctcc acctacgcca tgtcctgggt gcggcaggct    120
cccggcaagg gcctggaatg gtggccacc atctccgacg ccggctccta ctcctactac     180
cccgacaacg tgaagggcag attcaccatc agccgggaca cgccaagaa ctccctgtac     240 ctgcagatga actccctgcg ggccgaggac accgccgtgt actactgtgc cagacggggc    300
tccagatacg aagagtacta cgtgatggac tattggggcc agggcaccac cgtgacagtg    360
tcctcc                                                               366

<210> SEQ ID NO 546
<211> LENGTH: 452
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 546

Glu Val Gln Leu Val Glu Ser Gly Gly Gly Leu Val Lys Pro Gly Gly
 1               5                  10                  15

Ser Leu Arg Leu Ser Cys Ala Ala Ser Gly Phe Thr Phe Ser Thr Tyr
             20                  25                  30

Ala Met Ser Trp Val Arg Gln Ala Pro Gly Lys Gly Leu Glu Trp Val
         35                  40                  45

Ala Thr Ile Ser Asp Ala Gly Ser Tyr Ser Tyr Tyr Pro Asp Asn Val
     50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Arg Arg Gly Ser Arg Tyr Glu Glu Tyr Tyr Val Met Asp Tyr Trp
             100                 105                 110

Gly Gln Gly Thr Thr Val Thr Val Ser Ser Ala Ser Thr Lys Gly Pro

```
            115                 120                 125
Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Arg Val Glu Pro Lys Ser
    210                 215                 220

Cys Asp Lys Thr His Thr Cys Pro Pro Cys Pro Ala Pro Glu Leu Leu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Ala Val Ser
            260                 265                 270

His Glu Asp Pro Glu Val Lys Phe Asn Trp Tyr Val Asp Gly Val Glu
        275                 280                 285

Val His Asn Ala Lys Thr Lys Pro Arg Glu Glu Gln Tyr Asn Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Ala Ala Pro
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Arg Glu Glu Met Thr Lys Asn Gln Val
        355                 360                 365

Ser Leu Thr Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
                405                 410                 415

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
        435                 440                 445

Ser Pro Gly Lys
    450

<210> SEQ ID NO 547
<211> LENGTH: 1356
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 547
gaggtgcagc tggtggaatc tggcggaggc ctggtgaaac ccggcggatc cctgagactg    60
```

```
tcctgcgccg cctccggctt caccttctcc acctacgcca tgtcctgggt gcggcaggct    120
cccggcaagg gcctggaatg ggtggccacc atctccgacg ccggctccta ctcctactac    180
cccgacaacg tgaagggcag attcaccatc agccgggaca acgccaagaa ctccctgtac    240
ctgcagatga actccctgcg ggccgaggac accgccgtgt actactgtgc cagacggggc    300
tccagatacg aagagtacta cgtgatggac tattggggcc agggcaccac cgtgacagtg    360
tcctccgcta gcaccaaggg cccaagtgtg tttcccctgg cccccagcag caagtctact    420
tccggcggaa ctgctgccct gggttgcctg gtgaaggact acttccccga gcccgtgaca    480
gtgtcctgga actctggggc tctgacttcc ggcgtgcaca ccttccccgc cgtgctgcag    540
agcagcggcc tgtacagcct gagcagcgtg gtgacagtgc cctccagctc tctgggaacc    600
cagacctata tctgcaacgt gaaccacaag cccagcaaca ccaaggtgga caagagagtg    660
gagcccaaga gctgcgacaa gacccacacc tgccccccct gcccagctcc agaactgctg    720
ggagggcctt ccgtgttcct gttccccccc aagcccaagg acaccctgat gatcagcagg    780
acccccgagg tgacctgcgt ggtggtggcc gtgtcccacg aggacccaga ggtgaagttc    840
aactggtacg tggacggcgt ggaggtgcac aacgccaaga ccaagcccag agaggagcag    900
tacaacagca cctacagggt ggtgtccgtg ctgaccgtgc tgcaccagga ctggctgaac    960
ggcaaagaat acaagtgcaa agtctccaac aaggccctgg ctgccccaat cgaaaagaca   1020
atcagcaagg ccaagggcca gccacgggag ccccaggtgt acaccctgcc ccccagccgg   1080
gaggagatga ccaagaacca ggtgtccctg acctgtctgg tgaagggctt ctaccccagc   1140
gatatcgccg tggagtggga gagcaacggc cagcccgaga caactacaa gaccacccc    1200 ccagtgctgg acagcgacgg cagcttcttc ctgtacagca agctgaccgt ggacaagtcc   1260
aggtggcagc agggcaacgt gttcagctgc agcgtgatgc acgaggccct gcacaaccac   1320
tacacccaga gtccctgag cctgagcccc ggcaag                              1356
```

<210> SEQ ID NO 548
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 548

Arg Ala Ser Gln Ser Ile Ser Asn Asn Leu His
1               5                   10

<210> SEQ ID NO 549
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 549

Tyr Ala Ser Gln Ser Ile Ser
1               5

<210> SEQ ID NO 550
<211> LENGTH: 8
<212> TYPE: PRT
<213> ORGANISM: Artificial Sequence

```
<220> FEATURE:
<221> NAME/KEY: source
<223> OTHER INFORMATION: /note="Description of Artificial Sequence:
      Synthetic peptide"

<400> SEQUENCE: 550

Gln Gln Ser Ser Ser Trp Leu Thr
1               5

<210> SEQ ID NO 551
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 551

Arg Ala Ser Gln Ser Ile Ser Asn Asn Leu His
1               5                   10

<210> SEQ ID NO 552
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 552

Tyr Ala Ser Gln Ser Ile Ser
1               5

<210> SEQ ID NO 553
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 553

Gln Gln Ser Ser Ser Trp Leu Thr
1               5

<210> SEQ ID NO 554
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 554

Ser Gln Ser Ile Ser Asn Asn
1               5

<210> SEQ ID NO 555
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
```

```
<400> SEQUENCE: 555

Tyr Ala Ser
1

<210> SEQ ID NO 556
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 556

Ser Ser Ser Trp Leu
1               5

<210> SEQ ID NO 557
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 557

Gln Ser Ile Ser Asn Asn
1               5

<210> SEQ ID NO 558
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 558

Tyr Ala Ser
1

<210> SEQ ID NO 559
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 559

Gln Gln Ser Ser Ser Trp Leu Thr
1               5

<210> SEQ ID NO 560
<211> LENGTH: 106
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 560

Glu Ile Val Leu Thr Gln Ser Pro Ala Thr Leu Ser Val Ser Pro Gly
```

```
               1               5              10              15
            Glu Arg Val Thr Leu Ser Cys Arg Ala Ser Gln Ser Ile Ser Asn Asn
                            20                  25                  30

Leu His Trp Tyr Gln Gln Lys Pro Gly Gln Ala Pro Arg Leu Leu Ile
                        35                  40                  45

Lys Tyr Ala Ser Gln Ser Ile Ser Gly Ile Pro Ala Arg Phe Ser Gly
                    50                  55                  60

Ser Gly Ser Gly Thr Asp Phe Thr Leu Thr Ile Ser Ser Val Glu Pro
            65                  70                  75                  80

Glu Asp Phe Gly Val Tyr Phe Cys Gln Gln Ser Ser Ser Trp Leu Thr
                                85                  90                  95

Phe Gly Gln Gly Thr Lys Leu Glu Ile Lys
                            100                 105
```

<210> SEQ ID NO 561
<211> LENGTH: 318
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 561

```
gagatcgtgc tgacccagtc ccctgccacc ctgtccgtgt ctcccggcga gagagtgacc    60
ctgtcctgcc gggcctccca gtccatctcc aacaacctgc actggtatca gcagaagccc   120
ggccaggccc ctcggctgct gattaagtac gcctcccaga gcatctccgg catccctgcc   180
agattctccg gctccggcag cggcaccgac ttcaccctga ccatctccag cgtggaaccc   240
gaggacttcg gcgtgtactt ctgccagcag tcctcatcct ggctgacctt cggccagggc   300
accaagctgg aaatcaag                                                 318
```

<210> SEQ ID NO 562
<211> LENGTH: 213
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 562

```
            Glu Ile Val Leu Thr Gln Ser Pro Ala Thr Leu Ser Val Ser Pro Gly
            1               5                  10                  15

Glu Arg Val Thr Leu Ser Cys Arg Ala Ser Gln Ser Ile Ser Asn Asn
                            20                  25                  30

Leu His Trp Tyr Gln Gln Lys Pro Gly Gln Ala Pro Arg Leu Leu Ile
                        35                  40                  45

Lys Tyr Ala Ser Gln Ser Ile Ser Gly Ile Pro Ala Arg Phe Ser Gly
                    50                  55                  60

Ser Gly Ser Gly Thr Asp Phe Thr Leu Thr Ile Ser Ser Val Glu Pro
            65                  70                  75                  80

Glu Asp Phe Gly Val Tyr Phe Cys Gln Gln Ser Ser Ser Trp Leu Thr
                                85                  90                  95

Phe Gly Gln Gly Thr Lys Leu Glu Ile Lys Arg Thr Val Ala Ala Pro
                            100                 105                 110

Ser Val Phe Ile Phe Pro Pro Ser Asp Glu Gln Leu Lys Ser Gly Thr
                        115                 120                 125
```

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210

<210> SEQ ID NO 563
<211> LENGTH: 639
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 563
gagatcgtgc tgacccagtc ccctgccacc ctgtccgtgt ctcccggcga gagagtgacc      60
ctgtcctgcc gggcctccca gtccatctcc aacaacctgc actggtatca gcagaagccc     120
ggccaggccc ctcggctgct gattaagtac gcctcccaga gcatctccgg catccctgcc     180
agattctccg gctccggcag cggcaccgac ttcaccctga ccatctccag cgtggaaccc     240
gaggacttcg cgtgtacttc tgccagcag tcctcatcct ggctgacctt cggccagggc     300
accaagctgg aaatcaagcg tacggtggcc gctcccagcg tgttcatctt cccccccagc     360
gacgagcagc tgaagagtgg caccgccagc gtggtgtgcc tgctgaacaa cttctacccc     420
cgggaggcca aggtgcagtg gaaggtggac aacgccctgc agagcggcaa cagccaggag     480
agcgtcaccg agcaggacag caaggactcc acctacagcc tgagcagcac cctgaccctg     540
agcaaggccg actacgagaa gcataaggtg tacgcctgcg aggtgaccca ccagggcctg     600
tccagccccg tgaccaagag cttcaacagg ggcgagtgc                            639

<210> SEQ ID NO 564
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 564

Gly Phe Thr Phe Ser Ser Tyr Ala Met Ser
1               5                   10

<210> SEQ ID NO 565
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 565

```
Thr Ile Ser Ser Gly Gly Ser Phe Thr Tyr Tyr Pro Asp Ser Val Lys
1               5                   10                  15

Gly

<210> SEQ ID NO 566
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 566

Arg Ala Ser Thr Val Val Gly Thr Asp Phe Asp Val
1               5                   10

<210> SEQ ID NO 567
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 567

Ser Tyr Ala Met Ser
1               5

<210> SEQ ID NO 568
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 568

Thr Ile Ser Ser Gly Gly Ser Phe Thr Tyr Tyr Pro Asp Ser Val Lys
1               5                   10                  15

Gly

<210> SEQ ID NO 569
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 569

Arg Ala Ser Thr Val Val Gly Thr Asp Phe Asp Val
1               5                   10

<210> SEQ ID NO 570
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 570
```

```
Gly Phe Thr Phe Ser Ser Tyr
1               5

<210> SEQ ID NO 571
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 571

Ser Ser Gly Gly Ser Phe
1               5

<210> SEQ ID NO 572
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 572

Arg Ala Ser Thr Val Val Gly Thr Asp Phe Asp Val
1               5                   10

<210> SEQ ID NO 573
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 573

Gly Phe Thr Phe Ser Ser Tyr Ala
1               5

<210> SEQ ID NO 574
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 574

Ile Ser Ser Gly Gly Ser Phe Thr
1               5

<210> SEQ ID NO 575
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 575

Ala Arg Arg Ala Ser Thr Val Val Gly Thr Asp Phe Asp Val
1               5                   10
```

<210> SEQ ID NO 576
<211> LENGTH: 121
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 576

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Ile Arg Gln Ala Pro Gly Lys Gly Leu Glu Trp Val
        35                  40                  45

Ala Thr Ile Ser Ser Gly Gly Ser Phe Thr Tyr Tyr Pro Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Arg Ala Ser Thr Val Val Gly Thr Asp Phe Asp Val Trp Gly
            100                 105                 110

Gln Gly Thr Thr Val Thr Val Ser Ser
        115                 120

<210> SEQ ID NO 577
<211> LENGTH: 363
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 577
gaggtgcagc tggtggaatc tggcggaggc ctggtgaaac ccggcggatc cctgagactg      60
tcctgcgccg cctccggctt caccttctcc agctacgcca tgtcctggat ccggcaggct     120
cccggcaagg gcctggaatg ggtggccacc atctcctccg gcggcagctt cacctactac     180
cccgacagcg tgaagggcag attcaccatc agccgggaca acgccaagaa ctccctgtac     240
ctgcagatga actccctgcg ggccgaggac accgccgtgt actactgtgc cagacgggcc     300
tccaccgtcg tgggaaccga cttcgatgtg tggggccagg gcaccaccgt gacagtgtcc     360
tcc                                                                  363

<210> SEQ ID NO 578
<211> LENGTH: 451
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 578

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

```
Ala Met Ser Trp Ile Arg Gln Ala Pro Gly Lys Gly Leu Glu Trp Val
            35                  40                  45

Ala Thr Ile Ser Ser Gly Gly Ser Phe Thr Tyr Tyr Pro Asp Ser Val
 50                      55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Arg Arg Ala Ser Thr Val Val Gly Thr Asp Phe Asp Val Trp Gly
                100                 105                 110

Gln Gly Thr Thr Val Thr Val Ser Ser Ala Ser Thr Lys Gly Pro Ser
            115                 120                 125

Val Phe Pro Leu Ala Pro Ser Ser Lys Ser Thr Ser Gly Gly Thr Ala
        130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
                180                 185                 190

Pro Ser Ser Ser Leu Gly Thr Gln Thr Tyr Ile Cys Asn Val Asn His
                195                 200                 205

Lys Pro Ser Asn Thr Lys Val Asp Lys Arg Val Glu Pro Lys Ser Cys
210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Ala Val Ser His
                260                 265                 270

Glu Asp Pro Glu Val Lys Phe Asn Trp Tyr Val Asp Gly Val Glu Val
            275                 280                 285

His Asn Ala Lys Thr Lys Pro Arg Glu Glu Gln Tyr Asn Ser Thr Tyr
        290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Ala Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser
        355                 360                 365

Leu Thr Cys Leu Val Lys Gly Phe Tyr Pro Ser Asp Ile Ala Val Glu
370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445
```

Pro Gly Lys
    450

<210> SEQ ID NO 579
<211> LENGTH: 1353
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 579

```
gaggtgcagc tggtggaatc tggcggaggc ctggtgaaac cggcggatc cctgagactg      60
tcctgcgccg cctccggctt caccttctcc agctacgcca tgtcctggat ccggcaggct     120
cccggcaagg gcctggaatg ggtggccacc atctcctccg gcggcagctt cacctactac     180
cccgacagcg tgaagggcag attcaccatc agccgggaca cgccaagaa ctccctgtac      240
ctgcagatga actccctgcg ggccgaggac accgccgtgt actactgtgc agacgggcc      300
tccaccgtcg tgggaaccga cttcgatgtg tggggccagg gcaccaccgt gacagtgtcc     360
tccgctagca ccaagggccc aagtgtgttt cccctggccc ccagcagcaa gtctacttcc     420
ggcggaactg ctgccctggg ttgcctggtg aaggactact ccccgagcc cgtgacagtg      480
tcctggaact ctggggctct gacttccggc gtgcacacct tcccgccgt gctgcagagc     540
agcggcctgt acagcctgag cagcgtggtg acagtgccct ccagctctct gggaacccag    600
acctatatct gcaacgtgaa ccacaagccc agcaacacca aggtggacaa gagagtggag    660
cccaagagct gcgacaagac ccacacctgc cccccctgcc cagctccaga actgctggga    720
gggccttccg tgttcctgtt cccccccaag cccaaggaca ccctgatgat cagcaggacc    780
cccgaggtga cctgcgtggt ggtggccgtg tcccacgagg acccagaggt gaagttcaac    840
tggtacgtgg acggcgtgga ggtgcacaac gccaagacca gcccagaga ggagcagtac    900
aacagcacct acagggtggt gtccgtgctg accgtgctgc accaggactg gctgaacggc    960
aaagaataca agtgcaaagt ctccaacaag gccctggctg ccccaatcga aaagacaatc   1020
agcaaggcca agggccagcc acgggagccc caggtgtaca ccctgccccc cagccgggag   1080
gagatgacca gaaccaggt gtccctgacc tgtctggtga agggcttcta ccccagcgat   1140
atcgccgtgg agtgggagag caacggccag cccgagaaca actacaagac caccccccca   1200
gtgctggaca gcgacggcag cttcttcctg tacagcaagc tgaccgtgga caagtccagg   1260
tggcagcagg gcaacgtgtt cagctgcagc gtgatgcacg aggccctgca caaccactac   1320
acccagaagt ccctgagcct gagccccggc aag                                1353
```

<210> SEQ ID NO 580
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 580

Arg Ala Ser Gln Asp Ile Gly Ser Ser Leu Asn
1               5                   10

<210> SEQ ID NO 581
<211> LENGTH: 7

```
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 581

Ala Thr Ser Ser Leu Asp Ser
1               5

<210> SEQ ID NO 582
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 582

Leu Gln Tyr Ala Ser Ser Pro Pro Thr
1               5

<210> SEQ ID NO 583
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 583

Arg Ala Ser Gln Asp Ile Gly Ser Ser Leu Asn
1               5                   10

<210> SEQ ID NO 584
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 584

Ala Thr Ser Ser Leu Asp Ser
1               5

<210> SEQ ID NO 585
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 585

Leu Gln Tyr Ala Ser Ser Pro Pro Thr
1               5

<210> SEQ ID NO 586
<211> LENGTH: 7
<212> TYPE: PRT
<213> ORGANISM: Artificial Sequence
<220> FEATURE:
<221> NAME/KEY: source
```

<223> OTHER INFORMATION: /note="Description of Artificial Sequence:
     Synthetic peptide"

<400> SEQUENCE: 586

Ser Gln Asp Ile Gly Ser Ser
1               5

<210> SEQ ID NO 587
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
     Synthetic peptide"

<400> SEQUENCE: 587

Ala Thr Ser
1

<210> SEQ ID NO 588
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
     Synthetic peptide"

<400> SEQUENCE: 588

Tyr Ala Ser Ser Pro Pro
1               5

<210> SEQ ID NO 589
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
     Synthetic peptide"

<400> SEQUENCE: 589

Gln Asp Ile Gly Ser Ser
1               5

<210> SEQ ID NO 590
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
     Synthetic peptide"

<400> SEQUENCE: 590

Ala Thr Ser
1

<210> SEQ ID NO 591
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
     Synthetic peptide"

<400> SEQUENCE: 591

Leu Gln Tyr Ala Ser Ser Pro Pro Thr
1               5

<210> SEQ ID NO 592
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 592

Asp Ile Gln Met Thr Gln Ser Pro Ser Ser Leu Ser Ala Ser Val Gly
1               5                   10                  15

Asp Arg Val Thr Leu Thr Cys Arg Ala Ser Gln Asp Ile Gly Ser Ser
            20                  25                  30

Leu Asn Trp Leu Gln Gln Lys Pro Gly Lys Ala Ile Lys Arg Leu Ile
        35                  40                  45

Tyr Ala Thr Ser Ser Leu Asp Ser Gly Val Pro Ser Arg Phe Ser Gly
    50                  55                  60

Ser Arg Ser Gly Thr Asp Tyr Thr Leu Thr Ile Ser Ser Leu Gln Pro
65                  70                  75                  80

Glu Asp Phe Val Val Tyr Tyr Cys Leu Gln Tyr Ala Ser Ser Pro Pro
                85                  90                  95

Thr Phe Gly Gly Gly Thr Lys Leu Glu Ile Lys
            100                 105

<210> SEQ ID NO 593
<211> LENGTH: 321
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 593
gacatccaga tgacccagtc cccctccagc ctgtccgcct ccgtgggcga tagagtgacc      60
ctgacctgcc gggcctccca ggacatcggc tcctccctga actggctgca gcagaagccc    120
ggcaaggcca tcaagcggct gatctacgcc acctcctccc tggactccgg cgtgccctcc    180
cggttctccg gctctagatc cggcaccgac tacaccctga ccatctccag cctgcagccc    240
gaggacttcg tggtgtacta ctgcctgcag tacgcctcca gccccccac ctttggcgga    300 ggcaccaagc tggaaatcaa g                                              321

<210> SEQ ID NO 594
<211> LENGTH: 214
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 594

Asp Ile Gln Met Thr Gln Ser Pro Ser Ser Leu Ser Ala Ser Val Gly
1               5                   10                  15

Asp Arg Val Thr Leu Thr Cys Arg Ala Ser Gln Asp Ile Gly Ser Ser
            20                  25                  30

Leu Asn Trp Leu Gln Gln Lys Pro Gly Lys Ala Ile Lys Arg Leu Ile
            35                  40                  45

Tyr Ala Thr Ser Ser Leu Asp Ser Gly Val Pro Ser Arg Phe Ser Gly
 50                  55                  60

Ser Arg Ser Gly Thr Asp Tyr Thr Leu Thr Ile Ser Ser Leu Gln Pro
 65                  70                  75                  80

Glu Asp Phe Val Val Tyr Tyr Cys Leu Gln Tyr Ala Ser Ser Pro Pro
                 85                  90                  95

Thr Phe Gly Gly Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
            130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205

Phe Asn Arg Gly Glu Cys
            210

<210> SEQ ID NO 595
<211> LENGTH: 642
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 595
gacatccaga tgacccagtc ccctccagc ctgtccgcct ccgtgggcga tagagtgacc      60
ctgacctgcc gggcctccca ggacatcggc tcctccctga actggctgca gcagaagccc    120
ggcaaggcca tcaagcggct gatctacgcc acctcctccc tggactccgg cgtgccctcc    180
cggttctccg gctctagatc cggcaccgac tacaccctga ccatctccag cctgcagccc    240
gaggacttcg tggtgtacta ctgcctgcag tacgcctcca gccccccac ctttggcgga    300 ggcaccaagc tggaaatcaa gcgtacggtg gccgctccca gcgtgttcat cttccccccc    360
agcgacgagc agctgaagag tggcaccgcc agcgtggtgt gcctgctgaa caacttctac    420 ccccggagg ccaaggtgca gtggaaggtg gacaacgccc tgcagagcgg caacagccag    480
gagagcgtca ccgagcagga cagcaaggac tccacctaca gcctgagcag cacctgacc    540 ctgagcaagg ccgactacga gaagcataag gtgtacgcct gcgaggtgac ccaccagggc    600
ctgtccagcc ccgtgaccaa gagcttcaac agggcgagt gc                        642

<210> SEQ ID NO 596
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 596

Gly Phe Thr Phe Ser Asn Phe Ala Met Ser
1               5                   10

<210> SEQ ID NO 597
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 597

Thr Ile Ser Thr Gly Gly Thr Tyr Thr Tyr Tyr Pro Asp Ser Val Lys
1               5                   10                  15

Gly

<210> SEQ ID NO 598
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 598

Arg Gly Tyr Ser Gly Val Asp Lys
1               5

<210> SEQ ID NO 599
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 599

Ser Asn Phe Ala Met Ser
1               5

<210> SEQ ID NO 600
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 600

Thr Ile Ser Thr Gly Gly Thr Tyr Thr Tyr Tyr Pro Asp Ser Val Lys
1               5                   10                  15

Gly

<210> SEQ ID NO 601
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

```
<400> SEQUENCE: 601

Arg Gly Tyr Ser Gly Val Asp Lys
1               5

<210> SEQ ID NO 602
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 602

Gly Phe Thr Phe Ser Asn Phe
1               5

<210> SEQ ID NO 603
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 603

Ser Thr Gly Gly Thr Tyr
1               5

<210> SEQ ID NO 604
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 604

Arg Gly Tyr Ser Gly Val Asp Lys
1               5

<210> SEQ ID NO 605
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 605

Gly Phe Thr Phe Ser Asn Phe Ala
1               5

<210> SEQ ID NO 606
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 606

Ile Ser Thr Gly Gly Thr Tyr Thr
```

<210> SEQ ID NO 607
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 607

Thr Arg Arg Gly Tyr Ser Gly Val Asp Lys
1               5                   10

<210> SEQ ID NO 608
<211> LENGTH: 117
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 608

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asn Phe
            20                  25                  30

Ala Met Ser Trp Val Arg Gln Ala Pro Gly Lys Gly Leu Glu Trp Val
        35                  40                  45

Ser Thr Ile Ser Thr Gly Gly Thr Tyr Thr Tyr Tyr Pro Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Arg Gly Tyr Ser Gly Val Asp Lys Trp Gly Gln Gly Thr Thr
            100                 105                 110

Val Thr Val Ser Ser
        115

<210> SEQ ID NO 609
<211> LENGTH: 351
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 609
gaggtgcagc tggtggaatc tggcggaggc ctggtgaaac cggcggatc cctgagactg       60 tcctgcgccg cctccggctt caccttctcc aacttcgcca tgtcctgggt gcggcaggct      120
cccggcaagg gcctggaatg ggtgtccacc atctccaccg gcggaccta cacctactac      180 cccgacagcg tgaagggcag attcaccatc agccgggaca cgccaagaa ctccctgtac      240 ctgcagatga actccctgcg ggccgaggac accgccgtgt actactgtgc cagacggggc      300
tactcaggcg tggacaaatg gggccagggc accaccgtga cagtgtcctc c              351

<210> SEQ ID NO 610

```
<211> LENGTH: 447
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 610
```

| | | | | | | | | | | | | | | | |
|---|---|---|---|---|---|---|---|---|---|---|---|---|---|---|---|
| Glu | Val | Gln | Leu | Val | Glu | Ser | Gly | Gly | Gly | Leu | Val | Lys | Pro | Gly | Gly |
| 1 | | | | 5 | | | | | 10 | | | | | 15 | |
| Ser | Leu | Arg | Leu | Ser | Cys | Ala | Ala | Ser | Gly | Phe | Thr | Phe | Ser | Asn | Phe |
| | | | 20 | | | | | 25 | | | | | 30 | | |
| Ala | Met | Ser | Trp | Val | Arg | Gln | Ala | Pro | Gly | Lys | Gly | Leu | Glu | Trp | Val |
| | | 35 | | | | | 40 | | | | | 45 | | | |
| Ser | Thr | Ile | Ser | Thr | Gly | Gly | Thr | Tyr | Thr | Tyr | Tyr | Pro | Asp | Ser | Val |
| 50 | | | | | 55 | | | | | 60 | | | | | |
| Lys | Gly | Arg | Phe | Thr | Ile | Ser | Arg | Asp | Asn | Ala | Lys | Asn | Ser | Leu | Tyr |
| 65 | | | | | 70 | | | | | 75 | | | | | 80 |
| Leu | Gln | Met | Asn | Ser | Leu | Arg | Ala | Glu | Asp | Thr | Ala | Val | Tyr | Tyr | Cys |
| | | | | 85 | | | | | 90 | | | | | 95 | |
| Ala | Arg | Arg | Gly | Tyr | Ser | Gly | Val | Asp | Lys | Trp | Gly | Gln | Gly | Thr | Thr |
| | | | 100 | | | | | 105 | | | | | 110 | | |
| Val | Thr | Val | Ser | Ser | Ala | Ser | Thr | Lys | Gly | Pro | Ser | Val | Phe | Pro | Leu |
| | | 115 | | | | | 120 | | | | | 125 | | | |
| Ala | Pro | Ser | Ser | Lys | Ser | Thr | Ser | Gly | Gly | Thr | Ala | Ala | Leu | Gly | Cys |
| 130 | | | | | 135 | | | | | 140 | | | | | |
| Leu | Val | Lys | Asp | Tyr | Phe | Pro | Cys | Pro | Val | Thr | Val | Ser | Trp | Asn | Ser |
| 145 | | | | | 150 | | | | | 155 | | | | | 160 |
| Gly | Ala | Leu | Thr | Ser | Gly | Val | His | Thr | Phe | Pro | Ala | Val | Leu | Gln | Ser |
| | | | | 165 | | | | | 170 | | | | | 175 | |
| Ser | Gly | Leu | Tyr | Ser | Leu | Ser | Ser | Val | Val | Thr | Val | Pro | Ser | Ser | Ser |
| | | | 180 | | | | | 185 | | | | | 190 | | |
| Leu | Gly | Thr | Gln | Thr | Tyr | Ile | Cys | Asn | Val | Asn | His | Lys | Pro | Ser | Asn |
| | | 195 | | | | | 200 | | | | | 205 | | | |
| Thr | Lys | Val | Asp | Lys | Arg | Val | Glu | Pro | Lys | Ser | Cys | Asp | Lys | Thr | His |
| 210 | | | | | 215 | | | | | 220 | | | | | |
| Thr | Cys | Pro | Pro | Cys | Pro | Ala | Pro | Glu | Leu | Leu | Gly | Gly | Pro | Ser | Val |
| 225 | | | | | 230 | | | | | 235 | | | | | 240 |
| Phe | Leu | Phe | Pro | Pro | Lys | Pro | Lys | Asp | Thr | Leu | Met | Ile | Ser | Arg | Thr |
| | | | | 245 | | | | | 250 | | | | | 255 | |
| Pro | Glu | Val | Thr | Cys | Val | Val | Val | Ala | Val | Ser | His | Glu | Asp | Pro | Glu |
| | | | 260 | | | | | 265 | | | | | 270 | | |
| Val | Lys | Phe | Asn | Trp | Tyr | Val | Asp | Gly | Val | Glu | Val | His | Asn | Ala | Lys |
| | | 275 | | | | | 280 | | | | | 285 | | | |
| Thr | Lys | Pro | Arg | Glu | Glu | Gln | Tyr | Asn | Ser | Thr | Tyr | Arg | Val | Val | Ser |
| 290 | | | | | 295 | | | | | 300 | | | | | |
| Val | Leu | Thr | Val | Leu | His | Gln | Asp | Trp | Leu | Asn | Gly | Lys | Glu | Tyr | Lys |
| 305 | | | | | 310 | | | | | 315 | | | | | 320 |
| Cys | Lys | Val | Ser | Asn | Lys | Ala | Leu | Ala | Ala | Pro | Ile | Glu | Lys | Thr | Ile |
| | | | | 325 | | | | | 330 | | | | | 335 | |
| Ser | Lys | Ala | Lys | Gly | Gln | Pro | Arg | Glu | Pro | Gln | Val | Tyr | Thr | Leu | Pro |
| | | | 340 | | | | | 345 | | | | | 350 | | |
| Pro | Ser | Arg | Glu | Glu | Met | Thr | Lys | Asn | Gln | Val | Ser | Leu | Thr | Cys | Leu |
| | | 355 | | | | | 360 | | | | | 365 | | | |

Val Lys Gly Phe Tyr Pro Cys Asp Ile Ala Val Glu Trp Glu Ser Asn
370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
                420                 425                 430

His Asn His Tyr Thr Gln Lys Ser Leu Ser Leu Ser Pro Gly Lys
435                 440                 445

<210> SEQ ID NO 611
<211> LENGTH: 1341
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 611
gaggtgcagc tggtggaatc tgcggaggc ctggtgaaac cggcggatc cctgagactg      60 tcctgcgccg cctccggctt caccttctcc aacttcgcca tgtcctgggt gcggcaggct     120
cccggcaagg gcctggaatg ggtgtccacc atctccaccg gcggcaccta cacctactac     180
cccgacagcg tgaagggcag attcaccatc agccgggaca acgccaagaa ctccctgtac     240
ctgcagatga actccctgcg ggccgaggac accgccgtgt actactgtgc agacgggc      300 tactcaggcg tggacaaatg gggccaggc accaccgtga cagtgtcctc cgctagcacc     360
aagggcccaa gtgtgtttcc cctggcccc agcagcaagt ctacttccgg cggaactgct     420
gccctgggtt gcctggtgaa ggactactc ccctgtcccg tgacagtgtc ctggaactct     480
ggggctctga cttccggcgt gcacaccttc cccgccgtgc tgcagagcag cggcctgtac     540
agcctgagca gcgtggtgac agtgccctcc agctctctgg gaacccagac ctatatctgc     600
aacgtgaacc acaagcccag caacaccaag gtggacaaga gagtggagcc caagagctgc     660
gacaagaccc acacctgccc ccctgccca gctccagaac tgctgggagg gccttccgtg     720
ttcctgttcc cccccaagcc caaggacac ctgatgatca gcaggacccc cgaggtgacc     780
tgcgtggtgg tggccgtgtc ccacgaggac ccagaggtga agttcaactg gtacgtggac     840
ggcgtggagg tgcacaacgc caagaccaag cccagagagg agcagtacaa cagcacctac     900
agggtggtgt ccgtgctgac cgtgctgcac caggactggc tgaacggcaa gaatacaag     960 tgcaaagtct ccaacaaggc cctggctgcc caatcgaaa agacaatcag caaggccaag    1020
ggccagccac gggagcccca ggtgtacacc ctgcccccca gccggagga gatgaccaag    1080 aaccaggtgt ccctgacctg tctggtgaag ggcttctacc cctgtgatat cgccgtggag    1140
tgggagagca acggcagcc cgagaacaac tacaagacca ccccccagt gctggacagc    1200 gacggcagct tcttcctgta cagcaagctg accgtggaca agtccaggtg gcagcagggc    1260
aacgtgttca gctgcagcgt gatgcacgag gccctgcaca accactacac ccagaagtcc    1320
ctgagcctga gccccggcaa g                                             1341

<210> SEQ ID NO 612
<211> LENGTH: 16
<212> TYPE: PRT
<213> ORGANISM: Artificial Sequence
<220> FEATURE:

```
<221> NAME/KEY: source
<223> OTHER INFORMATION: /note="Description of Artificial Sequence:
      Synthetic peptide"

<400> SEQUENCE: 612

Lys Ser Gly Gln Ser Leu Leu Asp Ser Thr Gly Lys Thr Tyr Leu Asn
1               5                   10                  15

<210> SEQ ID NO 613
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 613

Leu Val Ser Lys Leu Asp Ser
1               5

<210> SEQ ID NO 614
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 614

Trp Gln Gly Thr His Phe Pro Gln Thr
1               5

<210> SEQ ID NO 615
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 615

Lys Ser Gly Gln Ser Leu Leu Asp Ser Thr Gly Lys Thr Tyr Leu Asn
1               5                   10                  15

<210> SEQ ID NO 616
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 616

Leu Val Ser Lys Leu Asp Ser
1               5

<210> SEQ ID NO 617
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
```

```
<400> SEQUENCE: 617

Trp Gln Gly Thr His Phe Pro Gln Thr
1               5

<210> SEQ ID NO 618
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 618

Gly Gln Ser Leu Leu Asp Ser Thr Gly Lys Thr Tyr
1               5                   10

<210> SEQ ID NO 619
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 619

Leu Val Ser
1

<210> SEQ ID NO 620
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 620

Gly Thr His Phe Pro Gln
1               5

<210> SEQ ID NO 621
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 621

Gln Ser Leu Leu Asp Ser Thr Gly Lys Thr Tyr
1               5                   10

<210> SEQ ID NO 622
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 622

Leu Val Ser
1
```

<210> SEQ ID NO 623
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
    Synthetic peptide"

<400> SEQUENCE: 623

Trp Gln Gly Thr His Phe Pro Gln Thr
1               5

<210> SEQ ID NO 624
<211> LENGTH: 112
<212> TYPE: PRT
<213> ORGANISM: Artificial Sequence
<220> FEATURE:
<221> NAME/KEY: source
<223> OTHER INFORMATION: /note="Description of Artificial Sequence:
    Synthetic polypeptide"

<400> SEQUENCE: 624

Asp Val Val Met Thr Gln Ser Pro Leu Ser Leu Pro Val Thr Leu Gly
1               5                   10                  15

Gln Pro Ala Ser Ile Ser Cys Lys Ser Gly Gln Ser Leu Leu Asp Ser
            20                  25                  30

Thr Gly Lys Thr Tyr Leu Asn Trp Phe Leu Gln Arg Pro Gly Gln Ser
        35                  40                  45

Pro Arg Arg Leu Ile Tyr Leu Val Ser Lys Leu Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Trp Gln Gly
                85                  90                  95

Thr His Phe Pro Gln Thr Phe Gly Gly Gly Thr Lys Leu Glu Ile Lys
            100                 105                 110

<210> SEQ ID NO 625
<211> LENGTH: 336
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic polynucleotide"

<400> SEQUENCE: 625
gacgtggtga tgacccagtc cccectgtcc ctgcctgtga ccctgggcca gcctgcctcc      60
atctcctgca gtccggcca gtccctgctg gactccactg gcaagaccta cctgaactgg     120
ttcctgcagc ggcctggcca gtcccctcgg cggctgatct acctggtgtc caagctggac     180
agcggcgtgc ccgacagatt ctccggctct ggctccggca ccgacttcac cctgaagatc     240
tcccgggtgg aagccgagga cgtgggcgtg tactactgct ggcagggcac ccacttcccc     300
cagaccttcg gcggaggcac caagctggaa atcaag                              336

<210> SEQ ID NO 626
<211> LENGTH: 219
<212> TYPE: PRT
<213> ORGANISM: Artificial Sequence
<220> FEATURE:

<221> NAME/KEY: source
<223> OTHER INFORMATION: /note="Description of Artificial Sequence:
      Synthetic polypeptide"

<400> SEQUENCE: 626

```
Asp Val Val Met Thr Gln Ser Pro Leu Ser Leu Pro Val Thr Leu Gly
1               5                   10                  15

Gln Pro Ala Ser Ile Ser Cys Lys Ser Gly Gln Ser Leu Leu Asp Ser
            20                  25                  30

Thr Gly Lys Thr Tyr Leu Asn Trp Phe Leu Gln Arg Pro Gly Gln Ser
        35                  40                  45

Pro Arg Arg Leu Ile Tyr Leu Val Ser Lys Leu Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Trp Gln Gly
                85                  90                  95

Thr His Phe Pro Gln Thr Phe Gly Gly Gly Thr Lys Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215
```

<210> SEQ ID NO 627
<211> LENGTH: 657
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 627

```
gacgtggtga tgacccagtc ccccctgtcc ctgcctgtga ccctgggcca gcctgcctcc    60
atctcctgca agtccggcca gtccctgctg gactccactg gcaagaccta cctgaactgg   120
ttcctgcagc ggcctggcca gtcccctcgg cggctgatct acctggtgtc caagctggac   180
agcggcgtgc ccgacagatt ctccggctct ggctccggca ccgacttcac cctgaagatc   240
tcccgggtgg aagccgagga cgtgggcgtg tactactgct ggcagggcac ccacttcccc   300
cagaccttcg gcggaggcac caagctggaa atcaagcgta cggtggccgc tcccagcgtg   360
ttcatcttcc cccccagcga cgagcagctg aagagtggca ccgccagcgt ggtgtgcctg   420
ctgaacaact ctacccccg ggaggccaag gtgcagtgga aggtggacaa cgccctgcag   480
agcggcaaca gccaggagag cgtcaccgag caggacagca aggactccac ctacagcctg   540
agcagcaccc tgaccctgag caaggccgac tacgagaagc ataaggtgta cgcctgcgag   600
```

```
gtgacccacc agggcctgtc cagccccgtg accaagagct tcaacagggg cgagtgc     657
```

<210> SEQ ID NO 628
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
  Synthetic 6xHis tag"

<400> SEQUENCE: 628

His His His His His His
1               5

<210> SEQ ID NO 629
<211> LENGTH: 22
<212> TYPE: PRT
<213> ORGANISM: Artificial Sequence
<220> FEATURE:
<221> NAME/KEY: source
<223> OTHER INFORMATION: /note="Description of Artificial Sequence:
  Synthetic peptide"

<400> SEQUENCE: 629

Tyr Gly Arg Lys Lys Arg Arg Gln Arg Arg Leu Tyr Arg Ser Pro
1               5                   10                  15

Ala Met Pro Glu Asn Leu
            20